US008658639B2

(12) United States Patent
Suetsugu et al.

(10) Patent No.: US 8,658,639 B2

(45) Date of Patent: Feb. 25, 2014

(54) N-SUBSTITUTED-CYCLIC AMINO DERIVATIVE

(75) Inventors: Satoshi Suetsugu, Suita (JP); Nobuhisa Fukuda, Suita (JP); Yoshio Nakai, Suita (JP); Takashi Takada, Osaka (JP); Yohei Ikuma, Suita (JP); Hiroyuki Nakahira, Osaka (JP)

(73) Assignee: Dainippon Sumitomo Pharma Co., Ltd, Osaka (JP)

( * ) Notice: Subject to any disclaimer, the term of this patent is extended or adjusted under 35 U.S.C. 154(b) by 68 days.

(21) Appl. No.: 13/380,376

(22) PCT Filed: Jun. 24, 2010

(86) PCT No.: PCT/JP2010/060716
§ 371 (c)(1),
(2), (4) Date: Dec. 22, 2011

(87) PCT Pub. No.: WO2010/150840
PCT Pub. Date: Dec. 29, 2010

(65) Prior Publication Data

US 2012/0122773 A1 May 17, 2012

(30) Foreign Application Priority Data

Jun. 24, 2009 (JP) ................................ 2009-150382

(51) Int. Cl.

| | |
|---|---|
| *A61K 31/538* | (2006.01) |
| *C07D 413/12* | (2006.01) |
| *C07D 413/14* | (2006.01) |
| *C07D 417/14* | (2006.01) |
| *A61K 31/5415* | (2006.01) |
| *A61K 31/5386* | (2006.01) |
| *C07D 401/12* | (2006.01) |

(52) U.S. Cl.
USPC .................... 514/230.5; 514/322; 514/224.2; 514/312; 514/323; 514/224.5; 544/105; 544/52; 544/73; 546/157; 546/201; 546/199

(58) Field of Classification Search
None
See application file for complete search history.

(56) References Cited

U.S. PATENT DOCUMENTS

| | | | |
|---|---|---|---|
| 2004/0204455 | A1 | 10/2004 | Cody et al. |
| 2005/0137229 | A1 | 6/2005 | Fish et al. |
| 2010/0056497 | A1 | 3/2010 | Nakahira et al. |
| 2010/0087427 | A1 | 4/2010 | Breitenstein et al. |
| 2011/0190278 | A1 | 8/2011 | Nakahira et al. |

FOREIGN PATENT DOCUMENTS

| | | | | |
|---|---|---|---|---|
| EP | 1908761 A1 | 4/2008 | | |
| EP | 2119702 A1 | 11/2009 | | |
| JP | 2010-037276 A | 2/2010 | | |
| JP | 2010-064982 A | 3/2010 | | |
| JP | 2011-026301 A | 2/2011 | | |
| WO | 2004/089903 A1 | 10/2004 | | |
| WO | 2004/110995 A1 | 12/2004 | | |
| WO | 2005/053663 A2 | 6/2005 | | |
| WO | 2006/020598 A2 | 2/2006 | | |
| WO | 2006/064336 A2 | 6/2006 | | |
| WO | 2006/066133 A2 | 6/2006 | | |
| WO | 2006/066896 A2 | 6/2006 | | |
| WO | 2006/069788 A1 | 7/2006 | | |
| WO | WO 2006/069788 | * | 7/2006 | ........... C07D 401/10 |
| WO | 2006/094763 A1 | 9/2006 | | |
| WO | 2006/103273 A1 | 10/2006 | | |
| WO | 2006/103275 A1 | 10/2006 | | |
| WO | 2006/103277 A2 | 10/2006 | | |
| WO | 2007/006534 A2 | 1/2007 | | |
| WO | 2007/038138 A2 | 4/2007 | | |
| WO | 2007/077005 A1 | 7/2007 | | |
| WO | 2007/082907 A1 | 7/2007 | | |
| WO | 2007/141318 A1 | 12/2007 | | |

(Continued)

OTHER PUBLICATIONS

Takeshi Kawakita et al., "Synthesis and Pharmacology of 3,4-Dihydro-3-oxo-1,4-benzoxazine-8-carboxamide Derivatives, a New Class of Potent Serotonin-3(5-$HT_3$)Receptor Antagonists", Chem. Pharm. Bull., vol. 40, No. 3, 1992, pp. 624-630.

Translation of the International Preliminary Report on Patentability mailed Jan. 26, 2012, in International Application No. PCT/JP2010/060716.

Extended European Search Report issued Nov. 14, 2012 in European Patent Application No. 10792158.7 to Dainippon Sumitomo Pharma Co., Ltd.

(Continued)

*Primary Examiner* — Dennis Heyer
(74) *Attorney, Agent, or Firm* — Sughrue Mion, PLLC

(57) ABSTRACT

The present invention provides a compound of formula (I):

(I)

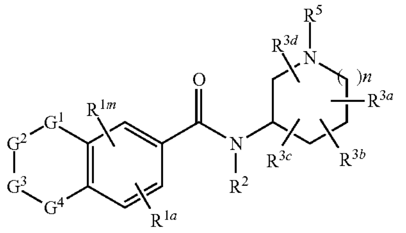

wherein $R^{1a}$ is optionally substituted $C_{1-6}$ alkyl, etc.; $R^{1m}$ is hydrogen atom, etc.; $G^1$, $G^2$, $G^3$ and $G^4$ are (i), etc. ((i) $G^1$ is —N($R^{1b}$)—, $G^2$ is —CO—, $G^3$ is —C($R^{1c}$)($R^{1d}$)—, and $G^4$ is oxygen, etc.); $R^{1b}$ is optionally substituted $C_{1-6}$ alkyl, etc.; $R^{1c}$ and $R^{1d}$ are each independently optionally substituted $C_{1-6}$ alkyl, etc.; $R^2$ is optionally substituted $C_{1-6}$ alkyl, etc.; $R^{3a}$, $R^{3b}$, $R^{3c}$ and $R^{3d}$ are each independently a group: -A-B (A is a single bond, etc., B is hydrogen atom, etc.), etc.; n is 1, etc.; $R^5$ is $C_{1-4}$ alkoxycarbonyl, etc., or a pharmaceutically acceptable salt thereof, which is useful as a renin inhibitor.

36 Claims, No Drawings

(56) References Cited

FOREIGN PATENT DOCUMENTS

| | | | |
|---|---|---|---|
| WO | 2008/017685 | A1 | 2/2008 |
| WO | 2008/040764 | A1 | 4/2008 |
| WO | WO 2008/093737 | A1 | 8/2008 |
| WO | 2008/136457 | A1 | 11/2008 |
| WO | WO 2008/136444 | A1 | 11/2008 |
| WO | 2008/153135 | A1 | 12/2008 |
| WO | 2008/153182 | A1 | 12/2008 |
| WO | 2009/005002 | A1 | 1/2009 |
| WO | 2009/014217 | A1 | 1/2009 |
| WO | 2009/050253 | A1 | 4/2009 |
| WO | 2009/051112 | A1 | 4/2009 |
| WO | 2009/053452 | A1 | 4/2009 |
| WO | 2009/056617 | A2 | 5/2009 |
| WO | 2009/070869 | A1 | 6/2009 |
| WO | 2009/071606 | A1 | 6/2009 |
| WO | 2009/072649 | A1 | 6/2009 |
| WO | 2009/074674 | A2 | 6/2009 |
| WO | WO 2009/078481 | A1 | 6/2009 |
| WO | 2009/154300 | A2 | 12/2009 |

* cited by examiner

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = Glu(EDANS)
<220> FEATURE:
<221> NAME/KEY: MISC_FEATURE
<222> LOCATION: (13)..(13)
<223> OTHER INFORMATION: Xaa = Lys(DABCYL)

<400> SEQUENCE: 1

Arg Xaa Ile His Pro Phe His Leu Val Ile His Thr Xaa Arg
1               5                   10


<210> SEQ ID NO 2
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = DABCYL-gamma-Abu
<220> FEATURE:
<221> NAME/KEY: MISC_FEATURE
```

-continued

```
<222> LOCATION: (11)..(11)
<223> OTHER INFORMATION: Xaa = Thr-EDANS

<400> SEQUENCE: 2

Xaa Ile His Pro Phe His Leu Val Ile His Xaa
1               5                   10
```

N-SUBSTITUTED-CYCLIC AMINO DERIVATIVE

CROSS REFERENCE TO RELATED APPLICATION

This application is a National Stage of International Application No. PCT/JP2010/060716 filed Jun. 24, 2010, claiming priority based on Japanese Patent Application No. 2009-150382, filed Jun. 24, 2009, the contents of all of which are incorporated herein by reference in their entirety.

TECHNICAL FIELD

The present invention relates to N-substituted cyclic amino derivatives which are useful as a medication. Specifically, it relates to N-substituted cyclic amino derivatives which are effective as a renin inhibitor. Further, it relates to a therapeutic agent for hypertension comprising N-substituted cyclic amino derivatives which are effective as a renin inhibitor.

BACKGROUND ART

A renin-angiotensin (RA) system is a hormone system which is important for maintaining electrolyte balance of blood pressure and within body, and plays an important role for development and progress of circulatory diseases such as hypertension, congestive heart failure, renal disorder.

Renin which is an important component of RA system is an aspartic protease which is secreted mainly from the kidney into the blood, and specifically breaks down angiotensinogen which is generated in the liver to produce angiotensin I. Angiotensin I is converted into angiotensin II by angiotensin converting enzyme (ACE) which exists in lung and vascular endothelial cells. Angiotensin II not only constricts a blood vessel, but also stimulates the adrenal gland to promote secretions of aldosterone. Aldosterone acts on the kidney to conserve sodium and eliminate potassium. These cascades cause increased blood pressure (Nonpatent Document 1).

Recently, it has been indicated that RA system components also exist in local sites including peripheral tissues or central tissues such as heart, blood vessel, kidney, adrenal gland, adipose, and (pro)renin receptor has the possibility to play an important role in activation of local RA system as an additional new component (Nonpatent Document 2), and the importance of local (tissue) RA system has been recognized. It has been indicated that circulating RA system involves in short-term circulation controls, while tissue RA system has the possibility to cause organ damages such as cardiomegaly, arteriosclerosis, renal disorder by inducing long-term various organ remodelings in heart, kidney, blood vessel, etc. (Nonpatent Document 3).

RA system inhibiting agents include ACE inhibitors and angiotensin II receptor antagonists (ARB). It has been shown that these agents (especially, the former) are useful as a therapeutic agent not only for hypertension, but also for cardiovascular diseases and renal diseases such as heart failure and diabetic nephropathy, and these agents have been applied in a wide clinical setting (Nonpatent Document 4, Nonpatent Document 5).

There are multiple RA system inhibiting steps, and among them, renin is located in upstream of RA system and limits the cascade. Thus, to inhibit renin is significantly attractive approach in theory (Nonpatent Document 6, Nonpatent Document 7). Actually, it has been shown that a renin inhibitor aliskiren which has been recently developed significantly inhibits plasma renin activity in clinical trial intended for hypertension patients, and shows excellent hypotensive effects comparable to other RA system inhibiting agents (Nonpatent Document 8, Nonpatent Document 9, Nonpatent Document 10).

As a compound group wherein nitrogen atom in the ring of cyclic amino is substituted, a compound group of the following formula:

[Chemical Formula 1]

(I)

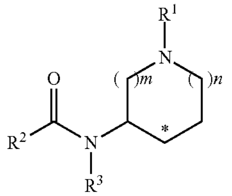

wherein $R^1$ is hydrogen atom, $C_{1-6}$ alkyl, —C(A)D, $C_{3-8}$ cycloalkyl, aryl, hetero, aryl-$C_{1-4}$ alkyl, or hetero-$C_{1-4}$ alkyl, $R^2$ is aryl or heteroaryl, A is S or O, D is hydrogen atom, halogen atom, $C_{1-6}$ alkyl, aryl, aryl-$C_{1-4}$ alkyl, or hetero-$C_{1-4}$ alkyl, n is 0 or 1, provided that if n is 1, m is 0 or 1, provided that if n is 2, m is 0, * is a chiral center, $R^3$ is hydrogen atom, $C_{1-6}$ alkyl, etc. has been known (Patent Document 1). However, this compound group is structurally different from the present compound in view of aryl or heteroaryl skeleton in "$R^2$".

As a renin inhibitor having cyclic amino, derivatives with a piperidine ring (Patent Documents 2 and 3), derivatives with a pyrrolidine ring (Patent Document 4) have been reported to be effective as a renin inhibitor. The compounds disclosed in these documents are structurally characterized in that they all have a partial structure wherein amino group binds to 3-position of piperidine ring and pyrrolidine ring via carbonyl group or methylene chain, and that nitrogen atom in the ring of piperidine ring and pyrrolidine ring is unsubstituted. It has been reported that a compound group having aminocarbonyl on 3-position of pyrrolidine ring or piperidine ring is effective as a renin inhibitor (Patent Documents 5 to 12). However, all these compound groups are structurally characterized in that nitrogen atom in the ring of cyclic amino (including pyrrolidine ring, piperidine ring) is unsubstituted. Hence, they are different from the present invention described hereinafter in that nitrogen atom in the ring of cyclic amino is unsubstituted or substituted by specific substituents.

[Patent Document 1] WO2006/064336 pamphlet
[Patent Document 2] WO2006/069788 pamphlet
[Patent Document 3] WO2006/094763 pamphlet
[Patent Document 4] WO2006/066896 pamphlet
[Patent Document 5] WO2008/093737 pamphlet
[Patent Document 6] WO2008/136457 pamphlet
[Patent Document 7] WO2008/153135 pamphlet
[Patent Document 8] WO2009/005002 pamphlet
[Patent Document 9] WO2009/014217 pamphlet
[Patent Document 10] WO2009/072649 pamphlet
[Patent Document 11] WO2009/078481 pamphlet
[Patent Document 12] WO2009/154300 pamphlet
[Nonpatent Document 1] Nat Rev Drug Discov. 1(8): p. 621-36 (2002)
[Nonpatent Document 2] Curr Hypertens Rep. 6(2): p. 129-32 (2004)
[Nonpatent Document 3] Physiol. Rev. 86: p. 747-803, (2006)
[Nonpatent Document 4] Curr Diab Rep. 6(1): p. 8-16, (2006)

[Nonpatent Document 5] J Hypertens Suppl. 23(1): S9-17, (2005)

[Nonpatent Document 6] J Exp Med. 106(3): p. 439-53, (1957)

[Nonpatent Document 7] J Am Soc Nephrol 16: p. 592-599 (2005)

[Nonpatent Document 8] Hypertension 42(6): p. 1137-43, (2003)

[Nonpatent Document 9] Circulation 111(8): p. 1012-8, (2005)

[Nonpatent Document 10] J Hypertens. 24(Suppl 4): S82. Abstract P4.269, (2006)

DISCLOSURE OF INVENTION

Problems to be Resolved by the Invention

The problem to be resolved by the present invention is to provide novel compounds having an excellent renin inhibitory effect as well as showing few side effects.

Means of Solving the Problems

According to the extensive studies to resolve the problem, the present inventors have found that the following compounds or pharmaceutically acceptable salts thereof wherein nitrogen atom in the ring of cyclic amino has specific substituents (which may be abbreviated as the present compound hereinafter, if needed) surprisingly show excellent renin inhibitory effects, and may reduce adverse effects such as actions or symptoms derived from inflammation-inducing effects, and have achieved the present invention.

The present invention is described as follows.

Item 1: A compound of formula (I):

[Chemical Formula 2]

(I)

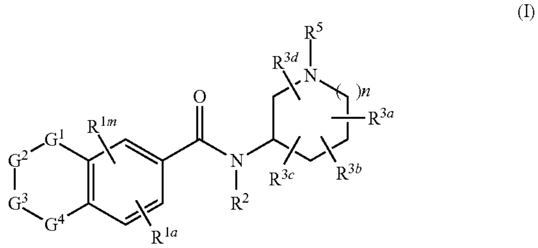

wherein $R^{1a}$ is halogen atom, hydroxyl, formyl, carboxy, cyano, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{5-6}$ cycloalkenyl, optionally substituted $C_{1-6}$ alkylthio, optionally substituted $C_{6-10}$ arylthio, optionally substituted $C_{1-6}$ alkylsulfonyl, optionally substituted $C_{1-6}$ alkoxy, optionally substituted $C_{3-6}$ cycloalkoxy, optionally substituted $C_{5-6}$ cycloalkenyloxy, optionally substituted amino, optionally substituted aminocarbonyl, optionally substituted $C_{1-4}$ alkoxycarbonyl, optionally substituted $C_{1-4}$ alkylcarbonyl, optionally substituted $C_{6-10}$ arylcarbonyl, optionally substituted $C_{6-10}$ aryl, optionally substituted $C_{6-10}$ aryloxy, optionally substituted $C_{7-14}$ aralkyloxy, or optionally substituted 5- to 10-membered monocyclic or polycyclic heteroaryl;

$R^{1m}$ is hydrogen atom, halogen atom, $C_{1-6}$ alkyl, $C_{3-6}$ cycloalkyl, $C_{1-6}$ alkoxy, or $C_{3-6}$ cycloalkoxy;

$G^1$, $G^2$, $G^3$ and $G^4$ are any of the following (i) to (v) (in which, (i) $G^1$ is —N($R^{1b}$)—, $G^2$ is —CO—, $G^3$ is —C($R^{1c}$)($R^{1d}$)—, and $G^4$ is —C($R^{1x}$)($R^{1y}$)—, —$SO_2$—, oxygen, sulfur, or absence, (ii) $G^1$ is —N($R^{1b}$)—, $G^2$ is —CO—, $G^3$ is —N($R^{1b}$)—, and $G^4$ is absence (wherein $R^{1b}$ in $G^1$ and $G^3$ are each independent), (iii) $G^1$ is oxygen, $G^2$ is —$CH_2$—, $G^3$ is oxygen, and $G^4$ is absence, (iv) $G^1$ is oxygen, $G^2$ is —$CH_2$—, $G^3$ is —$CH_2$—, and $G^4$ is oxygen, or (v) $G^1$ is —N($R^{1b}$)—, $G^2$ is —CO—, $G^3$ and $G^4$ are —C($R^{1d}$)=C($R^{1y}$)—);

$R^{1b}$ is optionally substituted $C_{1-6}$ alkyl, optionally substituted $C_{2-6}$ alkenyl, optionally substituted $C_{2-6}$ alkynyl, or optionally substituted 5- to 10-membered monocyclic or polycyclic heteroaryl $C_{1-4}$ alkyl;

$R^{1c}$ and $R^{1d}$ are each independently, same or different, hydrogen atom, halogen atom, hydroxyl, carboxy, optionally substituted $C_{2-6}$ alkenyl, optionally substituted $C_{5-6}$ cycloalkenyl, optionally substituted $C_{2-6}$ alkynyl, optionally substituted $C_{1-6}$ alkyl, optionally substituted $C_{3-6}$ cycloalkyl, optionally substituted aminocarbonyl, optionally substituted saturated heterocyclyl, optionally substituted $C_{1-6}$ alkoxy, optionally substituted $C_{3-6}$ cycloalkoxy, optionally substituted aminocarbonyl, optionally substituted $C_{1-4}$ alkoxycarbonyl, optionally substituted $C_{1-4}$ alkylcarbonyl, optionally substituted $C_{6-10}$ arylcarbonyl, optionally substituted 5- to 10-membered monocyclic or polycyclic heteroaryl, cyano, optionally substituted $C_{6-10}$ aryloxy, optionally substituted 5- to 10-membered monocyclic or polycyclic heteroaryloxy, optionally substituted $C_{7-14}$ aralkyloxy, optionally substituted $C_{7-14}$ aralkyl, optionally substituted amino, optionally substituted saturated heterocyclyloxy, optionally substituted 5- to 10-membered monocyclic or polycyclic heteroaryl $C_{1-4}$ alkyl, or a group of the following formula:

[Chemical Formula 3]

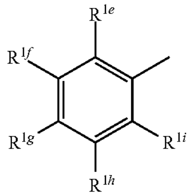

(wherein, $R^{1e}$, $R^{1f}$, $R^{1g}$, $R^{1h}$ and $R^{1i}$ are each independently, same or different, (a) hydrogen atom, (b) halogen atom, (c) cyano, (d) $C_{1-4}$ alkyl (in which the group may be optionally substituted by 5- to 6-membered saturated heterocyclyloxy, $C_{1-4}$ alkoxy (in which alkoxy may be optionally substituted by $C_{1-4}$ alkoxy or $C_{3-6}$ alkoxy), or 1 to 3 fluorine atoms), (e) $C_{1-4}$ alkoxy (in which the group may be optionally substituted by 1 to 3 halogen atoms, $C_{1-4}$ alkoxy or $C_{1-6}$ alkylaminocarbonyl), (f) $C_{3-6}$ cycloalkoxy (in which the group may be optionally substituted by $C_{1-4}$ alkoxy), (g) 5- to 6-membered saturated heterocyclyloxy, (h) $C_{1-6}$ alkylaminocarbonyl, (i) hydroxyl, or (j) $C_{1-4}$ alkylsulfonyl, or $R^{1e}$, $R^{1h}$ and $R^{1i}$ are each independently hydrogen atom, $R^{1f}$ and $R^{1g}$ combine each other to form a condensed ring), or alternatively, $R^{1c}$ and $R^{1d}$ combine each other to form a group of the following formula:

[Chemical Formula 4]

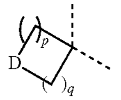

(wherein D is oxygen, sulfur, —$SO_2$—, —$NR^{4a}$—, —$NR^{4a}CO$—, $NR^{4a}SO_2$—, —$NR^{4a}CONR^{4a}$—, —$CH(R^{4b})$—, or —$CH(R^{4b})CH_2$—, $R^{4a}$ is hydrogen atom, optionally substituted $C_{1-6}$ alkyl, optionally substituted $C_{1-4}$ alkoxycarbonyl, optionally substituted $C_{1-4}$ alkylsulfonyl, or optionally substituted $C_{6-10}$ arylsulfonyl, $R^{4b}$ is hydrogen atom, halogen atom, hydroxyl, optionally substituted $C_{1-6}$ alkoxy, optionally substituted $C_{3-6}$ cycloalkoxy, optionally substituted $C_{7-14}$ aralkyloxy, or optionally substituted aminocarbonyloxy, p and q are each independently, same or different, 0, 1 or 2);

$R^{1x}$ and $R^{1y}$ are each independently, same or different, hydrogen atom, halogen atom, or $C_{1-4}$ alkyl, or alternatively, $R^{1x}$ and $R^{1y}$ combine each other to form a group of the following formula:

[Chemical Formula 5]

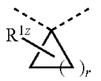

(wherein $R^{1z}$ is hydrogen atom, halogen atom, $C_{1-4}$ alkyl or $C_{1-4}$ alkoxy, r is 1, 2, 3 or 4);

$R^2$ is hydrogen atom, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted $C_{5-6}$ cycloalkenyl, optionally substituted $C_{6-10}$ aryl, optionally substituted $C_{7-14}$ aralkyl, or optionally substituted 5- to 10-membered monocyclic or polycyclic heteroaryl;

$R^{3a}$, $R^{3b}$, $R^{3a}$, and $R^{3d}$ are each independently, same or different, halogen atom, hydroxyl, formyl, carboxy, cyano, or a group: -A-B (wherein A is a single bond, —$(CH_2)_sO$—, —$(CH_2)_sN(R^{4c})$—, —$(CH_2)_sSO_2$—, —$(CH_2)_sCO$—, —$(CH_2)_sCOO$—, —$(CH_2)_sN(R^{4c})CO$—, —$(CH_2)_sN(R^{4c})SO_2$—, —$(CH_2)_sN(R^{4c})COO$—, —$(CH_2)_sOCON(R^{4c})$—, —$(CH_2)_sO$—CO—, —$(CH_2)_sCON(R^{4c})$—, —$(CH_2)_sN(R^{4c})CON(R^{4c})$—, or —$(CH_2)_sSO_2N(R^{4c})$—, B is hydrogen atom, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted $C_{5-6}$ cycloalkenyl, optionally substituted $C_{6-10}$ aryl, optionally substituted $C_{7-14}$ aralkyl, optionally substituted 5- to 10-membered monocyclic or polycyclic heteroaryl, optionally substituted 5- to 10-membered monocyclic or polycyclic heteroaryl $C_{1-4}$ alkyl, or optionally substituted saturated heterocyclyl, provided that if A is —$(CH_2)_sN(R^{4c})$—, —$(CH_2)_sOCON(R^{4c})$—, —$(CH_2)_sCON(R^{4c})$—, —$(CH_2)_sN(R^{4c})CON(R^{4c})$— and —$(CH_2)_sSO_2N(R^{4c})$—, $R^{4c}$ and B may combine each other to form a ring, $R^{4c}$ is hydrogen atom, optionally substituted $C_{1-6}$ alkyl, optionally substituted $C_{3-10}$ cycloalkyl, optionally substituted $C_{6-10}$ aryl, optionally substituted $C_{7-14}$ aralkyl, or optionally substituted 5- to 10-membered monocyclic or polycyclic heteroaryl, s is 0, 1 or 2, provided that if A is —$(CH_2)_sN(R^{4c})$—, s is 0 or 2, provided that if A is —$(CH_2)_sCON(R^{4c})$—, s is 1 or 2), or alternatively, any two of $R^{3a}$, $R^{3b}$, $R^{3c}$ and $R^{3d}$ are hydrogen atom, and the other two combine each other together with the adjacent heterocyclyl to form a bridged ring;

n is 0, 1 or 2;

$R^5$ is

1: $C_{1-6}$ alkyl (in which the group is substituted by (a) amino, (b) hydroxy, or (c) a group of the following formula:

[Chemical Formula 6]

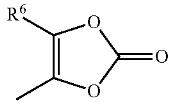

(wherein $R^6$ is (i) $C_{1-4}$ alkyl (in which the group may be optionally substituted by $C_{1-4}$ alkoxy), (ii) $C_{3-6}$ cycloalkyl, or (iii) $C_{6-10}$ aryl (in which the group may be optionally substituted by $C_{1-4}$ alkoxy))), 2: $C_{1-4}$ alkylcarbonyl (in which the group may be optionally substituted by (a) amino, or (b) hydroxy)

3: $C_{1-4}$ alkoxycarbonyl (in which the group is substituted by a group of the following formula:

[Chemical Formula 7]

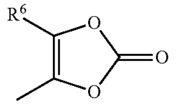

(wherein $R^6$ has the same meaning as defined above)), or

4: a group of the following formula:

[Chemical Formula 8]

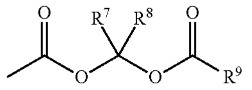

(wherein $R^7$ and $R^8$ are each independently, same or different, (a) hydrogen atom, (b) $C_{1-4}$ alkyl (in which the group may be optionally substituted by $C_{1-4}$ alkoxy, $C_{3-6}$ cycloalkyl (in which the group may be optionally substituted by $C_{1-4}$ alkoxy), 5- to 6-membered saturated heterocyclyl, or 5- to 6-membered saturated heterocyclyloxy), (c) $C_{3-10}$ cycloalkyl (in which the group may be optionally substituted by 1 to 2 fluorine atoms, or $C_{1-4}$ alkoxy),
(d) $C_{6-10}$ aryl (in which the group may be optionally substituted by halogen atom, or $C_{6-10}$ aryl (in which the aryl may be optionally substituted by halogen atom or $C_{1-4}$ alkoxy)),
(e) 5- to 6-membered saturated heterocyclyl, or
(f) 5- to 10-membered monocyclic or polycyclic heteroaryl (in which the group may be optionally substituted by $C_{1-4}$ alkyl, or $C_{1-4}$ alkoxy), $R^9$ is
(a) $C_{1-6}$ alkyl (in which the group may be optionally substituted by
1 to 3 fluorine atoms,
hydroxy,
$C_{1-4}$ alkoxy,
carboxy,
5- to 6-membered saturated heterocyclyl,
$C_{3-6}$ cycloalkyl,
$C_{1-4}$ alkoxycarbonyl,
$C_{1-4}$ alkoxycarbonylamino,
amino,
mono- or di-($C_{1-6}$ alkyl)amino,
5- to 7-membered cyclic amine,
1 to 2 nitroxy,
aminocarbonyl, or
5- to 7-membered cyclic aminocarbonyl),
(b) $C_{3-10}$ cycloalkyl (in which the group may be optionally substituted by hydroxy),
(c) $C_{6-10}$ aryl (in which the group is substituted by $C_{1-4}$ alkyl, $C_{1-4}$ alkoxy, or $C_{1-4}$ alkylcarbonyloxy),
(d) $C_{1-4}$ alkylcarbonyl (in which the group may be optionally substituted by hydroxy),
(e) 5- to 10-membered monocyclic or polycyclic heteroaryl,
(f) 5- to 6-membered saturated heterocyclyl (in which the group may be optionally substituted by $C_{1-4}$ alkyl optionally substituted by $C_{1-4}$ alkoxy),
(g) $C_{1-6}$ alkoxy (in which the group may be optionally substituted by $C_{3-6}$ cycloalkyl),
(h) $C_{3-6}$ cycloalkyloxy (in which the group may be optionally substituted by $C_{1-4}$ alkoxy), or
(i) 5- to 6-membered saturated heterocyclyloxy); or a pharmaceutically acceptable salt thereof Item 2: The compound of Item 1, wherein $G^1$, $G^2$, $G^3$ and $G^4$ are either of the following (i) or (ii) (in which,
(i) $G^1$ is —N($R^{1b}$)—, $G^2$ is —CO—, $G^3$ is —C($R^{1c}$)($R^{1d}$)—, and $G^4$ is —C($R^{1x}$)($R^{1y}$)—, —$SO_2$—, oxygen, sulfur, or absent, or
(ii) $G^1$ is —N($R^{1b}$)—, $G^2$ is —CO—, $G^3$ is —N($R^{1b}$)—, and $G^4$ is absent), or a pharmaceutically acceptable salt thereof.

Item 3: The compound of either Item 1 or 2, wherein $G^1$ is —N($R^{1b}$)—, $G^2$ is —CO—, $G^3$ is —C($R^{1c}$)($R^{1d}$)—, and $G^4$ is —$CH_2$—, —C($CH_3$)($CH_3$)—, —$SO_2$—, oxygen, or sulfur, or a pharmaceutically acceptable salt thereof.

Item 4: The compound of Item 3, wherein $G^4$ is oxygen, or a pharmaceutically acceptable salt thereof.

Item 5: The compound of Item 3, wherein $G^4$ is sulfur, or a pharmaceutically acceptable salt thereof.

Item 6: The compound of Item 3, wherein $G^4$ is —$CH_2$—, or a pharmaceutically acceptable salt thereof.

Item 7: The compound of Item 2, wherein $G^4$ is absent, or a pharmaceutically acceptable salt thereof.

Item 8: The compound of Item 2, wherein $G^1$ is —N($R^{1b}$)—, $G^2$ is —CO—, $G^3$ is —N($R^{1b}$)—, and $G^4$ is absent, or a pharmaceutically acceptable salt thereof.

Item 9: The compound of any one of Items 1 to 8, wherein $R^{1a}$ and $R^{1m}$ bind to the adjacent ring in any binding positions of the following formulae (A) to (C):

[Chemical Formula 9]

(A)

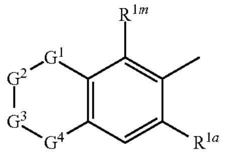

(B)

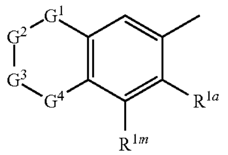

(C)

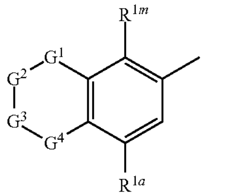

or a pharmaceutically acceptable salt thereof

Item 10: The compound of Item 9, wherein $R^{1a}$ and $R^{1m}$ bind to the adjacent ring in either binding position of the following formula (A) or (B):

[Chemical Formula 10]

(A)

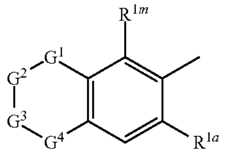

(B)

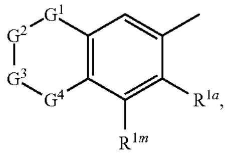

or a pharmaceutically acceptable salt thereof.

Item 11: The compound of any one of Items 1 to 10, wherein $R^{1a}$ is one group selected from the group consisting of
1: halogen atom;
2: cyano;
3: $C_{1-6}$ alkyl (in which the group may be optionally substituted by
(a) 1 to 3 fluorine atoms,
(b) $C_{1-4}$ alkoxy, or
(c) $C_{3-6}$ cycloalkoxy);
4: $C_{1-6}$ alkoxy (in which the group may be optionally substituted by
(a) 1 to 3 fluorine atoms, or
(b) $C_{3-6}$ cycloalkyl);
5: $C_{3-6}$ cycloalkyl;
6: $C_{3-6}$ cycloalkoxy (in which the group may be optionally substituted by
(a) 1 to 3 fluorine atoms, or
(b) $C_{1-4}$ alkoxy); and 7: 5- to 6-membered monocyclic heteroaryl (in which the group may be optionally substituted by $C_{1-4}$ alkyl); or a pharmaceutically acceptable salt thereof.

Item 12: The compound of any one of Items 1 to 11, wherein $R^{1a}$ is halogen atom, cyano, $C_{1-6}$ alkyl optionally substituted by 1 to 3 fluorine atoms, or $C_{1-6}$ alkoxy, or a pharmaceutically acceptable salt thereof.

Item 13: The compound of Item 12, wherein $R^{1a}$ is $C_{1-6}$ alkyl optionally substituted by 1 to 3 fluorine atoms, or a pharmaceutically acceptable salt thereof.

Item 14: The compound of Item 13, wherein $R^{1a}$ is methyl, or trifluoromethyl, or a pharmaceutically acceptable salt thereof.

Item 15: The compound of any one of Items 1 to 14, wherein $R^{1m}$ is hydrogen atom, halogen atom, or $C_{1-6}$ alkoxy, or a pharmaceutically acceptable salt thereof.

Item 16: The compound of Item 15, wherein $R^{1m}$ is hydrogen atom, or a pharmaceutically acceptable salt thereof.

Item 17: The compound of any one of Items 1 to 16, wherein $R^{1b}$ is

1: $C_{1-6}$ alkyl (in which the group may be optionally substituted by two groups selected from the group consisting of (a) hydroxy, (b) $C_{1-4}$ alkoxy (in which the group may be optionally substituted by 1 to 3 fluorine atoms, or $C_{1-4}$ alkoxy), (c) cyano, (d) trifluoromethyl, (e) trifluoromethoxy, (f) $C_{3-6}$ cycloalkyl (in which the group may be optionally substituted by 1 to 2 fluorine atoms, $C_{1-4}$ alkyl optionally substituted by $C_{1-4}$ alkoxy, or $C_{1-4}$ alkoxy), (g) $C_{3-6}$ cycloalkoxy, (h) formylamino, (i) $C_{1-4}$ alkylcarbonylamino (in which the group may be optionally substituted by 1 to 3 fluorine atoms), (j) N—($C_{1-4}$ alkylcarbonyl)-N—($C_{1-6}$ alkyl)-amino, (k) $C_{3-6}$ cycloalkylcarbonylamino, (l) ($C_{3-6}$ cycloalkyl$C_{1-4}$ alkyl)carbonylamino, (m) $C_{1-4}$ alkylthiocarbonylamino, (n) $C_{1-4}$ alkoxycarbonylamino (in which the group may be optionally substituted by 1 to 3 fluorine atoms), (o) N—($C_{1-4}$ alkoxycarbonyl)-N—($C_{1-6}$ alkyl)-amino, (p) mono- or di-($C_{1-6}$ alkyl)aminocarbonyloxy, (q) $C_{1-6}$ alkylaminocarbonyl (in which the group may be optionally substituted by 1 to 3 fluorine atoms), (r) di-($C_{1-6}$ alkyl)aminocarbonyl, (s) $C_{3-6}$ cycloalkylaminocarbonyl, (t) $C_{1-6}$ alkylaminocarbonylamino, (u) $C_{1-6}$ alkylaminothiocarbonylamino, (v) $C_{1-4}$ alkylcarbonyl (in which the group may be optionally substituted by $C_{1-4}$ alkoxy), (w) $C_{1-4}$ alkylcarbonyloxy, (x) $C_{1-4}$ alkoxycarbonyl, (y) $C_{1-6}$ alkylsulfonyl, (z) $C_{1-4}$ alkylsulfonylamino, (aa) 5- to 6-membered saturated heterocyclyl, (ab) carboxy, and (ac) $C_{1-6}$ alkylamino (in which alkyl may be optionally substituted by 1 to 3 fluorine atoms));

2: $C_{2-6}$ alkenyl (in which the group may be optionally substituted by halogen atom);

3: $C_{2-6}$ alkynyl (in which the group may be optionally substituted by $C_{1-4}$ alkoxy);

4: 5- to 6-membered monocyclic heteroaryl$C_{1-4}$ alkyl; or

5: $C_{3-6}$ cycloalkyl; or a pharmaceutically acceptable salt thereof

Item 18: The compound of any one of Items 1 to 17, wherein $R^{1b}$ is (a) $C_{1-6}$ alkyl, which is optionally substituted by $C_{1-4}$ alkoxy, $C_{1-4}$ alkylcarbonylamino optionally substituted by 1 to 3 fluorine atoms, or $C_{1-4}$ alkoxycarbonylamino; or (b) 5- to 6-membered heteroaryl$C_{1-4}$ alkyl; or a pharmaceutically acceptable salt thereof.

Item 19: The compound of Item 18, wherein $R^{1b}$ is $C_{1-6}$ alkyl optionally substituted by $C_{1-4}$ alkoxy, or a pharmaceutically acceptable salt thereof Item 20: The compound of Item 19, wherein $R^{1b}$ is 3-methoxypropyl, or a pharmaceutically acceptable salt thereof.

Item 21: The compound of Item 19, wherein $R^{1b}$ is 4-methoxybutyl, or a pharmaceutically acceptable salt thereof.

Item 22: The compound of Item 18, wherein $R^{1b}$ is $C_{1-6}$ alkyl which is optionally substituted by $C_{1-4}$ alkylcarbonylamino optionally substituted by 1 to 3 fluorine atoms, or a pharmaceutically acceptable salt thereof.

Item 23: The compound of Item 22, wherein $R^{1b}$ is 2-(ethylcarbonylamino)ethyl, or a pharmaceutically acceptable salt thereof.

Item 24: The compound of Item 22, wherein $R^{1b}$ is 2-(difluoroacetylamino)ethyl, or a pharmaceutically acceptable salt thereof.

Item 25: The compound of Item 18, wherein $R^{1b}$ is $C_{1-6}$ alkyl optionally substituted by $C_{1-4}$ alkoxycarbonylamino, or a pharmaceutically acceptable salt thereof.

Item 26: The compound of Item 25, wherein $R^{1b}$ is 2-(methoxycarbonylamino)ethyl, or a pharmaceutically acceptable salt thereof.

Item 27: The compound of any one of Items 1 to 26, wherein $R^{1c}$ is hydrogen atom, halogen atom, or $C_{1-6}$ alkyl optionally substituted by $C_{1-4}$ alkoxy, or a pharmaceutically acceptable salt thereof.

Item 28: The compound of any one of Items 1 to 27, wherein $R^{1c}$ is hydrogen atom, or $C_{1-6}$ alkyl, or a pharmaceutically acceptable salt thereof.

Item 29: The compound of Item 28, wherein $R^{1c}$ is $C_{1-6}$ alkyl, or a pharmaceutically acceptable salt thereof.

Item 30: The compound of any one of Items 1 to 29, wherein $R^{1d}$ is one group selected from the group consisting of 1: hydrogen atom;

2: halogen atom;

3: cyano;

4: $C_{2-6}$ alkenyl (in which the group may be optionally substituted by $C_{6-10}$ aryl optionally substituted by $C_{1-4}$ alkoxy);

5: $C_{2-6}$ alkynyl (in which the group may be optionally substituted by $C_{6-10}$ aryl optionally substituted by $C_{1-4}$ alkoxy);

6: $C_{1-6}$ alkyl (in which the group may be optionally substituted by same or different 1 to 2 groups selected from the group consisting of (a) 1 to 3 halogen atoms, (b) cyano, (c) $C_{3-6}$ cycloalkyl (in which the group may be optionally substituted by halogen atom, $C_{1-4}$ alkyl, or $C_{1-4}$ alkoxy), (d) hydroxy, (e) $C_{1-4}$ alkoxy (in which the group may be optionally substituted by same or different 1 to 3 groups selected from the group consisting of halogen atom, cyano, $C_{3-6}$ cycloalkoxy optionally substituted by mono- or di-($C_{1-6}$ alkyl)aminocarbonyl, mono- or di-($C_{1-6}$ alkyl)aminosulfonyl, $C_{1-6}$ alkylsulfonyl, aminocarbonyl optionally substituted by mono- or di-($C_{1-6}$ alkyl), $C_{1-4}$ alkylcarbonyl, 5- to 7-membered cyclic aminocarbonyl,
hydroxy,
$C_{1-4}$ alkoxy,
5- to 6-membered saturated heterocyclyl, and
$C_{1-4}$ alkoxycarbonyl),
(f) $C_{3-6}$ cycloalkoxy (in which the group may be optionally substituted by $C_{1-4}$ alkyl optionally substituted by $C_{1-4}$ alkoxy),
(g) $C_{6-10}$ aryloxy (in which the group may be optionally substituted by same or different 1 to 3 groups selected from the group consisting of halogen atom, cyano, and $C_{1-4}$ alkoxy),
(h) mono- or di-substituted amino (in which the group is substituted by same or different 1 to 2 groups selected from the group consisting of
$C_{1-6}$ alkyl,
$C_{3-6}$ cycloalkyl,
$C_{3-6}$ cycloalkyl$C_{1-4}$ alkyl optionally substituted by aminocarbonyl,
$C_{3-6}$ cycloalkyl$C_{1-4}$ alkoxycarbonyl,
$C_{1-4}$ alkylcarbonyl,
$C_{3-6}$ cycloalkylcarbonyl optionally substituted by $C_{1-4}$ alkylsulfonylamino,
5- to 6-membered saturated heterocyclyl$C_{1-4}$ alkyl optionally substituted by $C_{1-4}$ alkyl,
5- to 6-membered saturated heterocyclylcarbonyl,
5- to 6-membered saturated heterocyclyloxycarbonyl,
5- to 6-membered saturated heterocyclyl$C_{1-4}$ alkylcarbonyl, and
$C_{1-4}$ alkylsulfonyl),
(i) 5- to 7-membered cyclic amino (in which the group may be optionally substituted by same or different 1 to 4 groups selected from the group consisting of $C_{1-4}$ alkyl, $C_{7-14}$ aralkyl, and oxo),
(j) mono- or di-($C_{1-6}$ alkyl)aminocarbonyl,
(k) 4- to 7-membered cyclic aminocarbonyl (in which cyclic amino may be optionally substituted by $C_{1-4}$ alkyl),
(l) aminocarbonyloxy (in which amino is substituted by same or different 1 to 2 groups selected from the group consisting of
$C_{1-6}$ alkyl optionally substituted by 5- to 6-membered saturated heterocyclyl,
$C_{3-6}$ cycloalkyl optionally substituted by hydroxy, and
5- to 6-membered saturated heterocyclyl),
(m) 5- to 7-membered cyclic aminocarbonyloxy (in which cyclic amino may be optionally substituted by 1 to 2 fluorine atoms),
(n) 5- to 7-membered cyclic aminocarbonyl$C_{1-4}$ alkoxy,
(o) mono- or di-($C_{1-6}$ alkyl)aminocarbonyl$C_{1-4}$ alkoxy,
(p) 5- to 6-membered saturated heterocyclyl (in which the group may be optionally substituted by same or different groups selected from the group consisting of $C_{1-4}$ alkyl and oxo),
(q) 5- to 6-membered saturated heterocyclyl$C_{1-4}$ alkoxy (in which heterocyclyl may be optionally substituted by $C_{1-4}$ alkyl),
(r) 5- to 6-membered saturated heterocyclyloxy (in which heterocyclyl may be optionally substituted by same or different 1 to 2 groups selected from the group consisting of $C_{1-4}$ alkyl and oxo),
(s) mono- or di-$C_{1-4}$ alkylaminosulfonyl,
(t) carboxy,
(u) $C_{1-4}$ alkoxycarbonyl,
(v) $C_{6-10}$ arylcarbonyl (in which the group may be optionally substituted by $C_{1-4}$ alkoxy),
(w) $C_{1-4}$ alkoxycarbonylamino, (x) $C_{6-10}$ aryloxycarbonylamino (in which aryl may be optionally substituted by halogen atom),
(y) 5- to 6-membered monocyclic heteroaryloxycarbonylamino, and
(z) N—($C_{1-4}$ alkylaminocarbonyl)-N—($C_{1-6}$ alkyl) amino);
7: $C_{3-10}$ cycloalkyl (in which the group may be optionally substituted by
(a) halogen atom,
(b) hydroxy, or
(c) $C_{1-4}$ alkoxy);
8: $C_{7-14}$ aralkyl (in which the group may be optionally substituted by same or different 1 to 3 groups selected from the group consisting of
(a) halogen atom,
(b) cyano,
(c) hydroxy,
(d) $C_{1-4}$ alkoxy, and
(e) $C_{1-4}$ alkyl optionally substituted by $C_{1-4}$ alkoxy);
9: $C_{1-6}$ alkoxy (in which the group may be optionally substituted by
(a) $C_{1-4}$ alkoxycarbonylamino,
(b) N—($C_{1-6}$ alkylsulfonyl)-N—($C_{1-6}$ alkyl)aminocarbonyl,
(c) mono- or di-($C_{1-6}$ alkyl)aminocarbonyl, or
(d) 5- to 7-membered cyclic aminocarbonyl);
10: $C_{3-6}$ cycloalkoxy;
11: $C_{7-14}$ aralkyloxy optionally substituted by $C_{1-4}$ alkoxy;
12: mono- or di-substituted aminocarbonyl (in which amino may be optionally substituted by $C_{1-6}$ alkyl optionally substituted by 5- to 6-membered saturated heterocyclyl);
13: 5- to 7-membered cyclic aminocarbonyl (in which the group may be optionally substituted by a group selected from the group consisting of
(a) halogen atom,
(b) $C_{1-4}$ alkoxy, and
(c) $C_{6-10}$ aryl optionally substituted by halogen atom);
14: saturated heterocyclyl (in which the group may be optionally substituted by same or different 1 to 4 groups selected from the group consisting of
(a) $C_{1-4}$ alkyl,
(b) $C_{6-10}$ aryl optionally substituted by 1 to 3 halogen atoms, and
(c) oxo);
15: saturated heterocyclyloxy (in which the group may be optionally substituted by $C_{1-4}$ alkoxycarbonyl, or $C_{1-4}$ alkylcarbonyl);
16: 5- to 10-membered monocyclic or polycyclic heteroaryl (in which the group may be optionally substituted by same or different 1 to 2 groups selected from the group consisting of
(a) halogen atom,
(b) $C_{1-4}$ alkyl optionally substituted by 1 to 3 fluorine atoms, and
(c) $C_{1-4}$ alkoxy optionally substituted by mono- or di-($C_{1-6}$ alkyl)aminocarbonyl);
17: 5- to 10-membered monocyclic or polycyclic heteroaryl$C_{1-4}$ alkyl;
18: amino (in which amino may be optionally substituted by
(a) $C_{3-6}$ cycloalkyl$C_{1-4}$ alkyl (in which cycloalkyl may be optionally substituted by aminocarbonyl),
(b) $C_{1-4}$ alkylcarbonyl (in which alkyl may be optionally substituted by $C_{1-4}$ alkoxy),
(c) $C_{3-6}$ cycloalkylcarbonyl (in which cycloalkyl may be optionally substituted by $C_{1-4}$ alkylsulfonylamino), or
(d) 5- to 6-membered saturated heterocyclyloxycarbonyl);

19: hydroxyl, and

20: a group of the following formula:

[Chemical Formula 11]

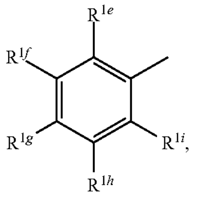

or a pharmaceutically acceptable salt thereof

Item 31: The compound of any one of Items 1 to 30, wherein $R^{1d}$ is one group selected from the group consisting of 1: hydrogen atom;

2: halogen atom;

3: $C_{1-6}$ alkyl (in which the group may be optionally substituted by (a) 1 to 3 halogen atoms, (b) hydroxy, (c) $C_{1-4}$ alkoxy (in which the group may be optionally substituted by 1 to 2 groups selected from the group consisting of hydroxy, $C_{1-4}$ alkoxy, 5- to 6-membered saturated heterocyclyl, and $C_{1-4}$ alkoxycarbonyl), (d) $C_{6-10}$ aryloxy (in which the group may be optionally substituted by same or different 1 to 3 groups selected from the group consisting of cyano and $C_{1-4}$ alkoxy), (e) $C_{1-6}$ alkylaminocarbonyloxy, (f) (5- to 6-membered saturated heterocyclyl$C_{1-4}$ alkyl) aminocarbonyloxy, or (g) 5- to 7-membered cyclic aminocarbonyloxy);

4: aminocarbonyl;

5: mono- or di-($C_{1-6}$ alkyl)aminocarbonyl;

6: N-(5- to 6-membered saturated heterocyclyl$C_{1-4}$ alkyl)-N—($C_{1-6}$ alkyl)-aminocarbonyl;

7: 5- to 7-membered cyclic aminocarbonyl;

8: $C_{7-14}$ aralkyl optionally substituted by $C_{1-4}$ alkoxy;

9: 5- to 6-membered saturated heterocyclyl;

10: $C_{3-6}$ cycloalkyl;

11: $C_{3-6}$ cycloalkoxy; and

12: a group of the following formula:

[Chemical Formula 12]

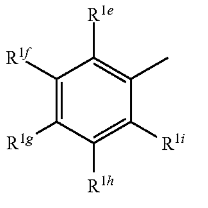

or a pharmaceutically acceptable salt thereof

Item 32: The compound of any one of Items 1 to 31, wherein $R^{1d}$ is $C_{1-6}$ alkyl optionally substituted by one group selected from the group consisting of 1: 1 to 3 halogen atoms, 2: hydroxy, 3: $C_{1-4}$ alkoxy (in which the group may be optionally substituted by 1 to 2 groups selected from the group consisting of (a) hydroxy, (b) $C_{1-4}$ alkoxy, (c) 5- to 6-membered saturated heterocyclyl, and (d) $C_{1-4}$ alkoxycarbonyl), 4: $C_{6-10}$ aryloxy (in which the group may be optionally substituted by same or different 1 to 3 groups selected from the group consisting of cyano and $C_{1-4}$ alkoxy), 5: $C_{1-6}$ alkylaminocarbonyloxy, 6: (5- to 6-membered saturated heterocyclyl$C_{1-4}$ alkyl)aminocarbonyloxy, and 7: 5- to 7-membered cyclic aminocarbonyloxy, or a pharmaceutically acceptable salt thereof.

Item 33: The compound of any one of Items 1 to 32, wherein $R^{1d}$ is $C_{1-6}$ alkyl optionally substituted by $C_{1-4}$ alkoxy, or a pharmaceutically acceptable salt thereof.

Item 34: The compound of any one of Items 1 to 31, wherein $R^{1d}$ is a group of the following formula:

[Chemical Formula 13]

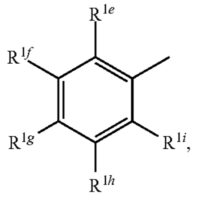

or a pharmaceutically acceptable salt thereof

Item 35: The compound of Item 34, wherein $R^{1e}$, $R^{1f}$, $R^{1g}$, $R^{1h}$ and $R^{1i}$ are each independently, same or different, a group selected from the group consisting of 1: hydrogen atom, 2: halogen atom, 3: cyano, 4: $C_{1-4}$ alkyl (in which the group may be optionally substituted by (a) 5- to 6-membered saturated heterocyclyloxy, (b) $C_{1-4}$ alkoxy (in which the group may be optionally substituted by $C_{1-4}$ alkoxy or $C_{3-6}$ cycloalkoxy), or (c) 1 to 3 fluorine atoms), 5: $C_{1-4}$ alkoxy (in which the group may be optionally substituted by (a) 1 to 3 halogen atoms, (b) $C_{1-4}$ alkoxy, or (c) $C_{1-6}$ alkylaminocarbonyl), 6: $C_{3-6}$ cycloalkoxy (in which the group may be optionally substituted by $C_{1-4}$ alkoxy), 7: 5- to 6-membered saturated heterocyclyloxy, 8: $C_{1-6}$ alkylaminocarbonyl, 9: hydroxyl, and 10: $C_{1-4}$ alkylsulfonyl, or a pharmaceutically acceptable salt thereof Item 36: The compound of Item 35, wherein $R^{1e}$, $R^{1f}$, $R^{1g}$, $R^{1h}$ and $R^{1i}$ are each independently, same or different, a group selected from the group consisting of hydrogen atom, halogen atom, cyano, $C_{1-4}$ alkyl optionally substituted by 1 to 3 fluorine atoms, $C_{1-4}$ alkoxy, hydroxyl, and $C_{1-4}$ alkylsulfonyl, or a pharmaceutically acceptable salt thereof Item 37: The compound of Item 36, wherein $R^{1e}$, $R^{1f}$, $R^{1g}$, $R^{1h}$ and $R^{1i}$ are each independently, same or different, selected from the group consisting of hydrogen atom, halogen atom, and $C_{1-4}$ alkoxy, or a pharmaceutically acceptable salt thereof Item 38: The compound of Item 36, wherein $R^{1d}$ is any group selected from the group consisting of

[Chemical Formula 14]

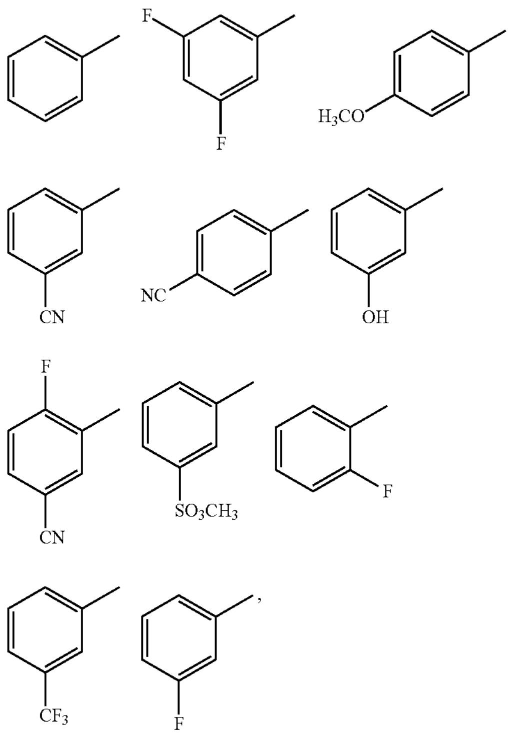

, or a pharmaceutically acceptable salt thereof.

Item 39: The compound of any one of Items 1 to 26, wherein $R^{1c}$ and $R^{1d}$ combine each other to form a group of the following formula:

[Chemical Formula 15]

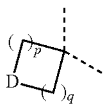

or a pharmaceutically acceptable salt thereof

Item 40: The compound of Item 39, wherein $R^{4a}$ is selected from the group consisting of hydrogen atom, $C_{1-6}$ alkyl, $C_{1-4}$ alkoxycarbonyl, $C_{1-4}$ alkylsulfonyl, and $C_{6-10}$ arylsulfonyl, or a pharmaceutically acceptable salt thereof.

Item 41: The compound of Item 39, wherein $R^{4b}$ is (a) hydrogen atom, (b) halogen atom, (c) $C_{1-4}$ alkoxy optionally substituted by $C_{1-4}$ alkoxy, (d) $C_{7-14}$ aralkyloxy optionally substituted by 1 to 3 groups selected from the group consisting of fluorine atom and cyano, or (e) aminocarbonyloxy optionally substituted by mono- or di-($C_{1-6}$ alkyl), or a pharmaceutically acceptable salt thereof.

Item 42: The compound of any one of Items 39 to 41, wherein D, p and q are any of the following (i) to (iii) (in which (i) D is oxygen, and p and q are the same and 2, (ii) D is $—CH_2—$, and p and q are the same and 1 or 2, or (iii) D is $—CH_2CH_2—$, and p and q are the same and 0 or 1), or a pharmaceutically acceptable salt thereof Item 43: The compound of any one of Items 1 to 26, wherein $R^{1c}$ and $R^{1d}$ combine each other to form a group of the following formula:

[Chemical Formula 16]

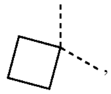

, or a pharmaceutically acceptable salt thereof

Item 44: The compound of any one of Items 1 to 43, wherein $R^2$ is one group selected from the group consisting of (a) $C_{1-6}$ alkyl optionally substituted by $C_{3-6}$ cycloalkyl (in which $C_{1-6}$ alkyl may be optionally substituted by 1 to 3 halogen atoms, and $C_{3-6}$ cycloalkyl may be optionally substituted by halogen atom, $C_{1-4}$ alkyl or $C_{1-4}$ alkoxy); (b) $C_{3-6}$ cycloalkyl optionally substituted by halogen atom or $C_{1-4}$ alkyl; (c) $C_{2-6}$ alkenyl; and (d) $C_{7-10}$ aralkyl optionally substituted by halogen atom, or a pharmaceutically acceptable salt thereof.

Item 45: The compound of Item 44, wherein $R^2$ is $C_{1-6}$ alkyl, or a pharmaceutically acceptable salt thereof.

Item 46: The compound of Item 45, wherein $R^2$ is isopropyl, or a pharmaceutically acceptable salt thereof.

Item 47: The compound of any one of Items 1 to 46, wherein $R^{3a}$, $R^{3b}$, $R^{3c}$ and $R^{3d}$ are each independently a group: -A-B (wherein A is a single bond, $—(CH_2)_sO—$, $—(CH_2)_sN(R^{4c})—$, $—(CH_2)_sCOO—$, $—(CH_2)_sN(R^{4c})CO—$, $—(CH_2)_sN(R^{4c})SO_2—$, $—(CH_2)_sN(R^{4c})COO—$, $—(CH_2)_sOCON(R^{4c})—$, $—(CH_2)_sCON(R^{4c})—$, or $—(CH_2)_sN(R^{4c})CON(R^{4c})—$, B is one group selected from the group consisting of 1: hydrogen atom;

2: $C_{1-6}$ alkyl (in which the group may be optionally substituted by same or different 1 to 3 groups selected from the group consisting of (a) halogen atom, (b) $C_{3-6}$ cycloalkyl (in which the group may be optionally substituted by same or different 1 to 2 groups selected from the group consisting of halogen atom, hydroxy, $C_{1-4}$ alkoxy and $C_{3-6}$ cycloalkylcarbonylamino), (c) hydroxy, (d) $C_{1-4}$ alkoxy, (e) carboxy, (f) $C_{1-4}$ alkoxycarbonyl, (g) saturated heterocyclyl (in which the ring may be optionally substituted by same or different 1 to 3 groups selected from the group consisting of $C_{1-4}$ alkyl, $C_{1-4}$ alkoxy, $C_{1-4}$ alkylcarbonylamino, and oxo), (h) aminocarbonyl (in which amino may be optionally substituted by $C_{1-4}$ alkyl, $C_{3-6}$ cycloalkyl, or $C_{3-6}$ cycloalkyl$C_{1-4}$ alkyl), and (i) 5- to 7-membered cyclic amino (in which the group may be optionally substituted by same or different 1 to 3 groups selected from the group consisting of halogen atom, $C_{1-4}$ alkyl, $C_6$ aryl optionally substituted by $C_{1-4}$ alkoxy, $C_6$ aryloxy optionally substituted by 1 to 3 halogen atoms and oxo));

3: $C_{2-6}$ alkenyl (in which the group may be optionally substituted by (a) fluorine, or (b) $C_{1-6}$ alkyl);

4: $C_{3-10}$ cycloalkyl (in which the group may be optionally substituted by (a) halogen atom, (b) $C_{1-4}$ alkyl optionally substituted by $C_{1-4}$ alkoxy, (c) hydroxy, or (d) $C_{1-4}$ alkoxy);

5: $C_6$ aryl (in which the group may be optionally substituted by same or different 1 to 4 groups selected from the group consisting of (a) halogen atom, (b) $C_{1-4}$ alkyl (in which $C_{1-4}$ alkyl may be optionally substituted by one group selected from the group consisting of 5- to 7-membered cyclic amino (in which the group may be optionally substituted by $C_6$ aryloxy optionally substituted by 1 to 3 halogen atoms), mono-$C_{1-6}$ alkylamino (in which $C_{1-6}$ alkyl may be optionally substituted by $C_6$ aryloxy optionally substituted by 1 to 3 halogen atoms), 5- to 6-membered saturated heterocyclylamino (in which saturated heterocyclyl may be optionally substituted by $C_6$ aryl), 5- to 6-membered saturated heterocyclyloxy (in which saturated heterocyclyl may be optionally substituted by $C_6$ aryl, or 5- to 10-membered monocyclic or polycyclic heteroaryl), $C_6$ aryloxy (in which the aryl may be optionally substituted by same or different 1 to 3 groups selected from the group consisting of halogen atom and $C_{1-4}$ alkyl), $C_{1-4}$ alkoxy, and $C_{3-6}$ cycloalkoxy), (c) $C_{1-4}$ alkoxy (in which $C_{1-4}$ alkoxy may be optionally substituted by one group selected from the group consisting of $C_{1-4}$ alkoxy, $C_6$ aryloxy (in which the aryl may be optionally substituted by $C_{1-4}$ alkyl or 1 to 3 halogen atoms), $C_{3-6}$ cycloalkyl optionally substituted by $C_{1-4}$ alkyl or $C_{1-4}$ alkoxy, $C_{3-6}$ cycloalkyloxy optionally substituted by $C_{1-4}$ alkyl, phenylamino (in which phenyl may be optionally substituted by 1 to 3 halogen atoms), and $C_{7-10}$ aralkyloxy optionally substituted by 1 to 3 halogen atoms), (d) $C_6$ aryloxy (in which the group may be optionally substituted by 1 to 3 groups selected from the group consisting of halogen atom, cyano, $C_{1-4}$ alkyl, and $C_{1-4}$ alkoxy), (e) $C_{7-10}$ aralkyloxy (in which the group may be optionally substituted by 1 to 3 groups selected from the group consisting of halogen atom and $C_{1-4}$ alkoxy), (f) 5- to 7-membered cyclic amino (in which cyclic amino may be optionally substituted by ($C_{1-6}$ alkyl)(phenylcarbonyl)amino, or $C_6$ aryloxy (in which the group may be optionally substituted by same or different 1 to 3 groups selected from the group consisting of halogen atom, and $C_{1-4}$ alkyl optionally substituted by hydroxy)), (g) 5- to 6-membered saturated heterocyclyloxy (in which the ring may be optionally substituted by $C_6$ aryl optionally substituted by 1 to 3 halogen atoms, 5- to 10-membered monocyclic or polycyclic heteroaryl, 5- to 6-membered saturated heterocyclylcarbonyl, or oxo), (h) 5- to 6-membered monocyclic heteroaryloxy (in which heteroaryl may be optionally substituted by $C_{1-4}$ alkyl), (i) 5- to 7-membered cyclic aminocarbonyl (in which cyclic amino may be optionally substituted by $C_6$ aryloxy optionally substituted by 1 to 3 halogen atoms), (j) 5- to 7-membered cyclic aminocarbonyloxy (in which cyclic amino may be optionally substituted by $C_6$ aryl), and (k) $C_6$ aryl);

6: $C_{7-14}$ aralkyl (in which the group may be optionally substituted by same or different 1 to 3 groups selected from the group consisting of (a) halogen atom, (b) cyano, (c) $C_{1-4}$ alkyl, (d) hydroxy, (e) $C_{1-4}$ alkoxy (in which the group may be optionally substituted by 1 to 3 fluorine atoms), (f) $C_{3-6}$ cycloalkoxy (in which the group may be optionally substituted by 1 to 2 halogen atoms), (g) $C_{1-4}$ alkoxycarbonyl, (h) aminocarbonyl, (i) $C_{6-10}$ aryl (in which the aryl may be optionally substituted by 1 to 3 halogen atoms) and (j) $C_{1-4}$ alkylsulfonyl);

7: 5- to 10-membered monocyclic or polycyclic heteroaryl (in which the group may be optionally substituted by halogen atom);

8: 5- to 10-membered monocyclic or polycyclic heteroaryl$C_{1-4}$ alkyl (in which the group may be optionally substituted by halogen atom, or $C_{1-4}$ alkyl (in which alkyl may be optionally substituted by 1 to 3 fluorine atoms)); and 9: saturated heterocyclyl (in which the group may be optionally substituted by $C_{1-4}$ alkyl optionally substituted by $C_{1-4}$ alkoxy), provided that if A is $-(CH_2)_sN(R^{4c})-$, $-(CH_2)_sOCON(R^{4c})-$, $-(CH_2)_sCON(R^{4c})-$, and $-(CH_2)_sN(R^{4c})CON(R^{4c})-$, $R^{4c}$ and B may combine each other to form a ring), or a pharmaceutically acceptable salt thereof.

Item 48: The compound of any one of Items 1 to 47, wherein $R^{3a}$, $R^{3b}$, $R^{3c}$ and $R^{3d}$ bind to piperidine ring on substitution positions represented by the following formula:

[Chemical Formula 17]

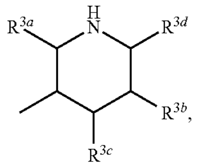

or a pharmaceutically acceptable salt thereof

Item 49: The compound of Item 48, wherein $R^{3a}$, $R^{3b}$) and $R^{3d}$ are all a group: -A-B (wherein A is a single bond, and B is hydrogen atom);

$R^{3c}$ is a group: -A-B (wherein A is a single bond, or $-(CH_2)_sO-$, and B is hydrogen atom, optionally substituted $C_{6-10}$ aryl, optionally substituted $C_{7-14}$ aralkyl, or optionally substituted 5- to 10-membered monocyclic or polycyclic heteroaryl), or a pharmaceutically acceptable salt thereof.

Item 50: The compound of Item 49, wherein $R^{3c}$ is a group: -A-B (wherein A is a single bond, and B is optionally substituted $C_{6-10}$ aryl), or a pharmaceutically acceptable salt thereof.

Item 51: The compound of Item 49, wherein B is optionally substituted $C_{6-10}$ aryl, or optionally substituted $C_{7-14}$ aralkyl, or a pharmaceutically acceptable salt thereof.

Item 52: The compound of Item 49, wherein $R^{3c}$ is a group: -A-B (wherein A is $-(CH_2)_sO-$, and B is hydrogen atom, optionally substituted $C_{6-10}$ aryl, or optionally substituted $C_{7-14}$ aralkyl), or a pharmaceutically acceptable salt thereof.

Item 53: The compound of Item 48, wherein $R^{3a}$, $R^{3c}$ and $R^{ad}$ are all a group: -A-B (wherein A is a single bond, and B is hydrogen atom);

$R^{3b}$ is a group: -A-B (wherein A is a single bond, $—(CH_2)_s—$, $—(CH_2)_sN(R^{4c})—$, $—(CH_2)_sCOO—$, $—(CH_2)_sN(R^{4c})CO—$, $—(CH_2)_sN(R^{4c})SO_2—$, $—(CH_2)_sN(R^{4c})COO—$, $—(CH_2)_sOCON(R^{4c})—$, $—(CH_2)_sCON(R^{4c})—$, $—(CH_2)_sN(R^{4c})CON(R^{4c})—$, or $—(CH_2)_sSO_2N(R^{4c})—$, B is hydrogen atom, optionally substituted $C_{1-6}$ alkyl, optionally substituted $C_{3-6}$ cycloalkyl, optionally substituted $C_{6-10}$ aryl, optionally substituted $C_{7-14}$ aralkyl, optionally substituted 5- to 10-membered monocyclic or polycyclic heteroaryl, or optionally substituted 5- to 6-membered saturated heterocyclyl), or a pharmaceutically acceptable salt thereof.

Item 54: The compound of Item 48, wherein $R^{3a}$, $R^{3b}$, and $R^{3c}$ are each independently a group: -A-B (wherein A is a single bond, and B is hydrogen atom);

$R^{3d}$ is a group: -A-B (wherein A is a single bond, $—(CH_2)_sO—$, $—(CH_2)_sN(R^{4c})—$, $—(CH_2)_sCOO—$, $—(CH_2)_sN(R^{4c})CO—$, $—(CH_2)_sN(R^{4c})SO_2—$, $—(CH_2)_sN(R^{4c})COO—$, $—(CH_2)_sOCON(R^{4c})—$, or $—(CH_2)_sN(R^{4c})CON(R^{4c})—$, B is hydrogen atom, optionally substituted $C_{1-6}$ alkyl, optionally substituted $C_{2-6}$ alkenyl, optionally substituted $C_{3-10}$ cycloalkyl, optionally substituted $C_{6-10}$ aryl, optionally substituted $C_{7-14}$ aralkyl, optionally substituted 5- to 10-membered monocyclic or polycyclic heteroaryl, optionally substituted 5- to 10-membered monocyclic or polycyclic heteroaryl$C_{1-4}$ alkyl or optionally substituted 5- to 6-membered saturated heterocyclyl), or a pharmaceutically acceptable salt thereof.

Item 55: The compound of Item 54, wherein A in $R^{ad}$ is $—(CH_2)_sN(R^{4c})CO—$, or a pharmaceutically acceptable salt thereof.

Item 56: The compound of either Item 54 or 55, wherein B in $R^{3d}$ is optionally substituted $C_{1-6}$ alkyl, or a pharmaceutically acceptable salt thereof.

Item 57: The compound of Item 55, wherein B in $R^{ad}$ is $C_{7-14}$ aralkyl optionally substituted by 1 to 3 halogen atoms, or a pharmaceutically acceptable salt thereof Item 58: The compound of any one of Items 54 to 57, wherein s is 2, or a pharmaceutically acceptable salt thereof.

Item 59: The compound of any one of Items 1 to 58, wherein $R^{4c}$ is hydrogen atom, $C_{1-6}$ alkyl substituted by 1 to 3 halogen atoms or $C_{3-6}$ cycloalkyl, $C_{3-6}$ cycloalkyl optionally substituted by 1 to 2 halogen atoms, or $C_7$ aralkyl, or a pharmaceutically acceptable salt thereof.

Item 60: The compound of Item 59, wherein $R^{4c}$ is $C_{1-6}$ alkyl substituted by 1 to 3 halogen atoms, or $C_{3-6}$ cycloalkyl, or a pharmaceutically acceptable salt thereof.

Item 61: The compound of Item 60, wherein $R^{4c}$ is $C_{3-6}$ cycloalkyl, or a pharmaceutically acceptable salt thereof.

Item 62: The compound of any one of Items 1 to 48, wherein $R^{3a}$, $R^{3b}$, $R^{3c}$ and $R^{3d}$ are all a group: -A-B (wherein A is a single bond, and B is hydrogen atom), or a pharmaceutically acceptable salt thereof.

Item 63: The compound of any one of Items 1 to 47, wherein n is 1, or a pharmaceutically acceptable salt thereof.

Item 64: The compound of any one of Items 1 to 63, wherein $R^5$ is $C_{1-4}$ alkoxycarbonyl (in which the group is substituted by a group of the following formula:

[Chemical Formula 18]

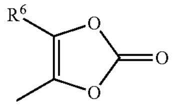

wherein $R^6$ is the same as defined above, or a pharmaceutically acceptable salt thereof Item 65: The compound of any one of Items 1 to 64, wherein $R^5$ is a group of the following formula:

[Chemical Formula 19]

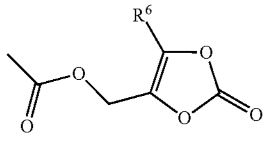

wherein $R^6$ is the same as defined above, or a pharmaceutically acceptable salt thereof Item 66: The compound of Item 65, wherein $R^6$ is methyl, or a pharmaceutically acceptable salt thereof.

Item 67: The compound of any one of Items 1 to 63, wherein $R^5$ is a group of the following formula:

[Chemical Formula 20]

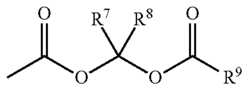

(in which $R^7$ and $R^8$ are each independently, same or different, hydrogen atom, or $C_{1-4}$ alkyl, and $R^9$ is (a) $C_{1-6}$ alkyl (in which the group may be optionally substituted by 1 to 3 fluorine atoms, amino, hydroxy, $C_{1-4}$ alkoxy, carboxy, $C_{1-4}$ alkoxycarbonyl, $C_{1-4}$ alkoxycarbonylamino, or 1 to 2 nitroxy), (b) $C_{3-10}$ cycloalkyl, (c) $C_{1-4}$ alkylcarbonyl (in which the group may be optionally substituted by hydroxy), (d) $C_{6-10}$ aryl (in which the group is substituted by $C_{1-4}$ alkyl, or $C_{1-4}$ alkylcarbonyloxy), (e) 5- to 10-membered monocyclic or polycyclic heteroaryl, (f) 5- to 6-membered saturated heterocyclyl, (g) $C_{1-6}$ alkoxy (in which the group may be optionally substituted by $C_{3-6}$ cycloalkyl), (h) $C_{3-6}$ cycloalkyloxy, or (i) 5- to 6-membered saturated heterocyclyloxy), or a pharmaceutically acceptable salt thereof.

Item 68: The compound of Item 67, wherein $R^7$ is hydrogen atom, and $R^8$ is methyl, or a pharmaceutically acceptable salt thereof.

Item 69: The compound of either Item 67 or 68, wherein $R^9$ is (a) $C_{1-4}$ alkyl (in which the group may be optionally substituted by amino, hydroxy, $C_{1-4}$ alkoxy, carboxy, $C_{1-4}$ alkoxycarbonyl, or $C_{1-4}$ alkoxycarbonylamino), (b) $C_{3-10}$ cycloalkyl, (c) $C_{1-4}$ alkylcarbonyl, (d) $C_{6-10}$ aryl (in which the group is substituted by $C_{1-4}$ alkylcarbonyloxy), (e) 5- to 10-membered monocyclic or polycyclic heteroaryl, (f) 5- to 6-membered saturated heterocyclyl, (g) $C_{1-6}$ alkoxy (in which the group may be optionally substituted by $C_{3-6}$ cycloalkyl), (h) $C_{3-6}$ cycloalkyloxy, or (i) 5- to 6-membered saturated heterocyclyloxy, or a pharmaceutically acceptable salt thereof.

Item 70: The compound of Item 69, wherein $R^9$ is

1: $C_{1-4}$ alkyl,

2: $C_{3-6}$ cycloalkyl,

3: $C_{1-6}$ alkoxy (in which the group may be optionally substituted by $C_{3-6}$ cycloalkyl), 4: $C_{3-6}$ cycloalkyloxy, or 5: 5- to 6-membered saturated heterocyclyloxy, or a pharmaceutically acceptable salt thereof Item 71: The compound of Item 70, wherein $R^9$ is 1: $C_{1-4}$ alkyl, or 2: $C_{1-6}$ alkoxy, or a pharmaceutically acceptable salt thereof.

Item 72: The compound of Item 1, selected from the group consisting of:

1-(isobutyryloxy)ethyl (3R)-3-[isopropyl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (5-methyl-2-oxo-1,3-dioxol-4-yl)methyl (3R)-3-[isopropyl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(cyclohexylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate,

[(2-methylpropanoyl)oxy]methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperazine-1-carboxylate, {[(propan-2-yloxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (acetyloxy)methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (2-oxo-5-phenyl-1,3-dioxol-4-yl)methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-{[(propan-2-yloxy)carbonyl]oxy}ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate,

[(methoxycarbonyl)oxy]methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate,

[(ethoxycarbonyl)oxy]methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, {[(cyclopropylmethoxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, {[(cyclobutyloxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, {[(tetrahydro-2H-pyran-4-yloxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]-piperidine-1-carboxylate, {[(pentane-3-yloxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, {[(cyclopentyloxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(acetyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(propanoyloxy)ethyl (3R)-3-[propan-2-yl({2,2,7-trimethyl-3-oxo-4-[2-(propanoylamino)-ethyl]-3,4-dihydro-2H-1,4-benzoxazin-6-yl}carbonyl)amino]piperidine-1-carboxylate, 1-(acetyloxy)-2-methylpropyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 2-methyl-1-(propanoyloxy)propyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 2-(acetyloxy)propan-2-yl (3R)-3-[propan-2-yl({2,2,7-trimethyl-3-oxo-4-[2-(propanoylamino)-ethyl]-3,4-dihydro-2H-1,4-benzoxazin-6-yl}carbonyl)amino]piperidine-1-carboxylate, 2,2-dimethyl-3-oxo-4-[2-(propanoylamino)ethyl]-N-(propan-2-yl)-7-(trifluoromethyl)-N-[(3R)-1-(L-valyl)piperidin-3-yl]-3,4-dihydro-2H-1,4-benzoxazine-6-carboxamide, N-[(3R)-1-(L-alanyl)piperidin-3-yl]-2,2-dimethyl-3-oxo-4-[2-(propanoylamino)ethyl]-N-(propan-2-yl)-7-(trifluoromethyl)-3,4-dihydro-2H-1,4-benzoxazine-6-carboxamide, N-{(3R)-1-[(2S)-2-hydroxypropanoyl]piperidin-3-yl}-2,2-dimethyl-3-oxo-4-[2-(propanoylamino)ethyl]-N-(propan-2-yl)-7-(trifluoromethyl)-3,4-dihydro-2H-1,4-benzoxazine-6-carboxamide, N-[(3R)-1-acetylpiperidine-3-yl]-2,2-dimethyl-3-oxo-4-[2-(propanoylamino)ethyl]-N-(propan-2-yl)-7-(trifluoromethyl)-3,4-dihydro-2H-1,4-benzoxazine-6-carboxamide, 1-[(2-methylpropanoyl)oxy]ethyl (3R)-3-[({2,2-dimethyl-3-oxo-4-[2-(propanoylamino)ethyl]-7-(trifluoromethyl)-3,4-dihydro-2H-1,4-benzoxazin-6-yl}carbonyl)(propan-2-yl)amino]-piperidine-1-carboxylate, (5-methyl-2-oxo-1,3-dioxol-4-yl)methyl (3R)-3-[({2,2-dimethyl-3-oxo-4-[2-(propanoylamino)-ethyl]-7-(trifluoromethyl)-3,4-dihydro-2H-1,4-benzoxazin-6-yl}carbonyl)(propan-2-yl)amino]-piperidine-1-carboxylate, {[(propan-2-yloxy)carbonyl]oxy}methyl (3R)-3-[({2,2-dimethyl-3-oxo-4-[2-(propanoylamino)ethyl]-7-(trifluoromethyl)-3,4-dihydro-2H-1,4-benzoxazin-6-yl}carbonyl)-(propan-2-yl)amino]piperidine-1-carboxylate, {[(tetrahydro-2H-pyran-4-yloxy)carbonyl]oxy}methyl (3R)-3-[({2,2-dimethyl-3-oxo-4-[2-(propanoylamino)

ethyl]-7-(trifluoromethyl)-3,4-dihydro-2H-1,4-benzoxazin-6-yl}carbonyl)-(propan-2-yl)amino]piperidine-1-carboxylate, (5-methyl-2-oxo-1,3-dioxol-4-yl)methyl (3R)-3-[({2,2-dimethyl-3-oxo-4-[2-(propanoylamino)-ethyl]-7-(trifluoromethyl)-3,4-dihydro-2H-1,4-benzothiazin-6-yl}carbonyl)(propan-2-yl)-amino]piperidine-1-carboxylate, 2,2-dimethyl-N-{(3R)-1-[(5-methyl-2-oxo-1,3-dioxol-4-yl)methyl]piperidin-3-yl}-3-oxo-4-[2-(propanoylamino)ethyl]-N-(propan-2-yl)-7-(trifluoromethyl)-3,4-dihydro-2H-1,4-benzoxazine-6-carboxamide, 2,2,7-trimethyl-3-oxo-N-{(3R)-1-[(2-oxo-5-phenyl-1,3-dioxol-4-yl)methyl]piperidin-3-yl}-4-[2-(propanoylamino)ethyl]-N-(propan-2-yl)-3,4-dihydro-2H-1,4-benzoxazine-6-carboxamide, 1-(acetyloxy)ethyl (3R)-3-[({7-methyl-3-oxo-4-[2-(propanoylamino)ethyl]-3,4-dihydrospiro-[1,4-benzoxazine-2,1'-cyclobutan]-6-yl}carbonyl)(propan-2-yl)amino]piperidine-1-carboxylate, 1-[(ethoxycarbonyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-(acetyloxy)-2-methylpropyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-(propanoyloxy)ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-(propanoyloxy)ethyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, 1-[(ethoxycarbonyl)oxy]ethyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, (5-methyl-2-oxo-1,3-dioxol-4-yl)methyl (3R)-3-{[(4-{2-[(difluoroacetyl)amino]ethyl}-7-methyl-3-oxo-3,4-dihydrospiro[1,4-benzoxazine-2,1'-cyclopropan]-6-yl)carbonyl](propan-2-yl)amino}piperidine-1-carboxylate, (5-methyl-2-oxo-1,3-dioxol-4-yl)methyl (3R)-3-[({7-methyl-3-oxo-4-[2-(propanoylamino)-ethyl]-3,4-dihydrospiro[1,4-benzoxazine-2,1'-cyclopropan]-6-yl}carbonyl)(propan-2-yl)-amino]piperidine-1-carboxylate, 1-(propanoyloxy)ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)(propan-2-yl)amino]-piperidine-1-carboxylate, 1-[(2-methylpropanoyl)oxy]ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)(propan-2-yl)amino]-piperidine-1-carboxylate, 1-[(tetrahydro-2H-pyran-4-ylcarbonyl)oxy]ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)-(propan-2-yl)amino]piperidine-1-carboxylate, (5-methyl-2-oxo-1,3-dioxol-4-yl)methyl (3R)-3-{[(4-{2-[(difluoroacetyl)amino]ethyl}-7-methyl-3-oxo-3,4-dihydrospiro[1,4-benzoxazine-2,1'-cyclobutan]-6-yl)carbonyl](propan-2-yl)amino}piperidine-1-carboxylate, 2-methyl-1-[(2-methylpropanoyl)oxy]propyl (3R)-3-[({7-methyl-3-oxo-4-[2-(propanoylamino)ethyl]-3,4-dihydrospiro[1,4-benzoxazine-2,1'-cyclobutan]-6-yl}carbonyl)-(propan-2-yl)amino]piperidine-1-carboxylate, 2-methyl-1-(propanoyloxy)propyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(2-methylpropanoyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(tetrahydro-2H-pyran-4-ylcarbonyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)-(propan-2-yl)amino]piperidine-1-carboxylate, 1-[(methoxyacetyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(3-hydroxy-3-methylbutanoyl)oxy]ethyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, 2-methyl-1-[(2-methylpropanoyl)oxy]propyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1S)-1-(propanoyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-(propanoyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-{[(cyclohexyloxy)carbonyl]oxy}ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, tert-butyl 1-[({(3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidin-1-yl}carbonyl)oxy]ethyl butanedioate, 4-oxo-4-{1-[({(3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidin-1-yl}carbonyl)oxy]ethoxy}-butanoic acid, 1-{[N-(tert-butoxycarbonyl)glycyl]oxy}ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(glycyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[({(3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidin-1-yl}carbonyl)oxy]ethylpyridine-3-carboxylate, 1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(methoxyacetyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(L-valyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(4-hydroxybutanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-({[2-(acetyloxy)phenyl]carbonyl}oxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(2-oxopropanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1S)-1-[(2-methylpropanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-[(2-methylpropanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(3-hydroxy-3-methylbutanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (5-methyl-2-oxo-1,3-dioxol-4-yl)methyl (3R)-3-[{[2-(hydroxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, (5-methyl-2-oxo-1,3-dioxol-4-yl)methyl (3R)-3-[{[2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, (5-methyl-2-oxo-1,3-dioxol-4-yl)methyl (3R)-3-[{[4-{2-[(difluoroacetyl)amino]ethyl}-3-oxo-7-(trifluoromethyl)-3,4-dihydrospiro[1,4-benzoxazine-2,1'-cyclopropan]-6-yl]carbonyl}-(propan-2-yl)amino]piperidine-1-carboxylate, 1-[(2-methylpropanoyl)oxy]ethyl (3R)-3-[{[4-{2-[(difluoroacetyl)amino]ethyl}-3-oxo-7-(trifluoromethyl)-3,4-dihydrospiro[1,4-benzoxazine-2,1'-cyclopropan]-6-yl]carbonyl}(propan-2-yl)amino]piperidine-1-carboxylate, (5-methyl-2-oxo-1,3-dioxol-4-yl)methyl (3R)-3-[{[(2R)-2-methyl-3-oxo-4-[2-(propanoylamino)ethyl]-2,7-bis(trifluoromethyl)-3,4-dihydro-2H-1,4-benzoxazin-6-yl]-carbonyl}(propan-2-yl)amino]piperidine-1-carboxylate, 1-[(2-methylpropanoyl)oxy]ethyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, 2-methyl-1-(propanoyloxy)propyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, 2-methyl-1-[(2-methylpropanoyloxy)oxy]propyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]-carbonyl}(propan-2-yl)amino]piperidine-1-carboxylate, (5-methyl-2-oxo-1,3-dioxol-4-yl)methyl (3R)-3-{[(4-{2-[(difluoroacetyl)amino]ethyl}-2,2,7-trimethyl-3-oxo-3,4-dihydro-2H-1,4-benzothiazin-6-yl)carbonyl](propan-2-yl)amino}-piperidine-1-carboxylate, (5-methyl-2-oxo-1,3-dioxol-4-yl)methyl (3R)-3-[({7-methyl-3-oxo-4-[2-(propanoylamino)-ethyl]-3,4-dihydrospiro[1,4-benzothiazine-2,1'-cyclobutan]-6-yl}carbonyl)(propan-2-yl)-amino]piperidine-1-carboxylate, 1-{[(4-methylphenyl)carbonyl]oxy}ethyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, (1R)-1-[(2-methylpropanoyl)oxy]ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]-piperidine-1-carboxylate, (5-methyl-2-oxo-1,3-dioxol-4-yl)methyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, (1R)-1-[(2-methylpropanoyl)oxy]ethyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, (1S)-1-[(2-methylpropanoyl)oxy]ethyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, 1-[(4-methoxybutanoyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(4-methoxybutanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(propanoyloxy)ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]-piperidine-1-carboxylate, (1R)-1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]-piperidine-1-carboxylate, (1S)-1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]-piperidine-1-carboxylate, 1-[({(3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidin-1-yl}carbonyl)-oxy]ethylpyridine-3-carboxylate, (1S)-1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]-piperidine-1-carboxylate, (1R)-1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)-amino]piperidine-1-carboxylate, (1S)-1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)-amino]piperidine-1-carboxylate, 1-[(tetrahydro-2H-pyran-4-ylcarbonyl)oxy]ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]piperidine-1-carboxylate, 1-{[(cyclohexyloxy)carbonyl]oxy}ethyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, 1-[(difluoroacetyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(cyclopropylacetyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-{[6,7-bis(nitroxy)heptanoyl]oxy}ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, and 1-[(cyclohexylcarbonyl)oxy]ethyl (3R)-3-[({2,2-dimethyl-3-oxo-4-[2-(propanoylamino)ethyl]-7-(trifluoromethyl)-3,4-dihydro-2H-1,4-benzoxazin-6-yl}carbonyl)(propan-2-yl)amino]-piperidine-1-carboxylate, or a pharmaceutically acceptable salt thereof.

Item 73: The compound of Item 1, selected from the group consisting of:

(5-methyl-2-oxo-1,3-dioxol-4-yl)methyl (3R)-3-[isopropyl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (5-methyl-2-oxo-1,3-dioxol-4-yl)methyl (3R)-3-[({2,2-dimethyl-3-oxo-4-[2-(propanoylamino)-ethyl]-7-(trifluoromethyl)-3,4-dihydro-2H-1,4-benzoxazin-6-yl}carbonyl)(propan-2-yl)amino]-piperidine-1-carboxylate, (5-methyl-2-oxo-1,3-dioxol-4-yl)methyl (3R)-3-[({2,2-dimethyl-3-oxo-4-[2-(propanoylamino)-ethyl]-7-(trifluoromethyl)-3,4-dihydro-2H-1,4-benzothiazin-6-yl}carbonyl)(propan-2-yl)-amino]piperidine-1-carboxylate, (5-methyl-2-oxo-1,3-dioxol-4-yl)methyl (3R)-3-{[(4-{2-[(difluoroacetyl)amino]ethyl}-7-methyl-3-oxo-3,4-dihydrospiro[1,4-benzoxazine-2,1'-cyclopropan]-6-yl)carbonyl](propan-2-yl)amino}piperidine-1-carboxylate, (5-methyl-2-oxo-1,3-dioxol-4-yl)methyl (3R)-3-[({7-methyl-3-oxo-4-[2-(propanoylamino)-ethyl]-3,4-dihydrospiro[1,4-benzoxazine-2,1'-cyclopropan]-6-yl}carbonyl)(propan-2-yl)-amino]piperidine-1-carboxylate, (5-methyl-2-oxo-1,3-dioxol-4-yl)methyl (3R)-3-{[(4-{2-[(difluoroacetyl)amino]ethyl}-7-methyl-3-oxo-3,4-dihydrospiro[1,4-benzoxazine-2,1'-cyclobutan]-6-yl)carbonyl](propan-2-yl)-amino}piperidine-1-carboxylate, (5-methyl-2-oxo-1,3-dioxol-4-yl)methyl (3R)-3-[{[2-(hydroxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, (5-methyl-2-oxo-1,3-dioxol-4-yl)methyl (3R)-3-[{[2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, (5-methyl-2-oxo-1,3-dioxol-4-yl)methyl (3R)-3-[{[4-{2-[(difluoroacetyl)amino]ethyl}-3-oxo-7-(trifluoromethyl)-3,4-dihydrospiro[1,4-benzoxazine-2,1'-cyclopropan]-6-yl]carbonyl}-(propan-2-yl)amino]piperidine-1-carboxylate, (5-methyl-2-oxo-1,3-dioxol-4-yl)methyl (3R)-3-[{[(2R)-2-methyl-3-oxo-4-[2-(propanoylamino)ethyl]-2,7-bis(trifluoromethyl)-3,4-dihydro-2H-1,4-benzoxazin-6-yl]-carbonyl}(propan-2-yl)amino]piperidine-1-carboxylate, (5-methyl-2-oxo-1,3-dioxol-4-yl)methyl (3R)-3-{[(4-{2-[(difluoroacetyl)amino]ethyl}-2,2,7-trimethyl-3-oxo-3,4-dihydro-2H-1,4-benzothiazin-6-yl)carbonyl](propan-2-yl)amino}-piperidine-1-carboxylate, (5-methyl-2-oxo-1,3-dioxol-4-yl)methyl (3R)-3-[({7-methyl-3-oxo-4-[2-(propanoylamino)-ethyl]-3,4-dihydrospiro[1,4-benzothiazine-2,1'-cyclobutan]-6-yl}carbonyl)(propan-2-yl)-amino]piperidine-1-carboxylate, and (5-methyl-2-oxo-1,3-dioxol-4-yl)methyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, or a pharmaceutically acceptable salt thereof.

Item 74: The compound of Item 1, selected from the group consisting of:

1-(isobutyryloxy)ethyl (3R)-3-[isopropyl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(propanoyloxy)ethyl (3R)-3-[propan-2-yl({2,2,7-trimethyl-3-oxo-4-[2-(propanoylamino)-ethyl]-3,4-dihydro-2H-1,4-benzoxazin-6-yl}carbonyl)amino]piperidine-1-carboxylate, 1-[(2-methylpropanoyl)oxy]ethyl (3R)-3-[({2,2-dimethyl-3-oxo-4-[2-(propanoylamino)ethyl]-7-(trifluoromethyl)-3,4-dihydro-2H-1,4-benzoxazin-6-yl}carbonyl)(propan-2-yl)amino]-piperidine-1-carboxylate, 1-[(ethoxycarbonyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-(propanoyloxy)ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-(propanoyloxy)ethyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, 1-[(ethoxycarbonyl)oxy]ethyl (3R)-3-[{[(2S)-2-(methoxymethyl)-2-methyl-3-oxo-4-[2-(propanoylamino)ethyl]-7-

(trifluoromethyl)-3,4-dihydro-2H-1,4-benzoxazin-6-yl]carbonyl}-(propan-2-yl)amino]piperidine-1-carboxylate, 1-(propanoyloxy)ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)(propan-2-yl)amino]-piperidine-1-carboxylate, 1-[(2-methylpropanoyl)oxy]ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)(propan-2-yl)amino]-piperidine-1-carboxylate, 1-[(tetrahydro-2H-pyran-4-ylcarbonyl)oxy]ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)-(propan-2-yl)amino]piperidine-1-carboxylate, 1-[(2-methylpropanoyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(tetrahydro-2H-pyran-4-ylcarbonyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)-(propan-2-yl)amino]piperidine-1-carboxylate, (1S)-1-(propanoyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-(propanoyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1S)-1-[(2-methylpropanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-[(2-methylpropanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(2-methylpropanoyl)oxy]ethyl (3R)-3-[{[4-{2-[(difluoroacetyl)amino]ethyl}-3-oxo-7-(trifluoromethyl)-3,4-dihydrospiro[1,4-benzoxazine-2,1'-cyclopropan]-6-yl]carbonyl}(propan-2-yl)amino]piperidine-1-carboxylate, 1-[(2-methylpropanoyl)oxy]ethyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, (1R)-1-[(2-methylpropanoyl)oxy]ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]-piperidine-1-carboxylate, (1R)-1-[(2-methylpropanoyl)oxy]ethyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, (1S)-1-[(2-methylpropanoyl)oxy]ethyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, 1-(propanoyloxy)ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]-piperidine-1-carboxylate, (1R)-1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]-piperidine-1-carboxylate, (1S)-1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]-piperidine-1-carboxylate, (1S)-1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]-piperidine-1-carboxylate, (1R)-1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)-amino]piperidine-1-carboxylate, (1S)-1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)-amino]piperidine-1-carboxylate, 1-[(tetrahydro-2H-pyran-4-ylcarbonyl)oxy]ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]piperidine-1-carboxylate, 1-{[(cyclohexyloxy)carbonyl]oxy}ethyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, 1-[(difluoroacetyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, and 1-[(cyclopropylacetyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, or a pharmaceutically acceptable salt thereof.

Item 75: A compound of formula (II):

[Chemical Formula 21]

(II)

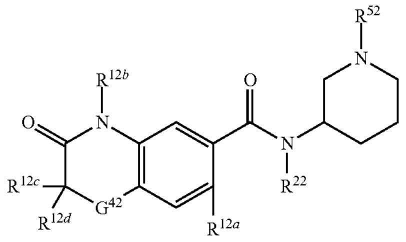

wherein $R^{12a}$ is $C_{1-6}$ alkyl optionally substituted by 1 to 3 fluorine atoms;

$G^{42}$ is oxygen, or sulfur;

$R^{12b}$ is $C_{1-6}$ alkyl optionally substituted by $C_{1-4}$ alkylcarbonylamino (in which alkyl may be optionally substituted by 1 to 3 fluorine atoms);

$R^{12c}$ is $C_{1-6}$ alkyl, $R^{12d}$ is $C_{1-6}$ alkyl optionally substituted by $C_{1-4}$ alkoxy, or alternatively, $R^{12c}$ and $R^{12d}$ combine each other to form a group of the following formula:

[Chemical Formula 22]

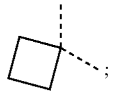

$R^{52}$ is

1: $C_{1-4}$ alkylcarbonyl (in which the group may be optionally substituted by (a) amino, or (b) hydroxy), 2: $C_{1-4}$ alkoxycarbonyl (in which the group is substituted by a group of the following formula:

[Chemical Formula 23]

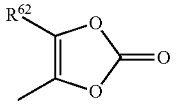

wherein $R^{62}$ is (a) $C_{1-4}$ alkyl, or (b) $C_{6-10}$ aryl), or

3: a group of the following formula:

[Chemical Formula 24]

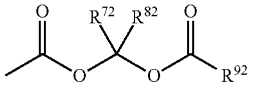

wherein $R^{72}$ and $R^{82}$ are each independently, same or different, (a) hydrogen atom, (b) $C_{1-4}$ alkyl, or (c) $C_{3-10}$ cycloalkyl, $R^{92}$ is (a) $C_{1-6}$ alkyl, (b) $C_{3-10}$ cycloalkyl, (c) $C_{1-6}$ alkoxy (in which the group may be optionally substituted by $C_{3-6}$ cycloalkyl), (d) $C_{3-6}$ cycloalkyloxy, or (e) 5- to 6-membered saturated heterocyclyloxy, or a pharmaceutically acceptable salt thereof.

Item 76: A pharmaceutical composition, comprising as the active ingredient the compound of any one of Items 1 to 75 or a pharmaceutically acceptable salt thereof.

Item 77: A renin inhibitor, comprising as the active ingredient the compound of any one of Items 1 to 75 or a pharmaceutically acceptable salt thereof.

Item 78: A therapeutic agent for diseases caused by renin inhibition, comprising as the active ingredient the compound of any one of Items 1 to 75 or a pharmaceutically acceptable salt thereof.

Item 79: Use of the compound of any one of Items 1 to 75 or a pharmaceutically acceptable salt thereof in the manufacture of a renin inhibitor.

Item 80: Use of the compound of any one of Items 1 to 75 or a pharmaceutically acceptable salt thereof in the manufacture of a therapeutic agent for diseases caused by renin inhibition.

Item 81: A method of treating diseases caused by renin inhibition, comprising administering an effective amount of the compound of any one of Items 1 to 75 or a pharmaceutically acceptable salt thereof to a patient in need thereof.

Item 82: A medication, comprising the compound of any one of Items 1 to 75 or a pharmaceutically acceptable salt thereof in combination with at least one or more drugs selected from the following Drug Group (A):

wherein Drug Group (A) is the group consisting of insulin formulation, an improving agent of insulin resistance, α-glucosidase inhibitor, biguanide preparation, insulin secretagogue, GLP-1, GLP-1 analog, protein tyrosine phosphatase inhibitor, β3 agonist, DPPIV inhibitor, aldose reductase inhibitor, neurotrophic factor, PKC inhibitor, AGE inhibitor, active oxygen-eliminating agent, cerebral vasodilator, HMG-CoA reductase inhibitor, squalene synthetase inhibitor, ACAT inhibitor, angiotensin converting enzyme inhibitor, angiotensin II antagonist, calcium antagonist, ACE/NEP inhibitor, β blocking agent, a blocking agent, αβ blocking agent, central anti-obesity drug, pancreatic lipase inhibitor, peptidic anorexiant, cholecystokinin agonist, xanthine derivative, thiazide preparation, anti-aldosterone preparation, carbonic anhydrase inhibitor, chlorobenzene sulfonamide preparation, azosemide, isosorbide, ethacrynic acid, piretanide, bumetanide, and furosemide.

Item 83: The medication of Item 82, wherein Drug Group (A) is the group consisting of angiotensin converting enzyme inhibitor, angiotensin II antagonist, calcium antagonist, ACE/NEP inhibitor, β blocking agent, a blocking agent, αβ blocking agent, thiazide preparation, and anti-aldosterone preparation.

Item 84: The medication of Item 83, wherein Drug Group (A) is the group consisting of angiotensin II antagonist, calcium antagonist, and thiazide preparation.

Item 85: A method of treating diseases caused by renin inhibitory effects, comprising administering an effective amount of the compound of any one of Items 1 to 75 or a pharmaceutically acceptable salt thereof in combination with at least one or more drugs selected from Drug Group (A) defined in Item 82 to a patient in need thereof Item 86: The method of Item 85, wherein Drug Group (A) is the group consisting of angiotensin converting enzyme inhibitor, angiotensin II antagonist, calcium antagonist, ACE/NEP inhibitor, β blocking agent, a blocking agent, αβ blocking agent, thiazide preparation, and anti-aldosterone preparation.

Item 87: The method of Item 86, wherein Drug Group (A) is the group consisting of angiotensin II antagonist, calcium antagonist, and thiazide preparation.

Item 88: Use of the compound of any one of Items 1 to 75 or a pharmaceutically acceptable salt thereof in a combined administration with at least one or more drugs selected from Drug Group (A) defined in Item 82.

Item 89: The use of Item 88, wherein Drug Group (A) is the group consisting of angiotensin converting enzyme inhibitor, angiotensin II antagonist, calcium antagonist, ACE/NEP inhibitor, β blocking agent, a blocking agent, αβ blocking agent, thiazide preparation, and anti-aldosterone preparation.

Item 90: The use of Item 89, wherein Drug Group (A) is the group consisting of angiotensin II antagonist, calcium antagonist, and thiazide preparation.

Item 91: An intermediate compound of formula (III):

[Chemical Formula 25]

(III)

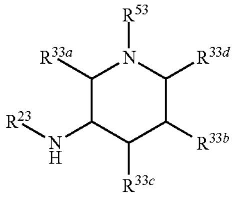

wherein $R^{23}$ is hydrogen atom, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted $C_{5-6}$ cycloalkenyl, optionally substituted $C_{6-10}$ aryl, optionally substituted $C_{7-14}$ aralkyl, or optionally substituted 5- to 10-membered monocyclic or polycyclic heteroaryl;

$R^{33a}$, $R^{33b}$, $R^{33c}$, and $R^{33d}$ are each independently, same or different, halogen atom, hydroxyl, formyl, carboxy, cyano, or the following group: $-A^3-B^3$ (wherein $A^3$ is a single bond, $—(CH_2)_{s3}O—$, $—(CH_2)_{s3}N(R^{43c})—$, $—(CH_2)_{s3}SO_2—$, $—(CH_2)_{s3}CO—$, $—(CH_2)_{s3}COO—$, $—(CH_2)_{s3}N(R^{43c})CO—$, $—(CH_2)_{s3}N(R^{43c})SO_2—$, $—(CH_2)_{s3}N(R^{43c})COO—$, $—(CH_2)_{s3}OCON(R^{43c})—$, $—(CH_2)_{s3}O—CO—$, $—(CH_2)_{s3}CON(R^{43c})—$, $—(CH_2)_{s3}N(R^{43c})CON(R^{43c})—$, or $—(CH_2)_{s3}SO_2N(R^{43c})—$, $B^3$ is hydrogen atom, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted $C_{5-6}$ cycloalkenyl, optionally substituted $C_{6-10}$ aryl, optionally substituted $C_{7-14}$ aralkyl, optionally substituted 5- to 10-membered monocyclic or polycyclic heteroaryl, optionally substituted 5- to 10-membered monocyclic or polycyclic heteroaryl$C_{1-4}$ alkyl, or optionally substituted saturated heterocyclyl, provided that if $A^3$ is $—(CH_2)_{s3}N(R^{43c})—$, $—(CH_2)_{s3}OCON(R^{43c})—$, $—(CH_2)_{s3}CON(R^{43c})—$, $—(CH_2)_{s3}N(R^{43c})CON(R^{43c})—$, and $—(CH_2)_{s3}SO_2N(R^{43c})—$, $R^{43c}$ and $B^3$ may combine each other to form a ring, $R^{43c}$ is hydrogen atom, optionally substituted $C_{1-6}$ alkyl, optionally substituted $C_{3-10}$ cycloalkyl, optionally substituted $C_{6-10}$ aryl, optionally substituted $C_{7-14}$ aralkyl, or optionally substituted 5- to 10-membered monocyclic or polycyclic heteroaryl, s3 is 0, 1 or 2, provided that if $A^3$ is $—(CH_2)_{s3}N(R^{43c})—$, s3 is 0 or 2, provided that if $A^3$ is $—(CH_2)_{s3}CON(R^{43c})—$, s3 is 1 or 2), or alternatively any two of $R^{33a}$, $R^{33b}$, $R^{33c}$ and $R^{33d}$ are hydrogen atom, the other two combine each other together with the adjacent heterocyclyl to form a bridged ring;

$R^{53}$ is

1: $C_{1-4}$ alkoxycarbonyl (in which the group is substituted by a group of the following formula:

[Chemical Formula 26]

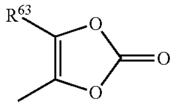

(in which $R^{63}$ is (a) $C_{1-4}$ alkyl (in which the group may be optionally substituted by $C_{1-4}$ alkoxy)

(b) $C_{3-6}$ cycloalkyl, or (c) $C_{6-10}$ aryl (in which the group may be optionally substituted by $C_{1-4}$ alkoxy))), or 2: a group of the following formula:

[Chemical Formula 27]

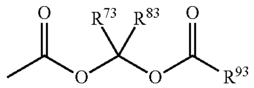

(wherein $R^{73}$ and $R^{83}$ are each independently, same or different, (a) hydrogen atom, (b) $C_{1-4}$ alkyl (in which the group may be optionally substituted by $C_{1-4}$ alkoxy, $C_{3-6}$ cycloalkyl (in which the group may be optionally substituted by $C_{1-4}$ alkoxy), 5- to 6-membered saturated heterocyclyl, or 5- to 6-membered saturated heterocyclyloxy), (c) $C_{3-10}$ cycloalkyl (in which the group may be optionally substituted by 1 to 2 fluorine atoms, or $C_{1-4}$ alkoxy), (d) $C_{6-10}$ aryl (in which the group may be optionally substituted by halogen atom, or $C_{6-10}$ aryl (in which the aryl may be optionally substituted by halogen atom or $C_{1-4}$ alkoxy)), (e) 5- to 6-membered saturated heterocyclyl, or (f) 5- to 10-membered monocyclic or polycyclic heteroaryl (in which the group may be optionally substituted by $C_{1-4}$ alkyl, or $C_{1-4}$ alkoxy), and $R^{93}$ is (a) $C_{1-6}$ alkyl (in which the group may be optionally substituted by 1 to 3 fluorine atoms, hydroxy, $C_{1-4}$ alkoxy, carboxy, 5- to 6-membered saturated heterocyclyl, $C_{3-6}$ cycloalkyl, $C_{1-4}$ alkoxycarbonyl, $C_{1-4}$ alkoxycarbonylamino, amino, mono- or di-($C_{1-6}$ alkyl)amino, 5- to 7-membered cyclic amine, 1 to 2 nitroxy, aminocarbonyl, or 5- to 7-membered cyclic aminocarbonyl), (b) $C_{3-10}$ cycloalkyl (in which the group may be optionally substituted by hydroxy), (c) $C_{6-10}$ aryl (in which the group is substituted by $C_{1-4}$ alkyl, $C_{1-4}$ alkoxy, or $C_{1-4}$ alkylcarbonyloxy), (d) $C_{1-4}$ alkylcarbonyl (in which the group may be optionally substituted by hydroxy), (e) 5- to 10-membered monocyclic or polycyclic heteroaryl, (f) 5- to 6-membered saturated heterocyclyl (in which the group may be optionally substituted by $C_{1-4}$ alkyl optionally substituted by $C_{1-4}$ alkoxy), (g) $C_{1-6}$ alkoxy (in which the group may be optionally substituted by $C_{3-6}$ cycloalkyl), (h) $C_{3-6}$ cycloalkyloxy (in which the group may be optionally substituted by $C_{1-4}$ alkoxy), or (i) 5- to 6-membered saturated heterocyclyloxy), or a pharmaceutically acceptable salt thereof.

Item 92: The compound of Item 91, wherein $R^{23}$ is $C_{1-6}$ alkyl, or $C_{3-6}$ cycloalkyl, or a pharmaceutically acceptable salt thereof.

Item 93: The compound of Item 92, wherein $R^{23}$ is $C_{1-6}$ alkyl, or a pharmaceutically acceptable salt thereof.

Item 94: The compound of Item 93, wherein $R^{23}$ is isopropyl, or a pharmaceutically acceptable salt thereof.

Item 95: The compound of any one of Items 91 to 94, wherein $R^{33a}$, $R^{33b}$, $R^{33c}$ and $R^{33d}$ are each independently a group: $-A^3-B^3$ (in which $A^3$ is a single bond, and $B^3$ is hydrogen atom), or a pharmaceutically acceptable salt thereof.

Item 96: The compound of any one of Items 91 to 94, wherein $R^{53}$ is $C_{1-4}$ alkoxycarbonyl (in which the group is substituted by a group of the following formula:

[Chemical Formula 28]

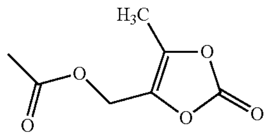

), or a pharmaceutically acceptable salt thereof

Item 97: The compound of any one of Items 91 to 94, wherein $R^{53}$ is a group of the following formula:

[Chemical Formula 29]

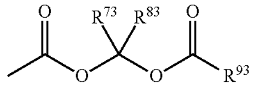

wherein $R^{73}$ and $R^{83}$ are each independently, same or different, hydrogen atom, or $C_{1-4}$ alkyl, $R^{93}$ is (a) $C_{1-6}$ alkyl (in which the group may be optionally substituted by 1 to 3 fluorine atoms, amino, hydroxy, $C_{1-4}$ alkoxy, carboxy, $C_{1-4}$ alkoxycarbonyl, $C_{1-4}$ alkoxycarbonylamino, or 1 to 2 nitroxy),
(b) $C_{3-10}$ cycloalkyl,
(c) $C_{1-4}$ alkylcarbonyl (in which the group may be optionally substituted by hydroxy),
(d) $C_{6-10}$ aryl (in which the group is substituted by $C_{1-4}$ alkyl, or $C_{1-4}$ alkylcarbonyloxy),
(e) 5- to 10-membered monocyclic or polycyclic heteroaryl,
(f) 5- to 6-membered saturated heterocyclyl,
(g) $C_{1-6}$ alkoxy (in which the group may be optionally substituted by $C_{3-6}$ cycloalkyl),
(h) $C_{3-6}$ cycloalkyloxy, or
(i) 5- to 6-membered saturated heterocyclyloxy, or a pharmaceutically acceptable salt thereof.

A compound of formula (I) or a pharmaceutically acceptable salt thereof is referred to as "the present compound" hereinafter, if necessary.

Effect of Invention

The present compound shows excellent renin inhibitory effects, and is useful as a therapeutic agent for hypertension. The present compound may reduce adverse effects such as actions or symptoms derived from inflammation-inducing effects in moieties which the compound is thought to come into the direct contact with (e.g., oral cavity, digestive tracts such as gastrointestinal tracts, etc. which is likely to be exposed by high concentrations of the compound, specifically). The present compound may also reduce adverse effects of cardiotoxic action, and have promise for improving pharmacokinetics. Therefore, the present compound is excellent as a therapeutic agent for diseases caused by renin inhibitory effects.

BEST MODE FOR CARRYING OUT THE INVENTION

The present invention is explained in further details as below. The number of carbons in the definition of "substituent" herein may be described as "$C_{1-6}$", etc., for example. Specifically, the description "$C_{1-6}$ alkyl" is synonymous with alkyl group with 1 to 6 carbon atoms. Herein, the group without specifying the term "optionally substituted" or "substituted" means an "unsubstituted" group. For example, "$C_{1-6}$ alkyl" means "unsubstituted $C_{1-6}$ alkyl".

The term "group" used herein means a monovalent group. For example, "alkyl group" means a monovalent saturated hydrocarbon group. The term "group" may be omitted in the description of substituents herein. The number of substituents in the "optionally substituted" or "substituted" group is 1 or more, but is not limited thereto, if possible. The definition for each group is also applicable to any group which is a part of other group or a substituent of other group, unless otherwise specified.

"Halogen atom" includes, for example, fluorine atom, chlorine atom, bromine atom or iodine atom, etc.

"$C_{1-6}$ alkyl" means a straight or branched-chain saturated hydrocarbon group having 1 to 6 carbon atoms. Preferable one includes "$C_{1-4}$ alkyl", etc. Concrete examples of "$C_{1-6}$ alkyl" include, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, etc.

"$C_{1-6}$ alkyl" in "B" includes groups wherein a ring is formed with $C_2$ to $C_4$ on one carbon of saturated hydrocarbon group. Concrete examples include, for example, the following groups, etc. Meanwhile, the same can be said for alkyl moiety of $C_{7-14}$ aralkyl group.

[Chemical Formula 30]

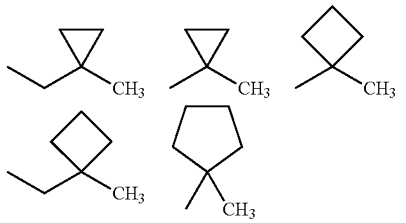

"$C_{2-6}$ alkenyl" means a straight or branched-chain unsaturated hydrocarbon group having 2 to 10 carbon atoms and 1 double bond. Concrete examples include, for example, vinyl, propenyl, methylpropenyl, butenyl or methylbutenyl, etc.

"$C_{2-6}$ alkenyl" in "B" includes the following group.

[Chemical Formula 31]

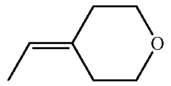

"$C_{2-6}$ alkynyl" means a straight or branched-chain unsaturated hydrocarbon having 2 to 6 carbon atoms and 1 triple bond. For example, concrete examples include ethynyl, 1-propynyl, 2-propynyl, 2-butyryl, pentynyl or hexynyl, etc.

"$C_{3-10}$ cycloalkyl" means a cyclic saturated hydrocarbon group having 3 to 10 carbon atoms. For example, preferable one includes "$C_{3-6}$ cycloalkyl", etc. Concrete examples of "$C_{3-10}$ cycloalkyl" include, for example, cyclopropyl, cyclobutyl, cyclopentyl, cyclohexyl, cycloheptyl, adamantyl or norbornyl, etc.

"$C_{3-10}$ cycloalkyl" in "B" includes saturated bicyclo ring. Concrete examples include, for example, the following groups, etc.

[Chemical Formula 32]

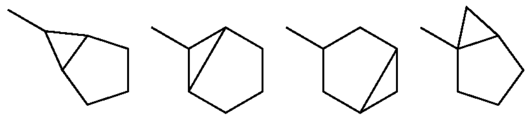

"$C_{3-10}$ cycloalkyl" in "B" includes compounds condensed with an aromatic ring. Concrete examples include, for example, the following group, etc.

[Chemical Formula 33]

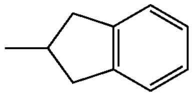

"$C_{3-6}$ cycloalkyl$C_{1-4}$ alkyl" means a group wherein "$C_{3-6}$ cycloalkyl" binds to "$C_{1-4}$ alkyl". Concrete examples include, for example, cyclopropylmethyl, cyclobutylmethyl, cyclopentylmethyl, cyclohexylmethyl, etc.

"$C_{5-6}$ cycloalkenyl" means a cyclic unsaturated hydrocarbon group having 1 double bond. Concrete examples include 1-cyclopentenyl, 1-cyclohexenyl, etc.

"$C_{6-10}$ aryl" means an aromatic hydrocarbon group having 6 to 10 carbon atoms. Preferable one includes "$C_6$ aryl" (phenyl), etc. Concrete examples of "$C_{6-10}$ aryl" include, for example, phenyl, 1-naphthyl or 2-naphthyl, etc.

"$C_{7-14}$ aralkyl" means "$C_{6-10}$ aryl$C_{1-4}$ alkyl" and a group wherein the "alkyl" is substituted by the "aryl". Preferable one includes "$C_{7-10}$ aralkyl" ($C_6$ aryl$C_{1-4}$ alkyl). Concrete examples of "$C_{7-14}$ aralkyl" include, for example, benzyl, 2-phenylethyl, 1-phenylpropyl or 1-naphthylmethyl, etc.

$C_{1-4}$ alkyl moiety of "$C_{7-14}$ aralkyl" in "B" includes groups wherein a ring is formed with $C_2$ to $C_4$ on any one carbon of $C_{1-4}$ alkyl group.

"Heteroaryl" includes, for example, 5- to 10-membered monocyclic or polycyclic group which contains same or different one or more (e.g., 1 to 4) heteroatoms selected from nitrogen, sulfur or oxygen. Preferable one includes, for example, 5- to 6-membered monocyclic group which contains one heteroatom selected from nitrogen, sulfur, oxygen. Concrete examples of "heteroaryl" include, for example, pyrrolyl, thienyl, benzothienyl, benzofuranyl, benzoxazolyl, benzthiazolyl, furyl, oxazolyl, thiazolyl, isooxazolyl, imidazolyl, pyrazolyl, pyridyl, pyrazyl, pyrimidyl, pyridazyl, quinolyl, isoquinolyl, triazolyl, triazinyl, tetrazolyl, indolyl, imidazo[1,2-a]pyridyl, dibenzofuranyl, benzimidazolyl, quinoxalyl, cinnolyl, quinazolyl, indazolyl, naphthylidyl, quinolinolyl or isoquinolinolyl, etc.

"Heteroaryl$C_{1-4}$ alkyl" means a group wherein the "alkyl" is substituted by the "heteroaryl". The heteroaryl moiety includes the same concrete examples as illustrated in the heteroaryl group. For example, it includes "heteroaryl$C_{1-4}$ alkyl". Particularly, it includes 2-pyridylmethyl, etc.

"$C_{1-6}$ alkyl" moiety of "$C_{1-6}$ alkoxy" is the same as defined in the "$C_{1-6}$ alkyl". Preferable one includes "$C_{1-4}$ alkoxy", etc. Concrete examples of "$C_{1-6}$ alkoxy" include methoxy, ethoxy, propoxy, isopropoxy, butoxy, isobutoxy, sec-butoxy, tert-butoxy, etc.

"$C_{1-6}$ alkyl" moiety of "$C_{1-6}$ alkylthio" is the same as defined in the "$C_{1-6}$ alkyl". Preferable one includes "$C_{1-4}$ alkylthio", etc. Concrete examples of "$C_{1-6}$ alkylthio" include, for example, methylthio, ethylthio, propylthio, isopropylthio, butylthio, sec-butylthio, tert-butylthio, pentylthio or hexylthio, etc.

"$C_{1-6}$ alkyl" moiety of "$C_{1-6}$ alkylsulfonyl" is the same as defined in the "$C_{1-6}$ alkyl". Preferable one includes "$C_{1-4}$ alkylsulfonyl", etc. Concrete examples of "$C_{1-6}$ alkylsulfonyl" include, for example, methylsulfonyl, ethylsulfonyl, propylsulfonyl, isopropylsulfonyl, butylsulfonyl, pentylsulfonyl or hexylsulfonyl, etc.

"$C_{6-10}$ aryl" moiety of "$C_{6-10}$ arylthio" is the same as defined in the "$C_{6-10}$ aryl". Concrete examples of "$C_{6-10}$ arylthio" include, for example, phenylthio, 1-naphthylthio or 2-naphthylthio, etc.

"$C_{3-10}$ cycloalkyl" moiety of "$C_{3-10}$ cycloalkoxy" is the same as defined in the "$C_{3-10}$ cycloalkyl". Preferable one includes "$C_{3-6}$ cycloalkoxy", etc. Concrete examples of "$C_{3-10}$ cycloalkoxy" include cyclopropyloxy, cyclobutyloxy, cyclopentyloxy, cyclohexyloxy, cycloheptyloxy, adamantyloxy or norbornyloxy, etc.

"$C_{5-6}$ cycloalkenyl" moiety of "$C_{5-6}$ cycloalkenyloxy" is the same as defined in the "$C_{5-6}$ cycloalkenyl". Concrete examples include 1-cyclopentenyloxy, etc.

"$C_{6-10}$ aryl" moiety of "$C_{6-10}$ aryloxy" is the same as defined in the "$C_{6-10}$ aryl". "$C_6$ aryloxy" (e.g., phenyloxy) is preferable. Concrete examples of "$C_{6-10}$ aryloxy" include phenoxy, 1-naphthyloxy or 2-naphthyloxy, etc.

"$C_{7-14}$ aralkyl" moiety of "$C_{7-14}$ aralkyloxy" (e.g., $C_{6-10}$ aryl$C_{1-4}$ alkyloxy) is the same as defined in the "$C_{7-14}$ aralkyl". Preferable one includes "$C_{7-10}$ aralkyloxy" (e.g., "phenyl$C_{1-4}$ alkyl"), etc. Concrete examples of "$C_{7-14}$ aralkyloxy" include, for example, benzyloxy, phenethyloxy, naphthylmethyloxy, etc.

"Heteroaryloxy" means a group wherein "aralkyl" moiety of the "aralkyloxy" is replaced with "heteroaryl". For example, it includes "5- to 10-membered monocyclic or polycyclic heteroaryloxy", etc.

"$C_{1-4}$ alkoxy" moiety of "$C_{1-4}$ alkoxysulfonyl" is the same as defined in the "$C_{1-4}$ alkoxy". For example, it includes methoxysulfonyl, etc.

"$C_{3-6}$ cycloalkoxy" moiety of "$C_{3-6}$ cycloalkoxysulfonyl" is the same as defined in the "$C_{3-6}$ cycloalkoxy". For example, it includes cyclopropyloxysulfonyl, etc.

"$C_{6-10}$ aryl" moiety of "$C_{6-10}$ aryloxysulfonyl" is the same as defined in the "$C_{6-10}$ aryl". For example, it includes phenoxysulfonyl, etc.

"$C_{1-4}$ alkoxycarbonyl" means a group wherein "$C_{1-4}$ alkoxy" binds to carbonyl group. Particularly, it includes methoxycarbonyl, ethoxycarbonyl, propoxycarbonyl, 2-propoxycarbonyl or tert-butoxycarbonyl, etc.

"$C_{3-6}$ cycloalkoxycarbonyl" means a group wherein the "$C_{3-6}$ cycloalkoxy" binds to carbonyl group. Particularly, $C_{3-6}$ cycloalkoxy moiety includes the same as illustrated in the cycloalkoxy group.

"$C_{1-4}$ alkylcarbonyl" means a group wherein the "$C_{1-4}$ alkyl" binds to carbonyl group. Particularly, it includes acetyl, propionyl or butyryl, etc.

"$C_{3-10}$ cycloalkylcarbonyl" means a group wherein the "$C_{3-10}$ cycloalkyl" binds to carbonyl group. Preferably, it includes "$C_{3-6}$ cycloalkylcarbonyl", etc., and concrete examples of "$C_{3-10}$ cycloalkylcarbonyl" include cyclopropylcarbonyl, cyclobutylcarbonyl, cyclopentylcarbonyl, cyclohexylcarbonyl, adamantylcarbonyl or norbornylcarbonyl, etc.

"$C_{3-10}$ cycloalkyl$C_{1-4}$ alkylcarbonyl" means a group wherein the "$C_{3-10}$ cycloalkyl$C_{1-4}$ alkyl" binds to carbonyl group. Concrete examples include cyclopropylmethylcarbonyl, etc.

"$C_{6-10}$ arylcarbonyl" means a group wherein the "$C_{6-10}$ aryl" binds to carbonyl group.

"$C_{6-10}$ aryl" moiety is the same as defined in the "$C_{6-10}$ aryl". Preferable one includes "$C_6$ arylcarbonyl" (e.g., phenylcarbonyl). Concrete examples of "$C_{6-10}$ arylcarbonyl" include, for example, benzoyl, 1-naphthoyl or 2-naphthoyl, etc.

"$C_{1-4}$ alkyl" moiety of "$C_{1-4}$ alkylcarbonyloxy" is the same as defined in the "$C_{1-4}$ alkyl". Concrete examples include, for example, methylcarbonyloxy, ethylcarbonyloxy, isopropylcarbonyloxy, etc.

"$C_{3-6}$ cycloalkyl" moiety of "$C_{3-6}$ cycloalkylcarbonyloxy" is the same as defined in the "$C_{3-6}$ cycloalkyl". Concrete examples include, for example, cyclopropylcarbonyloxy, cyclobutylcarbonyloxy, cyclopentylcarbonyloxy, etc.

"$C_{3-6}$ cycloalkyl$C_{1-4}$ alkoxy" means a group wherein "$C_{1-4}$ alkoxy" is substituted by the "$C_{3-6}$ cycloalkyl". Concrete examples include, for example, cyclopropylmethoxy, etc.

"$C_{3-6}$ cycloalkyl$C_{1-4}$ alkoxy" moiety of "$C_{3-6}$ cycloalkyl$C_{1-4}$ alkoxycarbonyl" is the same as defined above. Concrete examples include, for example, cyclopropylmethoxycarbonyl, etc.

"$C_{1-4}$ alkylcarbonylamino" means a group wherein amino group is substituted by one "$C_{1-4}$ alkylcarbonyl". Concrete examples include, for example, methylcarbonylamino, etc. Meanwhile, "$C_{1-4}$ alkyl" may be optionally substituted by 1 to 3 fluorine atoms.

"$C_{1-4}$ alkylthiocarbonylamino" means a group wherein carbonyl group of the "$C_{1-4}$ alkylcarbonyl" is replaced with thiocarbonyl group. Concrete examples include, for example, methylthiocarbonylamino, etc.

"N—($C_{1-4}$ alkylcarbonyl)-N—($C_{1-6}$ alkyl)-amino" means a group wherein amino group of the "$C_{1-4}$ alkylcarbonylamino" is substituted by the "$C_{1-6}$ alkyl". Concrete examples include, for example, N-methyl-N-ethylcarbonylamino, etc.

"$C_{3-6}$ cycloalkylcarbonylamino" means a group wherein amino group is substituted by one "$C_{3-6}$ cycloalkylcarbonyl". Concrete examples include, for example, cyclopropylcarbonylamino, etc.

"$C_{3-6}$ cycloalkyl$C_{1-4}$ alkylcarbonylamino" means a group wherein amino group is substituted by one "$C_{3-6}$ cycloalkyl$C_{1-4}$ alkylcarbonyl". Concrete examples include, for example, cyclopropylmethylcarbonylamino, etc.

"$C_{1-4}$ alkoxycarbonylamino" means a group wherein amino group is substituted by one "$C_{1-4}$ alkoxycarbonyl". Concrete examples include, for example, methoxycarbonylamino, ethoxycarbonylamino, etc. Meanwhile, "$C_{1-4}$ alkyl" may be optionally substituted by 1 to 3 fluorine atoms.

"N—($C_{1-6}$ alkyl)-N—($C_{1-4}$ alkoxycarbonyl)-amino" means a group wherein amino group of the "$C_{1-4}$ alkoxycarbonylamino" is substituted by "$C_{1-6}$ alkyl". Concrete examples include, for example, N-methyl-methoxycarbonylamino, etc.

"$C_{1-4}$ alkylsulfonylamino" means a group wherein amino group is substituted by one "$C_{1-4}$ alkylsulfonyl". Concrete examples include, for example, methylsulfonylamino, ethylsulfonylamino, etc.

"$C_{1-4}$ alkylsulfonylaminocarbonyl" means a group wherein carbonyl group is substituted by the "$C_{1-4}$ alkylsulfonylamino". Concrete examples include, for example, methylsulfonylamino, etc.

"Saturated heterocycle" includes, for example, 5- to 6-membered saturated heterocycle having same or different 1 to 3 atoms selected from nitrogen, oxygen or sulfur, etc. Each of the nitrogen, oxygen and sulfur is an atom which constitutes a ring. Particularly, it includes pyranyl, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, imidazolidinyl, oxoimidazolidinyl, dioxoimidazolidinyl, oxooxazolidinyl, dioxooxazolidinyl, dioxothiazolidinyl, tetrahydrofuranyl or tetrahydropyridinyl, etc. In the group, nitrogen atom which constitutes a ring is not a binding site of a "group". In other words, the group does not encompass the embodiment of pyrrolidino group, for example, etc.

"5- to 6-membered saturated heterocyclyl" includes saturated bicyclo ring and saturated spiro ring of which a basic skeleton is "5- to 6-membered saturated heterocyclyl". Concrete examples include the following "groups", etc.

[Chemical Formula 34]

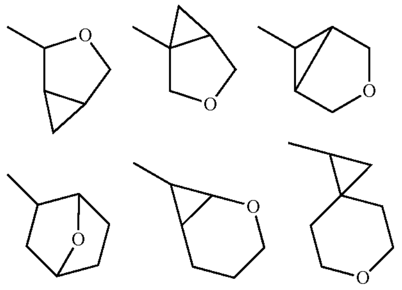

The "saturated heterocyclyl" may form a condensed ring with 6-membered aromatic hydrocarbon or 6-membered unsaturated heterocyclyl. For example, it includes bicyclic 11- or 12-membered "saturated heterocyclyl" wherein the 5- to 6-membered "saturated heterocycle" is condensed with 6-membered aromatic hydrocarbon or 6-membered unsaturated heterocyclyl. The 6-membered aromatic hydrocarbon includes benzene, etc. The 6-membered unsaturated heterocyclyl includes pyridine, pyrimidine or pyridazine, etc. Particularly, it includes dihydroindolyl, dihydroisoindolyl, dihydropurinyl, dihydrothiazolopyrimidinyl, dihydrobenzodioxanyl, isoindolinyl, indazolyl, pyrrolidinyl, tetrahydroquinolinyl, decahydroquinolinyl, tetrahydroisoquinolinyl, decahydroisoquinolinyl, tetrahydronaphthylidinyl or tetrahydropyridoazepinyl, etc.

"Saturated heterocyclyl" moiety of "saturated heterocyclyloxy" is the same as defined in the "saturated heterocyclyl". Particularly, it includes 4-pyranyloxy, etc.

"Saturated heterocyclylcarbonyl" means a group wherein the "saturated heterocyclyl" binds to carbonyl group. Particularly, it includes 4-pyranylcarbonyl, etc.

"Saturated heterocyclyl$C_{1-4}$ alkyl" means a group wherein the "saturated heterocyclyl" binds to "$C_{1-4}$ alkyl". Particularly, it includes 4-pyranylmethyl, etc.

"Saturated heterocyclyl$C_{1-4}$ alkoxy" means a group wherein the "saturated heterocyclyl" binds to "$C_{1-4}$ alkoxy". Particularly, it includes 4-pyranylmethoxy, etc.

"Saturated heterocyclyloxy" moiety of "saturated heterocyclyloxycarbonyl" is the same as defined above. Particularly, it includes 4-pyranyloxycarbonyl, etc.

"Saturated heterocyclyl$C_{1-4}$ alkyl" moiety of "saturated heterocyclyl$C_{1-4}$ alkylcarbonyl" is the same as defined above. Particularly, it includes 4-pyranylmethylcarbonyl, etc.

"Optionally substituted amino" means amino, mono- or di-substituted amino, and 5- to 7-membered cyclic amino.

"Mono- or di-substituted amino" means amino group substituted by same or different 1 to 2 groups selected from the group consisting of "$C_{1-6}$ alkyl", "$C_{3-6}$ cycloalkyl", "$C_{3-6}$ cycloalkyl$C_{1-4}$ alkyl", "$C_{3-6}$ cycloalkyl$C_{1-4}$ alkoxycarbonyl", "$C_{1-4}$ alkylcarbonyl", "saturated heterocyclyl", "saturated heterocyclyl$C_{1-4}$ alkyl", "saturated heterocyclylcarbonyl", "saturated heterocyclyloxycarbonyl", "saturated heterocyclyl$C_{1-4}$ alkylcarbonyl", and "benzyl".

Concrete examples of "mono- or di-substituted amino" include, for example,

"mono- or di-($C_{1-6}$ alkyl)-substituted amino" (e.g., methylamino, ethylamino, dimethylamino, diethylamino, etc.), "mono- or di-($C_{3-6}$ cycloalkyl)-substituted amino" (e.g., cyclopropylamino, cyclobutylamino, cyclopentylamino, dicyclopropylamino, dicyclobutylamino, cyclodipentylamino, etc.), "mono-($C_{3-6}$ cycloalkyl$C_{1-4}$ alkyl)-substituted amino" (e.g., cyclopropylmethylamino, cyclobutylmethylamino, cyclopentylmethylamino, etc.), "($C_{1-4}$ alkyl)(benzyl)-substituted amino" (e.g., N-methyl-N-benzylamino, N-ethyl-N-benzylamino, etc.), "($C_{3-6}$ cycloalkyl)(benzyl)-substituted amino" (e.g., N-cyclopropyl-N-benzylamino, N-cyclopentyl-N-benzylamino, N-cyclohexyl-N-benzylamino, etc.), "$C_{3-6}$ cycloalkyl$C_{1-4}$ alkoxycarbonylamino" (e.g., cyclopropylmethoxycarbonylamino, etc.), "5- to 6-membered saturated heterocyclylamino" (e.g., 3-pyrrolidinylamino, etc.), "saturated heterocyclyl$C_{1-4}$ alkylcarbonylamino" (e.g., (4-pyranylmethylcarbonyl)amino, etc.), "N—($C_{1-6}$ alkyl)-N-(saturated heterocyclyl$C_{1-4}$ alkylcarbonyl)-amino" (e.g., N-methyl-N-(4-pyranylmethylcarbonyl) amino, etc.), "saturated heterocyclylcarbonylamino" (e.g., 4-pyranylcarbonylamino, etc.), "N—($C_{1-6}$ alkyl)-N-(saturated heterocyclylcarbonyl)-amino" (e.g., N-methyl-N-(4-pyranylcarbonyl)amino, etc.), "N—($C_{1-4}$ alkylcarbonyl)-N—($C_{1-6}$ alkyl)-amino" (e.g., N-methyl-N-methylcarbonylamino, etc.), "(saturated heterocyclyloxycarbonyl)amino" (e.g., 3-tetrahydrofuryloxycarbonylamino, etc.), "N-(saturated heterocyclyl$C_{1-4}$ alkyl)-N—($C_{1-6}$ alkyl)-amino" (e.g., N-methyl-N-(4-pyranylmethyl)amino, etc.), "N-(saturated heterocyclylcarbonyl)-N—($C_{1-6}$ alkyl)-amino" (e.g., N-methyl-N-(4-pyranylcarbonyl)amino, etc.), "N-(saturated heterocyclyl$C_{1-4}$ alkylcarbonyl)-N—($C_{1-6}$ alkyl)-amino" (e.g., N-methyl-N-(4-pyranylmethylcarbonyl) amino, etc.), "N-(saturated heterocyclyloxycarbonyl)-N—($C_{3-6}$ cycloalkyl)-amino" (e.g., N-cyclopropyl-N-(4-pyranyloxycarbonyl)amino, etc.), "N-(saturated heterocyclyl$C_{1-4}$ alkylcarbonyl)-N—($C_{1-3-6}$ cycloalkyl)-amino" (e.g., N-cyclopropyl-N-(4-pyranylmethylcarbonyl)amino, etc.), etc.

Meanwhile, "$C_{1-6}$ alkyl" moiety of "mono- or di-($C_{1-6}$ alkyl)-substituted amino" may be optionally substituted by $C_{1-6}$ alkoxy, mono-$C_{1-6}$ alkylcarbonylamino (in which $C_{1-6}$ alkyl may be optionally substituted by 1 to 3 fluorine atoms), or mono-$C_{1-6}$ alkoxycarbonylamino.

"4- to 7-Membered cyclic amino" means 4- to 7-membered cyclic amino group. It means a group wherein nitrogen atom in the ring is directly a binding site of a "group". Preferable one is 5- to 7-membered group, more preferably 5- or 6-membered group. Concrete examples include, for example, pyrrolidino, piperidino, morpholino, thiomorpholino, thiomorpholinooxide, thiomorpholinodioxide, piperazino, 2-pyrrolidon-1-yl, etc. The ring may be optionally substituted by halogen atom, $C_{1-4}$ alkyl, or $C_6$ aryl optionally substituted by $C_{1-4}$ alkoxy, for example, etc.

"5- to 7-Membered cyclic amino" may form a condensed ring with 6-membered aromatic hydrocarbon or 6-membered unsaturated heterocyclyl. Concrete examples include the following "group", etc.

[Chemical Formula 35]

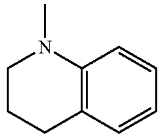

Substituents in "optionally substituted $C_{1-6}$ alkyl" include, for example, (a) halogen atom,
(b) cyano,
(c) $C_{3-6}$ cycloalkyl (in which the group may be optionally substituted by halogen atom, hydroxyl or $C_{1-4}$ alkoxy),
(d) hydroxyl,
(e) $C_{1-4}$ alkoxy (in which the group may be optionally substituted by fluorine atom, $C_{1-4}$ alkoxy or $C_{3-6}$ cycloalkyl),
(f) $C_{3-6}$ cycloalkyloxy,
(g) $C_6$ aryloxy (in which the group may be optionally substituted by same or different groups selected from the group consisting of halogen atom, cyano and $C_{1-4}$ alkoxy),
(h) benzyloxy,
(i) formyl,
(j) $C_{1-4}$ alkylcarbonyl,
(k) $C_{3-6}$ cycloalkylcarbonyl,
(l) phenylcarbonyl,
(m) benzylcarbonyl,
(n) formylcarbonyloxy,
(o)$C_{1-4}$ alkylcarbonyloxy,
(p) $C_{3-6}$ cycloalkylcarbonyloxy,
(q) carboxyl,
(r) $C_{1-4}$ alkoxycarbonyl,
(s) $C_{3-6}$ cycloalkoxycarbonyl,
(t) amino,
(u) mono-substituted amino (in which the group is substituted by
  (u1) $C_{1-6}$ alkyl,
  (u2) $C_{3-6}$ cycloalkyl,
  (u3) $C_{3-6}$ cycloalkyl$C_{1-4}$ alkyl,
  (u4) benzyl, (u5) $C_{3-6}$ cycloalkyl$C_{1-4}$ alkoxycarbonyl,
(u6) $C_{1-4}$ alkylcarbonyl,
(u7) $C_{3-6}$ cycloalkylcarbonyl,
(u8) saturated heterocyclyl$C_{1-4}$ alkyl,
(u9) saturated heterocyclylcarbonyl,
(u10) saturated heterocyclyloxycarbonyl,
(u11) saturated heterocyclyl$C_{1-4}$ alkylcarbonyl, or
(u12) $C_{1-4}$ alkylsulfonyl),
(v) di-substituted amino (in which the group is substituted by same or different 2 groups selected from the above (u1) to (u12)),
(w) 5- to 7-membered cyclic amino,
(x) optionally substituted aminocarbonyl,
(y) optionally substituted aminocarbonyloxy, or
(z) saturated heterocyclyl (in which the ring may be optionally substituted by $C_{1-4}$ alkyl optionally substituted by $C_{1-4}$ alkoxy, $C_{1-4}$ alkoxy, or $C_{1-4}$ alkylcarbonylamino, for example, etc.), etc. Meanwhile, the substituents are not limited to the above list of substituents. In other words, (f801) to (f826) and (b120) to (b128) as described below are also included in the substituents in addition to the above list.

The "optionally substituted aminocarbonyl" means a group wherein "optionally substituted amino" binds to carbonyl. Herein, "substituted amino" means mono-substituted amino, di-substituted amino or 5- to 7-membered cyclic amino.

Concrete examples of "mono- or di-substituted aminocarbonyl" include a group wherein "mono- or di-aminocarbonyl" moiety is the same as illustrated in the concrete examples of the "mono- or di-substituted amino".

"5- to 7-Membered cyclic aminocarbonyl" may be optionally substituted by $C_{6-10}$ aryloxy. Concrete examples include 3-phenyloxypyrrolidinocarbonyl, etc.

"$C_{1-6}$ alkylaminocarbonylamino" means amino group substituted by one "mono-($C_{1-6}$ alkyl)-substituted aminocarbonyl". Concrete examples include methylaminocarbonylamino, etc.

"N—($C_{1-6}$ alkylaminocarbonyl)-N—($C_{1-6}$ alkyl)-amino" means a group wherein amino group of the "$C_{1-6}$ alkylaminocarbonylamino" is substituted by "$C_{1-6}$ alkyl". Concrete examples include, for example, N-methylaminocarbonyl-N-methyl-amino, etc.

"$C_{1-6}$ alkylaminothiocarbonylamino" means a group wherein carbonyl in the "$C_{1-6}$ alkylaminocarbonylamino" is replaced with thiocarbonyl. Concrete examples include methylaminothiocarbonylamino, etc.

"Optionally substituted aminocarbonyl" moiety of the "optionally substituted aminocarbonyloxy" is the same as defined in the "optionally substituted aminocarbonyl". Concrete examples include, for example, aminocarbonyloxy, etc.

"5- to 7-Membered cyclic aminocarbonyl" moiety of "5- to 7-membered cyclic aminocarbonyloxy" is the same as defined above. Concrete examples include pyrrolidinocarbonyloxy, etc.

"5- to 7-Membered cyclic aminocarbonyl$C_{1-4}$ alkoxy" means a group wherein the "$C_{1-4}$ alkoxy" is substituted by the "5- to 7-membered cyclic aminocarbonyl". Concrete examples include 1-morpholinocarbonyl-1,1-dimethyl-methoxy, etc.

Preferable substituents of "optionally substituted $C_{1-6}$ alkyl" in "B" are a group selected from the group consisting of
(a2) halogen atom,
(b2) $C_{3-6}$ cycloalkyl (in which the group may be optionally substituted by same or different 1 to 2 groups selected from the group consisting of
(b21) halogen atom,
(b22) hydroxy,
(b23) $C_{1-4}$ alkoxy, and
(b24) $C_{3-6}$ cycloalkylcarbonylamino),
(c2) hydroxyl,
(d2) $C_{1-4}$ alkoxy,
(e2) $C_{3-6}$ cycloalkoxy,
(f2) $C_6$ aryloxy (in which the group may be optionally substituted by $C_{1-4}$ alkyl),
(g2) carboxy,
(h2) $C_{1-4}$ alkoxycarbonyl,
(i2) amino (in which the group may be optionally substituted by $C_{1-6}$ alkyl or benzyl),
(j2) aminocarbonyl (in which the amino moiety may be optionally substituted by
(j21) $C_{1-6}$ alkyl,
(j22) $C_{3-6}$ cycloalkyl, or
(j23) $C_{3-6}$ cycloalkyl$C_{1-4}$ alkyl),
(k2) $C_{3-6}$ cycloalkylcarbonylamino,
(l2) saturated heterocyclyl (in which the ring may be optionally substituted by same or different 1 to 2 groups selected from the group consisting of
(l21) $C_{1-4}$ alkyl,
(l22) $C_{1-4}$ alkoxy,
(l23) $C_{1-4}$ alkylcarbonylamino, and
(l24) oxo), and
(m2) 5- to 7-membered cyclic amino (in which the group may be optionally substituted by same or different 1 to 3 groups selected from the group consisting of
(m21) halogen atom,
(m22) $C_{1-4}$ alkyl,
(m23) $C_6$ aryl optionally substituted by $C_{1-4}$ alkoxy,
(m24) $C_6$ aryloxy optionally substituted by 1 to 3 halogen atoms, and
(m25) oxo).

In case where "A" is a single bond, and "B" is $C_{1-6}$ alkyl substituted by "mono-($C_{1-6}$ alkyl)-substituted amino", "$C_{1-6}$ alkyl" in the amino moiety may be optionally substituted by aminocarbonyl, mono- or di-($C_{1-6}$ alkyl)aminocarbonyl, or 5- to 6-membered cyclic aminocarbonyl, and concrete examples of "$C_{1-6}$ alkyl" in the amino moiety include the following groups.

[Chemical Formula 36]

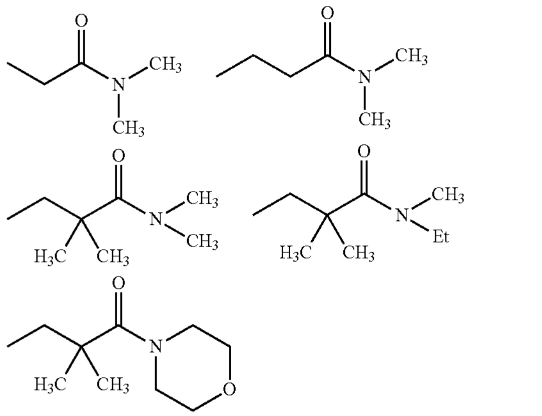

Substituents of "optionally substituted $C_{1-6}$ alkyl" in "B" may be optionally substituted by same or different at least 1 to 3 groups selected from the group consisting of the above (a2) to (m2). For example, in case where "A" is a single bond, the group may be simultaneously optionally substituted by 2 substituents of the above (b2) and (j2). Further, for example, in case where "A" is not a single bond, the group may be simultaneously optionally substituted by 2 substituents of the above (b2) and (d2).

Concrete examples of the case include, for example, the following "groups", etc.

[Chemical Formula 37]

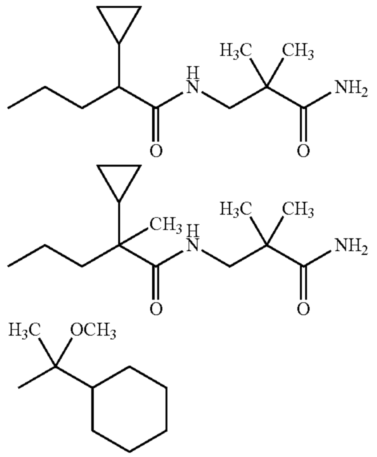

Substituents in "optionally substituted $C_{1-6}$ alkoxy" include, for example, one group selected from the group consisting of (a) to (z) in the "optionally substituted $C_{1-6}$ alkyl", etc. (in which substituents of the substituted amino group in (u), (v), (x) and (y) are limited to $C_{1-4}$ alkyl and $C_{3-6}$ cycloalkyl).

Substituents in "optionally substituted $C_{2-6}$ alkenyl" and "optionally substituted $C_{2-6}$ alkynyl" include, for example, one group selected from the group consisting of the groups of (a) to (s) in the "optionally substituted $C_{1-6}$ alkyl" and $C_{1-4}$ alkyl (in which $C_{1-4}$ alkyl may be optionally substituted by hydroxyl), etc.

Substituents in "optionally substituted $C_{3-10}$ cycloalkyl" and "optionally substituted $C_{3-10}$ cycloalkyloxy" include, for example, one group selected from the group consisting of the group of (x) in the "optionally substituted $C_{1-6}$ alkyl", halogen atom, $C_{1-4}$ alkyl optionally substituted by $C_{1-4}$ alkoxy, and $C_{6-10}$ aryl (in which the aryl may be optionally substituted by halogen atom, $C_{1-4}$ alkyl, hydroxyl, or $C_{1-4}$ alkoxy), etc.

Substituents in "optionally substituted $C_{5-6}$ cycloalkenyl" and "optionally substituted $C_{5-6}$ cycloalkenyloxy" include, for example, one group selected from the group consisting of the groups of (a) to (s) in the "optionally substituted $C_{1-6}$ alkyl" and nitro, etc.

Substituents in "optionally substituted $C_{1-4}$ alkylcarbonyl" and "optionally substituted $C_{3-10}$ cycloalkylcarbonyl" include, for example, one group selected from the group consisting of the groups of (a) to (h) in the "optionally substituted $C_{1-6}$ alkyl", nitro, $C_{1-4}$ alkylcarbonylamino and $C_{1-4}$ alkoxycarbonylamino, etc.

Substituents in "optionally substituted $C_{1-6}$ alkylthio", "optionally substituted $C_{1-6}$ alkylsulfonyl", and "optionally substituted $C_{1-4}$ alkoxycarbonyl" include, for example, one group selected from the group consisting of halogen atom, hydroxyl, nitro, cyano, or the groups of (d) to (h) in the "optionally substituted $C_{1-6}$ alkyl", etc.

Substituents in "optionally substituted $C_{6-10}$ aryl", "optionally substituted $C_{6-10}$ aryloxy", "optionally substituted $C_{6-10}$ arylcarbonyl", "optionally substituted 5- to 10-membered monocyclic or polycyclic heteroaryl" and "optionally substituted 5- to 10-membered monocyclic or polycyclic heteroaryloxy" include, for example, a group selected from the group consisting of (a3) halogen atom,
(b3) nitro,
(c3) cyano,
(d3) $C_{1-4}$ alkyl (in which the group may be optionally substituted by halogen atom, hydroxyl, or amino, for example),
(e3) hydroxyl,
(f3) $C_{1-4}$ alkoxy (in which the group may be optionally substituted by
 (f31) $C_{1-4}$ alkoxy,
 (f32) $C_{3-6}$ cycloalkyl optionally substituted by $C_{1-4}$ alkyl, or
 (f33) $C_6$ aryloxy optionally substituted by halogen atom),
(g3) $C_{3-6}$ cycloalkyloxy,
(h3) $C_{6-10}$ aryloxy (in which the group may be optionally substituted by same or different groups selected from the group consisting of halogen atom, cyano and $C_{1-4}$ alkoxy),
(i3) $C_{6-10}$ aryl (in which the group may be optionally substituted by
 (i31) halogen atom,
 (i32) $C_{1-4}$ alkyl optionally substituted by carboxy, or
 (i33) $C_{1-4}$ alkoxy optionally substituted by fluorine atom, hydroxyl, or carboxy, for example),
(j3) sulfonyl,
(k3) $C_{1-4}$ alkoxysulfonyl,
(l3) $C_{3-6}$ cycloalkoxysulfonyl,
(m3) $C_{6-10}$ aryloxysulfonyl (in which the aryl may be optionally substituted by same or different groups selected from the group consisting of halogen atom, cyano and $C_{1-4}$ alkoxy),
(n3) benzyloxysulfonyl,
(o3) 5- to 6-membered monocyclic heteroaryloxy (in which the group may be optionally substituted by $C_{1-4}$ alkyl),
(p3) saturated heterocyclyloxy (in which the group may be optionally substituted by
 (p31) $C_6$ aryl optionally substituted by halogen atom, or
 (p32) saturated heterocyclylcarbonyl),
(q3) amino (in which the group may be optionally substituted by same or different 1 to 2 groups selected from the above (u1) to (u12)),
(r3) 5- to 7-membered cyclic amino (in which the group may be optionally substituted by $C_6$ aryl),
(s3) optionally substituted aminocarbonyl, and
(t3) optionally substituted aminocarbonyloxy, etc. Meanwhile, the substituents are not limited to the above list of substituents, and (e1201) to (e1211) as described below are also included in the substituents in addition to the above list.

Substituents of the aryl moiety in "optionally substituted $C_{7-14}$ aralkyl" and "optionally substituted $C_{7-14}$ aralkyloxy" include, for example, a group selected from the group consisting of (a4) halogen atom,
(b4) cyano,
(c4) $C_{1-4}$ alkyl (in which the group may be optionally substituted by 1 to 3 halogen atoms),
(d4) hydroxyl,
(e4) $C_{1-4}$ alkoxy (in which the group may be optionally substituted by 1 to 3 halogen atoms),
(f4) $C_{3-6}$ cycloalkoxy (in which the group may be optionally substituted by 1 to 2 halogen atoms),
(g4) carboxy,
(h4) $C_{1-4}$ alkoxycarbonyl,
(i4) $C_{6-10}$ aryl (in which the group may be optionally substituted by 1 to 3 halogen atoms or $C_{1-4}$ alkoxy), (j4) $C_{6-10}$ aryloxy,
(k4) $C_{7-10}$ aralkyloxy,
(l4) aminocarbonyl (in which the amino moiety may be optionally substituted by $C_{1-6}$ alkyl),
(m4) $C_{1-4}$ alkylsulfonylamino, and
(n4) $C_{1-4}$ alkylsulfonyl, etc.

Substituents of the above (a4) to (n4) may be optionally substituted on $C_{1-4}$ alkyl moiety of $C_{7-14}$ aralkyl (e.g., $C_{6-10}$ aryl$C_{1-4}$ alkyl).

Substituents of the heteroaryl moiety of "optionally substituted 5- to 10-membered monocyclic or polycyclic heteroaryl$C_{1-4}$ alkyl" include groups which are listed as substituents in "optionally substituted 5- to 10-membered monocyclic or polycyclic heteroaryl".

Substituents of "saturated heterocyclyl" and "saturated heterocycle" include, for example,
(a5) halogen atom,
(b5) hydroxyl,
(c5) nitro,
(d5) cyano,
(e5) $C_{1-4}$ alkyl (in which the group may be optionally substituted by 1 to 3 halogen atoms, or $C_{1-4}$ alkoxy),
(f5) $C_{1-4}$ alkoxy (in which the group may be optionally substituted by 1 to 3 halogen atoms, etc.),
(g5) carboxyl,
(h5) $C_{1-4}$ alkoxycarbonyl,
(i5) $C_{3-6}$ cycloalkoxycarbonyl,
(j5) amino (in which the group may be optionally substituted by $C_{1-4}$ alkyl),
(k5) $C_6$ aryl (in which the group may be optionally substituted by $C_{1-4}$ alkoxy),
(l5) aminocarbonyl,
(m5) $C_{1-4}$ alkylcarbonylamino,
(n5) oxo, or
(o5) thioxo, etc.

The "saturated heterocyclyl" or "saturated heterocycle" may be optionally substituted by same or different two groups among the above substituents.

Preferable "optionally substituted saturated heterocyclyl" in "B" is, for example, "5- to 6-membered saturated heterocyclyl having same or different 1 to 3 atoms selected from the group consisting of nitrogen, oxygen and sulfur".

The definitions of "$G^1$", "$G^2$", "$G^3$" and "$G^4$" in a compound of formula (I) are illustrated. The compound wherein $G^1$ is —N($R^{1b}$)—, $G^2$ is —CO—, $G^3$ is —C($R^{1c}$)($R^{1d}$)—, and $G^4$ is absent means a compound of the following formula:

[Chemical Formula 38]

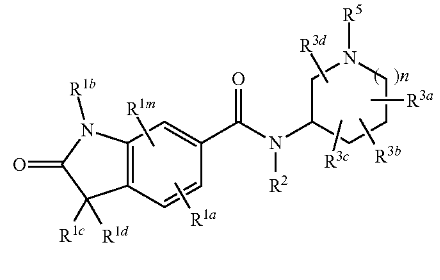

wherein each definition is the same as defined in Item 1.

The compound wherein $G^1$ is —N($R^{1b}$)—, $G^2$ is —CO—, $G^3$ is —N($R^{1b}$)—, and $G^4$ is absent means a compound of the following formula:

[Chemical Formula 39]

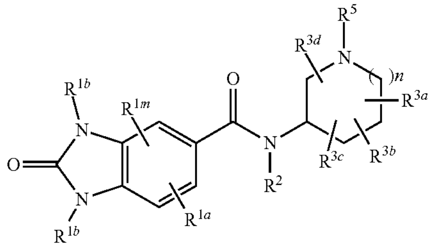

wherein each definition is the same as defined in Item 1.

The compound wherein $G^1$ is —N($R^{1b}$)—, $G^2$ is —CO—, $G^3$ is —C($R^{1c}$)($R^{1d}$)—, and $G^4$ is —C($R^{1x}$)($R^{1y}$)— means a compound of the following formula:

[Chemical Formula 40]

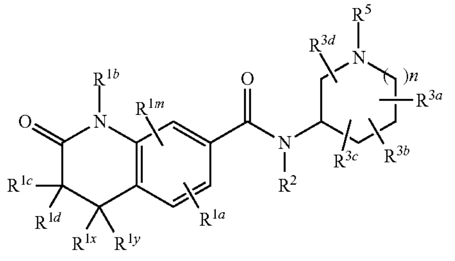

wherein each definition is the same as defined in Item 1. In the compound, "$R^{1c}$" and "$R^{1x}$" may combine each other to bind together. In other words, such definitions include a compound of the following formula wherein $G^1$ is —N($R^{1b}$)—, $G^2$ is —CO—, and $G^3$ and $G^4$ are —C($R^{1d}$)=C($R^{1y}$)—:

[Chemical Formula 41]

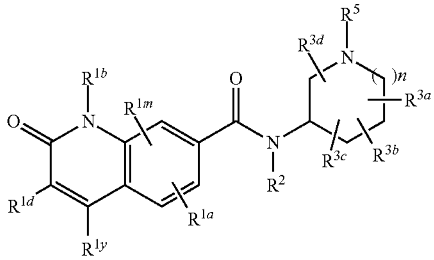

wherein each definition is the same as defined in Item 1.

The definition of "$R^{1x}$ and $R^{1y}$ combine each other to form a group of the following formula:

[Chemical Formula 42]

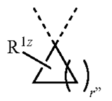

is illustrated. The definition means spiro rings of the following formulae (wherein solid lines are moieties defined by $R^{1x}$ and $R^{1y}$, and broken lines are skeleton moieties defined by $G^1$ to $G^4$).

[Chemical Formula 43]

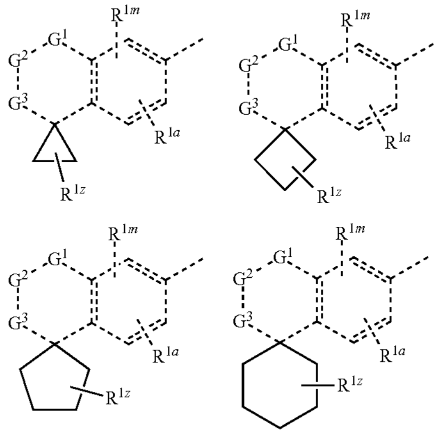

A binding position of "A" in the "group: -A-B" is illustrated. The "group: -A-B" wherein A is —$(CH_2)_s$O—, and B is hydrogen atom, for example, means a "group: —$(CH_2)_s$ O—H".

"If A is —$(CH_2)_s$N($R^{4c}$)—, —$(CH_2)_s$OCON($R^{4c}$)—, —$(CH_2)_s$CON($R^{4c}$)—, —$(CH_2)_s$N($R^{4c}$)CON($R^{4c}$)— and —$(CH_2)_s$$SO_2$N($R^{4c}$)—, $R^{4c}$ and B may combine each other to form a ring" means that "N($R^{4c}$)—" moiety forms "5- to 6-membered cyclic amino". Concrete examples include, for example, groups of the following formulae:

[Chemical Formula 44]

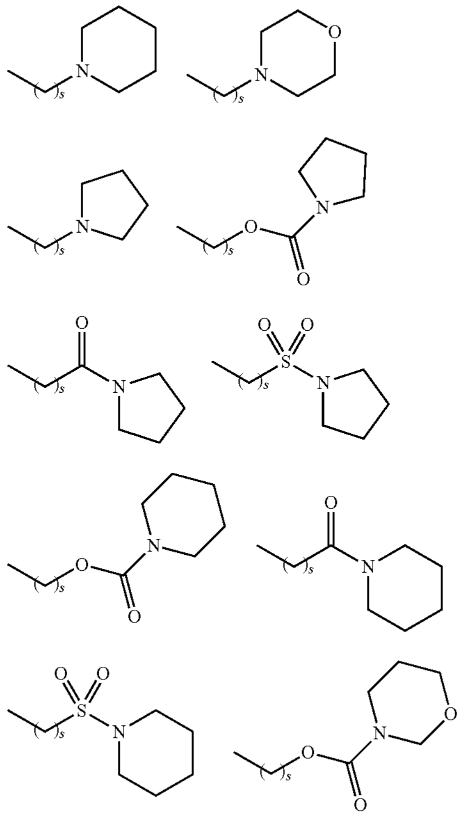

-continued

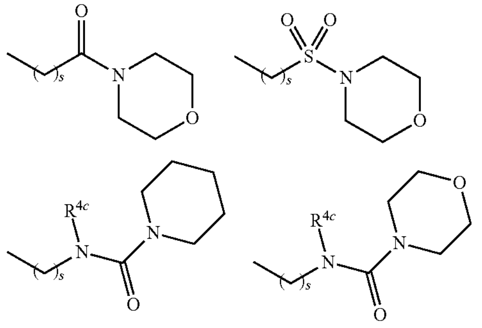

The ring in case that "$R^{4c}$ and B may combine each other to form a ring" may form a condensed ring with $C_6$ aryl, 5- to 6-membered heteroaryl, or 5- to 6-membered saturated heterocycle. Concrete examples include groups of the following formulae:

[Chemical Formula 45]

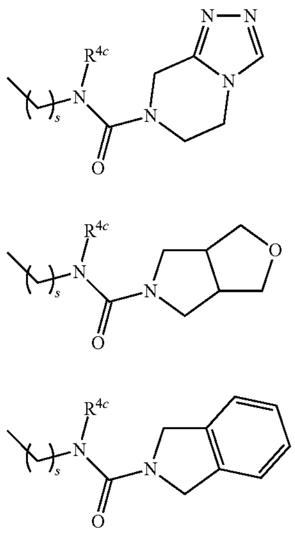

The cyclic amino may be optionally substituted by the same substituents as described in the "saturated heterocyclyl". Concrete examples include 4-hydroxypiperidino; 2-methoxymorpholino; 4-formyl-piperidino; 4-methoxycarbonylpiperidino; 4-aminocarbonylpiperidino; 4-N-methylaminopiperidino; 3-phenylpyrrolidino; 4-dimethylaminopiperidino, etc.

In a compound of formula (I), if A is —$(CH_2)_s$N($R^{4c}$)CON ($R^{4c}$)—, $R^{4c}$ may be each independent and different. Concrete examples in this case include an embodiment that A is "—$(CH_2)_s$NHCON($CH_3$)—", etc.

"Any two of $R^{3a}$, $R^{3b}$, $R^{3c}$ and $R^{3d}$ are hydrogen atom, and the other two combine each other together with the adjacent heterocyclyl to form a bridged ring" means that the other two groups form a bridged ring with heterocycle (pyrrolidine ring, piperidine ring, etc.) which the groups are substituted on. Concrete examples of the definition include groups of the following formulae.

[Chemical Formula 46]

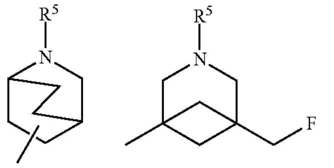

Preferable embodiments of the definitions in a compound of formula (I) are illustrated.

The definitions in a partial structure of the following formula:

[Chemical Formula 47]

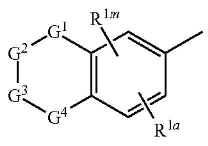

wherein each definition is the same as defined above are illustrated.

A preferable embodiment of "$G^1$", "$G^2$", "$G^3$" and "$G^4$" is (i) $G^1$ is —N($R^{1b}$)—, $G^2$ is —CO—, $G^3$ is —C($R^{1c}$)($R^{1d}$)—, and $G^4$ is —C($R^{1x}$)($R^{1y}$)—, —$SO_2$—, oxygen, sulfur, or absent, or (ii) $G^1$ is —N($R^{1b}$)—, $G^2$ is —CO—, $G^3$ is —N($R^{1b}$)—, and $G^4$ is absent.

A preferable embodiment of "$G^1$", "$G^2$", "$G^3$" and "$G^4$" is that $G^1$ is —N($R^{1b}$)—, $G^2$ is —CO—, $G^3$ is —N($R^{1b}$)—, and $G^4$ is absent.

More preferable embodiment of "$G^1$", "$G^2$", "$G^3$" and "$G^4$" is that $G^1$ is —N($R^{1b}$)—, $G^2$ is —CO—, $G^3$ is —C($R^{1c}$)($R^{1d}$)—, and $G^4$ is —C($R^{1x}$)($R^{1y}$)—, oxygen, or sulfur.

"$G^4$" is preferably —C($R^{1x}$)($R^{1y}$)—, and $R^{1x}$ and $R^{1y}$ are preferably hydrogen atom or $C_{1-4}$ alkyl.

"$G^4$" is preferably oxygen or sulfur.

"$R^{1a}$" includes one group selected from the group consisting of (a6) halogen atom, (b6) cyano, (c6) $C_{1-6}$ alkyl (in which the group may be optionally substituted by 1 to 3 fluorine atoms, $C_{1-4}$ alkoxy, or $C_{3-6}$ cycloalkoxy), (d6) $C_{1-6}$ alkoxy (in which the group may be optionally substituted by 1 to 3 fluorine atoms, or $C_{3-6}$ cycloalkyl), (e6) $C_{3-6}$ cycloalkyl, (f6) $C_{3-6}$ cycloalkoxy (in which the group may be optionally substituted by 1 to 2 fluorine atoms or $C_{1-4}$ alkoxy) and (g6) 5- to 6-membered monocyclic heteroaryl (in which the group may be optionally substituted by $C_{1-4}$ alkyl).

"$R^{1a}$" is preferably one group selected from the group consisting of halogen atom, cyano, $C_{1-6}$ alkyl optionally substituted by 1 to 3 fluorine atoms, and $C_{1-6}$ alkoxy. More preferable one is $C_{1-6}$ alkyl.

"$R^{1a}$" is preferably substituted on the position shown by the following formula:

[Chemical Formula 48]

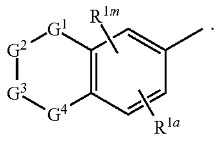

"$R^{1b}$" includes (a7) $C_{1-6}$ alkyl (in which the group may be optionally substituted by two groups selected from the group consisting of (a701) hydroxy, (a702) cyano, (a703) $C_{1-4}$ alkoxy (in which the group may be optionally substituted by 1 to 3 fluorine atoms, or $C_{1-4}$ alkoxy), (a704) trifluoromethyl, (a705) trifluoromethoxy, (a706) $C_{3-6}$ cycloalkyl (in which the group may be optionally substituted by 1 to 2 fluorine atoms, $C_{1-4}$ alkyl optionally substituted by $C_{1-4}$ alkoxy, or $C_{1-4}$ alkoxy), (a707) $C_{3-6}$ cycloalkoxy, (a708) formylamino, (a709) $C_{1-4}$ alkylcarbonylamino (in which alkyl may be optionally substituted by 1 to 3 fluorine atoms), (a710) N—($C_{1-4}$ alkylcarbonyl)-N—($C_{1-6}$ alkyl)-amino, (a711) $C_{3-6}$ cycloalkylcarbonylamino, (a712) ($C_{3-6}$ cycloalkyl$C_{1-4}$ alkyl)carbonylamino, (a713) $C_{1-6}$ alkylthiocarbonylamino, (a714) $C_{1-4}$ alkoxycarbonylamino (in which alkoxy may be optionally substituted by 1 to 3 fluorine atoms), (a715) N—($C_{1-4}$ alkoxycarbonyl)-N—($C_{1-6}$ alkyl)-amino, (a716) mono- or di-($C_{1-6}$ alkyl)aminocarbonyloxy, (a717) $C_{1-6}$ alkylaminocarbonyl (in which alkyl may be optionally substituted by 1 to 3 fluorine atoms), (a718) di-($C_{1-6}$ alkyl)aminocarbonyl, (a719) $C_{3-6}$ cycloalkylaminocarbonyl, (a720) $C_{1-6}$ alkylaminocarbonylamino, (a721) $C_{1-6}$ alkylaminothiocarbonylamino, (a722) $C_{1-4}$ alkylcarbonyl (in which the group may be optionally substituted by $C_{1-4}$ alkoxy), (a723) $C_{1-4}$ alkylcarbonyloxy, (a724) $C_{1-4}$ alkoxycarbonyl, (a725) $C_{1-6}$ alkylsulfonyl, (a726) $C_{1-4}$ alkylsulfonylamino, (a727) 5- to 6-membered saturated heterocyclyl, (a728) carboxy, and (a729) $C_{1-6}$ alkylamino (in which alkyl may be optionally substituted by 1 to 3 fluorine atoms)), (b7) $C_{2-6}$ alkenyl (in which the group may be optionally substituted by halogen atom), (c7) $C_{2-6}$ alkynyl (in which the group may be optionally substituted by $C_{1-4}$ alkoxy), (d7) 5- to 6-membered monocyclic heteroaryl$C_{1-4}$ alkyl, or (e7) $C_{3-6}$ cycloalkyl. The above (a7) $C_{1-6}$ alkyl may be optionally substituted by same or different substituents.

"$R^{1b}$" is preferably $C_{1-6}$ alkyl substituted by $C_{1-4}$ alkoxy, and more preferably 3-methoxypropyl or 4-methoxybutyl.

"$R^{1b}$" is preferably $C_{1-6}$ alkyl substituted by $C_{1-6}$ alkylcarbonylamino, and more preferably 2-(ethylcarbonylamino)ethyl.

"$R^{1b}$" is preferably $C_{1-6}$ alkyl substituted by $C_{1-4}$ alkoxycarbonylamino, and more preferably 2-(methoxycarbonylamino)ethyl.

"$R^{1c}$" and "$R^{1d}$" are each independently, same or different, one group selected from the group consisting of (a8) hydrogen atom, (b8) halogen atom, (c8) cyano, (d8) $C_{2-6}$ alkenyl (in which the group may be optionally substituted by $C_{6-10}$ aryl optionally substituted by $C_{1-4}$ alkoxy), (e8) $C_{2-6}$ alkynyl (in which the group may be optionally substituted by $C_{6-10}$ aryl optionally substituted by $C_{1-4}$ alkoxy), (f8) $C_{1-6}$ alkyl (in which the group may be optionally substituted by same or different 1 to 2 groups selected from the group consisting of (f801) 1 to 3 halogen atoms, (f802) cyano, (f803) $C_{3-6}$ cycloalkyl (in which the group may be optionally substituted by halogen atom, $C_{1-4}$ alkyl, or $C_{1-4}$ alkoxy), (f804) hydroxy, (f805) $C_{1-4}$ alkoxy (in which the group may be optionally substituted by same or different 1 to 3 groups selected from the group consisting of (f80511) halogen atom, (f80512) cyano, (f80513) $C_{3-6}$ cycloalkoxy (in which the group may be optionally substituted by mono- or di-($C_{1-6}$ alkyl)aminocarbonyl), (f80514) mono- or di-($C_{1-6}$ alkyl)aminosulfonyl, (f80515) $C_{1-6}$ alkylsulfonyl, (f80516) aminocarbonyl optionally substituted by mono- or di-($C_{1-6}$ alkyl), (f80517) $C_{1-4}$ alkylcarbonyl, (f80518) 5- to 7-membered cyclic aminocarbonyl, (f80519) hydroxy, (f80520) $C_{1-4}$ alkoxy, (f80521) 5- to 6-membered saturated heterocyclyl, and (f80522) $C_{1-4}$ alkoxycarbonyl), (f806) $C_{3-6}$ cycloalkoxy (in which the group may be optionally substituted by (f8061) $C_{1-4}$ alkyl (in which the group may be optionally substituted by $C_{1-4}$ alkoxy)), (f807) $C_{6-10}$ aryloxy (in which the group may be optionally substituted by same or different 1 to 3 groups selected from the group consisting of (f8071) halogen atom, (f8072) cyano, and (f8073) $C_{1-4}$ alkoxy)

(f808) amino (in which amino is substituted by same or different 1 to 2 groups selected from the group consisting of (f80811) $C_{1-6}$ alkyl, (f80812) $C_{3-6}$ cycloalkyl, (f80813) $C_{3-6}$ cycloalkyl$C_{1-4}$ alkyl (in which cycloalkyl may be optionally substituted by aminocarbonyl), (f80814) $C_{3-6}$ cycloalkyl$C_{1-4}$ alkoxycarbonyl, (f80815) $C_{1-4}$ alkylcarbonyl, (f80816) $C_{3-6}$ cycloalkylcarbonyl (in which cycloalkyl may be optionally substituted by $C_{1-4}$ alkylsulfonylamino), (f80817) 5- to 6-membered saturated heterocyclyl$C_{1-4}$ alkyl (in which heterocyclyl may be optionally substituted by $C_{1-4}$ alkyl), (f80818) 5- to 6-membered saturated heterocyclylcarbonyl, (f80819) 5- to 6-membered saturated heterocyclyloxycarbonyl, (f80820) 5- to 6-membered saturated heterocyclyl$C_{1-4}$ alkylcarbonyl, and (f80821) $C_{1-4}$ alkylsulfonyl), (f809) 5- to 7-membered cyclic amino (in which cyclic amino may be optionally substituted by 1 to 4 groups selected from the group consisting of $C_{1-4}$ alkyl, $C_{7-14}$ aralkyl, and oxo), (f810) mono- or di-($C_{1-6}$ alkyl)aminocarbonyl, (f811) 4- to 7-membered cyclic aminocarbonyl (in which cyclic amino may be optionally substituted by $C_{1-4}$ alkyl), (f812) aminocarbonyloxy (in which amino is substituted by same or different 1 to 2 groups selected from the group consisting of (f8121) $C_{1-6}$ alkyl (in which the group may be optionally substituted by 5- to 6-membered saturated heterocyclyl), (f8122) $C_{3-6}$ cycloalkyl (in which the group may be optionally substituted by hydroxy), and (f8123) 5- to 6-membered saturated heterocyclyl), (f813) 5- to 7-membered cyclic aminocarbonyloxy (in which cyclic amino may be optionally substituted by 1 to 2 fluorine atoms), (f814) 5- to 7-membered cyclic aminocarbonyl$C_{1-4}$ alkoxy, (f815) mono- or di-($C_{1-6}$ alkyl)aminocarbonyl$C_{1-4}$ alkoxy, (f816) 5- to 6-membered saturated heterocyclyl (in which the group may be optionally substituted by same or different 1 to 2 groups selected from the group consisting of $C_{1-4}$ alkyl and oxo), (f817) 5- to 6-membered saturated heterocyclyl$C_{1-4}$ alkoxy (in which heterocyclyl may be optionally substituted by $C_{1-4}$ alkyl), (f818) 5- to 6-membered saturated heterocyclyloxy (in which the group may be optionally substituted by same or different 1 to 2 groups selected from the group consisting of $C_{1-4}$ alkyl and oxo), (f819) mono- or di-$C_{1-4}$ alkylaminosulfonyl, (f820) carboxy, (f821) $C_{1-4}$ alkoxycarbonyl, (f822) $C_{6-10}$ arylcarbonyl (in which the group may be optionally substituted by $C_{1-4}$ alkoxy), (f823) $C_{1-4}$ alkoxycarbonylamino, (f824) $C_{6-10}$ aryloxycarbonylamino (in which aryl may be optionally substituted by halogen atoms), (f825) 5- to 6-membered monocyclic heteroaryloxycarbonylamino, and (f826) N—($C_{1-4}$ alkylaminocarbonyl)-N—($C_{1-6}$ alkyl)amino), (g8) $C_{3-10}$ cycloalkyl (in which the group may be optionally substituted by (g81) halogen atom, (g82) hydroxy, or (g83) $C_{1-4}$ alkoxy), (h8) $C_{7-14}$ aralkyl (in which the group may be optionally substituted by same or different 1 to 3 groups selected from the group consisting of (h81) halogen atom, (h82) cyano, (h83) hydroxy, (h84) $C_{1-4}$ alkoxy, and (h85) $C_{1-4}$ alkyl optionally substituted by $C_{1-4}$ alkoxy), (i8) $C_{1-6}$ alkoxy (in which the group may be optionally substituted by (i81) $C_{1-4}$ alkoxycarbonylamino, (i82) N—($C_{1-6}$ alkylsulfonyl)-N—($C_{1-6}$ alkyl)aminocarbonyl, (i83) mono- or di-($C_{1-6}$ alkyl)aminocarbonyl, or (i83) 5- to 7-membered cyclic aminocarbonyl), (j8) $C_{3-6}$ cycloalkoxy, (k8) $C_{7-14}$ aralkyloxy (in which the group may be optionally substituted by $C_{1-4}$ alkoxy), (l8) mono- or di-substituted aminocarbonyl (in which amino may be optionally substituted by $C_{1-6}$ alkyl optionally substituted by 5- to 6-membered saturated heterocyclyl), (m8) 5- to 7-membered cyclic aminocarbonyl (in which cyclic amino may be optionally substituted by a group selected from the group consisting of halogen atom, $C_{1-4}$ alkoxy, and $C_{6-10}$ aryl optionally substituted by halogen atoms), (n8) saturated heterocyclyl (in which the group may be optionally substituted by same or different 1 to 4 groups selected from the group consisting of (n81) $C_{1-4}$ alkyl, (n82) $C_{6-10}$ aryl optionally substituted by 1 to 3 halogen atoms, or (n83) oxo), (o8) saturated heterocyclyloxy (in which the group may be optionally substituted by $C_{1-4}$ alkoxycarbonyl, or $C_{1-4}$ alkylcarbonyl)

(p8) 5- to 10-membered monocyclic or polycyclic heteroaryl (in which the group may be optionally substituted by same or different 1 to 2 groups selected from the group consisting of (p81) halogen atom, (p82) $C_{1-4}$ alkyl optionally substituted by 1 to 3 fluorine atoms, and (p83) $C_{1-4}$ alkoxy (in which the group may be optionally substituted by mono- or di-($C_{1-6}$ alkyl)aminocarbonyl)), (q8) 5- to 10-membered monocyclic or polycyclic heteroaryl$C_{1-4}$ alkyl, (r8) amino (in which amino may be optionally substituted by (r81) $C_{3-6}$ cycloalkyl$C_{1-4}$ alkyl (in which cycloalkyl may be optionally substituted by aminocarbonyl), (r82) $C_{1-4}$ alkylcarbonyl (in which alkyl may be optionally substituted by $C_{1-4}$ alkoxy), (r83) $C_{3-6}$ cycloalkylcarbonyl (in which cycloalkyl may be optionally substituted by $C_{1-4}$ alkylsulfonylamino), or (r84) 5- to 6-membered saturated heterocyclyloxycarbonyl), (s8) hydroxyl, and (t8) a group of the following formula:

[Chemical Formula 49]

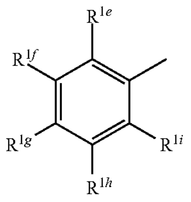

wherein $R^{1e}$, $R^{1f}$, $R^{1g}$, $R^{1h}$ and $R^{1i}$ are the same as defined above.

"$R^{1c}$" is preferably a group selected from the group consisting of (a9) hydrogen atom, (b9) halogen atom, and (c9) $C_{1-6}$ alkyl optionally substituted by $C_{1-4}$ alkoxy.

"$R^{1d}$" is preferably one group selected from the group consisting of the above (a8) to (t8).

"$R^{1d}$" is more preferably one group selected from the group consisting of (a10) hydrogen atom, (b10) halogen atom, (c10) $C_{1-6}$ alkyl (in which the group may be optionally substituted by (c101) 1 to 3 halogen atoms, (c102) hydroxy, (c103) $C_{1-4}$ alkoxy (in which the group may be optionally substituted by 1 to 2 groups selected from the group consisting of hydroxy, $C_{1-4}$ alkoxy, 5- to 6-membered saturated heterocyclyl, and $C_{1-4}$ alkoxycarbonyl), (c104) $C_{6-10}$ aryloxy (in which the group may be optionally substituted by same or different 1 to 3 groups selected from the group consisting of cyano and $C_{1-4}$ alkoxy), (c105) $C_{1-6}$ alkylaminocarbonyloxy, (c106) (5- to 6-membered saturated heterocyclyl$C_{1-4}$ alkyl)aminocarbonyloxy, or (c107) 5- to 7-membered cyclic aminocarbonyloxy), (d10) aminocarbonyl, (e10) mono- or di-($C_{1-6}$ alkyl)aminocarbonyl, (f10) N-(5- to 6-membered saturated heterocyclyl$C_{1-4}$ alkyl)-N—($C_{1-6}$ alkyl)-aminocarbonyl, (g10) 5- to 7-membered cyclic aminocarbonyl, (h10) $C_{7-14}$ aralkyl (in which the group may be optionally substituted by $C_{1-4}$ alkoxy), (i10) 5- to 6-membered saturated heterocyclyl, (j10) $C_{3-6}$ cycloalkyl, (k10) $C_{3-6}$ cycloalkoxy, and (l10) a group of the following formula:

[Chemical Formula 50]

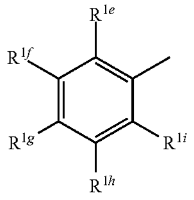

wherein $R^{1e}$, $R^{1f}$, $R^{1g}$, $R^{1h}$ and $R^{1i}$ are the same as defined above.

Preferably, "$R^{1e}$", "$R^{1f}$", "$R^{1g}$" and "$R^{1i}$" are each independently, same or different, (a11) hydrogen atom, (b11) halogen atom, (c11) cyano, (d11) $C_{1-4}$ alkyl (in which the group may be optionally substituted by (d111) 5- to 6-membered saturated heterocyclyloxy, (d112) $C_{1-4}$ alkoxy (in which the group may be optionally substituted by $C_{1-4}$ alkoxy, or $C_{3-6}$ alkoxy), or (d113) 1 to 3 fluorine atoms), (e11) $C_{1-4}$ alkoxy (in which the group may be optionally substituted by (e111) 1 to 3 halogen atoms, (e112) $C_{1-4}$ alkoxy, or (e113) $C_{1-6}$ alkylaminocarbonyl), (f11) $C_{3-6}$ cycloalkoxy (in which the group may be optionally substituted by (f111) $C_{1-4}$ alkoxy), (g11) 5- to 6-membered saturated heterocyclyloxy, (h11) $C_{1-6}$ alkylamino carbonyl, (i11) hydroxyl, or (j11) $C_{1-4}$ alkoxysulfonyl.

Preferably, $R^{1e}$, $R^{1f}$, $R^{1g}$, $R^{1h}$ and $R^{1i}$ are each independently, same or different, hydrogen atom, halogen atom, or $C_{1-4}$ alkoxy.

"$R^{1e}$, $R^{1h}$ and $R^{1i}$ are hydrogen atom, and $R^{1f}$ and $R^{1g}$ combine each other to form a condensed ring" means that $R^{1f}$ and $R^{1g}$ form a bicyclic or tricyclic condensed ring with phenyl group to which they bind. The condensed ring may be either 5- to 6-membered saturated ring or unsaturated ring, and the ring may contain at least one of nitrogen, oxygen, or sulfur. The ring may be optionally substituted by $C_{1-4}$ alkyl, hydroxyl, or oxo.

Concrete examples of "$R^{1e}$, $R^{1h}$ and $R^{1i}$ are hydrogen atom, and $R^{1f}$ and $R^{1g}$ combine each other to form a condensed ring" include one group selected from the following compound group, etc.

[Chemical Formula 51]

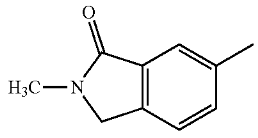
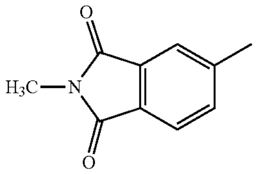
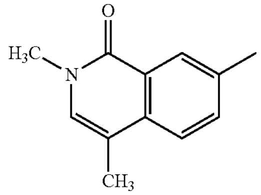
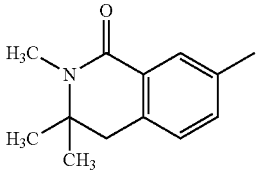
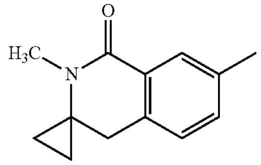
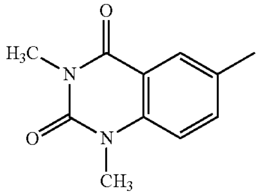
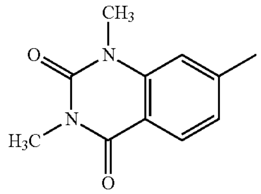
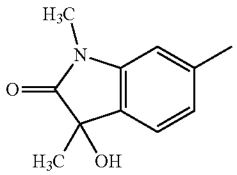
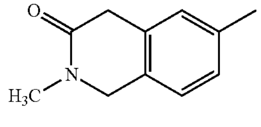
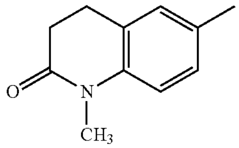
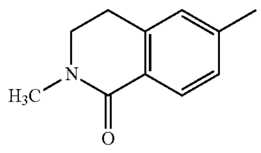
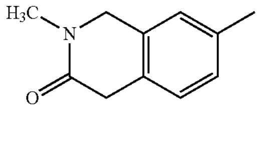
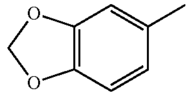
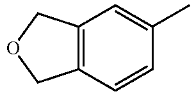
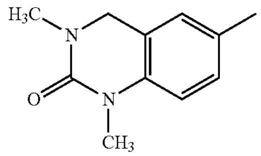
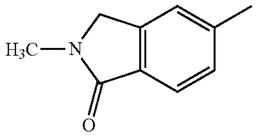

-continued

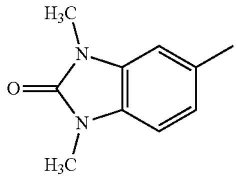
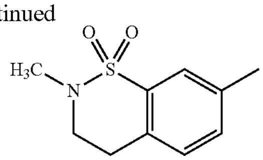
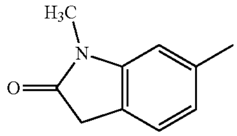
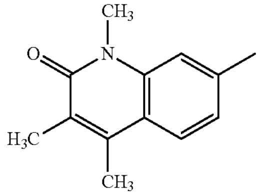
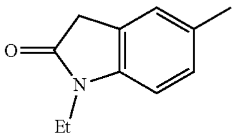
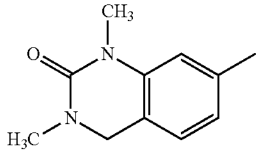
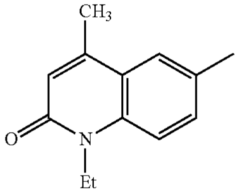
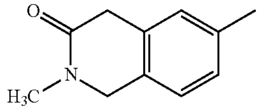
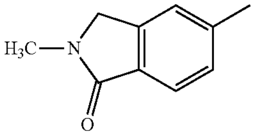
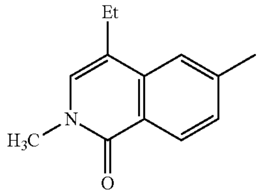
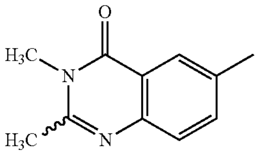
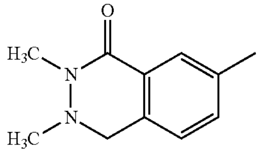
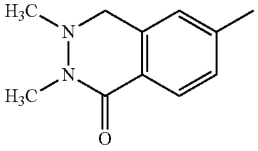
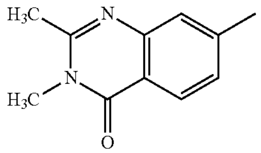
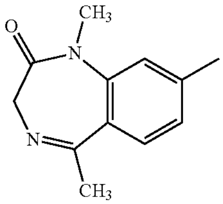
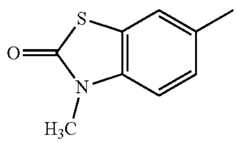
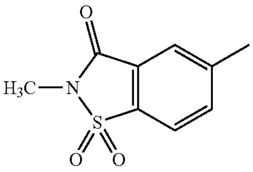
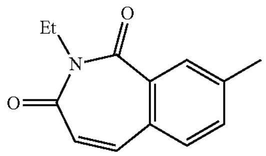

-continued
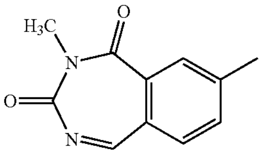
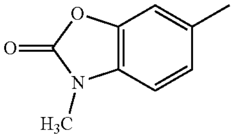
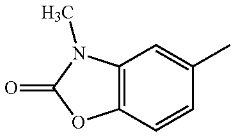
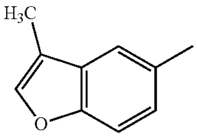
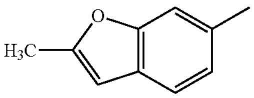
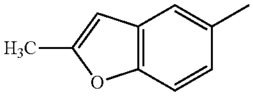
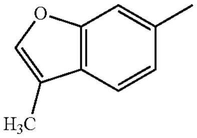
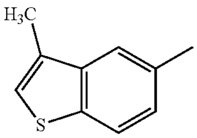
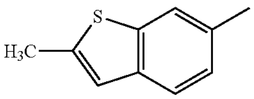
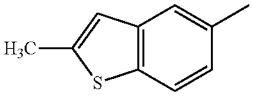
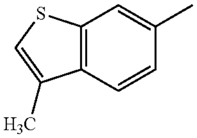
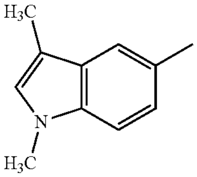
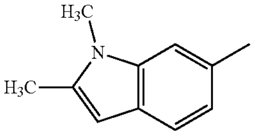
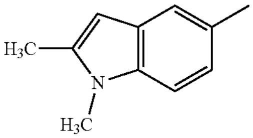
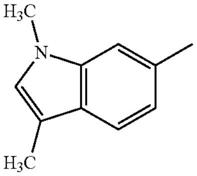
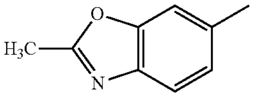
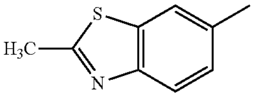
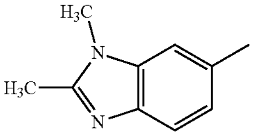
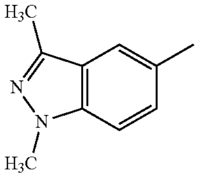
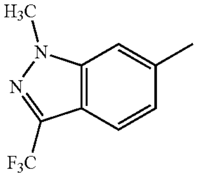
-continued
[Chemical Formula 52]
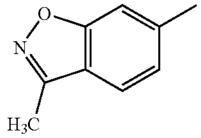
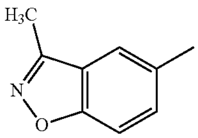
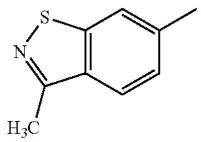
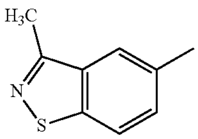
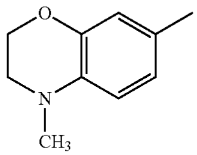
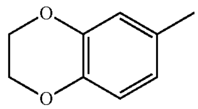
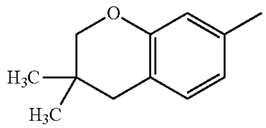
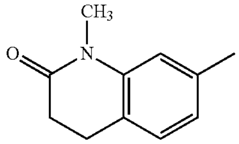
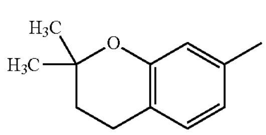
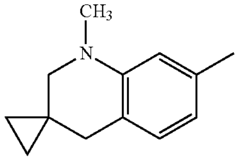
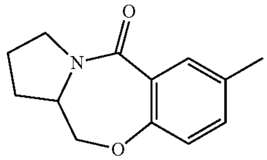
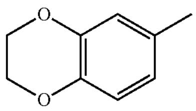
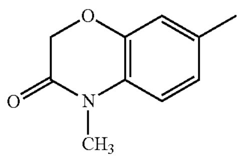
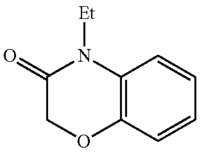
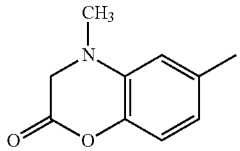
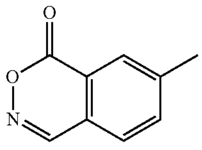
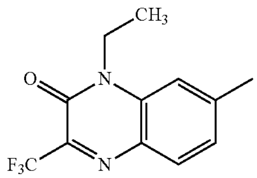
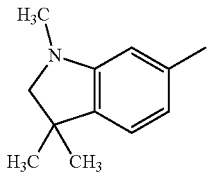
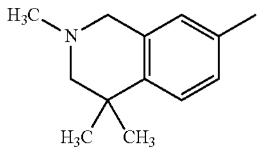
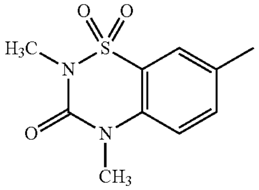

-continued

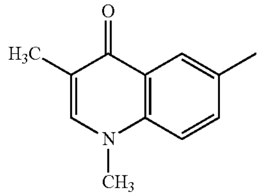

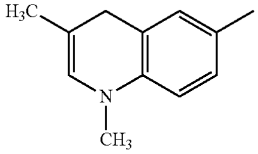

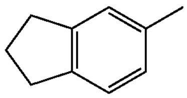

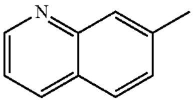

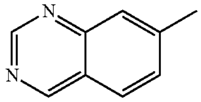

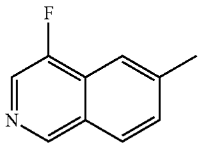

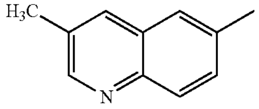

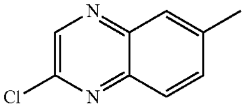

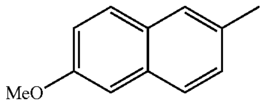

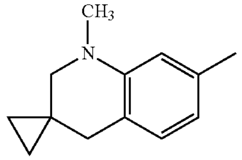

$R^{1c}$ and $R^{1d}$ preferably combine each other to form a group of the following formula:

[Chemical Formula 53]

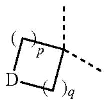

wherein solid lines are moieties defined by $R^{1c}$ and $R^{1d}$, and broken lines are skeleton moieties defined by $G^1$ to $G^4$.

The group wherein "D" is oxygen or sulfur and p and q are 0 means that $R^{1c}$ and $R^{1d}$ combine each other to form oxo or thioxo.

Each $R^{4a}$ in "—$NR^{4a}CONR^{4a}$—" in "D" is independent.

"—$CH(R^{4b})CH_2$—" in "D" may be "—$CH_2CH(R^{4b})$—". If "D" is —$SO_2$—, —$NR^{4a}CO$—, —$NR^{4a}SO_2$—, —$NR^{4a}CONR^{4a}$—, then neither "p" nor "q" are 0. If "D" is "—$CH(R^{4b})$—" and "$R^{4b}$" is halogen atom, then hydrogen atom of "—$CH(R^{4b})$—" may be replaced with halogen atom.

Concrete examples of the group which $R^{1c}$ and $R^{1d}$ combine each other to form include a structural formula of the following group.

[Chemical Formula 54]

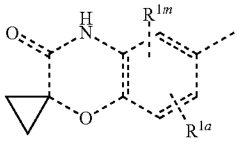

-continued

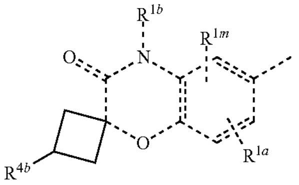

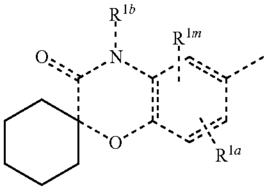

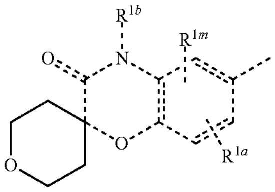

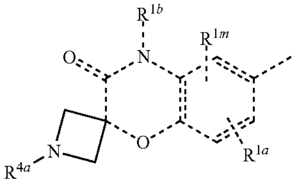

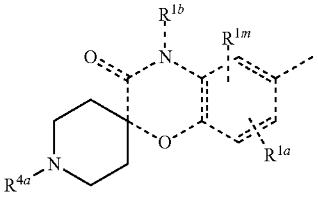

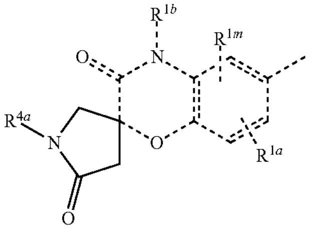

"$R^{4a}$" is preferably one group selected from the group consisting of hydrogen atom, $C_{1-6}$ alkyl, $C_{1-4}$ alkoxycarbonyl, $C_{1-4}$ alkylsulfonyl, and $C_{6-10}$ arylsulfonyl.

"$R^{4b}$" is preferably one group selected from the group consisting of hydrogen atom; halogen atom; $C_{1-4}$ alkoxy optionally substituted by $C_{1-4}$ alkoxy; $C_{7-14}$ aralkyloxy optionally substituted by 1 to 3 groups selected from the group consisting of fluorine atom and cyano; and aminocarbonyloxy optionally substituted by mono- or di-($C_{1-6}$ alkyl), and more preferably hydrogen atom.

"D", "p" and "q" are preferably any of the following (i) to (iii):

(i) "D" is oxygen, and "p" and "q" are the same and 2, (ii) "D" is —$CH_2$—, and "p" and "q" are 1 or 2, or (iii) "D" is —$CH_2CH_2$—, and "p" and "q" are 0 or 1. More preferably, "D" is —$CH_2$—, and "p" and "q" are 1.

In a compound of formula (I), a partial structure of the following formula:
[Chemical Formula 55]
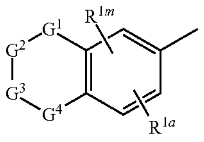
includes, for example, a partial structure selected from the following group.
[Chemical Formula 56]
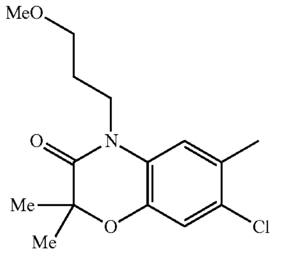
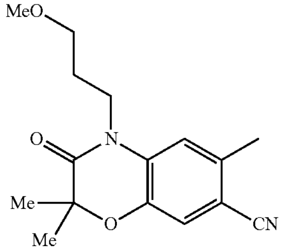
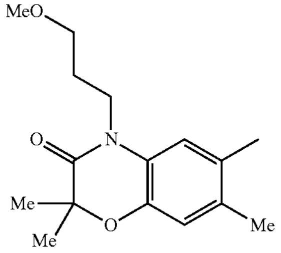
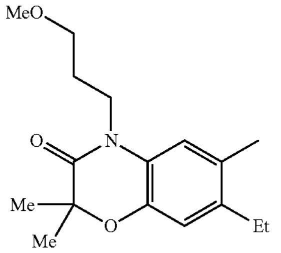
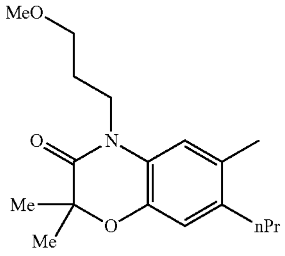
-continued
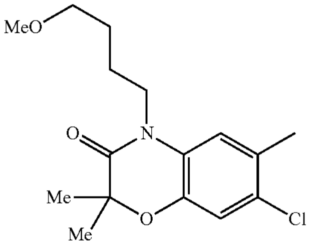
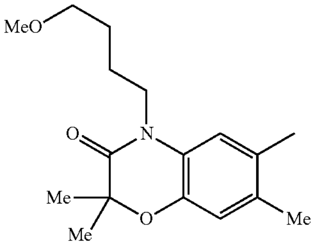
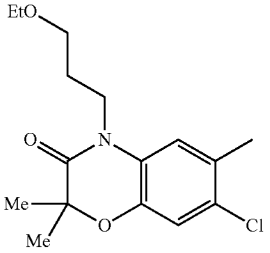
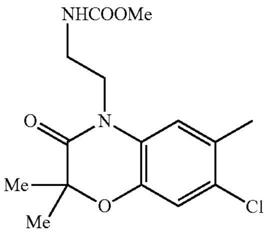
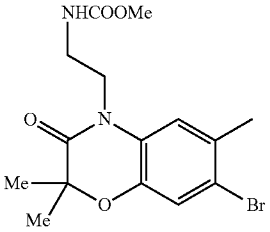
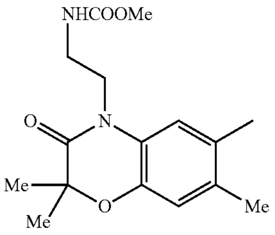
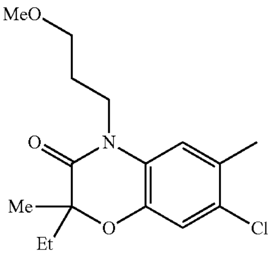

-continued
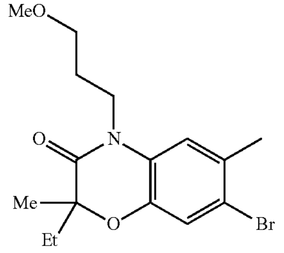
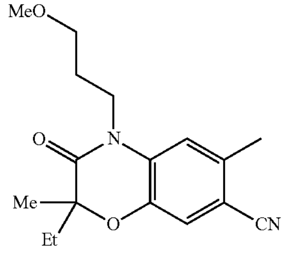
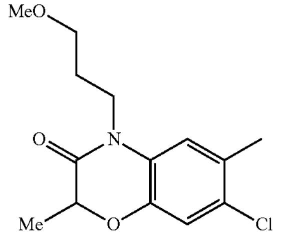
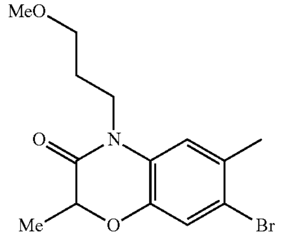
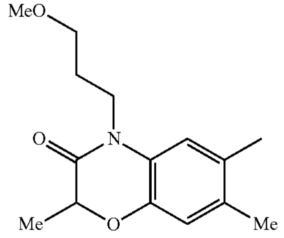
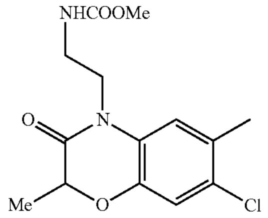
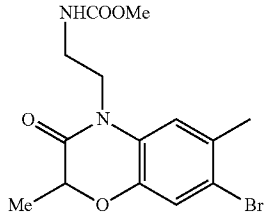
-continued
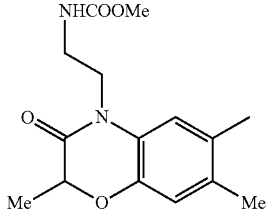
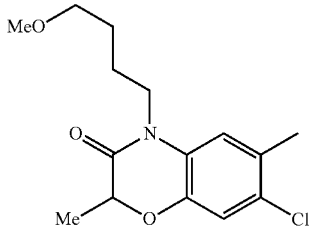
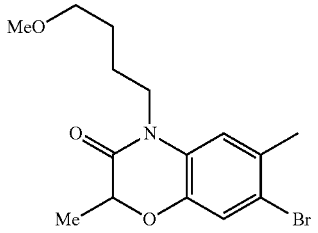
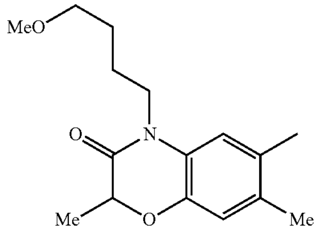
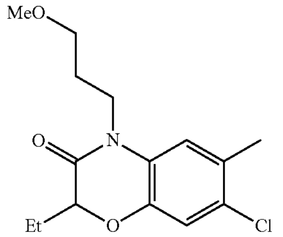
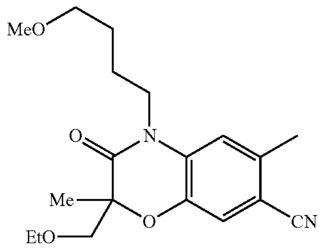
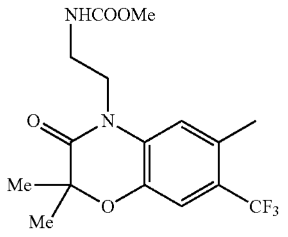

-continued
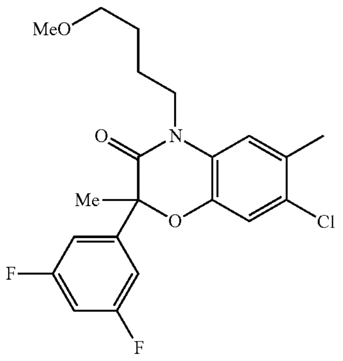
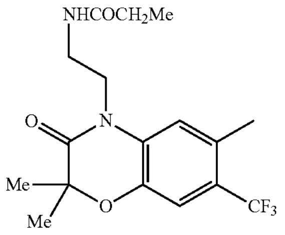
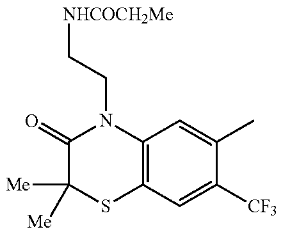
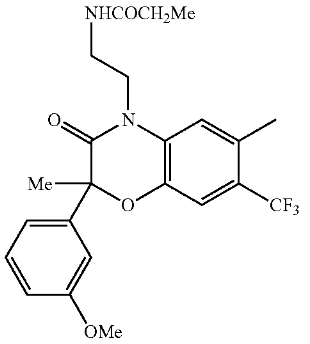
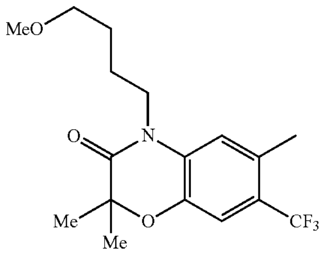
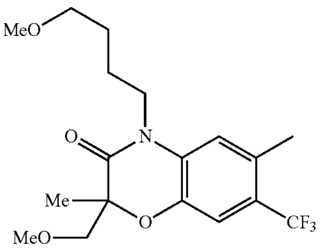
-continued
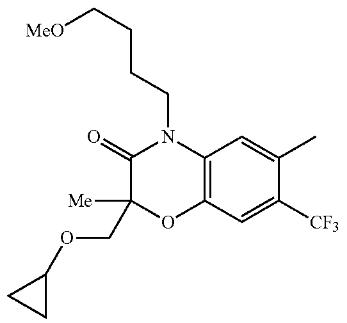
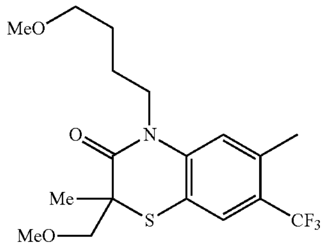
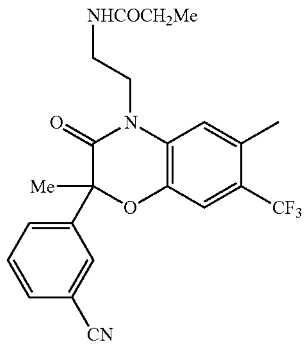
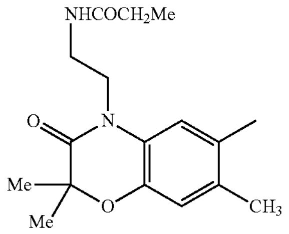
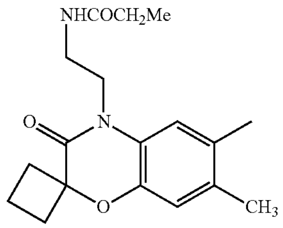
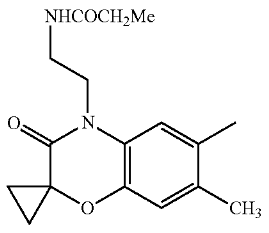

-continued

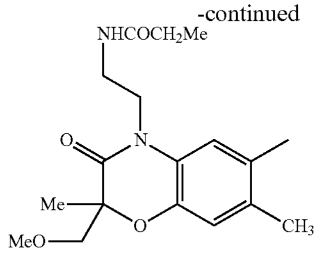

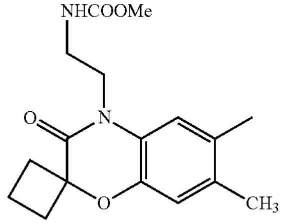

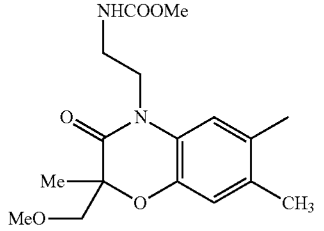

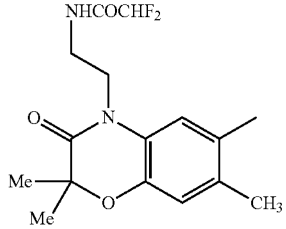

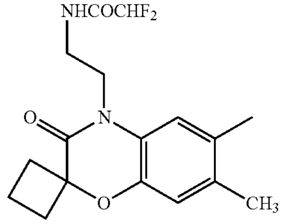

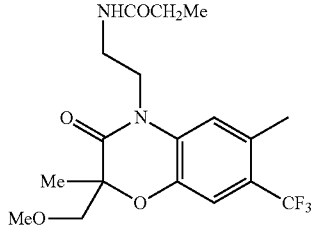

"$R^2$" includes one group selected from the group consisting of (a100) hydrogen atom, (b100) $C_{1-6}$ alkyl (in which the group may be optionally substituted by halogen atom; $C_{3-6}$ cycloalkyl optionally substituted by halogen atom, $C_{1-4}$ alkyl or $C_{1-4}$ alkoxy), (c100) $C_{3-6}$ cycloalkyl (in which the group may be optionally substituted by halogen atom or $C_{1-4}$ alkyl), (d100) $C_{2-6}$ alkenyl, and (e100) $C_{7-10}$ aralkyl (in which the group may be optionally substituted by halogen atom).

"$R^2$" is preferably $C_{1-6}$ alkyl, more preferably isopropyl.

Preferable "B" is one group selected from the group consisting of (a12) hydrogen atom, (b12) $C_{1-6}$ alkyl (in which the group may be optionally substituted by 1 to 3 groups selected from the group consisting of (b120) halogen atom, (b121) $C_{3-6}$ cycloalkyl (in which the group may be optionally substituted by same or different 1 to 2 groups selected from the group consisting of (i) halogen atom, (ii) hydroxy, (iii) $C_{1-4}$ alkoxy, and (iv) $C_{3-6}$ cycloalkylcarbonylamino), (b122) hydroxyl, (b123) $C_{1-4}$ alkoxy, (b124) carboxy, (b125) $C_{1-4}$ alkoxycarbonyl, (b126) saturated heterocyclyl (in which the ring may be optionally substituted by same or different 1 to 3 groups selected from the group consisting of (i) $C_{1-4}$ alkyl, (ii) $C_{1-4}$ alkoxy, (iii) $C_{1-4}$ alkylcarbonylamino, and (iv) oxo), (b127) aminocarbonyl (in which amino may be optionally substituted by (i) $C_{1-4}$ alkyl, (ii) $C_{3-6}$ cycloalkyl, or (iii) $C_{3-6}$ cycloalkyl$C_{1-4}$ alkyl), and (b128) 5- to 7-membered cyclic amino (in which the group may be optionally substituted by same or different 1 to 3 groups selected from the group consisting of (i) halogen atom, (ii) $C_{1-4}$ alkyl, (iii) $C_6$ aryl optionally substituted by $C_{1-4}$ alkoxy, (iv) $C_6$ aryloxy optionally substituted by 1 to 3 halogen atoms, and (v) oxo)), (c12) $C_{2-6}$ alkenyl (in which the group may be optionally substituted by 1 to 2 groups selected from the group consisting of fluorine atom and $C_{1-6}$ alkyl), (d12) $C_{3-10}$ cycloalkyl (in which the group may be optionally substituted by (d121) halogen atom, (d122) $C_{1-4}$ alkyl optionally substituted by $C_{1-4}$ alkoxy, (d123) hydroxy, or (d124) $C_{1-4}$ alkoxy), (e12) $C_6$ aryl (in which the group may be optionally substituted by same or different 1 to 3 groups selected from the group consisting of (e1201) halogen atom, (e1202) $C_{1-4}$ alkyl (in which $C_{1-4}$ alkyl may be optionally substituted by one group selected from the group consisting of (i) 5- to 7-membered cyclic amino (in which the group may be optionally substituted by $C_6$ aryl optionally substituted by 1 to 3 halogen atoms), (ii) mono-$C_{1-6}$ alkylamino (in which $C_{1-6}$ alkyl may be optionally substituted by $C_6$ aryloxy optionally substituted by 1 to 3 halogen atoms), (iii) 5- to 6-membered saturated heterocyclylamino (in which saturated heterocyclyl may be optionally substituted by $C_6$ aryl), (iv) 5- to 6-membered saturated heterocyclyloxy (in which saturated heterocyclyl may be optionally substituted by $C_6$ aryl or 5- to 10-membered monocyclic or polycyclic heteroaryl), (v) $C_6$ aryloxy (in which aryl may be optionally substituted by same or different 1 to 3 groups selected from the group consisting of halogen atom and $C_{1-4}$ alkyl), (vi) $C_{1-4}$ alkoxy, and (vii) $C_{3-6}$ cycloalkoxy), (e1203) $C_{1-4}$ alkoxy (in which $C_{1-4}$ alkoxy may be optionally substituted by one group selected from the group consisting of (i) $C_{1-4}$ alkoxy, (ii) $C_6$ aryloxy (in which aryl may be optionally substituted by 1 to 3 groups selected from the group consisting of $C_{1-4}$ alkyl and halogen atom), (iii) $C_{3-6}$ cycloalkyloxy (in which the group may be optionally substituted by $C_{1-4}$ alkyl), (iv) phenylamino (in which phenyl may be optionally substituted by 1 to 3 halogen atoms), and (v) $C_{7-10}$ aralkyloxy (in which the group may be optionally substituted by 1 to 3 halogen atoms)), (e1204) $C_6$ aryloxy (in which aryl may be optionally substituted by 1 to 3 groups selected from the group consisting of (i) halogen atom, (ii) cyano, (iii) $C_{1-4}$ alkyl and (iv) $C_{1-4}$ alkoxy), (e1205) $C_{7-10}$ aralkyloxy (in which the group may be optionally substituted by 1 to 3 groups selected from the group consisting of halogen atom and $C_{1-4}$ alkoxy), (e1206) 5- to 7-membered cyclic amino (in which the ring may be optionally substituted by (i) ($C_{1-6}$ alkyl)(phenylcarbonyl)amino, or (ii) $C_6$ aryloxy (in which aryl may be optionally substituted by same or different 1 to 3 groups selected from the group consisting of halogen atom and $C_{1-4}$ alkyl optionally substituted by hydroxy)), (e1207) 5- to 6-membered saturated heterocyclyloxy (in which the ring may be optionally substituted by (i) $C_6$ aryl optionally substituted by 1 to 3 halogen atoms, (ii) 5- to 10-membered monocyclic or polycyclic heteroaryl, (iii) 5- to 6-membered saturated heterocyclylcarbonyl, (iv) oxo), (e1208) 5- to 6-membered monocyclic heteroaryloxy (in which the group may be optionally substituted by $C_{1-4}$ alkyl)

(e1209) 5- to 7-membered cyclic aminocarbonyl (in which cyclic amino may be optionally substituted by $C_6$ aryloxy optionally substituted by 1 to 3 halogen atoms), (e1210) 5- to 7-membered cyclic aminocarbonyloxy (in which cyclic amino may be optionally substituted by $C_6$ aryl), and (e1211) $C_6$ aryl), (f12) $C_{7-14}$ aralkyl (in which the group may be optionally substituted by same or different 1 to 3 groups selected from the group consisting of (f120) halogen atom, (f121) cyano, (f122) $C_{1-4}$ alkyl, (f123) hydroxy, (f124) $C_{1-4}$ alkoxy (in which the group may be optionally substituted by 1 to 3 fluorine atoms), (f125) $C_{3-6}$ cycloalkoxy (in which the group may be optionally substituted by 1 to 2 halogen atoms), (f126) $C_{1-4}$ alkoxycarbonyl, (f127) aminocarbonyl, (f128) $C_{6-10}$ aryl (in which the group may be optionally substituted by 1 to 3 halogen atoms) and (f129) $C_{1-4}$ alkylsulfonyl), (g12) 5- to 10-membered monocyclic or polycyclic heteroaryl (in which the group may be optionally substituted by halogen atom), (h12) 5- to 10-membered monocyclic or polycyclic heteroaryl$C_{1-4}$ alkyl (in which the group may be optionally substituted by (h121) halogen atom, or (h122) $C_{1-4}$ alkyl (in which the group may be optionally substituted by 1 to 3 fluorine atoms)), and (i12) saturated heterocyclyl (in which the group may be optionally substituted by $C_{1-4}$ alkyl optionally substituted by $C_{1-4}$ alkoxy).

The substituent "$C_{1-4}$ alkoxy substituted by $C_{1-4}$ alkoxy" of (e1203) in "B" includes the following group.

[Chemical Formula 57]

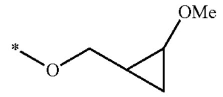

"$R^{4c}$" is preferably one group selected from the group consisting of hydrogen atom, $C_{1-6}$ alkyl substituted by 1 to 3 halogen atoms or $C_{3-6}$ cycloalkyl, $C_{3-6}$ cycloalkyl and $C_7$ aralkyl. More preferable one is hydrogen atom, or $C_{3-6}$ cycloalkyl.

"$R^5$" is preferably

1: $C_{1-4}$ alkoxycarbonyl (in which the group is substituted by a group of the following formula:

[Chemical Formula 58]

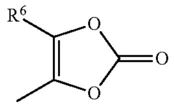

wherein $R^6$ is the same as defined above, or

2: a group of the following formula:

[Chemical Formula 59]

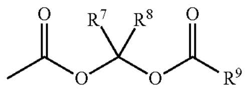

wherein $R^7$ and $R^8$ are the same as defined above.

"$R^5$" is preferably methoxycarbonyl substituted by a group of the following formula:

[Chemical Formula 60]

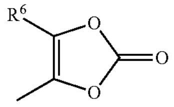

wherein $R^6$ is the same as defined above.

"$R^6$" is preferably $C_{1-4}$ alkyl.

"$R^5$" is preferably a group of the following formula:

[Chemical Formula 61]

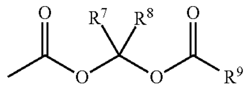

wherein $R^7$, $R^8$ and $R^9$ are the same as defined above.

Preferably, "$R^7$" and "$R^8$" are each independently, same or different, hydrogen atom or $C_{1-4}$ alkyl.

"$R^7$" is preferably hydrogen atom, and "$R^8$" is preferably $C_{1-4}$ alkyl.

"$R^9$" is preferably (a) $C_{1-6}$ alkyl (in which the group may be optionally substituted by 1 to 3 fluorine atoms, hydroxy, $C_{1-4}$ alkoxy, carboxy, $C_{1-4}$ alkoxycarbonyl, $C_{1-4}$ alkoxycarbonylamino, amino, or 1 to 2 nitroxy), (b) $C_{3-10}$ cycloalkyl, (c) $C_{6-10}$ aryl (in which the group is substituted by $C_{1-4}$ alkyl or $C_{1-4}$ alkylcarbonyloxy), (d) $C_{1-4}$ alkylcarbonyl (in which the group may be optionally substituted by hydroxy), (e) 5- to 10-membered monocyclic or polycyclic heteroaryl, (f) 5- to 6-membered saturated heterocyclyl, (g) $C_{1-6}$ alkoxy (in which the group may be optionally substituted by $C_{3-6}$ cycloalkyl), (h) $C_{3-6}$ cycloalkyloxy (in which the group may be optionally substituted by $C_{1-4}$ alkoxy), or (i) 5- to 6-membered saturated heterocyclyloxy.

"$R^9$" is more preferably (a) $C_{1-6}$ alkyl, (b) $C_{3-10}$ cycloalkyl, (c) $C_{1-6}$ alkoxy (in which the group may be optionally substituted by $C_{3-6}$ cycloalkyl), (d) $C_{3-6}$ cycloalkyloxy, or (e) 5- to 6-membered saturated heterocyclyloxy.

"$R^9$" is further preferably (a) $C_{1-6}$ alkyl, or (b) $C_{1-6}$ alkoxy (in which the group may be optionally substituted by $C_{3-6}$ cycloalkyl).

Further preferable embodiments of the present compound include compounds of the following formulae.

Specifically, the present invention is as follows.

(1) A compound of formula (IIa), or a pharmaceutically acceptable salt thereof

[Chemical Formula 62]

(IIa)

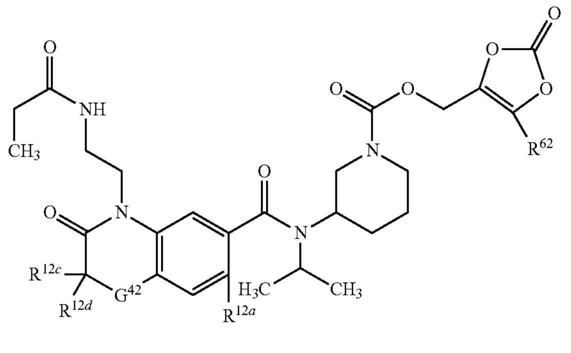

[In the formula, $G^{42}$, $R^{12a}$, $R^{12c}$, $R^{12d}$, and $R^{62}$ are the same as defined above.]

(2) A compound of formula (IIb), or a pharmaceutically acceptable salt thereof

[Chemical Formula 63]

(IIb)

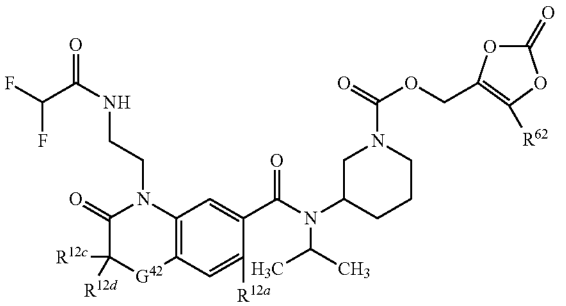

[In the formula, $G^{42}$, $R^{12a}$, $R^{12c}$, $R^{12d}$, and $R^{62}$ are the same as defined above.]

(3) A compound of formula (IIc), or a pharmaceutically acceptable salt thereof

[Chemical Formula 64]

(IIc)

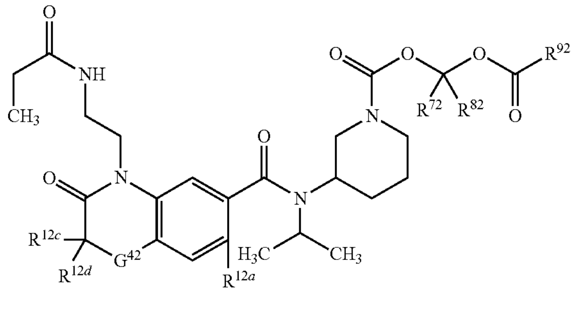

[In the formula, $G^{42}$, $R^{12a}$, $R^{12c}$, $R^{12d}$, $R^{72}$, $R^{82}$ and $R^{92}$ are the same as defined above.]

(4) A compound of formula (IId), or a pharmaceutically acceptable salt thereof

[Chemical Formula 65]

(IId)

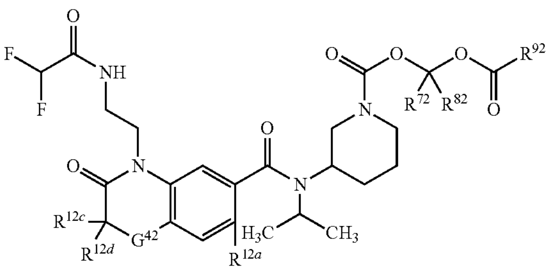

[In the formula, $G^{42}$, $R^{12a}$, $R^{12c}$, $R^{12d}$, $R^{72}$, $R^{82}$ and $R^{92}$ are the same as defined above.]

Each preferable embodiment of each substituent in the compounds of the above (1) to (4) (i.e., formula IIa to formula IId) is the same as each preferable embodiment of each substituent in a compound of formula (I).

A preferable intermediate compound of the above formula (III) includes the following illustrated compounds. Each definition of $R^{33a}$, $R^{33b}$, $R^{33c}$, $R^{33d}$, $R^{63}$, $R^{73}$, $R^{83}$ and $R^{93}$ in the compounds is the same as each preferable embodiment of each substituent in a compound of formula (I).

(5) A compound of formula (IIIa), or a pharmaceutically acceptable salt thereof

[Chemical Formula 66]

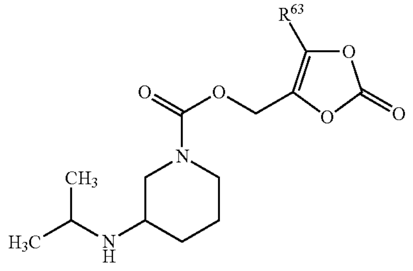

[In the formula, $R^{63}$ is the same as defined above.]

(6) A compound of formula (IIIb), or a pharmaceutically acceptable salt thereof

[Chemical Formula 67]

(IIIb)

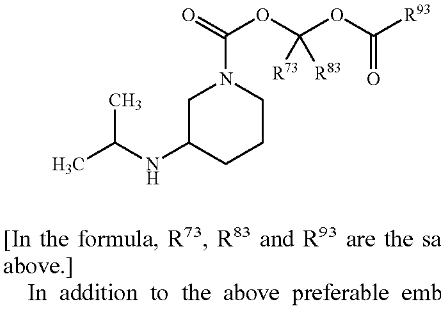

[In the formula, $R^{73}$, $R^{83}$ and $R^{93}$ are the same as defined above.]

In addition to the above preferable embodiments, the present invention also encompasses the following compounds.

(7) A compound of formula (Ia), or a pharmaceutically acceptable salt thereof.

[Chemical Formula 68]

(Ia)

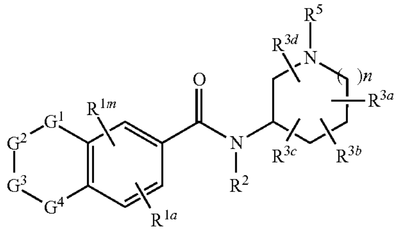

[In the formula $R^{1a}$, $R^{1m}$, $G^1$, $G^2$, $G^3$, $G^4$, $R^2$, $R^{3a}$, $R^{3b}$, $R^{3c}$, $R^{3d}$, n and $R^5$ are the same as defined in the above Item 1. Provided that if $R^{1c}$ and $R^{1d}$ in $G^3$ combine each other to form a group of the following formula of the above Item 1:

[Chemical Formula 69]

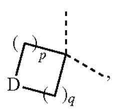

$R^{4b}$ is not hydroxyl. $R^9$ in $R^5$ is not $C_{1-6}$ alkyl substituted by 1 to 3 fluorine atoms, $C_{3-6}$ cycloalkyl or 1 to 2 nitroxy; $C_{6-10}$ aryl substituted by $C_{1-4}$ alkyl; and $C_{1-4}$ alkylcarbonyl substituted by hydroxy.]

(8) A compound of formula (Ib), or a pharmaceutically acceptable salt thereof

[Chemical Formula 70]

(Ib)

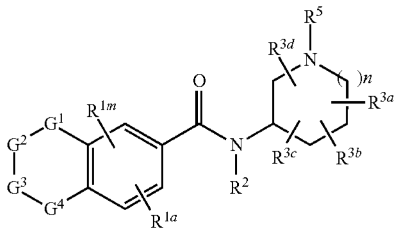

[In the formula $R^{1a}$, $R^{1m}$, $G^1$, $G^2$, $G^3$, $G^4$, $R^2$, $R^{3a}$, $R^{3b}$, $R^{3c}$, $R^{3d}$, n and $R^5$ are the same as defined in the above Item 1. Provided that if $R^{1c}$ and $R^{1d}$ in $G^3$ combine each other to form a group of the following formula of the above Item 1:

[Chemical Formula 71]

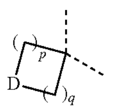

$R^{4b}$ is hydroxyl. $R^9$ in $R^5$ is $C_{1-6}$ alkyl substituted by 1 to 3 fluorine atoms, $C_{3-6}$ cycloalkyl or 1 to 2 nitroxy; $C_{6-10}$ aryl substituted by $C_{1-4}$ alkyl; and $C_{1-4}$ alkylcarbonyl substituted by hydroxy.]

Each definition and each preferable embodiment of each substituent in the compounds of the above (7) and (8) (i.e., formula (Ia) to formula (Ib)) are the same as each definition and each preferable embodiment of the definition in a compound of formula (I).

The "pharmaceutically acceptable salt" includes, for example, an inorganic acid salt such as hydrochloride, hydrobromide, sulfate, phosphate or nitrate, or an organic acid salt such as acetate, propionate, oxalate, succinate, lactate, malate, tartrate, citrate, maleate, fumarate, methanesulfonate, benzenesulfonate, p-toluenesulfonate or ascorbate, etc.

The present invention encompasses a compound of formula (I), or a pharmaceutically acceptable salt thereof. The present invention also encompasses a hydrate or a solvate thereof such as ethanolate. Further, the present invention encompasses every crystalline form.

A compound of formula (I) may also exist as a tautomer. Thus, the present invention also encompasses a tautomer of a compound of formula (I).

The present compound may have at least one asymmetric carbon atom. Thus, the present invention encompasses not only a racemate of the present compound, but also an optical isomer thereof. When the present compound has two or more asymmetric carbon atoms, a stereoisomer may exist. Thus, the present invention also encompasses a stereoisomer thereof and a mixture thereof.

The axial chirality may exist in the present compound due to a rotational hindrance between phenyl group and carbonyl. The present invention also encompasses stereoisomers of the following general formula due to the axial chirality.

[Chemical Formula 72]

(I)

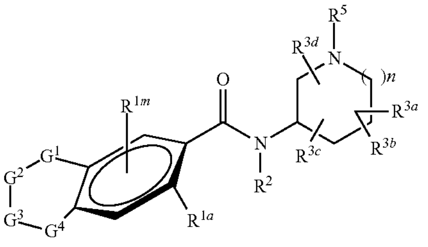

-continued (I)

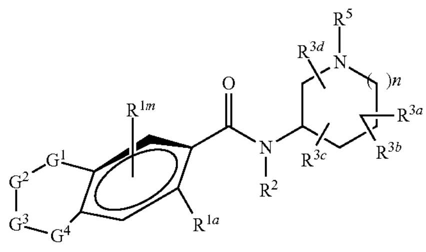

The present compound may be illustrated as Compounds No. 1 to 1304 of the following tables, and may be also illustrated as compounds wherein "$R^5$" is replaced with any one of the following partial structures P1 to P174. In the following tables, for example, a compound of No. 1 ($T^1$: Q144; $T^2$: Q144; $T^3$: Q182; $T^4$: Q263) means the following compound.

[Chemical Formula 73]

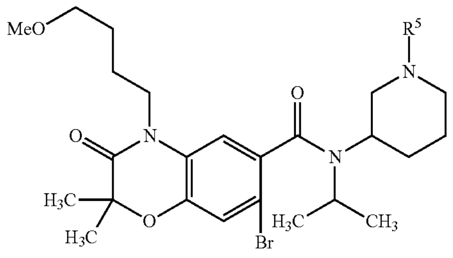

[Chemical Formula 74]

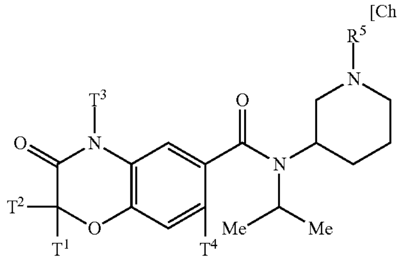

| No. | $T^1$ | $T^2$ | $T^3$ | $T^4$ |
|---|---|---|---|---|
| 1 | Q144 | Q144 | Q182 | Q263 |
| 2 | Q144 | Q144 | Q182 | Q262 |
| 3 | Q144 | Q144 | Q182 | Q143 |
| 4 | Q144 | Q144 | Q182 | Q144 |
| 5 | Q144 | Q144 | Q182 | Q145 |
| 6 | Q144 | Q144 | Q182 | Q261 |
| 7 | Q144 | Q144 | Q183 | Q262 |
| 8 | Q144 | Q144 | Q183 | Q144 |
| 9 | Q144 | Q144 | Q284 | Q262 |
| 10 | Q144 | Q144 | Q186 | Q263 |
| 11 | Q144 | Q144 | Q186 | Q262 |

-continued
| | | | | |
|---|---|---|---|---|
| 12 | Q144 | Q144 | Q186 | Q144 |
| 13 | Q145 | Q144 | Q182 | Q262 |
| 14 | Q145 | Q144 | Q182 | Q144 |
| 15 | Q145 | Q144 | Q182 | Q143 |
| 16 | H | Q144 | Q182 | Q262 |
| 17 | H | Q144 | Q182 | Q263 |
| 18 | H | Q144 | Q182 | Q144 |
| 19 | H | Q144 | Q183 | Q262 |
| 20 | H | Q144 | Q183 | Q263 |
| 21 | H | Q144 | Q183 | Q144 |
| 22 | H | Q144 | Q186 | Q262 |
| 23 | H | Q144 | Q186 | Q263 |
| 24 | H | Q144 | Q186 | Q144 |
| 25 | H | Q145 | Q182 | Q262 |
| 26 | Q285 | Q144 | Q183 | Q262 |
[Chemical Formula 75]
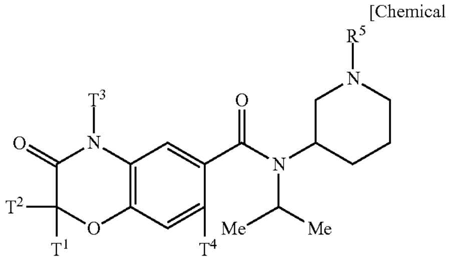
| No. | $T^1$ | $T^2$ | $T^3$ | $T^4$ |
|---|---|---|---|---|
| 27 | Q1 | H | Q183 | Q262 |
| 28 | Q2 | Q144 | Q183 | Q144 |
| 29 | Q3 | Q145 | Q183 | Q262 |
| 30 | Q4 | H | Q183 | Q144 |
| 31 | Q5 | Q144 | Q183 | Q143 |
| 32 | Q6 | Q145 | Q182 | Q262 |
| 33 | Q7 | H | Q183 | Q144 |
| 34 | Q8 | Q144 | Q183 | Q262 |
| 35 | Q9 | Q145 | 0183 | Q144 |
| 36 | Q10 | H | Q183 | Q143 |
| 37 | Q11 | Q144 | Q183 | Q262 |
| 38 | Q12 | Q145 | Q182 | Q144 |
| 39 | Q13 | H | Q183 | Q262 |
| 40 | Q14 | Q144 | Q183 | Q144 |
| 41 | Q15 | Q145 | Q183 | Q143 |
| 42 | Q16 | H | Q183 | Q262 |
| 43 | Q17 | Q144 | Q183 | Q144 |
| 44 | Q18 | Q145 | Q182 | Q262 |
| 45 | Q19 | H | Q183 | Q144 |
| 46 | Q20 | Q144 | Q183 | Q143 |
| 47 | Q21 | Q145 | Q183 | Q262 |
| 48 | Q22 | H | Q183 | Q144 |
| 49 | Q23 | Q144 | Q183 | Q262 |
| 50 | Q24 | Q145 | Q182 | Q144 |
| 51 | Q25 | H | Q183 | Q143 |
| 52 | Q26 | H | Q183 | Q262 |
| 53 | Q27 | Q144 | Q183 | Q144 |
| 54 | Q28 | Q145 | Q183 | Q262 |
| 55 | Q29 | H | Q183 | Q144 |
| 56 | Q30 | Q144 | Q183 | Q143 |
| 57 | Q31 | Q145 | Q182 | Q262 |
| 58 | Q32 | H | Q183 | Q144 |
| 59 | Q33 | Q144 | Q183 | Q262 |
| 60 | Q34 | Q145 | Q183 | Q144 |
| 61 | Q35 | H | Q183 | Q143 |
| 62 | Q36 | Q144 | Q183 | Q262 |
| 63 | Q37 | Q145 | Q182 | Q144 |
| 64 | Q38 | H | Q183 | Q262 |
| 65 | Q39 | Q144 | Q183 | Q144 |
| 66 | Q40 | Q145 | Q183 | Q143 |
| 67 | Q41 | H | Q183 | Q262 |
| 68 | Q42 | Q144 | Q183 | Q144 |
| 69 | Q43 | Q145 | Q182 | Q262 |
| 70 | Q44 | H | Q183 | Q144 |
| 71 | Q45 | Q144 | Q183 | Q143 |
| 72 | Q46 | Q145 | Q183 | Q262 |
| 73 | Q47 | H | Q183 | Q144 |

-continued
| | | | | |
|---|---|---|---|---|
| 74 | Q48 | Q144 | Q183 | Q262 |
| 75 | Q49 | Q145 | Q182 | Q144 |
| 76 | Q50 | H | Q183 | Q143 |
[Chemical Formula 76]
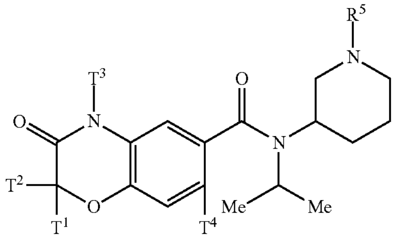
| No. | $T^1$ | $T^2$ | $T^3$ | $T^4$ |
|---|---|---|---|---|
| 77 | Q51 | H | Q183 | Q262 |
| 78 | Q52 | Q144 | Q183 | Q144 |
| 79 | Q53 | Q145 | Q183 | Q262 |
| 80 | Q54 | H | Q183 | Q144 |
| 81 | Q55 | Q144 | Q183 | Q143 |
| 82 | Q56 | Q145 | Q182 | Q262 |
| 83 | Q57 | H | Q183 | Q144 |
| 84 | Q58 | Q144 | Q183 | Q262 |
| 85 | Q59 | Q145 | Q183 | Q144 |
| 86 | Q60 | H | Q183 | Q143 |
| 87 | Q61 | Q144 | Q183 | Q262 |
| 88 | Q62 | Q145 | Q182 | Q144 |
| 89 | Q63 | H | Q183 | Q262 |
| 90 | Q64 | Q144 | Q183 | Q144 |
| 91 | Q65 | Q145 | Q183 | Q143 |
| 92 | Q66 | H | Q183 | Q262 |
| 93 | Q67 | Q144 | Q183 | Q144 |
| 94 | Q68 | Q145 | Q182 | Q262 |
| 95 | Q69 | H | Q183 | Q144 |
| 96 | Q70 | Q144 | Q183 | Q143 |
| 97 | Q71 | Q145 | Q183 | Q262 |
| 98 | Q72 | H | Q183 | Q144 |
| 99 | Q73 | Q144 | Q183 | Q262 |
| 100 | Q74 | Q145 | Q182 | Q144 |
| 101 | Q75 | H | Q183 | Q143 |
| 102 | Q76 | H | Q183 | Q262 |
| 103 | Q77 | Q144 | Q183 | Q144 |
| 104 | Q78 | Q145 | Q183 | Q262 |
| 105 | Q79 | H | Q183 | Q144 |
| 106 | Q80 | Q144 | Q183 | Q143 |
| 107 | Q81 | Q145 | Q182 | Q262 |
| 108 | Q82 | H | Q183 | Q144 |
| 109 | Q83 | Q144 | Q183 | Q262 |
| 110 | Q84 | Q145 | Q183 | 0144 |
| 111 | Q85 | H | Q183 | Q143 |
| 112 | Q86 | Q144 | Q183 | Q262 |
| 113 | Q87 | Q145 | Q182 | Q144 |
| 114 | Q88 | H | Q183 | Q262 |
| 115 | Q89 | Q144 | Q183 | Q144 |
| 116 | Q90 | Q145 | Q183 | Q143 |
| 117 | Q91 | H | Q183 | Q262 |
| 118 | Q92 | Q144 | Q183 | Q144 |
| 119 | Q93 | Q145 | Q182 | Q262 |
| 120 | Q94 | H | Q183 | Q144 |
| 121 | Q95 | Q144 | Q183 | Q143 |
| 122 | Q96 | Q145 | Q183 | Q262 |
| 123 | Q97 | H | Q183 | Q144 |
| 124 | Q98 | Q144 | Q183 | Q262 |
| 125 | Q99 | Q145 | Q182 | Q144 |
| 126 | Q100 | H | Q183 | Q143 |

-continued
[Chemical Formula 77]
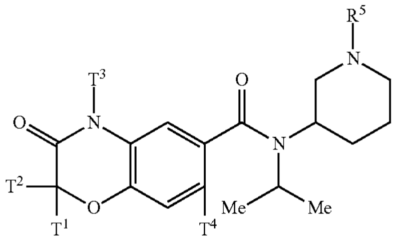
| No. | $T^1$ | $T^2$ | $T^3$ | $T^4$ |
|---|---|---|---|---|
| 127 | Q101 | H | Q183 | Q262 |
| 128 | Q102 | Q144 | Q183 | Q144 |
| 129 | Q103 | Q145 | Q183 | Q262 |
| 130 | Q104 | H | Q183 | Q144 |
| 131 | Q105 | Q144 | Q183 | Q143 |
| 132 | Q106 | Q145 | Q182 | Q262 |
| 135 | Q107 | H | Q183 | Q144 |
| 136 | Q108 | Q144 | Q183 | Q262 |
| 137 | Q109 | Q145 | Q183 | Q144 |
| 138 | Q110 | H | Q183 | Q143 |
| 139 | Q111 | Q144 | Q183 | Q262 |
| 140 | Q112 | Q145 | Q182 | Q144 |
| 141 | Q113 | H | Q183 | Q262 |
| 142 | Q114 | Q144 | Q183 | Q144 |
| 143 | Q115 | Q145 | Q183 | Q143 |
| 144 | Q116 | H | Q183 | Q262 |
| 145 | Q117 | Q144 | Q183 | Q144 |
| 146 | Q118 | Q145 | Q182 | Q262 |
| 147 | Q119 | H | Q183 | Q144 |
| 148 | Q120 | Q144 | Q183 | Q143 |
| 149 | Q121 | Q145 | Q183 | Q262 |
| 150 | Q122 | H | Q183 | Q144 |
| 151 | Q123 | Q144 | Q183 | Q262 |
| 152 | Q124 | Q145 | Q182 | Q144 |
| 153 | Q125 | H | Q183 | Q143 |
| 154 | Q126 | H | Q183 | Q262 |
| 155 | Q127 | Q144 | Q183 | Q144 |
| 156 | Q128 | Q145 | Q183 | Q262 |
| 157 | Q129 | H | Q183 | Q144 |
| 158 | Q130 | Q144 | Q183 | Q143 |
| 159 | Q131 | Q145 | Q182 | Q262 |
| 160 | Q132 | H | Q183 | Q144 |
| 161 | Q133 | Q144 | Q183 | Q262 |
| 162 | Q134 | Q145 | Q183 | Q144 |
| 163 | Q135 | H | Q183 | Q143 |
| 164 | Q136 | Q144 | Q183 | Q262 |
| 165 | Q10 | Q145 | Q186 | Q148 |
| 166 | Q138 | H | Q183 | Q262 |
| 167 | Q139 | Q144 | Q183 | Q144 |
| 168 | Q140 | Q145 | Q183 | Q143 |
| 169 | Q141 | H | Q183 | Q262 |
| 170 | Q142 | Q144 | Q183 | Q144 |
| 171 | Q144 | Q145 | Q182 | Q262 |
| 172 | Q145 | H | Q183 | Q144 |
| 173 | Q146 | H | Q183 | Q143 |
| 174 | Q147 | H | Q183 | Q262 |
| 175 | Q148 | H | Q183 | Q144 |
| 176 | Q149 | Q144 | Q183 | Q262 |
| 177 | Q150 | Q145 | Q182 | Q144 |
| 178 | Q151 | H | Q183 | Q143 |

-continued
[Chemical Formula 78]
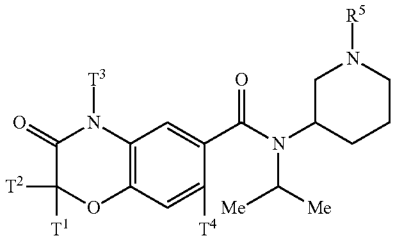
| No. | $T^1$ | $T^2$ | $T^3$ | $T^4$ |
|---|---|---|---|---|
| 179 | Q152 | H | Q183 | Q262 |
| 180 | Q153 | Q144 | Q183 | Q144 |
| 181 | Q154 | Q145 | Q183 | Q262 |
| 182 | Q155 | H | Q183 | Q144 |
| 183 | Q156 | Q144 | Q183 | Q143 |
| 184 | Q157 | Q145 | Q182 | Q262 |
| 185 | Q158 | H | Q183 | Q144 |
| 186 | Q159 | Q144 | Q183 | Q262 |
| 187 | Q160 | Q145 | Q183 | Q144 |
| 188 | Q161 | H | Q183 | Q143 |
| 189 | Q162 | Q144 | Q183 | Q262 |
| 190 | Q163 | Q145 | Q182 | Q144 |
| 191 | Q164 | H | Q183 | Q262 |
| 192 | Q165 | Q144 | Q183 | Q144 |
| 193 | Q166 | Q145 | Q183 | Q143 |
| 194 | Q167 | H | Q183 | Q262 |
| 195 | Q168 | Q144 | Q183 | Q144 |
| 196 | Q169 | Q145 | Q182 | Q262 |
| 197 | Q170 | H | Q183 | Q144 |
| 198 | Q171 | Q144 | Q183 | Q143 |
| 199 | Q172 | Q145 | Q183 | Q262 |
| 200 | Q173 | H | Q183 | Q144 |
| 201 | Q174 | Q144 | Q183 | Q262 |
| 202 | Q175 | Q145 | Q182 | Q144 |
| 203 | Q176 | H | Q183 | Q143 |
| 204 | Q177 | H | Q183 | Q262 |
| 205 | Q178 | Q144 | Q183 | Q144 |
| 206 | Q179 | Q145 | Q183 | Q262 |
| 207 | Q180 | H | Q183 | Q144 |
| 208 | Q181 | Q144 | Q183 | Q143 |
| 209 | Q182 | Q145 | Q182 | Q262 |
| 210 | Q183 | H | Q183 | Q144 |
| 211 | Q184 | Q144 | Q183 | Q262 |
| 212 | Q185 | Q145 | Q183 | Q144 |
| 213 | Q210 | H | Q183 | Q143 |
| 214 | Q223 | Q144 | Q183 | Q262 |
| 215 | Q137 | Q145 | Q182 | Q144 |
| 216 | Q236 | H | Q183 | Q262 |
| 217 | Q244 | H | Q183 | Q144 |
| 218 | Q238 | H | Q183 | Q143 |
| 219 | Q144 | Q144 | Q138 | Q262 |
| 220 | Q144 | Q144 | Q184 | Q144 |
| 221 | Q144 | Q144 | Q185 | Q262 |
| 222 | Q144 | Q144 | Q186 | Q144 |
| 223 | Q144 | H | Q183 | Q145 |
| 224 | Q144 | H | Q183 | Q148 |
| 225 | Q145 | H | Q183 | Q263 |
| 226 | Q144 | Q144 | Q183 | Q261 |
| 227 | Q144 | Q144 | Q182 | Q180 |
| 228 | Q182 | R144 | Q183 | Q149 |

-continued

[Chemical Formula 79]

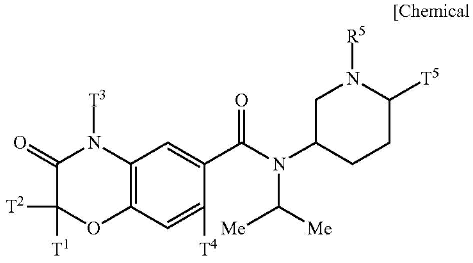

| No. | $T^1$ | $T^2$ | $T^3$ | $T^4$ | $T^5$ |
|---|---|---|---|---|---|
| 229 | Q144 | Q144 | Q183 | Q262 | Q191 |
| 230 | Q144 | H | Q183 | Q144 | Q192 |
| 231 | Q144 | Q144 | Q183 | Q143 | Q193 |
| 232 | Q145 | H | Q183 | Q143 | Q194 |
| 233 | Q144 | Q144 | Q183 | Q262 | Q195 |
| 234 | Q144 | H | Q183 | Q144 | Q196 |
| 235 | Q144 | Q144 | Q183 | Q143 | Q197 |
| 236 | Q145 | H | Q183 | Q143 | Q198 |
| 237 | Q144 | Q144 | Q183 | Q262 | Q199 |
| 238 | Q144 | H | Q183 | Q144 | Q200 |
| 239 | Q144 | Q144 | Q183 | Q143 | Q201 |
| 240 | Q145 | H | Q183 | Q143 | Q202 |
| 241 | Q144 | Q144 | Q183 | Q262 | Q203 |
| 242 | Q144 | H | Q183 | Q144 | Q204 |
| 243 | Q144 | Q144 | Q183 | Q143 | Q205 |
| 244 | Q145 | H | Q183 | Q143 | Q206 |
| 245 | Q144 | Q144 | Q183 | Q262 | Q207 |
| 246 | Q144 | H | Q183 | Q144 | Q208 |
| 247 | Q144 | Q144 | Q183 | Q143 | Q209 |
| 248 | Q145 | H | Q183 | Q143 | Q210 |
| 249 | Q144 | Q144 | Q183 | Q262 | Q211 |
| 250 | Q144 | H | Q183 | Q144 | Q212 |
| 251 | Q144 | Q144 | Q183 | Q143 | Q213 |
| 252 | Q145 | H | Q183 | Q143 | Q214 |
| 253 | Q145 | H | Q183 | Q143 | Q215 |

[Chemical Formula 80]

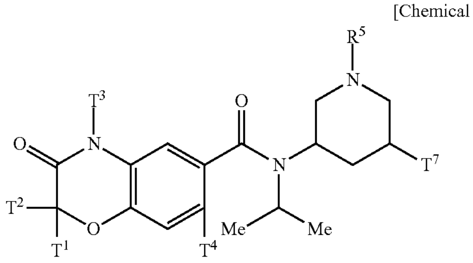

| No. | $T^1$ | $T^2$ | $T^3$ | $T^4$ | $T^7$ |
|---|---|---|---|---|---|
| 254 | Q144 | Q144 | Q183 | Q262 | Q216 |
| 255 | Q144 | H | Q183 | Q144 | Q217 |
| 256 | Q144 | Q144 | Q183 | Q143 | Q218 |
| 257 | Q145 | H | Q183 | Q143 | Q219 |
| 258 | Q144 | Q144 | Q183 | Q262 | Q220 |
| 259 | Q144 | H | Q183 | Q144 | Q221 |
| 260 | Q144 | Q144 | Q182 | Q143 | Q222 |
| 261 | Q145 | H | Q183 | Q143 | Q223 |
| 262 | Q144 | Q144 | Q183 | Q262 | Q224 |
| 263 | Q144 | H | Q183 | Q144 | Q225 |
| 264 | Q144 | Q144 | Q183 | Q143 | Q226 |
| 265 | Q145 | H | Q183 | Q143 | Q227 |
| 266 | Q144 | Q144 | Q182 | Q262 | Q228 |
| 267 | Q144 | H | Q183 | Q144 | Q229 |
| 268 | Q144 | Q144 | Q183 | Q143 | Q230 |
| 269 | Q145 | H | Q183 | Q143 | Q231 |
| 270 | Q144 | Q144 | Q183 | Q262 | Q232 |
| 271 | Q144 | H | Q183 | Q144 | Q233 |
| 272 | Q144 | Q144 | Q183 | Q143 | Q234 |
| 273 | Q145 | H | Q183 | Q143 | Q235 |

-continued
[Chemical Formula 81]
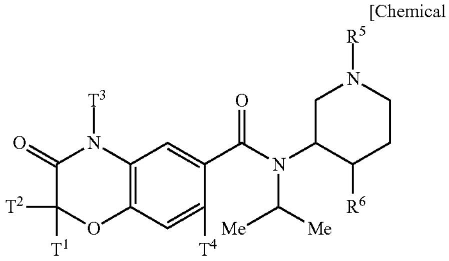
| No. | T1 | T2 | T3 | T4 | T6 |
|---|---|---|---|---|---|
| 274 | Q144 | Q144 | Q183 | Q262 | Q247 |
| 275 | Q144 | H | Q183 | Q144 | Q248 |
| 276 | Q144 | Q144 | Q183 | Q143 | Q249 |
| 277 | Q145 | H | Q183 | Q143 | Q250 |
| 278 | Q144 | Q144 | Q183 | Q262 | Q251 |
| 279 | Q144 | H | Q183 | Q144 | Q252 |
| 280 | Q144 | Q144 | Q182 | Q143 | Q253 |
| 281 | Q145 | H | Q183 | Q143 | Q254 |
| 282 | Q144 | Q144 | Q183 | Q262 | Q255 |
| 283 | Q144 | H | Q183 | Q144 | Q256 |
| 284 | Q144 | Q144 | Q183 | Q143 | Q257 |
| 285 | Q145 | H | Q183 | Q143 | Q258 |
| 286 | Q144 | Q144 | Q183 | Q262 | Q259 |
| 287 | Q144 | H | Q182 | Q144 | Q260 |
| 288 | Q144 | Q144 | Q183 | Q143 | Q187 |
[Chemical Formula 82]
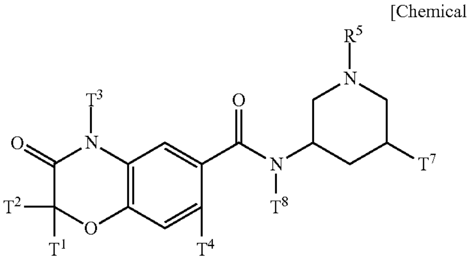
| No. | T1 | T2 | T3 | T4 | T8 | T7 |
|---|---|---|---|---|---|---|
| 309 | Q144 | Q144 | Q183 | Q262 | Q237 | Q210 |
| 310 | Q144 | H | Q183 | Q144 | Q238 | Q223 |
| 311 | Q144 | Q144 | Q182 | Q143 | Q115 | Q192 |
| 312 | Q145 | H | Q183 | Q143 | Q116 | Q193 |
| 313 | Q144 | Q144 | Q183 | Q262 | Q117 | Q194 |
| 314 | Q144 | H | Q183 | Q144 | Q118 | Q195 |
| 315 | Q144 | Q144 | Q183 | Q143 | Q119 | Q196 |
| 316 | Q145 | H | Q182 | Q143 | Q180 | Q197 |
| 317 | Q138 | H | Q183 | Q262 | Q180 | Q199 |
| 318 | Q139 | H | Q183 | Q144 | Q180 | Q200 |
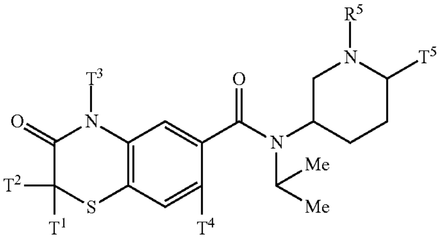
| No. | T1 | T2 | T3 | T4 | T5 |
|---|---|---|---|---|---|
| 319 | Q144 | Q144 | Q183 | Q262 | H |
| 320 | Q144 | H | Q183 | Q144 | H |
| 321 | Q179 | Q144 | Q183 | Q143 | H |
| 322 | Q138 | H | Q183 | Q143 | H |
| 323 | Q139 | Q144 | Q182 | Q262 | H |
| 324 | Q144 | H | Q183 | Q144 | Q223 |
| 325 | Q144 | Q144 | Q183 | Q143 | Q210 |
| 326 | Q145 | Q144 | Q183 | Q143 | Q215 |

-continued
| | | | | | |
|---|---|---|---|---|---|
| 327 | Q144 | H | Q182 | Q262 | Q216 |
| 328 | Q144 | H | Q183 | Q144 | Q203 |
[Chemical Formula 83]
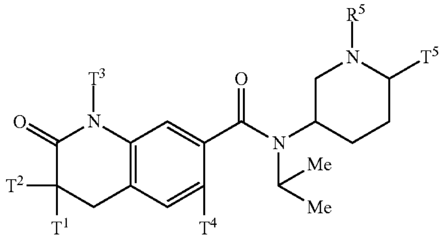
| No. | $T^1$ | $T^2$ | $T^3$ | $T^4$ | $T^5$ |
|---|---|---|---|---|---|
| 329 | Q144 | Q144 | Q183 | Q262 | H |
| 330 | Q144 | H | Q183 | Q144 | H |
| 331 | Q179 | Q144 | Q183 | Q143 | H |
| 332 | Q138 | Q144 | Q183 | Q143 | H |
| 333 | Q139 | Q144 | Q182 | Q262 | H |
| 334 | Q144 | H | Q183 | Q144 | Q223 |
| 335 | Q144 | Q144 | Q183 | Q143 | Q210 |
| 336 | Q145 | Q144 | Q183 | Q143 | Q215 |
| 337 | Q144 | H | Q182 | Q262 | Q216 |
| 338 | Q144 | H | Q183 | Q144 | Q203 |
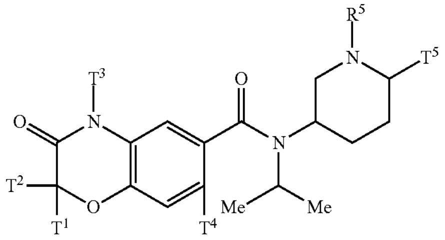
| No. | $T^1$ | $T^2$ | $T^3$ | $T^4$ | $T^5$ |
|---|---|---|---|---|---|
| 339 | Q144 | Q144 | Q183 | Q262 | Q264 |
| 340 | Q144 | H | Q183 | Q144 | Q265 |
| 341 | Q144 | Q144 | Q183 | Q143 | Q266 |
| 342 | Q145 | H | Q182 | Q143 | Q267 |
| 343 | Q144 | Q144 | Q183 | Q262 | Q268 |
[Chemical Formula 84]
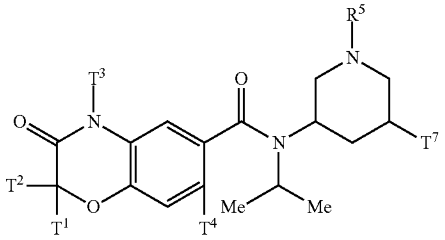
| No. | $T^1$ | $T^2$ | $T^3$ | $T^4$ | $T^7$ |
|---|---|---|---|---|---|
| 344 | Q144 | Q144 | Q183 | Q262 | Q264 |
| 345 | Q144 | H | Q183 | Q144 | Q265 |
| 346 | Q144 | Q144 | Q183 | Q143 | Q266 |
| 347 | Q145 | H | Q183 | Q143 | Q267 |
| 348 | Q144 | Q144 | Q183 | Q262 | Q268 |

-continued
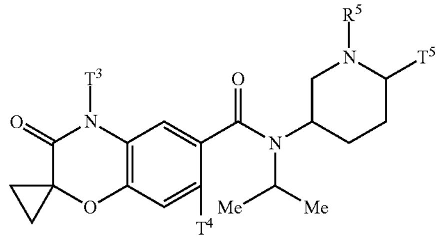
| No. | T3 | T4 | T5 |
|---|---|---|---|
| 349 | Q183 | Q262 | Q223 |
| 350 | Q183 | Q144 | Q210 |
| 351 | Q183 | Q143 | Q268 |
| 352 | Q183 | Q143 | H |
[Chemical Formula 85]
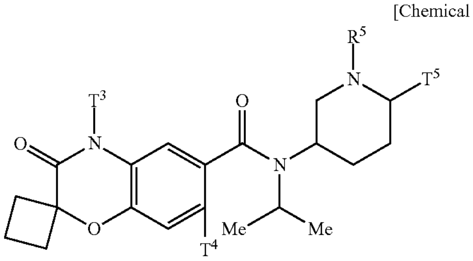
| No. | T3 | T4 | T5 |
|---|---|---|---|
| 353 | Q183 | Q262 | Q223 |
| 354 | Q183 | Q262 | Q210 |
| 355 | Q183 | Q143 | H |
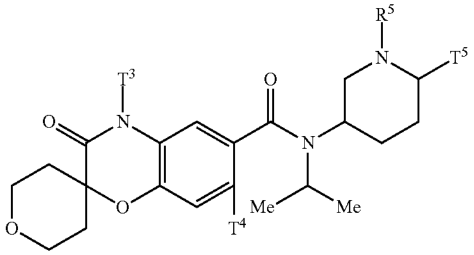
| No. | T3 | T4 | T5 |
|---|---|---|---|
| 356 | Q183 | Q262 | Q223 |
| 357 | Q183 | Q144 | Q210 |
| 358 | Q183 | Q143 | Q268 |
| 359 | Q183 | Q262 | Q223 |
| 360 | Q183 | Q262 | Q210 |
| 361 | Q183 | Q143 | H |
[Chemical Formula 86]
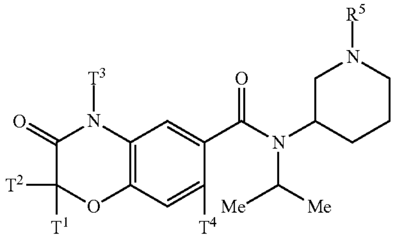
| No. | T1 | T2 | T3 | T4 |
|---|---|---|---|---|
| 362 | Q10 | Q144 | Q186 | Q148 |
| 363 | Q10 | Q144 | Q183 | Q144 |
| 364 | Q10 | Q144 | Q183 | Q143 |
| 365 | Q78 | Q144 | Q183 | Q144 |

-continued
| | | | | |
|---|---|---|---|---|
| 366 | Q80 | Q144 | Q183 | Q144 |
| 367 | Q82 | Q144 | Q183 | Q143 |
| 368 | Q83 | Q144 | Q186 | Q262 |
| 369 | Q91 | Q144 | Q183 | Q262 |
| 370 | Q144 | Q144 | Q186 | Q274 |
| 371 | Q144 | Q144 | Q186 | Q275 |
| 372 | Q277 | H | Q183 | Q262 |
| 373 | Q144 | Q144 | Q183 | Q272 |
| 374 | Q144 | Q144 | Q183 | Q273 |
| 375 | Q144 | Q144 | Q281 | Q262 |
| 376 | Q144 | Q144 | Q282 | Q262 |
| 377 | Q283 | Q144 | Q183 | Q262 |
| 378 | Q144 | Q144 | Q186 | Q148 |
| 379 | Q10 | Q144 | Q186 | Q147 |
| 380 | Q10 | Q144 | Q186 | Q146 |
| 381 | Q145 | Q144 | Q183 | Q262 |
| 382 | Q278 | H | Q183 | Q262 |
| 383 | Q143 | H | Q183 | Q262 |
[Chemical Formula 87]
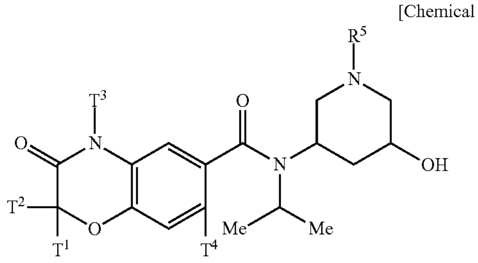
| No. | $T^1$ | $T^2$ | $T^3$ | $T^4$ |
|---|---|---|---|---|
| 384 | Q10 | Q144 | Q183 | Q148 |
| 385 | Q10 | Q144 | Q183 | Q144 |
| 386 | Q10 | Q144 | Q183 | Q262 |
| 387 | Q144 | Q144 | Q183 | Q263 |
| 388 | Q10 | Q144 | Q183 | Q147 |
[Chemical Formula 88]
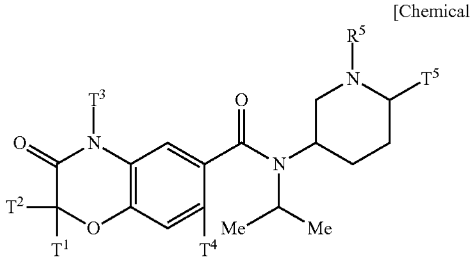
| No. | $T^1$ | $T^2$ | $T^3$ | $T^4$ | $T^5$ |
|---|---|---|---|---|---|
| 389 | Q144 | Q144 | Q183 | Q148 | Q286 |
| 390 | Q144 | Q144 | Q183 | Q148 | Q287 |
| 391 | Q144 | Q144 | Q183 | Q148 | Q288 |
| 392 | Q144 | Q144 | Q183 | Q148 | Q289 |
| 393 | Q144 | Q144 | Q183 | Q148 | Q290 |
| 394 | Q144 | Q144 | Q183 | Q148 | Q291 |
| 395 | Q144 | Q144 | Q183 | Q148 | Q296 |
| 396 | Q144 | Q144 | Q183 | Q148 | Q300 |
| 397 | Q144 | Q144 | Q183 | Q148 | Q301 |
| 398 | Q144 | Q144 | Q183 | Q148 | Q302 |
| 399 | Q144 | Q144 | Q183 | Q148 | Q303 |
| 400 | Q144 | Q144 | Q183 | Q148 | Q304 |
| 401 | Q144 | Q144 | Q183 | Q148 | Q305 |
| 402 | Q144 | Q144 | Q183 | Q148 | Q306 |
| 403 | Q144 | Q144 | Q183 | Q148 | Q307 |
| 404 | Q144 | Q144 | Q183 | Q148 | Q308 |
| 405 | Q144 | Q144 | Q183 | Q148 | Q309 |
| 406 | Q144 | Q144 | Q183 | Q148 | Q310 |
| 407 | Q144 | Q144 | Q183 | Q148 | Q311 |
| 408 | Q144 | Q144 | Q183 | Q148 | Q312 |
| 409 | Q144 | Q144 | Q183 | Q148 | Q313 |
| 410 | Q144 | Q144 | Q183 | Q148 | Q314 |
| 411 | Q144 | Q144 | Q183 | Q148 | Q315 |
| 412 | Q144 | Q144 | Q183 | Q148 | Q316 |

-continued

| | | | | | |
|---|---|---|---|---|---|
| 413 | Q144 | Q144 | Q183 | Q148 | Q317 |
| 414 | Q144 | Q144 | Q183 | Q148 | Q318 |
| 415 | Q144 | Q144 | Q183 | Q148 | Q319 |
| 416 | Q144 | Q144 | Q183 | Q148 | Q320 |
| 417 | Q144 | Q144 | Q183 | Q148 | Q321 |
| 418 | Q144 | Q144 | Q183 | Q148 | Q322 |
| 419 | Q144 | Q144 | Q183 | Q148 | Q323 |
| 420 | Q144 | Q144 | Q183 | Q148 | Q324 |
| 421 | Q144 | Q144 | Q183 | Q148 | Q325 |
| 422 | Q144 | Q144 | Q183 | Q148 | Q326 |
| 423 | Q144 | Q144 | Q183 | Q148 | Q327 |
| 424 | Q144 | Q144 | Q183 | Q148 | Q328 |
| 425 | Q144 | Q144 | Q183 | Q148 | Q329 |
| 426 | Q144 | Q144 | Q183 | Q148 | Q334 |
| 427 | Q144 | Q144 | Q183 | Q148 | Q338 |
| 428 | Q144 | Q144 | Q183 | Q148 | Q339 |
| 429 | Q144 | Q144 | Q183 | Q148 | Q340 |
| 430 | Q144 | Q144 | Q183 | Q148 | Q341 |
| 431 | Q144 | Q144 | Q183 | Q148 | Q342 |
| 432 | Q144 | Q144 | Q183 | Q148 | Q343 |
| 433 | Q144 | Q144 | Q183 | Q148 | Q344 |
| 434 | Q144 | Q144 | Q183 | Q148 | Q345 |
| 435 | Q144 | Q144 | Q183 | Q148 | Q346 |
| 436 | Q144 | Q144 | Q183 | Q148 | Q347 |
| 437 | Q144 | Q144 | Q183 | Q148 | Q348 |
| 438 | Q144 | Q144 | Q183 | Q148 | Q349 |
| 439 | Q144 | Q144 | Q183 | Q148 | Q350 |
| 440 | Q144 | Q144 | Q183 | Q148 | Q351 |
| 441 | Q144 | Q144 | Q183 | Q148 | Q352 |
| 442 | Q144 | Q144 | Q183 | Q148 | Q353 |
| 443 | Q144 | Q144 | Q183 | Q148 | Q354 |
| 444 | Q144 | Q144 | Q183 | Q148 | Q355 |
| 445 | Q144 | Q144 | Q183 | Q148 | Q356 |
| 446 | Q144 | Q144 | Q183 | Q148 | Q357 |

[Chemical Formula 89]

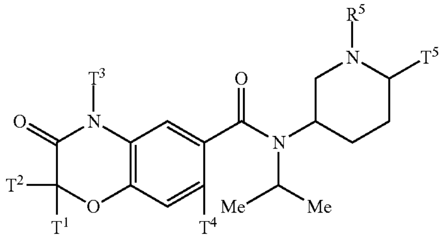

| No. | $T^1$ | $T^2$ | $T^3$ | $T^4$ | $T^5$ |
|---|---|---|---|---|---|
| 447 | Q144 | Q144 | Q183 | Q148 | Q358 |
| 448 | Q465 | Q144 | Q183 | Q148 | Q359 |
| 449 | Q14 | Q144 | Q183 | Q148 | Q360 |
| 450 | Q2 | H | Q183 | Q148 | Q361 |
| 451 | Q11 | Q144 | Q183 | Q148 | Q362 |
| 452 | Q468 | | Q183 | Q148 | Q363 |
| 453 | Q285 | Q144 | Q183 | Q148 | Q364 |
| 454 | Q181 | Q144 | Q183 | Q148 | Q365 |
| 455 | Q149 | Q144 | Q183 | Q148 | Q366 |
| 456 | Q103 | Q144 | Q183 | Q148 | Q367 |
| 457 | Q149 | Q144 | Q183 | Q148 | Q368 |
| 458 | Q182 | Q144 | Q183 | Q148 | Q369 |
| 459 | Q176 | Q144 | Q183 | Q148 | Q370 |
| 460 | Q116 | Q144 | Q183 | Q148 | Q371 |
| 461 | Q149 | Q144 | Q183 | Q148 | Q372 |
| 462 | Q547 | | Q183 | Q148 | Q373 |
| 463 | Q144 | Q144 | Q183 | Q148 | Q374 |
| 464 | Q465 | Q144 | Q183 | Q148 | Q375 |
| 465 | Q14 | Q144 | Q183 | Q148 | Q376 |
| 466 | Q2 | H | Q183 | Q148 | Q377 |
| 467 | Q11 | Q144 | Q183 | Q144 | Q288 |
| 468 | Q468 | | Q183 | Q262 | Q308 |
| 469 | Q285 | Q144 | Q183 | Q143 | Q288 |
| 470 | Q181 | Q144 | Q183 | Q147 | Q308 |
| 471 | Q149 | Q144 | Q183 | Q145 | Q288 |
| 472 | Q103 | Q144 | Q183 | Q277 | Q308 |
| 473 | Q149 | Q144 | Q183 | Q280 | Q288 |
| 474 | Q182 | Q144 | Q183 | Q478 | Q308 |
| 475 | Q176 | Q144 | Q183 | Q479 | Q288 |

-continued

| | | | | | |
|---|---|---|---|---|---|
| 476 | Q116 | Q144 | Q183 | Q480 | Q308 |
| 477 | Q149 | Q144 | Q183 | Q481 | Q288 |
| 478 | Q547 | | Q183 | Q482 | Q308 |
| 479 | Q144 | Q144 | Q427 | Q148 | Q353 |
| 480 | Q465 | Q144 | Q186 | Q148 | Q264 |
| 481 | Q14 | Q144 | Q445 | Q148 | Q223 |
| 482 | Q2 | H | Q427 | Q148 | Q353 |
| 483 | Q11 | Q144 | Q427 | Q148 | Q264 |
| 484 | Q468 | | Q186 | Q148 | Q223 |
| 485 | Q285 | Q144 | Q427 | Q148 | Q353 |
| 486 | Q181 | Q144 | Q186 | Q148 | Q264 |
| 487 | Q149 | Q144 | Q445 | Q148 | Q223 |
| 488 | Q103 | Q144 | Q427 | Q148 | Q353 |
| 489 | Q149 | Q144 | Q427 | Q148 | Q264 |
| 490 | Q182 | Q144 | Q186 | Q148 | Q223 |
| 491 | Q176 | Q144 | Q427 | Q148 | Q353 |
| 492 | Q116 | Q144 | Q186 | Q148 | Q264 |
| 493 | Q149 | Q144 | Q445 | Q148 | Q353 |
| 494 | Q547 | | Q427 | Q262 | Q353 |
| 495 | Q144 | Q144 | Q445 | Q144 | Q264 |
| 496 | Q465 | Q144 | Q186 | Q143 | Q223 |
| 497 | Q14 | Q144 | Q427 | Q145 | Q353 |
| 498 | Q2 | H | Q445 | Q147 | Q264 |
| 499 | Q11 | Q144 | Q186 | Q277 | Q223 |
| 500 | Q468 | | Q427 | Q280 | Q353 |
| 501 | Q285 | Q144 | Q445 | Q279 | Q264 |
| 502 | Q181 | Q144 | Q186 | Q261 | Q223 |
| 503 | Q149 | Q144 | Q445 | Q263 | Q353 |
| 504 | Q103 | Q144 | Q186 | Q180 | Q264 |

[Chemical Formula 90]

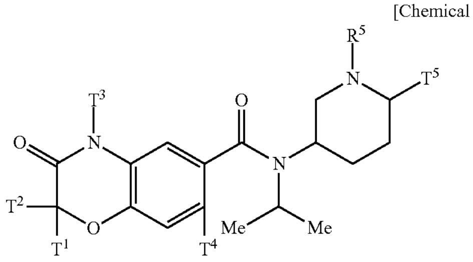

| No. | $T^1$ | $T^2$ | $T^3$ | $T^4$ | $T^5$ |
|---|---|---|---|---|---|
| 505 | Q269 | Q144 | Q183 | Q148 | Q358 |
| 506 | Q270 | Q144 | Q183 | Q148 | Q359 |
| 507 | Q271 | Q145 | Q183 | Q148 | Q360 |
| 508 | Q272 | H | Q183 | Q148 | Q361 |
| 509 | Q273 | Q144 | Q183 | Q148 | Q362 |
| 510 | Q274 | Q144 | Q183 | Q148 | Q363 |
| 511 | Q283 | Q144 | Q183 | Q148 | Q364 |
| 512 | Q390 | Q144 | Q183 | Q148 | Q365 |
| 513 | Q404 | H | Q183 | Q148 | Q366 |
| 514 | Q405 | Q144 | Q183 | Q148 | Q367 |
| 515 | Q408 | Q145 | Q183 | Q148 | Q368 |
| 516 | Q410 | Q144 | Q183 | Q148 | Q369 |
| 517 | Q411 | H | Q183 | Q148 | Q370 |
| 518 | Q412 | Q144 | Q183 | Q148 | Q371 |
| 519 | Q413 | Q144 | Q183 | Q148 | Q372 |
| 520 | Q414 | Q144 | Q183 | Q148 | Q373 |
| 521 | Q415 | Q145 | Q183 | Q148 | Q374 |
| 522 | Q447 | Q144 | Q183 | Q148 | Q375 |
| 523 | Q448 | Q144 | Q183 | Q148 | Q376 |
| 524 | Q449 | H | Q183 | Q148 | Q377 |
| 525 | Q450 | Q144 | Q183 | Q144 | Q288 |
| 526 | Q451 | Q144 | Q183 | Q262 | Q308 |
| 527 | Q452 | Q145 | Q183 | Q143 | Q288 |
| 528 | Q453 | Q144 | Q183 | Q147 | Q308 |
| 529 | Q454 | H | Q183 | Q145 | Q288 |
| 530 | Q455 | Q144 | Q183 | Q277 | Q308 |
| 531 | Q456 | Q145 | Q183 | Q280 | Q288 |
| 532 | Q457 | Q144 | Q183 | Q478 | Q308 |
| 533 | Q458 | Q144 | Q183 | Q479 | Q288 |
| 534 | Q459 | Q145 | Q183 | Q480 | Q308 |
| 535 | Q460 | Q144 | Q183 | Q481 | Q288 |
| 536 | Q461 | Q144 | Q183 | Q482 | Q308 |
| 537 | Q462 | Q144 | Q427 | Q148 | Q353 |
| 538 | Q463 | Q145 | Q186 | Q148 | Q264 |
| 539 | Q464 | Q144 | Q445 | Q148 | Q223 |

-continued

| | | | | | |
|---|---|---|---|---|---|
| 540 | Q465 | H | Q427 | Q148 | Q353 |
| 541 | Q466 | | Q427 | Q148 | Q264 |
| 542 | Q467 | | Q186 | Q148 | Q223 |
| 543 | Q468 | | Q427 | Q148 | Q353 |
| 544 | Q469 | | Q186 | Q148 | Q264 |
| 545 | Q470 | | Q445 | Q148 | Q223 |
| 546 | Q471 | Q145 | Q427 | Q148 | Q353 |
| 547 | Q472 | Q144 | Q427 | Q148 | Q264 |
| 548 | Q473 | | Q186 | Q148 | Q223 |
| 549 | Q474 | Q144 | Q427 | Q148 | Q353 |
| 550 | Q475 | Q144 | Q186 | Q148 | Q264 |
| 551 | Q476 | Q144 | Q445 | Q148 | Q353 |
| 552 | Q477 | Q144 | Q427 | Q262 | Q353 |
| 553 | Q483 | Q144 | Q445 | Q144 | Q264 |
| 554 | Q484 | Q144 | Q186 | Q143 | Q223 |
| 555 | Q485 | Q145 | Q427 | Q145 | Q353 |
| 556 | Q486 | H | Q445 | Q147 | Q264 |
| 557 | Q487 | Q144 | Q186 | Q277 | Q223 |
| 558 | Q488 | Q144 | Q427 | Q280 | Q353 |
| 559 | Q489 | Q144 | Q445 | Q279 | Q264 |
| 560 | Q490 | Q144 | Q186 | Q261 | Q223 |
| 561 | Q491 | Q144 | Q445 | Q263 | Q353 |
| 562 | Q492 | Q145 | Q186 | Q180 | Q264 |

[Chemical Formula 91]

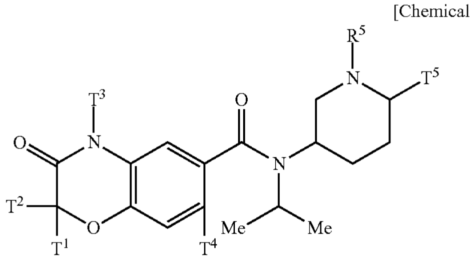

| No. | $T^1$ | $T^2$ | $T^3$ | $T^4$ | $T^5$ |
|---|---|---|---|---|---|
| 563 | Q493 | Q144 | Q183 | Q148 | Q358 |
| 564 | Q494 | Q144 | Q183 | Q148 | Q359 |
| 565 | Q495 | Q145 | Q183 | Q148 | Q360 |
| 566 | Q496 | | Q183 | Q148 | Q361 |
| 567 | Q497 | | Q183 | Q148 | Q362 |
| 568 | Q498 | | Q183 | Q148 | Q363 |
| 569 | Q499 | | Q183 | Q148 | Q364 |
| 570 | Q500 | Q144 | Q183 | Q148 | Q365 |
| 571 | Q501 | H | Q183 | Q148 | Q366 |
| 572 | Q502 | Q144 | Q183 | Q148 | Q367 |
| 573 | Q503 | Q145 | Q183 | Q148 | Q368 |
| 574 | Q504 | Q144 | Q183 | Q148 | Q369 |
| 575 | Q505 | H | Q183 | Q148 | Q370 |
| 576 | Q506 | Q144 | Q183 | Q148 | Q371 |
| 577 | Q507 | | Q183 | Q148 | Q372 |
| 578 | Q508 | | Q183 | Q148 | Q373 |
| 579 | Q509 | | Q183 | Q148 | Q374 |
| 580 | Q510 | Q144 | Q183 | Q148 | Q375 |
| 581 | Q511 | Q144 | Q183 | Q148 | Q376 |
| 582 | Q512 | H | Q183 | Q148 | Q377 |
| 583 | Q513 | Q144 | Q183 | Q144 | Q288 |
| 584 | Q514 | Q144 | Q183 | Q262 | Q308 |
| 585 | Q515 | Q145 | Q183 | Q143 | Q288 |
| 586 | Q516 | | Q183 | Q147 | Q308 |
| 587 | Q517 | | Q183 | Q145 | Q288 |
| 588 | Q518 | | Q183 | Q277 | Q308 |
| 589 | Q519 | | Q183 | Q280 | Q288 |
| 590 | Q520 | | Q183 | Q478 | Q308 |
| 591 | Q521 | | Q183 | Q479 | Q288 |
| 592 | Q522 | | Q183 | Q480 | Q308 |
| 593 | Q523 | | Q183 | Q481 | Q288 |
| 594 | Q524 | | Q183 | Q482 | Q308 |
| 595 | Q525 | Q144 | Q427 | Q148 | Q353 |
| 596 | Q526 | Q145 | Q186 | Q148 | Q264 |
| 597 | Q527 | Q144 | Q445 | Q148 | Q223 |
| 598 | Q528 | H | Q427 | Q148 | Q353 |
| 599 | Q529 | | Q427 | Q148 | Q264 |
| 600 | Q530 | | Q186 | Q148 | Q223 |
| 601 | Q531 | Q144 | Q427 | Q148 | Q353 |
| 602 | Q532 | Q144 | Q186 | Q148 | Q264 |
| 603 | Q533 | Q144 | Q445 | Q148 | Q223 |

-continued

| | | | | | |
|---|---|---|---|---|---|
| 604 | Q534 | Q145 | Q427 | Q148 | Q353 |
| 605 | Q535 | Q144 | Q427 | Q148 | Q264 |
| 606 | Q536 | Q144 | Q186 | Q148 | Q223 |
| 607 | Q537 | Q144 | Q427 | Q148 | Q353 |
| 608 | Q538 | Q144 | Q186 | Q148 | Q264 |
| 609 | Q539 | Q144 | Q445 | Q148 | Q353 |
| 610 | Q540 | Q144 | Q427 | Q262 | Q353 |
| 611 | Q541 | Q144 | Q445 | Q144 | Q264 |
| 612 | Q542 | Q144 | Q186 | Q143 | Q223 |
| 613 | Q543 | Q145 | Q427 | Q145 | Q353 |
| 614 | Q544 | H | Q445 | Q147 | Q264 |
| 615 | Q545 | Q144 | Q186 | Q277 | Q223 |
| 616 | Q546 | Q144 | Q427 | Q280 | Q353 |
| 617 | Q547 | | Q445 | Q279 | Q264 |
| 618 | Q269 | Q144 | Q183 | Q148 | H |
| 619 | Q270 | Q144 | Q183 | Q148 | H |
| 620 | Q271 | Q145 | Q183 | Q148 | H |

[Chemical Formula 92]

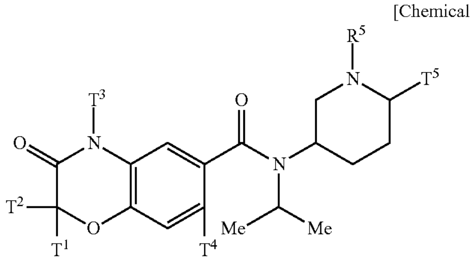

| No. | $T^1$ | $T^2$ | $T^3$ | $T^4$ | $T^5$ |
|---|---|---|---|---|---|
| 621 | Q272 | H | Q183 | Q148 | H |
| 622 | Q273 | Q144 | Q183 | Q148 | H |
| 623 | Q274 | Q144 | Q183 | Q148 | H |
| 624 | Q283 | Q144 | Q183 | Q148 | H |
| 625 | Q390 | Q144 | Q183 | Q148 | H |
| 626 | Q404 | H | Q183 | Q148 | H |
| 627 | Q405 | Q144 | Q183 | Q148 | H |
| 628 | Q408 | Q145 | Q183 | Q148 | H |
| 629 | Q410 | Q144 | Q183 | Q148 | H |
| 630 | Q411 | H | Q183 | Q148 | H |
| 631 | Q412 | Q144 | Q183 | Q148 | H |
| 632 | Q413 | Q144 | Q183 | Q148 | H |
| 633 | Q414 | Q144 | Q183 | Q148 | H |
| 634 | Q415 | Q145 | Q183 | Q148 | H |
| 635 | Q447 | Q144 | Q183 | Q148 | H |
| 636 | Q448 | Q144 | Q183 | Q148 | H |
| 637 | Q449 | H | Q183 | Q148 | H |
| 638 | Q450 | Q144 | Q183 | Q144 | H |
| 639 | Q451 | Q144 | Q183 | Q262 | H |
| 640 | Q452 | Q145 | Q183 | Q143 | H |
| 641 | Q453 | Q144 | Q183 | Q147 | H |
| 642 | Q454 | H | Q183 | Q145 | H |
| 643 | Q455 | Q144 | Q183 | Q277 | H |
| 644 | Q456 | Q145 | Q183 | Q280 | H |
| 645 | Q457 | Q144 | Q183 | Q478 | H |
| 646 | Q458 | Q144 | Q183 | Q479 | H |
| 647 | Q459 | Q145 | Q183 | Q480 | H |
| 648 | Q460 | Q144 | Q183 | Q481 | H |
| 649 | Q461 | Q144 | Q183 | Q482 | H |
| 650 | Q462 | Q144 | Q427 | Q148 | H |
| 651 | Q463 | Q145 | Q186 | Q148 | H |
| 652 | Q464 | Q144 | Q445 | Q148 | H |
| 653 | Q465 | H | Q427 | Q148 | H |
| 654 | Q466 | | Q427 | Q148 | H |
| 655 | Q467 | | Q186 | Q148 | H |
| 656 | Q468 | | Q427 | Q148 | H |
| 657 | Q469 | | Q186 | Q148 | H |
| 658 | Q470 | | Q445 | Q148 | H |
| 659 | Q471 | Q145 | Q427 | Q148 | H |
| 660 | Q472 | Q144 | Q427 | Q148 | H |
| 661 | Q473 | | Q186 | Q148 | H |
| 662 | Q474 | Q144 | Q427 | Q148 | H |
| 663 | Q475 | Q144 | Q186 | Q148 | H |
| 664 | Q476 | Q144 | Q445 | Q148 | H |
| 665 | Q477 | Q144 | Q427 | Q262 | H |
| 666 | Q483 | Q144 | Q445 | Q144 | H |
| 667 | Q484 | Q144 | Q186 | Q143 | H |

-continued

| | | | | | |
|---|---|---|---|---|---|
| 668 | Q485 | Q145 | Q427 | Q145 | H |
| 669 | Q486 | H | Q445 | Q147 | H |
| 670 | Q487 | Q144 | Q186 | Q277 | H |
| 671 | Q488 | Q144 | Q427 | Q280 | H |
| 672 | Q489 | Q144 | Q445 | Q279 | H |
| 673 | Q490 | Q144 | Q186 | Q261 | H |
| 674 | Q491 | Q144 | Q445 | Q263 | H |
| 675 | Q492 | Q145 | Q186 | Q180 | H |
| 676 | Q490 | Q144 | Q186 | Q148 | H |
| 677 | Q491 | Q144 | Q445 | Q148 | H |
| 678 | Q492 | Q145 | Q186 | Q148 | H |

[Chemical Formula 93]

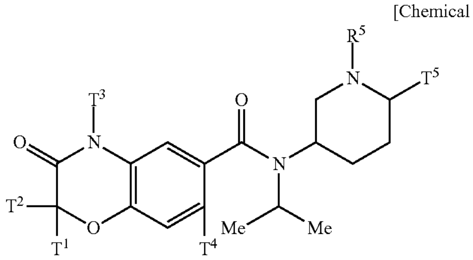

| No. | $T^1$ | $T^2$ | $T^3$ | $T^4$ | $T^5$ |
|---|---|---|---|---|---|
| 679 | Q493 | Q144 | Q183 | Q148 | H |
| 680 | Q494 | Q144 | Q183 | Q148 | H |
| 681 | Q495 | Q145 | Q183 | Q148 | H |
| 682 | Q496 | | Q183 | Q148 | H |
| 683 | Q497 | | Q183 | Q148 | H |
| 684 | Q498 | | Q183 | Q148 | H |
| 685 | Q499 | | Q183 | Q148 | H |
| 686 | Q500 | Q144 | Q183 | Q148 | H |
| 687 | Q501 | H | Q183 | Q148 | H |
| 688 | Q502 | Q144 | Q183 | Q148 | H |
| 689 | Q503 | Q145 | Q183 | Q148 | H |
| 690 | Q504 | Q144 | Q183 | Q148 | H |
| 691 | Q505 | H | Q183 | Q148 | H |
| 692 | Q506 | Q144 | Q183 | Q148 | H |
| 693 | Q507 | | Q183 | Q148 | H |
| 694 | Q508 | | Q183 | Q148 | H |
| 695 | Q509 | | Q183 | Q148 | H |
| 696 | Q510 | Q144 | Q183 | Q148 | H |
| 697 | Q511 | Q144 | Q183 | Q148 | H |
| 698 | Q512 | H | Q183 | Q148 | H |
| 699 | Q513 | Q144 | Q183 | Q144 | H |
| 700 | Q514 | Q144 | Q183 | Q262 | H |
| 701 | Q515 | Q145 | Q183 | Q143 | H |
| 702 | Q516 | | Q183 | Q147 | H |
| 703 | Q517 | | Q183 | Q145 | H |
| 704 | Q518 | | Q183 | Q277 | H |
| 705 | Q519 | | Q183 | Q280 | H |
| 706 | Q520 | | Q183 | Q478 | H |
| 707 | Q521 | | Q183 | Q479 | H |
| 709 | Q523 | | Q183 | Q481 | H |
| 710 | Q524 | | Q183 | Q482 | H |
| 711 | Q525 | Q144 | Q427 | Q148 | H |
| 712 | Q526 | Q145 | Q186 | Q148 | H |
| 713 | Q527 | Q144 | Q445 | Q148 | H |
| 714 | Q528 | H | Q427 | Q148 | H |
| 715 | Q529 | | Q427 | Q148 | H |
| 716 | Q530 | | Q186 | Q148 | H |
| 717 | Q531 | Q144 | Q427 | Q148 | H |
| 718 | Q532 | Q144 | Q186 | Q148 | H |
| 719 | Q533 | Q144 | Q445 | Q148 | H |
| 720 | Q534 | Q145 | Q427 | Q148 | H |
| 721 | Q535 | Q144 | Q427 | Q148 | H |
| 722 | Q536 | Q144 | Q186 | Q148 | H |
| 723 | Q537 | Q144 | Q427 | Q148 | H |
| 724 | Q538 | Q144 | Q186 | Q148 | H |
| 725 | Q539 | Q144 | Q445 | Q148 | H |
| 726 | Q540 | Q144 | Q427 | Q262 | H |
| 727 | Q541 | Q144 | Q445 | Q144 | H |
| 728 | Q542 | Q144 | Q186 | Q143 | H |
| 729 | Q543 | Q145 | Q427 | Q145 | H |
| 730 | Q544 | H | Q445 | Q147 | H |
| 731 | Q545 | Q144 | Q186 | Q277 | H |
| 732 | Q546 | Q144 | Q427 | Q280 | H |

-continued

| | | | | | |
|---|---|---|---|---|---|
| 733 | Q547 | | Q445 | Q279 | H |
| 734 | Q149 | Q144 | Q445 | Q148 | H |
| 735 | Q149 | Q144 | Q186 | Q148 | H |
| 736 | Q149 | Q144 | Q186 | Q144 | H |

[Chemical Formula 94]

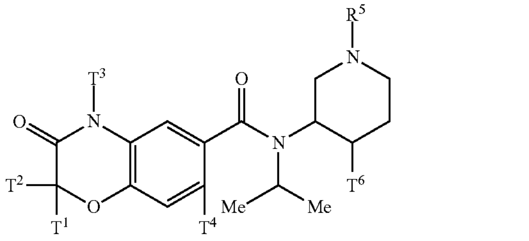

| No. | $T^1$ | $T^2$ | $T^3$ | $T^4$ | $T^6$ |
|---|---|---|---|---|---|
| 752 | Q468 | | Q427 | Q148 | Q292 |
| 753 | Q144 | Q144 | Q427 | Q148 | Q293 |
| 754 | Q149 | Q144 | Q183 | Q148 | Q294 |
| 755 | Q144 | Q144 | Q427 | Q143 | Q295 |
| 756 | Q149 | Q144 | Q186 | Q148 | Q297 |
| 757 | Q144 | Q144 | Q183 | Q148 | Q298 |
| 758 | Q547 | | Q427 | Q148 | Q299 |
| 759 | Q144 | Q144 | Q427 | Q148 | Q330 |
| 760 | Q144 | Q144 | Q427 | Q144 | Q331 |
| 761 | Q2 | Q144 | Q183 | Q148 | Q332 |
| 762 | Q182 | Q144 | Q427 | Q148 | Q333 |
| 763 | Q144 | Q144 | Q186 | Q148 | Q335 |
| 764 | Q103 | Q144 | Q183 | Q262 | Q336 |
| 765 | Q2 | Q144 | Q427 | Q148 | Q337 |
| 766 | Q144 | Q144 | Q427 | Q148 | Q387 |
| 767 | Q547 | | Q186 | Q147 | Q388 |
| 768 | Q144 | Q144 | Q183 | Q148 | Q389 |
| 769 | Q285 | Q144 | Q427 | Q148 | Q391 |
| 770 | Q144 | Q144 | Q427 | Q148 | Q392 |
| 771 | Q144 | Q144 | Q183 | Q148 | Q393 |
| 772 | Q11 | Q144 | Q427 | Q148 | Q394 |
| 773 | Q468 | | Q186 | Q148 | Q395 |
| 774 | Q144 | Q144 | Q183 | Q147 | Q396 |
| 775 | Q144 | Q145 | Q427 | Q148 | Q397 |
| 776 | Q144 | Q144 | Q427 | Q148 | Q398 |
| 777 | Q468 | | Q183 | Q148 | Q399 |
| 778 | Q144 | Q144 | Q427 | Q148 | Q400 |
| 779 | Q176 | Q144 | Q186 | Q148 | Q401 |
| 780 | Q11 | Q144 | Q183 | Q148 | Q402 |
| 781 | Q144 | Q144 | Q427 | Q148 | Q403 |

[Chemical Formula 95]

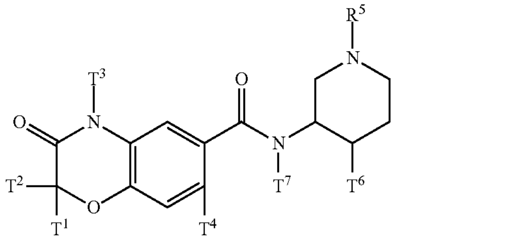

| No. | $T^1$ | $T^2$ | $T^3$ | $T^4$ | $T^6$ | $T^7$ |
|---|---|---|---|---|---|---|
| 782 | Q468 | | Q427 | Q148 | Q250 | Q144 |
| 783 | Q144 | Q144 | Q427 | Q148 | Q257 | Q145 |
| 784 | Q149 | Q144 | Q183 | Q148 | Q294 | Q180 |
| 785 | Q144 | Q144 | Q427 | Q143 | Q295 | Q261 |
| 786 | Q149 | Q144 | Q186 | Q148 | Q297 | Q115 |
| 787 | Q144 | Q144 | Q183 | Q148 | Q298 | Q144 |
| 788 | Q547 | | Q427 | Q148 | Q335 | Q145 |
| 789 | Q144 | Q144 | Q427 | Q148 | Q336 | Q145 |
| 790 | Q144 | Q144 | Q427 | Q144 | Q388 | Q180 |
| 791 | Q2 | Q144 | Q183 | Q148 | Q397 | Q261 |
| 792 | Q182 | Q144 | Q427 | Q148 | Q402 | Q115 |

-continued

[Chemical Formula 96]

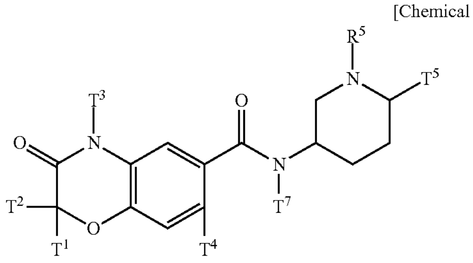

| No. | T1 | T2 | T3 | T4 | T5 | T7 |
|---|---|---|---|---|---|---|
| 793 | Q468 | | Q427 | Q148 | Q223 | Q406 |
| 794 | Q149 | Q144 | Q427 | Q148 | Q264 | Q407 |
| 795 | Q11 | Q144 | Q183 | Q148 | Q353 | Q409 |
| 796 | Q14 | Q145 | Q427 | Q143 | Q215 | Q416 |
| 797 | Q149 | Q144 | Q186 | Q148 | Q307 | Q417 |
| 798 | Q144 | Q144 | Q183 | Q148 | Q339 | Q418 |
| 799 | Q547 | | Q427 | Q148 | Q223 | Q419 |
| 800 | Q144 | Q144 | Q427 | Q148 | Q264 | Q180 |
| 801 | Q144 | Q145 | Q427 | Q144 | Q353 | Q406 |
| 802 | Q2 | Q144 | Q445 | Q148 | Q215 | Q416 |
| 803 | Q182 | Q144 | Q427 | Q148 | Q307 | Q416 |
| 804 | Q468 | | Q427 | Q148 | H | Q406 |
| 805 | Q149 | Q144 | Q427 | Q148 | H | Q407 |
| 806 | Q11 | Q144 | Q183 | Q148 | H | Q409 |
| 807 | Q14 | Q145 | Q427 | Q143 | H | Q416 |
| 808 | Q149 | Q144 | Q186 | Q148 | H | Q417 |
| 809 | Q144 | Q144 | Q183 | Q148 | H | Q418 |
| 810 | Q547 | | Q427 | Q148 | H | Q419 |
| 811 | Q144 | Q144 | Q427 | Q148 | H | Q180 |
| 812 | Q144 | Q145 | Q427 | Q144 | H | Q406 |
| 813 | Q2 | Q144 | Q445 | Q148 | H | Q416 |
| 814 | Q182 | Q144 | Q427 | Q148 | H | Q416 |

[Chemical Formula 97]

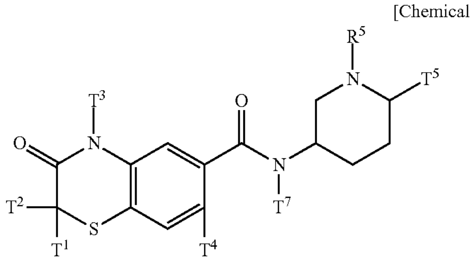

| No. | T1 | T2 | T3 | T4 | T5 | T7 |
|---|---|---|---|---|---|---|
| 815 | Q468 | | Q427 | Q148 | Q223 | Q236 |
| 816 | Q149 | Q144 | Q427 | Q148 | Q264 | Q236 |
| 817 | Q11 | Q144 | Q183 | Q148 | Q353 | Q236 |
| 818 | Q14 | Q145 | Q427 | Q143 | Q215 | Q237 |
| 819 | Q149 | Q144 | Q186 | Q148 | Q307 | Q416 |
| 820 | Q144 | Q144 | Q183 | Q148 | Q339 | Q180 |
| 821 | Q547 | | Q427 | Q148 | Q223 | Q236 |
| 822 | Q144 | Q144 | Q427 | Q148 | Q264 | Q236 |
| 823 | Q144 | Q145 | Q427 | Q144 | Q353 | Q236 |
| 824 | Q2 | Q144 | Q445 | Q148 | Q215 | Q236 |
| 825 | Q182 | Q144 | Q427 | Q148 | Q307 | Q236 |
| 826 | Q473 | | Q427 | Q148 | Q223 | Q236 |
| 827 | Q469 | | Q427 | Q148 | Q264 | Q236 |
| 828 | Q467 | | Q183 | Q148 | Q353 | Q236 |
| 829 | Q496 | | Q427 | Q143 | Q215 | Q237 |
| 830 | Q461 | Q144 | Q186 | Q148 | Q307 | Q416 |
| 831 | Q465 | Q144 | Q183 | Q148 | Q339 | Q180 |
| 832 | Q466 | | Q427 | Q148 | Q223 | Q236 |
| 833 | Q493 | Q144 | Q427 | Q148 | Q264 | Q236 |
| 834 | Q500 | Q145 | Q427 | Q144 | Q353 | Q236 |
| 835 | Q135 | Q144 | Q445 | Q148 | Q215 | Q236 |
| 836 | Q138 | Q144 | Q427 | Q148 | Q307 | Q236 |
| 837 | Q468 | | Q427 | Q148 | H | Q236 |
| 838 | Q149 | Q144 | Q427 | Q148 | H | Q236 |
| 839 | Q11 | Q144 | Q183 | Q148 | H | Q236 |
| 840 | Q14 | Q145 | Q427 | Q143 | H | Q237 |

-continued

| | | | | | | |
|---|---|---|---|---|---|---|
| 841 | Q149 | Q144 | Q186 | Q148 | H | Q416 |
| 842 | Q144 | Q144 | Q183 | Q148 | H | Q180 |
| 843 | Q547 | | Q427 | Q148 | H | Q236 |
| 844 | Q548 | Q144 | Q183 | Q148 | H | Q236 |
| 845 | Q144 | Q145 | Q427 | Q144 | H | Q236 |
| 846 | Q2 | Q144 | Q445 | Q148 | H | Q236 |
| 847 | Q182 | Q144 | Q427 | Q148 | H | Q236 |
| 848 | Q473 | | Q427 | Q148 | H | Q236 |
| 849 | Q469 | | Q427 | Q148 | H | Q236 |
| 850 | Q467 | | Q183 | Q148 | H | Q236 |
| 851 | Q496 | | Q427 | Q143 | H | Q237 |
| 852 | Q461 | Q144 | Q186 | Q148 | H | Q416 |
| 853 | Q465 | Q144 | Q183 | Q148 | H | Q180 |
| 854 | Q466 | | Q427 | Q148 | H | Q236 |
| 855 | Q493 | Q144 | Q427 | Q148 | H | Q236 |
| 856 | Q500 | Q145 | Q427 | Q144 | H | Q236 |
| 857 | Q135 | Q144 | Q445 | Q148 | H | Q236 |
| 858 | Q138 | Q144 | Q427 | Q148 | H | Q236 |

[Chemical Formula 98]

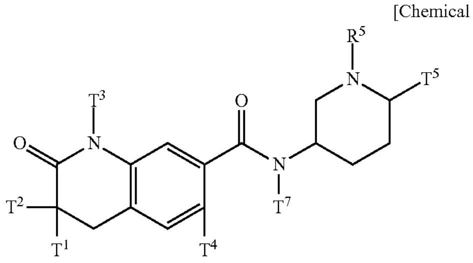

| No. | $T^1$ | $T^2$ | $T^3$ | $T^4$ | $T^5$ | $T^7$ |
|---|---|---|---|---|---|---|
| 859 | Q468 | | Q427 | Q148 | Q223 | Q236 |
| 860 | Q149 | Q144 | Q427 | Q148 | Q264 | Q236 |
| 861 | Q11 | Q144 | Q183 | Q148 | Q353 | Q236 |
| 862 | Q14 | Q145 | Q427 | Q143 | Q215 | Q237 |
| 863 | Q149 | Q144 | Q186 | Q148 | Q307 | Q416 |
| 864 | Q144 | Q144 | Q183 | Q148 | Q339 | Q180 |
| 865 | Q547 | | Q427 | Q148 | Q223 | Q236 |
| 866 | Q144 | Q144 | Q427 | Q148 | Q264 | Q236 |
| 867 | Q144 | Q145 | Q427 | Q144 | Q353 | Q236 |
| 868 | Q2 | Q144 | Q445 | Q148 | Q215 | Q236 |
| 869 | Q182 | Q144 | Q427 | Q148 | Q307 | Q236 |
| 870 | Q473 | | Q427 | Q148 | Q223 | Q236 |
| 871 | Q469 | | Q427 | Q148 | Q264 | Q236 |
| 872 | Q467 | | Q183 | Q148 | Q353 | Q236 |
| 873 | Q496 | | Q427 | Q143 | Q215 | Q237 |
| 874 | Q461 | Q144 | Q186 | Q148 | Q307 | Q416 |
| 875 | Q465 | Q144 | Q183 | Q148 | Q339 | Q180 |
| 876 | Q466 | | Q427 | Q148 | Q223 | Q236 |
| 877 | Q493 | Q144 | Q427 | Q148 | Q264 | Q236 |
| 878 | Q500 | Q145 | Q427 | Q144 | Q353 | Q236 |
| 879 | Q135 | Q144 | Q445 | Q148 | Q215 | Q236 |
| 880 | Q138 | Q144 | Q427 | Q148 | Q307 | Q236 |
| 881 | Q468 | | Q427 | Q148 | H | Q236 |
| 882 | Q149 | Q144 | Q427 | Q148 | H | Q236 |
| 883 | Q11 | Q144 | Q183 | Q148 | H | Q236 |
| 884 | Q14 | Q145 | Q427 | Q143 | H | Q237 |
| 885 | Q149 | Q144 | Q186 | Q148 | H | Q416 |
| 886 | Q144 | Q144 | Q183 | Q148 | H | Q180 |
| 887 | Q547 | | Q427 | Q148 | H | Q236 |
| 888 | Q144 | Q144 | Q427 | Q148 | H | Q236 |
| 889 | Q144 | Q145 | Q427 | Q144 | H | Q236 |
| 890 | Q2 | Q144 | Q445 | Q148 | H | Q236 |
| 891 | Q182 | Q144 | Q427 | Q148 | H | Q236 |
| 892 | Q473 | | Q427 | Q148 | H | Q236 |
| 893 | Q469 | | Q427 | Q148 | H | Q236 |
| 894 | Q467 | | Q183 | Q148 | H | Q236 |
| 895 | Q496 | | Q427 | Q143 | H | Q237 |
| 896 | Q461 | Q144 | Q186 | Q148 | H | Q416 |
| 897 | Q465 | Q144 | Q183 | Q148 | H | Q180 |
| 898 | Q466 | | Q427 | Q148 | H | Q236 |
| 899 | Q493 | Q144 | Q427 | Q148 | H | Q236 |
| 900 | Q500 | Q145 | Q427 | Q144 | H | Q236 |
| 901 | Q135 | Q144 | Q445 | Q148 | H | Q236 |
| 902 | Q138 | Q144 | Q427 | Q148 | H | Q236 |

-continued
[Chemical Formula 99]
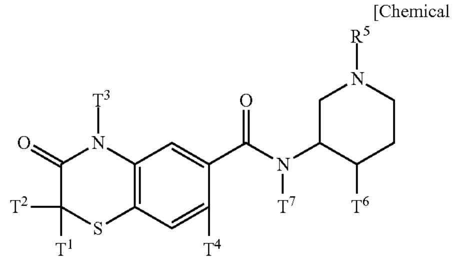
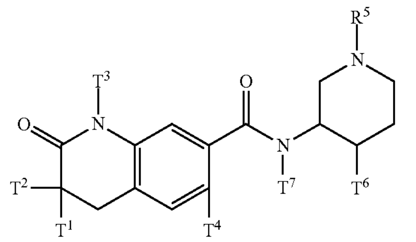
| No. | T1 | T2 | T3 | T4 | T6 | T7 |
|---|---|---|---|---|---|---|
| 903 | Q468 | | Q427 | Q148 | Q292 | Q236 |
| 904 | Q149 | Q144 | Q427 | Q148 | Q293 | Q236 |
| 905 | Q11 | Q144 | Q183 | Q148 | Q294 | Q144 |
| 906 | Q14 | Q145 | Q427 | Q143 | Q295 | Q145 |
| 907 | Q149 | Q144 | Q186 | Q148 | Q297 | Q145 |
| 908 | Q144 | Q144 | Q183 | Q148 | Q298 | Q180 |
| 909 | Q547 | | Q427 | Q148 | Q299 | Q180 |
| 910 | Q144 | Q144 | Q427 | Q148 | Q330 | Q419 |
| 911 | Q144 | Q145 | Q427 | Q144 | Q331 | Q236 |
| 912 | Q2 | Q144 | Q445 | Q148 | Q332 | Q236 |
| 913 | Q182 | Q144 | Q427 | Q148 | Q333 | Q144 |
| 914 | Q473 | | Q427 | Q148 | Q335 | Q145 |
| 915 | Q469 | | Q427 | Q148 | Q336 | Q145 |
| 916 | Q467 | | Q183 | Q148 | Q337 | Q180 |
| 917 | Q496 | | Q427 | Q143 | Q387 | Q180 |
| 918 | Q468 | | Q427 | Q148 | Q292 | Q236 |
| 919 | Q149 | Q144 | Q427 | Q148 | Q293 | Q236 |
| 920 | Q11 | Q144 | Q183 | Q148 | Q294 | Q144 |
| 921 | Q14 | Q145 | Q427 | Q143 | Q295 | Q145 |
| 922 | Q149 | Q144 | Q186 | Q148 | Q297 | Q145 |
| 923 | Q144 | Q144 | Q183 | Q148 | Q298 | Q180 |
| 924 | Q547 | | Q427 | Q148 | Q299 | Q180 |
| 925 | Q144 | Q144 | Q427 | Q148 | Q330 | Q419 |
| 926 | Q144 | Q145 | Q427 | Q144 | Q331 | Q236 |
| 927 | Q2 | Q144 | Q445 | Q148 | Q332 | Q236 |
| 928 | Q182 | Q144 | Q427 | Q148 | Q333 | Q144 |
| 929 | Q473 | | Q427 | Q148 | Q335 | Q145 |
| 930 | Q469 | | Q427 | Q148 | Q336 | Q145 |
| 931 | Q467 | | Q183 | Q148 | Q337 | Q180 |
| 932 | Q496 | | Q427 | Q143 | Q387 | Q180 |
[Chemical Formula 100]
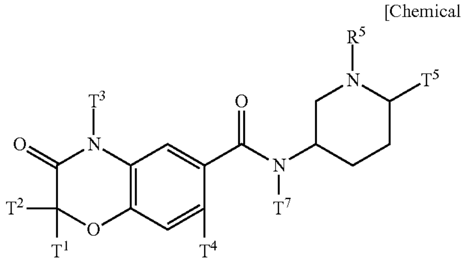
| No. | T1 | T2 | T3 | T4 | T5 | T7 |
|---|---|---|---|---|---|---|
| 933 | Q468 | | Q281 | Q148 | Q233 | Q236 |
| 934 | Q149 | Q144 | Q282 | Q148 | Q264 | Q236 |
| 935 | Q11 | Q144 | Q284 | Q148 | Q353 | Q236 |
| 936 | Q14 | Q145 | Q378 | Q143 | Q215 | Q236 |
| 937 | Q149 | Q144 | Q379 | Q148 | Q307 | Q236 |
| 938 | Q144 | Q144 | Q380 | Q148 | Q339 | Q236 |

-continued

| | | | | | | |
|---|---|---|---|---|---|---|
| 939 | Q547 | | Q381 | Q148 | Q223 | Q236 |
| 940 | Q144 | Q144 | Q382 | Q148 | Q264 | Q180 |
| 941 | Q144 | Q145 | Q383 | Q144 | Q353 | Q236 |
| 942 | Q2 | Q144 | Q384 | Q148 | Q215 | Q236 |
| 943 | Q182 | Q144 | Q385 | Q148 | Q307 | Q236 |
| 944 | Q468 | | Q386 | Q148 | Q223 | Q416 |
| 945 | Q149 | Q144 | Q420 | Q148 | Q264 | Q236 |
| 946 | Q11 | Q144 | Q421 | Q148 | Q353 | Q236 |
| 947 | Q14 | Q145 | Q422 | Q143 | Q215 | Q236 |
| 948 | Q149 | Q144 | Q423 | Q148 | Q307 | Q236 |
| 949 | Q144 | Q144 | Q424 | Q148 | Q339 | Q416 |
| 950 | Q547 | | Q425 | Q148 | Q223 | Q180 |
| 951 | Q144 | Q144 | Q426 | Q148 | Q264 | Q236 |
| 952 | Q144 | Q145 | Q428 | Q144 | Q353 | Q236 |
| 953 | Q2 | Q144 | Q429 | Q148 | Q215 | Q236 |
| 954 | Q182 | Q144 | Q430 | Q148 | Q307 | Q236 |
| 955 | | Q468 | Q431 | Q148 | Q223 | Q236 |
| 956 | Q149 | Q144 | Q432 | Q148 | Q264 | Q236 |
| 957 | Q11 | Q144 | Q433 | Q148 | Q353 | Q236 |
| 958 | Q14 | Q145 | Q434 | Q143 | Q215 | Q236 |
| 959 | Q149 | Q144 | Q435 | Q148 | Q307 | Q236 |
| 960 | Q144 | Q144 | Q436 | Q148 | Q339 | Q180 |
| 961 | Q11 | Q144 | Q437 | Q148 | Q353 | Q236 |
| 962 | Q14 | Q145 | Q438 | Q143 | Q215 | Q236 |
| 963 | Q149 | Q144 | Q439 | Q148 | Q307 | Q236 |
| 964 | Q144 | Q144 | Q440 | Q148 | Q339 | Q416 |
| 965 | Q547 | | Q441 | Q148 | Q223 | Q236 |
| 966 | Q144 | Q144 | Q442 | Q148 | Q264 | Q236 |
| 967 | Q144 | Q145 | Q443 | Q144 | Q353 | Q416 |
| 968 | Q2 | Q144 | Q444 | Q148 | Q215 | Q236 |
| 969 | Q182 | Q144 | Q446 | Q148 | Q307 | Q416 |
| 970 | Q468 | | Q281 | Q148 | H | Q236 |
| 971 | Q149 | Q144 | Q282 | Q148 | H | Q236 |
| 972 | Q11 | Q144 | Q284 | Q148 | H | Q236 |
| 973 | Q14 | Q145 | Q378 | Q143 | H | Q236 |
| 974 | Q149 | Q144 | Q379 | Q148 | H | Q236 |
| 975 | Q144 | Q144 | Q380 | Q148 | H | Q236 |
| 976 | Q547 | | Q381 | Q148 | H | Q236 |
| 977 | Q144 | Q144 | Q382 | Q148 | H | Q180 |
| 978 | Q144 | Q145 | Q383 | Q144 | H | Q236 |
| 979 | Q2 | Q144 | Q384 | Q148 | H | Q236 |
| 980 | Q182 | Q144 | Q385 | Q148 | H | Q236 |
| 981 | Q468 | | Q386 | Q148 | H | Q416 |
| 982 | Q149 | Q144 | Q420 | Q148 | H | Q236 |
| 983 | Q11 | Q144 | Q421 | Q148 | H | Q236 |
| 984 | Q14 | Q145 | Q422 | Q143 | H | Q236 |
| 985 | Q149 | Q144 | Q423 | Q148 | H | Q236 |
| 986 | Q144 | Q144 | Q424 | Q148 | H | Q416 |
| 987 | Q547 | | Q425 | Q148 | H | Q180 |
| 988 | Q144 | Q144 | Q426 | Q148 | H | Q236 |
| 989 | Q144 | Q145 | Q428 | Q144 | H | Q236 |
| 990 | Q2 | Q144 | Q429 | Q148 | H | Q236 |
| 991 | Q182 | Q144 | Q430 | Q148 | H | Q236 |
| 992 | Q468 | | Q431 | Q148 | H | Q236 |
| 993 | Q149 | Q144 | Q432 | Q148 | H | Q236 |
| 994 | Q11 | Q144 | Q433 | Q148 | H | Q236 |
| 995 | Q14 | Q145 | Q434 | Q143 | H | Q236 |
| 996 | Q149 | Q144 | Q435 | Q148 | H | Q236 |
| 997 | Q144 | Q144 | Q436 | Q148 | H | Q180 |
| 998 | Q11 | Q144 | Q437 | Q148 | H | Q236 |
| 999 | Q14 | Q145 | Q438 | Q143 | H | Q236 |
| 1000 | Q149 | Q144 | Q439 | Q148 | H | Q236 |
| 1001 | Q144 | Q144 | Q440 | Q148 | H | Q416 |
| 1002 | Q547 | | Q441 | Q148 | H | Q236 |
| 1003 | Q144 | Q144 | Q442 | Q148 | H | Q236 |
| 1004 | Q144 | Q145 | Q443 | Q144 | H | Q416 |
| 1005 | Q2 | Q144 | Q444 | Q148 | H | Q236 |
| 1006 | Q182 | Q144 | Q446 | Q148 | H | Q416 |

-continued

[Chemical Formula 101]

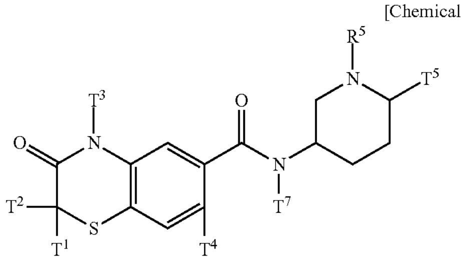

| No. | T1 | T2 | T3 | T4 | T5 | T7 |
|---|---|---|---|---|---|---|
| 1007 | Q468 | | Q281 | Q148 | Q223 | Q236 |
| 1008 | Q149 | Q144 | Q282 | Q148 | Q264 | Q236 |
| 1009 | Q11 | Q144 | Q284 | Q148 | Q353 | Q236 |
| 1010 | Q14 | Q145 | Q378 | Q143 | Q215 | Q236 |
| 1011 | Q149 | Q144 | Q379 | Q148 | Q307 | Q236 |
| 1012 | Q144 | Q144 | Q380 | Q148 | Q339 | Q236 |
| 1013 | Q547 | | Q381 | Q148 | Q223 | Q236 |
| 1014 | Q144 | Q144 | Q382 | Q148 | Q264 | Q180 |
| 1015 | Q144 | Q145 | Q383 | Q144 | Q353 | Q236 |
| 1016 | Q2 | Q144 | Q384 | Q148 | Q215 | Q236 |
| 1017 | Q182 | Q144 | Q385 | Q148 | Q307 | Q236 |
| 1018 | Q468 | | Q386 | Q148 | Q223 | Q416 |
| 1019 | Q149 | Q144 | Q420 | Q148 | Q264 | Q236 |
| 1020 | Q11 | Q144 | Q421 | Q148 | Q353 | Q236 |
| 1021 | Q14 | Q145 | Q422 | Q143 | Q215 | Q236 |
| 1022 | Q149 | Q144 | Q423 | Q148 | Q307 | Q236 |
| 1023 | Q144 | Q144 | Q424 | Q148 | Q339 | Q416 |
| 1024 | Q547 | | Q425 | Q148 | Q223 | Q180 |
| 1025 | Q144 | Q144 | Q426 | Q148 | Q264 | Q236 |
| 1026 | Q144 | Q145 | Q428 | Q144 | Q353 | Q236 |
| 1027 | Q2 | Q144 | Q429 | Q148 | Q215 | Q236 |
| 1028 | Q182 | Q144 | Q430 | Q148 | Q307 | Q236 |
| 1029 | Q468 | | Q431 | Q148 | Q223 | Q236 |
| 1030 | Q149 | Q144 | Q432 | Q148 | Q264 | Q236 |
| 1031 | Q11 | Q144 | Q433 | Q148 | Q353 | Q236 |
| 1032 | Q14 | Q145 | Q434 | Q143 | Q215 | Q236 |
| 1033 | Q149 | Q144 | Q435 | Q148 | Q307 | Q236 |
| 1034 | Q144 | Q144 | Q436 | Q148 | Q339 | Q180 |
| 1035 | Q11 | Q144 | Q437 | Q148 | Q353 | Q236 |
| 1036 | Q14 | Q145 | Q438 | Q143 | Q215 | Q236 |
| 1037 | Q149 | Q144 | Q439 | Q148 | Q307 | Q236 |
| 1038 | Q144 | Q144 | Q440 | Q148 | Q339 | Q416 |
| 1039 | Q547 | | Q441 | Q148 | Q223 | Q236 |
| 1040 | Q144 | Q144 | Q442 | Q148 | Q264 | Q236 |
| 1041 | Q144 | Q145 | Q443 | Q144 | Q353 | Q416 |
| 1042 | Q2 | Q144 | Q444 | Q148 | Q215 | Q236 |
| 1043 | Q182 | Q144 | Q446 | Q148 | Q307 | Q416 |
| 1044 | Q468 | | Q281 | Q148 | H | Q236 |
| 1045 | Q149 | Q144 | Q282 | Q148 | H | Q236 |
| 1046 | Q11 | Q144 | Q284 | Q148 | H | Q236 |
| 1047 | Q14 | Q145 | Q378 | Q143 | H | Q236 |
| 1048 | Q149 | Q144 | Q379 | Q148 | H | Q236 |
| 1049 | Q144 | Q144 | Q380 | Q148 | H | Q236 |
| 1050 | Q547 | | Q381 | Q148 | H | Q236 |
| 1051 | Q144 | Q144 | Q382 | Q148 | H | Q180 |
| 1052 | Q144 | Q145 | Q383 | Q144 | H | Q236 |
| 1053 | Q2 | Q144 | Q384 | Q148 | H | Q236 |
| 1054 | Q182 | Q144 | Q385 | Q148 | H | Q236 |
| 1055 | Q468 | | Q386 | Q148 | H | Q416 |
| 1056 | Q149 | Q144 | Q420 | Q148 | H | Q236 |
| 1057 | Q11 | Q144 | Q421 | Q148 | H | Q236 |
| 1058 | Q14 | Q145 | Q422 | Q143 | H | Q236 |
| 1059 | Q149 | Q144 | Q423 | Q148 | H | Q236 |
| 1060 | Q144 | Q144 | Q424 | Q148 | H | Q416 |
| 1061 | Q547 | | Q425 | Q148 | H | Q180 |
| 1062 | Q144 | Q144 | Q426 | Q148 | H | Q236 |
| 1063 | Q144 | Q145 | Q428 | Q144 | H | Q236 |
| 1064 | Q2 | Q144 | Q429 | Q148 | H | Q236 |
| 1065 | Q182 | Q144 | Q430 | Q148 | H | Q236 |
| 1066 | Q468 | | Q431 | Q148 | H | Q236 |
| 1067 | Q149 | Q144 | Q432 | Q148 | H | Q236 |
| 1068 | Q11 | Q144 | Q433 | Q148 | H | Q236 |
| 1069 | Q14 | Q145 | Q434 | Q143 | H | Q236 |
| 1070 | Q149 | Q144 | Q435 | Q148 | H | Q236 |
| 1071 | Q144 | Q144 | Q436 | Q148 | H | Q180 |

-continued

| | | | | | | |
|---|---|---|---|---|---|---|
| 1072 | Q11 | Q144 | Q437 | Q148 | H | Q236 |
| 1073 | Q14 | Q145 | Q438 | Q143 | H | Q236 |
| 1074 | Q149 | Q144 | Q439 | Q148 | H | Q236 |
| 1075 | Q144 | Q144 | Q440 | Q148 | H | Q416 |
| 1076 | Q547 | | Q441 | Q148 | H | Q236 |
| 1077 | Q144 | Q144 | Q442 | Q148 | H | Q236 |
| 1078 | Q144 | Q145 | Q443 | Q144 | H | Q416 |
| 1079 | Q2 | Q144 | Q444 | Q148 | H | Q236 |
| 1080 | Q182 | Q144 | Q446 | Q148 | H | Q416 |

[Chemical Formula 102]

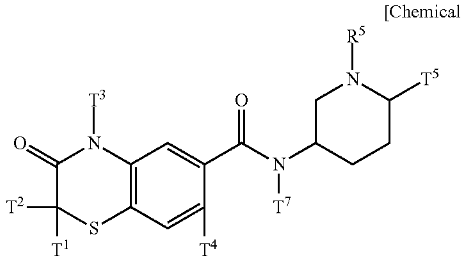

| No. | $T^1$ | $T^2$ | $T^3$ | $T^4$ | $T^5$ | $T^7$ |
|---|---|---|---|---|---|---|
| 1081 | Q468 | | Q281 | Q148 | Q223 | Q236 |
| 1082 | Q149 | Q144 | Q282 | Q148 | Q264 | Q236 |
| 1083 | Q11 | Q144 | Q284 | Q148 | Q353 | Q236 |
| 1084 | Q14 | Q145 | Q378 | Q143 | Q215 | Q236 |
| 1085 | Q149 | Q144 | Q379 | Q148 | Q307 | Q236 |
| 1086 | Q144 | Q144 | Q380 | Q148 | Q339 | Q236 |
| 1087 | Q547 | | Q381 | Q148 | Q223 | Q236 |
| 1088 | Q144 | Q144 | Q382 | Q148 | Q264 | Q180 |
| 1089 | Q144 | Q145 | Q383 | Q144 | Q353 | Q236 |
| 1090 | Q2 | Q144 | Q384 | Q148 | Q215 | Q236 |
| 1091 | Q182 | Q144 | Q385 | Q148 | Q307 | Q236 |
| 1092 | Q468 | | Q386 | Q148 | Q223 | Q416 |
| 1093 | Q149 | Q144 | Q420 | Q148 | Q264 | Q236 |
| 1094 | Q11 | Q144 | Q421 | Q148 | Q353 | Q236 |
| 1095 | Q14 | Q145 | Q422 | Q143 | Q215 | Q236 |
| 1096 | Q149 | Q144 | Q423 | Q148 | Q307 | Q236 |
| 1097 | Q144 | Q144 | Q424 | Q148 | Q339 | Q416 |
| 1098 | Q547 | | Q425 | Q148 | Q223 | Q180 |
| 1099 | Q144 | Q144 | Q426 | Q148 | Q264 | Q236 |
| 1100 | Q144 | Q145 | Q428 | Q144 | Q353 | Q236 |
| 1101 | Q2 | Q144 | Q429 | Q148 | Q215 | Q236 |
| 1102 | Q182 | Q144 | Q430 | Q148 | Q307 | Q236 |
| 1103 | Q468 | | Q431 | Q148 | Q223 | Q236 |
| 1104 | Q149 | Q144 | Q432 | Q148 | Q264 | Q236 |
| 1105 | Q11 | Q144 | Q433 | Q148 | Q353 | Q236 |
| 1106 | Q14 | Q145 | Q434 | Q143 | Q215 | Q236 |
| 1107 | Q149 | Q144 | Q435 | Q148 | Q307 | Q236 |
| 1108 | Q144 | Q144 | Q436 | Q148 | Q339 | Q180 |
| 1109 | Q11 | Q144 | Q437 | Q148 | Q353 | Q236 |
| 1110 | Q14 | Q145 | Q438 | Q143 | Q215 | Q236 |
| 1111 | Q149 | Q144 | Q439 | Q148 | Q307 | Q236 |
| 1112 | Q144 | Q144 | Q440 | Q148 | Q339 | Q416 |
| 1113 | Q547 | | Q441 | Q148 | Q223 | Q236 |
| 1114 | Q144 | Q144 | Q442 | Q148 | Q264 | Q236 |
| 1115 | Q144 | Q145 | Q443 | Q144 | Q353 | Q416 |
| 1116 | Q2 | Q144 | Q444 | Q148 | Q215 | Q236 |
| 1117 | Q182 | Q144 | Q446 | Q148 | Q307 | Q416 |
| 1118 | Q468 | | Q281 | Q148 | H | Q236 |
| 1119 | Q149 | Q144 | Q282 | Q148 | H | Q236 |
| 1120 | Q11 | Q144 | Q284 | Q148 | H | Q236 |
| 1121 | Q14 | Q145 | Q378 | Q143 | H | Q236 |
| 1122 | Q149 | Q144 | Q379 | Q148 | H | Q236 |
| 1123 | Q144 | Q144 | Q380 | Q148 | H | Q236 |
| 1124 | Q547 | | Q381 | Q148 | H | Q236 |
| 1125 | Q144 | Q144 | Q382 | Q148 | H | Q180 |
| 1126 | Q144 | Q145 | Q383 | Q144 | H | Q236 |
| 1127 | Q2 | Q144 | Q384 | Q148 | H | Q236 |
| 1128 | Q182 | Q144 | Q385 | Q148 | H | Q236 |
| 1129 | Q468 | | Q386 | Q148 | H | Q416 |
| 1130 | Q149 | Q144 | Q420 | Q148 | H | Q236 |
| 1131 | Q11 | Q144 | Q421 | Q148 | H | Q236 |
| 1132 | Q14 | Q145 | Q422 | Q143 | H | Q236 |
| 1133 | Q149 | Q144 | Q423 | Q148 | H | Q236 |
| 1134 | Q144 | Q144 | Q424 | Q148 | H | Q416 |
| 1135 | Q547 | | Q425 | Q148 | H | Q180 |

-continued

| | | | | | | |
|---|---|---|---|---|---|---|
| 1136 | Q144 | Q144 | Q426 | Q148 | H | Q236 |
| 1137 | Q144 | Q145 | Q428 | Q144 | H | Q236 |
| 1138 | Q2 | Q144 | Q429 | Q148 | H | Q236 |
| 1139 | Q182 | Q144 | Q430 | Q148 | H | Q236 |
| 1140 | Q468 | | Q431 | Q148 | H | Q236 |
| 1141 | Q149 | Q144 | Q432 | Q148 | H | Q236 |
| 1142 | Q11 | Q144 | Q433 | Q148 | H | Q236 |
| 1143 | Q14 | Q145 | Q434 | Q143 | H | Q236 |
| 1144 | Q149 | Q144 | Q435 | Q148 | H | Q236 |
| 1145 | Q144 | Q144 | Q436 | Q148 | H | Q180 |
| 1146 | Q11 | Q144 | Q437 | Q148 | H | Q236 |
| 1147 | Q14 | Q145 | Q438 | Q143 | H | Q236 |
| 1148 | Q149 | Q144 | Q439 | Q148 | H | Q236 |
| 1149 | Q144 | Q144 | Q440 | Q148 | H | Q416 |
| 1150 | Q547 | | Q441 | Q148 | H | Q236 |
| 1151 | Q144 | Q144 | Q442 | Q148 | H | Q236 |
| 1152 | Q144 | Q145 | Q443 | Q144 | H | Q416 |
| 1153 | Q2 | Q144 | Q444 | Q148 | H | Q236 |
| 1154 | Q182 | Q144 | Q446 | Q148 | H | Q416 |

[Chemical Formula 103]

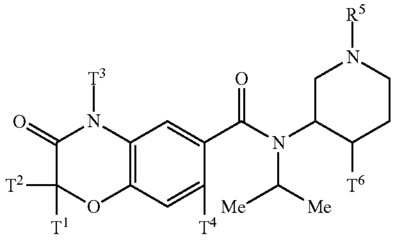

| No. | $T^1$ | $T^2$ | $T^3$ | $T^4$ | $T^6$ |
|---|---|---|---|---|---|
| 1155 | Q468 | | Q428 | Q148 | Q292 |
| 1156 | Q144 | Q144 | Q428 | Q148 | Q293 |
| 1157 | Q149 | Q144 | Q428 | Q148 | Q294 |
| 1158 | Q144 | Q144 | Q428 | Q143 | Q295 |
| 1159 | Q149 | Q144 | Q430 | Q148 | Q297 |
| 1160 | Q144 | Q144 | Q430 | Q148 | Q298 |
| 1161 | Q547 | | Q430 | Q148 | Q299 |
| 1162 | Q144 | Q144 | Q425 | Q148 | Q330 |
| 1163 | Q144 | Q144 | Q425 | Q144 | Q331 |
| 1164 | Q2 | Q144 | Q425 | Q148 | Q332 |
| 1165 | Q182 | Q144 | Q437 | Q148 | Q333 |
| 1166 | Q144 | Q144 | Q437 | Q148 | Q335 |
| 1167 | Q103 | Q144 | Q437 | Q262 | Q336 |
| 1168 | Q2 | Q144 | Q428 | Q148 | Q337 |
| 1169 | Q144 | Q144 | Q428 | Q148 | Q387 |
| 1170 | Q547 | | Q428 | Q147 | Q388 |
| 1171 | Q144 | Q144 | Q428 | Q148 | Q389 |
| 1172 | Q285 | Q144 | Q428 | Q148 | Q391 |
| 1173 | Q144 | Q144 | Q428 | Q148 | Q392 |
| 1174 | Q144 | Q144 | Q430 | Q148 | Q393 |
| 1175 | Q11 | Q144 | Q430 | Q148 | Q394 |
| 1176 | Q468 | | Q430 | Q148 | Q395 |
| 1177 | Q144 | Q144 | Q425 | Q147 | Q396 |
| 1178 | Q144 | Q145 | Q425 | Q148 | Q397 |
| 1179 | Q144 | Q144 | Q425 | Q148 | Q398 |
| 1180 | Q468 | | Q437 | Q148 | Q399 |
| 1181 | Q144 | Q144 | Q437 | Q148 | Q400 |
| 1182 | Q176 | Q144 | Q437 | Q148 | Q401 |
| 1183 | Q11 | Q144 | Q428 | Q148 | Q402 |
| 1184 | Q144 | Q144 | Q428 | Q148 | Q403 |

-continued
[Chemical Formula 104]
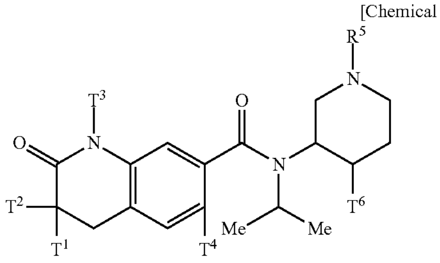
| No. | T1 | T2 | T3 | T4 | T6 |
|---|---|---|---|---|---|
| 1185 | Q468 | | Q428 | Q148 | Q292 |
| 1186 | Q144 | Q144 | Q428 | Q148 | Q293 |
| 1187 | Q149 | Q144 | Q428 | Q148 | Q294 |
| 1188 | Q144 | Q144 | Q428 | Q143 | Q295 |
| 1189 | Q149 | Q144 | Q430 | Q148 | Q297 |
| 1190 | Q144 | Q144 | Q430 | Q148 | Q298 |
| 1191 | Q547 | | Q430 | Q148 | Q299 |
| 1192 | Q144 | Q144 | Q425 | Q148 | Q330 |
| 1193 | Q144 | Q144 | Q425 | Q144 | Q331 |
| 1194 | Q2 | Q144 | Q425 | Q148 | Q332 |
| 1195 | Q182 | Q144 | Q437 | Q148 | Q333 |
| 1196 | Q144 | Q144 | Q437 | Q148 | Q335 |
| 1197 | Q103 | Q144 | Q437 | Q262 | Q336 |
| 1198 | Q2 | Q144 | Q428 | Q148 | Q337 |
| 1199 | Q144 | Q144 | Q428 | Q148 | Q387 |
| 1200 | Q547 | | Q428 | Q147 | Q388 |
| 1201 | Q144 | Q144 | Q428 | Q148 | Q389 |
| 1202 | Q285 | Q144 | Q428 | Q148 | Q391 |
| 1203 | Q144 | Q144 | Q428 | Q148 | Q392 |
| 1204 | Q144 | Q144 | Q430 | Q148 | Q393 |
| 1205 | Q11 | Q144 | Q430 | Q148 | Q394 |
| 1206 | Q468 | | Q430 | Q148 | Q395 |
| 1207 | Q144 | Q144 | Q425 | Q147 | Q396 |
| 1208 | Q144 | Q145 | Q425 | Q148 | Q397 |
| 1209 | Q144 | Q144 | Q425 | Q148 | Q398 |
| 1210 | Q468 | | Q437 | Q148 | Q399 |
| 1211 | Q144 | Q144 | Q437 | Q148 | Q400 |
| 1212 | Q176 | Q144 | Q437 | Q148 | Q401 |
| 1213 | Q11 | Q144 | Q428 | Q148 | Q402 |
| 1214 | Q144 | Q144 | Q428 | Q148 | Q403 |
[Chemical Formula 105]
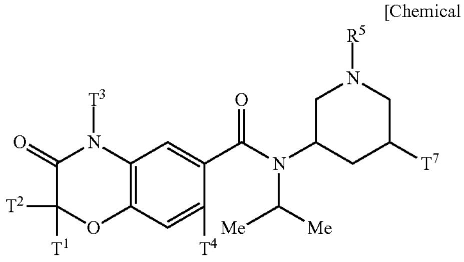
| No. | T1 | T2 | T3 | T4 | T7 |
|---|---|---|---|---|---|
| 1215 | Q468 | | Q183 | Q148 | Q223 |
| 1216 | Q144 | Q144 | Q186 | Q148 | Q204 |
| 1217 | Q149 | Q144 | Q183 | Q148 | Q210 |
| 1218 | Q144 | Q144 | Q183 | Q143 | Q212 |
| 1219 | Q149 | Q144 | Q186 | Q148 | Q227 |
| 1220 | Q144 | Q144 | Q183 | Q148 | Q228 |
| 1221 | Q547 | | Q427 | Q148 | Q219 |
| 1222 | Q144 | Q144 | Q445 | Q148 | Q220 |
| 1223 | Q144 | Q144 | Q427 | Q144 | Q219 |
| 1224 | Q2 | Q144 | Q445 | Q148 | Q221 |
| 1225 | Q182 | Q144 | Q427 | Q148 | Q205 |
| 1226 | Q144 | Q144 | Q427 | Q148 | Q195 |
| 1227 | Q103 | Q144 | Q427 | Q262 | Q234 |
| 1228 | Q2 | Q144 | Q186 | Q148 | Q235 |
| 1229 | Q144 | Q144 | Q186 | Q148 | Q200 |
| 1230 | Q547 | | Q183 | Q147 | Q314 |
| 1231 | Q144 | Q144 | Q186 | Q148 | Q307 |
| 1232 | Q285 | Q144 | Q183 | Q148 | Q322 |

-continued

| | | | | | |
|---|---|---|---|---|---|
| 1233 | Q144 | Q144 | Q183 | Q148 | Q327 |
| 1234 | Q144 | Q144 | Q186 | Q148 | Q344 |
| 1235 | Q11 | Q144 | Q183 | Q148 | Q368 |
| 1236 | Q468 | | Q427 | Q148 | Q376 |
| 1237 | Q144 | Q144 | Q445 | Q147 | Q353 |
| 1238 | Q144 | Q145 | Q427 | Q148 | Q361 |
| 1239 | Q144 | Q144 | Q445 | Q148 | Q338 |
| 1240 | Q468 | | Q427 | Q148 | Q349 |
| 1241 | Q144 | Q144 | Q427 | Q148 | Q318 |
| 1242 | Q176 | Q144 | Q427 | Q148 | Q366 |
| 1243 | Q11 | Q144 | Q186 | Q148 | Q123 |
| 1244 | Q144 | Q144 | Q186 | Q148 | Q323 |

[Chemical Formula 106]

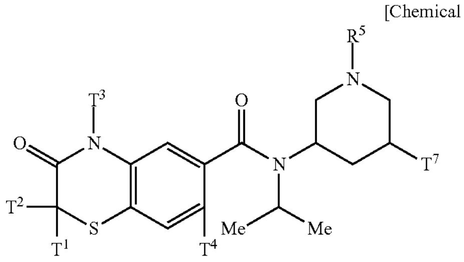

| No. | $T^1$ | $T^2$ | $T^3$ | $T^4$ | $T^7$ |
|---|---|---|---|---|---|
| 1245 | Q468 | | Q183 | Q148 | Q223 |
| 1246 | Q144 | Q144 | Q186 | Q148 | Q204 |
| 1247 | Q149 | Q144 | Q183 | Q148 | Q210 |
| 1248 | Q144 | Q144 | Q183 | Q143 | Q212 |
| 1249 | Q149 | Q144 | Q186 | Q148 | Q227 |
| 1250 | Q144 | Q144 | Q183 | Q148 | Q228 |
| 1251 | Q547 | | Q427 | Q148 | Q219 |
| 1252 | Q144 | Q144 | Q445 | Q148 | Q220 |
| 1253 | Q144 | Q144 | Q427 | Q144 | Q219 |
| 1254 | Q2 | Q144 | Q445 | Q148 | Q221 |
| 1255 | Q182 | Q144 | Q427 | Q148 | Q205 |
| 1256 | Q144 | Q144 | Q427 | Q148 | Q195 |
| 1257 | Q103 | Q144 | Q427 | Q262 | Q234 |
| 1258 | Q2 | Q144 | Q186 | Q148 | Q235 |
| 1259 | Q144 | Q144 | Q186 | Q148 | Q200 |
| 1260 | Q547 | | Q183 | Q147 | Q314 |
| 1261 | Q144 | Q144 | Q186 | Q148 | Q307 |
| 1262 | Q285 | Q144 | Q183 | Q148 | Q322 |
| 1263 | Q144 | Q144 | Q183 | Q148 | Q327 |
| 1264 | Q144 | Q144 | Q186 | Q148 | Q344 |
| 1265 | Q11 | Q144 | Q183 | Q148 | Q368 |
| 1266 | Q468 | | Q427 | Q148 | Q376 |
| 1267 | Q144 | Q144 | Q445 | Q147 | Q353 |
| 1268 | Q144 | Q145 | Q427 | Q148 | Q361 |
| 1269 | Q144 | Q144 | Q445 | Q148 | Q338 |
| 1270 | Q468 | | Q427 | Q148 | Q349 |
| 1271 | Q144 | Q144 | Q427 | Q148 | Q318 |
| 1272 | Q176 | Q144 | Q427 | Q148 | Q366 |
| 1273 | Q11 | Q144 | Q186 | Q148 | Q123 |
| 1274 | Q144 | Q144 | Q186 | Q148 | Q323 |

[Chemical Formula 107]

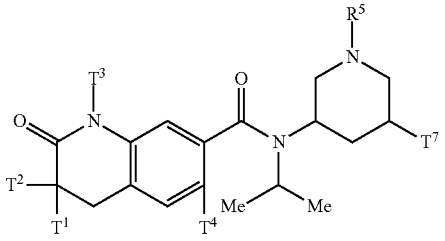

| No. | $T^1$ | $T^2$ | $T^3$ | $T^4$ | $T^7$ |
|---|---|---|---|---|---|
| 1275 | Q468 | | Q183 | Q148 | Q223 |
| 1276 | Q144 | Q144 | Q186 | Q148 | Q204 |
| 1277 | Q149 | Q144 | Q183 | Q148 | Q210 |
| 1278 | Q144 | Q144 | Q183 | Q143 | Q212 |
| 1279 | Q149 | Q144 | Q186 | Q148 | Q227 |

-continued

| | | | | | |
|---|---|---|---|---|---|
| 1280 | Q144 | Q144 | Q183 | Q148 | Q228 |
| 1281 | Q547 | | Q427 | Q148 | Q219 |
| 1282 | Q144 | Q144 | Q445 | Q148 | Q220 |
| 1283 | Q144 | Q144 | Q427 | Q144 | Q219 |
| 1284 | Q2 | Q144 | Q445 | Q148 | Q221 |
| 1285 | Q182 | Q144 | Q427 | Q148 | Q205 |
| 1286 | Q144 | Q144 | Q427 | Q148 | Q195 |
| 1287 | Q103 | Q144 | Q427 | Q262 | Q234 |
| 1288 | Q2 | Q144 | Q186 | Q148 | Q235 |
| 1289 | Q144 | Q144 | Q186 | Q148 | Q200 |
| 1290 | Q547 | | Q183 | Q147 | Q314 |
| 1291 | Q144 | Q144 | Q186 | Q148 | Q307 |
| 1292 | Q285 | Q144 | Q183 | Q148 | Q322 |
| 1293 | Q144 | Q144 | Q183 | Q148 | Q327 |
| 1294 | Q144 | Q144 | Q186 | Q148 | Q344 |
| 1295 | Q11 | Q144 | Q183 | Q148 | Q368 |
| 1296 | Q468 | | Q427 | Q148 | Q376 |
| 1297 | Q144 | Q144 | Q445 | Q147 | Q353 |
| 1298 | Q144 | Q145 | Q427 | Q148 | Q361 |
| 1299 | Q144 | Q144 | Q445 | Q148 | Q338 |
| 1300 | Q468 | | Q427 | Q148 | Q349 |
| 1301 | Q144 | Q144 | Q427 | Q148 | Q318 |
| 1302 | Q176 | Q144 | Q427 | Q148 | Q366 |
| 1303 | Q11 | Q144 | Q186 | Q148 | Q123 |
| 1304 | Q144 | Q144 | Q186 | Q148 | Q323 |

Abbreviated symbols in the above tables refer to partial structures optionally selected from the group consisting of the following partial structural formulae.

[Chemical Formula 108]

P1:

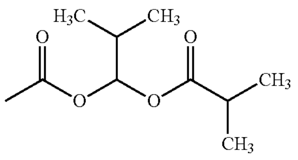

P2:

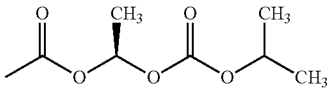

P3:

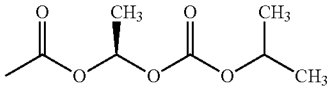

P4:

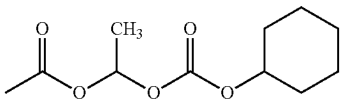

P5:

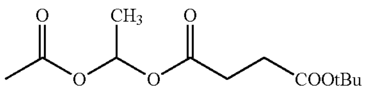

P6:

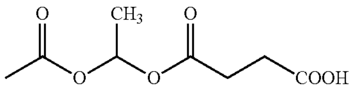

P7:

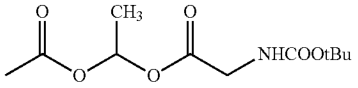

-continued

P8:

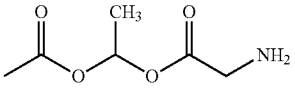

P9:

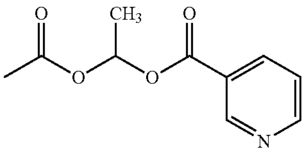

P10:

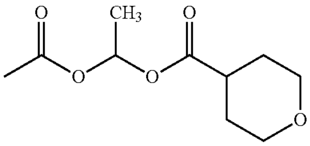

P11:

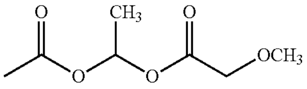

P12:

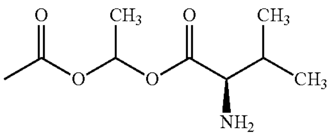

P13:

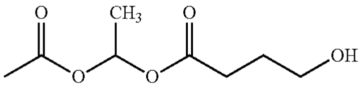

P14:

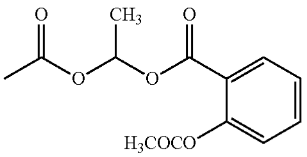

-continued
P15:
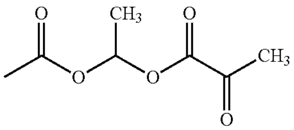
P16:
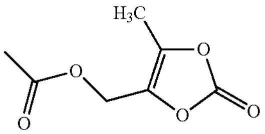
P17:
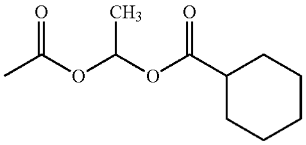
P18:
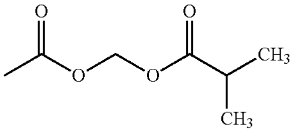
P19:
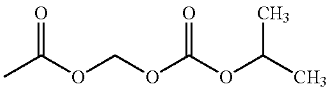
P20:
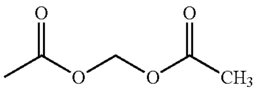
P21:
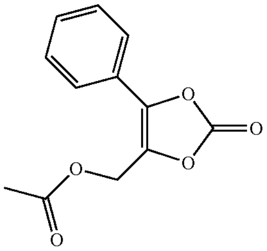
P22:
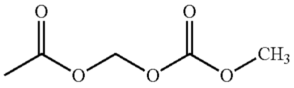
P23:
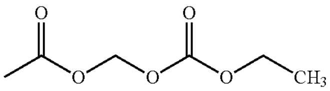
P24:
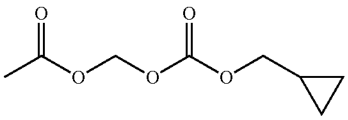
P25:
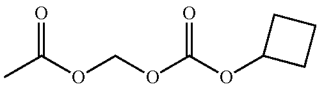
-continued
P26:
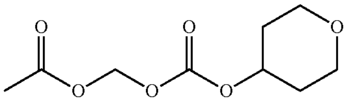
P27:
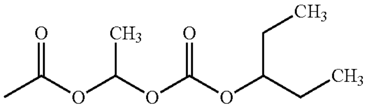
P28:
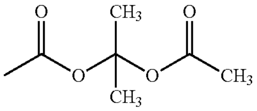
P29:
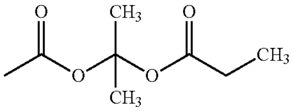
P30:
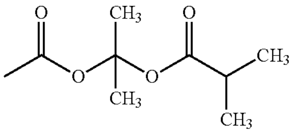
P31:
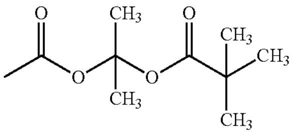
P32:
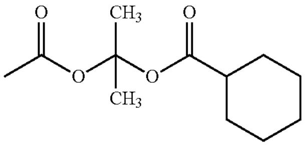
P33:
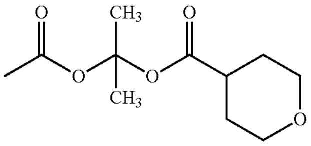
P34:
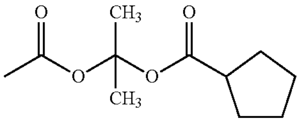
P35:
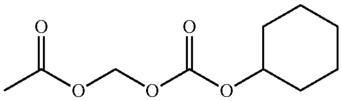
P36:
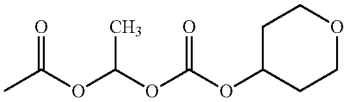

-continued
[Chemical Formula 109]
P37:
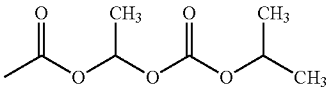
P38:
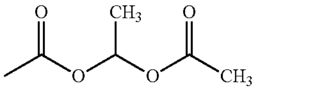
P39:
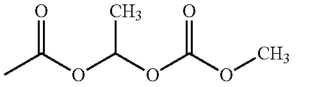
P40:
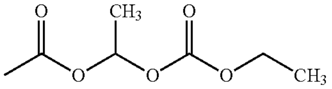
P41:
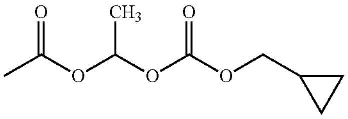
P42:
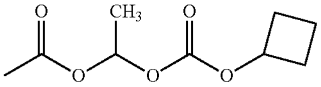
P43:
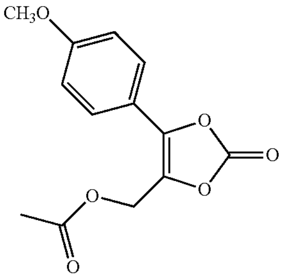
P44:
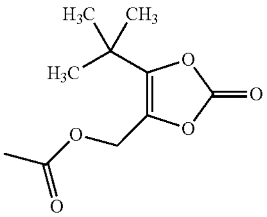
P45:
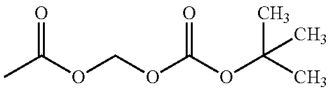
P46:
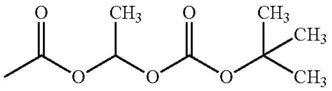
P47:
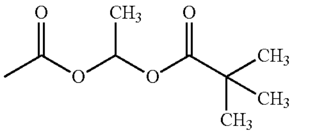
-continued
P48:
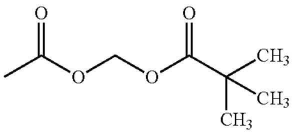
P49:
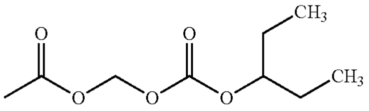
P50:
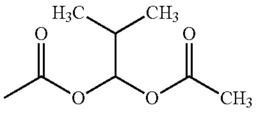
P51:
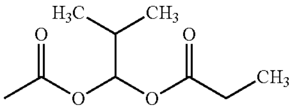
P52:
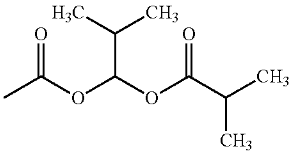
P53:
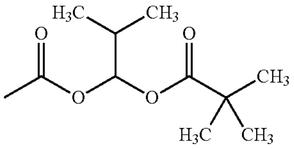
P54:
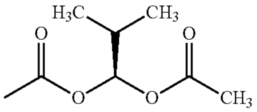
P55:
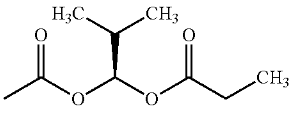
P56:
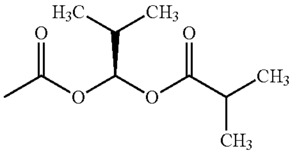
P57:
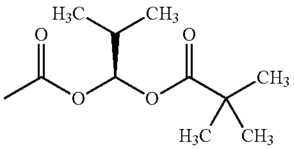

-continued
P58:
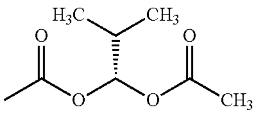
P59:
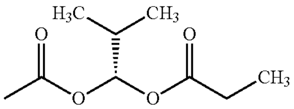
P60:
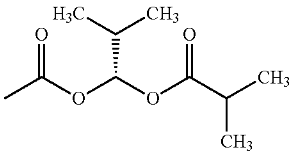
P61:
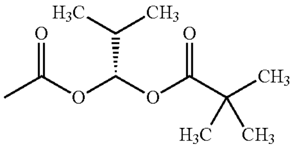
P62:
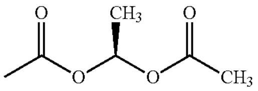
P63:
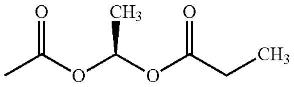
P64:
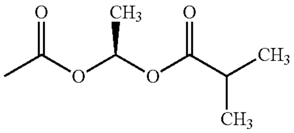
P65:
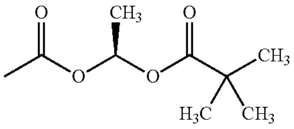
P66:
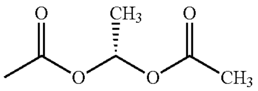
P67:
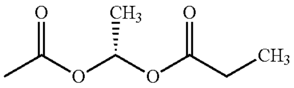
P68:
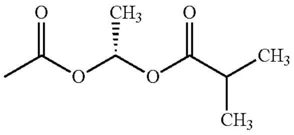
-continued
P69:
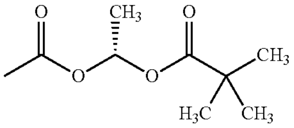
P70:
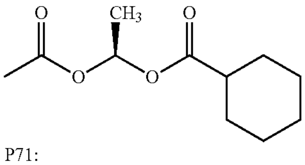
P71:
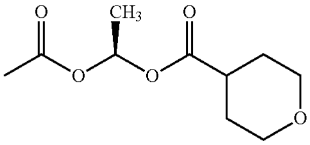
P72:
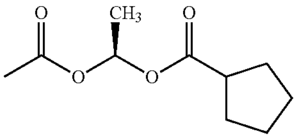
P73:
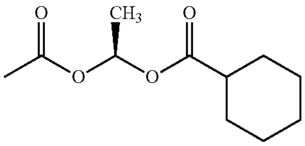
P74:
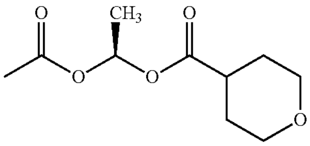
P75:
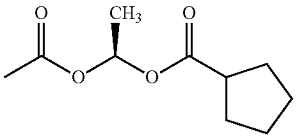
[Chemical Formula 110]
P76:
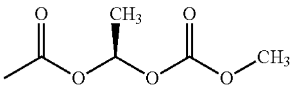
P77:
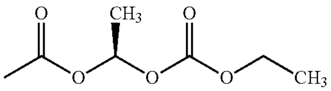
P78:
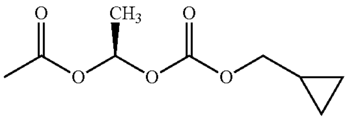
P79:
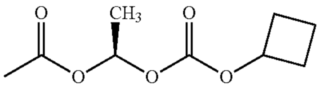

-continued
P80:
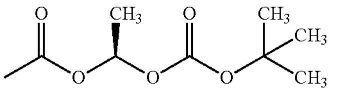
P81:
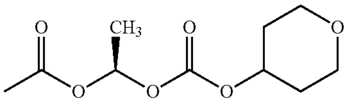
P82:
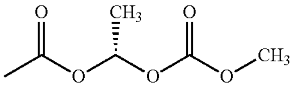
P83:
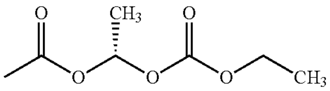
P84:
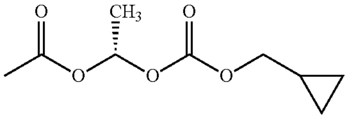
P85:
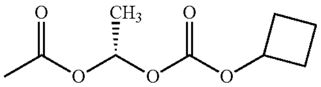
P86:
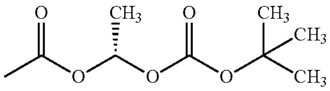
P87:
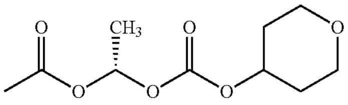
P88:
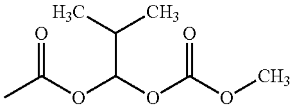
P89:
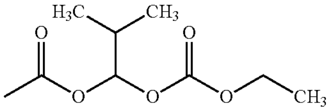
P90:
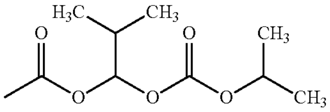
P91:
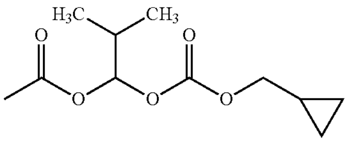
-continued
P92:
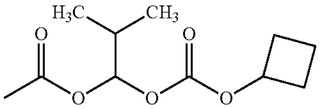
P93:
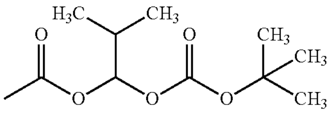
P94:
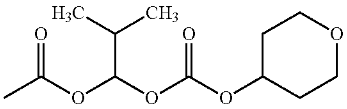
P95:
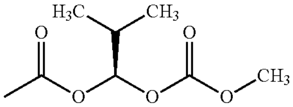
P96:
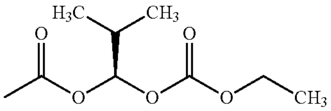
P97:
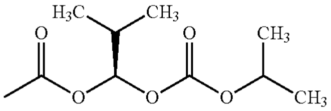
P98:
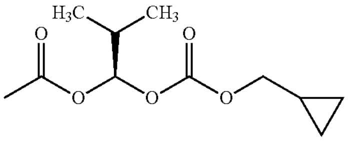
P99:
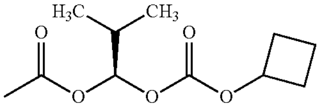
P100:
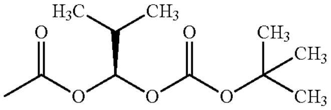
P101:
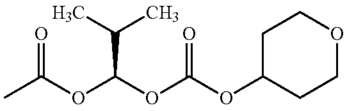
P102:
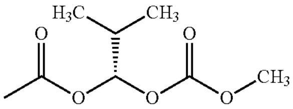
P103:
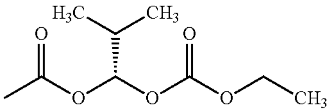

-continued
P104:
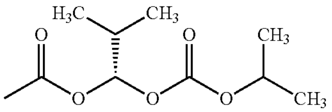
P105:
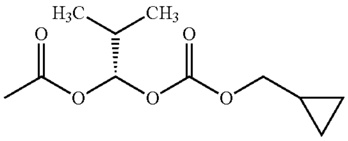
P106:
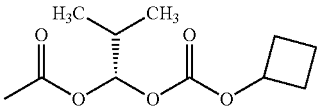
P107:
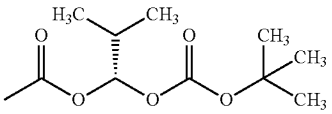
P108:
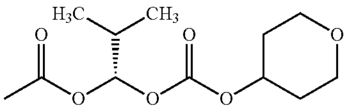
P109:
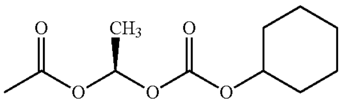
P110:
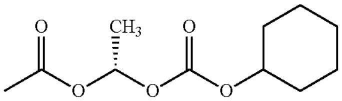
P111:
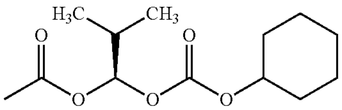
P112:
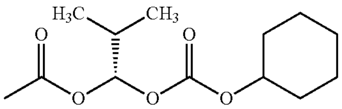
P113:
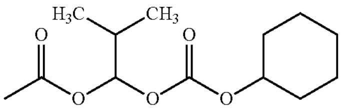
P114:
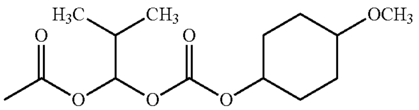
-continued
[Chemical Formula 111]
P115:
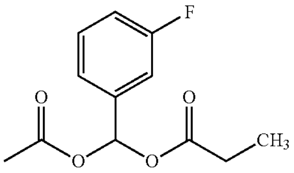
P116:
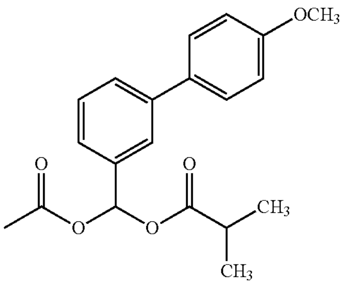
P117:
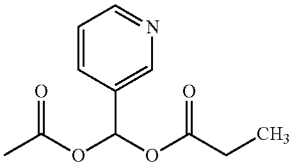
P118:
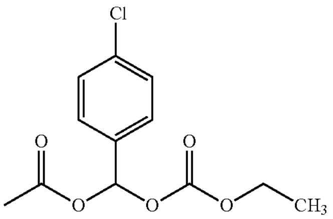
P119:
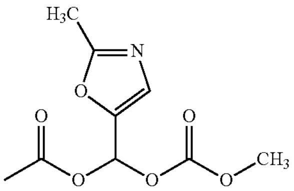
P120:
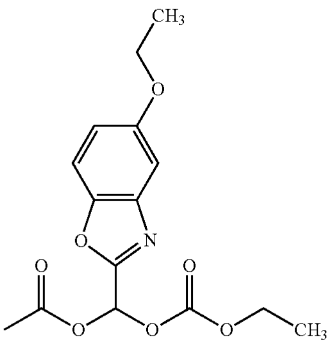

-continued
P121:
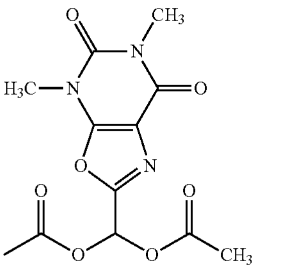
P122:
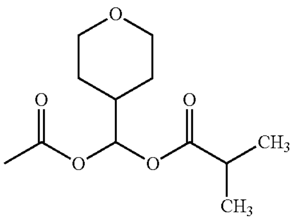
P123:
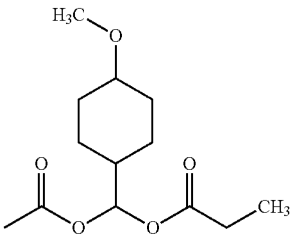
P124:
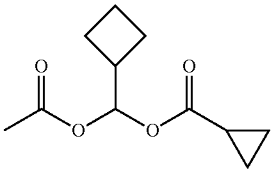
P125:
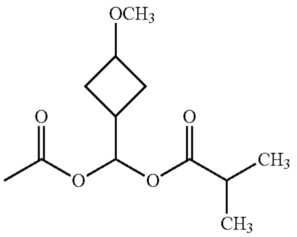
P126:
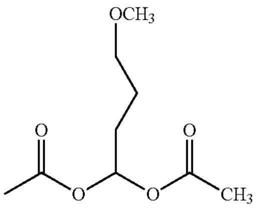
-continued
P127:
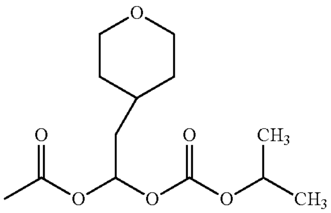
P128:
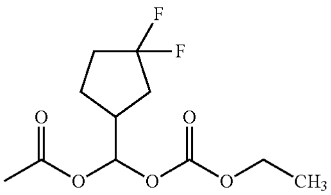
P129:
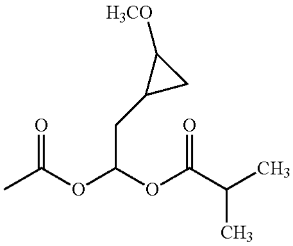
P130:
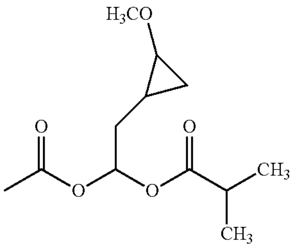
P131:
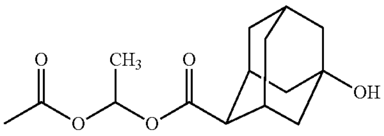
P132:
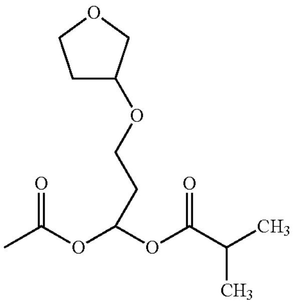
P133:
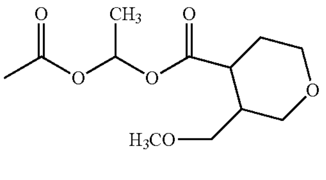

-continued
P134:
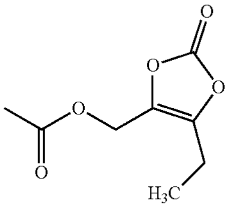
P135:
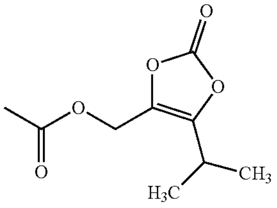
P136:
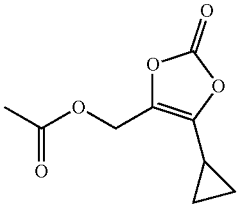
P137:
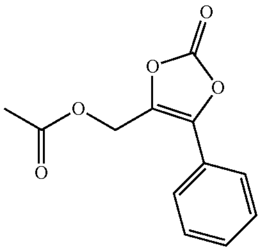
P138:
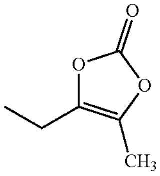
P139:
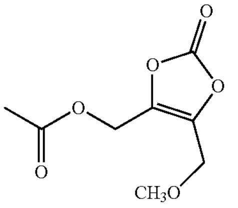
P140:
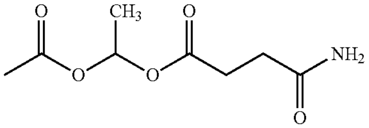
-continued
P141:
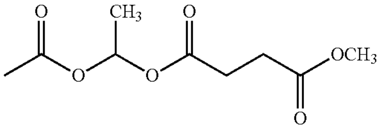
P142:
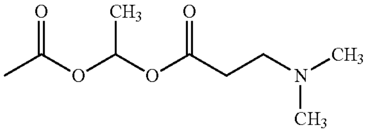
P143:
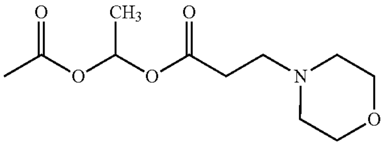
P144:
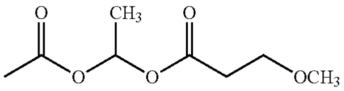
P145:
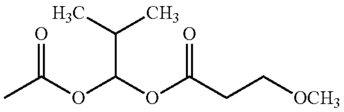
P146:
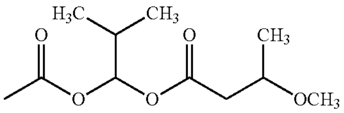
P147:
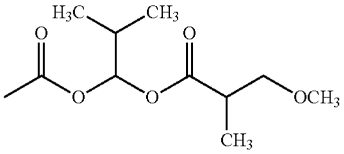
P148:
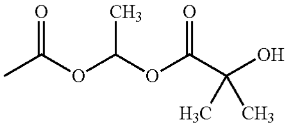
P149:
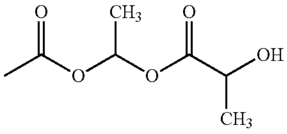
[Chemical Formula 112]
P150:
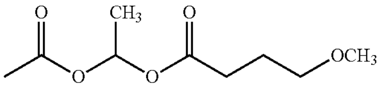
P151:
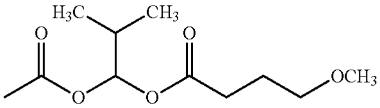

-continued
P152:
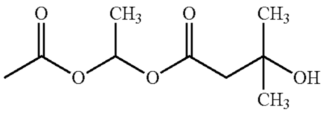
P153:
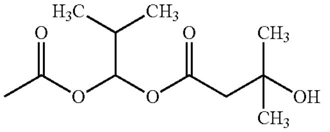
P154:
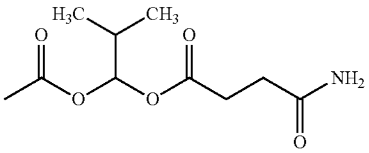
P155:
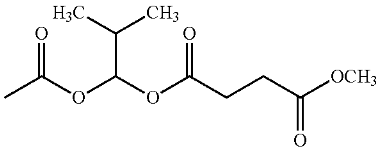
P156:
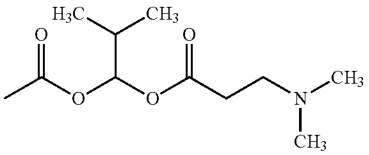
P157:
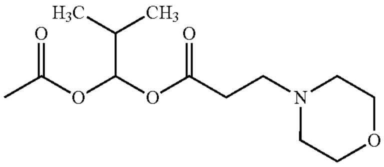
P158:
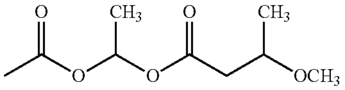
P159:
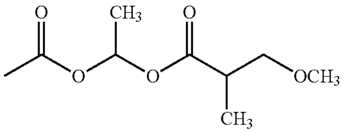
P160:
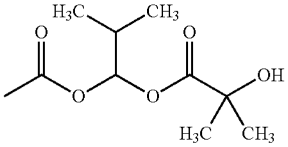
P161:
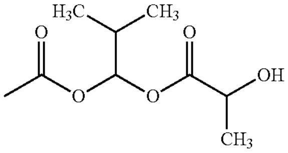
-continued
P162:
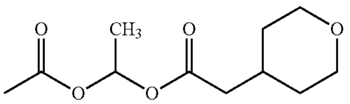
P163:
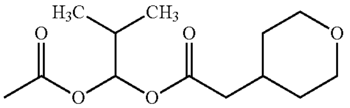
P164:
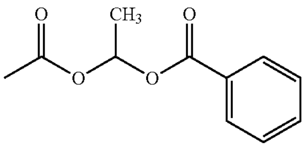
P165:
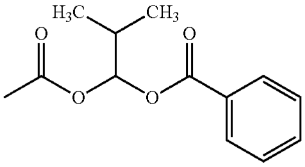
P166:
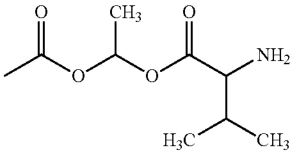
P167:
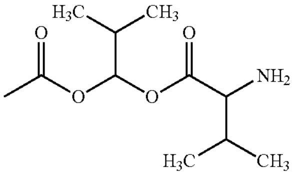
P168:
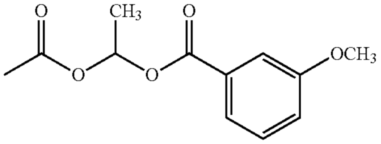
P169:
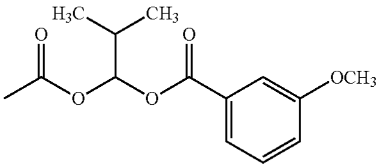
P170:
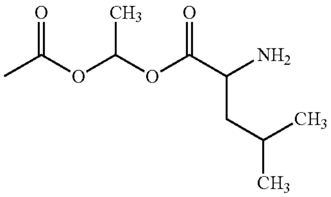

-continued
P171:
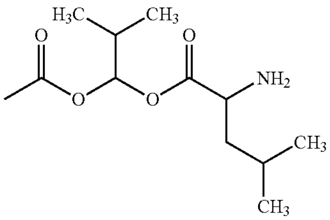
P172:
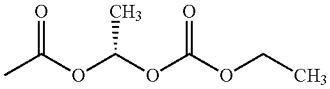
P173:
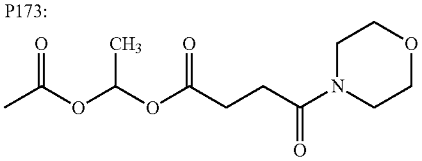
P174:
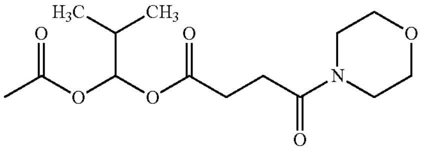
[Chemical Formula 113]
Q1:
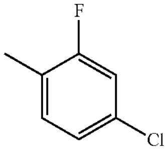
Q2:
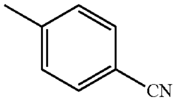
Q3:
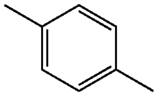
Q4:
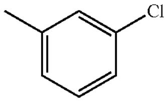
Q5:
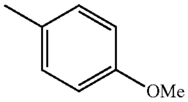
Q6:
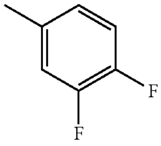
-continued
Q7:
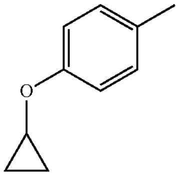
Q8:
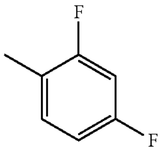
Q9:
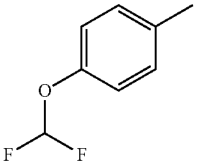
Q10:
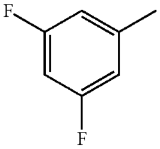
Q11:
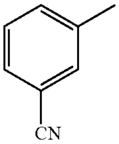
Q12:
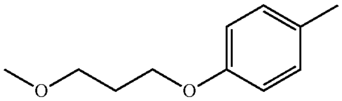
Q13:
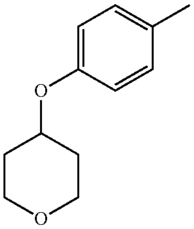
Q14:
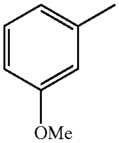

-continued
Q15:
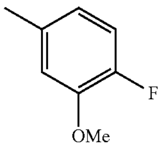
Q16:
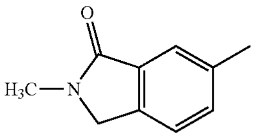
Q17:
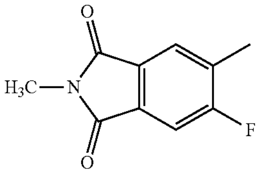
Q18:
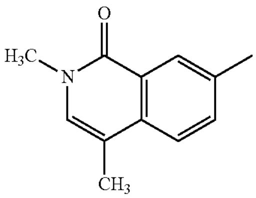
Q19:
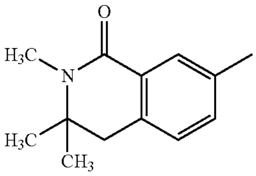
Q20:
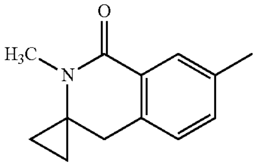
Q21:
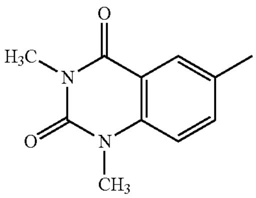
Q22:
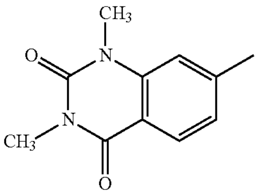
-continued
Q23:
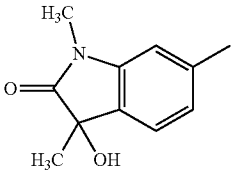
Q24:
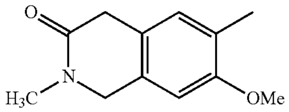
Q25:
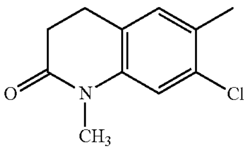
Q26:
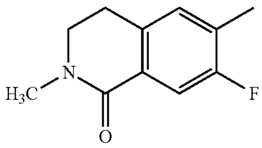
Q27:
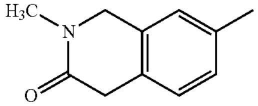
Q28:
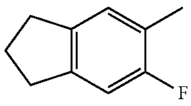
Q29:
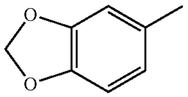
Q30:
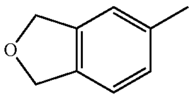
Q31:
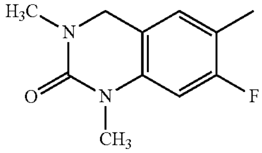
Q32:
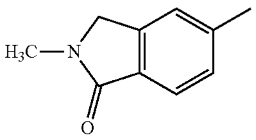

-continued
Q33:
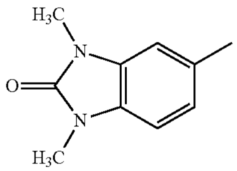
Q34:
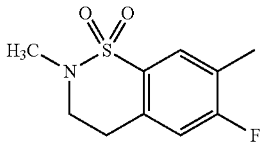
Q35:
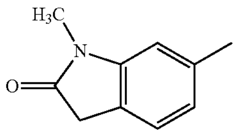
[Chemical Formula 114]
Q36:
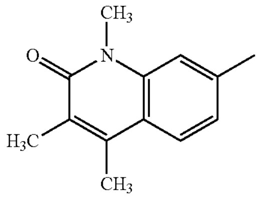
Q37:
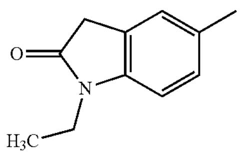
Q38:
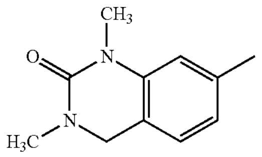
Q39:
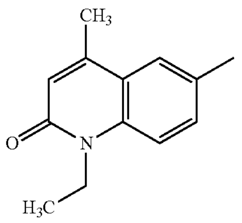
Q40:
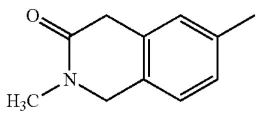
-continued
Q41:
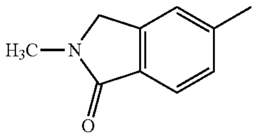
Q42:
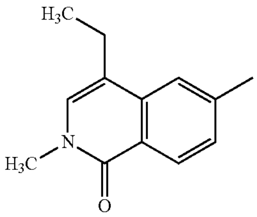
Q43:
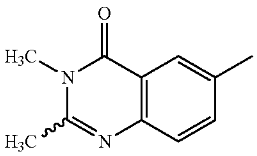
Q44:
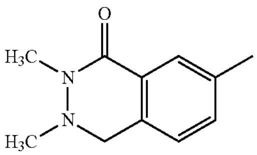
Q45:
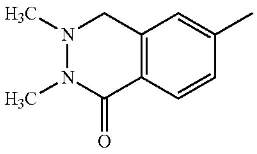
Q46:
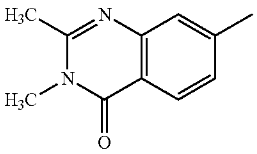
Q47:
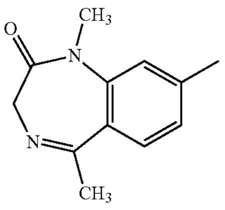
Q48:
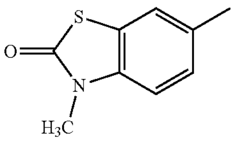

-continued
Q49:
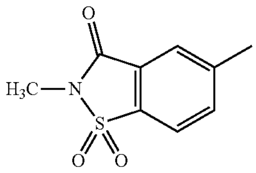
Q50:
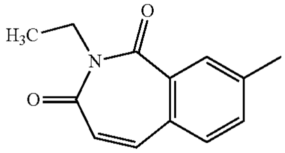
Q51:
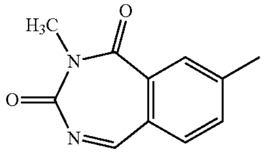
Q52:
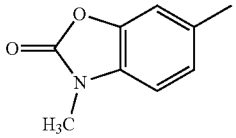
Q53:
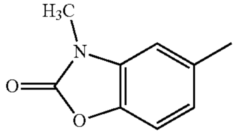
Q54:
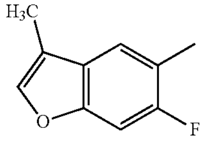
Q55:
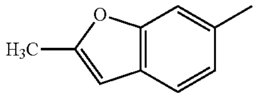
Q56:
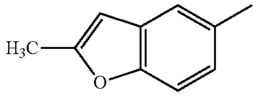
Q57:
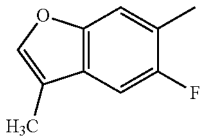
-continued
Q58:
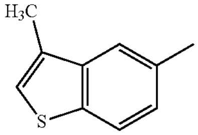
Q59:
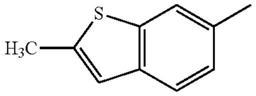
Q60:
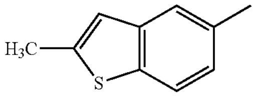
Q61:
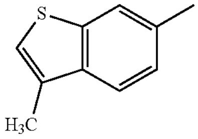
Q62:
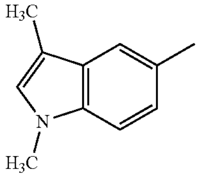
Q63:
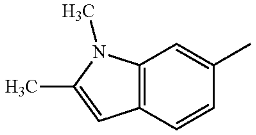
Q64:
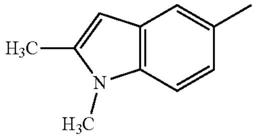
Q65:
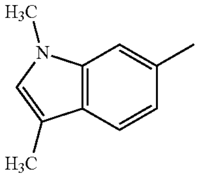
Q66:
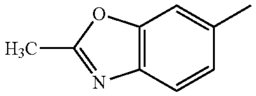
Q67:
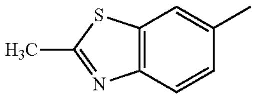

-continued
Q68:
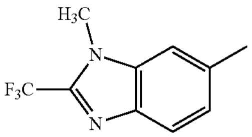
Q69:
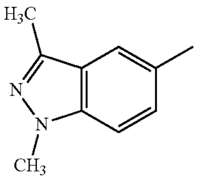
Q70:
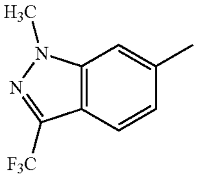
[Chemical Formula 115]
Q71:
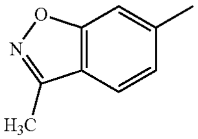
Q72:
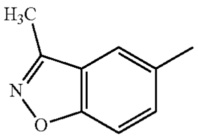
Q73:
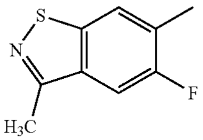
Q74:
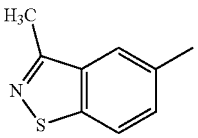
Q75:
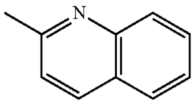
Q76:
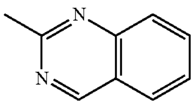
-continued
Q77:
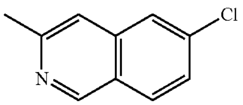
Q78:
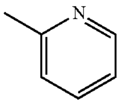
Q79:
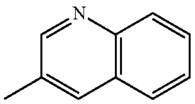
Q80:
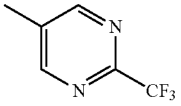
Q81:
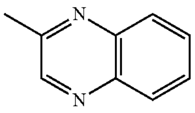
Q82:
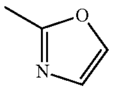
Q83:
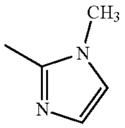
Q84:
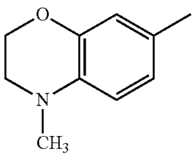
Q85:
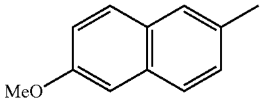
Q86:
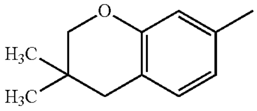
Q87:
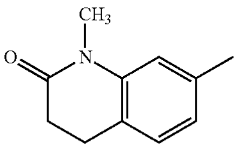

-continued
Q88:
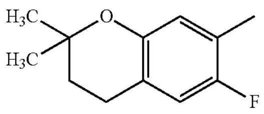
Q89:
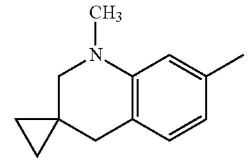
Q90:
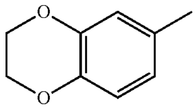
Q91:
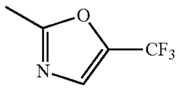
Q92:
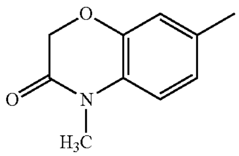
Q93:
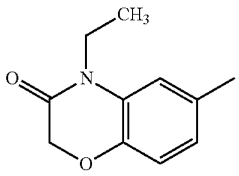
Q94:
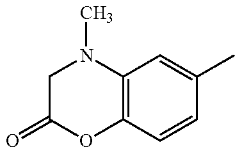
Q95:
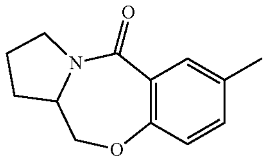
Q96:
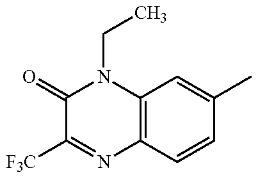
-continued
Q97:
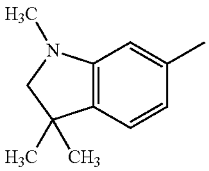
Q98:
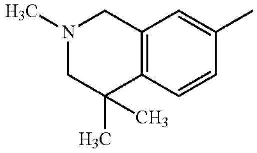
Q99:
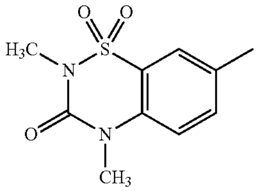
Q100:
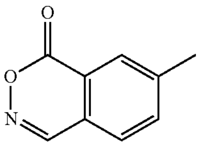
Q101:
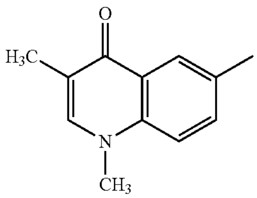
Q102:
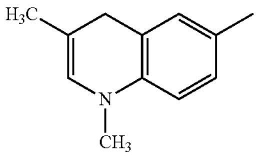
Q103:
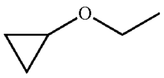
Q104:
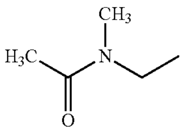
Q105:
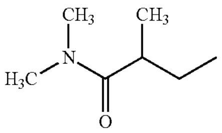

-continued
[Chemical Formula 116]
Q106:
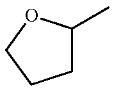
Q107:
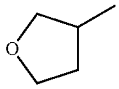
Q108:
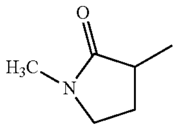
Q109:
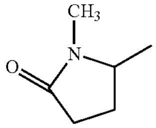
Q110:
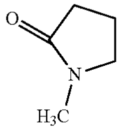
Q111:
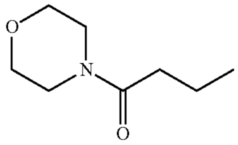
Q112:
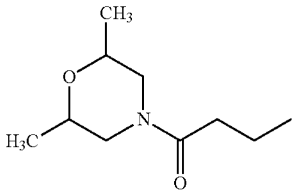
Q113:
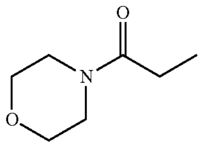
Q114:
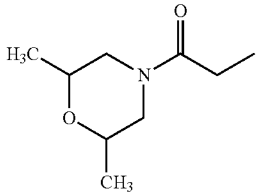
Q115:
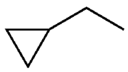
-continued
Q116:
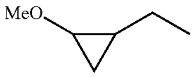
Q117:
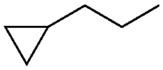
Q118:
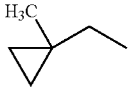
Q119:
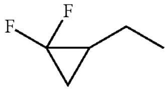
Q120:
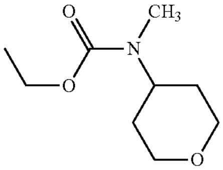
Q121:
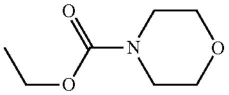
Q122:
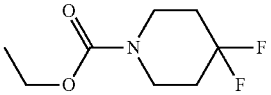
Q123:
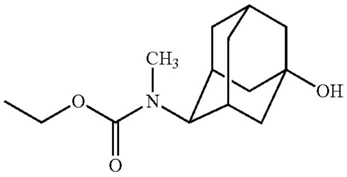
Q124:
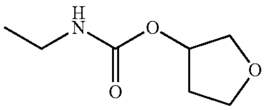
Q125:
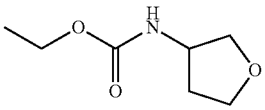
Q126:
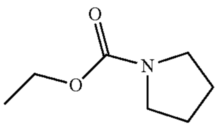

-continued
Q127:
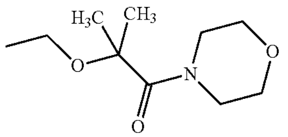
Q128:
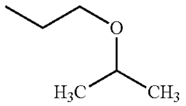
Q129:
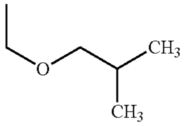
Q130:
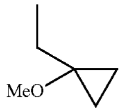
Q131:
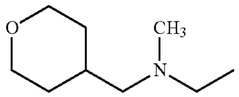
Q132:
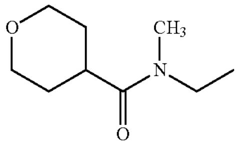
Q133:
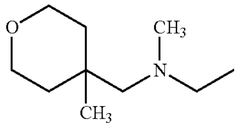
Q134:
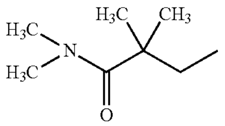
Q135:
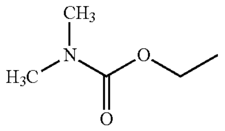
Q136:
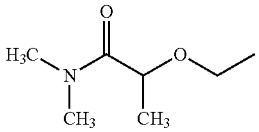
-continued
Q137:
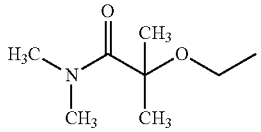
Q138:
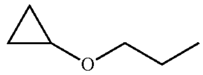
Q139:
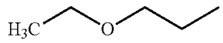
Q140:
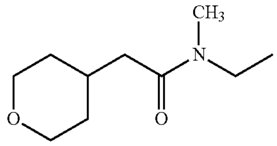
Q141:
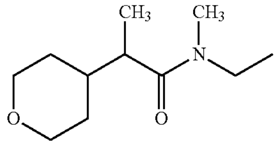
Q142:
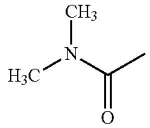
Q143:
CN
Q144:
Me
Q145:
Et
[Chemical Formula 117]
Q146:
$FH_2C$
Q147:
$F_2HC$
Q148:
$F_3C$
Q149:
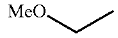
Q150:
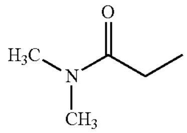
Q151:
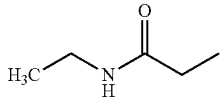

-continued
Q152:
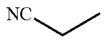
Q153:
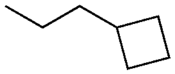
Q154:
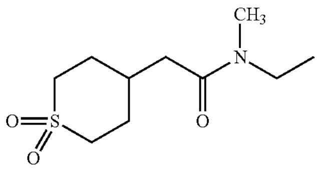
Q155:
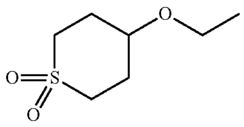
Q156:
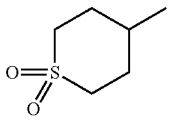
Q157:
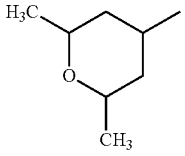
Q158:
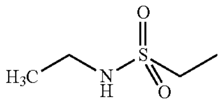
Q159:
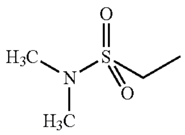
Q160:
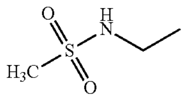
Q161:
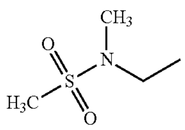
Q162:
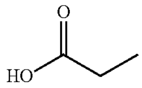
-continued
Q163:
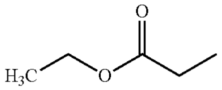
Q164:
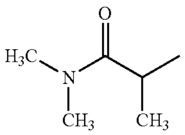
Q165:
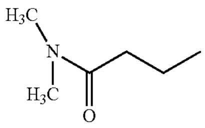
Q166:
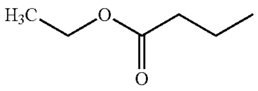
Q167:
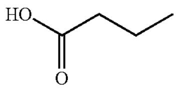
Q168:
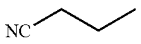
Q169:
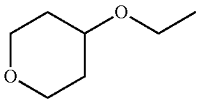
Q170:
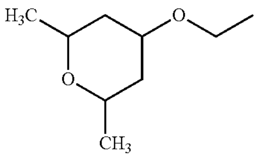
Q171:
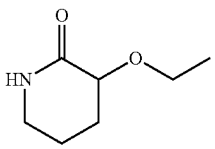
Q172:
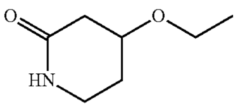
Q173:
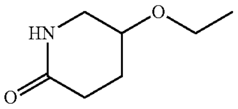

-continued
Q174:
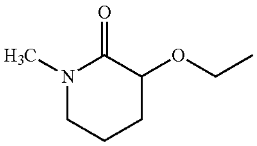
Q175:
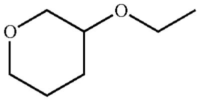
Q176:
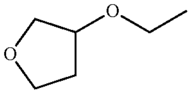
Q177:
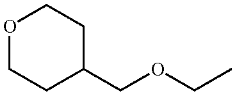
Q178:
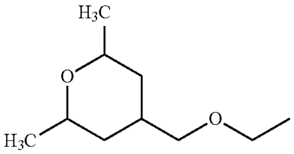
Q179:
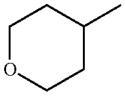
Q180:
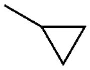
Q181:
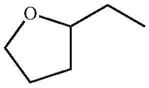
Q182:
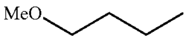
Q183:
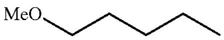
Q184:
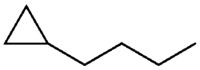
Q185:
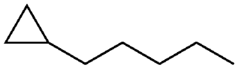
Q186:
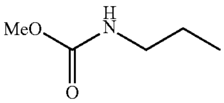
-continued
[Chemical Formula 118]
Q187:
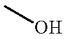
Q188:
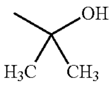
Q189:
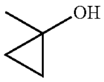
Q190:
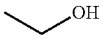
Q191:
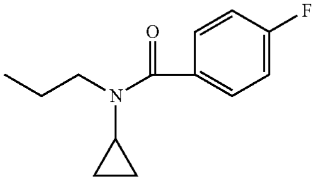
Q192:
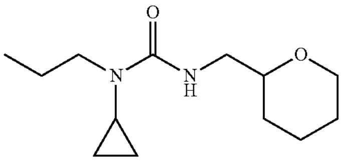
Q193:
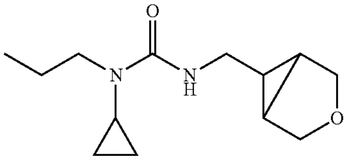
Q194:
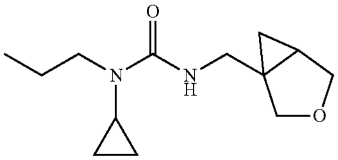
Q195:
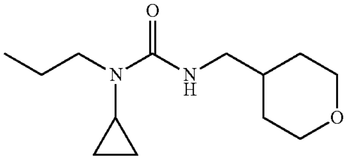
Q196:
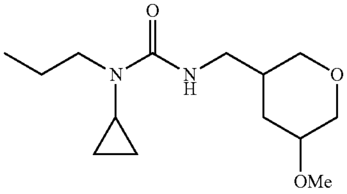

-continued
Q197:
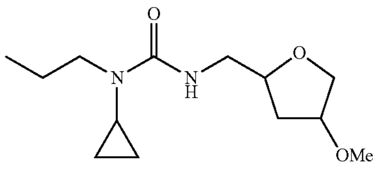
Q198:
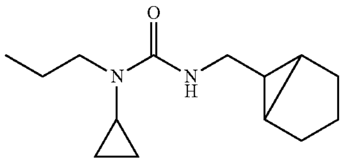
Q199:
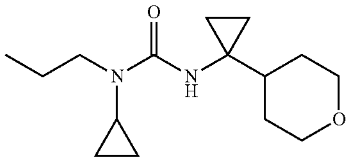
Q200:
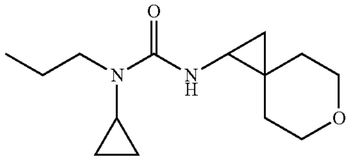
Q201:
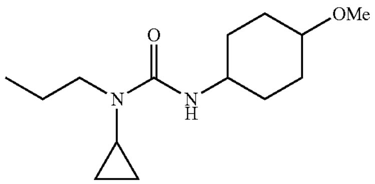
Q202:
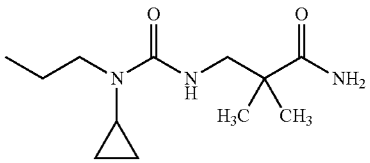
Q203:
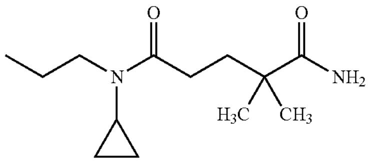
Q204:
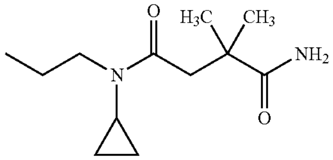
-continued
Q205:
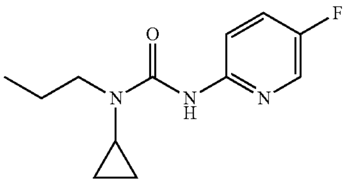
Q206:
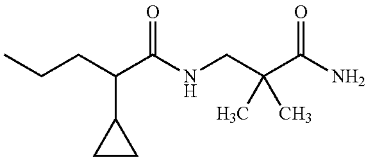
Q207:
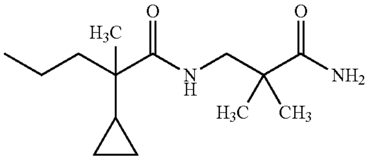
Q208:
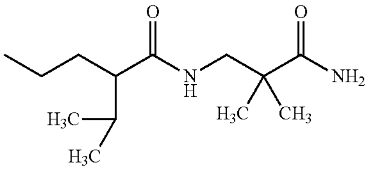
Q209:
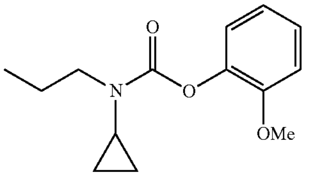
Q210:
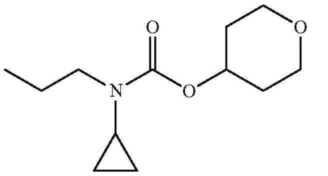
Q211:
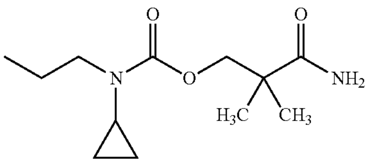
Q212:
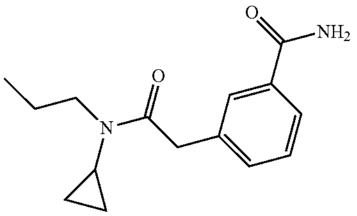

-continued
Q213:
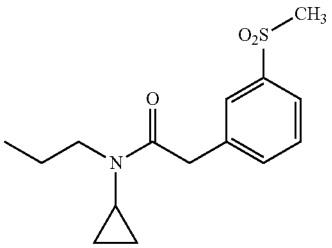
Q214:
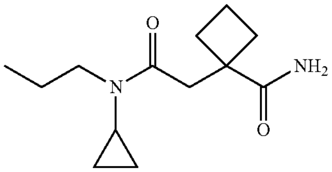
Q215:
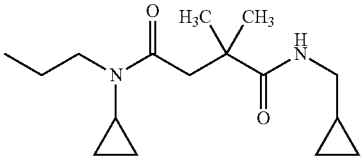
Q216:
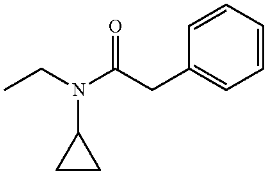
Q217:
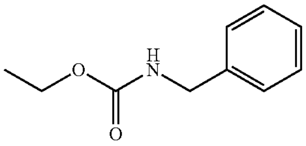
Q218:
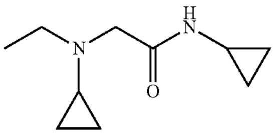
Q219:
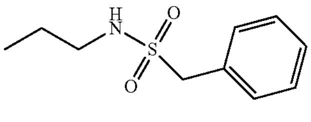
Q220:
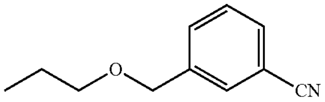
-continued
Q221:
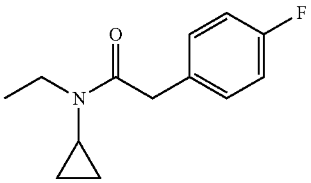
Q222:
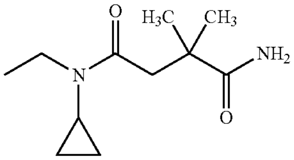
Q223:
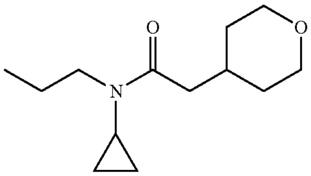
Q224:
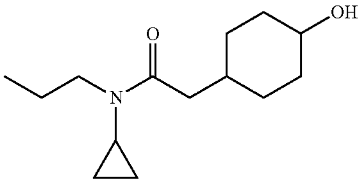
[Chemical Formula 119]
Q225:
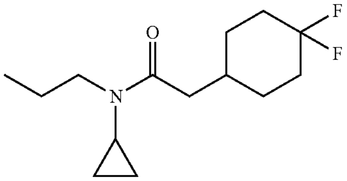
Q226:
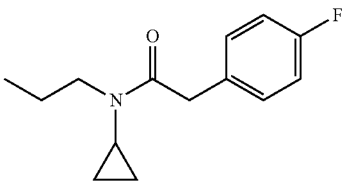
Q227:
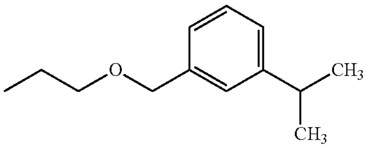

-continued
Q228:
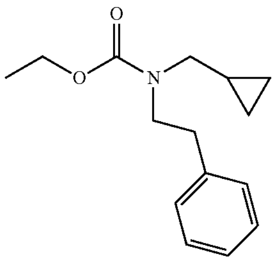
Q229:
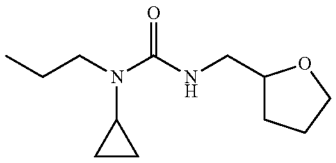
Q230:
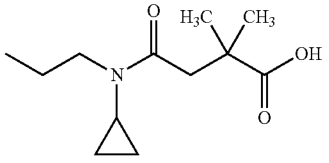
Q231:
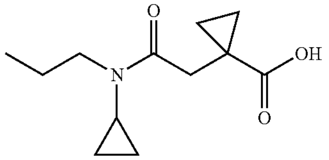
Q232:
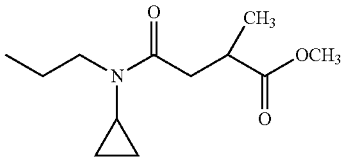
Q233:
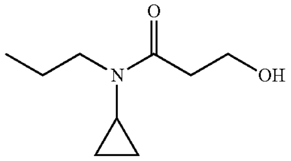
Q234:
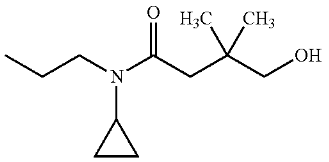
Q235:
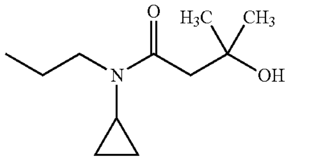
-continued
Q236:
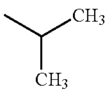
Q237:
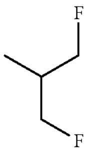
Q238:
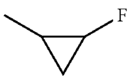
Q239:
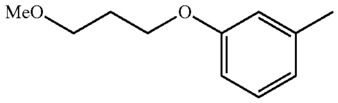
Q240:
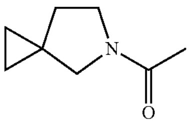
Q241:
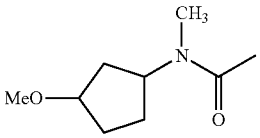
Q242:
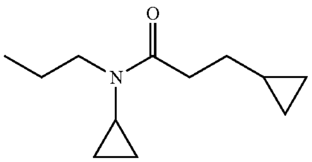
Q243:
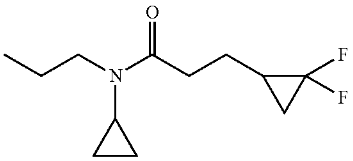
Q244:
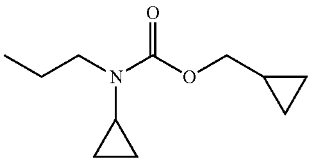
Q245:
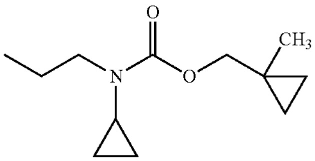

-continued
Q246:
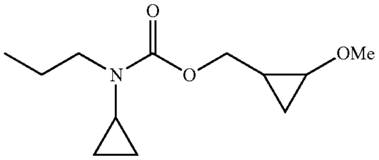
Q247:
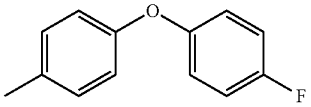
Q248:
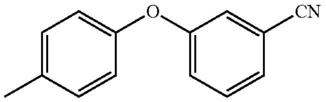
Q249:
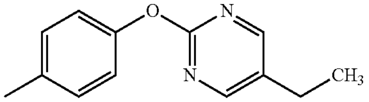
Q250:
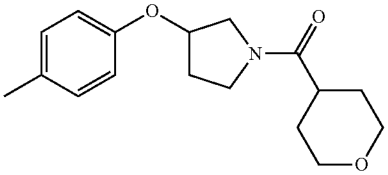
Q251:
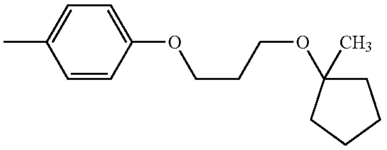
Q252:
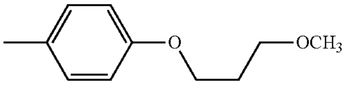
Q253:
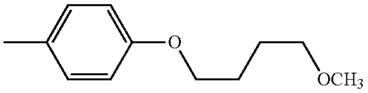
Q254:
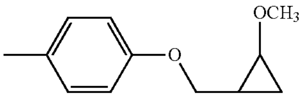
Q255:
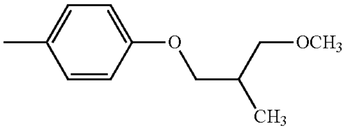
-continued
Q256:
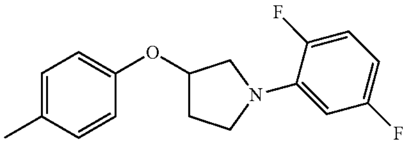
Q257:
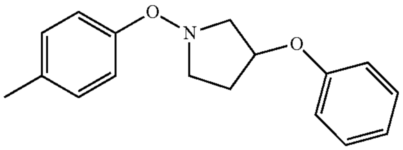
Q258:
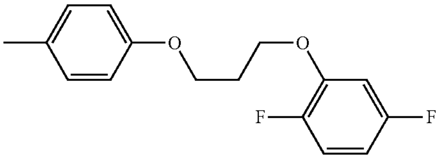
Q259:
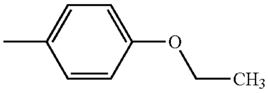
Q260:
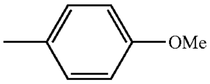
Q261:
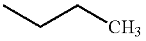
Q262:
Cl
Q263:
Br
[Chemical Formula 120]
Q264:
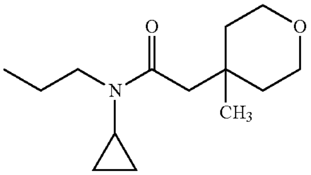
Q265:
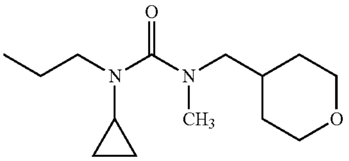
Q266:
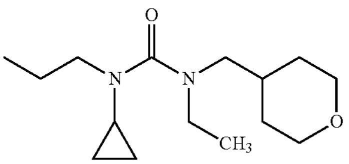

-continued
Q267:
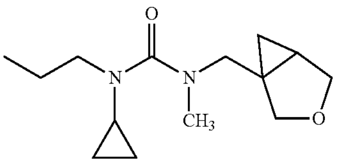
Q268:
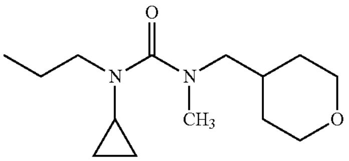
Q269:
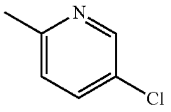
Q270:
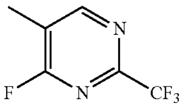
Q271:
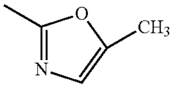
Q272:
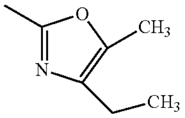
Q273:
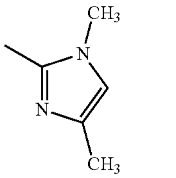
Q274:
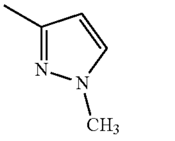
Q275:
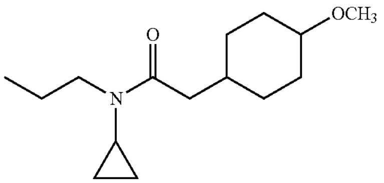
-continued
Q276:
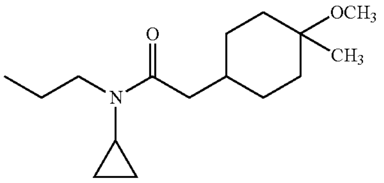
Q277:
OMe
Q278:
OEt
Q279:
$OCHF_2$
Q280:
$OCF_3$
Q281:
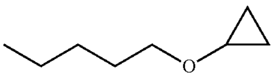
Q282:
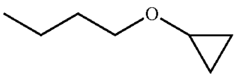
Q283:
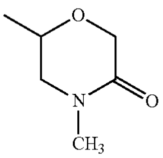
Q284:
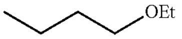
Q285:
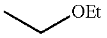
Q286:
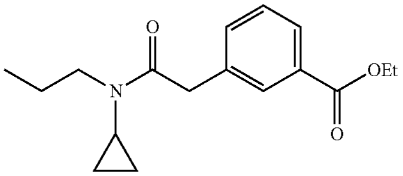
Q287:
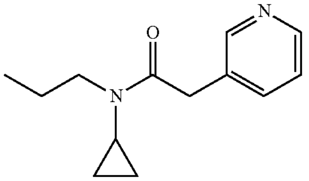
Q288:
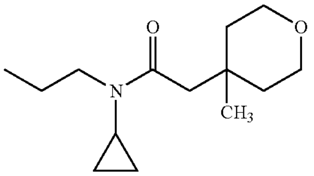

-continued
Q289:
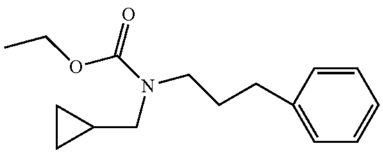
Q290:
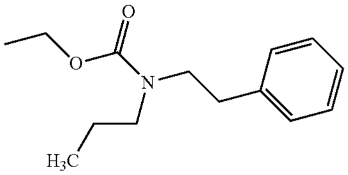
Q291:
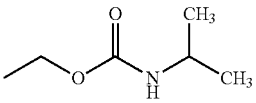
Q292:
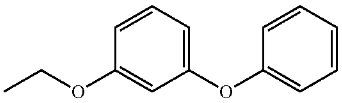
Q293:
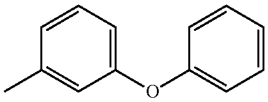
Q294:
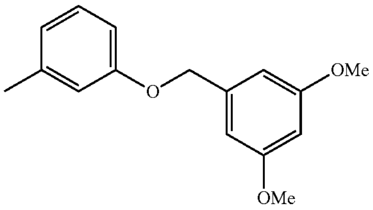
Q295:
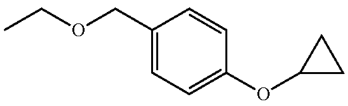
Q296:
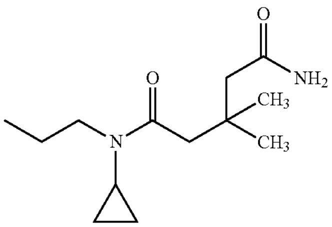
Q297:
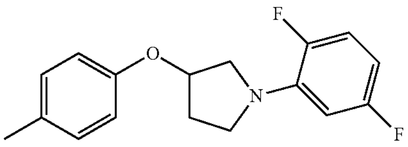
-continued
Q298:
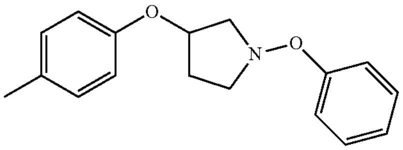
Q299:
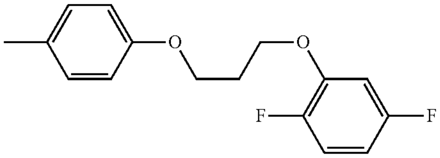
Q300:
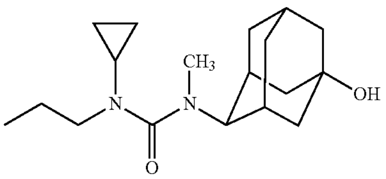
Q301:
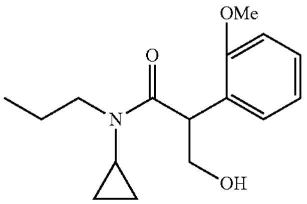
Q302:
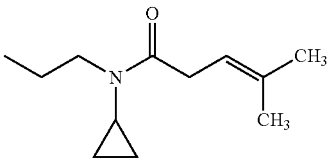
Q303:
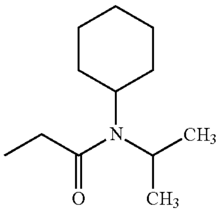
Q304:
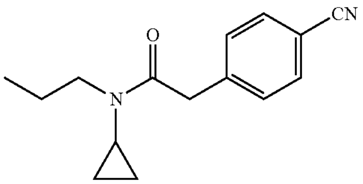
Q305:
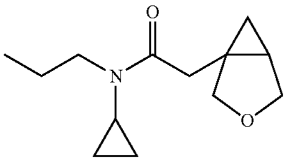

-continued
Q306:
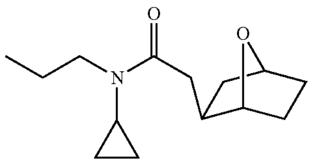
Q307:
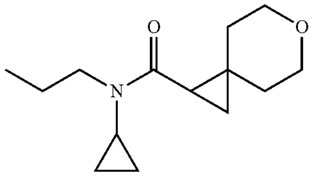
Q308:
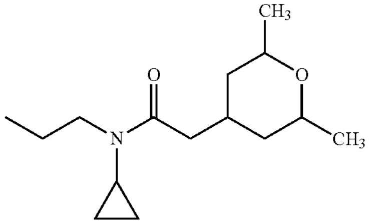
Q309:
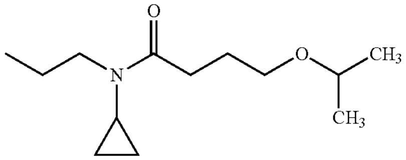
Q310:
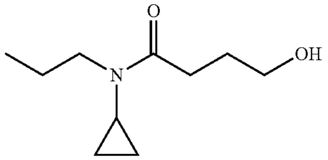
Q311:
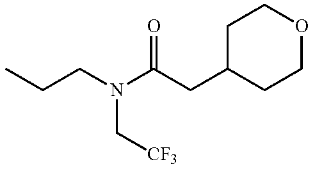
Q312:
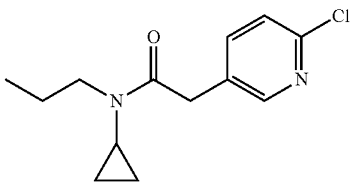
Q313:
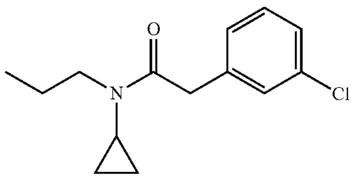
-continued
Q314:
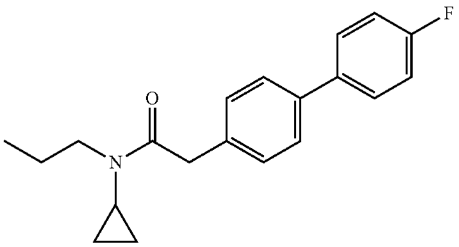
[Chemical Formula 121]
Q315:
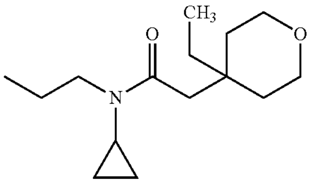
Q316:
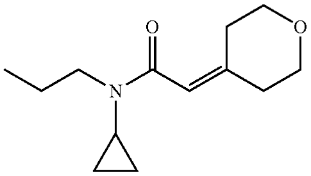
Q317:
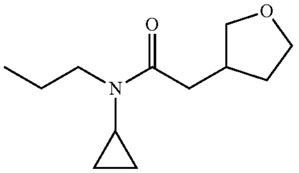
Q318:
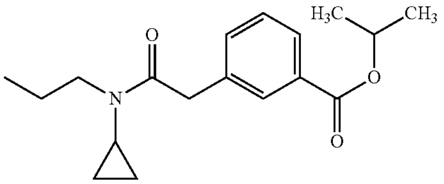
Q319:
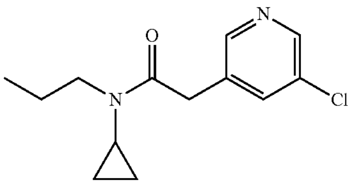
Q320:
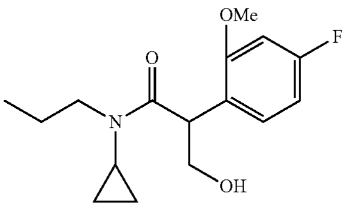

-continued
Q321:
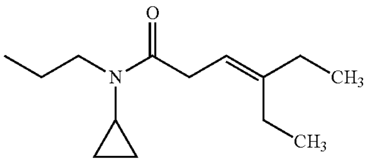
Q322:
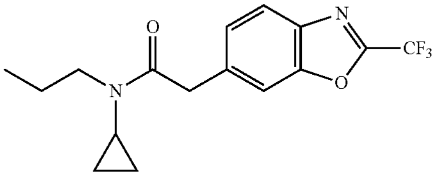
Q323:
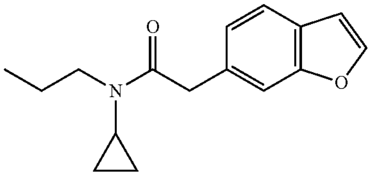
Q324:
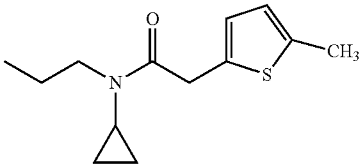
Q325:
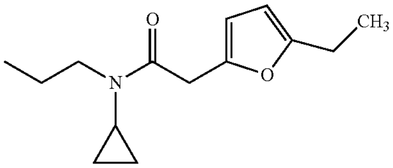
Q326:
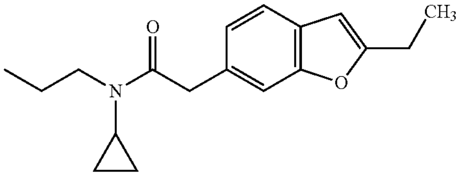
Q327:
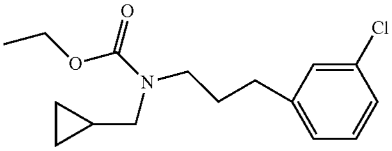
Q328:
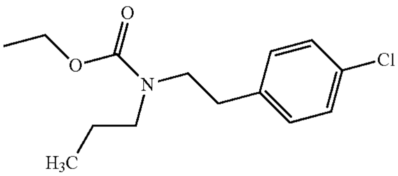
-continued
Q329:
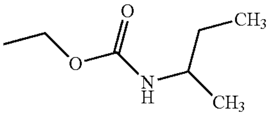
Q330:
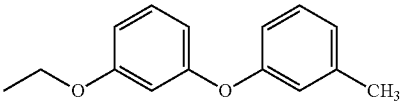
Q331:
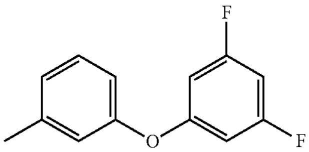
Q332:
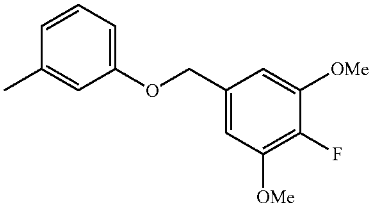
Q333:
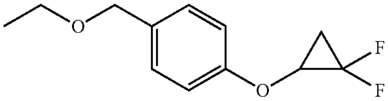
Q334:
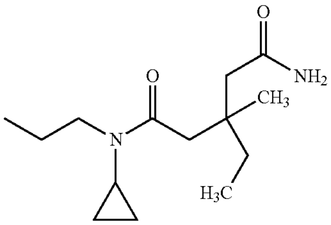
Q335:
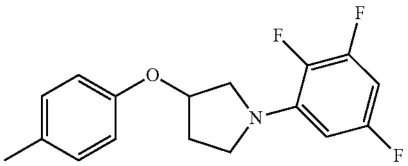
Q336:
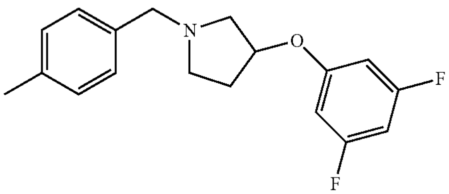

-continued
Q337:
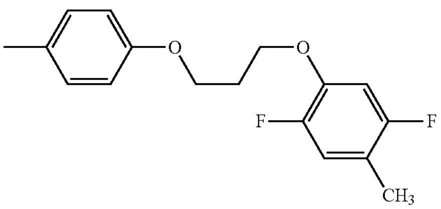
Q338:
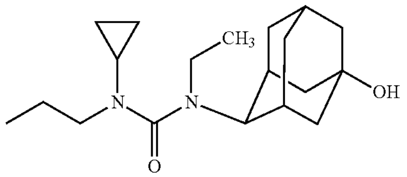
Q339:
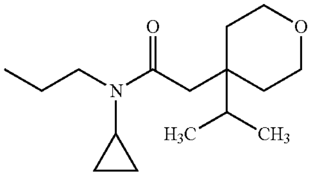
Q340:
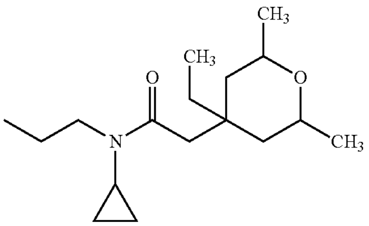
Q341:
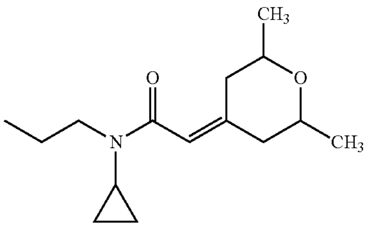
Q342:
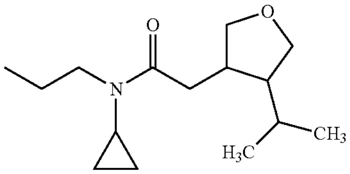
Q343:
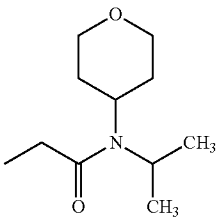
-continued
Q344:
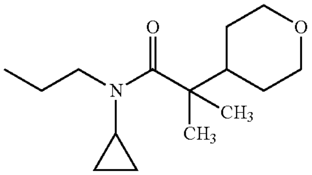
Q345:
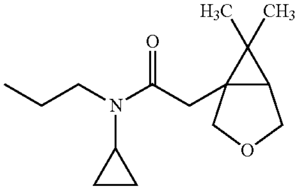
Q346:
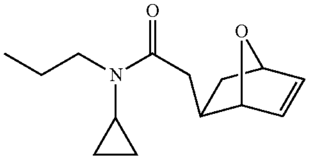
Q347:
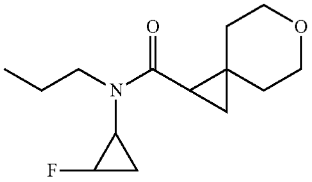
Q348:
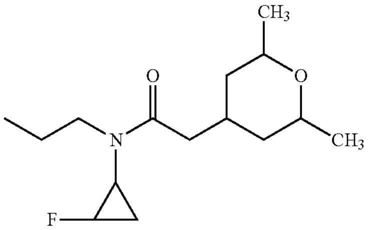
Q349:
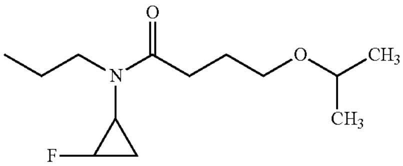
[Chemical Formula 122]
Q350:
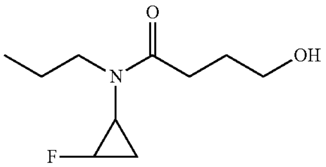

-continued
Q351:
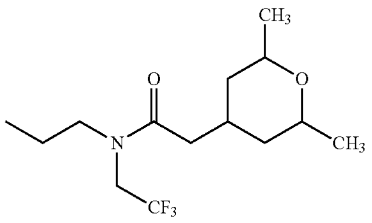
Q352:
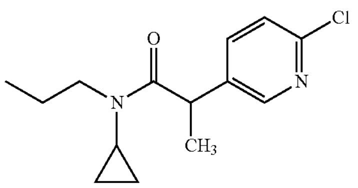
Q353:
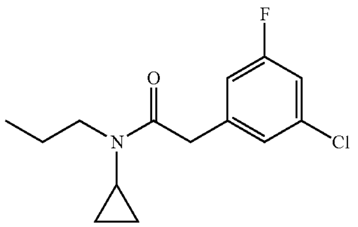
Q354:
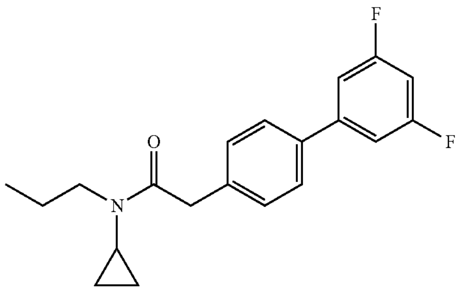
Q355:
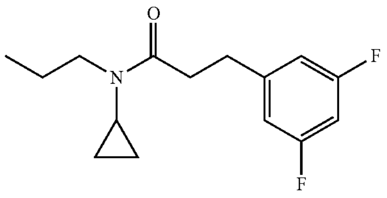
Q356:
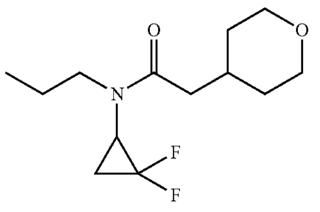
-continued
Q357:
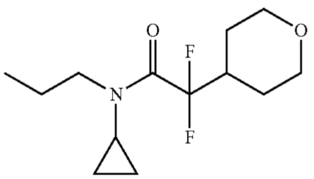
Q358:
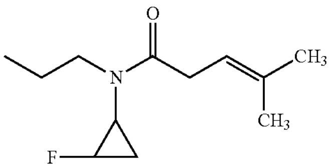
Q359:
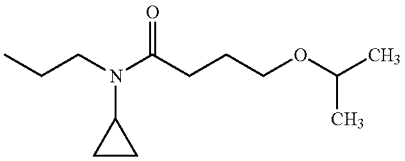
Q360:
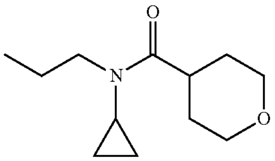
Q361:
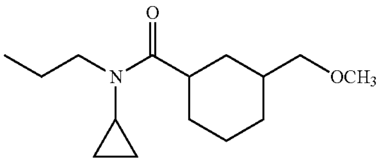
Q362:
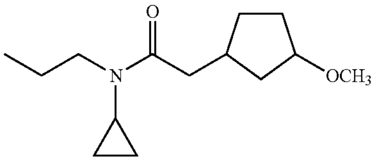
Q363:
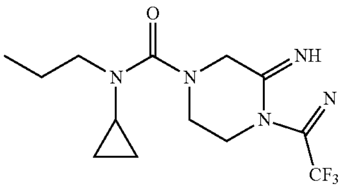
Q364:
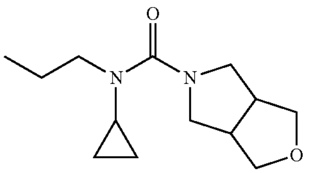

-continued
Q365:
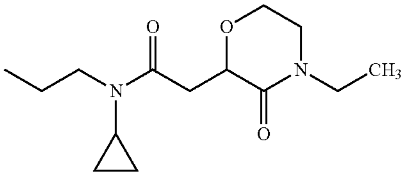
Q366:
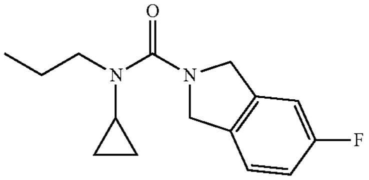
Q367:
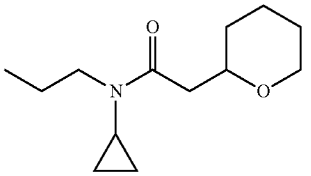
Q368:
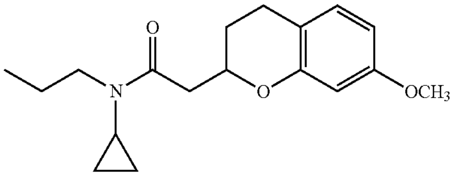
Q369:
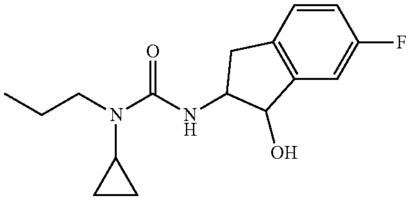
Q370:
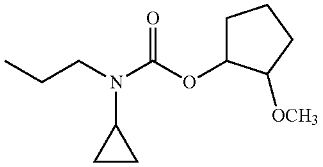
Q371:
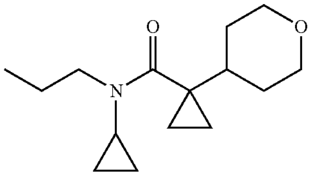
-continued
Q372:
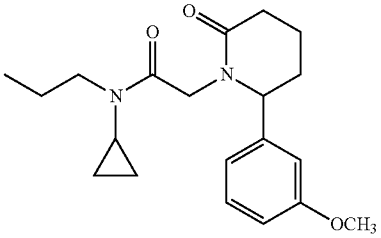
Q373:
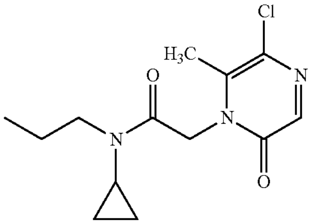
Q374:
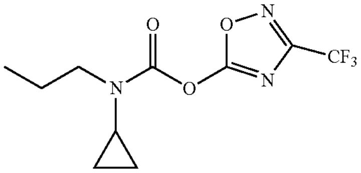
Q375:
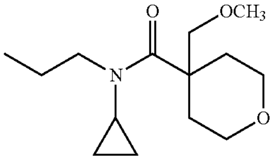
Q376:
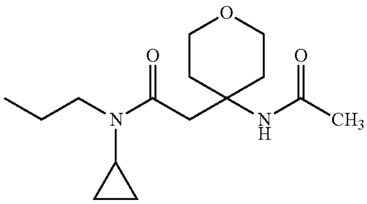
Q377:
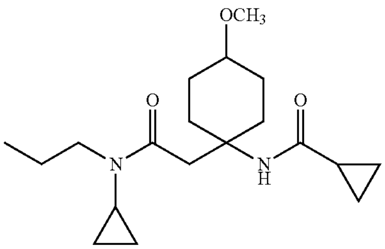
Q378:
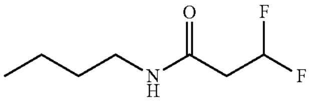

-continued
Q379:
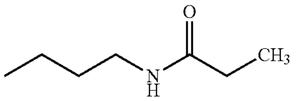
Q380:
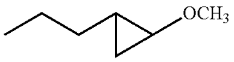
Q381:
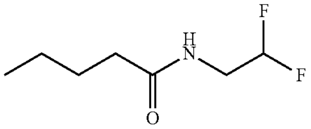
Q382:
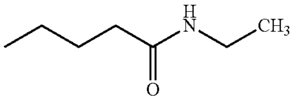
Q383:
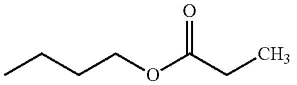
Q384:
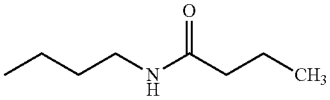
[Chemical Formula 123]
Q385:
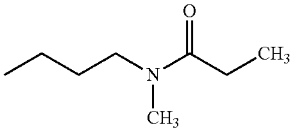
Q386:
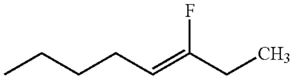
Q387:
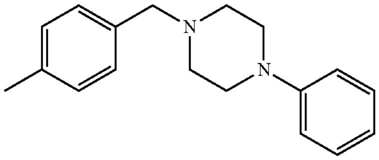
Q388:
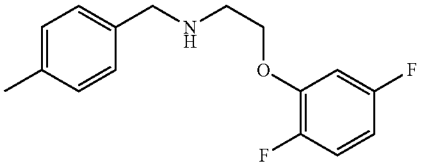
Q389:
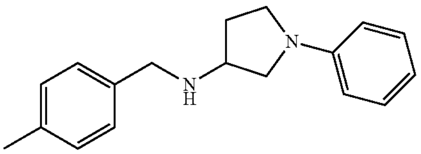
-continued
Q390:
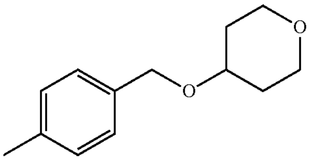
Q391:
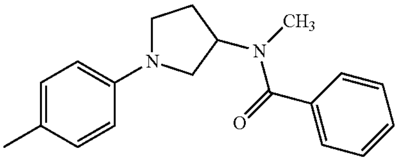
Q392:
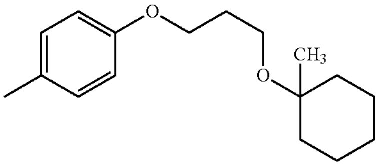
Q393:
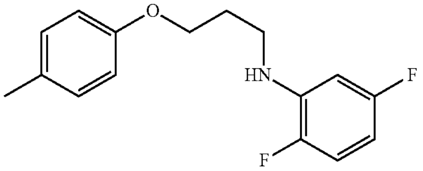
Q394:
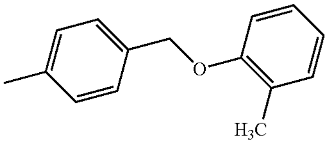
Q395:
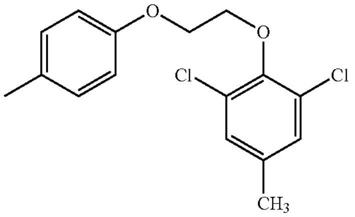
Q396:
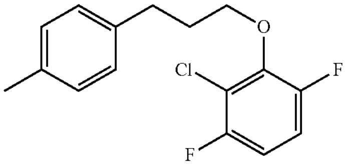
Q397:
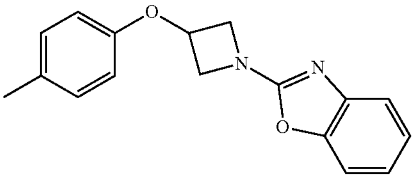

-continued
Q398:
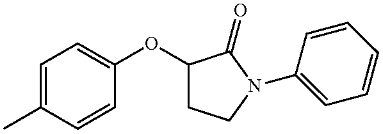
Q399:
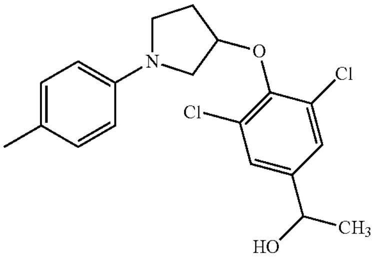
Q400:
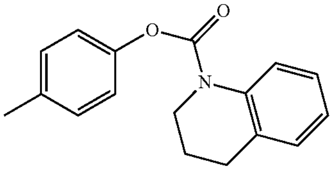
Q401:
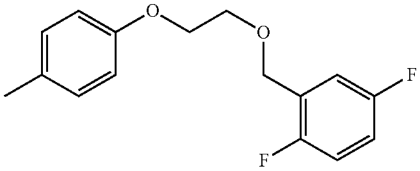
Q402:
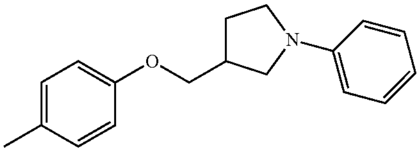
Q403:
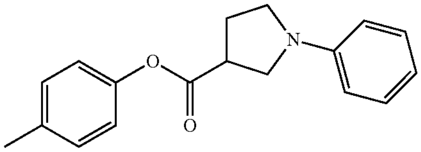
Q404:
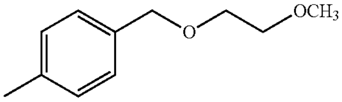
Q405:
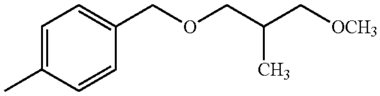
Q406:
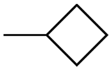
-continued
Q407:
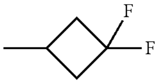
Q408:
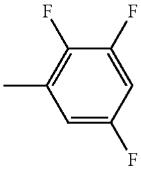
Q409:
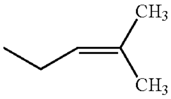
Q410:
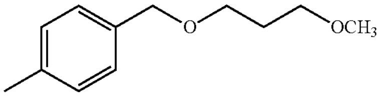
Q411:
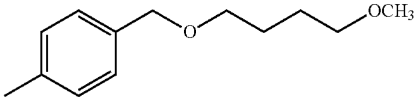
Q412:
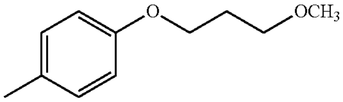
Q413:
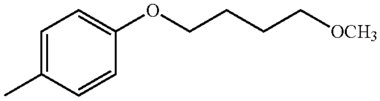
Q414:
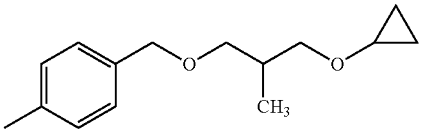
Q415:
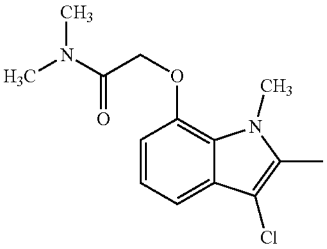
[Chemical Formula 124]
Q416:
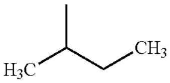

-continued
Q417:
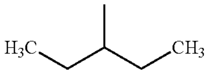
Q418:
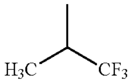
Q419:
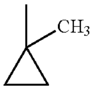
Q420:
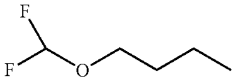
Q421:
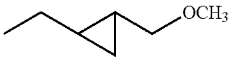
Q422:
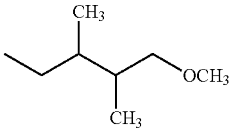
Q423:
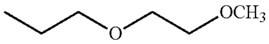
Q424:
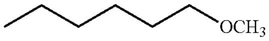
Q425:
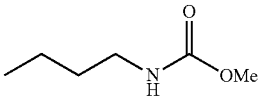
Q426:
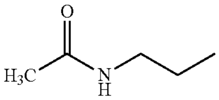
Q427:
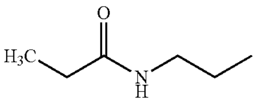
Q428:
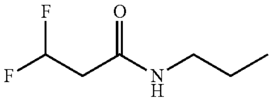
Q429:
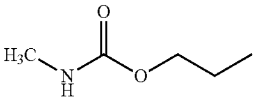
-continued
Q430:
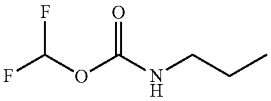
Q431:
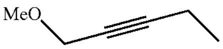
Q432:
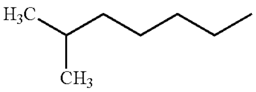
Q433:
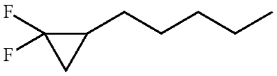
Q434:
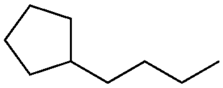
Q435:
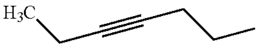
Q436:
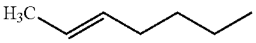
Q437:
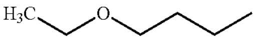
Q438:
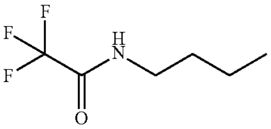
Q439:
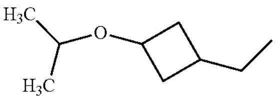
Q440:
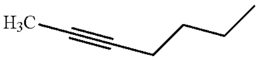
Q441:
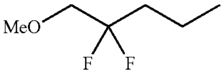
Q442:
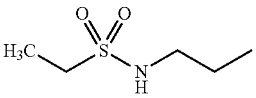
Q443:
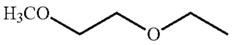
Q444:
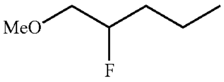

-continued
Q445:
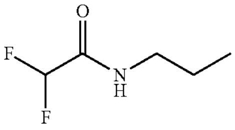
Q446:
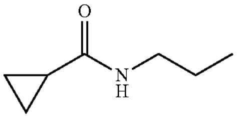
[Chemical Formula 125]
Q447:
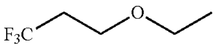
Q448:
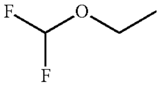
Q449:
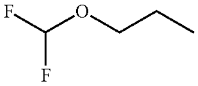
Q450:
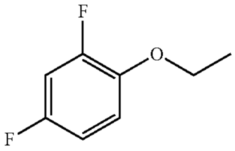
Q451:
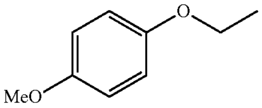
Q452:
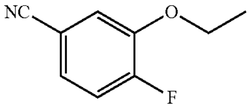
Q453:
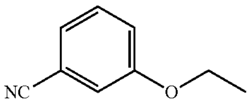
Q454:
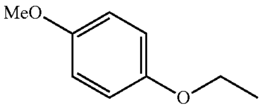
Q455:
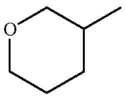
Q456:
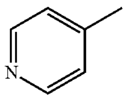
-continued
Q457:
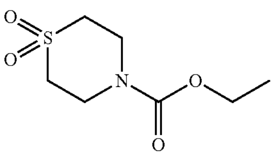
Q458:
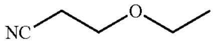
Q459:
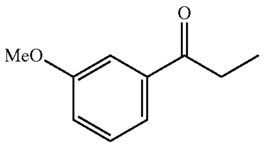
Q460:
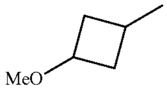
Q461:
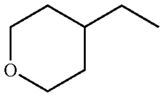
Q462:
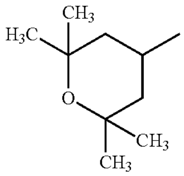
Q463:
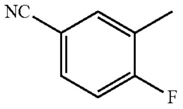
Q464:
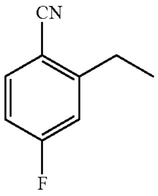
Q465:
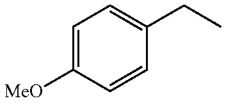
Q466:
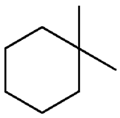

-continued
Q467:
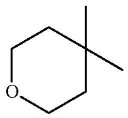
Q468:
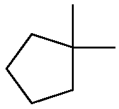
Q469:
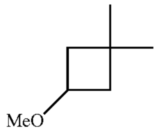
Q470:
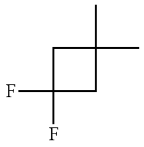
Q471:
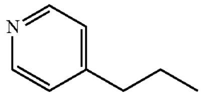
Q472:
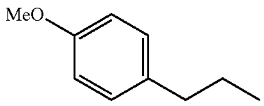
Q473:
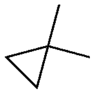
Q474:
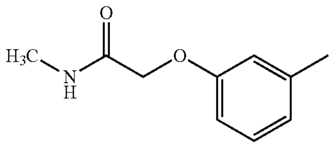
Q475:
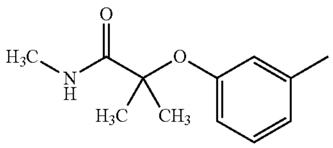
Q476:
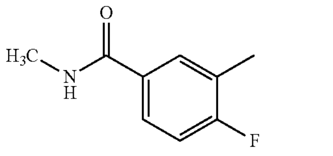
-continued
Q477:
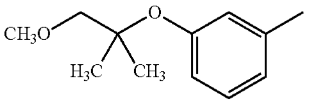
Q478:
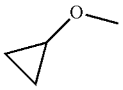
Q479:
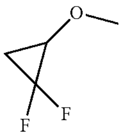
Q480:
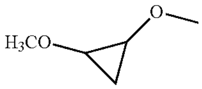
Q481:
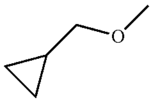
Q482:
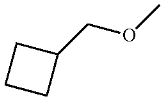
[Chemical Formula 126]
Q483:
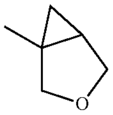
Q484:
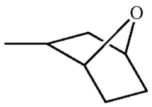
Q485:
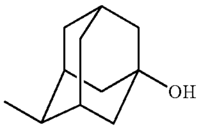
Q486:
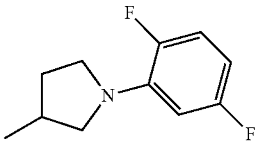
Q487:
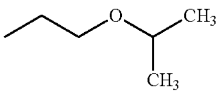

-continued
Q488:
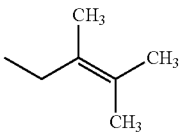
Q489:
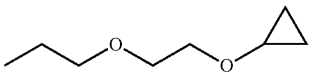
Q490:
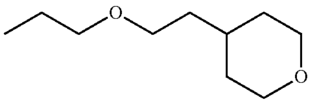
Q491:
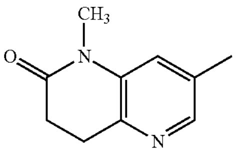
Q492:
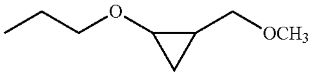
Q493:
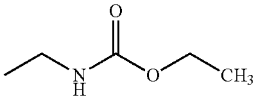
Q494:
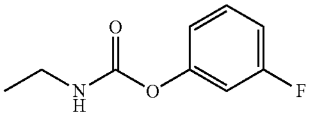
Q495:
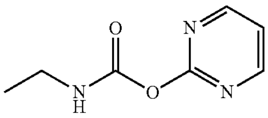
Q496:
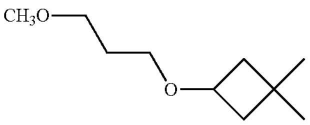
Q497:
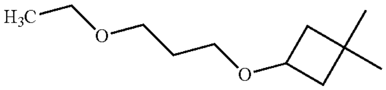
Q498:
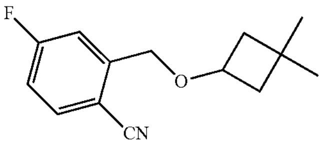
-continued
Q499:
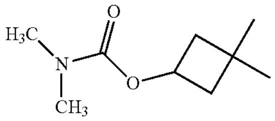
Q500:
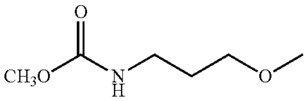
Q501:
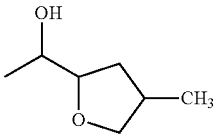
Q502:
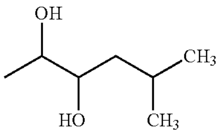
Q503:
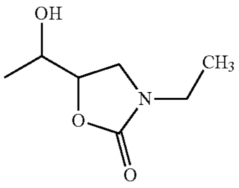
Q504:
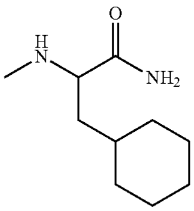
Q505:
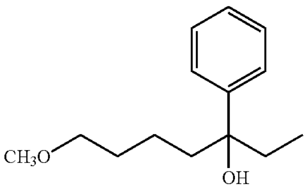
Q506:
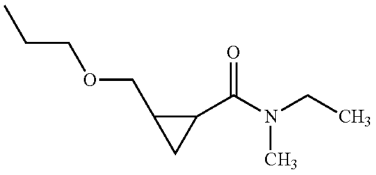
Q507:
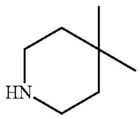

-continued
Q508:
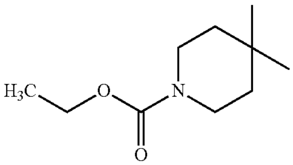
Q509:
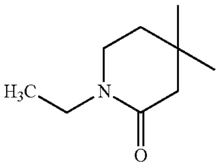
Q510:
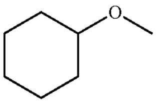
Q511:
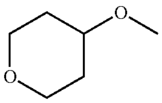
Q512:
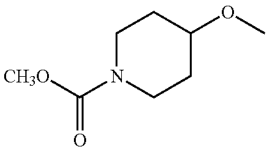
Q513:
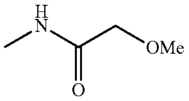
Q514:
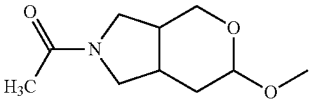
Q515:
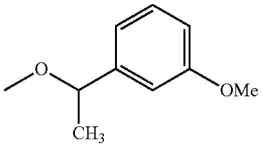
Q516:
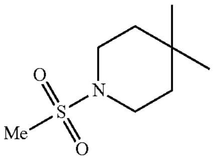
Q517:
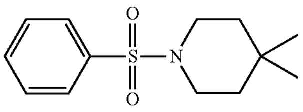
-continued
Q518:
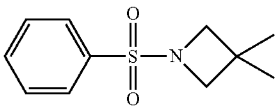
Q519:
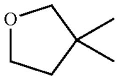
Q520:
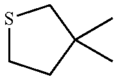
Q521:
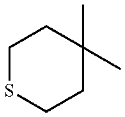
Q522:
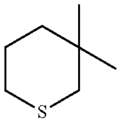
Q523:
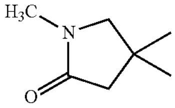
Q524:
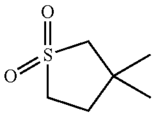
Q525:
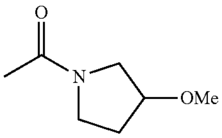
Q526:
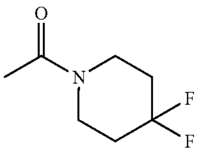
Q527:
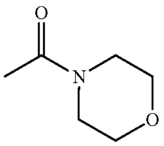

-continued
Q528:
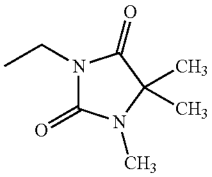
Q529:
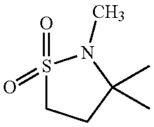
Q530:
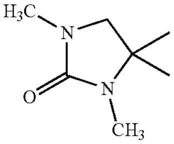
Q531:
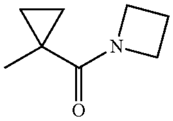
Q532:
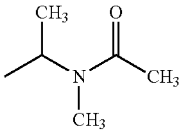
Q533:
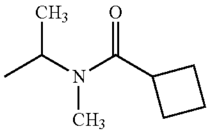
Q534:
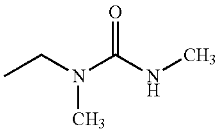
Q535:
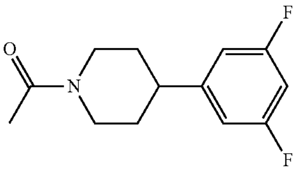
Q536:
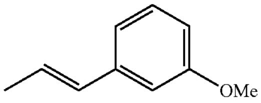
-continued
Q537:
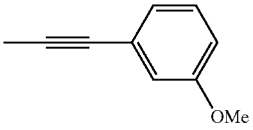
Q538:
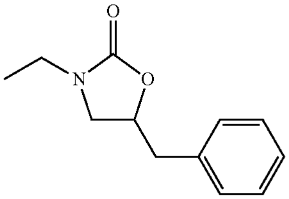
Q539:
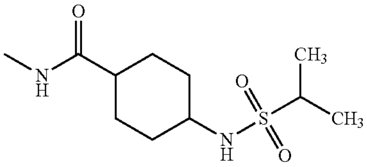
Q540:
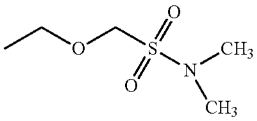
Q541:
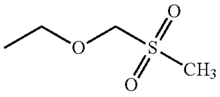
Q542:
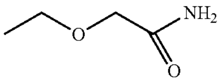
Q543:
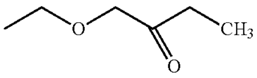
Q544:
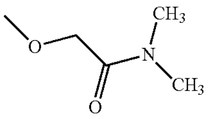
Q545:
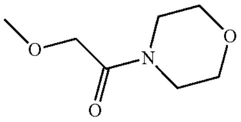
Q546:
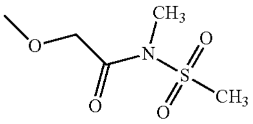
Q547:
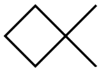

-continued

Q548:

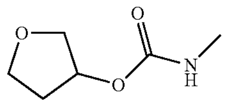

Preparations of a compound of formula (I) of the present invention are illustrated as below, but the present invention is not intended to be limited thereto. In addition, the following abbreviations may be used herein in order to simplify the description of the present invention.

Boc: tert-butoxycarbonyl
Cbz: benzyloxycarbonyl
TMS: trimethylsilyl
TBS: tert-butyldimethylsilyl
SEM: 2-[(trimethylsilyl)ethoxy]methyl
Ac: acetyl
Me: methyl
Et: ethyl
Pr: propyl
i-Pr: isopropyl
Bu: butyl
i-Bu: isobutyl
t-Bu: tert-butyl
Ph: phenyl
Bn: benzyl
Ms: methanesulfonyl
TFA: trifluoroacetic acid
Alloc: allyloxycarbonyl
Tf: trifluoromethanesulfonate A compound of formula (I) may be synthesized by a combination of known synthetic methods from known compounds. For example, it may be synthesized in the following manners. A compound of formula (I) may be synthesized by a combination of optionally selected following methods depending on the types of starting materials.

Preparation 1

A compound of formula (I) or a salt thereof is prepared by the following method, for example.

[Chemical Formula 128]
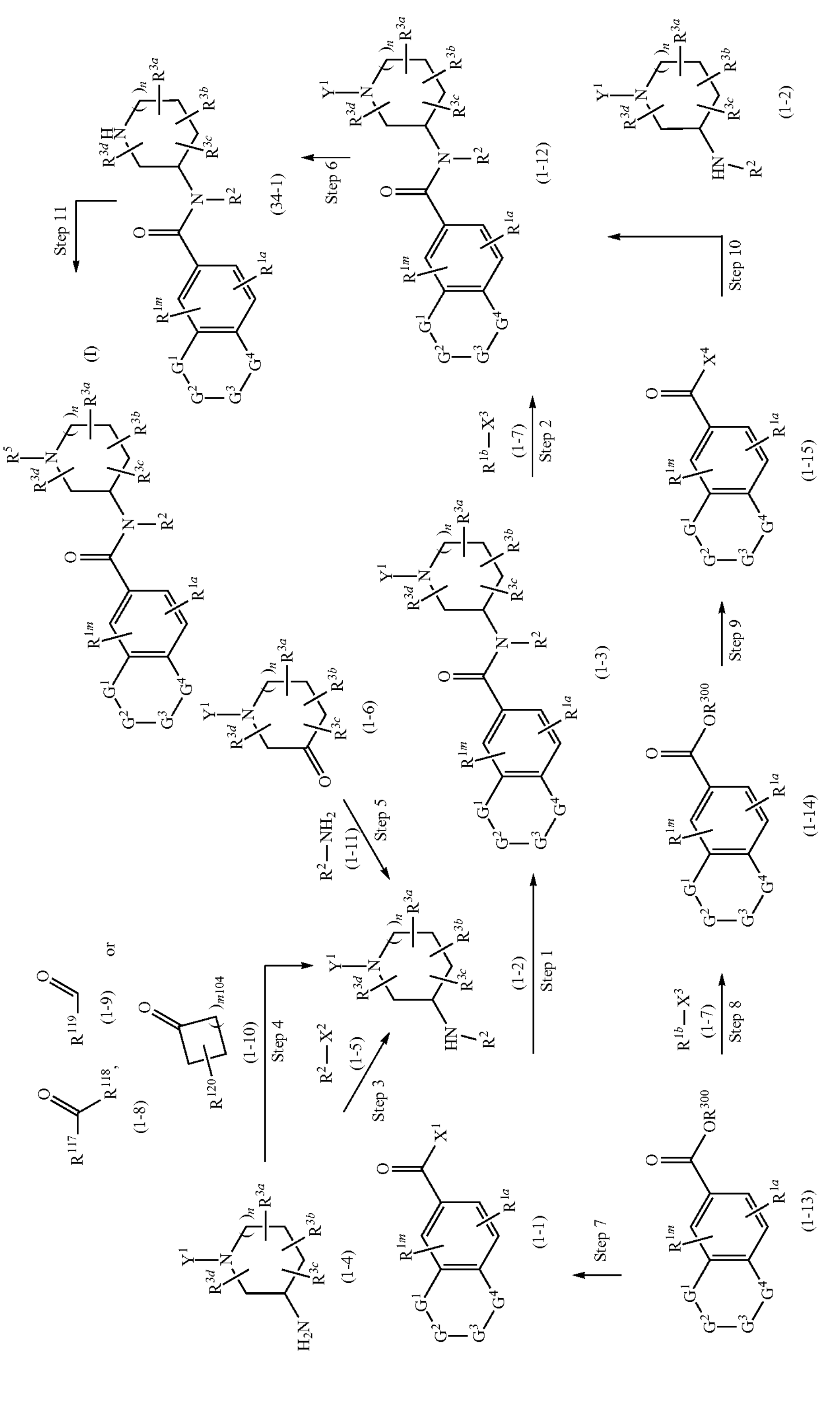

[In the scheme, n, $G^1$, $G^2$, $G^3$, $G^4$, $R^{1a}$, $R^{1m}$, $R^{3a}$, $R^{3b}$, $R^{3c}$, $R^{3d}$, $R^2$ and $R^5$ are the same as defined in the above Item 1, $R^{300}$ is $C_{1-6}$ alkyl, $X^1$ is hydroxyl or chlorine atom, $X^2$ is iodine atom, bromine atom, chlorine atom, methanesulfonyloxy, trifluoromethanesulfonyloxy or p-toluenesulfonyloxy, $X^3$ is iodine atom, methanesulfonyloxy, bromine atom or trifluoromethanesulfonyloxy, $X^4$ is hydroxyl or chlorine atom, $R^{120}$ is fluorine atom or $C_{1-3}$ alkoxy, $m_{104}$ is an integer of 0, 1, 2 or 3, and $Y^1$ is Cbz, Boc or Alloc.]

1) Step 1

When $X^1$ is hydroxyl, Compound (1-3) may be synthesized by reacting Compound (1-1) with Compound (1-2) in an inert solvent by use of a condensing agent in the presence of a base, if needed. A phase-transfer catalyst may be also used in some cases.

The base may be any conventional ones which are usually used as a conventional reactions, but is not limited. It includes, for example, an organic base such as N-methylmorpholine, triethylamine, diisopropylethylamine, tributylamine, 1,8-diazabicyclo[5.4.0]undec-7-ene, 1,5-diazabicyclo[4.3.0]non-5-ene, 1,4-diazabicyclo[5.4.0]undec-7-ene, pyridine, dimethylaminopyridine, or picoline, or an inorganic base such as sodium hydrogencarbonate, potassium hydrogencarbonate, sodium carbonate, potassium carbonate, sodium hydroxide, or sodium hydride, etc. The phase-transfer catalyst includes, for example, a quaternary ammonium salt such as tetrabutylammonium bromide or benzyltriethylammonium bromide, or a crown ether such as 18-crown-6-ether, etc.

The condensing agent may be ones disclosed in the Jikken-Kagaku-Koza (edited by The Chemical Society of Japan, Maruzen) vol. 22, etc.

The inert solvent includes, for example, an ether type solvent such as tetrahydrofuran, diethylether, 1,4-dioxane or 1,2-dimethoxyethane, a hydrocarbon type solvent such as hexane, heptane, toluene, benzene or xylene, a halogenated hydrocarbon type solvent such as dichloromethane, chloroform or 1,2-dichloroethane, a ketone type solvent such as acetone, or an aprotic solvent such as acetonitrile, N,N'-dimethylformamide, dimethylsulfoxide or hexamethylene phosphoamide, etc., and may be a mixed solvent thereof. The reaction temperature is selected in the range of about −70° C. to about 80° C.

When $X^1$ is chlorine atom, Compound (1-3) may be synthesized by reacting Compound (1-2) with Compound (1-1) in an inert solvent in the presence of a base, if needed. The base includes, for example, an organic base such as N-methylmorpholine, triethylamine, diisopropylethylamine, tributylamine, 1,8-diazabicyclo[5.4.0]undec-7-ene, 1,5-diazabicyclo[4.3.0]non-5-ene, 1,4-diazabicyclo[5.4.0]undec-7-ene, pyridine, dimethylaminopyridine, or picoline. The base is usually used in the amount of 1 to 20 equivalents to Compound (1-1) wherein $X^1$ is chlorine atom. The inert solvent includes a halogenated hydrocarbon type solvent such as dichloromethane, chloroform or 1,2-dichloroethane, etc. The reaction temperature is selected in the range of about −10° C. to about 50° C.

Compound (1-1) wherein $X^1$ is chlorine atom may be synthesized by reacting Compound (1-1) wherein $X^1$ is hydroxyl with oxalyl chloride or thionyl chloride in an inert solvent in the presence or absence of an additive. The additive includes dimethylformamide, diethylformamide, etc. The inert solvent includes a halogenated hydrocarbon type solvent such as dichloromethane, dichloroethane or chloroform, etc. The reaction temperature is selected in the range of about −10° C. to about 50° C. Compound (1-1) wherein $X^1$ is chlorine atom may be obtained after the completion of the reaction by concentrating the reaction solution under reduced pressure in the presence of a hydrocarbon type solvent such as benzene or toluene.

The step may be also carried out by reference to the method of literature (e.g., Tetrahedron 61, 10827 (2005), etc.).

The substituents of Compound (1-3), $R^{3a}$, $R^{3b}$, $R^{3a}$ and $R^{3d}$, may be also converted into the substituents of Preparations 2 to 18 by using the methods of Preparations 2 to 18, 21, 31 and 32.

2) Step 2

Compound (1-12) may be prepared from Compound (1-3) in the similar manner to Step 8 of Preparation 1.

3) Step 3

Compound (1-2) may be prepared from Compound (1-4) in the similar manner to Step 8 of Preparation 1. When $R^2$ is optionally substituted aryl or optionally substituted heteroaryl in Compound (1-5), Compound (1-2) may be prepared from Compound (1-4) in the similar manner to the method of literature (J. Org. Chem. 71, 6522 (2006), etc.).

4) Step 4

Compound (1-2) may be prepared from Compound (1-4) in the similar manner to the method of literatures (e.g., J. Org. Chem. 61, 3849 (1996), J. Org. Chem. 68, 4120 (2003), J. Org. Chem. 63, 370 (1998), J. Org. Chem. 70, 2195 (2005), etc.). Specifically, the following preparation is exemplified.

Compound (1-2) may be prepared by a reductive amination with Compound (1-4) using one compound selected from Compound (1-8), Compound (1-9) and Compound (1-10), and a borohydride compound such as sodium triacetoxyborohydride or sodium cyanoborohydride in an inert solvent in the presence or absence of acetic acid. The inert solvent includes a halogenated hydrocarbon type solvent such as dichloromethane or dichloroethane, an alcohol solvent such as methanol or ethanol, an ether type solvent such as tetrahydrofuran or 1,4-dioxane or 1,2-dimethoxyethane, etc. The borohydride compound is usually used in the amount of 1 to 3 equivalents to Compound (1-4). The reaction temperature is selected in the range of about −10° C. to about 40° C.

5) Step 5

Compound (1-2) may be prepared from Compound (1-6) in the similar manner to Step 4 of Preparation 1.

6) Step 6

Compound (34-1) may be prepared from Compound (1-12) in the similar manner to the method of literature (e.g., Protective Groups in Organic Synthesis 2nd Edition (John Wiley & Sons, Inc.), etc.).

7) Step 7

Compound (1-1) wherein $X^1$ is chlorine atom may be prepared from Compound (1-13) in the similar manner to Step 1 of Preparation 1.

8) Step 8

Compound (1-14) may be prepared by reacting Compound (1-7) with Compound (1-13) in an inert solvent in the presence of a base. The base includes an alkali metal salt such as sodium hydrogencarbonate, potassium carbonate or sodium hydroxide, an organic base such as triethylamine or 1,8-diazabicyclo[5.4.0]undec-7-ene (DBU), an alkali metal hydride such as sodium hydride or potassium hydride, or an alkali metal alkoxide such as potassium t-butoxide, etc. When $X^3$ is chlorine atom or bromine atom, an additive such as sodium iodide or potassium iodide may be used. The inert solvent includes, for example, an ether type solvent such as tetrahydrofuran or 1,4-dioxane, an aprotic solvent such as dimethylformamide or dimethylsulfoxide, or a halogenated hydrocarbon type solvent such as dichloromethane or dichloroethane, etc., and may be a mixed solvent thereof. The reaction temperature is selected in the range of about 0° C. to about 150° C.

9) Step 9

Compound (1-15) may be prepared from Compound (1-14) in the similar manner to Step 1 of Preparation 1.

10) Step 10

Compound (1-12) may be prepared from Compound (1-15) in the similar manner to Step 1 of Preparation 1.

11) Step 11

A compound of formula (I) or a salt thereof may be prepared from Compound (34-1) by the method of Preparation 34, 35, 36 or 37, for example.

Preparation 2

Among a compound of formula (1-4), a compound of formula (2-3) or a salt thereof is prepared by the following method, for example.

[Chemical Formula 129]

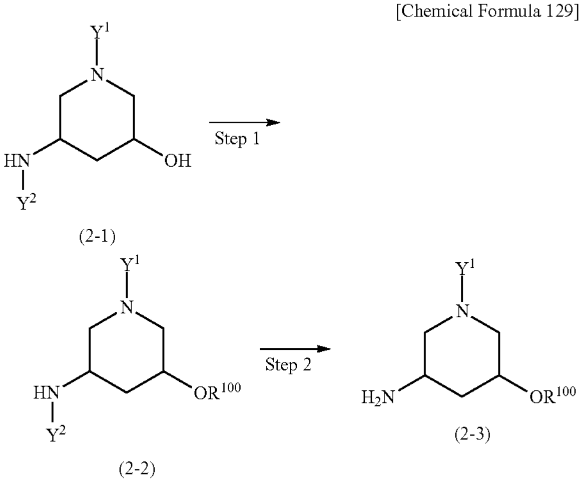

(2-1) (2-2) (2-3)

[In the scheme, $Y^1$ is the same as defined above, $Y^2$ is Cbz, Boc or Alloc, and $R^{100}$ is the same as B defined in the above Item 1.]

1) Step 1

Compound (2-2) may be prepared from Compound (2-1) in the similar manner to the method of literature (e.g., Comprehensive Organic transformation, R. C. Larock, VCH publisher Inc., 1989, etc.). Compound (2-1) may be prepared in the similar manner to the method of literature (e.g., WO05/028467, etc.).

2) Step 2

Compound (2-3) may be prepared from Compound (2-2) in the similar manner to the method of literature (e.g., Protective Groups in Organic Synthesis 2nd Edition (John Wiley & Sons, Inc.), etc.).

Preparation 3

Among a compound of formula (1-4), a compound of formula (3-6) or a salt thereof is prepared by the following method, for example.

[Chemical Formula 130]

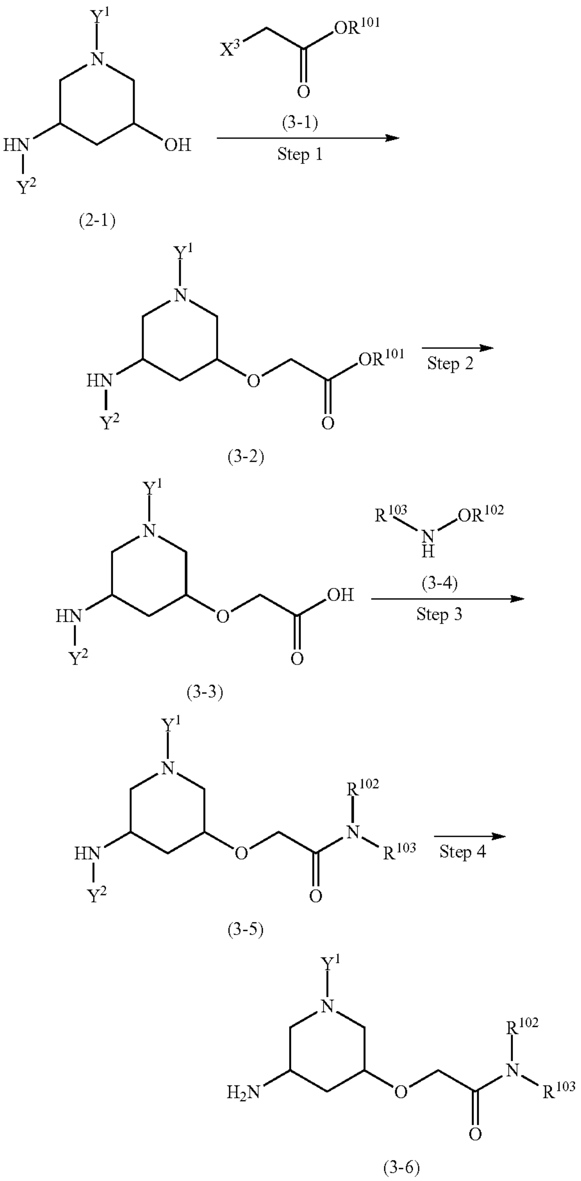

(2-1) (3-2) (3-3) (3-5) (3-6)

[In the scheme, $Y^1$ and $Y^2$ are the same as defined above, $X^3$ is chlorine atom or bromine atom, $R^{101}$ is $C_{1-4}$ alkyl, and $R^{102}$ and $R^{103}$ are each, same or different, hydrogen atom, $C_{1-4}$ alkyl, $C_{3-6}$ cycloalkyl or $C_{3-6}$ cycloalkyl$C_{1-4}$ alkyl.]

1) Step 1

Compound (3-2) may be prepared from Compound (2-1) in the similar manner to the method of literature (e.g., Comprehensive Organic transformation, R. C. Larock, VCH publisher Inc., 1989, etc.). Compound (2-1) may be prepared in the similar manner to the method of literature (e.g., WO05/028467, etc.).

2) Steps 2 to 3

Compound (3-5) may be prepared from Compound (3-2) in the similar manner to the method of literature (e.g., Comprehensive Organic transformation, R. C. Larock, VCH publisher Inc., 1989, etc.).

3) Step 4

Compound (3-6) may be prepared from Compound (3-5) in the similar manner to the method of literature (e.g., Protective Groups in Organic Synthesis 2nd Edition (John Wiley & Sons, Inc.), etc.).

Preparation 4

Among a compound of formula (1-4), compounds of formulae (4-3) and (4-6) or salts thereof are prepared by the following method, for example.

4) Step 4

Compound (4-6) may be prepared from Compound (4-5) in the similar manner to the method of literature (e.g., Protective Groups in Organic Synthesis 2nd Edition (John Wiley & Sons, Inc.), etc.).

Preparation 5

Among a compound of formula (1-4), a compound of formula (5-4) or a salt thereof is prepared by the following method, for example.

[Chemical Formula 131]

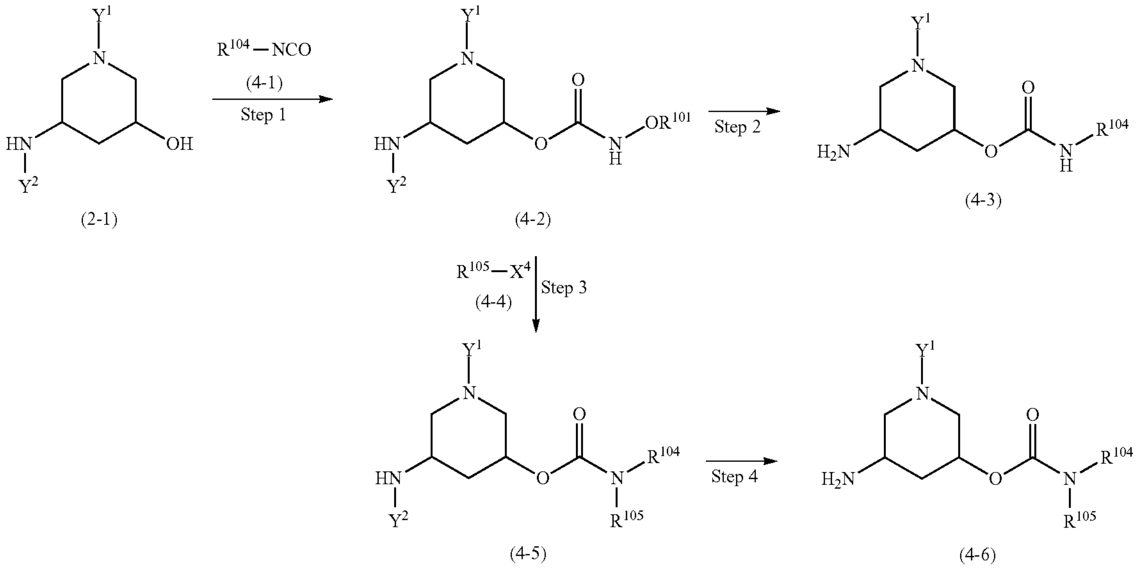

[In the scheme, $Y^1$ and $Y^2$ are the same as defined above, $R^{104}$ is the same as B defined in the above Item 1, $R^{105}$ is the same as $R^{4c}$ defined in the above Item 1, or $R^{104}$ and $R^{105}$ may combine each other to form a ring, and $X^4$ is iodine atom, bromine atom, chlorine atom, methanesulfonyloxy, trifluoromethanesulfonyloxy, or p-toluenesulfonyloxy.]

1) Step 1

Compound (4-2) may be prepared from Compound (2-1) in the similar manner to the method of literature (e.g., Comprehensive Organic transformation, R. C. Larock, VCH publisher Inc., 1989, etc.). Compound (2-1) may be prepared in the similar manner to the method of literature (e.g., WO05/028467, etc.).

2) Step 2

Compound (4-3) may be prepared from Compound (4-2) in the similar manner to the method of literature (e.g., Protective Groups in Organic Synthesis 2nd Edition (John Wiley & Sons, Inc.), etc.).

3) Step 3

Compound (4-5) may be prepared from Compound (4-2) in the similar manner to the method of literature (e.g., Comprehensive Organic transformation, R. C. Larock, VCH publisher Inc., 1989, etc.).

[Chemical Formula 132]

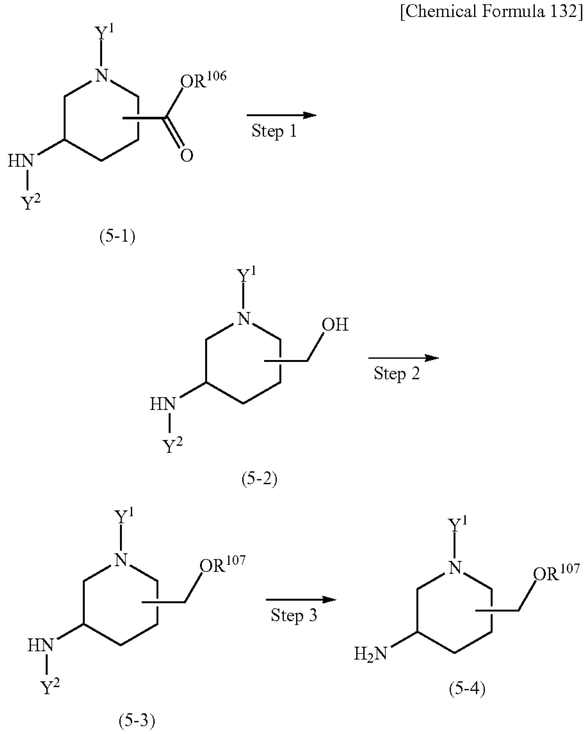

[In the scheme, $Y^1$ and $Y^2$ are the same as defined above, $R^{106}$ is $C_{1-4}$ alkyl, and $R^{107}$ is the same as B defined in the above Item 1. A substituent across a bond means that it is substituted on any position of $R^{3a}$, $R^{3b}$, $R^{3c}$ or $R^{3d}$ in Item 48. The same can be said for the following general scheme.]

1) Step 1

Compound (5-2) may be prepared from Compound (5-1) in the similar manner to the method of literature (e.g., Comprehensive Organic transformation, R. C. Larock, VCH publisher Inc., 1989, etc.). Compound (5-1) may be prepared in the similar manner to the method of literature (e.g., WO97/18813, WO02/10172, Tetrahedron Letters 46, 7495 (2005), WO02/02525, etc.).

2) Step 2

Compound (5-3) may be prepared from Compound (5-2) in the similar manner to the method of literature (e.g., Comprehensive Organic transformation, R. C. Larock, VCH publisher Inc., 1989, etc.).

3) Step 3

Compound (5-4) may be prepared from Compound (5-3) in the similar manner to the method of literature (e.g., Protective Groups in Organic Synthesis 2nd Edition (John Wiley & Sons, Inc.), etc.).

Preparation 6

Among a compound of formula (1-4), a compound of formula (6-5) or a salt thereof is prepared by the following method, for example.

[Chemical Formula 133]

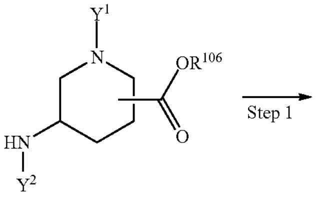

(5-1)

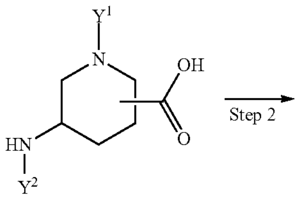

(6-1)

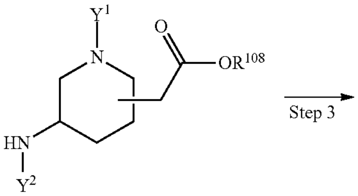

(6-2)

-continued

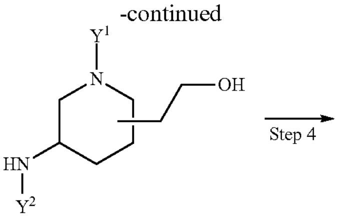

(6-3)

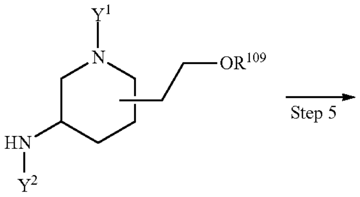

(6-4)

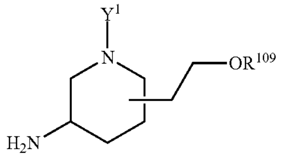

(6-5)

[In the scheme, $Y^1$, $Y^2$ and $R^{106}$ are the same as defined above, $R^{108}$ is $C_{1-4}$ alkyl, and $R^{109}$ is the same as B defined in the above Item 1.]

1) Step 1

Compound (6-1) may be prepared from Compound (5-1) in the similar manner to the method of literature (e.g., Comprehensive Organic transformation, R. C. Larock, VCH publisher Inc., 1989, etc.). Compound (5-1) may be prepared in the similar manner to the method of literature (e.g., WO97/18813, WO02/10172, Tetrahedron Letters 46, 7495 (2005), WO02/02525, J. Org. Chem. 70, 6956 (2005), etc.).

2) Step 2

Compound (6-2) may be prepared from Compound (6-1) in the similar manner to the method of literature (e.g., Comprehensive Organic transformation, R. C. Larock, VCH publisher Inc., 1989, J. Org. Chem. 57, 7194 (1992), etc.).

3) Steps 3 to 4

Compound (6-4) may be prepared from Compound (6-2) in the similar manner to the method of literature (e.g., Comprehensive Organic transformation, R. C. Larock, VCH publisher Inc., 1989, etc.).

4) Step 5

Compound (6-5) may be prepared from Compound (6-4) in the similar manner to the method of literature (e.g., Protective Groups in Organic Synthesis 2nd Edition (John Wiley & Sons, Inc.), etc.).

Preparation 7

Among a compound of formula (1-4), compounds of formulae (7-4), (7-6) and (7-8) or salts thereof are prepared by the following method, for example.

[Chemical Formula 134]

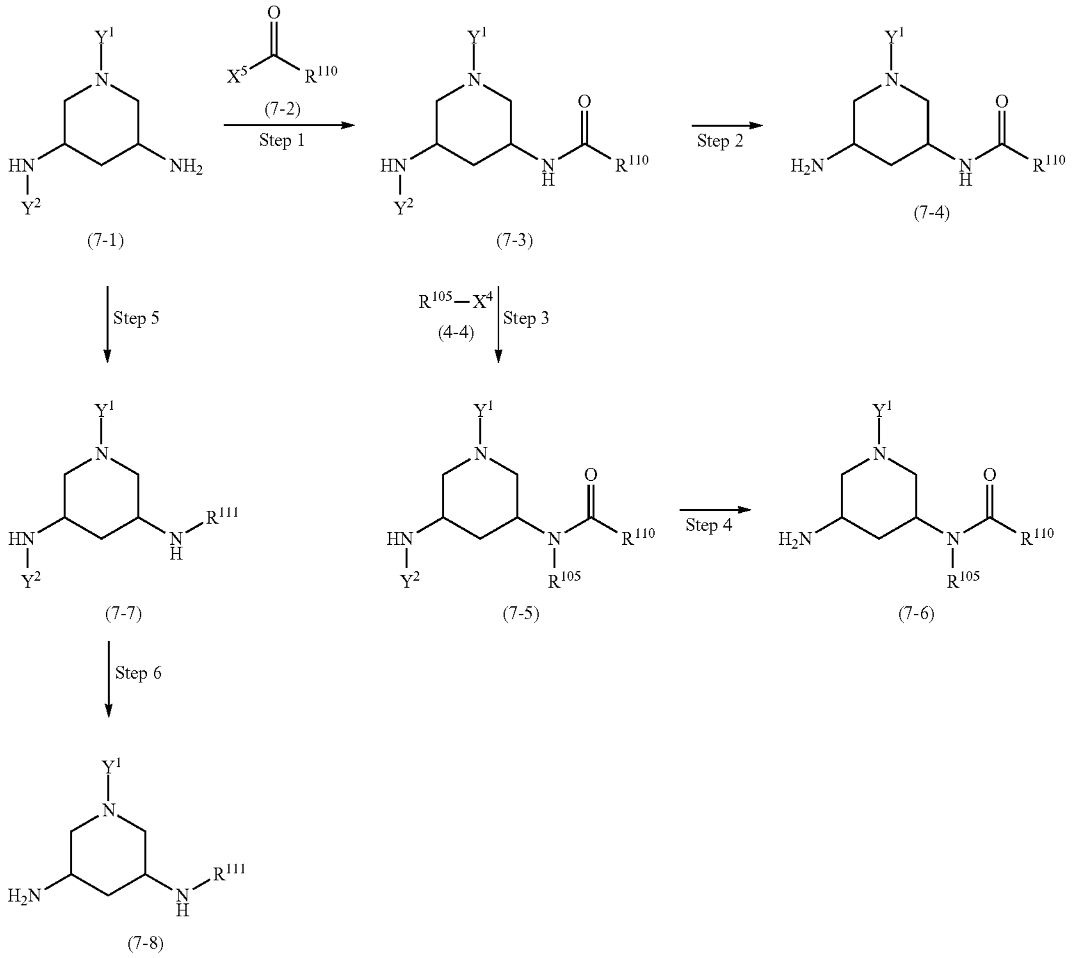

[In the scheme, $R^{105}$, $X^4$, $Y^1$ and $Y^2$ are the same as defined above, $X^5$ is hydroxyl or chlorine atom, and $R^{110}$ and $8^{111}$ are each independently the same as B defined in the above Item 1.]

1) Step 1

Compound (7-3) may be prepared from Compound (7-1) in the similar manner to the method of literature (e.g., Comprehensive Organic transformation, R. C. Larock, VCH publisher Inc., 1989, Chem. Pharm. Bull. 40, 102 (1992), J. Med. Chem. 26, 507 (1983), etc.). Compound (7-1) may be prepared in the similar manner to the method of literature (e.g., WO05/028467, etc.).

2) Step 2

Compound (7-4) may be prepared from Compound (7-3) in the similar manner to the method of literature (e.g., Protective Groups in Organic Synthesis 2nd Edition (John Wiley & Sons, Inc.), etc.).

3) Step 3

Compound (7-5) may be prepared from Compound (7-3) in the similar manner to the method of literature (e.g., Comprehensive Organic transformation, R. C. Larock, VCH publisher Inc., 1989, etc.).

4) Step 4

Compound (7-6) may be prepared from Compound (7-5) in the similar manner to the method of literature (e.g., Protective Groups in Organic Synthesis 2nd Edition (John Wiley & Sons, Inc.), etc.).

5) Step 5

Compound (7-7) may be prepared from Compound (7-1) in the similar manner to the method of literature (e.g., Comprehensive Organic transformation, R. C. Larock, VCH publisher Inc., 1989, J. Org. Chem. 61, 3849 (1996), J. Org. Chem. 68, 4120 (2003), J. Org. Chem. 63, 370 (1998), J. Org. Chem. 70, 2195 (2005), etc.).

6) Step 6

Compound (7-8) may be prepared from Compound (7-7) in the similar manner to the method of literature (e.g., Protective Groups in Organic Synthesis 2nd Edition (John Wiley & Sons, Inc.), etc.).

Preparation 8

Among a compound of formula (1-4), a compound of formula (8-4) or a salt thereof is prepared by the following method, for example.

[Chemical Formula 135]

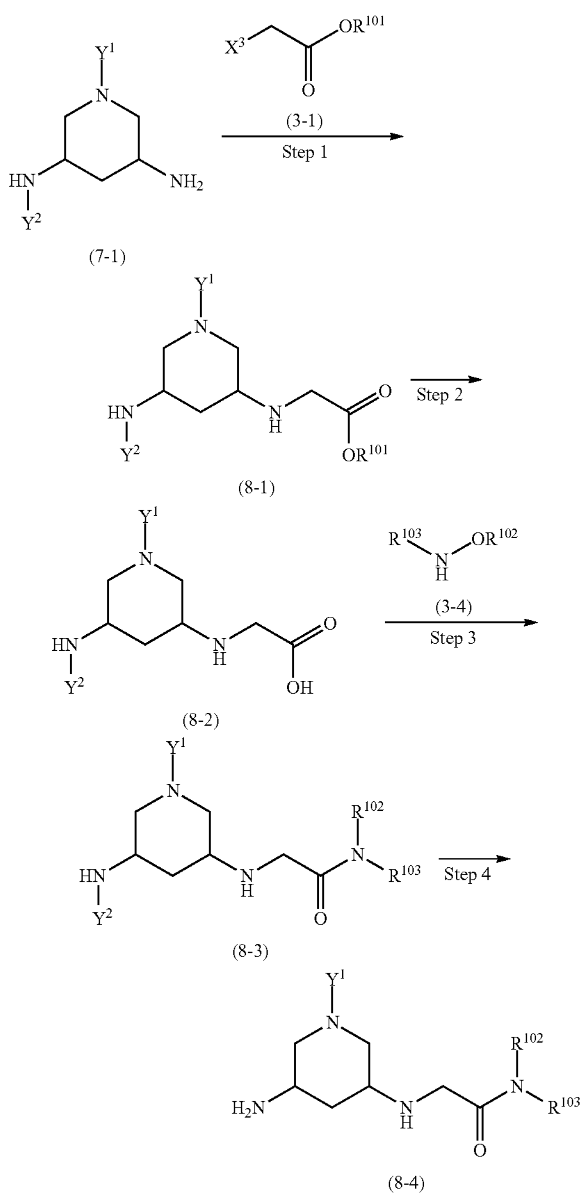

[In the scheme, $R^{101}$, $R^{102}$, $R^{103}$, $X^3$, $Y^1$ and $Y^2$ are the same as defined above.]

1) Step 1

Compound (8-1) may be prepared from Compound (7-1) in the similar manner to the method of literature (e.g., Comprehensive Organic transformation, R. C. Larock, VCH publisher Inc., 1989, Synthetic Communications 34, 219 (2004), etc.). Compound (7-1) may be prepared in the similar manner to the method of literature (e.g., WO05/028467, etc.).

2) Steps 2 to 3

Compound (8-3) may be prepared from Compound (8-1) in the similar manner to the method of literature (e.g., Comprehensive Organic transformation, R. C. Larock, VCH publisher Inc., 1989, etc.).

3) Step 4

Compound (8-4) may be prepared from Compound (8-3) in the similar manner to the method of literature (e.g., Protective Groups in Organic Synthesis 2nd Edition (John Wiley & Sons, Inc.), etc.).

Preparation 9

Among a compound of formula (1-4), a compound of formula (9-4) or a salt thereof is prepared by the following method, for example.

[Chemical Formula 136]

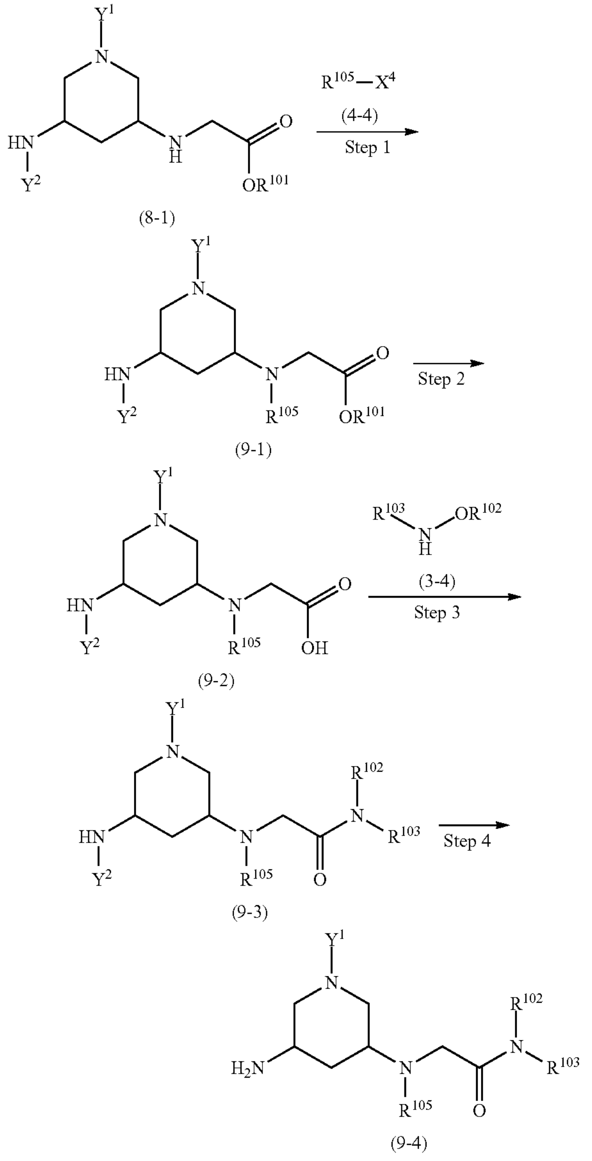

[In the scheme, $R^{101}$, $R^{102}$, $R^{103}$, $R^{105}$, $X^4$, $Y^1$ and $Y^2$ are the same as defined above.]

1) Steps 1 to 3

Compound (9-3) may be prepared from Compound (8-1) in the similar manner to the method of literature (e.g., Comprehensive Organic transformation, R. C. Larock, VCH publisher Inc., 1989, etc.).

2) Step 4

Compound (9-4) may be prepared from Compound (9-3) in the similar manner to the method of literature (e.g., Protective Groups in Organic Synthesis 2nd Edition (John Wiley & Sons, Inc.), etc.).

Preparation 10

Among a compound of formula (1-4), compounds of formulae (10-4) and (10-6) or salts thereof are prepared by the following method, for example.

3) Step 3

Compound (10-4) may be prepared from Compound (10-3) in the similar manner to the method of literature (e.g., Protective Groups in Organic Synthesis 2nd Edition (John Wiley & Sons, Inc.), etc.).

[Chemical Formula 137]

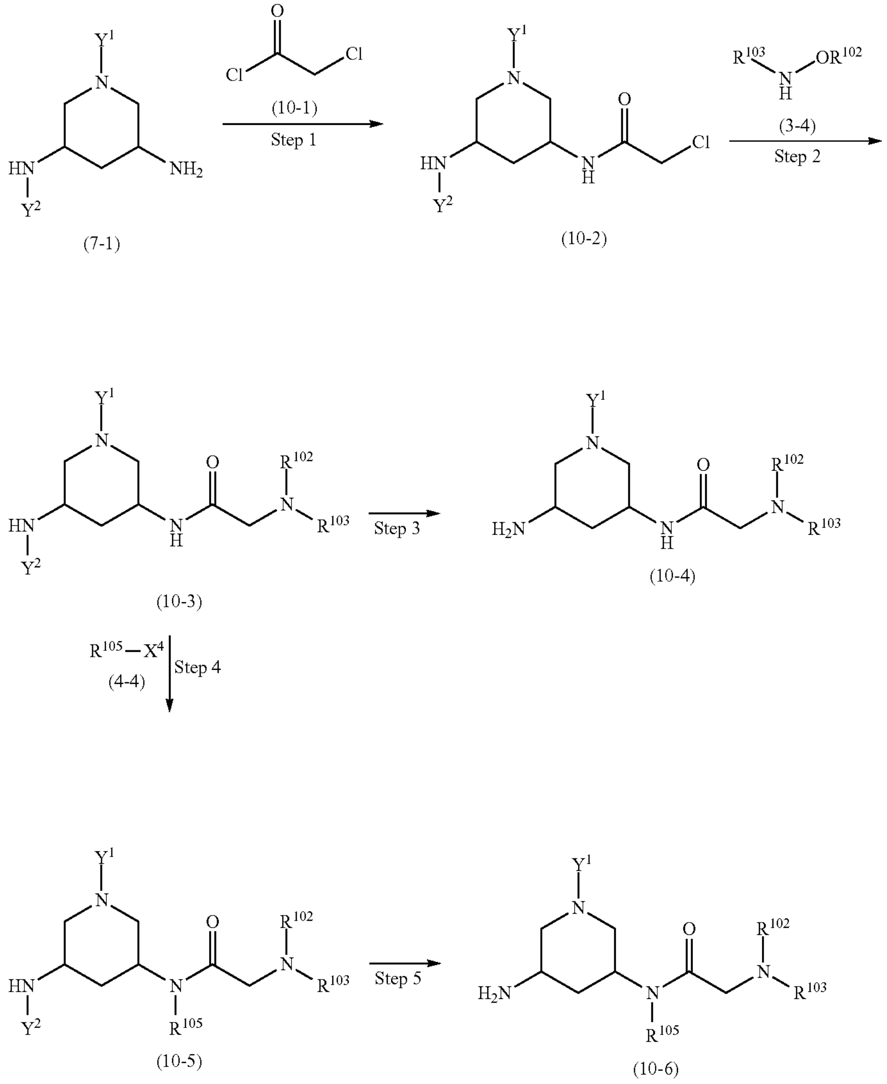

(7-1)
(10-2)
(10-3)
(10-4)
(10-5)
(10-6)

[In the scheme, $R^{102}$, $R^{103}$, $R^{105}$, $X^4$, $Y^1$ and $Y^2$ are the same as defined above.]

1) Step 1

Compound (10-2) may be prepared from Compound (7-1) in the similar manner to the method of literature (e.g., Tetrahedron: Asymmetry 16, 2599 (2005), etc.). Compound (7-1) may be prepared in the similar manner to the method of literature (e.g., WO05/028467, etc.).

2) Step 2

Compound (10-3) may be prepared from Compound (10-2) in the similar manner to the method of literature (e.g., Tetrahedron: Asymmetry 16, 2599 (2005), etc.).

4) Step 4

Compound (10-5) may be prepared from Compound (10-3) in the similar manner to the method of literature (e.g., Comprehensive Organic transformation, R. C. Larock, VCH publisher Inc., 1989, etc.).

5) Step 5

Compound (10-6) may be prepared from Compound (10-5) in the similar manner to the method of literature (e.g., Protective Groups in Organic Synthesis 2nd Edition (John Wiley & Sons, Inc.), etc.).

Preparation 11

Among a compound of formula (1-4), compounds of formulae (11-3) and (11-5) or salts thereof are prepared by the following method, for example.

[Chemical Formula 138]

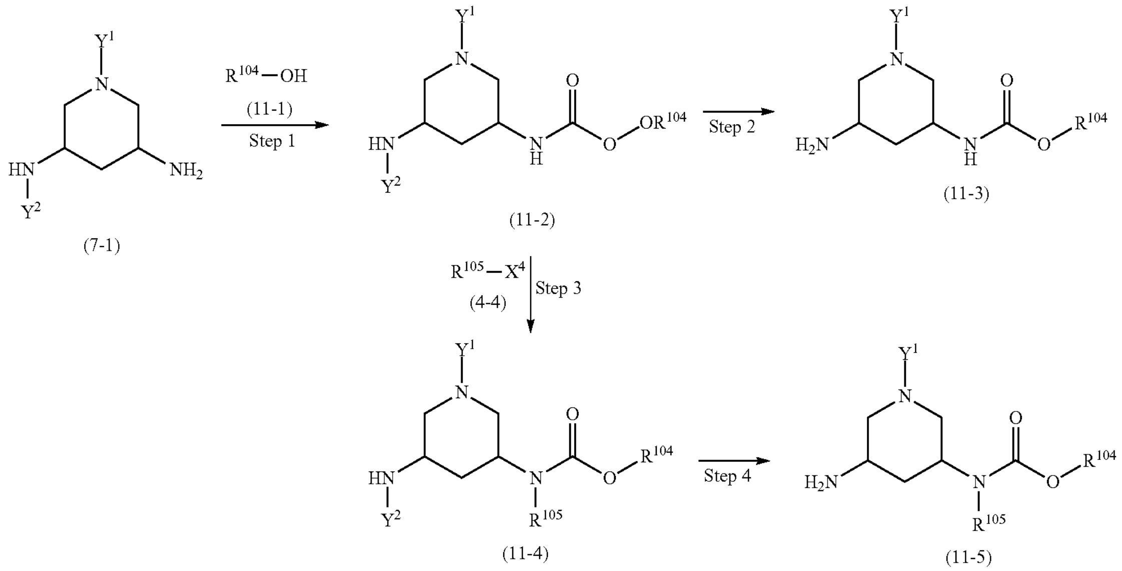

[In the scheme, $R^{104}$, $R^{105}$, $X^4$, $Y^1$ and $Y^2$ are the same as defined above.]

1) Step 1

Compound (11-2) may be prepared by reacting Compound (7-1) with Compound (11-1) in the similar manner to the method of literature (e.g., WO01/057044, etc.).

2) Step 2

Compound (11-3) may be prepared from Compound (11-2) in the similar manner to the method of literature (e.g., Protective Groups in Organic Synthesis 2nd Edition (John Wiley & Sons, Inc.), etc.).

3) Step 3

Compound (11-4) may be prepared from Compound (11-2) in the similar manner to the method of literature (e.g., Comprehensive Organic transformation, R. C. Larock, VCH publisher Inc., 1989, etc.).

4) Step 4

Compound (11-5) may be prepared from Compound (11-4) in the similar manner to the method of literature (e.g., Protective Groups in Organic Synthesis 2nd Edition (John Wiley & Sons, Inc.), etc.).

Preparation 12

Among a compound of formula (1-4), a compound of formula (12-3) or a salt thereof is prepared by the following method, for example.

[Chemical Formula 139]

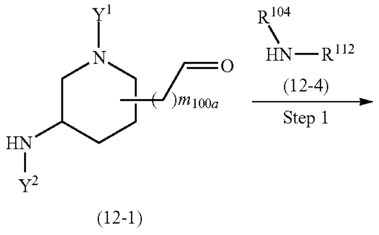

-continued

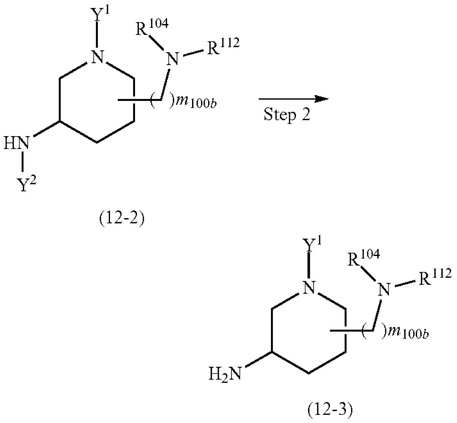

[In the scheme, $R^{104}$, $Y^1$ and $Y^2$ are the same as defined above, $R^{112}$ is the same as $R^{4c}$ defined in the above Item 1, in which $R^{104}$ and $8^{112}$ may combine each other to form a ring, $m_{100a}$ is 0 or 1, and $m_{100b}$ is 1 or 2.]

1) Step 1

Compound (12-2) may be prepared from Compound (12-1) in the similar manner to the method of literature (e.g., Comprehensive Organic transformation, R. C. Larock, VCH publisher Inc., 1989, etc.).

2) Step 2

Compound (12-3) may be prepared from Compound (12-2) in the similar manner to the method of literature (e.g., Protective Groups in Organic Synthesis 2nd Edition (John Wiley & Sons, Inc.), etc.).

Preparation 13

Among a compound of formula (1-4), compounds of formulae (13-4) and (13-6) or salts thereof are prepared by the following method, for example.

[Chemical Formula 140]

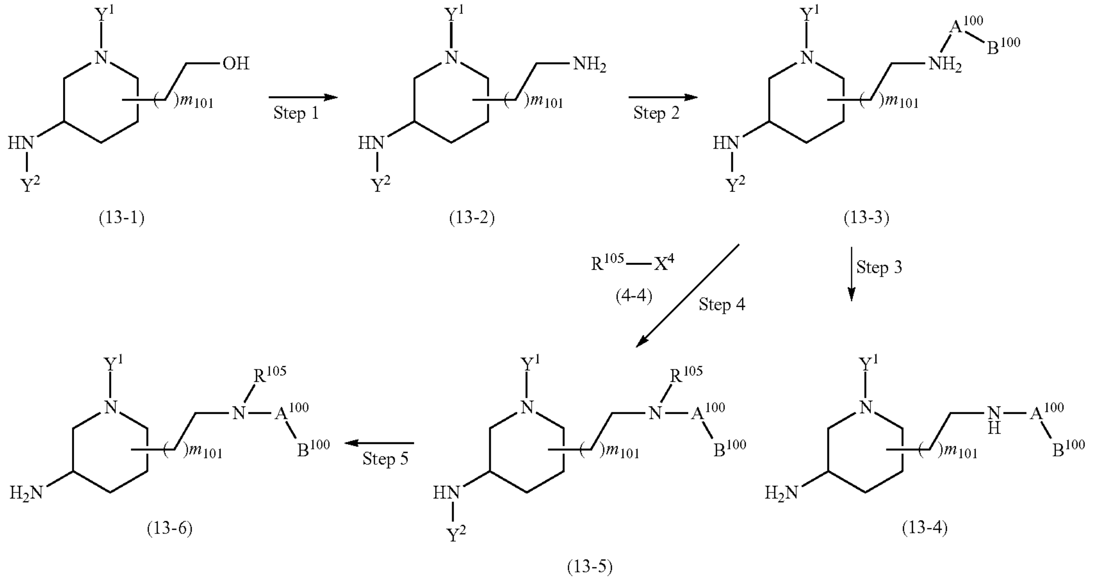

(13-1) (13-2) (13-3) (4-4) (13-6) (13-5) (13-4)

[In the scheme, $R^{105}$, $X^4$, $Y^1$ and $Y^2$ are the same as defined above, $A^{100}$ is —$SO_2$— or —CO—, $B^{100}$ is the same as B defined in the above Item 1, and $m_{101}$ is an integer of 0 or 1.]

1) Steps 1 to 2

Compound (13-3) may be prepared from Compound (13-1) in the similar manner to the method of literature (e.g., Comprehensive Organic transformation, R. C. Larock, VCH publisher Inc., 1989, etc.).

2) Step 3

Compound (13-4) may be prepared from Compound (13-3) in the similar manner to the method of literature (e.g., Protective Groups in Organic Synthesis 2nd Edition (John Wiley & Sons, Inc.), etc.).

3) Step 4

Compound (13-5) may be prepared from Compound (13-3) in the similar manner to the method of literature (e.g., Comprehensive Organic transformation, R. C. Larock, VCH publisher Inc., 1989, etc.).

4) Step 5

Compound (13-6) may be prepared from Compound (13-5) in the similar manner to the method of literature (e.g., Protective Groups in Organic Synthesis 2nd Edition (John Wiley & Sons, Inc.), etc.).

Preparation 14

Among a compound of formula (1-4), a compound of formula (14-2) or a salt thereof is prepared by the following method, for example.

[Chemical Formula 141]

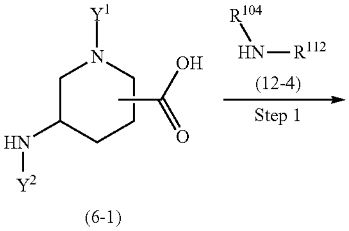

(6-1) (12-4)

-continued

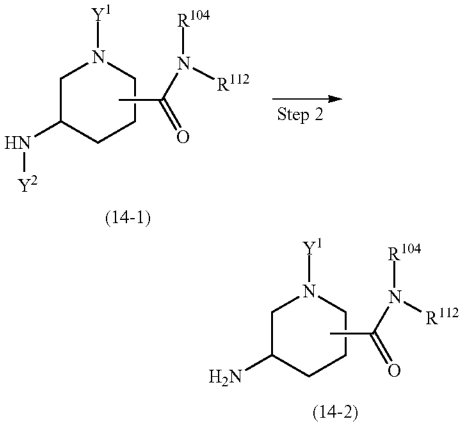

(14-1) (14-2)

[In the scheme, $R^{104}$, $R^{112}$, $Y^1$ and $Y^2$ are the same as defined above.]

1) Step 1

Compound (14-1) may be prepared from Compound (6-1) in the similar manner to the method of literature (e.g., Comprehensive Organic transformation, R. C. Larock, VCH publisher Inc., 1989, etc.).

2) Step 2

Compound (14-2) may be prepared from Compound (14-1) in the similar manner to the method of literature (e.g., Protective Groups in Organic Synthesis 2nd Edition (John Wiley & Sons, Inc.), etc.).

Preparation 15

Among a compound of formula (1-4), a compound of formula (15-3) or a salt thereof is prepared by the following method, for example.

[Chemical Formula 142]

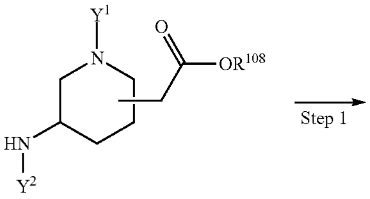

(6-2)

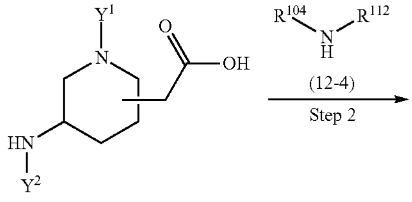

(15-1)

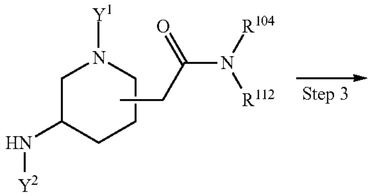

(15-2)

-continued

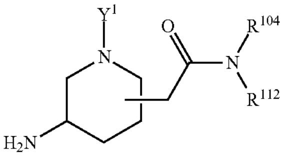

(15-3)

[In the scheme, $R^{104}$, $R^{112}$, $R^{108}$, $Y^1$ and $Y^2$ are the same as defined above.]

1) Steps 1 to 2

Compound (15-2) may be prepared from Compound (6-2) in the similar manner to the method of literature (e.g., Comprehensive Organic transformation, R. C. Larock, VCH publisher Inc., 1989, etc.).

2) Step 3

Compound (15-3) may be prepared from Compound (15-2) in the similar manner to the method of literature (e.g., Protective Groups in Organic Synthesis 2nd Edition (John Wiley & Sons, Inc.), etc.).

Preparation 16

Among a compound of formula (1-4), compounds of formulae (16-4) and (16-6) or salts thereof are prepared by the following method, for example.

[Chemical Formula 143]

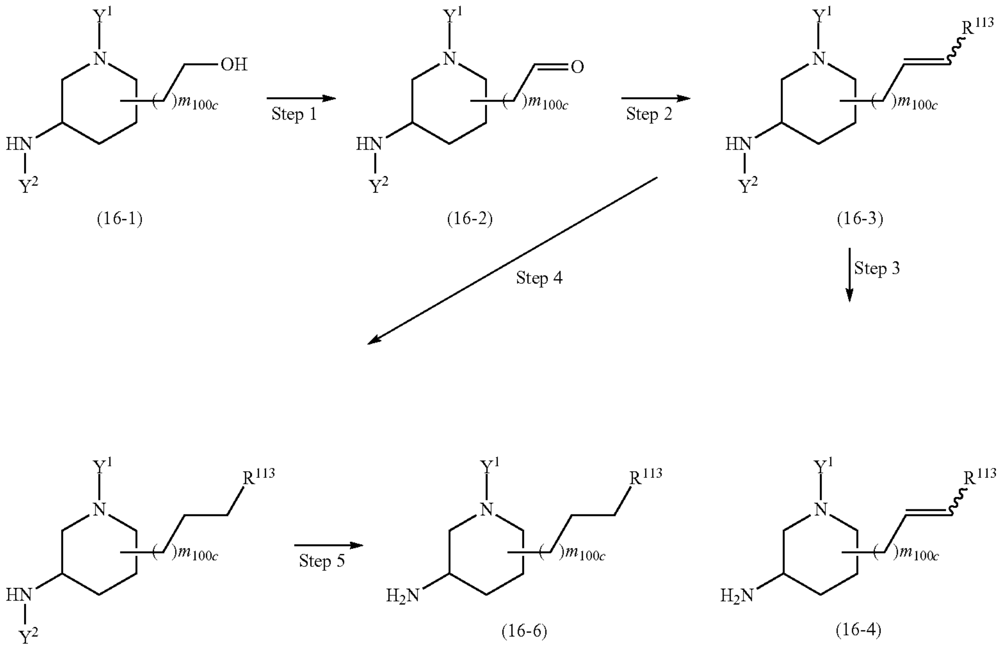

[In the scheme, $Y^1$ and $Y^2$ are the same as defined above, $m_{100c}$ is an integer of 0 to 4, and $R^{113}$ is any of the above (a) to (z), provided that it is limited to any of the above (a) to (s) in Compound (16-4).]

1) Step 1

Compound (16-2) may be prepared from Compound (16-1) in the similar manner to the method of literature (e.g., Tetrahedron: Asymmetry 17, 993 (2006), Comprehensive Organic transformation, R. C. Larock, VCH publisher Inc., 1989, etc.).

2) Step 2

Compound (16-3) may be prepared from Compound (16-2) in the similar manner to the method of literature (e.g., Tetrahedron: Asymmetry 8, 3685 (1997), J. Org. Chem. 61, 6033 (1996), JP-A-8-12605, Comprehensive Organic transformation, R. C. Larock, VCH publisher Inc., 1989, etc.).

3) Step 3

Compound (16-4) may be prepared from Compound (16-3) in the similar manner to the method of literature (e.g., Protective Groups in Organic Synthesis 2nd Edition (John Wiley & Sons, Inc.), etc.).

4) Step 4

Compound (16-5) may be prepared from Compound (16-3) in the similar manner to the method of literature (e.g., Comprehensive Organic transformation, R. C. Larock, VCH publisher Inc., 1989, etc.).

5) Step 5

Compound (16-6) may be prepared from Compound (16-5) in the similar manner to the method of literature (e.g., Protective Groups in Organic Synthesis 2nd Edition (John Wiley & Sons, Inc.), etc.).

Preparation 17

Among a compound of formula (1-4), compounds of formulae (17-3) and (17-5) or salts thereof are prepared by the following method, for example.

[Chemical Formula 144]

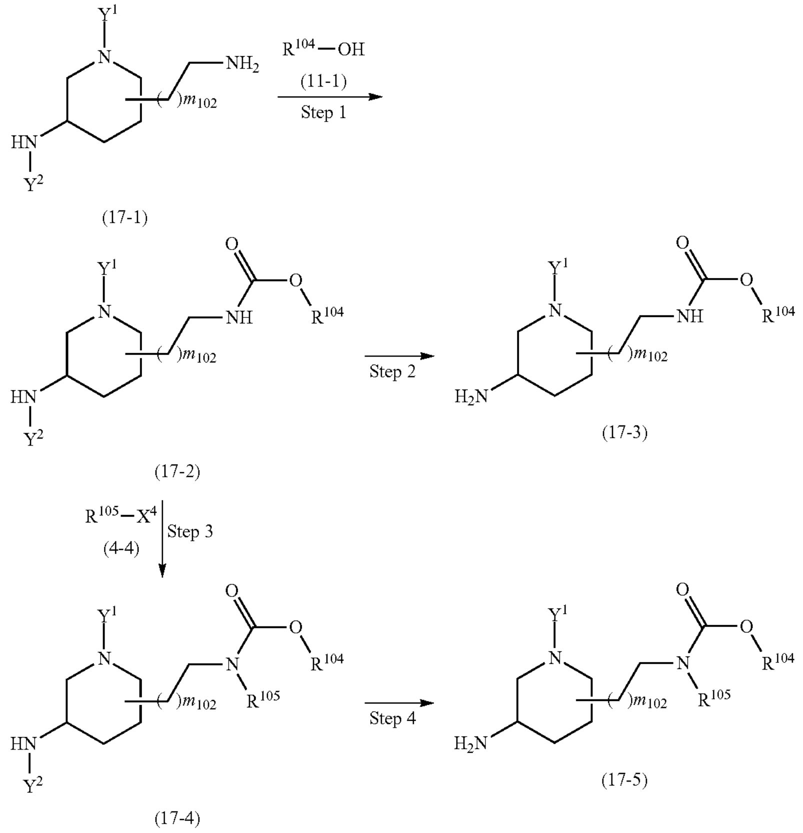

(17-1) (17-2) (17-3) (17-4) (17-5)

[In the scheme, $R^{104}$, $R^{105}$, $X^4$, $Y^1$ and $Y^2$ are the same as defined above, and $m_{102}$ is an integer of 0 or 1.]

1) Step 1

Compound (17-2) may be prepared by reacting Compound (17-1) with Compound (11-1) in the similar manner to the method of literature (e.g., WO01/057044, etc.).

2) Step 2

Compound (17-3) may be prepared from Compound (17-2) in the similar manner to the method of literature (e.g., Protective Groups in Organic Synthesis 2nd Edition (John Wiley & Sons, Inc.), etc.).

3) Step 3

Compound (17-4) may be prepared from Compound (17-2) in the similar manner to the method of literature (e.g., Comprehensive Organic transformation, R. C. Larock, VCH publisher Inc., 1989, etc.).

4) Step 4

Compound (17-5) may be prepared from Compound (17-4) in the similar manner to the method of literature (e.g., Protective Groups in Organic Synthesis 2nd Edition (John Wiley & Sons, Inc.), etc.).

Preparation 18

Among a compound of formula (1-4), compounds of formulae (18-5) and (18-7) or salts thereof are prepared by the following method, for example.

[Chemical Formula 145]

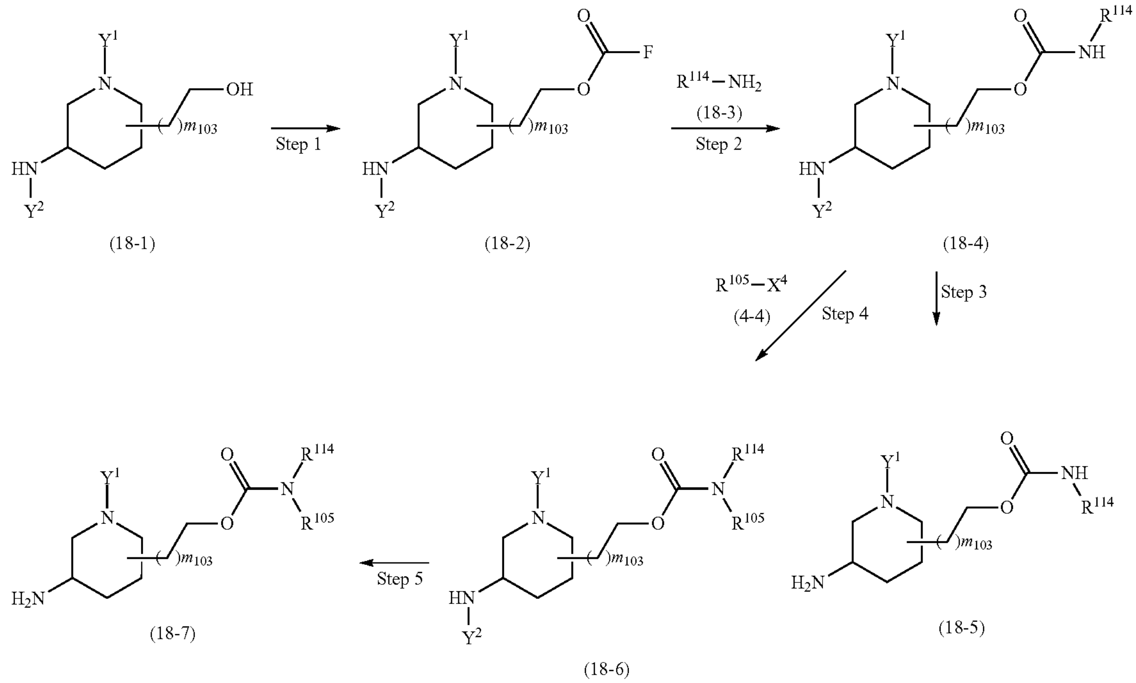

(18-1) (18-2) (18-4) (18-5) (18-6) (18-7)

[In the scheme, $R^{105}$, $X^4$, $Y^1$ and $Y^2$ are the same as defined above, $m_{103}$ is an integer of 0 or 1, and $R^{114}$ is the same as B defined in the above Item 1.]

1) Step 1

Compound (18-2) may be prepared from Compound (18-1) in the similar manner to the method of literature (e.g., Tetrahedron Letters 43, 4275 (2002), etc.).

2) Step 2

Compound (18-4) may be prepared from Compound (18-2) in the similar manner to the method of literature (e.g., Comprehensive Organic transformation, R. C. Larock, VCH publisher Inc., 1989, etc.).

3) Step 3

Compound (18-5) may be prepared from Compound (18-4) in the similar manner to the method of literature (e.g., Protective Groups in Organic Synthesis 2nd Edition (John Wiley & Sons, Inc.), etc.).

4) Step 4

Compound (18-6) may be prepared from Compound (18-4) in the similar manner to the method of literature (e.g., Comprehensive Organic transformation, R. C. Larock, VCH publisher Inc., 1989, etc.).

5) Step 5

Compound (18-7) may be prepared from Compound (18-6) in the similar manner to the method of literature (e.g., Protective Groups in Organic Synthesis 2nd Edition (John Wiley & Sons, Inc.), etc.).

Preparation 19

Among a compound of formula (1-4), a compound of formula (19-13) or a salt thereof is prepared by the following method, for example.

[Chemical Formula 146]

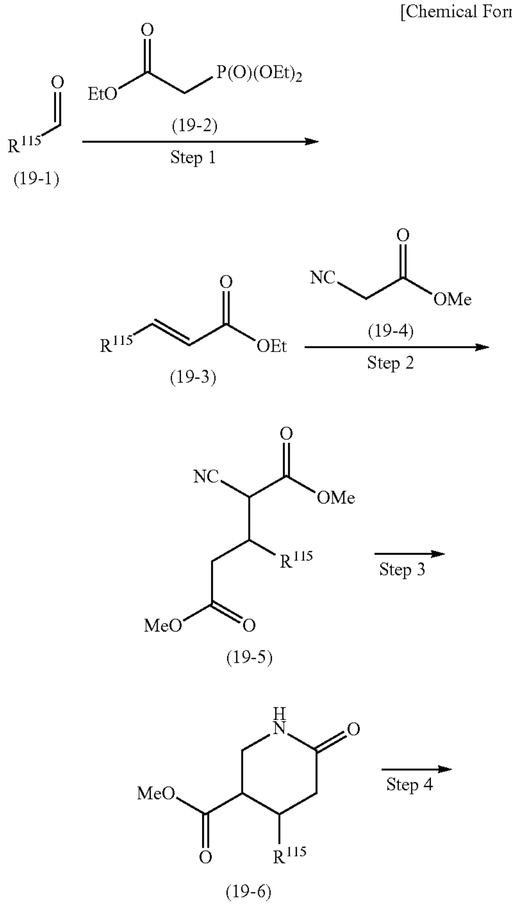

(19-1) (19-3) (19-5) (19-6)

-continued

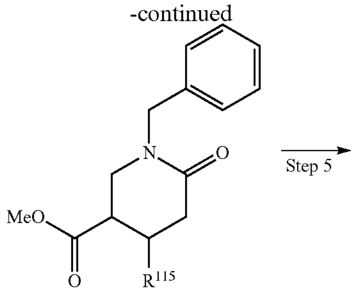

(19-7)

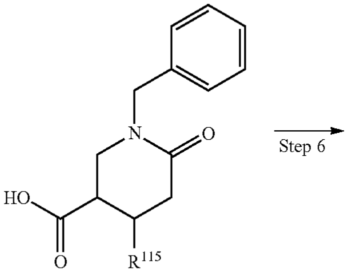

(19-8)

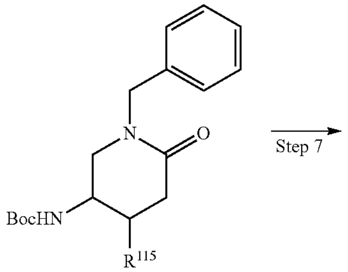

(19-9)

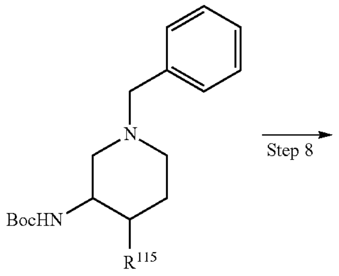

(19-10)

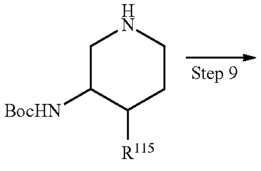

(19-11)

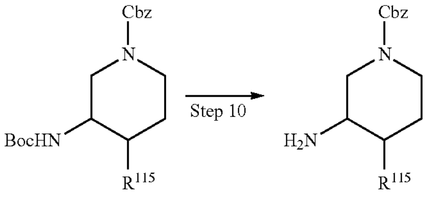

(19-12) (19-13)

[In the scheme, $R^{115}$ is the same as B defined in the above Item 1.]

1) Steps 1 to 8

Compound (19-11) may be prepared from Compound (19-1) in the similar manner to

[Chemical Formula 148]

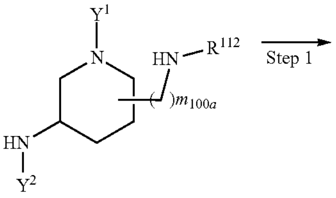

(21-1)

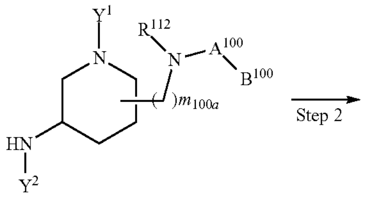

(21-2)

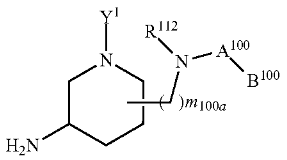

(21-3)

[In the scheme, $m_{100a}$, $R^{112}$, $A^{100}$, $B^{100}$, $Y^1$ and $Y^2$ are the same as defined above.]

1) Step 1

Compound (21-2) may be prepared from Compound (21-1) in the similar manner to Step 2 of Preparation 13. Compound (21-1) may be prepared in the similar manner to the method of Preparation 12.

2) Step 2

Compound (21-3) may be prepared from Compound (21-2) in the similar manner to the method of literature (e.g., Protective Groups in Organic Synthesis 2nd Edition (John Wiley & Sons, Inc.), etc.).

Preparation 22

Among a compound of formula (1-14), a compound of formula (22-2) or a salt thereof is prepared by the following method, for example.

[Chemical Formula 149]

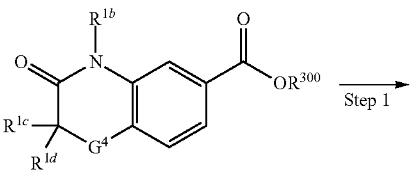

(22-1)

-continued

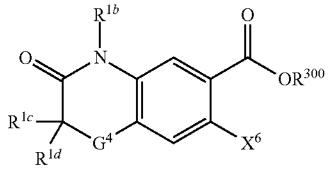

(22-2)

[In the scheme, $G^4$, $R^{1b}$, $R^{1c}$, $R^{1d}$ and $R^{300}$ are the same as defined above, and $X^6$ is halogen atom.]

1) Step 1

Compound (22-2) may be prepared by reacting Compound (22-1) with one compound selected from N-chlorosuccinimide, N-bromosuccinimide and N-iodosuccinimide in an inert solvent in the presence of sodium acetate. The inert solvent includes, for example, an organic the method of literature (e.g., WO06/039325, etc.).

2) Steps 9 to 10

Compound (19-13) may be prepared from Compound (19-11) in the similar manner to the method of literature (e.g., Protective Groups in Organic Synthesis 2nd Edition (John Wiley & Sons, Inc.), etc.).

Preparation 20

Among a compound of formula (1-4), a compound of formula (20-8) or a salt thereof is prepared by the following method, for example.

[Chemical Formula 147]

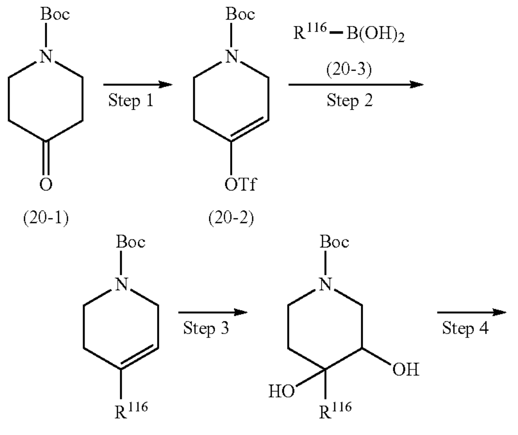

(20-1) (20-2) (20-4) (20-5)

-continued

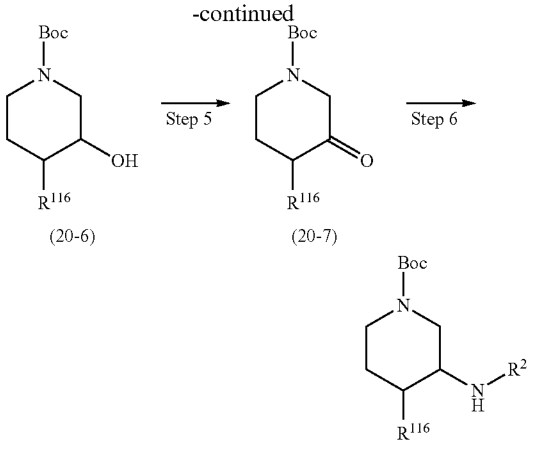

(20-6) (20-7) (20-8)

[In the scheme, $R^2$ is the same as defined in Item 1, and $R^{116}$ is optionally substituted $C_{6-10}$ aryl, or optionally substituted 5- to 10-membered monocyclic or polycyclic heteroaryl.]

1) Steps 1 to 5

Compound (20-7) may be prepared from Compound (20-1) in the similar manner to the method of literature (e.g., Bioorganic & Medicinal Chemistry 13, 59 (2005), etc.).

2) Step 6

Compound (20-8) may be prepared from Compound (20-7) in the similar manner to the method of literature (e.g., Protective Groups in Organic Synthesis 2nd Edition (John Wiley & Sons, Inc.), etc.).

Preparation 21

Among a compound of formula (1-4), a compound of formula (21-3) or a salt thereof is prepared by the following method, for example.

acid such as acetic acid or propionic acid. The reaction temperature is selected in the range of about −20° C. to about 50° C.

Preparation 23

Among a compound of formula (1-14), compounds of formulae (23-3) and (23-6) or salts thereof are prepared by the following method, for example.

[Chemical Formula 150]

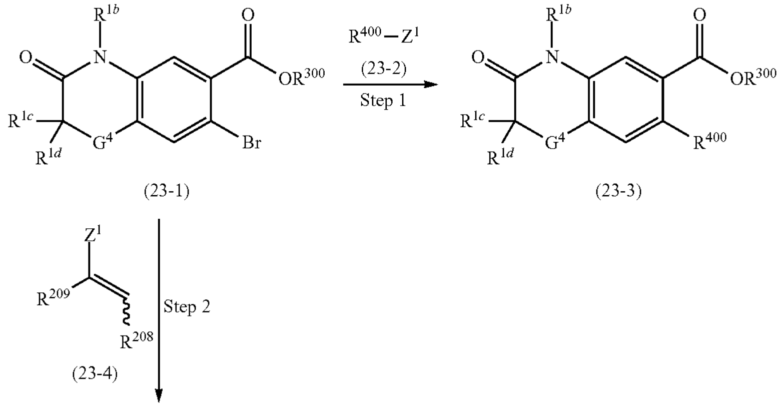

(23-1) (23-3) (23-4)

-continued

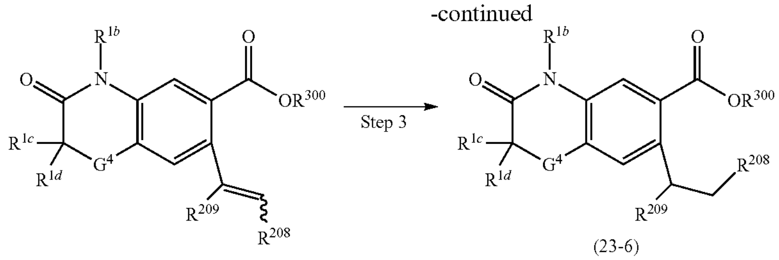

(23-5) (23-6)

[In the scheme, $G^4$, $R^{1b}$, $R^{1c}$, $R^{1d}$ and $R^{300}$ are the same as defined above, $R^{208}$ and $R^{209}$ are hydrogen atom and alkyl, $R^{400}$ is alkyl, and $Z^1$ is a group of formula:

[Chemical Formula 151]

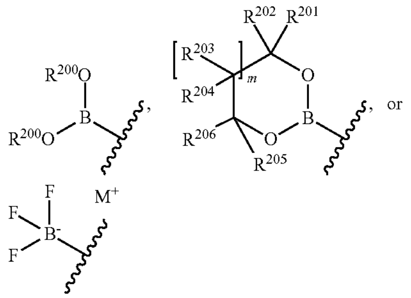

[wherein $R^{200}$ is hydrogen atom or $C_{1-4}$ alkyl, or two $R^{200}$ may combine each other to form 1,2-phenylene, $R^{201}$, $R^{202}$, $R^{203}$, $R^{204}$, $R^{205}$ and $R^{206}$ are each independently hydrogen atom or $C_{1-2}$ alkyl, m is an integer of 0 or 1, and $M^+$ is potassium ion, sodium ion, or ammonium ion.]

1) Step 1

Compound (23-3) may be prepared by reacting Compound (23-1) with Compound (23-2) in an inert solvent in the presence of Pd catalyst and an inorganic base. The inorganic base includes sodium hydrogencarbonate, potassium hydrogencarbonate, sodium carbonate, or potassium carbonate, etc. The Pd catalyst includes [1,1'-bis(diphenylphosphino)-ferrocene]palladium dichloride, or [1,1'-bis(diphenylphosphino)ferrocene]palladium dichloride dichloromethane complex, etc. The inert solvent includes water, tetrahydrofuran, or an ether type solvent such as 1,4-dioxane or 1,2-dimethoxyethane, etc. A mixed solvent of water and an ether type solvent is usually selected. The reaction temperature is selected in the range of about 50° C. to about 120° C.

2) Step 2

Compound (23-5) may be prepared from Compound (23-1) in the similar manner to the method of literature (e.g., Eur. J. Org. Chem. 5, 1075 (2004), WO07/39142, J. Org. Chem. 67, 8424 (2002), Organic Letters 4, 107 (2002), Organic Letters 3, 393 (2001), Tetrahedron 58, 465 (2002), etc.). An example of preparation method is illustrated as below.

Compound (23-5) may be prepared by reacting Compound (23-1) with Compound (23-4) wherein $Z^1$ is $B(OH)_2$ in the presence of Pd catalyst and a base in an inert solvent. The inert solvent includes water, or an ether type solvent such as tetrahydrofuran, 1,4-dioxane or 1,2-dimethoxyethane, and a mixed solvent of water and an ether type solvent is usually selected. The base includes sodium carbonate, sodium hydrogencarbonate, potassium carbonate or potassium hydrogencarbonate, etc. Pd catalyst includes palladium diphenylphosphinodichloride, or tetrakistriphenylphosphine palladium, etc. The reaction temperature is selected in the range of about 50° C. to about 150° C.

3) Step 3

Compound (23-6) may be prepared by hydrogenating Compound (23-5) in the presence of palladium carbon or palladium hydroxide in an inert solvent. The inert solvent includes, for example, an alcohol solvent such as methanol, ethanol or 2-propanol, etc. The reaction temperature is selected in the range of about 0° C. to about 50° C.

Preparation 24

Among a compound of formula (1-14), a compound of formula (24-1) or a salt thereof is prepared by the following method, for example.

[Chemical Formula 152]

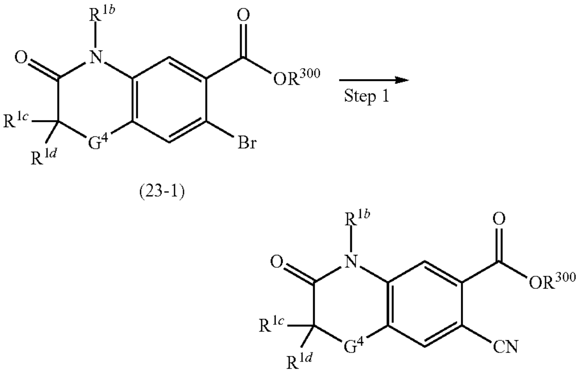

(23-1)

(24-1)

[In the scheme, $G^4$, $R^{1b}$, $R^{1c}$, $R^{1d}$ and $R^{300}$ are the same as defined above.]

1) Step 1

Compound (24-1) may be prepared from Compound (23-1) in the similar manner to the method of literature (e.g., Synth. Commun. 24, 887 (1994), Organic Letters 9, 1711 (2007), Tetrahedron Lett. 40, 8193 (1999), Tetrahedron Lett. 45, 1441 (2004), etc.).

Preparation 25

Among a compound of formula (1-13), a compound of formula (25-4) or a salt thereof is prepared by the following method, for example.

[Chemical Formula 153]

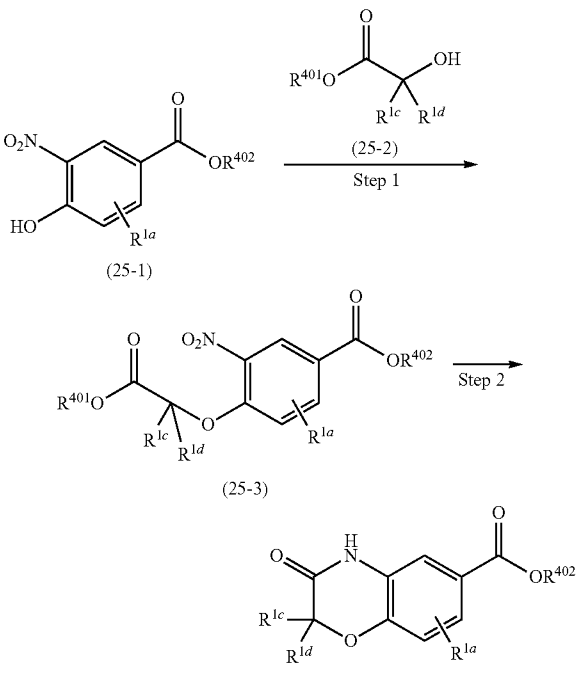

(25-1) (25-3) (25-4)

[In the scheme, $R^{1a}$, $R^{1c}$ and $R^{1d}$ are the same as defined above, $R^{401}$ is $C_{1-6}$ alkyl, and $R^{402}$ is $C_{1-2}$ alkyl.]

1) Step 1

Compound (25-3) may be prepared by reacting Compound (25-1) with Compound (25-2) in the presence of phosphine and a condensing agent in an inert solvent. The phosphine includes triphenylphosphine, etc., the inert solvent includes, for example, an ether type solvent such as tetrahydrofuran, diethylether, 1,4-dioxane or 1,2-dimethoxyethane, etc., and the condensing agent includes diisopropyl azodicarboxylate, etc. The reaction temperature is selected in the range of about 0° C. to about 80° C.

2) Step 2

For example, it can be carried out by the following preparation (i. or ii.).

i. Compound (25-4) may be prepared by reacting iron and Compound (25-3) in an inert solvent. The inert solvent includes, for example, water, acetic acid, or an alcohol solvent such as methanol, ethanol or 2-propanol, etc., and may be a mixed solvent thereof. The reaction temperature is selected in the range of about 30° C. to about 100° C.

ii. Compound (25-4) may be prepared by hydrogenating Compound (25-3) in the presence of palladium carbon or palladium hydroxide in an inert solvent. The inert solvent includes, for example, an alcohol solvent such as methanol, ethanol or 2-propanol, or an ether type solvent such as tetrahydrofuran, diethylether, 1,4-dioxane or 1,2-dimethoxyethane, etc. The reaction temperature is selected in the range of about 0° C. to about 50° C.

Preparation 26

Among a compound of formula (1-14), a compound of formula (26-5) or a salt thereof is prepared by the following method, for example.

[Chemical Formula 154]

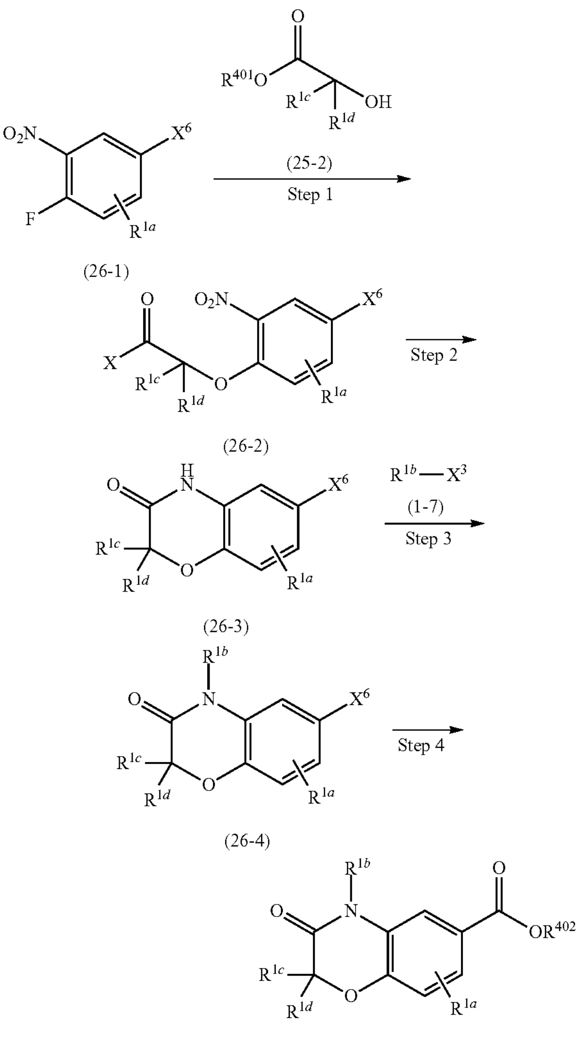

(26-1) (26-2) (26-3) (26-4) (26-5)

[In the scheme, $X^3$, $R^{1a}$, $R^{1b}$, $R^{1c}$, $R^{1d}$, $R^{401}$ and $R^{402}$ are the same as defined above, and $X^6$ is bromine atom or iodine atom.]

1) Step 1

Compound (26-2) may be prepared by reacting Compound (26-1) with Compound (25-2) and sodium hydride in the presence or absence of a crown ether in an inert solvent. The crown ether includes 15-crown, etc., and the inert solvent includes, for example, an ether type solvent such as tetrahydrofuran, diethylether, 1,4-dioxane, or 1,2-dimethoxyethane, etc. The reaction temperature is selected in the range of about 0° C. to about 50° C.

2) Step 2

Compound (26-3) may be prepared from Compound (26-2) in the similar manner to Step 2 of Preparation 25.

3) Step 3

Compound (26-4) may be prepared by reacting Compound (26-3) with Compound (1-7) in the presence of an inorganic base in an inert solvent. The inorganic base includes potassium carbonate or sodium hydride, etc. The inert solvent includes, for example, an ether type solvent such as tetrahydrofuran, diethylether, 1,4-dioxane or 1,2-dimethoxyethane, or a nitrile type solvent such as acetonitrile or propionitrile, etc. The reaction temperature is selected in the range of about 30° C. to about 100° C.

4) Step 4

Compound (26-5) may be prepared by treating Compound (26-4) under carbon monoxide with methanol or ethanol, an organic base, an auxiliary ligand and palladium acetate in an inert solvent. The auxiliary ligand includes diphenylphosphinopropane, etc. The organic base includes N,N-diisopropylethylamine, etc. The inert solvent includes, for example, an amide type solvent such as dimethylacetamide, etc. The reaction temperature is selected in the range of about 70° C. to about 150° C.

Preparation 27

Among a compound of formula (1-3), a compound of formula (27-7) or a salt thereof is prepared by the following method, for example.

[Chemical Formula 155]

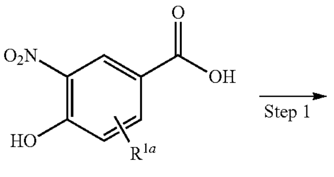

(27-1)

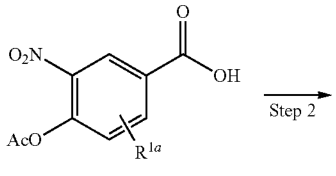

(27-2)

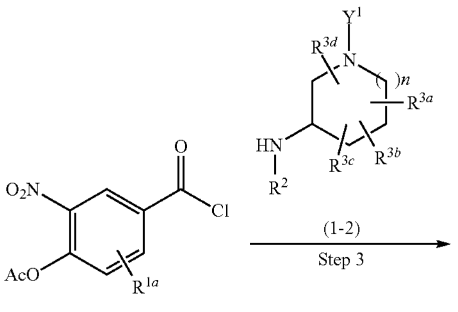

(27-3)

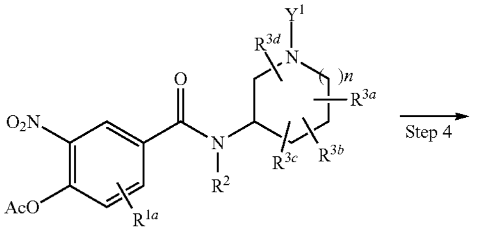

(27-4)

-continued

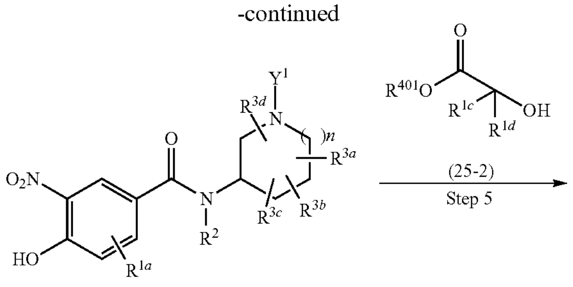

(27-5)

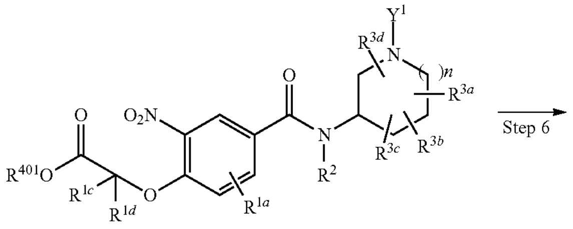

(27-6)

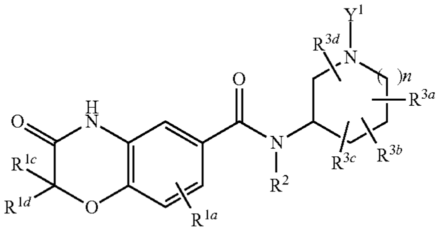

(27-7)

[In the scheme, n, $R^{401}$, $Y^1$, $R^{1a}$, $R^{1c}$, $R^{1d}$, $R^{3a}$, $R^{3b}$, $R^{3c}$, $R^{3d}$ and $R^2$ are the same as defined above.]

1) Step 1

Compound (27-2) may be prepared by reacting Compound (27-1) with acetic anhydride in pyridine solvent, for example. The reaction temperature is selected in the range of about 10° C. to about 40° C.

2) Step 2

Compound (27-3) may be prepared from Compound (27-2) in the similar manner to Step 1 of Preparation 1.

3) Step 3

Compound (27-4) may be prepared from Compound (27-3) in the similar manner to Step 1 of Preparation 1.

4) Step 4

Compound (27-5) may be prepared by reacting Compound (27-4) with a base in the presence or absence of Amberlite® in an inert solvent. The base includes an inorganic base such as sodium hydrogencarbonate, potassium hydrogencarbonate, sodium carbonate, potassium carbonate, sodium hydroxide, or sodium hydride, etc. The inert solvent includes, for example, an alcohol such as methanol, ethanol or 2-propanol, etc. The reaction temperature is selected in the range of about 10° C. to about 40° C.

5) Step 5

Compound (27-6) may be prepared from Compound (27-5) in the similar manner to Step 1 of Preparation 1.

6) Step 6

Compound (27-7) may be prepared from Compound (27-6) in the similar manner to Step 6 of Preparation 1.

Preparation 28

Among a compound of formula (1-13), a compound of formula (28-3) or a salt thereof is prepared by the following method, for example.

[Chemical Formula 156]

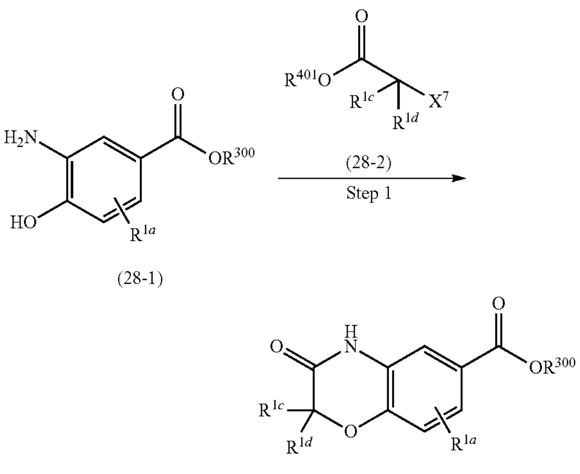

(28-1) (28-2) (28-3)

[In the scheme, $R^{1a}$, $R^{1c}$, $R^{1d}$, $R^{401}$ and $R^{300}$ are the same as defined above, and $X^7$ is bromine atom or chlorine atom.]

1) Step 1

Compound (28-3) may be prepared from Compound (28-1) in the similar manner to the method of literature (e.g., Chem. Pharm. Bull. 46, 1716 (1998), etc.).

Preparation 29

Among a compound of formula (1-13), a compound of formula (29-4) or a salt thereof is prepared by the following method, for example.

[Chemical Formula 157]

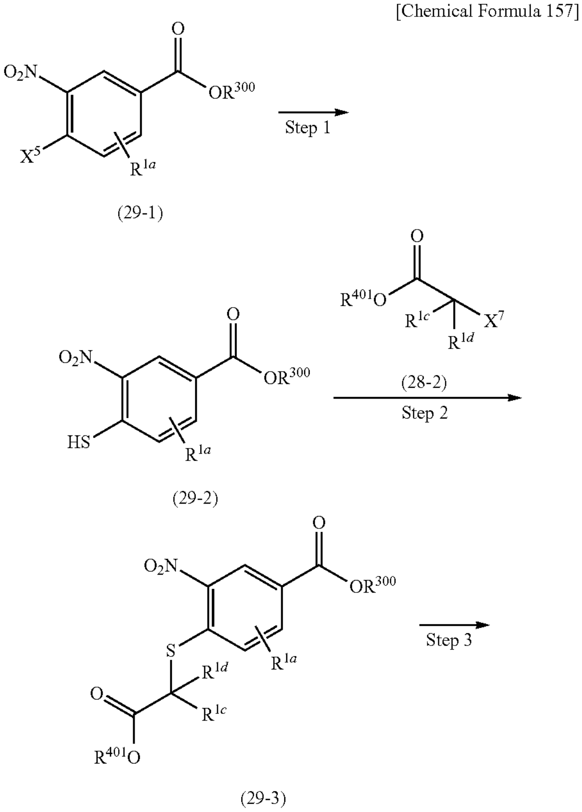

(29-1) (28-2) (29-2) (29-3)

-continued

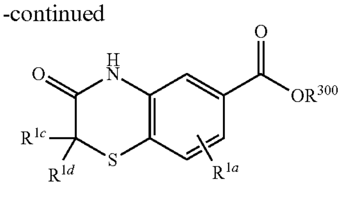

(29-4)

[In the scheme, $X^5$, $X^7$, $R^{1a}$, $R^{1c}$, $R^{1d}$, $R^{401}$ and $R^{300}$ are the same as defined above.]

1) Step 1

Compound (29-2) may be prepared from Compound (29-1) in the similar manner to the method of literature (e.g., Synth. Commun. 27, 2943 (1997), J. Chem. Soc. Perkin Trans 2, 691 (1988), etc.).

2) Steps 2 and 3

Compound (29-4) may be prepared from Compound (29-2) in the similar manner to the method of literature (e.g., WO2005/082872, etc.).

Preparation 30

Among a compound of formula (1-13), a compound of formula (30-5) or a salt thereof is prepared by the following method, for example.

[Chemical Formula 158]

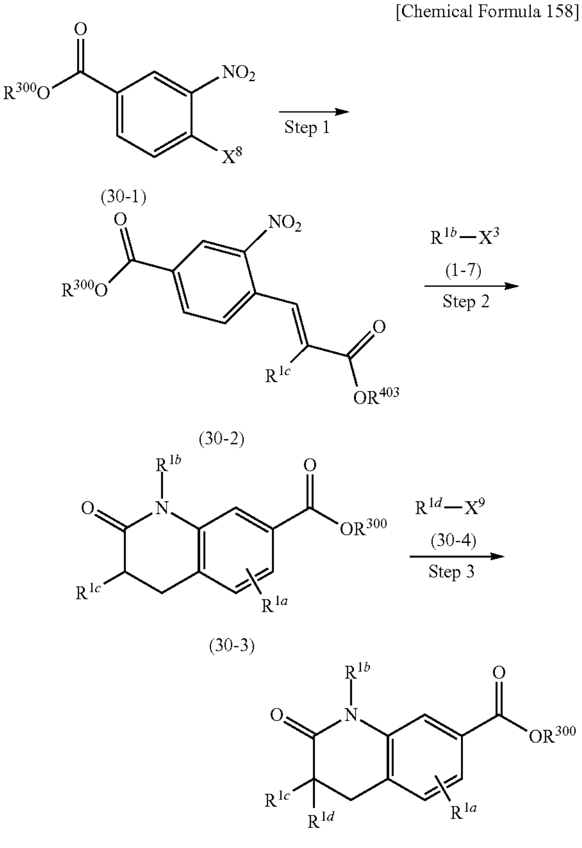

(30-1) (1-7) (30-2) (30-4) (30-3) (30-5)

[In the scheme, $X^3$, $R^{1a}$, $R^{1b}$, $R^{1c}$, $R^{1d}$ and $R^{300}$ are the same as defined above, $R^{403}$ is $C_{1-6}$ alkyl, $X^8$ is iodine atom, bromine atom, chlorin atom e or trifluoromethanesulfonyloxy, and $X^9$ is iodine atom, bromine atom, chlorine atom, methanesulfonyloxy, trifluoromethanesulfonyloxy or p-toluenesulfonyloxy.]

1) Step 1

Compound (30-2) may be prepared from Compound (30-1) in the similar manner to the method of literature (e.g., J. Am. Chem. Soc. 123, 6989 (2001), J. Org. Chem. 70, 4360 (2005), Synth. Commun. 29, 591 (1999), etc.).

2) Step 2

Compound (30-3) may be prepared from Compound (30-2) in the similar manner to Step 8 of Preparation 1.

3) Step 3

Compound (30-5) may be prepared from Compound (30-3) in the similar manner to the method of literature (e.g., WO2004/096773, etc.).

Preparation 31

Among a compound of formula (1-4), a compound of formula (31-3) or a salt thereof is prepared by the following method, for example.

[Chemical Formula 159]

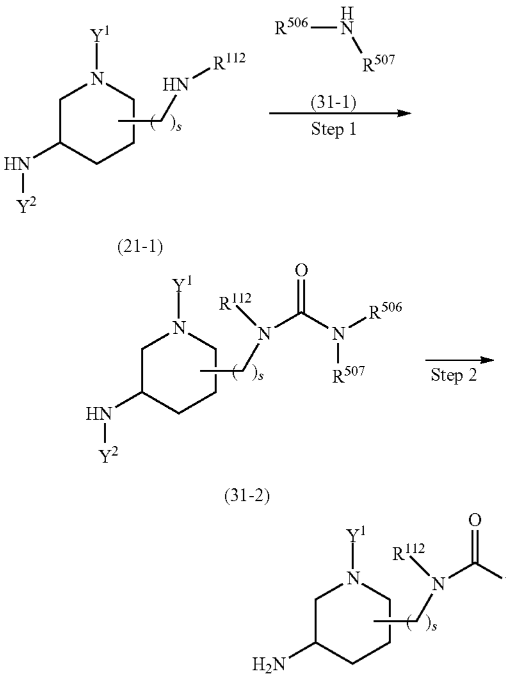

(21-1) (31-2) (31-3)

[In the scheme, $R^{112}$, s, $Y^1$ and $Y^2$ are the same as defined above, $R^{506}$ is the same as B, and $R^{507}$ is the same as $R^{4c}$.]

1) Step 1

Compound (31-2) may be prepared from Compound (21-1) in the similar manner to the method of literature (e.g., Bioorganic & Medicinal Chemistry Letters 1621, 16 (2006), WO99/054321, etc.).

2) Step 2

Compound (31-3) may be prepared from Compound (31-2) in the similar manner to the method of literature (e.g., Protective Groups in Organic Synthesis 2nd Edition (John Wiley & Sons, Inc.), etc.).

Preparation 32

Among a compound of formula (I), a compound of formula (32-17) or a salt thereof is prepared by the following method, for example.

[Chemical Formula 160]

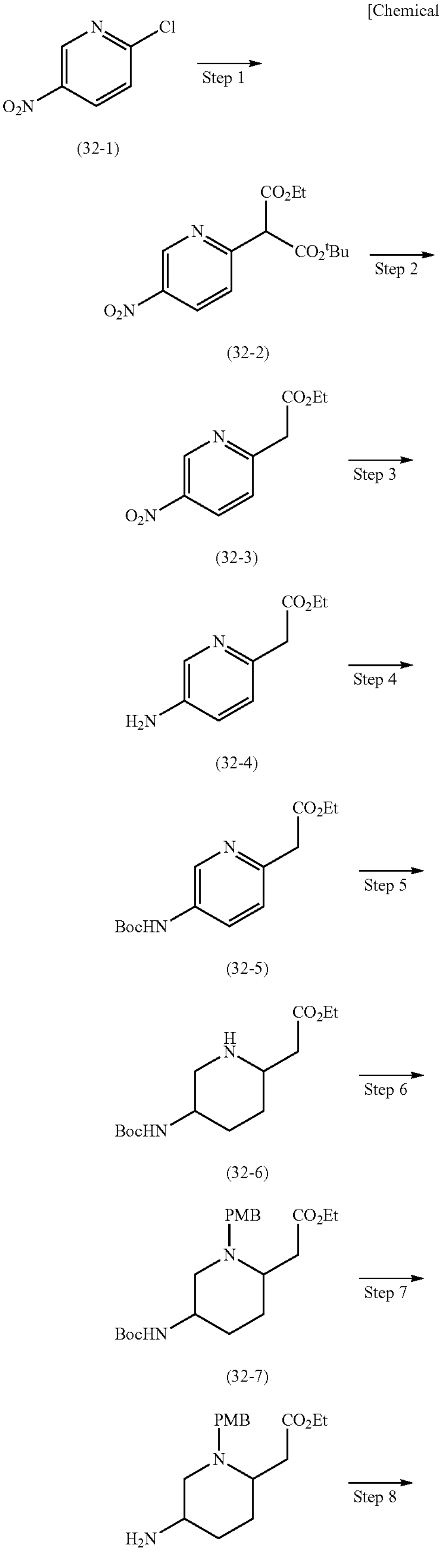

(32-1) (32-2) (32-3) (32-4) (32-5) (32-6) (32-7) (32-8)

-continued

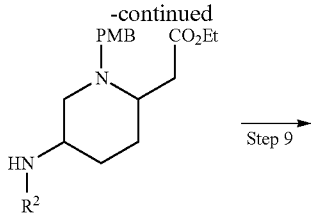

(32-9)

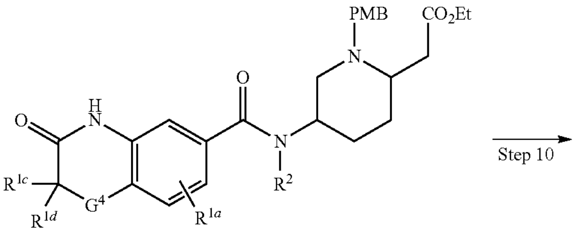

(32-10)

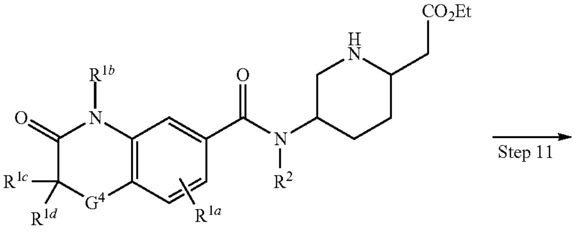

(32-11)

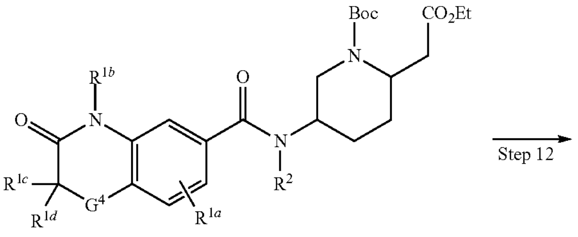

(32-12)

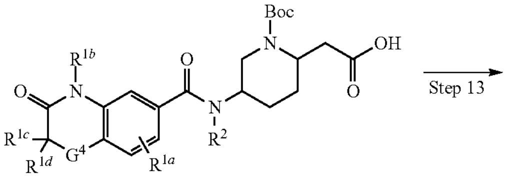

(32-13)

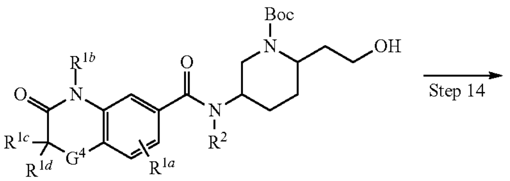

(32-14)

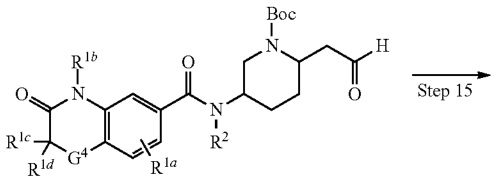

(32-15)

-continued

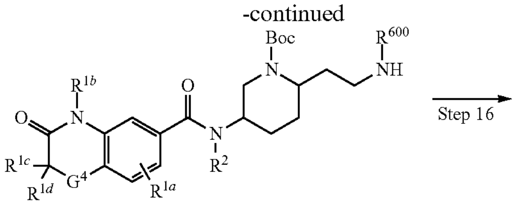

(32-16)

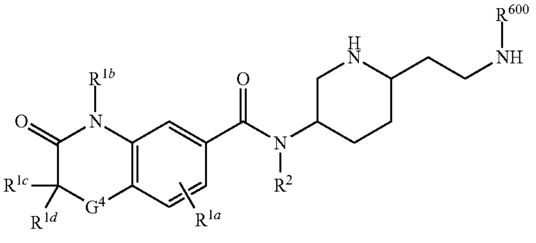

(32-17)

[In the scheme, $G^4$, $R^{1a}$, $R^{1b}$, $R^{1c}$, $R^{1d}$ and $R^2$ are the same as defined above, and $R^{600}$ is the same as B defined in Item 1.]

1) Step 1

Compound (32-2) may be prepared by reacting tert-butyl ethyl malonate with a base in an inert solvent, followed by reacting with Compound (32-1). The base includes an inorganic base such as potassium hydride or sodium hydride, etc. The inert solvent includes, for example, an aprotic solvent such as N,N'-dimethylformamide, dimethylsulfoxide or hexamethylene phosphoamide, etc. The reaction temperature is selected in the range of about 10° C. to about 40° C.

2) Step 2

Compound (32-3) may be prepared by reacting Compound (32-2) with trifluoroacetic acid in an inert solvent. The inert solvent includes, for example, a halogenated hydrocarbon type solvent such as dichloromethane, chloroform or 1,2-dichloroethane, etc. The reaction temperature is selected in the range of about 10° C. to about 40° C.

3) Step 3

Compound (32-4) may be prepared by reducing Compound (32-3) under hydrogen in the presence of palladium carbon in an inert solvent. The inert solvent includes, for example, an alcohol solvent such as methanol or ethanol, etc. The reaction temperature is selected in the range of about 10° C. to about 40° C.

4) Step 4

Compound (32-5) may be prepared by reacting Compound (32-4) with di-tert-butyl dicarbonate in an inert solvent. The inert solvent includes, for example, an ether type solvent such as dioxane or tetrahydrofuran, etc. The reaction temperature is selected in the range of about 10° C. to about 40° C.

5) Step 5

Compound (32-6) may be prepared by reducing Compound (32-5) under hydrogen in the presence of platinum oxide in an inert solvent. The inert solvent includes, for example, an alcohol solvent such as methanol or ethanol, etc. The reaction temperature is selected in the range of about 10° C. to about 40° C.

6) Step 6

Compound (32-7) may be prepared by reacting Compound (32-6) with p-methoxybenzyl chloride in an inert solvent in the presence of an inorganic base. The inorganic base includes potassium carbonate or cesium carbonate, etc. The inert solvent includes, for example, an aprotic solvent such as N,N'-dimethylformamide, dimethylsulfoxide or hexamethylene phosphoamide, etc. The reaction temperature is selected in the range of about 10° C. to about 40° C. In the present step, sodium iodide or potassium iodide may be added.

7) Step 7

Compound (32-8) may be prepared from Compound (32-7) in the similar manner to Step 6 of Preparation 1.

8) Step 8

Compound (32-9) may be prepared from Compound (32-8) in the similar manner to Step 4 of Preparation 1.

9) Step 9

Compound (32-10) may be prepared from Compound (32-9) in the similar manner to Step 10 of Preparation 1.

10) Step 10

Compound (32-11) may be prepared by reducing Compound (32-10) under hydrogen in the presence of palladium carbon in an inert solvent. The inert solvent includes, for example, an alcohol solvent such as methanol or ethanol, etc. The reaction temperature is selected in the range of about 10° C. to about 40° C.

11) Step 11

Compound (32-12) may be prepared from Compound (32-11) in the similar manner to Step 4 of Preparation 32.

12) Step 12

Compound (32-13) may be prepared from Compound (32-12) in the similar manner to Step 2 of Preparation 3.

13) Step 13

Compound (32-14) may be prepared by sequentially carrying out the following reactions (i. to ii.) from Compound (32-13) in an inert solvent. The inert solvent includes, for example, an ether type solvent such as dioxane or tetrahydrofuran, etc.

i. Compound (32-13) is reacted with ethyl chloroformate in the presence of triethylamine. The reaction temperature is selected in the range of about −10° C. to about 20° C.

ii. To the reaction mixture of i. is added sodium borohydride to react. The reaction temperature is selected in the range of about 0° C. to about 20° C.

14) Step 14

Compound (32-15) may be prepared by Swern oxidation of Compound (32-14). Specifically, to oxalyl chloride in a halogenated hydrocarbon type solvent such as dichloromethane, chloroform or 1,2-dichloroethane is added dimethylsulfoxide, and then thereto is added Compound (32-14), followed by adding diisopropylethylamine. The reaction temperature is selected in the range of about −80° C. to about −30° C.

15) Step 15

Compound (32-16) may be prepared from Compound (32-15) in the similar manner to Step 4 of Preparation 1.

16) Step 16

Compound (32-17) may be prepared from Compound (32-16) in the similar manner to Step 6 of Preparation 1.

Preparation 33

Among a compound of formula (I), a compound of formula (33-2) or a salt thereof is prepared by the following method, for example.

[Chemical Formula 161]

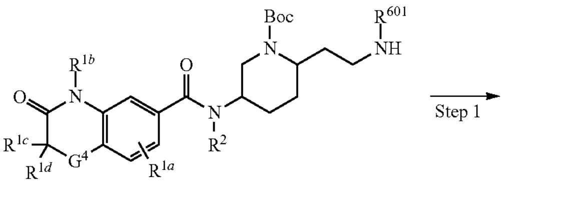

(32-16)

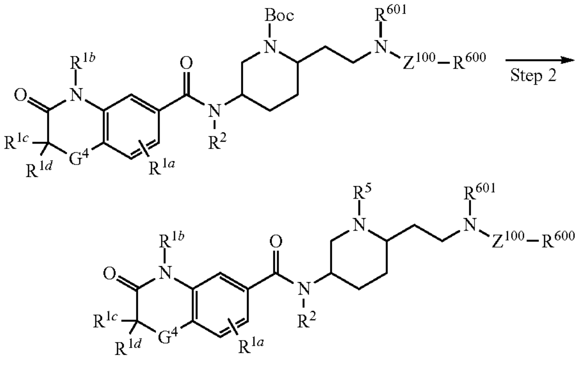

(33-2)

[In the scheme, $G^4$, $R^{600}$, $R^{1a}$, $R^{1b}$, $R^{1c}$, $R^{1d}$, $R^2$ and $R^5$ are the same as defined above, $Z^{100}$ is C(O), $S(O)_2$ or $C(O)N(R^{601})$, and $R^{601}$ is the same as $R^{4c}$ defined in Item 1.]

1) Step 1

Compound (33-1) may be prepared from Compound (32-16) in the similar manner to the method of literature (e.g., Comprehensive Organic transformation, R. C. Larock, VCH publisher Inc., 1989, etc.).

2) Step 2

Compound (33-2) may be prepared from Compound (33-1) in the similar manner to Step 6 of Preparation 1.

Preparation 34

Among a compound of formula (I), a compound of formula (34-5) or a salt thereof is prepared by the following method, for example.

[Chemical Formula 162]

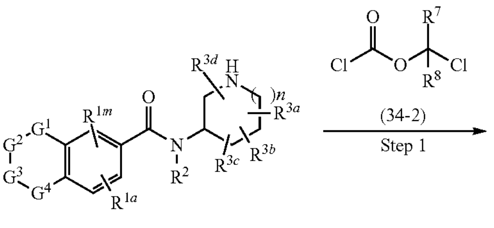

(34-1)

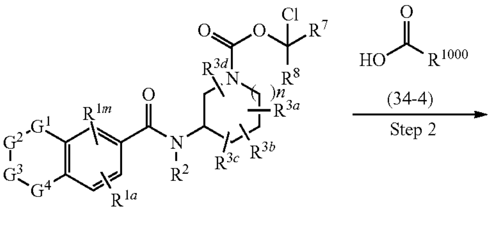

(34-3)

-continued

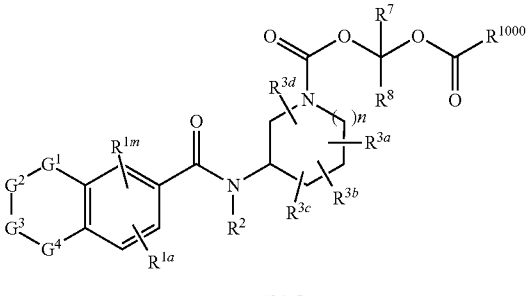

(34-5)

[In the scheme, n, $G^1$, $G^2$, $G^3$, $G^4$, $R^{1a}$, $R^{1m}$, $R^{3a}$, $R^{3b}$, $R^{3c}$, $R^{3d}$, $R^2$, $R^7$ and $R^8$ are the same as defined in the above Item 1, and $R^{1000}$ is the same as $R^9$ defined in the above Item 1.]

1) Step 1

Compound (34-3) may be prepared by reacting Compound (34-1) with Compound (34-2) in an inert solvent in the presence of a base. The base includes, for example, an organic base such as triethylamine, N-methylmorpholine, diisopropylethylamine, tributylamine, 1,8-diazabicyclo[5.4.0]undec-7-ene, 1,5-diazabicyclo[4.3.0]non-5-ene, 1,4-diazabicyclo [5.4.0]undec-7-ene, pyridine, dimethylaminopyridine, or picoline. The inert solvent includes, for example, an ether type solvent such as tetrahydrofuran or 1,4-dioxane, an aprotic solvent such as dimethylformamide or dimethylsulfoxide, or a halogenated hydrocarbon type solvent such as chloroform, dichloromethane or dichloroethane, etc., and may be a mixed solvent thereof. The reaction temperature is selected in the range of about −20° C. to about 40° C.

Compound (34-2) may be prepared by using the method of literatures, etc. For example, it may be prepared by a method wherein triphosgene is treated with the corresponding ketone and aldehyde (Tetrahedron Letters 30, 2033 (1989) or Tetrahedron Letters 42, 7751 (2001), etc.). etc.

2) Step 2

Compound (34-5) may be prepared by reacting Compound (34-3) with Compound (34-4) in an inert solvent in the presence of silver carbonate. The inert solvent includes, for example, an ether type solvent such as tetrahydrofuran or 1,4-dioxane, an aprotic solvent such as dimethylformamide or dimethylsulfoxide, or a halogenated hydrocarbon type solvent such as chloroform, dichloromethane or dichloroethane, etc., and may be a mixed solvent thereof. The reaction temperature is selected in the range of about 20° C. to about 80° C.

Preparation 35

Among a compound of formula (I), a compound of formula (35-3) or a salt thereof is prepared by the following method, for example.

[Chemical Formula 163]

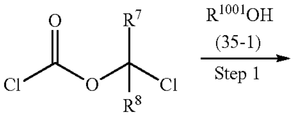

(34-2)

-continued

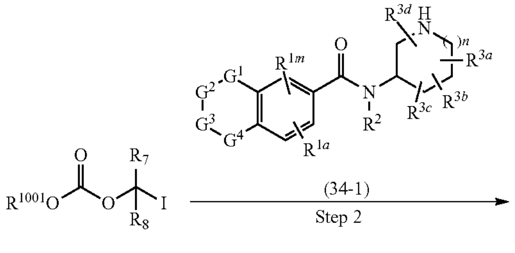

(35-2)

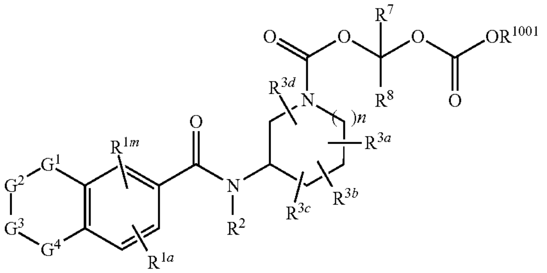

(35-3)

[In the scheme, n, $G^1$, $G^2$, $G^3$, $G^4$, $R^{1a}$, $R^{1m}$, $R^{3a}$, $R^{3b}$, $R^{3c}$, $R^{3d}$, $R^2$, $R^7$ and $R^8$ are the same as defined in the above Item 1, and $R^{1001}$ is $C_{1-6}$ alkoxy optionally substituted by $C_{3-6}$ cycloalkyl, $C_{3-6}$ cycloalkyl optionally substituted by $C_{1-4}$ alkoxy, or 5- to 6-membered saturated heterocyclyl.]

1) Step 1

Compound (35-2) may be prepared by sequentially carrying out the following reactions (i. to ii.) from Compound (34-2) in an inert solvent. The inert solvent includes, for example, an ether type solvent such as diethylether, dioxane or tetrahydrofuran, etc.

i. Compound (34-2) is reacted with Compound (35-1) in the presence of pyridine. The reaction temperature is selected in the range of about −10° C. to about 30° C.

ii. The reaction mixture of i. is filtered, and the filtrate is concentrated. Then, to the residue is added toluene, and then to the resulting solution are added sodium iodide and tetrabutylammonium bromide, and the mixture is reacted. The reaction temperature is selected in the range of about 80° C. to about 150° C.

2) Step 2

Compound (35-3) may be prepared by reacting carbon dioxide gas and Compound (35-2) with Compound (34-1) in an inert solvent in the presence of an inorganic base. The inorganic base includes cesium carbonate, sodium hydrogencarbonate, potassium hydrogencarbonate, sodium carbonate or potassium carbonate, etc. The inert solvent includes, for example, dimethylformamide, etc. The reaction temperature is selected in the range of about 0° C. to about 40° C.

Preparation 36

Among a compound of formula (I), a compound of formula (36-2) or a salt thereof is prepared by the following method, for example.

[Chemical Formula 164]

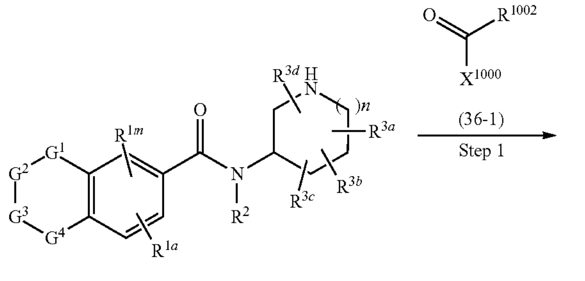

(34-1)

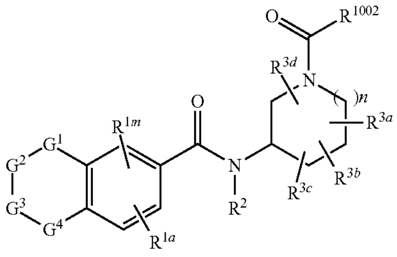

(36-2)

[In the scheme, n, $G^1$, $G^2$, $G^3$, $G^4$, $R^{1a}$, $R^{1m}$, $R^{3a}$, $R^{3b}$, $R^{3c}$, $R^{3d}$ and $R^2$ are the same as defined in the above Item 1, $R^{1002}$ is $C_{1-4}$ alkyl optionally substituted by amino or hydroxy, or $C_{1-4}$ alkoxy substituted by a group of the following formula:

[Chemical Formula 165]

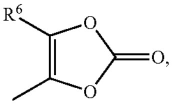

wherein $R^6$ is the same as defined above, and $X^{1000}$ is chlorine atom, hydroxyl or p-nitrophenoxy.]

1) Step 1

Compound (36-2) may be prepared from Compound (34-1) in the similar manner to the method of literature (e.g., Comprehensive Organic transformation, R. C. Larock, VCH publisher Inc., 1989, etc.).

Preparation 37

Among a compound of formula (I), a compound of formula (37-3) or a salt thereof is prepared by the following method, for example.

[Chemical Formula 166]

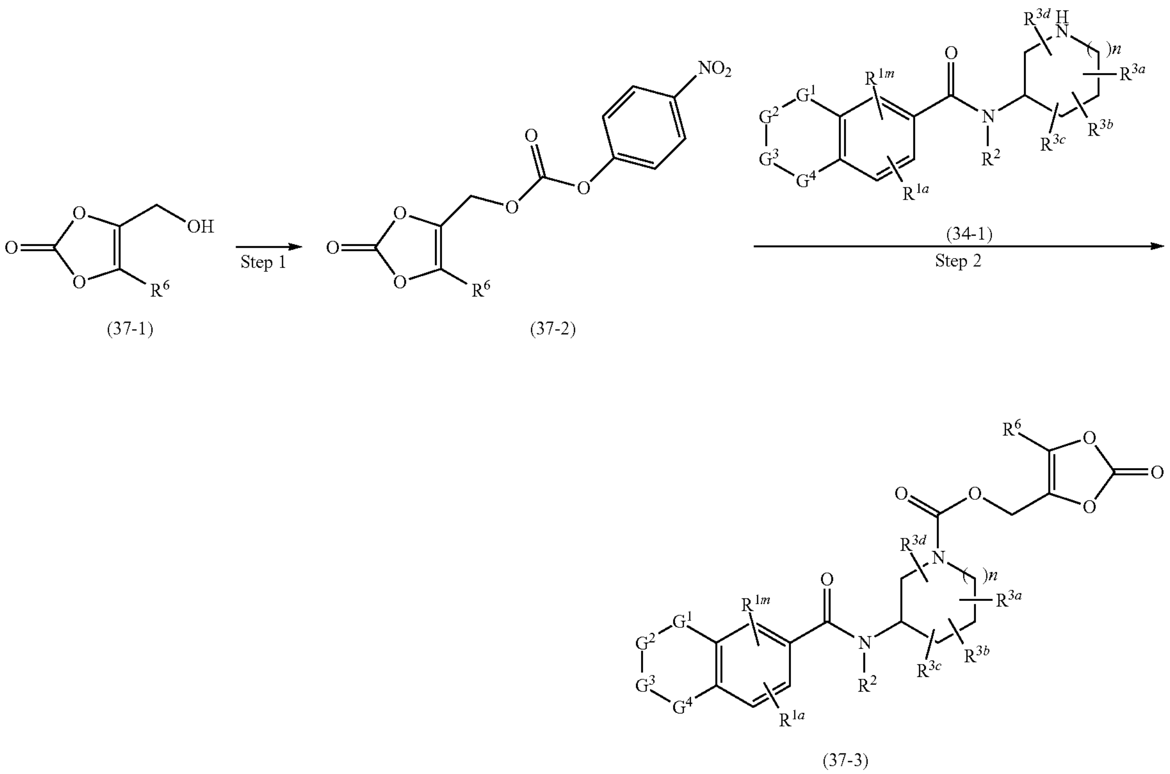

(37-1) (37-2) (37-3)

[In the scheme, n, $G^1$, $G^2$, $G^3$, $G^4$, $R^{1a}$, $R^{1m}$, $R^{3a}$, $R^{3b}$, $R^{3c}$, $R^{3d}$, $R^2$ and $R^6$ are the same as defined in the above Item 1.]

1) Step 1

Compound (37-2) may be prepared by reacting Compound (37-1) with nitrophenyl chloroformate in the presence of a base in an inert solvent. The base includes, for example, an organic base such as triethylamine, N-methylmorpholine, diisopropylethylamine, tributylamine, 1,8-diazabicyclo [5.4.0]undec-7-ene, 1,5-diazabicyclo[4.3.0]non-5-ene, 1,4-diazabicyclo[5.4.0]undec-7-ene, pyridine, dimethylaminopyridine or picoline. The inert solvent includes, for example, an ether type solvent such as tetrahydrofuran or 1,4-dioxane, an aprotic solvent such as dimethylformamide or dimethylsulfoxide, or a halogenated hydrocarbon type solvent such as chloroform, dichloromethane or dichloroethane, etc., and may be a mixed solvent thereof. The reaction temperature is selected in the range of about −20° C. to about 40° C.

Compound (37-1) may be prepared by the method of literature (e.g., Tetrahedron Letters 43, 1161 (2002), etc.).

2) Step 2

Compound (37-3) may be prepared by reacting Compound (34-1) with Compound (37-2) in the presence of an additive and a base in an inert solvent. The base includes, for example, an organic base such as triethylamine, N-methylmorpholine, diisopropylethylamine, tributylamine, 1,8-diazabicyclo [5.4.0]undec-7-ene, 1,5-diazabicyclo[4.3.0]non-5-ene, 1,4-diazabicyclo[5.4.0]undec-7-ene, pyridine, dimethylaminopyridine or picoline. The inert solvent includes, for example, an ether type solvent such as tetrahydrofuran or 1,4-dioxane, an aprotic solvent such as dimethylformamide or dimethylsulfoxide, or a halogenated hydrocarbon type solvent such as chloroform, dichloromethane or dichloroethane, etc., and may be a mixed solvent thereof. The additive includes dimethylaminopyridine, etc. The reaction temperature is selected in the range of about −10° C. to about 40° C.

In the above each preparation step, when each starting compound has reactive groups such as hydroxyl, amino or carboxyl, the desired compound may be obtained by reacting after optionally protecting these groups, except for a moiety to be reacted, with an appropriate protective group, and removing the protective group after carrying out each reaction or several reactions. The protective group which protects hydroxyl, amino, carboxyl, etc. includes conventional protective groups used in the synthetic organic chemistry field, and the introduction and removal of the protective group may be carried out in accordance with the conventional method (e.g., Protective Groups in Organic Synthesis, T. W. Greene, P. G. M. Wuts, 2nd Ed., John Wiley & Sons, Inc. (1991)).

For example, the protective group for hydroxyl includes tert-butyldimethylsilyl, methoxymethyl, tetrahydropyranyl, etc., and the protective group for amino includes tert-butyloxycarbonyl, benzyloxycarbonyl, etc. The protective group for hydroxyl may be removed by treating in the presence of a base, an acid such as sulfuric acid, acetic acid in a solvent such as aqueous methanol, aqueous ethanol, aqueous tetrahydrofuran. When tert-butyldimethylsilyl is used, then it may be also removed in the presence of tetrabutylammonium fluoride in a solvent such as tetrahydrofuran. The protective group for amino may be removed, for example, when such a protective group is tert-butyloxycarbonyl, then it may be removed by treating in the presence of an acid such as hydrochloric acid, trifluoroacetic acid in a solvent such as aqueous tetrahydrofuran, methylene chloride, chloroform, aqueous methanol, and when benzyloxycarbonyl is used, then it may be removed by treating in the presence of an acid such as hydrobromic acid in a solvent such as acetic acid.

The protective group for carboxyl includes tert-butyl ester, ortho ester, acid amide, etc. These protective groups may be removed, for example, when such a protective group is tert-butyl ester, then it may be removed by treating in the presence of hydrochloric acid in an aqueous solvent. When ortho ester is used, then it may be removed, for example, by treating with an acid in a solvent such as aqueous methanol, aqueous tetrahydrofuran, aqueous 1,2-dimethoxyethane, followed by treatment with an alkali such as sodium hydroxide, etc. When acid amide is used, then it may be removed, for example, by treating in the presence of an acid such as hydrochloric acid, sulfuric acid, etc. in a solvent such as water, aqueous methanol, aqueous tetrahydrofuran, etc.

A compound of formula (I) includes a compound having an optically-active center, and such compound may be obtained in a mixture of racemates, or in the form of an optically active compound when an optically active starting compound is used. If necessary, the obtained racemate may be physically or chemically resolved into optical enantiomer thereof by a conventional method, or preferably by resolution of diastereomers formed by treating with an optically active resolving agent. Diastereomers in a different form may be resolved by a conventional method such as fractional crystallization.

The present compound may be converted into a salt thereof, for example, by mixing with a pharmaceutically acceptable acid in a solvent such as water, methanol, ethanol, acetone, etc. The pharmaceutically acceptable acid includes, for example, an inorganic acid such as hydrochloric acid, hydrobromic acid, sulfuric acid, phosphoric acid, nitric acid, etc., or an organic acid such as acetic acid, propionic acid, oxalic acid, succinic acid, lactic acid, malic acid, tartaric acid, citric acid, maleic acid, fumaric acid, methanesulfonic acid, p-toluenesulfonic acid, ascorbic acid, etc.

The present compound may be possibly applied to the treatment of various diseases because of its renin inhibitory activity. The compounds disclosed in the present specification are useful as a therapeutic agent for hypertension. These compounds are also useful in the control of acute and chronic congestive heart failure. These compounds can be expected to be useful in the treatment of primary and secondary pulmonary hypertension, primary and secondary aldosteronism, renovascular hypertension, primary and secondary renal disease (e.g., glomerulonephritis, IgA nephropathy, diabetic nephropathy, hypertensive nephropathy (nephrosclerosis), nephrotic syndrome, kidney failure, etc.), left ventricular hypertrophy, left ventricular fibrosis, left ventricular diastolic failure, left ventricular failure, atrial fibrillation, unstable angina, cardiac infarction, cardiomyopathy, apoplexy, restenosis after angioplasty, diabetic retinopathy, cognitive disorder (e.g., Alzheimer's disease, cerebrovascular dementia, etc.), and for the minimization or prevention of vascular diseases (e.g., migraine, Raynaud's disease, etc.) or atherosclerosis process. In addition, these compounds are also useful in the treatment of diseases relating to elevated intraocular pressure (e.g., glaucoma, etc.). Additionally, these compounds are effective for improvement of therapeutic effects on these diseases.

When the present compound is used in the therapy, it may be administered orally or parenterally (e.g., intravenously, subcutaneously or intramuscularly, locally, rectally, percutaneously, or transnasally) in the form of a pharmaceutical composition. The composition for oral administration includes, for example, tablets, capsules, pills, granules, powders, solutions, suspensions, etc. The composition for parenteral administration includes, for example, aqueous solutions for injection, or oils, ointments, creams, lotions, aerosols, suppositories, adhesive preparations, etc. These preparations may be prepared by a conventional known method, and may contain a nontoxic and inactive carrier or excipient that is usually used in the pharmaceutical field.

The dosage may vary depending on each compound, or diseases, ages, body weights, sexes, conditions of each patient, or administration routes, etc., and the present compound or a pharmaceutically acceptable salt thereof may be usually administered to an adult (body weight: 50 kg) at a dose of 0.1 to 1000 mg/day, preferably at a dose of 1 to 300 mg/day, which may be administered once a day or divided into 2 or 3 dosage forms. In addition, the present compound can be administered once in several days to once in several weeks.

Aiming at the enhancement of the pharmacological activity, the present compound may be used in a combination with a medicament such as an antidiabetic agent, a therapeutic agent for diabetic complications, an antilipidemic agent, a hypotensive agent, an antiobesity agent, a diuretic agent (hereinafter referred to as combined medicine). The administration timing of the present compound and a combined medicine is not necessarily limited, and they may be administered to a subject simultaneously or administered with time-interval. In addition, the present compound and a combined medicine may be used in the form of a combination drug. The dosage of a combined medicine may be optionally selected based on the dosage in the clinical use. In addition, the mixing ratio of the present compound and a combined medicine may be optionally determined depending on the subject to be administered, the administration route, the disease to be treated, the conditions of a patient, and a kind of combination. For example, when the subject to be administered is human, then a combined medicine may be used an amount of 0.01 to 100 parts for weight of one part of the present compound.

The antidiabetic agent includes insulin formulations (e.g., animal insulin formulations extracted from the bovine pancreas or swine pancreas; genetically-engineered human insulin formulations using *Escherichia coli* or yeast, etc.), improving agents of insulin resistance (e.g., pioglitazone or a hydrochloride salt thereof, troglitazon, rosiglitazone or a maleate salt thereof, GI-262570, JTT-501, CC-555, YM-440, KRP-297, S-011, etc.), α-glucosidase inhibitors (e.g., voglibose, acarbose, miglitol, emiglitate, etc.), biguanides (e.g., metformine, etc.), insulin secretagogues (e.g., sulfonylureas such as tolbutamide, glibenclamide, gliclazide, chlorpropamide, tolazamide, acetohexamide, glyclopyramide, glimepiride, etc.; repaglinide, senaglinide, nateglinide, mitiglinide, etc.), GLP-1, GLP-1 analogues (exenatide, liraglutide, SUN-E7001, AVE010, BIM-51077, CJC1131, etc.), protein tyrosine phosphatase inhibitors (e.g., vanadic acid, etc.), β3 agonists (e.g., GW-427353B, N-5984, etc.), DPPIV inhibitors (e.g., sitagliptin, vildagliptin, saxagliptin, SYR-322, etc.).

The therapeutic agent for diabetic complications includes aldose reductase inhibitors (e.g., tolrestat, epalrestat, zenarestat, zopolrestat, minarestat, fidarestat, SK-860, CT-112, etc.), neurotrophic factors (e.g., NGF, NT-3, BDNF, etc.), PKC inhibitors (e.g., LY-333531, etc.), AGE inhibitors (e.g., ALT946, pimagedine, pyratoxatin, N-phenacylthiazolium bromide (ALT766), etc.), active oxygen scavengers (e.g., thioctic acid, etc.), cerebral vasodilators (e.g., tiapride, mexiletine, etc.). The antilipidemic agent includes HMG-CoA reductase inhibitors (e.g., pravastatin, simvastatin, lovastatin, atorvastatin, fluvastatin, itavastatin or a sodium salt thereof, etc.), squalene synthetase inhibitors, ACAT inhibitors, etc. The hypotensive agent includes angiotensin-converting enzyme inhibitors (e.g., captopril, enalapril fumarate, alacepril, delapril hydrochloride, lisinopril, imidapril, benazepril, cilazapril, temocapril, trandolapril, fosinopril sodium salt, moexipril hydrochloride, perindopril, quinapril hydrochloride, ramipril, spirapril, zofenopril calcium salt, etc.), angiotensin II antagonists (e.g., olmesartan medoxomil, candesartan cilexetil, losartan, eprosartan mesylate, valsartan, telmisartan, irbesartan, tasosartan, azilsartan medoxomil (TAK-491), azilsartan (TAK-536), fimasartan, pratosartan, etc.), calcium antagonists (e.g., nicardipine hydrochloride, manidipine hydrochloride, nisoldipine, nitrendipine, nilvadipine, amlodipine besylate, aranidipine, azelnidipine, barnidipine hydrochloride, benidipine hydrochloride, cilnidipine, clevidipine, diltiazem hydrochloride, efonidipine hydrochloride ethanol adduct, felodipine, isradipine, lacidipine, lercanidipine hydrochloride, levamlodipine, nifedipine, verapamil, etc.), ACE/NEP inhibitors (e.g., omapatrilat, fasidotril, etc.), β blocking agents (e.g., atenolol, bisoprolol, betaxolol, metoprolol, etc.), a blocking agents (e.g., urapidil, terazosin, doxazosin, bunazosin, etc.), aP blocking agents (e.g., amosulalol, arotinolol, labetalol, carvedilol, etc.).

The antiobesity agent includes, for example, central antiobesity drugs (e.g., phentermine, sibutramine, amfepramone, dexamphetamine, Mazindol, SR-141716A, etc.), pancreatic lipase inhibitors (e.g., Orlistat, etc.), peptidic anorexiants (e.g., leptin, CNTF (ciliary neurotrophic factor), etc.), cholecystokinin agonists (e.g., lintitript, FPL-15849, etc.). The diuretic agent includes, for example, xanthine derivatives (e.g., theobromine sodium salicylate, theobromine calcium salicylate. etc.), thiazide preparations (e.g., ethiazide, cyclopenthiazide, trichloromethiazide, hydrochlorothiazide, hydroflumethiazide, bentylhydrochlorothiazide, penflutizide, polythiazide, methychlothiazide, bendroflumethiazide, chlorothiazide, etc.), antialdosterone preparations (e.g., spironolactone, triamterene, eplerenone, etc.), carbonic anhydrase inhibitors (e.g., acetazolamide, etc.), chlorbenzenesulfonamide preparations (e.g., chlorthalidone, mefruside, indapamide, metolazone, etc.), azosemide, isosorbide, ethacrynic acid, piretanide, bumetanide, furosemide, etc.

The combined medicine is preferably a drug selected from the following Drug Group (A):

Drug Group (A) is the group consisting of insulin formulation, an improving agent of insulin resistance, α-glucosidase inhibitor, biguanide preparation, insulin secretagogue, GLP-1, GLP-1 analog, protein tyrosine phosphatase inhibitor, β3 agonist, DPPIV inhibitor, aldose reductase inhibitor, neurotrophic factor, PKC inhibitor, AGE inhibitor, active oxygen-eliminating agent, cerebral vasodilator, HMG-CoA reductase inhibitor, squalene synthetase inhibitor, ACAT inhibitor, angiotensin converting enzyme inhibitor, angiotensin II antagonist, calcium antagonist, ACE/NEP inhibitor, β blocking agent, α blocking agent, αβ blocking agent, central anti-obesity drug, pancreatic lipase inhibitor, peptidic anorexiant, cholecystokinin agonist, xanthine derivative, thiazide preparation, anti-aldosterone preparation, carbonic anhydrase inhibitor, chlorobenzene sulfonamide preparation, azosemide, isosorbide, ethacrynic acid, piretanide, bumetanide, and furosemide.

Preferable Drug Group (A) is the group consisting of angiotensin converting enzyme inhibitor, angiotensin II antagonist, calcium antagonist, ACE/NEP inhibitor, β blocking agent, a blocking agent, αβ blocking agent, thiazide preparation, and anti-aldosterone preparation.

More preferable one is the group consisting of angiotensin II antagonist, calcium antagonist, and thiazide preparation.

The above mentioned combined medicines may be used in a mixture of at least one or more, preferably one to four, more preferably one to two, further preferably one of these drugs in any ratios.

When the present compound is used in a combination of a combined medicine, the dosage of these drugs can be lessened within the safe range in view of the side effects of the drugs. Accordingly, any possible side effects caused by these drugs may be safely inhibited.

EXAMPLES

The present invention is illustrated in more detail by Reference Examples, Examples and Experiments, but the present invention should not be construed to be limited thereto. In addition, the compound names used in the following Reference Examples and Examples are not necessarily based on IUPAC nomenclature. Further, in order to simplify the description, some abbreviations may be used, and these abbreviations are as defined in the above-mentioned description.

Reference Example 1

1-Methyl-2-oxo-2-phenylethyl formate

[Chemical formula 167]

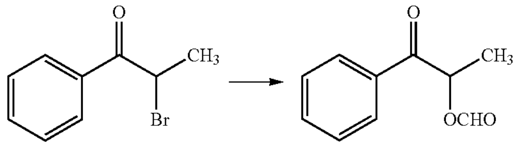

To a solution of 2-bromo-1-phenylpropan-1-one (25 g) in acetonitrile (250 ml) was added formic acid (7.7 ml), and thereto was added dropwise triethylamine (25 ml) under ice-cooling. Then, the mixture was stirred at room temperature for 5 hours. After the reaction was completed, water was added to the reaction solution, and the mixture was extracted with ethyl acetate. The ethyl acetate solution was washed with water and aqueous sodium chloride solution, dried over magnesium sulfate, and filtered and concentrated to give the title compound (19 g). The obtained crude product was used in the next reaction without further purification.

MS (ESI+) 179 (M+1, 10%)

Reference Example 2

2-Hydroxy-1-phenylpropan-1-one

[Chemical formula 168]

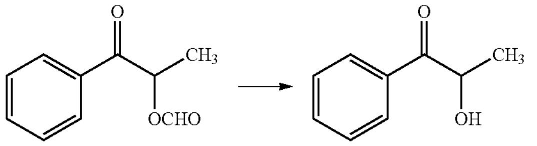

To the compound of Reference Example 1 (19 g) were added methanol (200 ml), water (60 ml) and conc. hydrochloric acid (2.3 ml), and the mixture was stirred at room temperature for 2 hours, then the mixture was warmed to 50° C., and further stirred for 2 hours. After the reaction was completed, water was added to the reaction solution, and the mixture was extracted with ethyl acetate. The ethyl acetate solution was washed with water and aqueous sodium chloride solution, dried over magnesium sulfate, filtered and concentrated to give the title compound (17 g). The obtained crude product was used without further purification in the next reaction.

MS (ESI+) 151 (M+1, 9%)

Reference Example 3

4-Methyl-5-phenyl-1,3-dioxol-2-one

[Chemical formula 169]

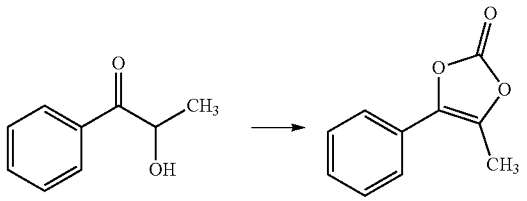

To a solution of the compound of Reference Example 2 (8.5 g) in toluene (75 ml) was added triphosgene (6.4 g), and thereto was added dropwise dimethylaniline (15 g) under ice-cooling, and the mixture was stirred at room temperature for 3 hours. Then, the mixture was further stirred for 4 hours under reflux. After the reaction was completed, water was added to the reaction solution, and the mixture was extracted with ethyl acetate. The ethyl acetate solution was washed with 1N aqueous hydrochloric acid solution, dried over magnesium sulfate, filtered and concentrated. The obtained residue was purified by column chromatography (hexane:ethyl acetate=4:1) to give the desired product as white crystal (6.16 g).

MS (ESI+) 177 (M+1, 14%)

Reference Example 4

4-(Bromomethyl)-5-phenyl-1,3-dioxol-2-one

[Chemical formula 170]

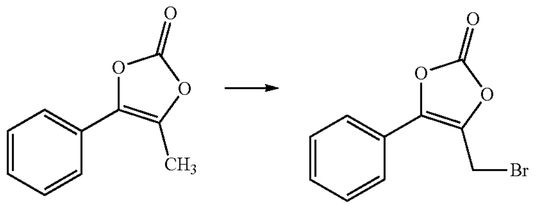

To a solution of the compound of Reference Example 3 (6.16 g) in carbon tetrachloride (150 ml) were added NBS (6.85 g) and benzoyl peroxide (850 mg), and the mixture was stirred at 77° C. for 6 hours. After the reaction was completed, water was added to the reaction solution, and the mixture was extracted with chloroform. The chloroform solution was washed with water and a saturated aqueous sodium chloride solution, dried over magnesium sulfate, filtered and concentrated to give the title compound (9g). The obtained crude product was used in the next reaction without further purification.

MS (ESI+) 254 (M+1, 5%)

Reference Example 5

(2-Oxo-5-phenyl-1,3-dioxol-4-yl)methylformate

[Chemical formula 171]

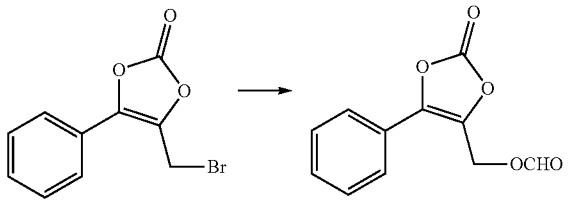

According to the method disclosed in Reference Example 1, the title compound (3.3 g) was synthesized from the compound obtained in Reference Example 4.

MS (ESI+) 221 (M+1, 15%)

Reference Example 6

4-(Hydroxymethyl)-5-phenyl-1,3-dioxol-2-one

[Chemical formula 172]

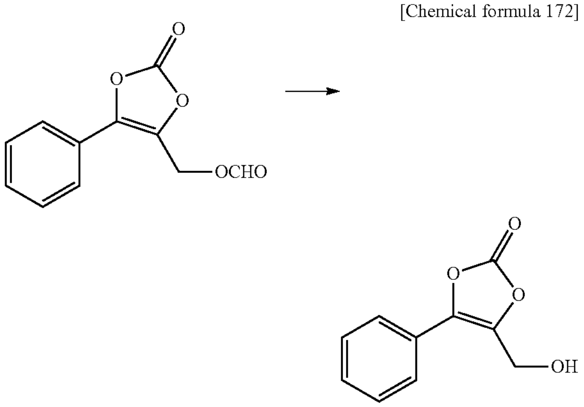

According to the method disclosed in Reference Example 2, the title compound (2.04 g) was synthesized from the compound obtained in Reference Example 5.

MS (ESI+) 193 (M+1, 10%)

Reference Example 7

4-Nitrophenyl (2-oxo-5-phenyl-1,3-dioxol-4-yl)methylcarbamate

[Chemical formula 173]

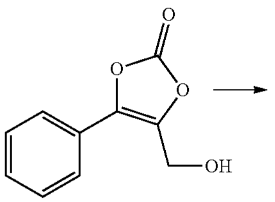

-continued

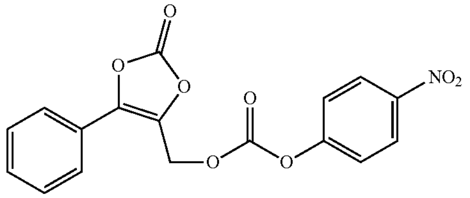

To the compound of Reference Example 6 (2.04 g) were added nitrophenyl chloroformate (2.0 g) and chloroform (30 ml), and thereto was added dropwise pyridine under ice-cooling. Then, the mixture was warmed to room temperature, and stirred overnight. After the reaction was completed, water was added the reaction solution, and the mixture was extracted with chloroform. This chloroform solution was washed with water and a saturated aqueous sodium chloride solution, dried over magnesium sulfate, filtered and concentrated. The obtained residue was purified by column chromatography (hexane:ethyl acetate=1:1) to give the title compound (1.95 g).

MS (ESI+) 344 (M+1, 13%)

Reference Example 8

4-(Bromomethyl)-5-methyl-1,3-dioxol-2-one

[Chemical formula 174]

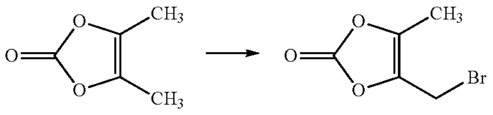

According to the method disclosed in Reference Example 4, the title compound was synthesized from 4,5-dimethyl-1,3-dioxol-2-one.

$R_f$=0.35 (hexane:ethyl acetate=3:1).

Reference Example 9

(5-Methyl-2-oxo-1,3-dioxol-4-yl)methyl formate

[Chemical formula 175]

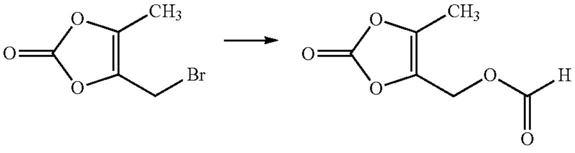

According to the method disclosed in Reference Example 1, the title compound was synthesized from the compound of Reference Example 8.

$R_f$=0.42 (hexane:ethyl acetate=3:1).

Reference Example 10

4-(Hydroxymethyl)-5-methyl-1,3-dioxol-2-one

[Chemical formula 176]

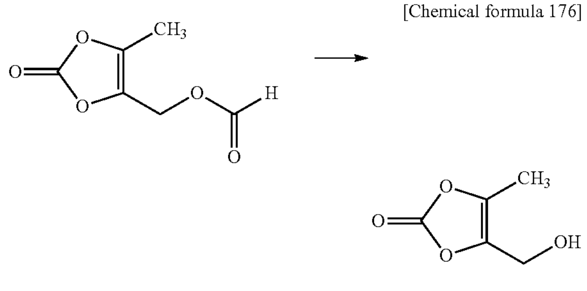

According to the method disclosed in Reference Example 2, the title compound was synthesized from the compound of Reference Example 9.

$R_f$=0.26 (hexane:ethyl acetate=1:1).

Reference Example 11

(5-Methyl-2-oxo-1,3-dioxol-4-yl)methyl 4-nitrophenyl carbonate

[Chemical formula 177]

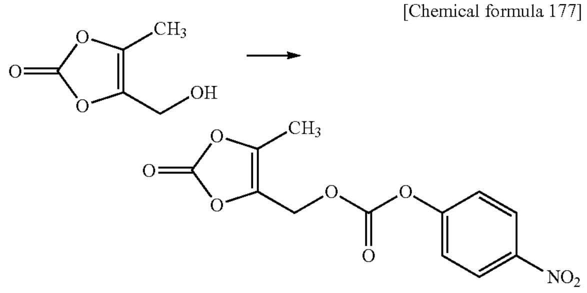

According to the method disclosed in Reference Example 7, the title compound was synthesized from the compound of Reference Example 10.

1H NMR (400 MHz, $d_6$-DMSO) δ 8.37 (ddd, J=9.2, 3.3, 2.2 Hz, 2H), 7.63 (ddd, J=9.2, 3.3, 2.1 Hz, 2H), 5.23 (s, 2H), 2.23 (s, 3H).

Reference Example 12

Isopropenyl 4-nitrophenyl carbonate

[Chemical formula 178]

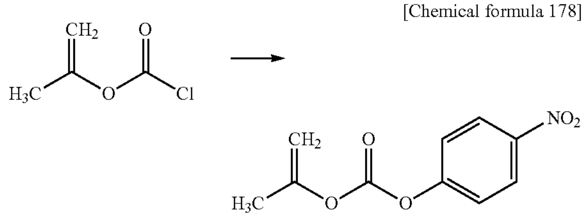

To isopropenyl chloride carbonate (6.68 g) were added 4-nitrophenol (5 g) and chloroform (150 ml), and thereto was added drowpise pyridine (2.9 ml) under ice-cooling over a period of 20 minutes. Then, the mixture was stirred under ice-cooling for 15 minutes, then warmed to room temperature, and further stirred overnight. After the reaction was completed, the reaction solution was washed succesively with 1N aqueous hydrochloric acid solution, water and a satureated aqueous sodium chloride solution, dried over magnesium sulfate, filtered and concentrated. The obtained residue was purified by column chromatography (hexane:ethyl acetate=4:1) to give the title compound (1.41 g).

1H NMR (300 MHz, $CDCl_3$) δ 8.31-8.25 (m, 2H), 7.43-7.24 (m, 2H), 4.94-4.80 (m, 2H), 2.04-2.00 (s, 3H)

Reference Example 13

1-Chloro-1-methylethyl 4-nitrophenylcarbonate

[Chemical formula 179]

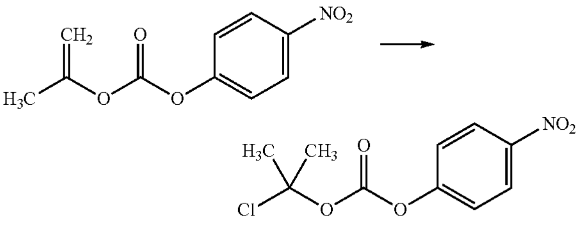

To the compound of Reference Example 12 (1.41 g) was added 4N solution of hydrochloric acid in dioxane (30 ml), and the mixture was stirred at room temperature overnight. After the reaction was completed, the reaction solution was concentrated to give the title compound. The obtained crude product was used in the next reaction without further purification.

1H NMR (300 MHz, $CDCl_3$) δ 8.28-8.24 (m, 2H), 7.41-7.36 (m, 2H), 2.09 (s, 6H)

Reference Example 14

1-Methyl-1-{[(4-nitrophenoxy)carbonyl]oxy}ethylacetate

[Chemical formula 180]

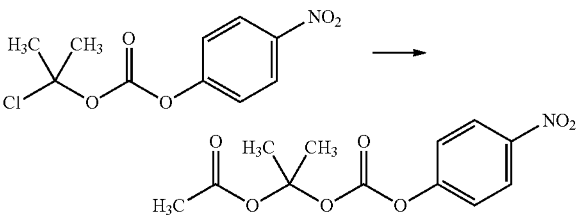

To the compound of Reference Example 13 (1.88 g) were added mercury acetate (3.76 g) and chloroform (180 ml), and the mixture was stirred at room temperature for 6 hours. After the reaction was completed, the reaction solution was washed successively with water, saturated aqueous sodium chloride solution and saturated aqueous sodium hydrogen carbonate solution, dried over magnesium sulfate, filtered and concentrated to give the title compound (1.96 g). The obtained crude product was used in the next reaction without further purification.

1H NMR (300 MHz, $CDCl_3$) δ 8.29-8.24 (m, 2H), 7.41-7.35 (m, 2H), 2.06 (s, 3H), 1.91 (s, 6H)

Reference Example 15

1-Iodoethyl isopropyl carbonate

[Chemical formula 181]

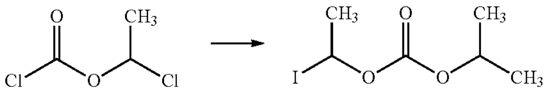

To 2-chloroethyl chloroformate (10 ml) were added isopropyl alcohol (8.6 ml), diethyl ether (200 ml), and thereto was added dropwise pyridine under ice-cooling. Then, the mixture was stirred under ice-cooling for one hour, and warmed to room temperature, and further stirred for 3 hours. After the reaction was completed, the precipitated salt was removed with a filter, and the obtained filtrate was concentrated to give the residue (11.7 g), which was used in the next reaction without purification. To the crude product, 1-chloroethyl isopropylcarbonate, were added sodium iodide (26.3 g), tetrabutylammonium bromide (456 mg), and toluene (150 ml), and the reaction mixture was refluxed for 7 hours. After the reaction was completed, water was added to the reaction solution, and extracted with ethyl acetate. This ethyl acetate solution was washed with water, 5% aqueous sodium hydrogen carbonate solution and 1% aqueous sodium thiosulfate solution, dried over magnesium sulfate, filtered and concentrated to give the title compound (2.04 g). The obtained crude product was used in the next reaction without further purification.

1H NMR (300 MHz, $CDCl_3$) δ 6.77-6.71 (q, J=6.2 Hz, 1H), 4.96-4.88 (quint, J=6.4 Hz, 1H), 2.22-2.20 (d, J=6.2 Hz, 3H), 1.33-1.29 (t, J=6.4 Hz, 6H)

Reference Example 16

Iodo methylmethylcarbonate

[Chemical formula 182]

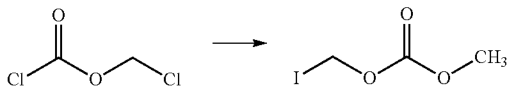

Using chloromethyl chloroformate, the title compound was obtained according to the method disclosed in Reference Example 15.

1H NMR (300 MHz, $CDCl_3$) δ 5.94 (s, 2H), 3.85 (s, 3H)

Reference Example 17

Ethyl Iodomethylcarbonate

[Chemical formula 183]

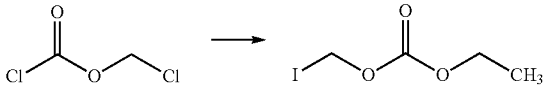

Using chloromethyl chloroformate, the title compound was obtained according to the method disclosed in Reference Example 15.

1H NMR (300 MHz, $CDCl_3$) δ5.93 (s, 2H), 4.30-4.23 (q, J=6.8 Hz, 2H), 1.34-1.28 (t, 6.8 Hz, 3H)

Reference Example 18

Iodo methylisopropylcarbonate

[Chemical formula 184]

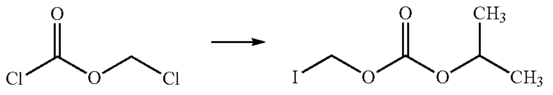

Using chloromethyl chloroformate, the title compound was obtained according to the method disclosed in Reference Example 15.

1H NMR (300 MHz, $CDCl_3$) δ 5.93 (s, 2H), 4.97-4.89 (m, 1H), 1.32-1.29 (d, 6.4 Hz, 6H)

Reference Example 19

Iodomethyl 2-methylbutylcarbonate

[Chemical formula 185]

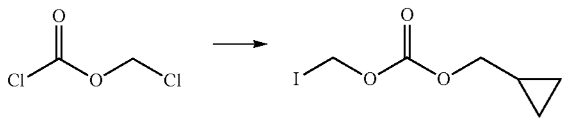

Using chloromethyl chloroformate, the title compound was obtained according to the method disclosed in Reference Example 15.

1H NMR (300 MHz, $CDCl_3$) δ 5.64-5.60 (m, 2H), 3.72-3.70 (m, 2H), 0.88-0.85 (m, 1H), 0.30-0.26 (m, 2H), 0.05-0.02 (m, 2H)

Reference Example 20

Cyclobutyl iodomethylcarbonate

[Chemical formula 186]

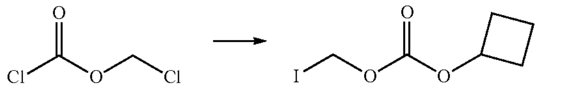

Using chloromethyl chloroformate, the title compound was obtained according to the method disclosed in Reference Example 15.

1H NMR (300 MHz, $CDCl_3$) δ 5.62 (s, 2H), 4.74-4.64 (m, 1H), 2.15-2.06 (m, 2H), 1.93-1.80 (m, 2H), 1.60-1.48 (m, 1H), 1.41-1.23 (m, 1H)

Reference Example 21

Iodomethyl tetrahydro-2H-pyran-4-yl carbonate

[Chemical formula 187]

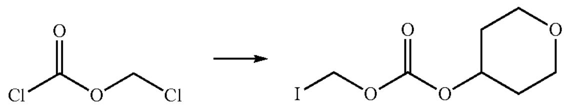

Using chloromethyl chloroformate, the title compound was obtained according to Reference Example 15.

1H NMR (300 MHz, $CDCl_3$) δ 5.93 (s, 2H), 4.92-4.83 (m, 1H), 3.94-3.87 (m, 2H), 3.56-3.48 (m, 2H), 2.02-1.94 (m, 2H), 1.80-1.63 (m, 2H)

Reference Example 22

1-Ethylpropyliodomethyl carbonate

[Chemical formula 188]

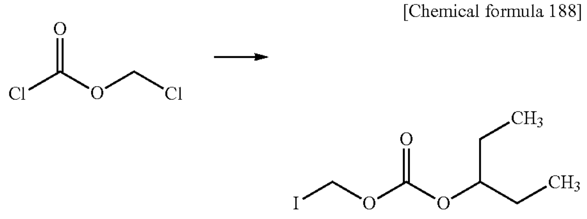

Using chloromethyl chloroformate, the title compound was obtained according to Reference Example 15.

1H NMR (300 MHz, $CDCl_3$) δ 5.93 (s, 2H), 4.69-4.60 (quint, J=6.8 Hz, 1H), 1.66-1.57 (quint, J=6.8 Hz, 4H), 0.93-0.88 (t, J=6.8 Hz, 6H)

Reference Example 23

Cyclopentyl iodomethyl carbonate

[Chemical formula 189]

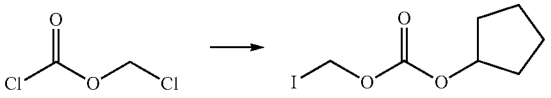

Using chloromethyl chloroformate, the title compound was obtained according to the method disclosed in Reference Example 15.

1H NMR (300 MHz, $CDCl_3$) δ 5.91 (s, 2H), 5.16-5.14 (m, 1H), 1.93-1.56 (m, 8H)

Reference Example 24

Ethyl 1-iodoethylcarbonate

[Chemical formula 190]

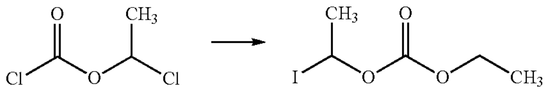

Using 1-chloroethyl chloroformate, the title compound was obtained according to the method disclosed in Reference Example 15.

1H NMR (300 MHz, $CDCl_3$) δ 6.78-6.72 (q, J=6.4 Hz, 1H), 4.28-4.21 (q, J=7.2 Hz, 2H), 2.23-2.21 (d, J=6.2 Hz, 3H), 1.34-1.30 (t, J=7.2 Hz, 3H)

Reference Example 25

Cyclohexyl 1-iodoethyl carbonate

[Chemical formula 191]

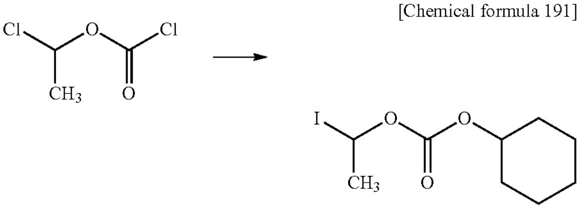

Using 1-chloroethyl chloroformate, the title compound was obtained according to the method disclosed in Reference Example 15.

1H NMR (300 MHz, $CDCl_3$) δ 6.76 (q, J=6.2 Hz, 1H), 4.74-4.61 (m, 1H), 2.24 (d, J=6.2 Hz, 3H), 2.13-1.29 (m, 10H)

Reference Example 26 tert-Butyl [(1S)-1-({(3R)-3-[{[2,2-dimethyl-3-oxo-4-[2-(propionylamino)ethyl]-7-(trifluoromethyl)-3,4-dihydro-2H-1,4-benzoxazin-6-yl]carbonyl}(isopropyl)amino]piperidin-1-yl}carbonyl)-2-methylpropyl] carbamate

[Chemical formula 192]

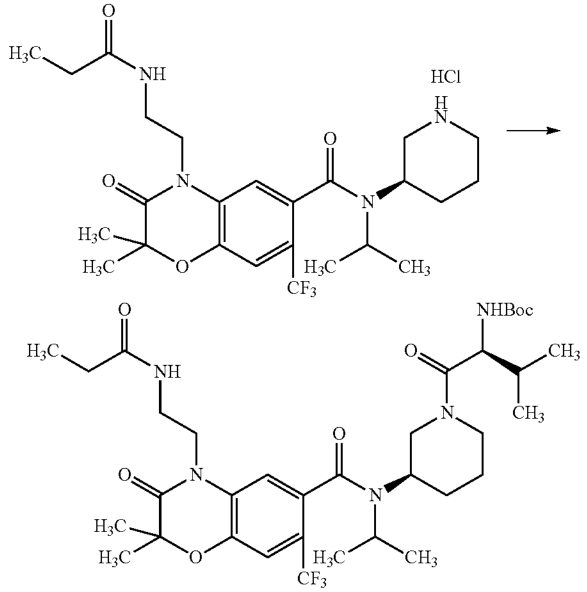

To N-isopropyl-2,2-dimethyl-3-oxo-N-[(3R)-piperidin-3-yl]-4-[2-(propionylamino)ethyl]-7-(trifluoromethyl)-3,4-dihydro-2H-1,4-benzoxazine-6-carboxamide hydrochloride (300 mg) were added N-Boc valine (158 mg), WSC (210 mg), HOBt (150 mg), triethylamine (0.30 ml) and chloroform (5 ml), and the mixture was stirred at room temperature overnight. After the reaction is completed, the solvent was concentrated, and the obtained residue was purified by column chromatography (hexane:ethyl acetate=1:2) to give the desired title compound (440 mg) as white amorphous.

MS (ESI+) 712 (M+1, 15%)

Reference Example 27 tert-Butyl ((1S)-2-{(3R)-3-[{[2,2-dimethyl-3-oxo-4-[2-(propionylamino)ethyl]-7-(trifluoromethyl)-3,4-dihydro-2H-1,4-benzoxazin-6-yl]carbonyl}(isopropyl)amino]piperidin-1-yl}-1-methyl-2-oxoethyl) carbamate

[Chemical formula 193]

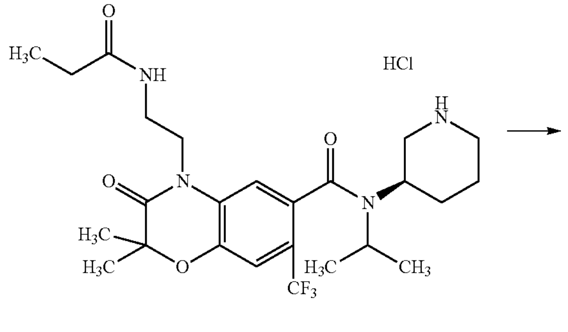

-continued

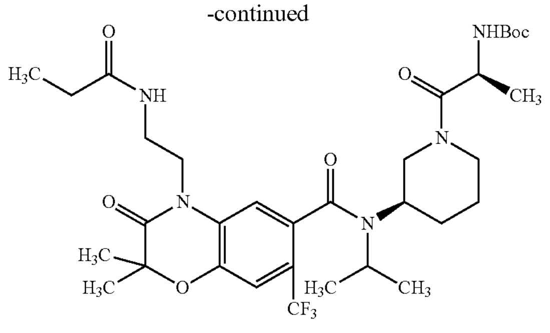

Using N-isopropyl-2,2-dimethyl-3-oxo-N-[(3R)-piperidin-3-yl]-4-[2-(propionylamino)ethyl]-7-(trifluoromethyl)-3,4-dihydro-2H-1,4-benzoxazine-6-carboxamine hydrochloride, the title compound was obtained according to the method disclosed in Reference Example 26

MS (ESI+) 684 (M+1, 15%)

Reference Example 28

1-Chloroethyl (3R)-3-[{[2,2-dimethyl-3-oxo-4-[2-(propionylamino)ethyl]-7-(trifluoromethyl)-3,4-dihydro-2H-1,4-benzoxazin-6-yl]carbonyl}(isopropyl) amino]piperidine-1-carboxylate

[Chemical formula 194]

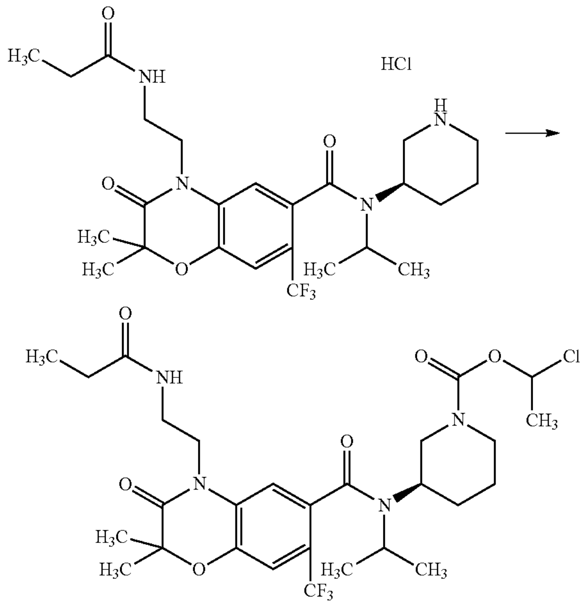

To a solution of N-isopropyl-2,2-dimethyl-3-oxo-N-[(3R)-piperidin-3-yl]-4-[2-(propionylamino)ethyl]-7-(trifluoromethyl)-3,4-dihydro-2H-1,4-benzoxazine-6-carboxamide hydrochloride (3.0 g) in chloroform (25 ml) were added successively triethylamine (0.98 ml) and 1-chloroethyl chloroformate (0.63 ml) under ice-cooling, and the mixture was stirred at room temperature overnight. After the reaction was completed, the reaction solution was washed with water and a saturated aqueous sodium chloride solution, dried over magnesium sulfate, and the solvent was concentrated to give the title compound (3.55 g) as white amorphous. The obtained title compound was used in the next reaction without further purification.

MS (ESI+) 619 (M+1, 8%)

Reference Example 29

1-Chloroethyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate

[Chemical formula 195]

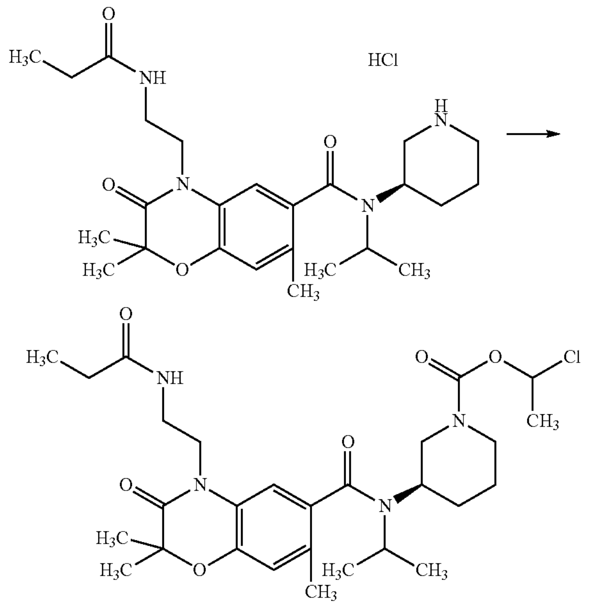

Using N-isopropyl-2,2,7-trimethyl-3-oxo-N-[(3R)-piperidin-3-yl]-4-[2-(propionylamino)ethyl]-3,4-dihydro-2H-1,4-benzoxazine-6-carboxamide hydrochloride, the title compound was obtained according to the method disclosed in Reference Example 28.

MS (ESI+) 565 (M+1, 10%)

Reference Example 30

Chloromethyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate

[Chemical formula 196]

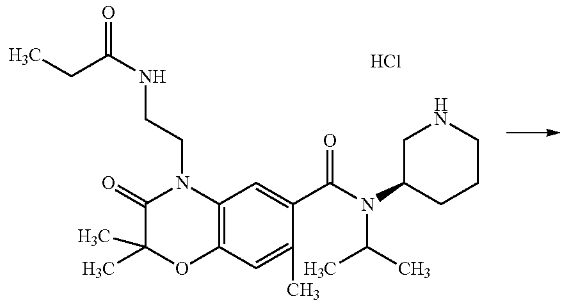

-continued

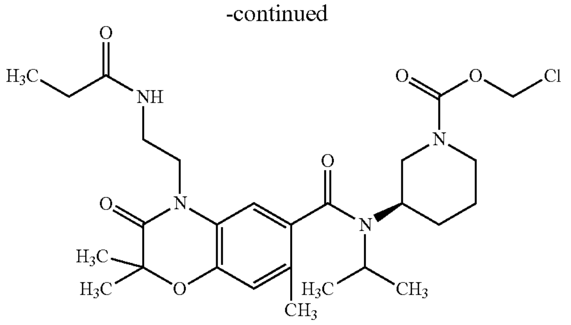

Using N-isopropyl-2,2,7-trimethyl-3-oxo-N-[(3R)-piperidin-3-yl]-4-[2-(propionylamino)ethyl]-3,4-dihydro-2H-1,4-benzoxazine-6-carboxamide hydrochloride, the title compound was obtained according to the method disclosed in Reference Example 28.

MS (ESI+) 551 (M+1, 10%)

Reference Example 31

1-Chloro-2-methylpropyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate

[Chemical formula 197]

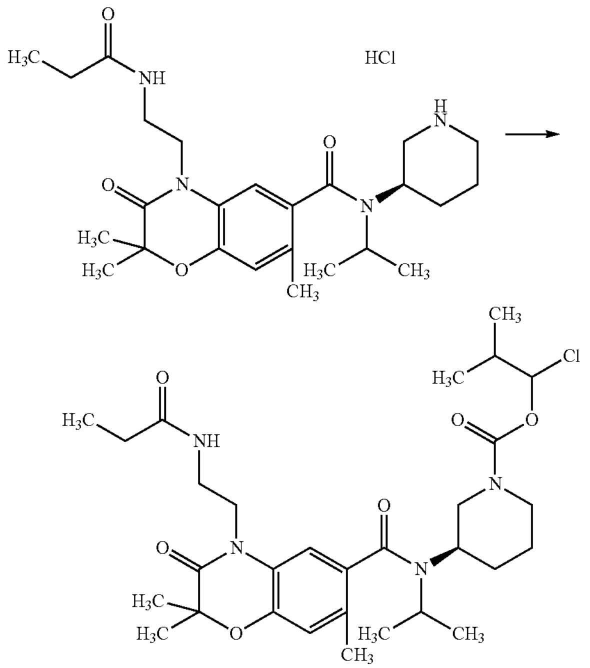

Using N-isopropyl-2,2,7-trimethyl-3-oxo-N-[(3R)-piperidin-3-yl]-4-[2-(propionylamino)ethyl]-3,4-dihydro-2H-1,4-benzoxazine-6-carboxamide hydrochloride, the title compound was obtained according to the method disclosed in Reference Example 28.

MS (ESI+) 593 (M+1, 11%)

Reference Example 32

1-Chloroethyl (3R)-3-[isopropyl({7-methyl-3-oxo-4-[2-(propionylamino)ethyl]-3,4-dihydrospiro[1,4-benzoxazine-2,1'-cyclobutan]-6-yl}carbonyl)amino] piperidine-1-carboxylate

[Chemical formula 198]

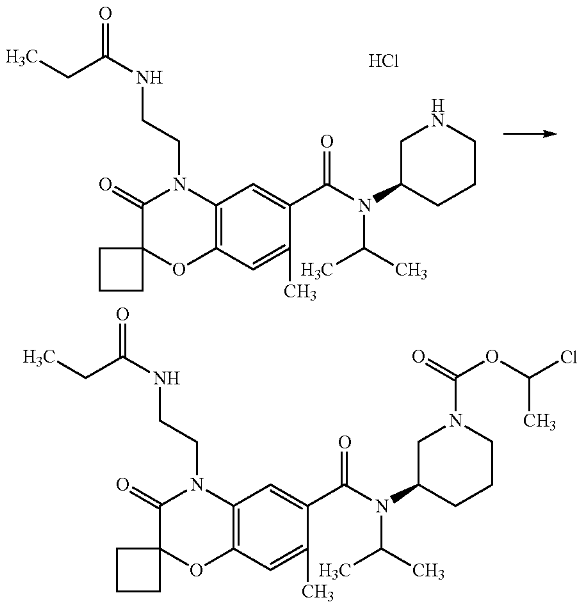

Using N-isopropyl-7-methyl-3-oxo-N-[(3R)-piperidin-3-yl]-4-[2-(propionylamino)ethyl]-3,4-dihydrospiro[1,4-benzoxazine-2,1'-cyclobutane]-6-carboxamide hydrochloride, the title compound was obtained according to the method disclosed in Reference Example 28.

MS (ESI+) 577 (M+1, 8%)

Reference Example 33

1-Chloro-2-methylpropyl (3R)-3-[isopropyl({7-methyl-3-oxo-4-[2-(propionylamino)ethyl]-3,4-dihydrospiro[1,4-benzoxazine-2,1'-cyclobutan]-6-yl}carbonyl)amino]piperidine-1-carboxylate

[Chemical formula 199]

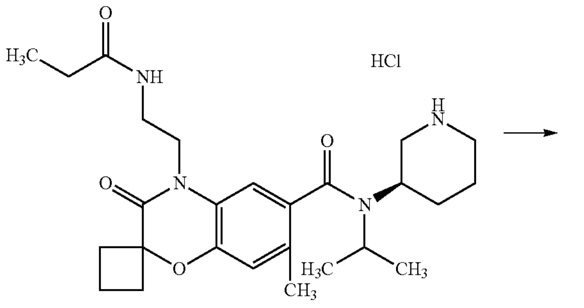

-continued

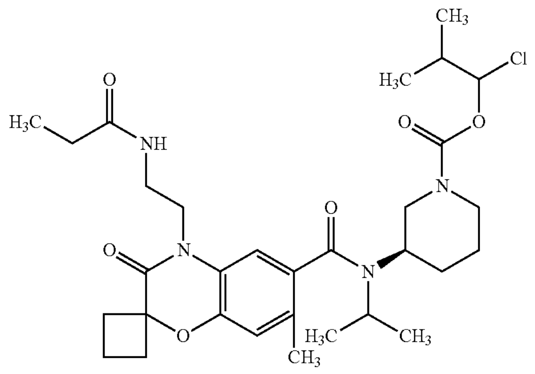

Using N-isopropyl-7-methyl-3-oxo-N-[(3R)-piperidin-3-yl]-4-[2-(propionylamino)ethyl]-3,4-dihydrospiro[1,4-benzoxazine-2,1'-cyclobutane]-6-carboxamide hydrochloride, the title compound was obtained according to the method disclosed in Reference Example 28.

MS (ESI+) 605 (M+1, 12%)

Reference Example 34

1-Chloroethyl (3R)-3-[isopropyl({(2S)-2-(methoxymethyl)-2-methyl-3-oxo-4-[2-(propionyl-amino) ethyl]-7-(trifluoromethyl)-3,4-dihydro-2H-1,4-benzoxazin-6-yl}carbonyl)amino]piperidine-1-carboxylate

[Chemical formula 200]

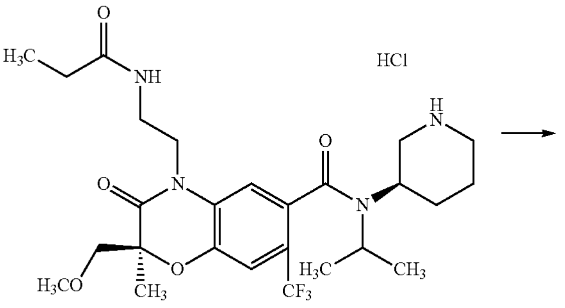

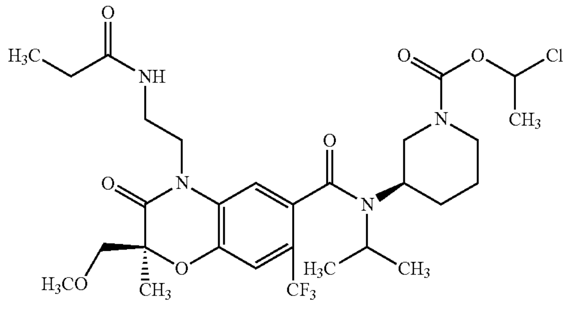

Using (2S)—N-isopropyl-2-(methoxymethyl)-2-methyl-3-oxo-N-[(3R)-piperidin-3-yl]-4-[2-(propionylamino)ethyl]-7-(trifluoromethyl)-3,4-dihydro-2H-1,4-benzoxazine-6-carboxamide hydrochloride, the title compound was obtained according to the method disclosed in Reference Example 28.

MS (ESI+) 605 (M+1, 12%)

Reference Example 35

1-Chloro-2-methylpropyl (3R)-3-(isopropyl{[(2S)-2-(methoxymethyl)-2-methyl-3-oxo-4-[2-(propionylamino)ethyl]-7-(trifluoromethyl)-3,4-dihydro-2H-1,4-benzoxazin-6-yl]carbonyl}-amino)piperidine-1-carboxylate

[Chemical formula 201]

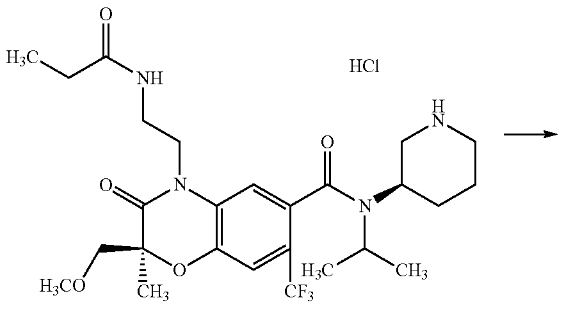

-continued

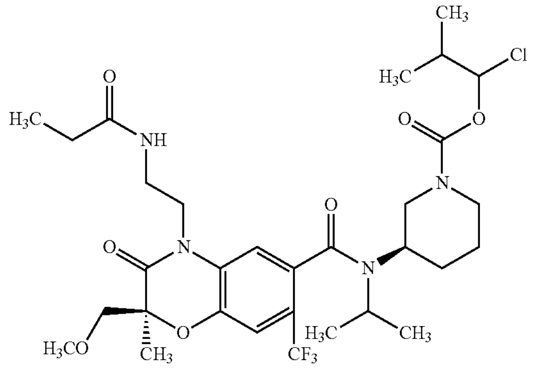

Using (2S)—N-isopropyl-2-(methoxymethyl)-2-methyl-3-oxo-N-[(3R)-piperidin-3-yl]-4-[2-(propionylamino)ethyl]-7-(trifluoromethyl)-3,4-dihydro-2H-1,4-benzoxazine-6-carboxamide hydrochloride, the title compound was obtained according to the method disclosed in Reference Example 28.

$R_f$=0.65 (chloroform:methanol=10:1).

Reference Example 36

1-{[N-(tert-Butoxycarbonyl)-L-valyl]oxy}ethyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate

[Chemical formula 202]

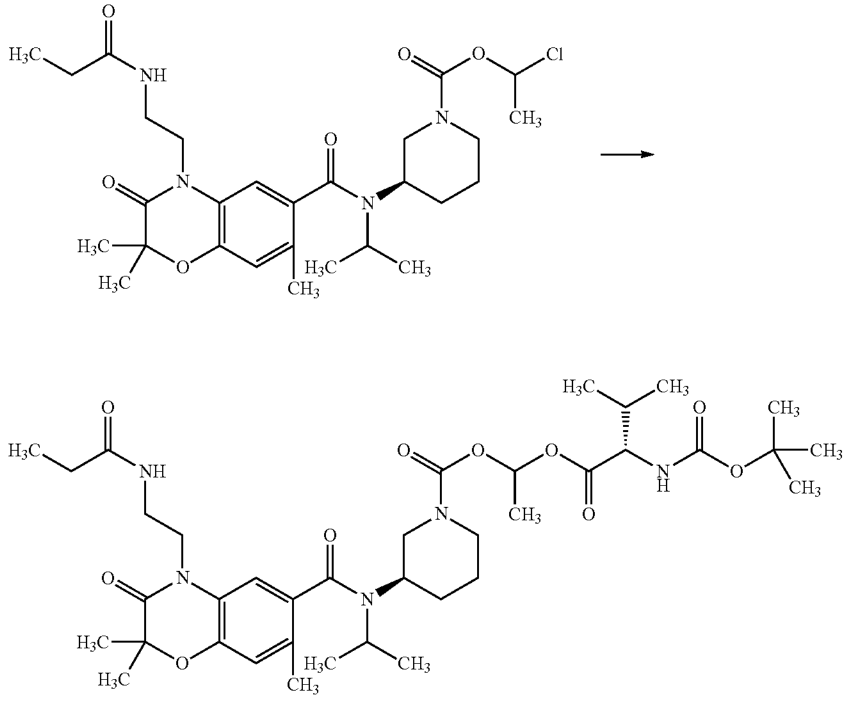

To a solution of the compound of Reference Example 29 (300 mg) in chloroform (3 ml) were added N-Boc valine (231 mg) and silver carbonate (220 mg), and the mixture was stirred at 50° C. for 2 hours. The reaction solution was filtered through celite, and concentrated under reduced pressure. The obtained residue was purified by silica gel column chromatography (hexane/ethyl acetate=10/90) to give the title compound (208 mg).

MS (ESI+) 746 (M+1, 100%)

Reference Example 37

1-{[4-(Benzyloxy)butanoyl]oxy}ethyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate

[Chemical formula 203]

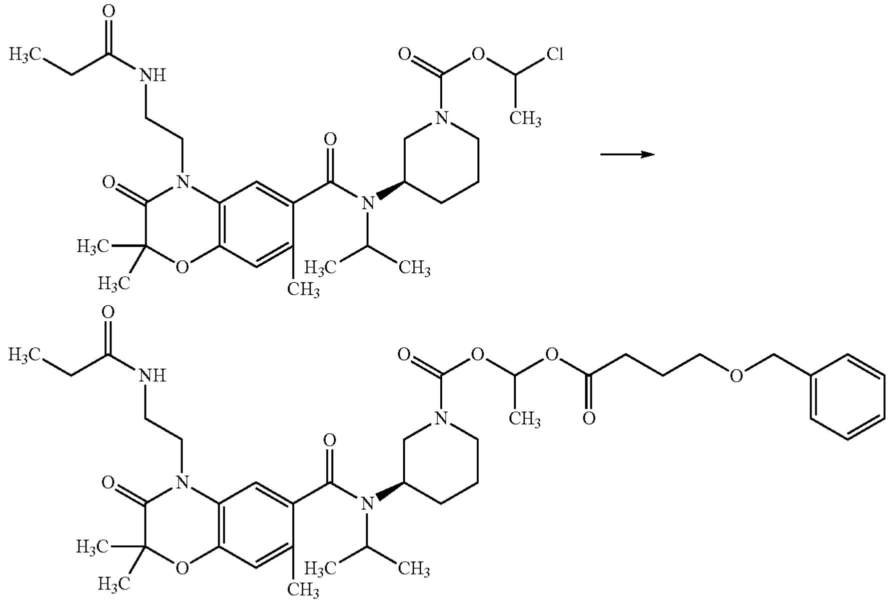

Using the compound of Reference Example 29, the title compound was obtained according to the method disclosed in Reference Example 36. $R_f$=0.36 (ethyl acetate).

Reference Example 38

1-Chloroethyl (3R)-3-[isopropyl({7-methyl-3-oxo-4-[2-(propionylamino)ethyl]-3,4-dihydrospiro[1,4-benzoxazine-2,1'-cyclopropan]-6-yl}carbonyl)amino]piperidine-1-carboxylate

[Chemical formula 204]

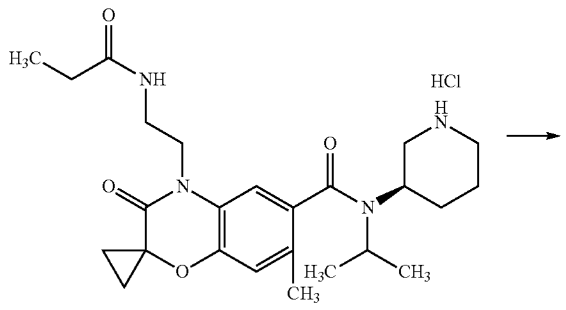

-continued

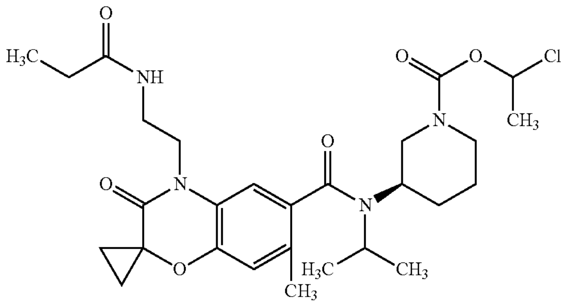

Using N-isopropyl-7-methyl-3-oxo-N-[(3R)-piperidin-3-yl]-4-[2-(propionylamino)ethyl]-3,4-dihydrospiro[1,4-benzoxazine-2,1'-cyclopropane]-6-carboxamide hydrochloride, the title compound was obtained according to the method disclosed in Reference Example 28.

$R_f$=0.47 (chloroform:methanol=10:1).

Reference Example 39

N-Isopropyl-2-(methoxymethyl)-2,7-dimethyl-3-oxo-N-[(3R)-piperidin-3-yl]-4-[2-(propionyl-amino)ethyl]-3,4-dihydro-2H-1,4-benzoxazine-6-carboxamide hydrochloride

[Chemical formula 205]

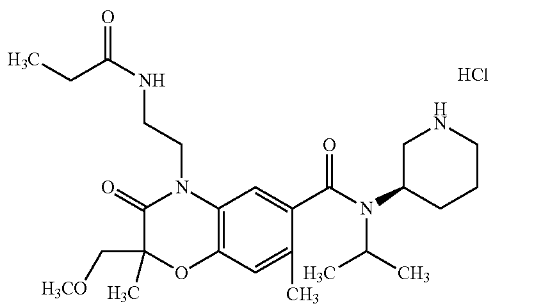

The title compound (7.9 g) was obtained from the compound of Reference Example 65 (8.9 g) according to the method disclosed in Reference Example 50.

1H NMR (400 MHz, $d_6$-DMSO) δ 9.13 (brs, 2H), 8.17-8.03 (m, 1H), 7.29-7.12 (m, 1H), 6.87-6.85 (m, 1H), 3.87-3.76 (m, 3H), 3.66-3.62 (m, 2H), 3.47-3.44 (m, 1H), 3.29-3.19 (m, 7H), 2.80-2.63 (m, 2H), 2.13 (s, 3H), 2.05-2.03 (m, 2H), 1.88-1.71 (m, 3H), 1.49-1.40 (m, 2H), 1.29-1.23 (m, 2H), 1.15-1.05 (m, 6H), 0.97-0.94 (m, 3H).

MS (ESI+) 489 (M++1, 100%).

Reference Example 40

1-Chloroethyl (3R)-3-[isopropyl({2-(methoxymethyl)-2,7-dimethyl-3-oxo-4-[2-(propionylamino)ethyl]-3,4-dihydro-2H-1,4-benzoxazin-6-yl}carbonyl)amino]piperidine-1-carboxylate

[Chemical formula 206]

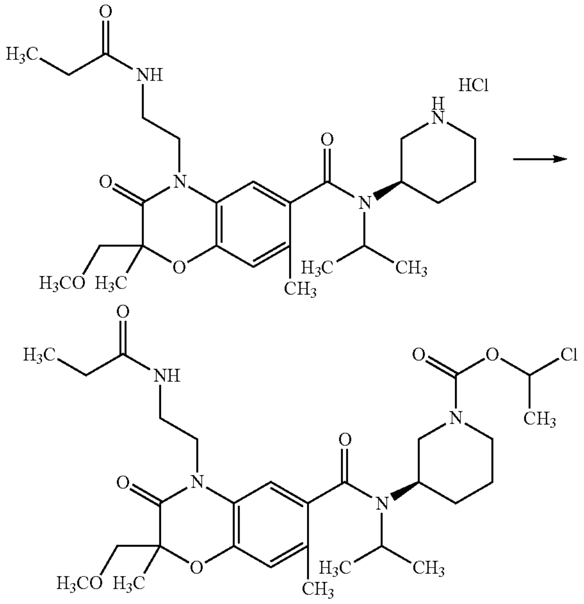

Using the compound of Reference Example 39, the title compound was obtained according to the method disclosed in Reference Example 28.

$R_f$=0.32 (hexane:ethyl acetate=1:3).

Reference Example 41

2-(Hydroxymethyl)-N-isopropyl-2-methyl-3-oxo-N-[(3R)-piperidin-3-yl]-4-[2-(propionylamino)ethyl]-7-(trifluoromethyl)-3,4-dihydro-2H-1,4-benzoxazine-6-carboxamide hydrochloride

[Chemical formula 207]

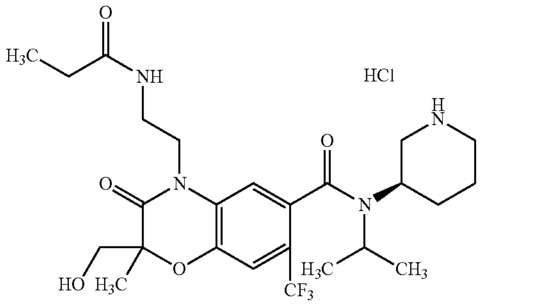

RT 2.709 min (Shim-pack XR-ODS, 0.1% trifluoroacetic acid in water/acetonitrile, acetonitrile 20-80% 7.1 min, 1.0 ml/min, UV 254 nm).

MS (ESI+) 529 (M+1, 8%).

The synthetic methods for preparing N-isopropyl-2,2,7-trimethyl-3-oxo-N-[(3R)-piperidin-3-yl]-4-[2-(propionylamino)ethyl]-3,4-dihydro-2H-1,4-benzoxazine-6-carboxamide hydrochloride and N-isopropyl-7-methyl-3-oxo-N-[(3R)-piperidin-3-yl]-4-[2-(propionylamino)ethyl]-3,4-dihydrospiro[1,4-benzoxazine-2,1'-cyclobutane]-6-carboxamide hydrochloride are disclosed below. The other derivatives were also synthesized according the method disclosed below.

Reference Example 42

Benzyl (2-bromoethyl)carbamate

[Chemical formula 208]

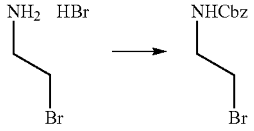

To a solution of 2-bromoethylamine hydrobromide (120.0 g) in chloroform (1400 ml) was added triethylamine (204 ml), and thereto was added dropwise benzyl chloroformate (100 ml) under ice-cooling slowly. The mixture was stirred at 0° C. for one hour, and warmed to room temperature, and further stirred overnight. To the reaction mixture was added water, and the mixture was extracted twice with chloroform. The organic layer was washed with a saturated aqueous sodium hydrogen carbonate solution and saturated aqueous sodium chloride solution, dried over sodium sulfate, filtered and dried under reduced pressure. The obtained residue was purified by silica gel column chromatography (developing solvent: hexane/ethyl acetate=3/1) to give the title compound (110 g).

Reference Example 43

2,2,7-Trimethyl-2H-1,4-benzoxazin-3(4H)-one

[Chemical formula 209]

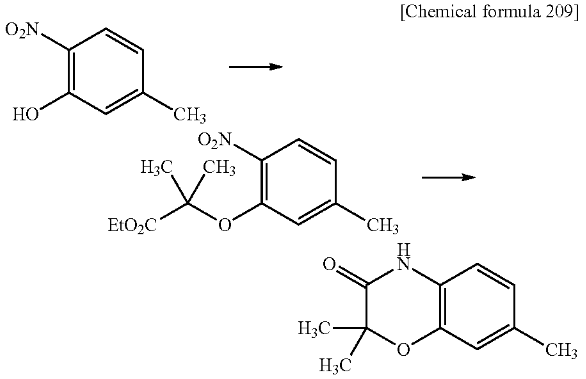

6-Nitro-m-cresol (30.6 g) was dissolved in acetonitrile (400 ml), and thereto was added cesium carbonate (163.3 g), and the mixture was warmed to 80° C. To the mixture was added dropwise ethyl 2-bromoisobutyric acid (60 ml), and the mixture was stirred at 80° C. for 6 hours. To the mixture was added dropwise again ethyl 2-bromoisobutyric acid (60 ml), and the mixture was further stirred at 80° C. for 8 hours. The reaction solution was cooled to room temperature, and filtered through celite. The filtrate was concentrated under reduced pressure. The residue was dissolved in ethyl acetate, washed with water (twice) and saturated aqueous sodium chloride solution (once), and dried over sodium sulfate. The mixture was filtered, and concentrated under reduced pressure to give a crude product. The obtained crude product was dissolved in ethanol (100 ml), and added dropwise in to a solution of iron (90 g) in acetic acid (300 ml), wherein the suspension was previously and separately warmed to 75° C. After the addition was completed, the mixture was stirred at 80° C. for 5 hours, and filtered through celite. The filtrate was concentrated under reduced pressure, and the residue was dissolved in ethyl acetate, washed successively with water and saturated aqueous sodium hydrogen carbonate solution, dried over sodium sulfate, filtered and concentrated under reduced pressure to give a crude product. The obtained crude product was washed with hexane, and collected by filtration to give the title compound (32 g) as whited crystal.

MS (ESI+) 192 ($M^+$+1, 100%).

Reference Example 44

Methyl 2,2,7-trimethyl-3-oxo-3,4-dihydro-2H-1,4-benzoxazine-6-carboxylate

[Chemical formula 210]

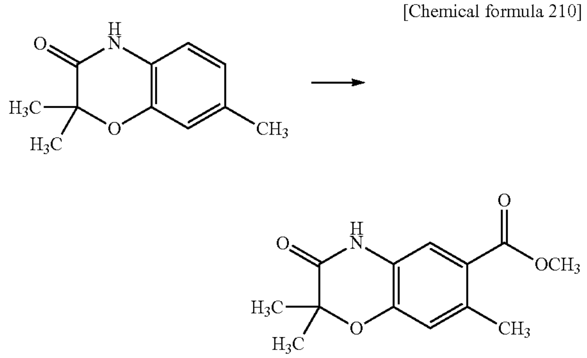

The compound of Reference Example 43 (9.6 g) and aluminum chloride (13.6 g) were dissolved in methylene chloride (100 ml), and the mixture was stirred at 0° C. for 30 minutes. Then, to the mixture was added oxalyl chloride (6.4 ml), and the mixture was stirred at 0° C. for 2 hours. To the mixture was added methanol (20 ml) at 0° C., and the mixture was stirred at room temperature for one hour, and water (20 ml) was added dropwise thereto. To the mixture were added chloroform and water, and extracted. The organic layer was washed with a saturated aqueous sodium chloride solution. Then, the organic layer was dried over sodium sulfate, filtered and concentrated under reduced pressure. To the obtained residue was added hexane, and the mixture was stirred at 50° C. for one hour. The mixture was cooled to room temperature, and the precipitate was collected by filtration, dried to give the title compound (11.4 g).

MS (ESI+) 250 ($M^+$+1, 100%).

Reference Example 45

Methyl 4-(2-{[(benzyloxy)carbonyl]amino}ethyl)-2,2,7-trimethyl-3-oxo-3,4-dihydro-2H-1,4-benzoxazine-6-carboxylate

[Chemical formula 211]

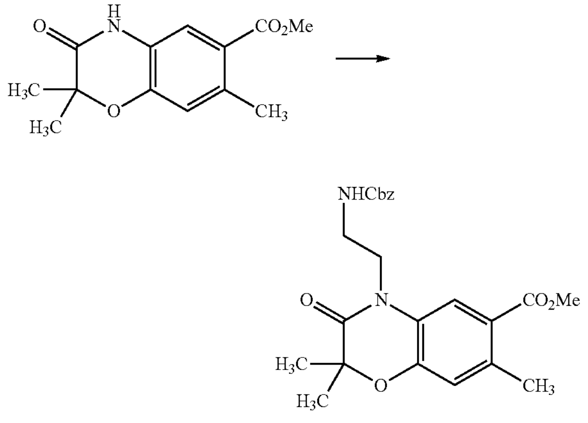

The compound of Reference Example 44 (75 g) was dissolved in dimethylformamide (150 ml) and acetonitrile (750 ml), and thereto were added cesium carbonate (198 g), potassium iodide (20 g), and the compound of Reference Example 42 (102 g), and the mixture was vigorously stirred with heating at 100° C. for 5 hours. The reaction solution was filtered, and water was added to the filtrate, and extracted with ethyl acetate. The organic layer was washed with aqueous hydrochloric acid solution and saturated aqueous sodium chloride solution, dried over sodium sulfate, filtered and concentrated under reduced pressure. The obtained residue was purified by silica gel column chromatography (ethyl acetate/hexane=1:3) to give the title compound (99 g).

MS (ESI+) 427 ($M^+$+1, 37%).

Reference Example 46

4-(2-{[(Benzyloxy)carbonyl]amino}ethyl)-2,2,7-trimethyl-3-oxo-3,4-dihydro-2H-1,4-benzoxazine-6-carboxylic acid

[Chemical formula 212]

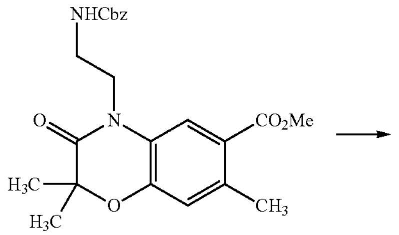

-continued

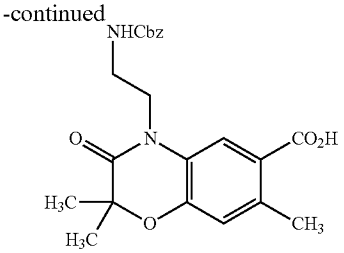

The compound of Reference Example 45 (94 g) was dissolved in tetrahydrofuran (400 ml) and 1,4-dioxane (200 ml), and thereto was added 10% aqueous sodium hydroxide solution (440 ml), and the mixture was warmed to 70° C., and further stirred vigorously for 5 hours. The reaction suspension was cooled to room temperature, and the organic solvent of the reaction mixture was concentrated under reduced pressure. To the residue was added hexane-diisopropyl ether (1:1), and the mixture was stirred. The precipitated white solid was collected by filtration. The solid was washed with hexane-diisopropyl ether (1:1), and the solid was mixed with ethyl acetate and tetrahydrofuran to give a slurry. The pH value of the obtained mixture was adjusted to pH 1 with 2N aqueous hydrochloric acid solution, and stirred for one hour. The organic layer was extracted, washed with saturated aqueous sodium chloride solution, dried over sodium sulfate, filtered and concentrated under reduced pressure to give the title compound (84 g).

MS (ESI+) 413 ($M^{+}$+1, 100%).

Reference Example 47 tert-Butyl (3R)-3-[{[4-(2-{[(benzyloxy)carbonyl]amino}ethyl)-2,2,7-trimethyl-3-oxo-3,4-dihydro-2H-1,4-benzoxazin-6-yl]carbonyl}(isopropyl)amino]piperidine-1-carboxylate

[Chemical formula 213]

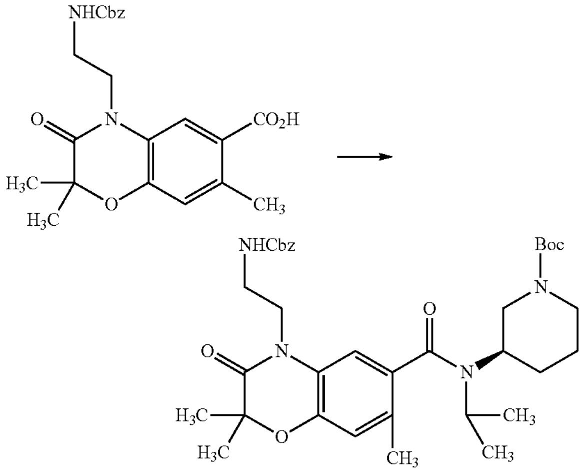

To a solution of the compound of Reference Example 46 (80 g) in dichloromethane (500 ml) were added oxalyl chloride (34 ml) and dimethylformamide (2 ml), and the mixture was stirred at room temperature for one hour. The solvent was evaporated under reduced pressure, and thereto was added toluene, and the mixture was concentrated under reduced pressure. The obtained residue was dissolved in dichloromethane (300 ml), and added dropwise into a solution of tert-butyl (3R)-3-(isopropylamino)piperidine-1-carboxylate (51 g) and triethylamine (80 ml) in dichloromethane (200 ml), and the mixture was stirred at room temperature for 2 hours. Water was added to the reaction mixture, and extracted with ethyl acetate. The organic layer was washed with saturated aqueous sodium chloride solution, dried over magnesium sulfate, filtered, and concentrated under reduced pressure. The obtained residue was purified by silica gel column chromatography (developing solvent: hexane/ethyl acetate=2/1) to give the title compound (92 g).

MS (ESI+) 637 ($M^{+}$+1, 38%).

Reference Example 48 tert-Butyl (3R)-3-[{[4-(2-aminoethyl)-2,2,7-trimethyl-3-oxo-3,4-dihydro-2H-1,4-benzoxazin-6-yl]carbonyl}(isopropyl)amino]piperidine-1-carboxylate

[Chemical formula 214]

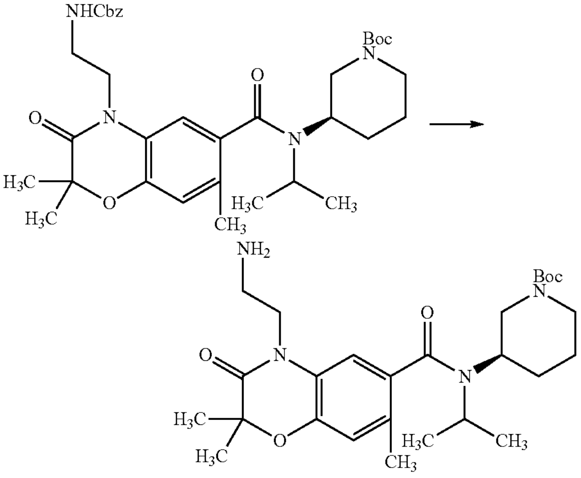

To the compound of Reference Example 47 (1.14 g) were added 10% palladium/carbon (500 mg) and methanol (30 ml), and the mixture was stirred at room temperature in the presence of hydrogen for 2 hours. After the reaction was completed, the mixture was filtered and concentrated. The obtained residue (900 mg) was used in the next reaction without purification.

MS (ESI+) 503 ($M^{+}$+1, 29%).

Reference Example 49 tert-Butyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate

[Chemical formula 215]

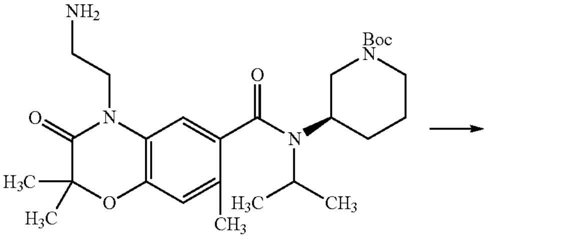

-continued

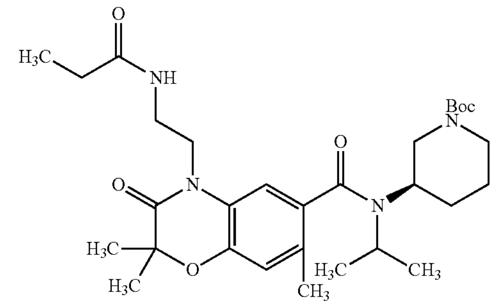

To the compound of Reference Example 48 (40 g) were added triethylamine (16 ml), tetrahydrofuran (170 ml) and propionyl chloride (8.8 ml) under ice-cooling, and the mixture was stirred at room temperature for one hour. After the reaction was completed, the mixture was concentrated, and the obtained residue was purified by silica gel column chromatography (hexane/ethyl acetate=1/6) to give the title compound (41 g) as colorless amorphous.

MS (ESI+) 559 ($M^{+}$+1, 32%).

Reference Example 50

N-Isopropyl-2,2,7-trimethyl-3-oxo-N-[(3R)-piperidin-3-yl]-4-[2-(propionylamino)ethyl]-3,4-dihydro-2H-1,4-benzoxazine-6-carboxamide hydrochloride

[Chemical formula 216]

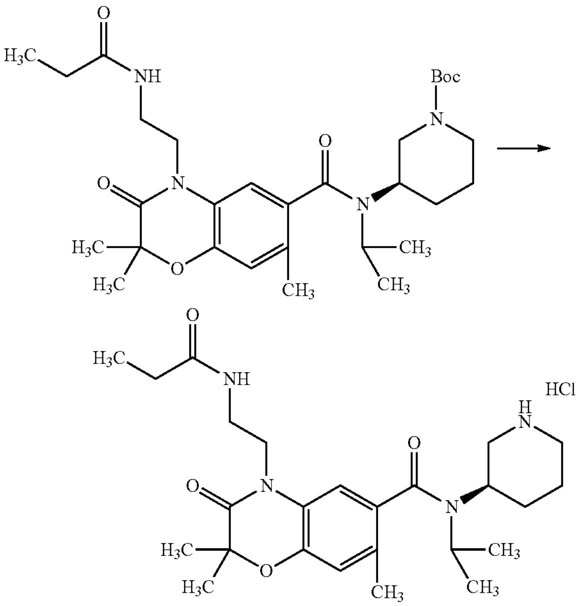

To a solution of the compound of Reference Example 49 (36 g) in dioxane (130 ml) was added 4N solution of hydrochloric acid in dioxane (65 ml), and the mixture was stirred at 25° C. for 7 hours. The reaction solution was concentrated under reduced pressure, and thereto was added chloroform, and concentrated under reduced pressure, and these procedure were repeated twice to give the title compound (31 g).

1H NMR (300 MHz, DMSO-$d_6$) δ 9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H)

Reference Example 51

Methyl 4-(benzyloxy)-2-methyl-5-nitrobenzoate

[Chemical formula 217]

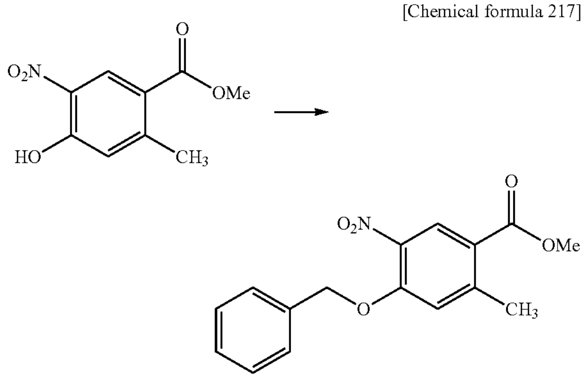

Methyl 4-hydroxy-2-methyl-5-nitrobenzoate (12.9 g) was dissolved in dimethylformamide (200 ml), and thereto were added potassium carbonate (20.1 g) and benzyl bromide (13.7 g), and the mixture was stirred at 70° C. for 4 hours. Water was added to the reaction mixture, and extracted with ethyl acetate. The obtained organic layer was washed with 1N aqueous hydrochloric acid solution, and saturated aqueous sodium chloride solution, dried over sodium sulfate, and the organic layer was concentrated under reduced pressure. The obtained solid was washed with hexane/ethyl acetate=10/1 to give the title compound (13 g).

1H NMR (400 MHz, $CDCl_3$) δ 8.55 (s, 1H), 8.00-7.30 (m, 5H), 6.91 (s, 1H), 5.26 (s, 2H), 3.87 (s, 3H), 2.65 (s, 3H).

Reference Example 52

4-(Benzyloxy)-2-methyl-5-nitrobenzoic acid

[Chemical formula 218]

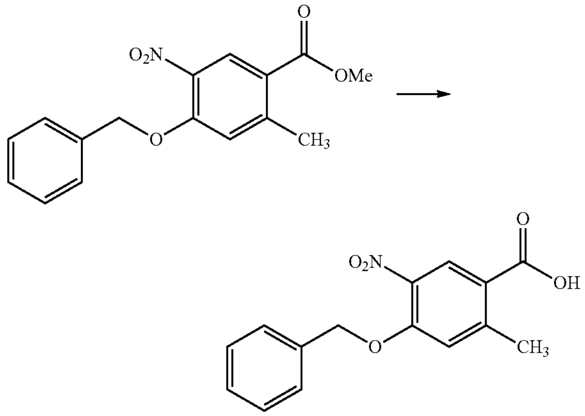

The compound of Reference Example 51 (21.3 g) was dissolved in tetrahydrofuran (80 ml) and methanol (80 ml), and thereto was added 10% aqueous sodium hydroxide solution (42.4 ml), and the mixture was warmed to 70° C. and vigorously stirred for 5 hours. The reaction solution was cooled to room temperature, and the reaction solvent was concentrated under reduced pressure to a half volume thereof.

The pH value of the remaining reaction solution was adjusted to pH=1, and extracted with ethyl acetate. The organic layer was washed with saturated aqueous sodium chloride solution, dried over sodium sulfate, and the organic layer was concentrated under reduced pressure to give the title compound (20 g).

1H NMR (400 MHz, $d_6$-DMSO) δ 8.82 (brs, 1H), 8.39 (s, 1H), 7.51-7.33 (m, 6H), 5.39 (s, 2H), 2.64 (s, 3H).

Reference Example 53 tert-Butyl (3R)-3-[[4-(benzyloxy)-2-methyl-5-nitrobenzoyl](isopropyl)amino]piperidine-1-carboxylate

[Chemical formula 219]

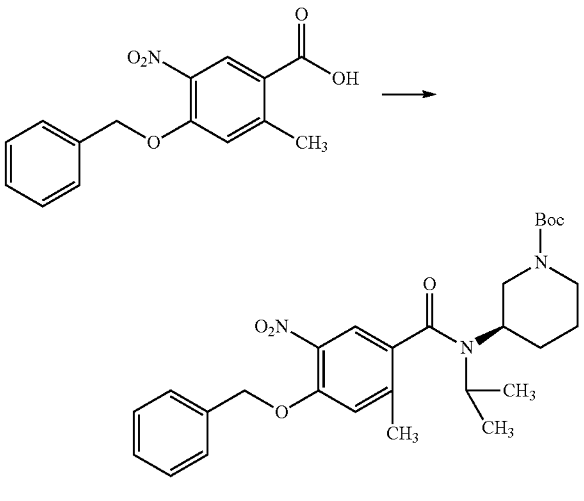

The compound of Reference Example 53 was synthesized according to the method disclosed in the corresponding Reference Example 47.

1H NMR (400 MHz, $CDCl_3$) δ 7.72-7.65 (m, 1H), 7.49-7.32 (m, 5H), 6.98 (s, 1H), 5.24 (s, 2H), 4.20-3.78 (m, 3H), 3.76-3.62 (m, 1H), 3.28-2.97 (m, 1H), 2.94-2.62 (m, 2H), 2.34 (brs, 3H), 1.85-1.67 (m, 2H), 1.48 (s, 9H), 1.44-1.33 (m, 1H), 1.26-1.06 (m, 6H).

Reference Example 54 tert-Butyl (3R)-3-[(5-amino-4-hydroxy-2-methylbenzoyl)(isopropyl)amino]piperidine-1-carboxylate

[Chemical formula 220]

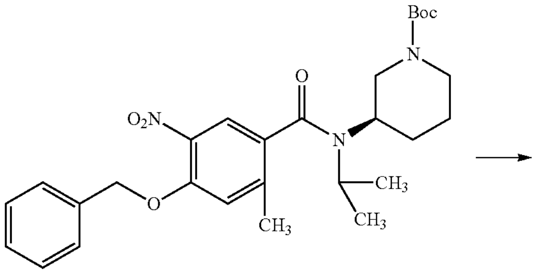

-continued

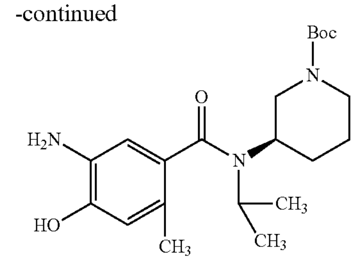

The compound of Reference Example 53 (31.1 g) was dissolved in methanol (300 ml), and thereto was added 10% palladium/carbon (30 g), and the mixture was vigorously stirred at room temperature for 8 hours under hydrogen atmosphere. After the reaction was completed, the mixture was filtered through celite, and the filtrate was concentrated under reduced pressure. The residue was dissolved in tetrahydrofuran, dried over sodium sulfate, filtered and concentrated under reduced pressure to give the title compound (23 g).

MS (ESI+) 392 ($M^+$+1, 93%).

Reference Example 55 tert-Butyl (3R)-3-{isopropyl[(7-methyl-3-oxo-3,4-dihydrospiro[1,4-benzoxazine-2,1'-cyclobutan]-6-yl)carbonyl]amino}piperidine-1-carboxylate

[Chemical formula 221]

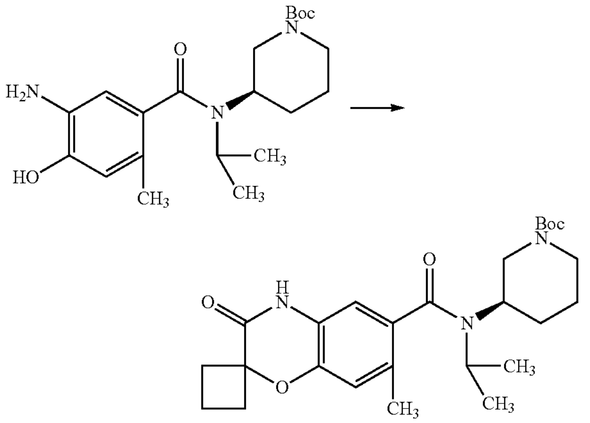

The compound of Reference Example 54 (23.5 g) was dissolved in chloroform (200 ml), and thereto was added a solution of sodium hydrogen carbonate (101 g) in water (1200 ml), and the mixture was cooled to 0° C. To the mixture was added dropwise a solution of 1-bromocyclobutanecarbonyl chloride (70 mmol) in dichloromethane (50 ml) slowly. The mixture was vigorously stirred at 0° C. for one hour, and then, further vigorously stirred at 25° C. for 2 hours. Water was added to the reaction mixture, and extracted twice with chloroform. The organic layer was washed with a saturated aqueous sodium chloride solution, dried over sodium sulfate, and the organic layer was concentrated under reduced pressure. The obtained residue was dissolved in dimethylformamide (400 ml) without further purification, and thereto was added potassium carbonate (21 g), and the mixture was vigorously stirred at 80° C. for 4 hours. Water was added to the reaction solution, and stirred for one hour, and then, extracted with ethyl acetate. The organic layer was washed with 10% aqueous potassium hydrogen sulfate solution and a saturated sodium chloride solution, dried over sodium sulfate, and the organic layer was concentrated under reduced pressure. The obtained residue was purified by silica gel column chromatography (developing solvent: hexane/ethyl acetate=1/1) to give the title compound (12.5 g).

MS (ESI+) 472 ($M^{+}$+1, 30%).

Reference Example 56 tert-Butyl (3R)-3-[{[4-(2-{[(benzyloxy)carbonyl]amino}ethyl)-7-methyl-3-oxo-3,4-dihydrospiro[1,4-benzoxazine-2,1'-cyclobutan]-6-yl]carbonyl}(isopropyl)amino]piperidine-1-carboxylate

[Chemical formula 222]

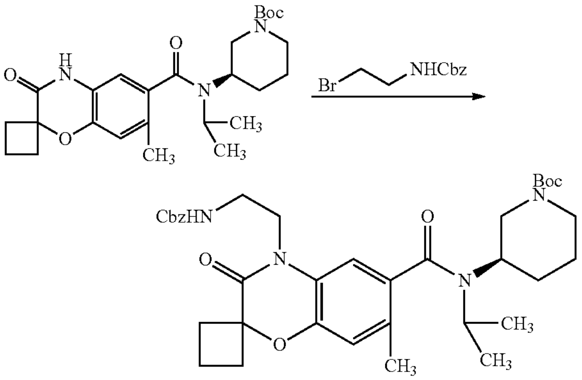

The compound of Reference Example 55 (12.3 g) was dissolved in dimethylformamide (100 ml), and thereto were added cesium carbonate (15.3 g) and the compound of Reference Example 42 (8.75 g), and the mixture was vigorously stirred at 80° C. for 5 hours. The mixture was filtered to remove the cesium carbonate, and water was added to the filtrate, and extracted with ethyl acetate. The organic layer was washed with 1N hydrochloric acid and saturated aqueous sodium chloride solution, dried over sodium sulfate, filtered and concentrated under reduced pressure. The obtained residue was purified by silica gel column (ethyl acetate/hexane=1:2) to give the title compound (10.7 g).

MS (ESI+) 649 ($M^{+}$+1, 40%).

Reference Example 57

N-Isopropyl-7-methyl-3-oxo-N-[(3R)-piperidin-3-yl]-4-[2-(propionylamino)ethyl]-3,4-dihydrospiro[1,4-benzoxazine-2,1'-cyclobutane]-6-carboxamide hydrochloride

[Chemical formula 223]

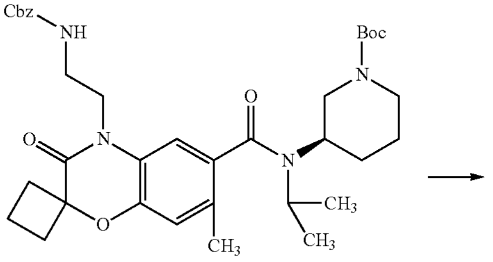

-continued

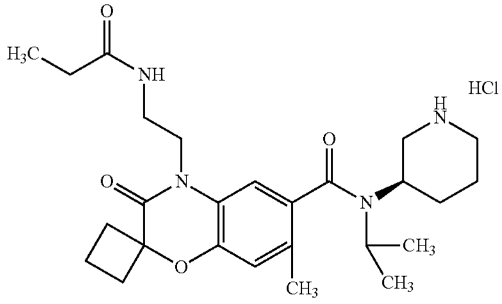

The title compound was synthesized according to the methods disclosed in Reference Examples 48, 49, 50.

1H NMR (400 MHz, $CDCl_3$) δ 9.89-9.38 (br, 2H), 7.37-7.08 (m, 2H), 6.49 (br, 0.5H), 5.93 (br, 0.5H), 4.33-3.29 (m, 12H), 2.88-2.66 (m, 4H), 2.58-1.78 (m, 6H), 2.10 (s, 3H), 1.46-0.89 (m, 9H)

Reference Example 58

N,N-Dibenzyl-2-bromoethanamine

[Chemical formula 224]

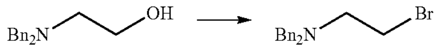

To N,N-dibenzyl-2-aminoethanol (80.68 g) were added cyclohexane (500 ml) and DMF (12.9 ml), and thereto was added dropwise thionyl bromide (83.4 g). The mixture was stirred for 15 hours, and to the reaction solution was added an saturated aqueous sodium hydrogen carbonate solution in an ice-bath, and the mixture was extracted with ethyl acetate. The organic layer was washed with water (three times) and saturated aqueous sodium chloride solution, dried over sodium sulfate, filtered and concentrated under reduced pressure to give the title compound (72.1 g).

1H NMR (400 MHz, $CDCl_3$) δ 7.48-7.39 (m, 8H), 7.36-7.33 (m, 2H), 3.74 (s, 4H), 3.43 (m, 2H), 2.97 (m, 2H).

Reference Example 59

Methyl 2-methyl-5-nitro-4-(2-propen-1-yloxy)benzoate

[Chemical formula 225]

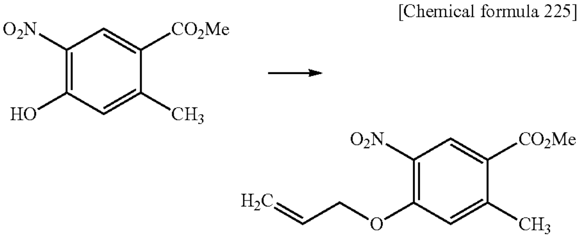

To a solution of methyl 4-hydroxy-2-methyl-5-nitrobenzoate (6.3 g) in N,N-dimethyl-formamide (150 ml) were added at room temperature 18-crown-6 (79 mg) and potassium carbonate (8.3 g), and the mixture was stirred at 80° C. for one hour. The mixture was cooled to room temperature, and to the reaction solution were added water and ethyl acetate, and the mixture was extracted with ethyl acetate. The organic layer was dried over sodium sulfate, filtered and concentrated under reduced pressure to give the title compound (7.5 g).

1H NMR (400 MHz, $CDCl_3$) δ 8.27 (s, 1H), 6.90 (s, 1H), 6.08-6.01 (m, 1H), 5.55-5.50 (m, 1H), 5.39-5.36 (m, 1H), 4.75-4.73 (m, 2H), 3.90 (s, 3H), 2.68 (s, 3H).

Reference Example 60

2-Methyl-5-nitro-4-(2-propen-1-yloxy)benzoic acid

[Chemical formula 226]

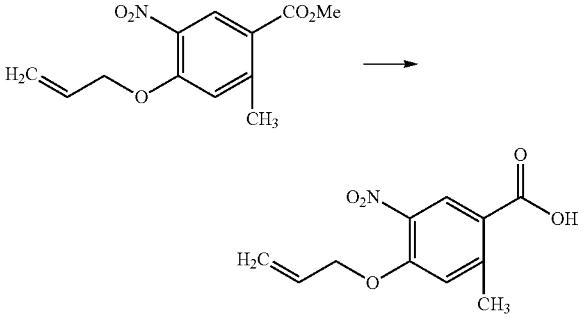

To a solution of the compound of Reference Example 59 (7.5 g) in tetrahydrofuran (60 ml) was added 5N aqueous sodium hydroxide solution (7.8 ml), and the mixture was stirred at 80° C. for 10 hours. The reaction solution was allowed to cool, and concentrated under reduced pressure to remove tetrahydrofuran. To the resultant were added water and chloroform, and the chloroform layer was removed. The pH value of the aqueous layer was adjusted to about pH 4 with 1N aqueous hydrochloric acid solution to give crystals. The resulting crystals were collected by filtration, and dried to give the title compound (7.1 g).

1H NMR (400 MHz, DMSO) δ 8.37 (s, 1H), 7.31 (s, 1H), 6.08-6.01 (m, 1H), 5.48 (d, J=9.4 Hz, 1H), 5.33 (d, J=7.2 Hz, 1H), 4.83-4.81 (m, 2H), 2.62 (s, 3H).

Reference Example 61

2-Methyl-2-propanyl (3R)-3-[{[2-methyl-5-nitro-4-(2-propen-1-yloxy)phenyl]carbonyl}(2-propanyl)amino]-1-piperidinecarboxylate

[Chemical formula 227]

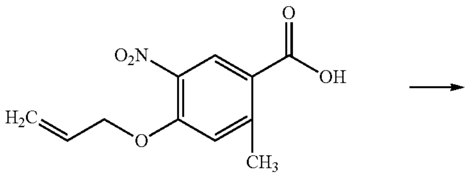

-continued

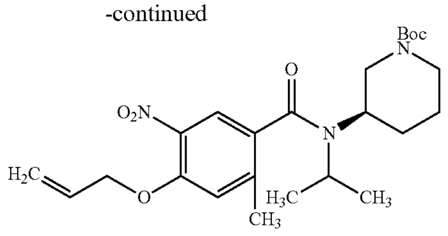

The title compound (163 g) was obtained from the compound of Reference Example 60 (98.4 g) according to the method disclosed in the corresponding Reference Example 47.

1H NMR (400 MHz, $CDCl_3$) δ 7.63 (s, 1H), 6.92 (s, 1H), 6.10-6.01 (m, 1H), 5.55-6.35 (m, 2H), 4.70 (d, J=4.4 Hz, 2H), 4.21-3.79 (m, 3H), 3.77-3.63 (m, 1H), 3.12-2.64 (m, 3H), 2.33 (brs, 3H), 1.86-1.68 (m, 2H), 1.62-1.37 (m, 10H), 1.26-1.09 (m, 6H).

Reference Example 62

Ethyl 2,7-dimethyl-6-{[(3R)-1-{[(2-methyl-2-propanyl)oxy]carbonyl}-3-piperidinyl](2-propanyl)carbamoyl}-3-oxo-3,4-dihydro-2H-1,4-benzoxazine-2-carboxylate

[Chemical formula 228]

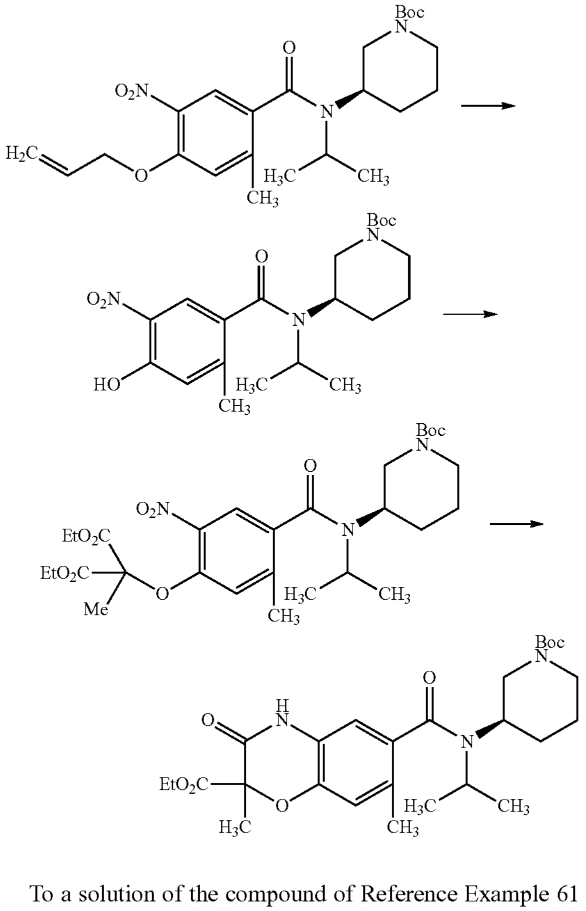

To a solution of the compound of Reference Example 61 (176 g) in tetrahydrofuran (1000 ml) were added tetrakistriphenylphosphine palladium (2.21 g) and morpholine (200 g), and the mixture was stirred at room temperature. Twenty-five minutes later, to the reaction solution were added a 5% aqueous potassium hydrogen sulfate solution and ethyl acetate, and extracted with ethyl acetate. The organic layer was washed with a saturated aqueous sodium chloride solution, dried over sodium sulfate, filtered and concentrated under reduced pressure to give 2-methyl-2-propanyl (3R)-3-{[(4-hydroxy-2-methyl-5-nitrophenyl)carbonyl](2-propanyl)amino}-1-piperidinecarboxylate (156 g).

To a solution of the obtained 2-methyl-2-propanyl (3R)-3-{[(4-hydroxy-2-methyl-5-nitrophenyl)carbonyl](2-propanyl)amino}-1-piperidinecarboxylate (138 g) in N,N-dimethylformamide (1000 ml) were added potassium carbonate (91 g), diethyl 2-bromo-2-methylmalonate (94 g), and the mixture was stirred at 80° C. for 8 hours. The reaction solution was allowed to cool to room temperature, filtered through celite, and to the filtrate were added a 5% aqueous sodium hydrogen sulfate solution and ethyl acetate, and extracted with ethyl acetate. The organic layer was washed with water, a saturated aqueous sodium chloride solution, and then dried over sodium sulfate. The sodium sulfate was removed by filtration, and the filtrate was concentrated under reduced pressure to give diethyl methyl(5-methyl-4-{[(3R)-1-{[(2-methyl-2-propanyl)oxy]carbonyl}-3-piperidinyl](2-propanyl)carbamoyl}-2-nitrophenoxy)propanedioate (205 g).

Subsequently, to a suspension of iron (110 g) in acetic acid (500 ml) was added dropwise a solution of the obtained diethyl methyl(5-methyl-4-{[(3R)-1-{[(2-methyl-2-propanyl)oxy]carbonyl}-3-piperidinyl](2-propanyl)carbamoyl}-2-nitrophenoxy)propanedioate (205 g) in acetic acid (200 ml) slowly at 90° C. Ten hours later, the mixture was allowed to cool to room temperature, filtered through celite, and the filtrate was concentrated under reduced pressure. To the obtained residue was added a saturated aqueous sodium hydrogen carbonate solution, and the mixture was extracted with chloroform. The organic layer was washed with water and a saturated aqueous sodium chloride solution, dried over sodium sulfate, and filtered. The filtrate was concentrated under reduced pressure, and the resulting residue was purified by silica gel chromatography to give the title compound (102 g).

$R_f$=0.25 (n-hexane/ethyl acetate=1/1)

Reference Example 63

Ethyl 4-[2-(dibenzylamino)ethyl]-2,7-dimethyl-6-{[(3R)-1-{[(2-methyl-2-propanyl)oxy]carbonyl}-3-piperidinyl](2-propanyl)carbamoyl}-3-oxo-3,4-dihydro-2H-1,4-benzoxazine-2-carboxylate

[Chemical formula 229]

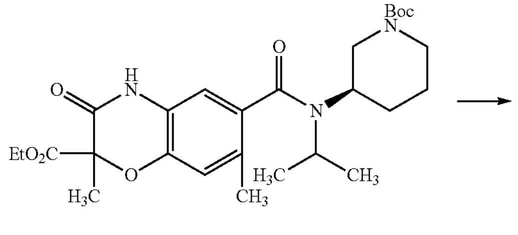

-continued

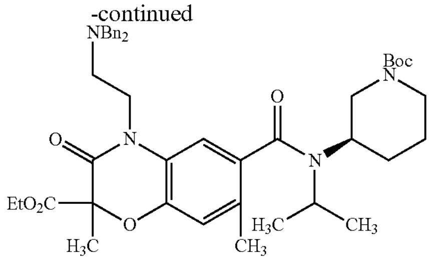

To a solution of the compound of Reference Example 62 (107 g) in acetonitrile (450 ml) were added potassium carbonate (43 g), 18-crown-6 (5.5 g), and the compound of Reference Example 58 (67 g) at room temperature, and the mixture was stirred at 80° C. for 8 hours. The mixture was allowed to cool to room temperature, and to the reaction solution was added an aqueous saturated ammonium chloride solution, and extracted with ethyl acetate. The organic layer was washed with a saturated aqueous sodium chloride solution, and dried over sodium sulfate. The sodium sulfate was removed by filtration, and the filtrate was concentrated under reduced pressure. The obtained residue was purified by silica gel chromatography to give the title compound (133 g).

$R_f$=0.51 (n-hexane/ethyl acetate=1/1)

Reference Example 64

2-Methyl-2-propanyl (3R)-3-[({4-[2-(dibenzylamino)ethyl]2-(methoxymethyl)-2,7-dimethyl-3-oxo-3,4-dihydro-2H-1,4-benzoxazin-6-yl}carbonyl)(2-propanyl)amino]-1-piperidinecarboxylate

[Chemical formula 230]

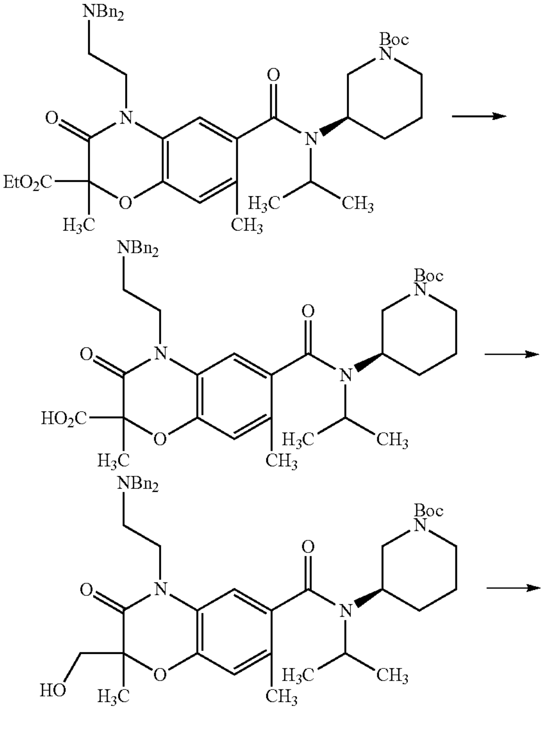

-continued

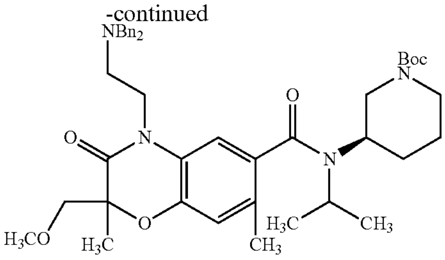

To a solution of the compound of Reference Example 63 (2 g) in a mixture of tetrahydrofuran-water (5 ml-3.5 ml) was added lithium hydroxide monohydrate (147 mg) at room temperature. Then, the mixture was stirred at 60° C. for 5 hours. The mixture was allowed to cool to room temperature, and thereto was added a 5% aqueous potassium hydrogen sulfate solution, and extracted with ethyl acetate. The organic layer was washed with a saturated aqueous sodium chloride solution, and dried over sodium sulfate. The sodium sulfate was removed by filtration, and the filtrate was concentrated under reduced pressure to give 4-[2-(dibenzylamino)ethyl]-2,7-dimethyl-6-{[(3R)-1-{[(2-methyl-2-propanyl)-oxy]carbonyl}-3-piperidinyl](2-propanyl)carbamoyl}-3-oxo-3,4-dihydro-2H-1,4-benzoxazine-2-carboxylic acid (1.9 g).

Under nitrogen atmosphere, the mixture was cooled with ice-bath, and to a solution of the obtained 4-[2-(dibenzylamino)ethyl]-2,7-dimethyl-6-{[(3R)-1-{[(2-methyl-2-propanyl)oxy]carbonyl}-3-piperidinyl](2-propanyl)carbamoyl}-3-oxo-3,4-dihydro-2H-1,4-benzoxazine-2-carboxylic acid (27.2 g) in tetrahydrofuran (75 ml) were added triethylamine (5.8 g) and chloroformic acid isobutyl ester (6.2 g), and the mixture was stirred for one hour. The precipitated salt was filtered, and the filtrate was added dropwise into a suspension of sodium borohydride (2.9 g) in tetrahydrofuran-ethanol (50 ml-50 ml) under ice-cooling. The mixture was stirred for one hour, and thereto was added a saturated aqueous ammonium chloride solution, and the mixture was extracted with ethyl acetate. The organic layer was washed with a saturated aqueous sodium chloride solution, and dried over sodium sulfate. The sodium sulfate was removed by filtration, and the filtrate was concentrated under reduced pressure. The obtained residue was purified by silica gel chromatography to give 2-methyl-2-propanyl (3R)-3-[({4-[2-(dibenzylamino)ethyl]-2-(hydroxymethyl)-2,7-dimethyl-3-oxo-3,4-dihydro-2H-1,4-benzoxazin-6-yl}carbonyl)(2-propanyl)amino]-1-piperidinecarboxylate (22.5 g).

To a solution of the obtained 2-methyl-2-propanyl (3R)-3-[({4-[2-(dibenzylamino)ethyl]-2-(hydroxymethyl)-2,7-dimethyl-3-oxo-3,4-dihydro-2H-1,4-benzoxazin-6-yl}carbonyl)(2-propanyl)amino]-1-piperidine carboxylate (22.5 g) in N,N-dimethylformamide (80 ml) were added sodium hydride (1.6 g) and methyl iodide (5.5 g) under ice-cooling. The mixture was stirred for 30 minutes, and then, cooled to room temperature, and further stirred for 2 hours. To the reaction solution was added a saturated aqueous ammonium chloride solution, and the mixture was ethyl acetate. The organic layer was washed with a saturated aqueous sodium chloride solution, and dried over sodium sulfate. The sodium sulfate was removed by filtration, and the filtrate was concentrated under reduced pressure, followed by purification with silica gel chromatography to give the title compound (19.2 g).

$R_f$=0.59 (n-hexane/ethyl acetate=1/1)

Reference Example 65

2-Methyl-2-propanyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(2-propanyl)amino]-1-piperidinecarboxylate

[Chemical formula 231]

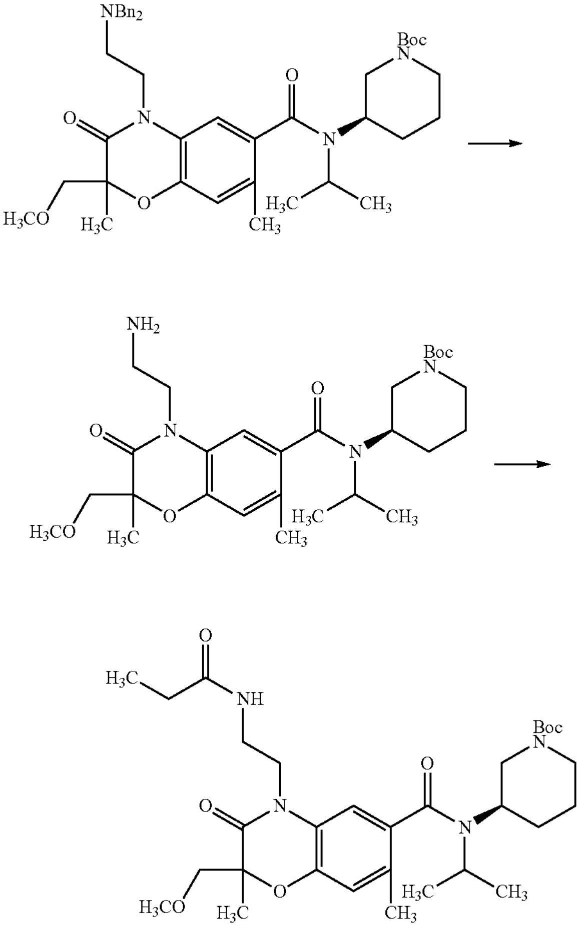

To a solution of the compound of Reference Example 64 (19.2 g) in ethanol (100 ml) was added palladium-carbon (9.6 g), and the mixture was stirred under hydrogen atmosphere at room temperature for 5 hours. The palladium-carbon was removed by filtration, and the filtrate was concentrated under reduced pressure, and the residue was purified by silica gel chromatography to give 2-methyl-2-propanyl (3R)-3-[{[4-(2-aminoethyl)-2-(methoxymethyl)-2,7-dimethyl-3-oxo-3,4-dihydro-2H-1,4-benzoxazin-6-yl]carbonyl}(2-propanyl)amino]-1-piperidinecarboxylate (10.1 g).

The title compound (8.9 g) was obtained from the obtained 2-methyl-2-propanyl (3R)-3-[{[4-(2-aminoethyl)-2-(methoxymethyl)-2,7-dimethyl-3-oxo-3,4-dihydro-2H-1,4-benzoxazin-6-yl]carbonyl}(2-propanyl)amino]-1-piperidine carboxylate (10.1 g) according to the method disclosed in Reference Example 49.

$R_f$=0.32 (n-hexane/ethyl acetate=1/3)

Reference Example 66

(2S)-2-(Methoxymethyl)-2,7-dimethyl-3-oxo-N-[(3R)-3-piperidinyl]-4-[2-(propanoylamino)ethyl]-N-(2-propanyl)-3,4-dihydro-2H-1,4-benzoxazine-6-carboxamide

[Chemical formula 232]

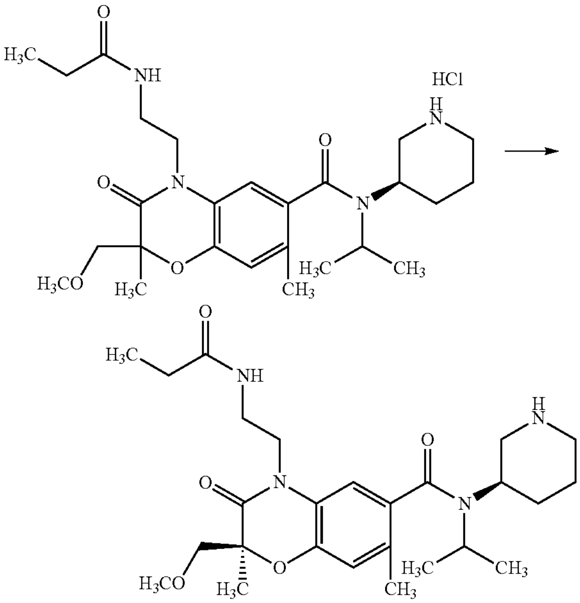

N-Isopropyl-2-(methoxymethyl)-2,7-dimethyl-3-oxo-N-[(3R)-piperidin-3-yl]-4-[2-(propionylamino)ethyl]-3,4-dihydro-2H-1,4-benzoxazine-6-carboxamide hydrochloride was separated and collected by HPLC under the following conditions to give the title compound.

CHIRALCEL (registered trademark) OD-H (0.46 cm I.D.×25 cm L), Mobile phase: n-hexane/2-propanol/diethylamine (50/50/0.1), Flow rate: 1.0 ml/min, Temperature: 40° C., Wave length: 294 nm RT 4.252 min 1H NMR (400 MHz, $CDCl_3$) δ 6.92-6.72 (m, 2H), 6.30-6.03 (m, 1H), 4.14-3.66 (m, 4H), 3.65-2.61 (m, 10H), 2.30-2.04 (m, 5H), 1.97-1.68 (m, 3H), 1.62-1.43 (m, 3H), 1.31-0.98 (m, 9H).

MS (ESI+) 489 ($M^+$+1, 100%).

Reference Example 67

(2R)-2-(Methoxymethyl)-2,7-dimethyl-3-oxo-N-[(3R)-3-piperidyl]-4-[2-(propanoylamino)ethyl]-N-(2-propanyl)-3,4-dihydro-2H-1,4-benzoxazine-6-carboxamide

[Chemical formula 233]

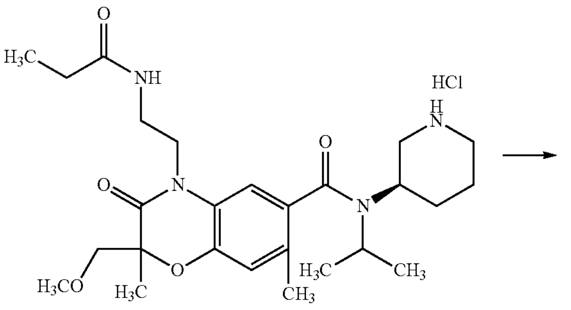

-continued

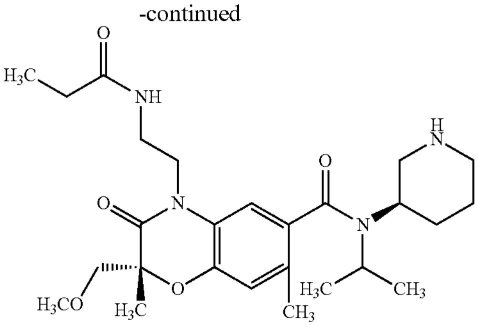

N-Isopropyl-2-(methoxymethyl)-2,7-dimethyl-3-oxo-N-[(3R)-piperidin-3-yl]-4-[2-(propionylamino)ethyl]-3,4-dihydro-2H-1,4-benzoxazine-6-carboxamide hydrochloride was separated and collected by HPLC to give the title compound.

CHIRALCEL (registered trademark) OD-H (0.46 cm I.D.×25 cm L), Mobile phase: n-hexane/2-propanol/diethylamine (50/50/0.1), Flow rate: 1.0 ml/min, Temperature: 40° C., Wave length: 294 nm RT 6.501 min 1H NMR (400 MHz, $CDCl_3$) δ 7.27 (s, 0.66H), 6.91 (s, 0.34H), 6.83 (s, 0.66H), 6.81 (s, 0.34H), 6.62-6.54 (m, 0.66H), 6.07-6.01 (m, 0.34H), 4.26-3.60 (m, 6H), 3.56-3.29 (m, 5H), 3.12-2.76 (m, 4H), 2.25-1.80 (m, 7H), 1.53-1.42 (m, 3H), 1.40-1.26 (m, 3H), 1.23-1.04 (m, 6H). MS (ESI+) 489 ($M^+$+1, 100%).

Example 1

1-(Isobutyryloxy)ethyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate

[Chemical formula 234]

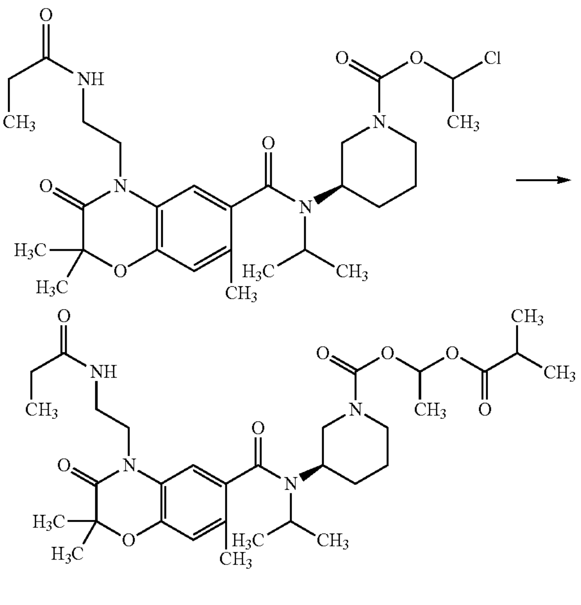

To a solution of the compound of Reference Example 29 (4 g) in chloroform (35 ml) were added propionic acid (2 mL)

and silver carbonate (2.93 g), and the mixture was stirred at room temperature for 2 hours. The reaction solution was filtered on celite, and the filtrate was concentrated under reduced pressure. The obtained residue was purified by silica gel column chromatography (hexane/ethyl acetate=20/80) to give the title compound (2.5 g).

1H NMR (300 MHz, $d_6$-DMSO) δ 8.01-7.94 (m, 1H), 7.33-7.10 (m, 1H), 6.86-6.84 (m, 1H), 6.67-6.65 (m, 1H), 3.85-3.62 (m, 3H), 3.34-3.01 (m, 3H), 2.78-2.70 (m, 2H), 2.16-2.14 (m, 3H), 2.04-1.98 (m, 2H), 1.50-1.35 (m, 13H), 1.13-0.81 (m, 18H).

MS (ESI+) 617 (M+1, 37%).

Example 2

(5-Methyl-2-oxo-1,3-dioxol-4-yl)methyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate

[Chemical formula 235]

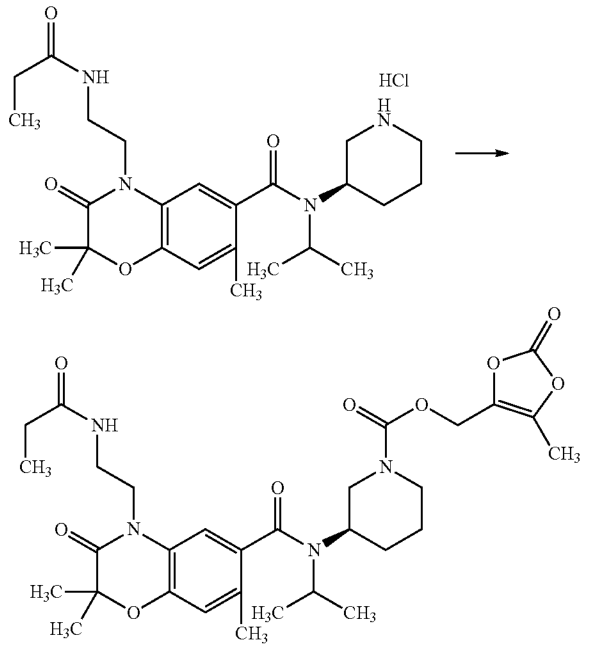

To a solution of N-isopropyl-2,2,7-trimethyl-3-oxo-N-[(3R)-piperidin-3-yl]-4-[2-(propionylamino)ethyl]-3,4-dihydro-2H-1,4-benzoxazine-6-carboxamide hydrochloride (24 g) in tetrahydrofuran (250 ml) were added triethylamine (8 ml), dimethylaminopyridine (1.2 g) and the compound of Reference Example 11 (15.9 g), and the mixture was stirred at 25° C. for 2 hours. Water was added to the mixture, and extracted with ethyl acetate. The organic layer was washed with a saturated aqueous sodium chloride solution, dried over sodium sulfate, filtered and concentrated under reduced pressure. The obtained residue was purified by silica gel column chromatography (chloroform/methanol=20/1) to give the title compound (9.5 g).

1H NMR (300 MHz, $d_6$-DMSO) δ 8.03-7.94 (m, 1H), 7.23-7.08 (m, 1H), 6.88-6.86 (m, 1H), 5.02-4.82 (m, 2H), 3.96-3.83 (m, 4H), 3.26-3.12 (m, 3H), 2.78-2.73 (m, 2H), 2.17-1.98 (m, 7H), 2.04-1.98 (m, 2H), 1.50-1.33 (m, 10H), 1.11-0.98 (m, 11H).

MS (ESI+) 615 (M+1, 54%).

Examples 3 to 20

According to the methods disclosed in the corresponding Reference Example and Example 1, the compounds of Examples 3, 4, 6, 18, 19 and 20 were synthesized. Using N-isopropyl-2,2,7-trimethyl-3-oxo-N-[(3R)-piperidin-3-yl]-4-[2-(propionylamino)ethyl]-3,4-dihydro-2H-1,4-benzoxazine-6-carboxamide hydrochloride, the compound of Example 7 was synthesized according to the method disclosed in the corresponding Reference Example and Example 2. Further, according to the method disclosed in the corresponding Reference Example and Example 5, the compounds of Examples 8, 9, 10, 11, 12, 13, 14, 15, 16 and 17 were synthesized.

TABLE 1

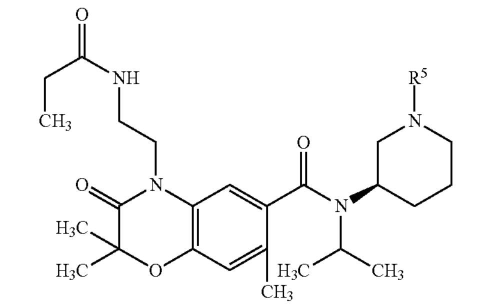

| Ex. No. | $R^5$ |
|---|---|
| 3 | 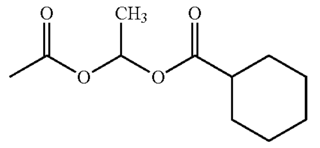 |
| 4 | 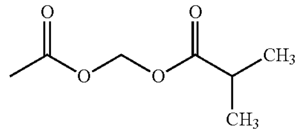 |
| 5 | 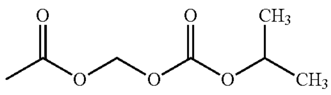 |
| 6 | 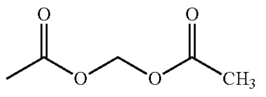 |
| 7 | 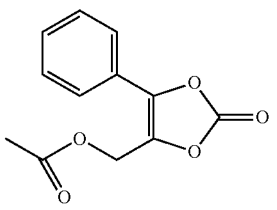 |
| 8 | 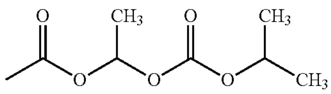 |

TABLE 1-continued
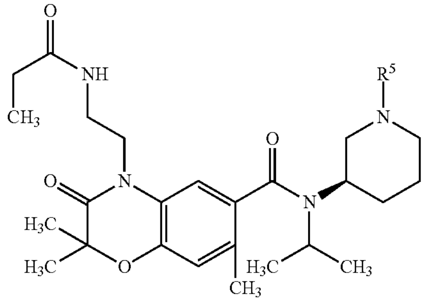
| Ex. No. | $R^5$ |
|---|---|
| 9 | 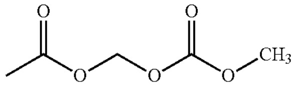 |
| 10 | 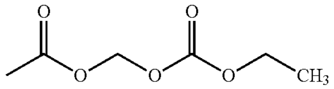 |
| 11 | 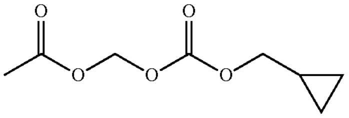 |
| 12 | 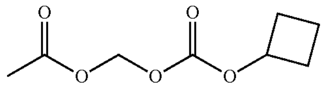 |
| 13 | 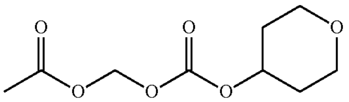 |
| 14 | 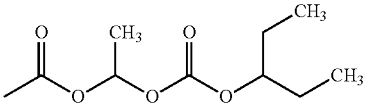 |
| 15 | 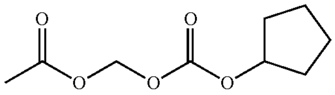 |
| 16 | 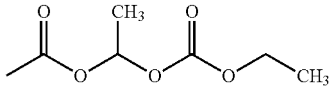 |
| 17 | 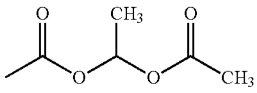 |
| 18 | 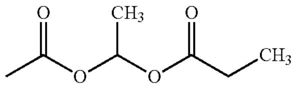 |
| 19 | 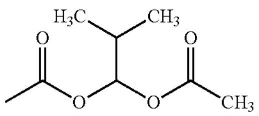 |
TABLE 1-continued
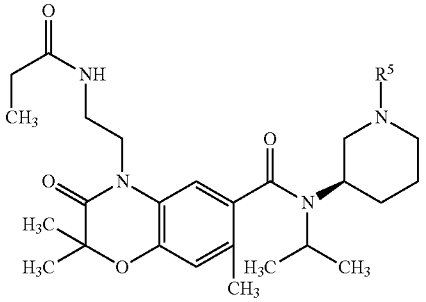
| Ex. No. | $R^5$ |
|---|---|
| 20 | 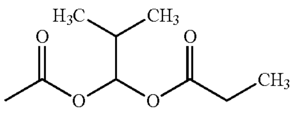 |
TABLE 2
| Ex. | Analytical Data |
|---|---|
| 3 | 1H NMR (300 MHz, $d_6$-DMSO) δ7.00-6.82 (m, 3H), 6.11-5.87 (m, 1H), 4.30-3.85 (m, 5H), 3.85-3.66 (m, 1H), 3.67-3.36 (m, 2H), 3.18-2.68 (m, 2H), 2.41-2.10 (m, 6H), 2.00-0.98 (m, 32H). MS (ESI+) 657 (M + 1, 8%). |
| 4 | 1H NMR (300 MHz, $d_6$-DMSO) δ8.00-7.95 (m, 1H), 7.36-7.07 (m, 1H), 6.88-6.82 (m, 1H), 5.72-5.51 (m, 2H), 3.97-3.62 (m, 3H), 3.41-3.10 (m, 3H), 2.73-2.50 (m, 5H), 2.12-1.91 (m, 5H), 1.50-1.35 (m, 9H), 1.17-0.93 (m, 16H). MS (ESI+) 603 (M + 1, 35%). |
Example 5
[(Isopropoxycarbonyl)oxy]methyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate
[Chemical formula 236]
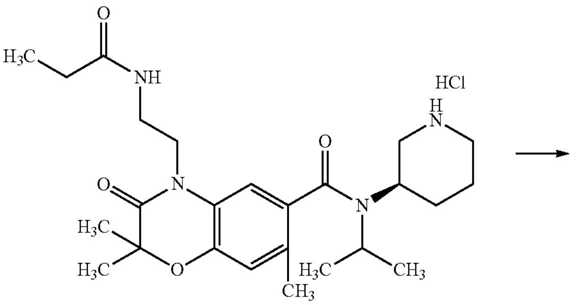

-continued

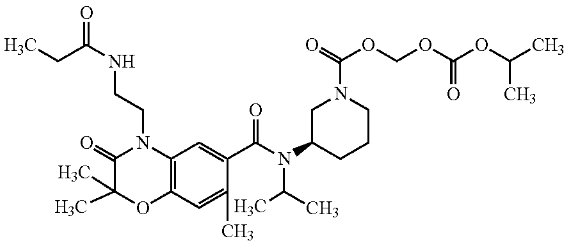

N-Isopropyl-2,2,7-trimethyl-3-oxo-N-[(3R)-piperidin-3-yl]-4-[2-(propionylamino)-ethyl]-3,4-dihydro-2H-1,4-benzoxazine-6-carboxamide hydrochloride (540 mg) was dissolved in chloroform (10 mL), and thereto was added a saturated aqueous sodium hydrogen carbonate solution (7.5 mL), and the mixture was stirred at room temperature for 30 minutes. The reaction mixture was extracted three times with chloroform (7.5 mL). The organic layer was dried over sodium sulfate, filtered and concentrated under reduced pressure to give a free amine compound. Then, the obtained amine compound was dissolved in DMF (10 ml), and thereto was added cesium carbonate (1.07 g). The reaction solution was stirred at room temperature for one hour while the reaction solution was subjected to bubbling with $CO_2$ gas. Further, to the mixture was added the compound of Reference Example 18 (266 mg), and the mixture was stirred for 30 minutes while the mixture was subjected to bubbling with $CO_2$ gas. Then, the bubbling was quenched, and further the mixture was stirred at room temperature for 90 minutes. After the reaction was completed, water was added to the reaction solution, and extracted with ethyl acetate. The ethyl acetate solution was washed with water and aqueous sodium chloride solution, dried over magnesium sulfate, filtered and concentrated. The obtained residue was purified by column chromatography (hexane:ethyl acetate=1:2) to give the title compound (430 mg) as white amorphous.

1H NMR (300 MHz, $d_6$-DMSO) δ 8.03-7.94 (m, 1H), 5.71-5.51 (m, 2H), 4.85-4.73 (m, 1H), 4.02-3.86 (m, 4H), 3.66-3.63 (m, 1H), 3.34-3.11 (m, 4H), 2.82-2.71 (m, 1H), 2.16-2.14 (m, 3H), 2.07-2.00 (m, 2H), 1.54-0.93 (m, 25H).

MS (ESI+) 619 (M+1, 31%).

TABLE 3

| Ex. | Analytical Data |
|---|---|
| 6 | 1H NMR (300 MHz, $d_6$-DMSO) δ8.01-7.96 (m, 1H), 7.34-7.08 (m, 1H), 6.88-6.85 (m, 1H), 5.71-5.53 (m, 2H), 4.07-3.86 (m, 4H), 3.68-3.60 (m, 1H), 3.34-3.12 (m, 3H), 2.78-2.70 (m, 1H), 2.14-1.99 (m, 8H), 1.78-1.66 (m, 2H), 1.51-1.33 (m, 8H), 1.11-0.93 (m, 10H). MS (ESI+) 575 (M + 1, 29%). |
| 7 | 1H NMR (300 MHz, $d_6$-DMSO) δ8.01-7.93 (m, 1H), 7.69-7.52 (m, 5H), 7.26-7.03 (m, 1H), 6.87-6.86 (m, 1H), 5.28-5.07 (m, 2H), 3.98-3.63 (m, 5H), 3.23-3.15 (m, 3H), 2.78-2.71 (m, 2H), 2.14-2.00 (m, 5H), 1.88-1.66 (m, 2H), 1.50-1.31 (m, 8H), 1.05-0.94 (m, 9H). MS (ESI+) 677 (M + 1, 27%). |
| 8 | 1H NMR (300 MHz, $d_6$-DMSO) δ8.02-7.98 (m, 1H), 7.27-7.10 (m, 1H), 6.88-6.84 (m, 1H), 6.58-6.55 (m, 1H), 4.78-4.75 (m, 1H), 3.98-3.63 (m, 3H), 3.34-3.01 (m, 3H), 2.79-2.75 (m, 2H), 2.16-2.14 (m, 3H), 2.07-1.99 (m, 2H), 1.44-0.93 (m, 30H). MS (ESI+) 633 (M + 1, 25%). |
| 9 | 1H NMR (300 MHz, $d_6$-DMSO) δ8.00-7.94 (m, 1H), 7.33-7.07 (m, 1H), 6.87-6.82 (m, 1H), 5.74-5.51 (m, 2H), 4.00-3.60 (m, 6H), 3.34-3.12 (m, 4H), 2.81-2.67 (m, 2H), 2.14-2.11 (m, 3H), 2.04-1.98 (m, 2H), 1.63-1.18 (m, 10H), 1.09-0.87 (m, 10H). MS (ESI+) 591 (M + 1, 18%). |

TABLE 3-continued

| Ex. | Analytical Data |
|---|---|
| 10 | 1H NMR (300 MHz, $d_6$-DMSO) δ7.99-7.93 (m, 1H), 7.34-7.06 (m, 1H), 6.87-6.80 (m, 1H), 5.73-5.50 (m, 2H), 4.18-3.63 (m, 6H), 3.31-2.68 (m, 5H), 2.13-2.11 (m, 3H), 2.05-1.98 (m, 2H), 1.55-1.34 (m, 10H), 1.22-0.91 (m, 13H). MS (ESI+) 605 (M + 1, 22%). |
| 11 | 1H NMR (300 MHz, $d_6$-DMSO) δ7.71-7.65 (m, 1H), 7.05-6.78 (m, 1H), 6.58-6.55 (m, 1H), 5.43-5.30 (m, 2H), 3.70-3.32 (m, 7H), 3.04-2.84 (m, 2H), 2.57-2.44 (m, 2H), 1.84-1.70 (m, 5H), 1.48-1.44 (m, 2H), 1.21-1.05 (m, 9H), 0.84-0.63 (m, 9H), 0.25-0.23 (m, 2H), 0.02-0.00 (m, 2H). MS (ESI+) 631 (M + 1, 17%). |
| 12 | 1H NMR (300 MHz, $d_6$-DMSO) δ7.50-7.44 (m, 1H), 6.73-6.57 (m, 1H), 6.36-6.34 (m, 1H), 5.20-4.99 (m, 2H), 4.42-4.29 (m, 1H), 3.47-3.11 (m, 3H), 2.88-2.59 (m, 4H), 2.34-2.18 (m, 1H), 1.78-1.74 (m, 2H), 1.64-1.48 (m, 8H), 1.04-0.84 (m, 11H), 0.72-0.42 (m, 11H). MS (ESI+) 631 (M + 1, 31%). |
| 13 | 1H NMR (300 MHz, $d_6$-DMSO) δ8.00-7.95 (m, 1H), 7.35-7.08 (m, 1H), 6.88-6.86 (m, 1H), 5.74-5.57 (m, 2H), 4.79-4.75 (m, 1H), 4.04-3.62 (m, 7H), 3.34-2.73 (m, 5H), 2.13-1.24 (m, 19H), 1.18-0.86 (m, 11H). MS (ESI+) 661 (M + 1, 32%). |

TABLE 4

| | |
|---|---|
| 14 | 1H NMR (300 MHz, $d_6$-DMSO) δ7.50-7.43 (m, 1H), 6.85-6.58 (m, 1H), 6.37-6.32 (m, 1H), 5.25-5.01 (m, 2H), 4.09-4.02 (m, 1H), 3.52-3.12 (m, 5H), 2.81-2.63 (m, 3H), 2.31-2.19 (m, 2H), 1.67-1.49 (m, 5H), 1.23-0.83 (m, 14H), 0.59-0.31 (m, 15H). MS (ESI+) 647 (M + 1, 100%). |
| 15 | 1H NMR (300 MHz, $d_6$-DMSO) δ7.98-7.94 (m, 1H), 7.22-7.09 (m, 1H), 6.86-6.84 (m, 1H), 5.69-5.54 (m, 2H), 5.02-4.99 (m, 1H), 3.93-3.59 (m, 5H), 3.34-3.10 (m, 3H), 2.76-2.68 (m, 2H), 2.13-2.11 (m, 3H), 2.04-1.98 (m, 2H), 1.79-1.22 (m, 17H), 1.13-0.91 (m, 10H). MS (ESI+) 645 (M + 1, 43%). |
| 16 | 1H NMR (300 MHz, $d_6$-DMSO) δ8.01-7.97 (m, 1H), 7.25-7.12 (m, 1H), 6.88-6.86 (m, 1H), 6.58-6.44 (m, 1H), 4.13-3.64 (m, 7H), 3.30-3.00 (m, 3H), 2.76-2.70 (m, 2H), 2.15-1.99 (m, 5H), 1.44-1.36 (m, 12H), 1.21-0.96 (m, 13H). MS (ESI+) 619 (M + 1, 40%). |
| 17 | 1H NMR (300 MHz, $d_6$-DMSO) δ8.04-7.99 (m, 1H), 7.25-7.12 (m, 1H), 6.88-6.86 (m, 1H), 6.67-6.55 (m, 1H), 3.95-3.66 (m, 5H), 3.34-2.99 (m, 3H), 2.79-2.66 (m, 2H), 2.16-2.14 (m, 3H), 2.05-2.02 (m, 2H), 1.89-1.65 (m, 2H), 1.51-1.35 (m, 11H), 1.15-0.92 (m, 10H). MS (ESI+) 589 (M + 1, 23%). |
| 18 | 1H NMR (300 MHz, $d_6$-DMSO) δ8.06-8.01 (m, 1H), 7.28-7.10 (m, 1H), 6.88-6.86 (m, 1H), 6.70-6.56 (m, 1H), 3.89-3.60 (m, 5H), 3.34-2.99 (m, 3H), 2.82-2.68 (m, 2H), 2.36-2.30 (m, 2H), 2.20-2.14 (m, 3H), 2.08-2.00 (m, 2H), 1.88-1.68 (m, 2H), 1.48-1.36 (m, 11H), 1.12-0.94 (m, 12H). MS (ESI+) 603 (M + 1, 19%). |
| 19 | 1H NMR (300 MHz, $d_6$-DMSO) δ8.01-7.97 (m, 1H), 7.22-7.11 (m, 1H), 6.88-6.83 (m, 1H), 6.55-6.25 (m, 1H), 3.96-3.64 (m, 5H), 3.33-3.01 (m, 3H), 2.79-2.71 (m, 2H), 2.15-1.99 (m, 9H), 1.86-1.68 (m, 2H), 1.55-1.37 (m, 8H), 1.11-0.78 (m, 15H). MS (ESI+) 617 (M + 1, 16%). |
| 20 | 1H NMR (300 MHz, $d_6$-DMSO) δ8.01-7.98 (m, 1H), 7.23-7.13 (m, 1H), 6.88-6.83 (m, 1H), 6.53-6.28 (m, 1H), 3.94-3.64 (m, 5H), 3.34-2.96 (m, 3H), 2.81-2.66 (m, 2H), 2.34-2.32 (m, 2H), 2.15-2.13 (m, 3H), 2.05-1.98 (m, 2H), 1.73-1.65 (m, 2H), 1.51-1.36 (m, 8H), 1.10-0.82 (m, 18H). MS (ESI+) 631 (M + 1, 17%). |

Example 21

1-(Acetyloxy)-1-methylethyl (3R)-3-[isopropyl({2,2,7-trimethyl-3-oxo-4-[2-(propionylamino)ethyl]-3,4-dihydro-2H-1,4-benzoxazin-6-yl}carbonyl)amino] piperidine-1-carboxylate

[Chemical formula 237]

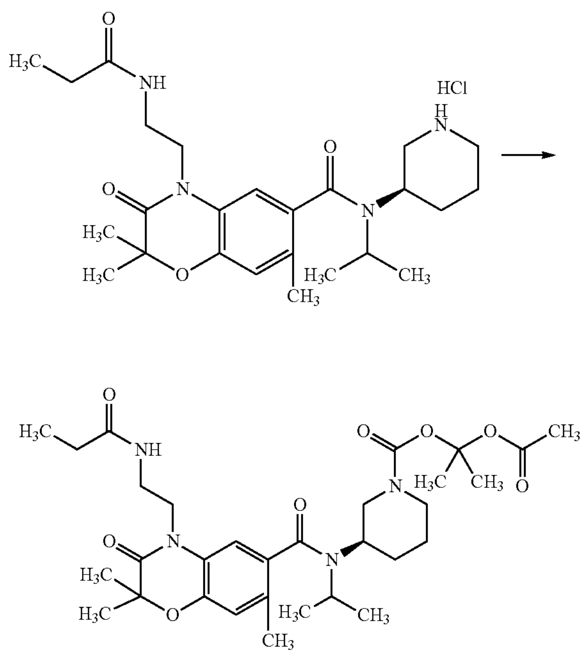

N-Isopropyl-2,2,7-trimethyl-3-oxo-N-[(3R)-piperidin-3-yl]-4-[2-(propionylamino)-ethyl]-3,4-dihydro-2H-1,4-benzoxazine-6-carboxamide hydrochloride (2.7 g) was dissolved in chloroform (10 mL), and thereto was added a saturated aqueous sodium hydrogen carbonate solution (7.5 mL), and the mixture was stirred at room temperature for 30 minutes. The reaction mixture was extracted three times with chloroform (7.5 mL). The organic layer was dried over sodium sulfate, filtered, and concentrated under reduced pressure to give a free amine compound. Then, the obtained amine compound was dissolved in DMF (35 ml), and thereto was added the compound of Reference Example 14 (1.58 g), and the mixture was stirred at room temperature overnight. After the reaction was completed, to the mixture was added ethyl acetate, and washed with water and a saturated aqueous sodium chloride solution. The obtained organic layer was dried over magnesium sulfate, and concentrated under reduced pressure. The obtained residue was purified by silica gel column chromatography (hexane/ethyl acetate=1/2) to give the title compound (1.21 g).

1H NMR (300 MHz, $d_6$-DMSO) δ 8.02-7.99 (m, 1H), 7.32-7.12 (m, 1H), 6.88-6.86 (m, 1H), 4.67-4.56 (m, 2H), 4.07-3.56 (m, 5H), 3.22-3.11 (m, 4H), 2.75-2.53 (m, 2H), 2.18-2.14 (m, 3H), 2.04-1.63 (m, 8H), 1.52-1.36 (m, 9H), 1.16-0.93 (m, 10H).

MS (ESI+) 603 (M+1, 2%).

Example 22

N-Isopropyl-2,2-dimethyl-3-oxo-4-[2-(propionylamino)ethyl]-7-(trifluoromethyl)-N-[(3R)-1-L-valylpiperidin-3-yl]-3,4-dihydro-2H-1,4-benzoxazine-6-carboxamide hydrochloride

[Chemical formula 238]

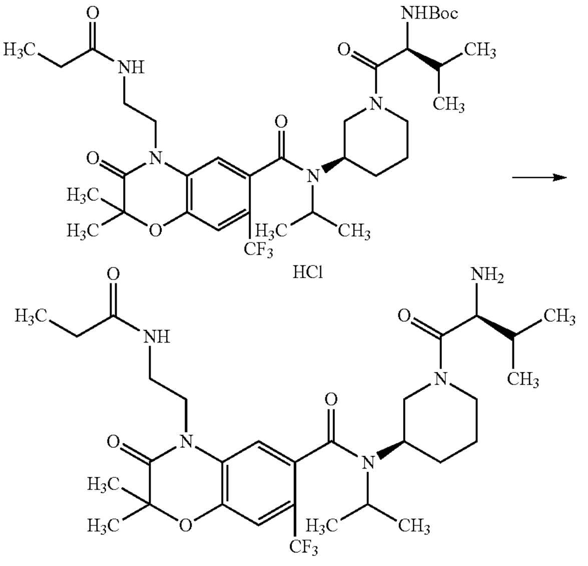

To the compound of Reference Example 26 (200 mg) was added a 4N hydrochloric acid in ethyl acetate solution (10 ml), and the mixture was stirred at room temperature for 15 minutes. After the reaction was completed, the solvent was concentrated, and to the obtained residue was added diisopropyl ether. The precipitated solid was collected by filtration, and dried to give the desired title compound (160 mg) as white amorphous.

1H NMR (300 MHz, $d_6$-DMSO) δ 8.17-8.01 (m, 4H), 7.53-7.32 (m, 2H), 4.60-3.55 (m, 4H), 2.74-2.71 (m, 1H), 2.06-1.90 (m, 6H), 1.75-1.68 (m, 2H), 1.52-1.35 (m, 9H), 1.18-0.82 (m, 16H)

MS (ESI+) 611 (M+1, 100%)

Examples 23 to 29

According to the method disclosed in Reference Example and Example 22, the compound of Example 23 was synthesized. According to the method disclosed in the corresponding Reference Example and Example 24, the compound of Example 25 was synthesized. According to the method disclosed in the corresponding Reference Example Example 1, the compound of Example 26 was synthesized. Using N-isopropyl-2,2-dimethyl-3-oxo-N-[(3R)-piperidin-3-yl]-4-[2-(propionylamino)ethyl]-7-(trifluoromethyl)-3,4-dihydro-2H-1,4-benzoxazine-6-carboxamide hydrochloride, the compound of Example 27 was synthesized according to the method disclosed in the corresponding Reference Example and Example 2. According to the method disclosed in the corresponding Reference Example and Example 5, the compounds of Examples 28 and 29 were synthesized.

TABLE 5

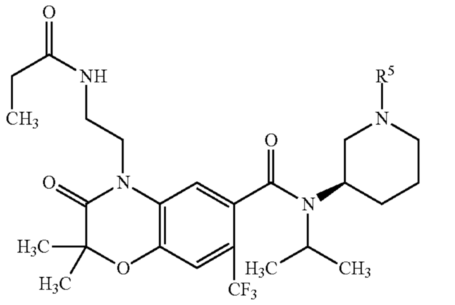

| Ex. No. | $R^5$ |
|---|---|
| 23 | 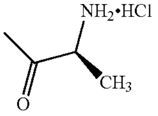 |
| 24 | 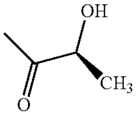 |
| 25 | 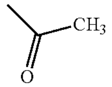 |
| 26 | 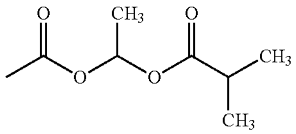 |
| 27 | 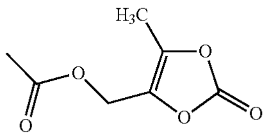 |
| 28 | 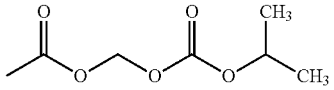 |
| 29 | 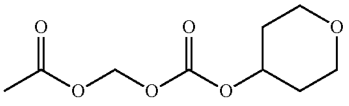 |

TABLE 6

| Ex. | Analytical Data |
|---|---|
| 23 | 1H NMR (300 MHz, $d_6$-DMSO) δ 8.40-8.02 (m, 2H), 7.56-7.30 (m, 2H), 4.37-3.85 (m, 3H), 3.71-3.57 (m, 4H), 3.34-2.71 (m, 4H), 2.06-1.97 (m, 4H), 1.77-1.67 (m, 3H), 1.57-1.30 (m, 7H), 1.22-0.91 (m, 10H). MS (ESI+) 584 (M + 1, 100%). |

Example 24

(1R)-1-Hydroxy-2-methylpropyl (3R)-3-[{[2,2-dimethyl-3-oxo-4-[2-(propionylamino)ethyl]-7-(trifluoromethyl)-3,4-dihydro-2H-1,4-benzoxazin-6-yl]carbonyl}(isopropyl)amino]piperidine-1-carboxylate

[Chemical formula 239]

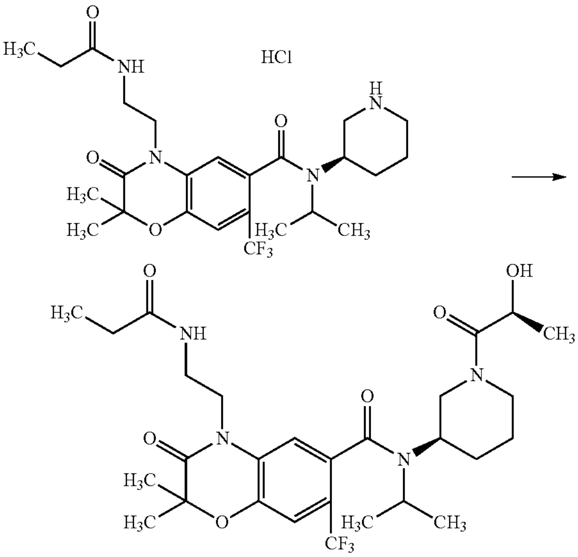

To N-isopropyl-2,2-dimethyl-3-oxo-N-[(3R)-piperidin-3-yl]-4-[2-(propionylamino)-ethyl]-7-trifluoromethyl)-3,4-dihydro-2H-1,4-benzoxazine-6-carboxamide hydrochloride (100 mg) were added 2-hydroxypropionic acid (0.08 ml), WSC (70 mg), HOBt (50 mg), triethylamine (0.10 ml) and chloroform (4 ml), and the mixture was stirred at room temperature overnight. After the reaction was completed, the solvent was concentrated, and the obtained residue was purified by column chromatography (chloroform:methanol=95:5) to give the title compound (80 mg) as white amorphous. 1H NMR (300 MHz, $d_6$-DMSO) δ 8.13-7.96 (m, 1H), 7.49-7.27 (m, 2H), 4.53-3.85 (m, 3H), 3.70-3.45 (m, 2H), 3.25-3.18 (m, 2H), 3.03-2.68 (m, 2H), 2.08-1.89 (m, 2H), 1.53-1.40 (m, 10H), 1.26-0.83 (m, 14H)

MS (ESI+) 585 (M+1, 100%)

TABLE 7

| Ex. | Analytical Data |
|---|---|
| 25 | 1H NMR (300 MHz, $d_6$-DMSO) δ7.42-7.27 (m, 2H), 4.55-4.28 (m, 1H), 3.98-3.90 (m, 3H), 3.59-3.53 (m, 1H), 3.27-3.21 (m, 2H), 3.05-2.87 (m, 1H), 2.06-1.74 (m, 7H), 1.55-1.37 (m, 9H), 1.18-0.90 (m, 10H). MS (ESI+) 555 (M + 1, 100%). |
| 26 | 1H NMR (300 MHz, $d_6$-DMSO) δ8.15-7.97 (m, 1H), 7.75-7.27 (m, 2H), 6.69-6.46 (m, 1H), 3.92-3.61 (m, 3H), 3.34-2.98 (m, 3H), 2.75-2.69 (m, 2H), 2.08-2.00 (m, 2H), 1.77-1.33 (m, 13H), 1.18-0.81 (m, 18H). MS (ESI+) 671 (M + 1, 32%). |
| 27 | 1H NMR (300 MHz, $d_6$-DMSO) δ8.05-7.98 (m, 1H), 7.77-7.30 (m, 2H), 4.49-4.76 (m, 2H), 3.98-3.47 (m, 4H), 3.33-2.98 (m, 3H), 2.81-2.72 (m, 2H), 2.15-2.00 (m, 5H), 1.69-1.36 (m, 10H), 1.22-0.93 (m, 10H). MS (ESI+) 678 (M + 1, 46%). |
| 28 | 1H NMR (300 MHz, $d_6$-DMSO) δ8.05-7.97 (m, 1H), 7.73-7.29 (m, 2H), 5.73-5.46 (m, 2H), 4.81-4.72 (m, 1H), 4.17-3.57 (m, 5H), 3.31-2.65 (m, 5H), 2.06-1.96 (m, 2H), 1.76-0.92 (m, 25H). MS (ESI+) 673 (M + 1, 64%). |
| 29 | 1H NMR (300 MHz, $d_6$-DMSO) δ8.05-7.99 (m, 1H), 7.75-7.29 (m, 2H), 5.77-5.49 (m, 2H), 4.79-4.76 (m, 1H), 3.97-3.44 (m, 6H), |

TABLE 7-continued

| Ex. | Analytical Data |
|---|---|
| | 3.34-2.99 (m, 3H), 2.83-2.51 (m, 2H), 2.05-1.73 (m, 4H), 1.56-1.42 (m, 13H), 1.15-0.93 (m, 11H). MS (ESI+) 715 (M + 1, 68%). |

Example 30

(5-Methyl-2-oxo-1,3-dioxol-4-yl)methyl (3R)-3-[{[2,2-dimethyl-3-oxo-4-[2-(propionylamino)-ethyl]-7-(trifluoromethyl)-3,4-dihydro-2H-1,4-benzothiazin-6-yl]carbonyl}(isopropyl)amino]-piperidine-1-carboxylate

[Chemical formula 240]

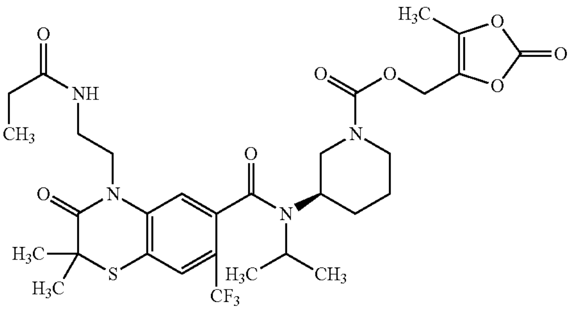

Using N-isopropyl-2,2-dimethyl-3-oxo-N-[(3R)-piperidin-3-yl]-4-[2-(propionylamino)-ethyl]-7-(trifluoromethyl)-3,4-dihydro-2H-1,4-benzothiazine-6-carboxamide hydrochloride, the title compound was synthesized according to the method disclosed in Example 2.

1H NMR (300 MHz, $d_6$-DMSO) δ 8.15-8.13 (m, 1H), 7.83-7.61 (m, 2H), 5.01-4.77 (m, 2H), 4.04-3.58 (m, 4H), 3.30-3.15 (m, 3H), 2.75-2.70 (m, 2H), 2.16-2.03 (m, 5H), 1.75-1.30 (m, 10H), 1.14-0.94 (m, 10H).

MS (ESI+) 685 (M+1, 54%).

Example 31

N-Isopropyl-2,2-dimethyl-N-{(3R)-1-[(5-methyl-2-oxo-1,3-dioxol-4-yl)methyl]piperidin-3-yl}-3-oxo-4-[2-(propionylamino)ethyl]-7-(trifluoromethyl)-3,4-dihydro-2H-1,4-benzoxazine-6-carboxamide

[Chemical formula 241]

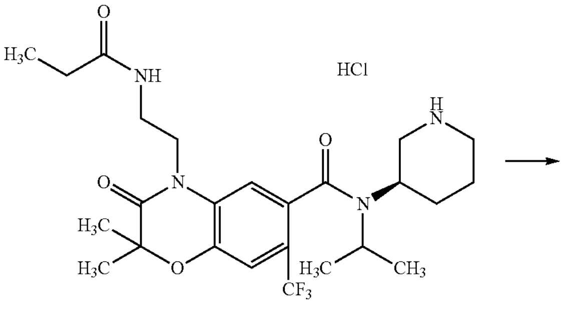

-continued

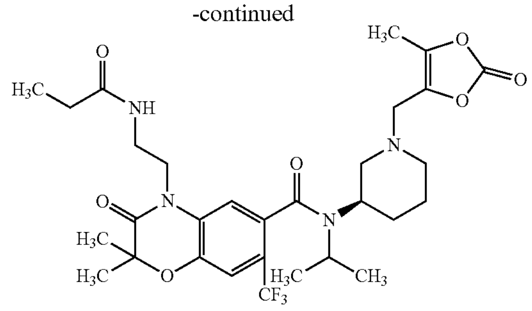

To N-isopropyl-2,2-dimethyl-3-oxo-N-[(3R)-piperidin-3-yl]-4-[2-(propionylamino)-ethyl]-7-(trifluoromethyl)-3,4-dihydro-2H-1,4-benzoxazine-6-carboxamide hydrochloride (1.0 g) were added the compound of Reference Example 8 (344 mg), potassium carbonate (45 mg) and DMF (30 ml), and the mixture was stirred at room temperature overnight. After the reaction was completed, water was added to the reaction solution, and the mixture was extracted with ethyl acetate. The ethyl acetate solution was washed with water and aqueous sodium chloride solution, dried over magnesium sulfate, filtered and concentrated. The obtained residue was purified by column chromatography (hexane:ethyl acetate=1:2) to give the title compound (300 mg) as white amorphous.

1H NMR (300 MHz, $d_6$-DMSO) δ 8.14-8.10 (m, 1H), 7.52-7.31 (m, 2H), 4.43-4.32 (m, 2H), 4.10-3.80 (m, 4H), 3.71-3.23 (m, 5H), 2.25-2.22 (m, 3H), 2.10-1.94 (m, 4H), 1.54-1.42 (m, 9H), 1.23-1.87 (m, 9H).

MS (ESI+) 625 (M+1, 91%).

Example 32

(2-Oxo-5-phenyl-1,3-dioxol-4-yl)methyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate

[Chemical formula 242]

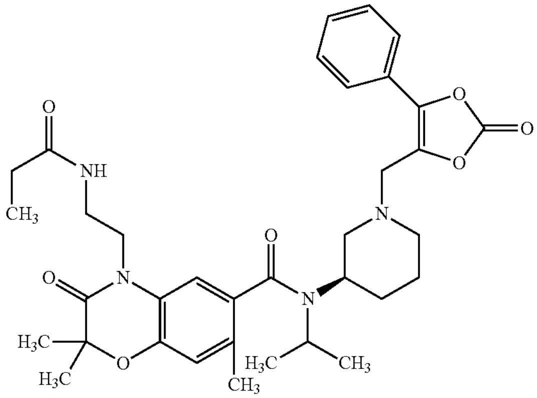

Using N-isopropyl-2,2,7-trimethyl-3-oxo-N-[(3R)-piperidin-3-yl]-4-[2-(propionylamino)ethyl]-3,4-dihydro-2H-1,4-benzoxazine-6-carboxamide hydrochloride, the title compound was synthesized according to the method disclosed in the corresponding Reference Example and Example 31.

1H NMR (300 MHz, $d_6$-DMSO) δ8.09-8.03 (m, 1H), 7.79-7.75 (m, 1H), 7.56-7.53 (m, 3H), 7.17-7.11 (m, 1H), 6.87-

6.85 (m, 1H), 3.87-2.51 (m, 13H), 2.14-1.82 (m, 8H), 1.45-1.35 (m, 6H), 1.23-1.01 (m, 9H).

MS (ESI+) 633 (M+1, 87%).

Examples 33 to 36

The compounds of Examples 33, 35 and 36 were synthesized according to the method disclosed in the corresponding Reference Example and Example 1. The compound of Example 34 was synthesized according to the method disclosed in the corresponding Reference Example and Example 5.

TABLE 8

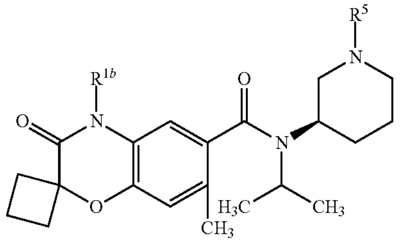

| Ex. No. | $R^{1b}$ | $R^5$ |
|---|---|---|
| 33 | $CH_3CH_2C(O)NH(CH_2)_2$ | 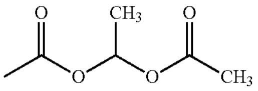 |
| 34 | $CH_3CH_2C(O)NH(CH_2)_2$ | 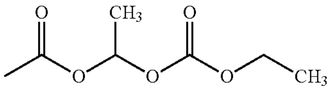 |
| 35 | $CH_3CH_2C(O)NH(CH_2)_2$ | 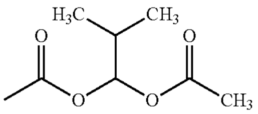 |
| 36 | $CH_3CH_2C(O)NH(CH_2)_2$ | 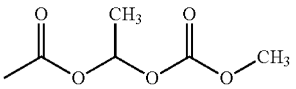 |

TABLE 9

| Ex. | Analytical Data |
|---|---|
| 33 | 1H NMR (300 MHz, $d_6$-DMSO) δ8.04-8.01 (m, 1H), 7.20-7.09 (m, 1H), 6.96-6.94 (m, 1H), 6.72-6.55 (m, 1H), 3.96-3.61 (m, 3H), 3.34-3.16 (m, 3H), 2.82-2.58 (m, 2H), 2.38-1.30 (m, 17H), 1.12-0.93 (m, 13H). MS (ESI+) 601 (M + 1, 8%). |
| 34 | 1H NMR (300 MHz, $d_6$-DMSO) δ8.03-7.98 (m, 1H), 7.23-7.04 (m, 1H), 6.96-6.92 (m, 1H), 6.59-6.54 (m, 1H), 4.14-3.58 (m, 7H), 3.34-3.01 (m, 3H), 2.72-2.62 (m, 2H), 2.38-1.71 (m, 11H), 1.20-0.92 (m, 15H). MS (ESI+) 632 (M + 1, 7%). |
| 35 | 1H NMR (300 MHz, $d_6$-DMSO) δ8.08-8.04 (m, 1H), 7.30-7.19 (m, 1H), 6.98-6.89 (m, 1H), 6.60-6.51 (m, 1H), 4.06-4.57 (m, 3H), 3.34-3.16 (m, 3H), 2.72-2.53 (m, 2H), 2.18-1.40 (m, 18H), 1.11-0.73 (m, 17H). MS (ESI+) 629 (M + 1, 17%). |
| 36 | 1H NMR (300 MHz, $d_6$-DMSO) δ7.54-7.46 (m, 1H), 7.23-6.76 (m, 2H), 6.04-5.91 (m, 1H), 3.61-3.03 (m, 8H), 2.73-2.35 (m, 8H), 2.20-2.11 (m, 2H), 1.54-1.40 (m, 2H), 1.21-0.88 (m, 9H), 0.67-0.45 (m, 15H). MS (ESI+) 615 (M + 1, 17%). |

Examples 37 to 38

The compound of Example 37 was synthesized according to the method disclosed in the corresponding Reference Example and Example 1. The compound of Example 38 was synthesized according to the method disclosed in the corresponding Reference Example and Example 5.

TABLE 10

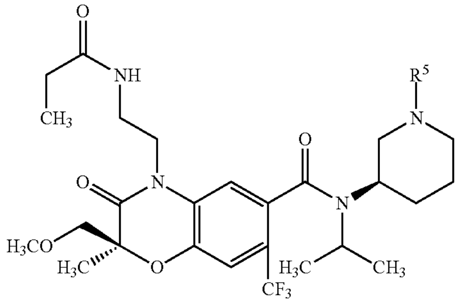

| Ex. No. | $R^5$ |
|---|---|
| 37 | 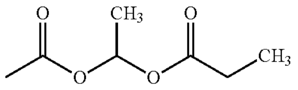 |
| 38 | 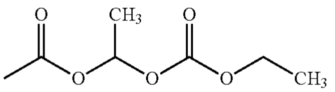 |

TABLE 11

| Ex. | Analytical Data |
|---|---|
| 37 | 1H NMR (300 MHz, $d_6$-DMSO) δ8.01-7.99 (m, 1H), 7.25-7.18 (m, 1H), 6.95-6.93 (m, 1H), 6.68-6.61 (m, 1H), 3.97-3.62 (m, 5H), 3.25-2.97 (m, 3H), 2.75-2.62 (m, 2H), 2.32-1.40 (m, 20H), 1.11-0.90 (m, 12H). MS (ESI+) 687 (M + 1, 19%). |
| 38 | 1H NMR (300 MHz, $d_6$-DMSO) δ8.06-7.98 (m, 1H), 7.62-7.27 (m, 2H), 6.70-6.55 (m, 1H), 4.13-3.54 (m, 8H), 3.34-2.97 (m, 6H), 2.75-2.68 (m, 2H), 2.33-2.30 (m, 2H), 2.09-2.01 (m, 3H), 1.76-1.38 (m, 11H), 1.13-0.95 (m, 12H). MS (ESI+) 703 (M + 1, 15%). |

Examples 39 to 43

Using 4-{2-[(difluoroacetyl)amino]ethyl}-N-isopropyl-7-methyl-3-oxo-N-[(3R)-piperidin-3-yl]-3,4-dihydrospiro[1,4-benzoxazine-2,1'-cyclopropane]-6-carboxamide hydrochloride and N-isopropyl-7-methyl-3-oxo-N-[(3R)-piperidin-3-yl]-4-[2-(propionylamino)ethyl]-3,4-dihydrospiro[1,4-benzoxazine-2,1'-cyclopropane]-6-carboxamide hydrochloride, the compounds of Examples 39 and 40 were synthesized according to the method disclosed in the corresponding Reference Example and Example 2, respectively. The compounds of Examples 41, 42, 43 were synthesized according to the method disclosed in Reference Example and Example 1.

TABLE 12

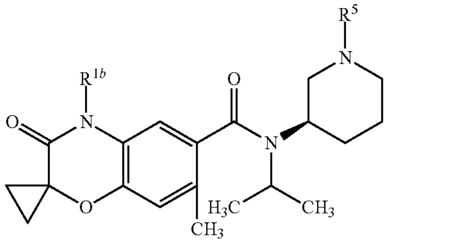

| Ex. No. | $R^{1b}$ | $R^5$ |
|---|---|---|
| 39 | $CHF_2C(O)NH(CH_2)_2$ | 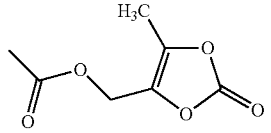 |
| 40 | $CH_3CH_2C(O)NH(CH_2)_2$ | 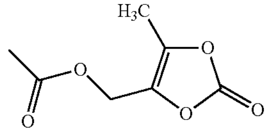 |
| 41 | $CH_3CH_2C(O)NH(CH_2)_2$ | 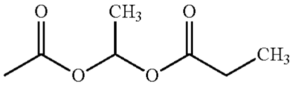 |
| 42 | $CH_3CH_2C(O)NH(CH_2)_2$ | 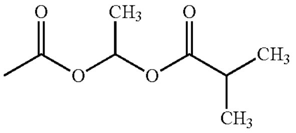 |
| 43 | $CH_3CH_2C(O)NH(CH_2)_2$ | 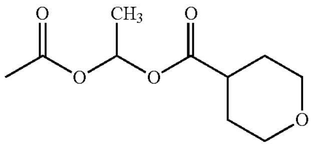 |

TABLE 13

| Ex. | Analytical Data |
|---|---|
| 39 | 1H NMR (400 MHz, $CDCl_3$) δ 7.09 (brs, 1H), 6.92-6.69 (m, 2H), 6.07-5.70 (m, 1H), 4.94-4.79 (m, 2H), 4.26-3.88 (m, 6H), 3.83-3.70 (m, 1H), 3.70-3.52 (m, 2H), 3.14-2.99 (m, 1H), 2.98-2.75 (m, 2H), 2.29-2.11 (m, 6H), 1.90-1.70 (m, 2H), 1.45-1.30 (m, 2H), 1.29-1.08 (m, 6H). MS (ESI+) 635 (M + 1, 47%). |
| 40 | 1H NMR (400 MHz, $CDCl_3$) δ7.02-6.85 (m, 1H), 6.78-6.69 (m, 1H), 6.11-5.58 (m, 1H), 4.90 (d, J = 13.8 Hz, 1H), 4.83 (d, J = 13.8 Hz, 1H), 4.21-3.86 (m, 6H), 3.86-3.70 (m, 1H), 3.68-3.43 (m, 2H), 3.15-3.00 (m, 1H), 3.00-2.74 (m, 2H), 2.33-2.11 (m, 8H), 1.92-1.70 (m, 2H), 1.46-1.30 (m, 2H), 1.28-1.06 (m, 11H). MS (ESI+) 613 (M + 1, 51%). |
| 41 | 1H NMR (400 MHz, $CDCl_3$) δ6.97-6.78 (m, 2H), 6.75-6.67 (m, 1H), 6.12-5.94 (m, 1H), 4.20-3.88 (m, 5H), 3.33-3.20 (m, 1H), 3.62-3.42 (m, 2H), 3.16-2.72 (m, 3H), 2.40-2.12 (m, 7H), 1.92-1.71 (m, 2H), 1.67-1.30 (m, 7H), 1.28-1.05 (m, 13H). MS (ESI+) 601 (M + 1, 4%). |
| 42 | 1H NMR (400 MHz, $CDCl_3$) δ6.98-6.78 (m, 2H), 6.75-6.67 (m, 1H), 6.12-5.95 (m, 1H), 4.21-3.88 (m, 5H), 3.84-3.70 (m, 1H), 3.63-3.43 (m, 2H), 3.18-2.74 (m, 3H), 2.51-2.46 (m, 1H), 2.29-2.11 (m, 6H), 1.92-1.31 (m, 9H), 1.28-1.04 (m, 15H). MS (ESI+) 615 (M + 1, 11%). |
| 43 | 1H NMR (400 MHz, $CDCl_3$) δ6.97-6.79 (m, 2H), 6.72 (brs, 1H), 6.14-5.95 (m, 1H), 4.21-3.87 (m, 5H), 3.32-3.20 (m, 1H), |

TABLE 13-continued

| Ex. | Analytical Data |
|---|---|
| | 3.62-3.34 (m, 5H), 3.16-2.72 (m, 3H), 2.62-2.47 (m, 1H), 2.27-2.12 (m, 6H), 1.92-1.70 (m, 8H), 1.56-1.32 (m, 5H), 1.29-1.07 (m, 10H). MS (ESI+) 657 (M + 1, 10%). |

Examples 44 to 50

According to the method disclosed in Example 2, the compound of Example 44 was synthesized using 4-{2-[(difluoroacetyl)amino]ethyl}-N-isopropyl-7-methyl-3-oxo-N-[(3R)-piperidin-3-yl]-3,4-dihydrospiro[1,4-benzoxazine-2,1'-cyclopropane]-6-carboxamide hydrochloride. The compounds of Examples 45, 46, 47, 48, 49 and 50 were synthesized according to the corresponding Reference Example and Example 1.

TABLE 14

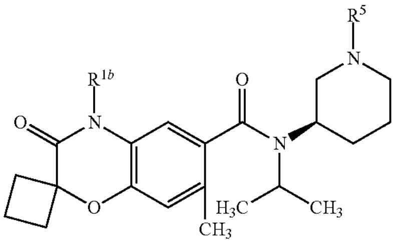

| Ex. No. | $R^{1b}$ | $R^5$ |
|---|---|---|
| 44 | $CHF_2C(O)NH(CH_2)_2$ | 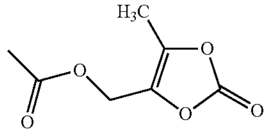 |
| 45 | $CH_3CH_2C(O)NH(CH_2)_2$ | 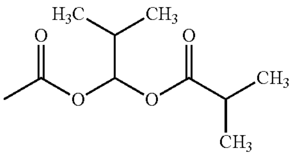 |
| 46 | $CH_3CH_2C(O)NH(CH_2)_2$ | 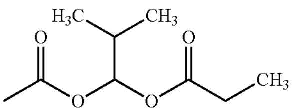 |
| 47 | $CH_3CH_2C(O)NH(CH_2)_2$ | 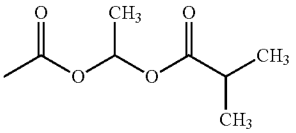 |
| 48 | $CH_3CH_2C(O)NH(CH_2)_2$ | 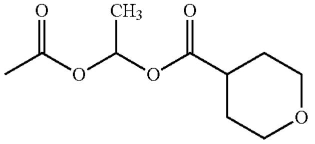 |

TABLE 14-continued

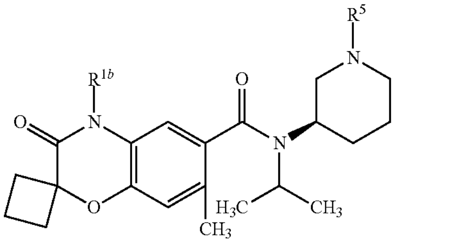

| Ex. No. | $R^{1b}$ | $R^5$ |
|---|---|---|
| 49 | $CH_3CH_2C(O)NH(CH_2)_2$ | 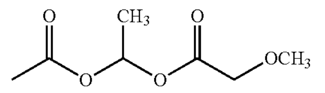 |
| 50 | $CH_3CH_2C(O)NH(CH_2)_2$ | 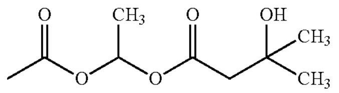 |

TABLE 15

| Ex. | Analytical Data |
|---|---|
| 44 | 1H NMR (400 MHz, $CDCl_3$) δ7.05 (s, 1H), 6.91-6.72 (m, 2H), 6.06-5.70 (m, 1H), 4.95-4.79 (m, 2H), 4.25-3.88 (m, 3H), 3.81-3.46 (m, 3H), 3.15-2.61 (m, 4H), 2.52-2.41 (m, 1H), 2.49-2.07 (m, 9H), 2.04-1.72 (m, 4H), 1.67-1.45 (m, 2H), 1.25-1.051 (m, 6H). MS (ESI+) 649 (M + 1, 48%). |
| 45 | 1H NMR (400 MHz, $CDCl_3$) δ6.90-6.78 (m, 2H), 6.71-6.54 (m, 1H), 6.10-5.94 (m, 1H), 4.24-3.88 (m, 8H), 3.82-3.68 (m, 1H), 3.62-3.40 (m, 4H), 3.18-2.77 (m, 5H), 2.73-2.50 (m, 4H), 2.39-2.11 (m, 14H), 2.11-1.70 (m, 8H), 1.26-0.84 (m, 14H). MS (ESI+) 657 (M + 1, 12%). |
| 46 | 1H NMR (400 MHz, $CDCl_3$) δ6.90-6.76 (m, 2H), 6.72-6.56 (m, 1H), 6.09-5.92 (m, 1H), 4.25-3.88 (m, 5H), 3.82-3.39 (m, 3H), 3.18-2.62 (m, 4H), 2.50-2.12 (m, 11H), 2.11-1.71 (m, 5H), 1.24-0.81 (m, 18H). MS (ESI+) 643 (M + 1, 6%). |
| 47 | 1H NMR (400 MHz, $CDCl_3$) δ6.92-6.78 (m, 3H), 6.09-5.94 (m, 1H), 4.21-3.88 (m, 5H), 3.82-3.40 (m, 3H), 3.16-2.75 (m, 3H), 2.73-2.39 (m, 3H), 2.38-2.11 (m, 8H), 2.03-1.71 (m, 4H), 1.68-1.44 (m, 5H), 1.24-1.07 (m, 13H). MS (ESI+) 629 (M + 1, 10%). |
| 48 | 1H NMR (400 MHz, $CDCl_3$) δ6.91-6.78 (m, 3H), 6.09-5.94 (m, 1H), 4.20-3.86 (m, 7H), 3.82-3.67 (m, 1H), 3.62-3.36 (m, 5H), 3.15-2.75 (m, 3H), 2.73-2.40 (m, 3H), 2.38-2.12 (m, 8H), 2.03-1.70 (m, 8H), 1.55-1.45 (m, 2H), 1.22-1.07 (m, 9H). MS (ESI+) 671 (M + 1, 11%). |
| 49 | 1H NMR (400 MHz, $CDCl_3$) δ6.98-6.79 (m, 2H), 6.08-5.93 (m, 1H), 4.21-3.88 (m, 8H), 3.82-3.69 (m, 1H), 3.62-3.49 (m, 6H), 3.16-2.64 (m, 4H), 2.49-2.12 (m, 8H), 2.03-1.71 (m, 4H), 1.62-1.45 (m, 2H), 1.22-1.06 (m, 9H). MS (ESI+) 631 (M + 1, 12%). |
| 50 | 1H NMR (400 MHz, $CDCl_3$) δ6.90-6.79 (m, 3H), 6.12-5.97 (m, 1H), 4.20-3.87 (m, 3H), 3.82-3.67 (m, 1H), 3.61-3.25 (m, 3H), 3.15-2.62 (m, 4H), 2.58-2.39 (m, 3H), 2.38-2.12 (m, 8H), 2.04-1.78 (m, 3H), 1.63-1.40 (m, 5H), 1.24-1.05 (m, 9H). MS (ESI+) 659 (M + 1, 22%). |

Examples 51 to 68

The compounds of Examples 51, 55, 57, 59, 60, 61, 64, 65 and 68 were synthesized according to the method disclosed in the corresponding Reference Example and Example 1. The compounds of Examples 66 and 67 were synthesized according to the method disclosed in Examples 52 and 53 using the compound of Example 1. According to the method disclosed in the corresponding Reference Example and Example 5, the compound of Example 54 was synthesized. According to the method disclosed in Example 56, the compounds of Examples 58 and 62 were synthesized using the compounds of Example 57 and Reference Example 36, respectively.

TABLE 16

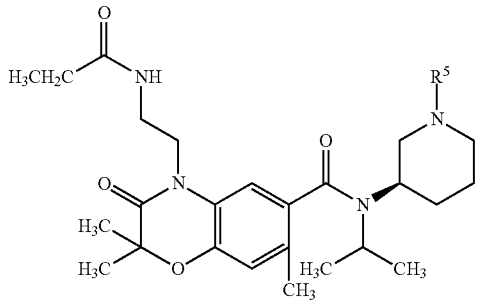

| Ex. No. | $R^5$ |
|---|---|
| 51 | 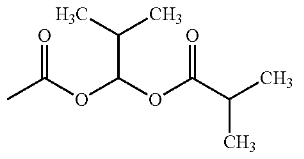 |
| 52 | 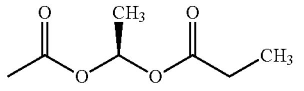 |
| 53 | 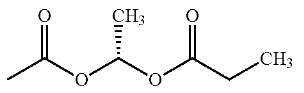 |
| 54 | 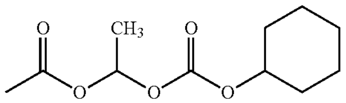 |
| 55 | 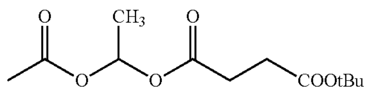 |
| 56 | 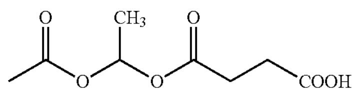 |
| 57 | 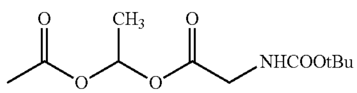 |
| 58 | 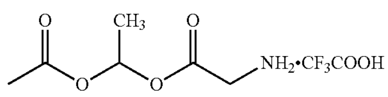 |
| 59 | 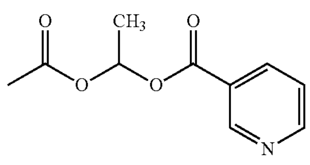 |

TABLE 16-continued
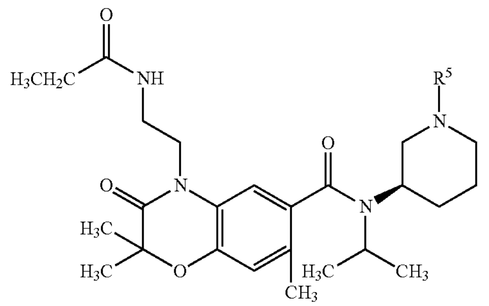
| Ex. No. | $R^5$ |
|---|---|
| 60 | 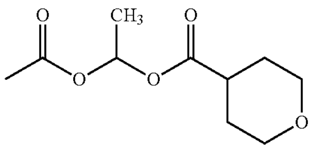 |
| 61 | 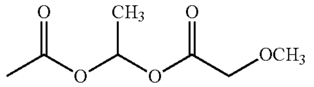 |
| 62 | 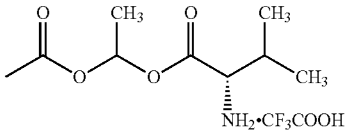 |
| 63 | 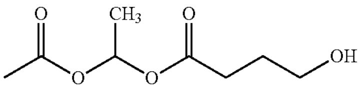 |
| 64 | 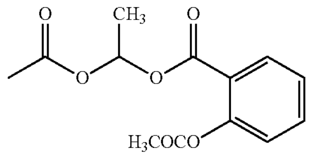 |
TABLE 16-continued
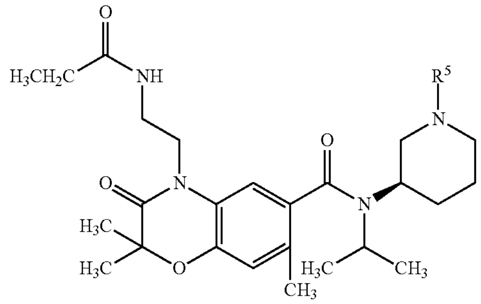
| Ex. No. | $R^5$ |
|---|---|
| 65 | 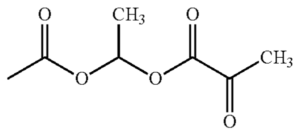 |
| 66 | 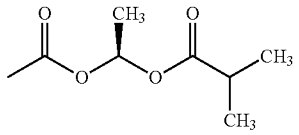 |
| 67 | 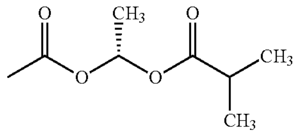 |
| 68 | 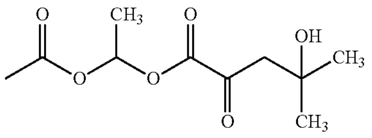 |
TABLE 17
| Ex. | Analytical Data |
|---|---|
| 51 | 1H NMR (400 MHz, $CD_3OD$) δ7.19-6.81 (m, 3H), 6.64-6.48 (m, 1H), 4.20-3.67 (m, 8H), 3.54-3.11 (m, 3H), 2.95-2.52 (m, 4H), 2.32-1.76 (m, 11H), 1.67-1.34 (m, 10H), 1.27-0.82 (m, 15H). MS (ESI+) 645 (M + 1, 11%). |
Example 52
[Chemical formula 243]
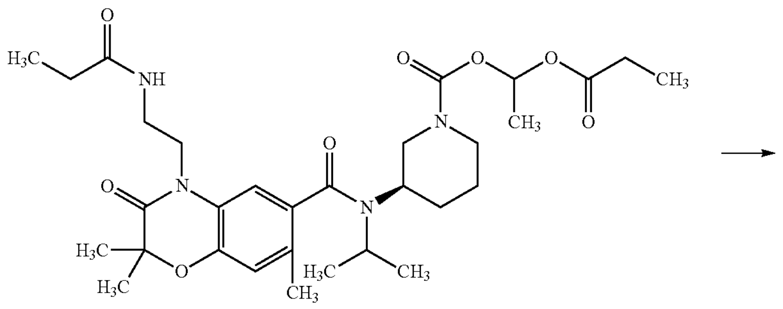

-continued

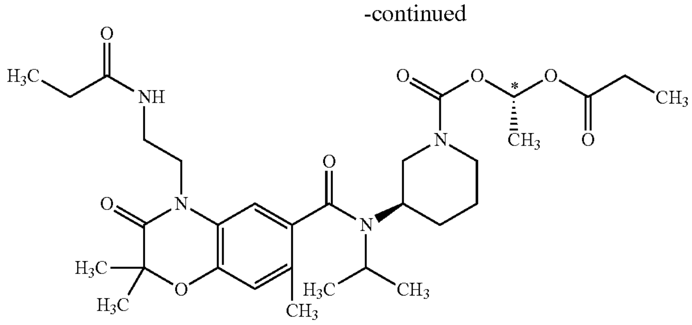

The compound of Example 18 was resolved with using a Chiral Column (CHIRALPAK (registered trade mark) IC) under the following analytical conditions to give the title compound and the compound of Example 53.

Column: CHIRALPAK (registered trade mark) IC (0.46 cm I.D.×25 cmL)

Mobile phase: hexane/ethanol/methanol=70/20/10 (v/v)

Flow rate: 1.0 mL/min

Temperature: 40° C.

Wave length: 294 nm

RT: 12.185 min

1H NMR (400 MHz, $CDCl_3$) δ 6.95-6.76 (m, 3H), 6.06-5.91 (m, 1H), 4.21-3.88 (m, 5H), 3.82-3.38 (m, 3H), 3.18-2.71 (m, 3H), 2.42-2.01 (m, 7H), 1.91-2.36 (m, 11H), 1.23-1.02 (m, 13H).

MS (ESI+) 603 (M+1, 11%).

TABLE 18

| Ex. | Analytical Data |
|---|---|
| 53 | 1H NMR (400 MHz, $CDCl_3$) δ.6.92-6.76 (m, 3H), 6.00 (brs, 1H), 4.20-3.86 (m, 5H), 3.29-3.37 (m, 3H), 3.14-2.71 (m, 3H), 2.39-2.11 (m, 7H), 1.89-1.37 (m, 11H), 1.21-1.05 (m, 13H).<br>MS (ESI+) 603 (M + 1, 7%).<br>CHIRALPAK ® IC (0.46 cm I.D. × 25 cm L), Mobile phase: hexane/ethanol/methanol = 70/20/10 (v/v), Flow rate: 1.0 mL/min, Temperature: 40° C., Wave length: 294 nm<br>RT: 15.241 min |
| 54 | 1H NMR (400 MHz, $CDCl_3$) δ 6.91-6.68 (m, 3H), 6.02-5.91 (m, 1H), 4.69-4.56 (m, 1H), 4.26-3.88 (m, 5H), 3.82-3.37 (m, 4H), 3.18-2.72 (m, 3H), 2.31-2.11 (m, 5H), 2.00-1.32 (m, 18H), 1.23-1.05 (m, 12H).<br>MS (ESI+) 673 (M + 1, 12%). |
| 55 | 1H NMR (400 MHz, $CDCl_3$) δ6.95-6.77 (m, 3H), 6.00 (brs, s), 4.20-3.89 (m, 5H), 3.81-3.68 (m, 1H), 3.18-2.71 (m, 3H), 2.65-2.42 (m, 4H), 2.31-2.11 (m, 6H), 1.90-1.71 (m, 2H), 1.68-1.36 (m, 20H), 1.23-1.06 (m, 9H).<br>MS (ESI+) 703 (M + 1, 30%). |

Example 56

[Chemical formula 244]

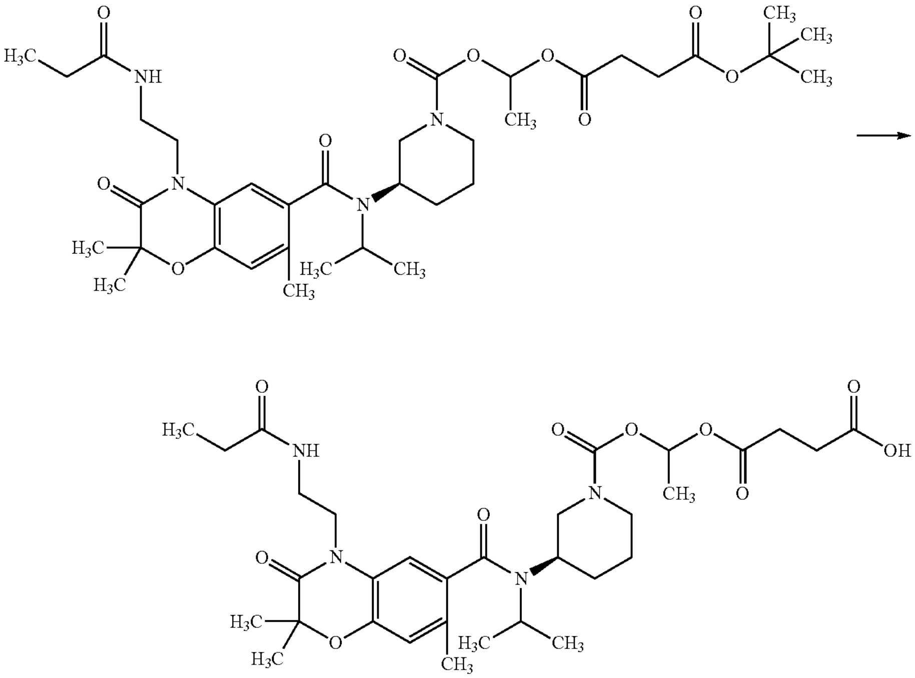

To a solution of the compound of Example 55 (110 mg) in chloroform (1 ml) was added trifluoroacetic acid (1 ml), and the mixture was stirred at 25° C. for 5 hours. The mixture was concentrated under reduced pressure to give the title compound (98 mg).

1H NMR (400 MHz, $d_6$-DMSO) δ 8.91-8.30 (m, 1H), 8.09-7.90 (m, 1H), 7.29-7.02 (m, 1H), 7.90-7.78 (m, 1H), 6.75-6.48 (m, 1H), 4.06-3.38 (m, 5H), 3.32-2.94 (m, 4H), 2.89-2.61 (m, 2H), 2.55-2.34 (m, 2H), 2.20-1.62 (m, 9H), 1.52-1.22 (m, 10H), 1.13-0.85 (m, 9H).

MS (ESI+) 647 (M+1, 25%).

TABLE 19

| Ex. | Analytical Data |
|---|---|
| 57 | 1H NMR (400 MHz, $CDCl_3$) δ6.98-6.78 (m, 4H), 6.06-5.94 (m, 1H), 5.13-4.94 (m, 1H), 4.18-3.68 (m, 8H), 3.62-3.37 (m, 2H), 3.21-2.71 (m, 3H), 2.30-2.12 (m, 6H), 1.92-1.70 (m, 5H), 1.64-1.34 (m, 14H), 1.22-1.06 (m, 9H). MS (ESI+) 704 (M + 1, 20%). |
| 58 | 1H NMR (400 MHz, $d_6$-DMSO) δ8.97-8.38 (m, 1H), 8.32-7.93 (m, 3H), 7.26-7.08 (m, 1H), 6.86 (s, 1H), 3.97-2.98 (m, 15H), 2.87-2.55 (m, 2H), 2.28-1.63 (m, 7H), 1.53-1.28 (m, 7H), 1.16-0.88 (m, 8H). MS (ESI+) 604 (M + 1, 57%). |

TABLE 19-continued

| Ex. | Analytical Data |
|---|---|
| 59 | 1H NMR (400 MHz, $CDCl_3$) δ9.28-9.15 (m, 1H), 8.83-8.75 (m, 1H), 8.38-8.25 (m, 1H), 7.46-7.35 (m, 1H), 7.20-7.06 (m, 1H), 6.95-6.75 (m, 2H), 6.06-5.88 (brs, 1H), 4.22-3.88 (m, 5H), 3.83-3.28 (m, 3H), 3.18-2.73 (m, 3H), 2.29-2.08 (m, 6H), 1.91-1.47 (m, 8H), 1.22-0.91 (m, 12H). MS (ESI+) 652 (M + 1, 38%). |
| 60 | 1H NMR (400 MHz, $CDCl_3$) δ6.92-6.77 (m, 3H), 6.05-5.90 (m, 1H), 4.20-3.88 (m, 7H), 3.81-3.69 (m, 1H), 3.62-3.38 (m, 5H), 3.15-2.76 (m, 3H), 2.63-2.49 (m, 1H), 2.28-2.11 (m, 6H), 1.91-1.71 (m, 7H), 1.68-1.37 (m, 7H), 1.22-1.05 (m, 9H). MS (ESI+) 659 (M + 1, 12%). |
| 61 | 1H NMR (400 MHz, $CDCl_3$) δ6.98-6.77 (m, 3H), 6.05-5.91 (m, 1H), 4.21-3.86 (m, 8H), 3.31-3.20 (m, 1H), 3.64-3.39 (m, 5H), 3.17-2.74 (m, 3H), 2.30-2.12 (m, 5H), 1.90-1.71 (m, 2H), 1.68-1.38 (m, 9H), 1.22-1.06 (m, 9H). MS (ESI+) 619 (M + 1, 6%). |
| 62 | 1H NMR (400 MHz, $CDCl_3$) δ7.01-6.76 (m, 3H), 4.28-3.71 (m, 6H), 3.64-3.37 (m, 2H), 3.28-2.70 (m, 3H), 2.41-2.10 (m, 6H), 1.92-1.68 (m, 2H), 1.64-1.35 (m, 11H), 1.23-0.92 (m, 16H). MS (ESI+) 646 (M + 1, 100%). |

Example 63

1-[(4-Hydroxybutanoyl)oxy]ethyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate

[Chemical formula 245]

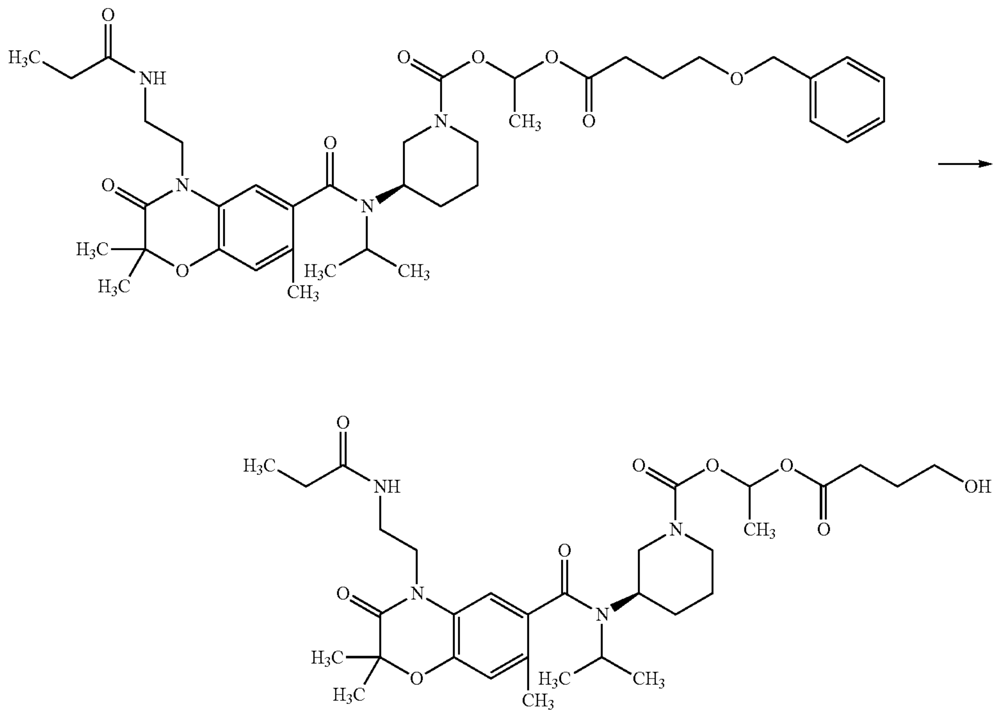

To a solution of the compound of Reference Example 37 (267 mg) in ethyl acetate (3.7 ml) was added a 10% palladium carbon (130 mg), and the mixture was stirred at room temperature for 16 hours under hydrogen atmosphere. The insoluble materials were removed by filtration, and the filtrate was concentrated under reduced pressure to give the title compound (165 mg).

RT 3.432 min (Shim-pack XR-ODS, 0.1% trifluoracetic acid in water/acetonitrile, acetonitrile 20-80% 7.1 min, 1.0 ml/min, UV 254 nm).

MS (ESI+) 633 (M+1, 8%).

TABLE 20

| Ex. | Analytical Data |
|---|---|
| 64 | 1H NMR (400 MHz, $CDCl_3$) δ 8.09-7.91 (m, 1H), 7.62-7.52 (m, 1H), 7.38-7.23 (m, 1H), 7.14-7.01 (m, 2H), 6.92-6.76 (m, 2H), 6.06-5.89 (m, 1H), 4.22-3.88 (m, 5H), 3.81-3.35 (m, 3H), 3.19-2.71 (m, 3H), 2.39-2.09 (m, 7H), 1.92-1.35 (m, 13H), 1.22-0.87 (m, 9H).<br>MS (ESI+) 709 (M + 1, 20%). |
| 65 | 1H NMR (400 MHz, $CDCl_3$) δ 6.99-6.72 (m, 3H), 6.41-5.94 (m, 1H), 4.23-3.84 (m, 4H), 3.81-3.21 (m, 4H), 3.17-2.72 (m, 3H), 2.29-2.08 (m, 5H), 2.03-1.71 (m, 3H), 1.63-1.34 (m, 12H), 1.28-1.01 (m, 9H).<br>MS (ESI+) 617 (M + 1, 5%). |
| 66 | 1H NMR (400 MHz, $CDCl_3$) δ 6.91-6.75 (m, 3H), 6.05-5.90 (m, 1H), 4.22-3.90 (m, 6H), 3.81-3.69 (m, 1H), 3.62-3.38 (m, 2H), 3.14-2.75 (m, 3H), 2.61-2.45 (m, 1H), 2.29 (s, 3H), 2.19 (q, J = 7.6 Hz, 2H), 1.91-1.70 (m, 2H), 1.54-1.44 (m, 9H), 1.18-1.09 (m, 15H).<br>MS (ESI+) 617 (M + 1, 34%).<br>CHIRALPAK ® IC (0.46 cmI.D. × 25 cmL), Mobile phase: hexane/ethanol = 50/50 (v/v), flow rate: 1.0 mL/min, temperature: 25° C., wave length: 254 nm<br>RT 9.474 min |

TABLE 20-continued

| Ex. | Analytical Data |
|---|---|
| 67 | 1H NMR (400 MHz, $CDCl_3$) δ 6.93-6.77 (m, 3H), 6.03-5.88 (m, 1H), 4.17-3.86 (m, 6H), 3.80-3.69 (m, 1H), 3.63-3.49 (m, 2H), 3.13-2.72 (m, 3H), 2.58-2.47 (m, 1H), 2.22 (s, 3H), 2.17 (q, J = 7.6 Hz, 2H), 1.89-1.70 (m, 2H), 1.54-1.41 (m, 9H), 1.17-1.09 (m, 15H).<br>MS (ESI+) 617 (M + 1, 7%).<br>CHIRALPAK ® IC (0.46 cmI.D. × 25 cmL), Mobile phase: hexane/ethanol = 50/50 (v/v), flow rate: 1.0 mL/min, temperature: 25° C., wave length: 254 nm<br>RT 13.706 min |
| 68 | 1H NMR (400 MHz, $CDCl_3$) δ 6.92-6.77 (m, 3H), 6.06-5.92 (m, 1H), 4.21-3.87 (m, 5H), 3.81-3.69 (m, 1H), 3.66-3.24 (m, 3H), 3.17-2.74 (m, 3H), 2.60-2.42 (m, 2H), 2.30-2.12 (m, 5H), 1.92-1.37 (m, 13H), 1.35-1.06 (m, 13H).<br>MS (ESI+) 647 (M + 1, 33%). |

Examples 69 to 76

According to the method disclosed in Example 2, the compounds of Examples 69, 70, 71, 73 were synthesized using the compound of Reference Example 41, N-isopropyl-2-(methoxymethyl)-2-methyl-3-oxo-N-[(3R)-piperidin-3-yl]-4-[2-(propionylamino)ethyl]-7-(trifluoromethyl)-3,4-dihydro-2H-1,4-benzoxazine-6-carboxamide hydrochloride, 4-{2-[(difluoroacetyl)amino]ethyl}-N-isopropyl-3-oxo-N-[(3R)-piperidin-3-yl]-7-(trifluoromethyl)-3,4-dihydrospiro[1,4-benzoxazine-2,1'-cyclopropane]-6-carboxamide hydrochloride, (2R)—N-isopropyl-2-methyl-3-oxo-N-[(3R)-piperidin-3-yl]-4-[2-(propionylamino)ethyl]-2,7-bis(trifluoromethyl)-3,4-dihydro-2H-1,4-benzoxazine-6-carboxamide hydrochloride, respectively. The compounds of Examples 72, 74, 75 and 76 were synthesized according to the methods disclosed in the corresponding Reference Example and Example 1.

TABLE 21

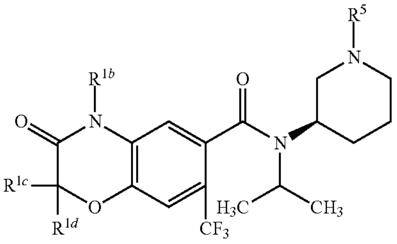

| Ex. No. | $R^{1b}$ | $R^{1c}$ | $R^{1d}$ | $R^5$ |
|---|---|---|---|---|
| 69 | $CH_3CH_2C(O)NH(CH_2)_2$ | Me | 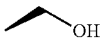 | 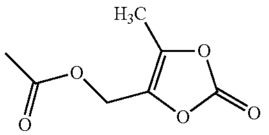 |
| 70 | $CH_3CH_2C(O)NH(CH_2)_2$ | Me | 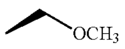 | 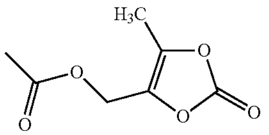 |
| 71 | $CHF_2C(O)NH(CH_2)_2$ | | 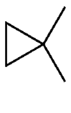 | 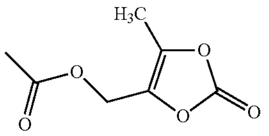 |

TABLE 21-continued

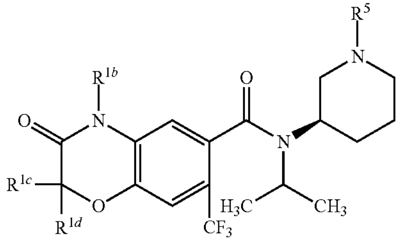

| Ex. No. | $R^{1b}$ | $R^{1c}$ | $R^{1d}$ | $R^5$ |
|---|---|---|---|---|
| 72 | $CHF_2C(O)NH(CH_2)_2$ | 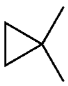 | | 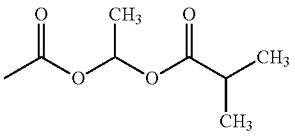 |
| 73 | $CH_3CH_2C(O)NH(CH_2)_2$ |  | 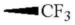 | 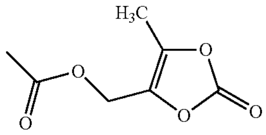 |
| 74 | $CH_3CH_2C(O)NH(CH_2)_2$ | 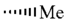 | 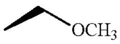 | 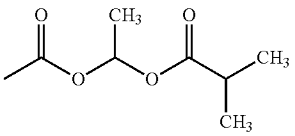 |
| 75 | $CH_3CH_2C(O)NH(CH_2)_2$ |  | 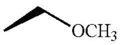 | 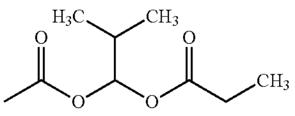 |
| 76 | $CH_3CH_2C(O)NH(CH_2)_2$ |  | 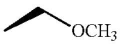 | 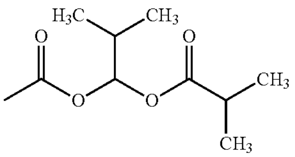 |

TABLE 22

| Ex. | Analytical Data |
|---|---|
| 69 | 1H NMR (400 MHz, $CDCl_3$) δ7.44-7.09 (m, 2H), 6.26-6.17 (m, 1H), 4.96-4.68 (m, 2H), 4.14-3.96 (m, 6H), 3.87-3.76 (m, 1H), 3.68-3.65 (m, 1H), 3.54-3.37 (m, 4H), 2.92-2.75 (m, 2H), 2.20-2.07 (m, 5H), 1.65-1.45 (m, 2H), 1.22-1.03 (m, 12H). MS (ESI+) 685 (M + 1, 90%). |
| 70 | 1H NMR (400 MHz, $CDCl_3$) δ7.30-7.19 (m, 3H), 5.90-5.80 (m, 1H), 4.99-4.74 (m, 2H), 4.21-3.88 (m, 5H), 3.72-3.26 (m, 8H), 3.16-2.99 (m, 1H), 2.94-2.74 (m, 2H), 2.25-2.09 (m, 5H), 2.00-1.71 (m, 2H), 1.59-1.34 (m, 3H), 1.27-1.04 (m, 9H). MS (ESI+) 699 (M + 1, 22%). |
| 71 | 1H NMR (400 MHz, $CDCl_3$) δ7.09-7.21 (m, 2H), 6.87 (brs, 1H), 6.09-5.73 (m, 1H), 4.97-4.73 (m, 2H), 4.92-4.73 (m, 5H), 3.72-3.49 (m, 4H), 3.17-2.74 (m, 3H), 2.20 (s, 3H), 1.92-1.68 (m, 2H), 1.52-1.08 (m, 10H). MS (ESI+) 689 (M + 1, 47%). |
| 72 | 1H NMR (400 MHz, $CDCl_3$) δ7.19-6.77 (m, 4H), 6.06-5.71 (m, 1H), 4.23-3.47 (m, 9H), 3.31-2.46 (m, 4H), 1.95-0.98 (m, 21H). MS (ESI+) 691 (M + 1, 100%). |
| 73 | 1H NMR (400 MHz, $CDCl_3$) δ7.62-7.29 (m, 2H), 5.97-5.81 (m, 1H), 4.99-4.71 (m, 2H), 4.28-3.84 (m, 5H), 3.69-3.33 (m, 3H), 3.15-2.70 (m, 3H), 2.27-1.94 (m, 5H), 1.90-1.43 (m, 6H), 1.35-0.96 (m, 9H). MS (ESI+) 723 (M + 1, 31%). |
| 74 | 1H NMR (400 MHz, $CDCl_3$) δ7.28-7.12 (m, 2H), 6.91-6.75 (m, 1H), 5.90-5.77 (m, 1H), 4.21-3.84 (m, 7H), 3.64-3.41 (m, 4H), 3.32 (s, 3H), 3.18-2.97 (m, 1H), 2.95-2.68 (m, 2H), 2.61-2.47 (m, 1H), 2.20-2.10 (m, 2H), 1.95-1.49 (m, 8H), 1.26-1.08 (m, 15H). MS (ESI+) 701 (M + 1, 12%). |
| 75 | 1H NMR (400 MHz, $CDCl_3$) δ7.30-7.02 (m, 2H), 6.72-6.23 (m, 1H), 5.88 (brs, 1H), 4.24-3.84 (m, 6H), 3.73-3.28 (m, 7H), 3.19-2.71 (m, 3H), 2.42-2.00 (m, 7H), 1.90-1.44 (m, 4H), 1.28-0.79 (m, 18H). MS (ESI+) 715 (M + 1, 8%). |
| 76 | 1H NMR (400 MHz, $CDCl_3$) δ7.30-7.02 (m, 2H), 6.71-6.22 (m, 1H), 5.89 (brs, 1H), 4.25-3.78 (m, 6H), 3.72-3.28 (m, 7H), 3.19-2.70 (m, 3H), 2.62-2.50 (m, 1H), 2.25-1.69 (m, 8H), 1.64-1.38 (m, 3H), 1.26-0.82 (m, 19H). MS (ESI+) 729 (M + 1, 10%). |

Examples 77 to 78

According to the method disclosed in Example 2, the compounds of Examples 77 and 78 were synthesized using 4-{2-[(difluoroacetyl)amino]ethyl}-N-isopropyl-2,2,7-trimethyl-3-oxo-N-[(3R)-piperidin-3-yl]-3,4-dihydro-2H-1,4-benzothiazin-6-carboxamide hydrochloride and N-isopropyl-7-methyl-3-oxo-N-[(3R)-piperidin-3-yl]-4-[2-(propionylamino)ethyl]-3,4-dihydrospiro[1,4-benzothiazine-2,1'-cyclobutane]-6-carboxamide hydrochloride, respectively.

TABLE 23

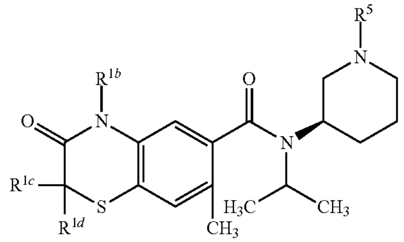

| Ex. No. | $R^{1b}$ | $R^{1c}$ | $R^{1d}$ | $R^5$ |
|---|---|---|---|---|
| 77 | $CHF_2C(O)NH(CH_2)_2$ | Me | Me | 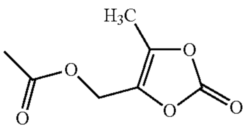 |
| 78 | $CH_3CH_2C(O)NH(CH_2)_2$ | 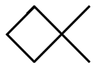 | | 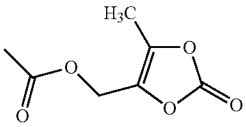 |

TABLE 24

| Ex. | Analytical Data |
|---|---|
| 77 | 1H NMR (400 MHz, $CDCl_3$) δ7.22-6.92 (m, 3H), 6.04-5.67 (m, 1H), 4.96-4.78 (m, 2H), 4.27-3.85 (m, 5H), 3.78-3.42 (m, 3H), 3.16-2.72 (m, 3H), 2.32-2.02 (m, 6H), 1.94-1.68 (m, 4H), 1.54-1.28 (m, 5H), 1.25-1.03 (m, 6H). MS (ESI+) 653 (M + 1, 100%). |
| 78 | 1H NMR (400 MHz, $CDCl_3$) δ7.18-7.12 (m, 1H), 7.10-6.90 (m, 1H), 6.19-6.02 (m, 1H), 4.94-4.78 (m, 2H), 4.23-3.85 (m, 6H), 3.77-3.62 (m, 1H), 3.59-3.33 (m, 2H), 3.12-2.72 (m, 5H), 2.49-1.43 (m, 15H), 1.35-0.98 (m, 9H). MS (ESI+) 643 (M + 1, 69%). |

Example 79

1-{[(4-Methylphenyl)carbonyl]oxy}ethyl 3-[({7-methyl-3-oxo-4-[2-(propanoylamino)ethyl]-3,4-dihydrospiro[1,4-benzoxazine-2,1'-cyclobutan]-6-yl}carbonyl)(2-propanyl)amino]-1-piperidinecarboxylate

[Chemical formula 246]

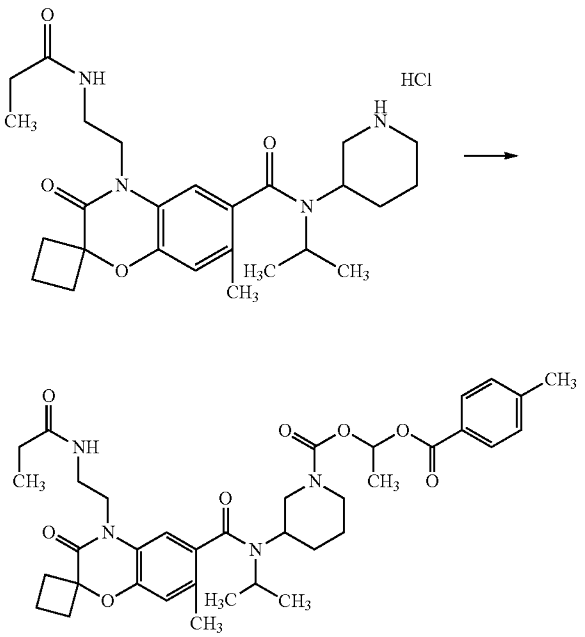

The title compound (203 mg) was obtained from the compound of Reference Example 32 (300 mg) according to the method disclosed in Example 1.

1H NMR (400 MHz, $CDCl_3$) δ. 7.99-7.88 (m, 2H), 7.30-7.18 (m, 2H), 7.15-7.02 (m, 1H), 6.91-6.77 (m, 2H), 6.03 (brs, 1H), 4.25-3.89 (m, 5H), 3.82-3.39 (m, 2H), 3.18-2.60 (m, 3H), 2.51-2.09 (m, 12H), 2.03-1.56 (m, 9H), 1.22-0.96 (m, 9H).

MS (ESI+) 677 ($M^+$+1, 49%).

Examples 80 to 86

The compounds of Examples 80, 84, 85, 86 were synthesized according to the method disclosed in the corresponding Reference Example and Example 1. The compound of Example 81 was synthesized according to the method disclosed in Example 2 using N-isopropyl-7-methyl-3-oxo-N-[(3R)-piperidin-3-yl]-4-[2-(propionylamino)ethyl]-3,4-dihydrospiro[1,4-benzoxazine-2,1'-cyclobutane]-6-carboxamide hydrochloride. The compounds of Examples 82, 83 were synthesized according to the method disclosed in Example 52, 53 using the compound of Example 47.

TABLE 25

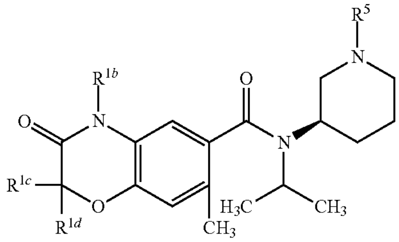

| Ex. No. | $R^{1b}$ | $R^{1c}$ | $R^{1d}$ | $R^5$ |
|---|---|---|---|---|
| 80 | $CH_3CH_2C(O)NH(CH_2)_2$ | Me | 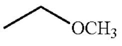 | 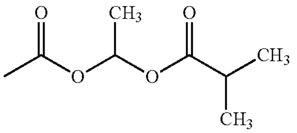 |
| 81 | $CH_3CH_2C(O)NH(CH_2)_2$ | | 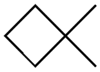 | 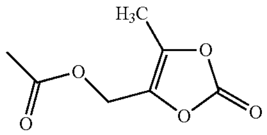 |
| 82 | $CH_3CH_2C(O)NH(CH_2)_2$ | | 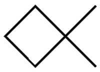 | 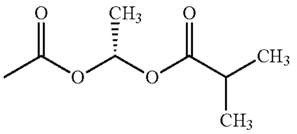 |
| 83 | $CH_3CH_2C(O)NH(CH_2)_2$ | | 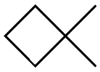 | 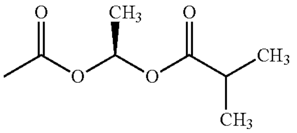 |
| 84 | $CH_3CH_2C(O)NH(CH_2)_2$ | | 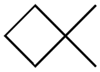 | 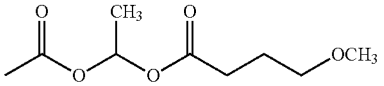 |
| 85 | $CH_3CH_2C(O)NH(CH_2)_2$ | Me | Me | 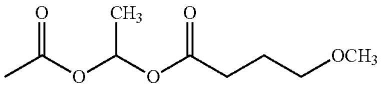 |
| 86 | $CH_3CH_2C(O)NH(CH_2)_2$ | Me | 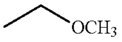 | 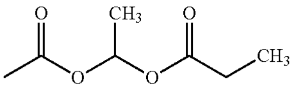 |

TABLE 26

| Ex. | Analytical Data |
|---|---|
| 80 | 1H NMR (400 MHz, $d_6$-DMSO) δ7.99 (m, 1H), 7.15-7.10 (m, 1H), 6.87-6.84 (m, 1H), 6.69-6.51 (m, 1H), 4.04-3.64 (m, 8H), 3.54-3.43 (m, 1H), 3.25-3.01 (m, 7H), 2.74-2.71 (m, 2H), 2.14-2.12 (m, 2H), 2.04-1.93 (m, 2H), 1.84-1.66 (m, 2H), 1.57-1.30 (m, 7H), 1.12-0.84 (m, 14H). MS (ESI+) 647 ($M^+$ + 1, 100%). |
| 81 | 1H NMR (400 MHz, $CDCl_3$) δ6.94-6.78 (m, 2H), 6.02 (brs, 1H), 4.94-4.78 (m, 2H), 4.21-3.87 (m, 5H), 3.81-3.68 (m, 1H), 3.62-3.40 (m, 2H), 3.24-2.62 (m, 4H), 2.48-2.38 (m, 1H), 2.37-2.08 (m, 10H), 2.04-1.72 (m, 4H), 1.70-1.46 (m, 2H), 1.23-1.04 (m, 8H). MS (ESI+) 627 (M + 1, 36%). |
| 82 | 1H NMR (400 MHz, $CDCl_3$) δ6.92-6.78 (m, 3H), 6.06-5.96 (m, 1H), 4.21-3.87 (m, 6H), 3.81-3.42 (m, 3H), 3.12-2.15 (m, 13H), 2.04-1.80 (m, 4H), 1.54-1.45 (m, 3H), 1.25-1.09 (m, 15H). MS (ESI+) 630 (M + 1, 100%). CHIRALPAK ® IC (0.46 cmI.D. × 25 cmL), Mobile phase: hexane/ethanol = 50/50 (v/v), flow rate: 1.0 mL/min, temperature: 25° C., wave length: 254 nm RT 15.809 min |
| 83 | 1H NMR (400 MHz, $CDCl_3$) δ6.91-6.78 (m, 3H), 6.14-6.00 (m, 1H), 4.21-3.88 (m, 6H), 3.82-3.68 (m, 1H), 3.62-49 (m, 2H), 3.14-2.98 (m, 1H), 2.97-2.74 (m, 2H), 2.73-2.64 (m, 1H), 2.62-2.49 (m, 1H), 2.48-2.38 (m, 1H), 2.47-2.13 (m, 5H), 2.05-1.71 (m, 4H), 1.62-1.38 (m, 3H), 1.77-1.08 (m, 15H). MS (ESI+) 630 (M + 1, 100%). CHIRALPAK ® IC (0.46 cmI.D. × 25 cmL), Mobile phase: hexane/ethanol = 50/50 (v/v), flow rate: 1.0 mL/min, temperature: 25° C., wave length: 254 nm RT 9.675 min |

TABLE 26-continued

| Ex. | Analytical Data |
|---|---|
| 84 | 1H NMR (400 MHz, $CDCl_3$) δ6.94-6.76 (m, 3H), 6.08-5.92 (m, 1H), 4.20-3.87 (m, 5H), 3.81-3.68 (m, 1H), 3.64-3.34 (m, 4H), 3.31 (s, 3H), 3.18-2.65 (m, 4H), 2.49-2.12 (m, 10H), 2.06-1.70 (m, 6H), 1.57-1.36 (m, 4H), 1.23-1.01 (m, 9H). MS (ESI+) 659 (M + 1, 12%). |
| 85 | 1H NMR (400 MHz, $CDCl_3$) δ6.94-6.75 (m, 3H), 6.02-5.88 (m, 1H), 4.20-3.86 (m, 5H), 3.81-3.67 (m, 1H), 3.66-3.34 (m, 4H), 3.31 (s, 3H), 3.18-2.70 (m, 3H), 2.48-2.32 (m, 2H), 2.29-2.12 (m, 5H), 1.96-1.72 (m, 4H), 1.66-1.36 (m, 10H), 1.23-1.05 (m, 9H). MS (ESI+) 647 (M + 1, 12%). |
| 86 | 1H NMR (400 MHz, $d_6$-DMSO) δ8.00 (m, 1H), 7.25-7.10 (m, 1H), 6.87-6.84 (m, 1H), 6.75-6.69 (m, 1H), 3.93-3.76 (m, 5H), 3.66-3.62 (m, 1H), 3.54-3.44 (m, 1H), 3.25-3.16 (m, 6H), 2.78-2.67 (m, 2H), 2.32-2.29 (m, 2H), 2.17-2.12 (m, 3H), 2.04-2.01 (m, 2H), 1.74-1.66 (m, 2H), 1.50-1.37 (m, 6H), 1.50-1.37 (m, 6H), 1.30-1.24 (m, 3H), 1.12-0.93 (m, 11H). MS (ESI+) 633 (M + 1, 100%). |

Examples 87 to 88

The compounds of Examples 87 and 88 were obtained by subjecting the compound of Example 60 to resolution under the following HPLC conditions.

TABLE 27

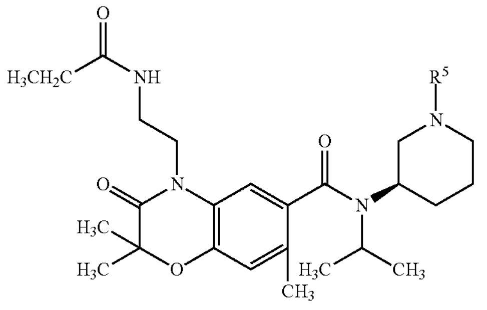

| Ex. No. | $R^5$ |
|---|---|
| 87 | 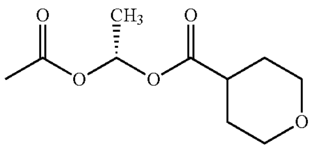 |
| 88 | 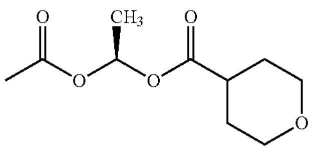 |

TABLE 28

| Ex. | Analytical Data |
|---|---|
| 87 | 1H NMR (400 MHz, $CDCl_3$) δ6.92-6.76 (m, 3H), 6.05-5.89 (m, 1H), 4.20-3.86 (m, 7H), 3.82-3.68 (m, 1H), 3.62-3.24 (m, 5H), 3.16-2.73 (m, 3H), 2.26-2.09 (m, 4H), 1.91-1.70 (m, 5H), 1.54 (s, 3H), 1.53-1.36 (m, 8H), 1.31-1.03 (m, 10H). MS (ESI+) 659 (M + 1, 100%). CHIRALPAK ® IC (0.46 cmI.D. × 25 cmL), Mobile phase: n-hexane/ethanol/methanol = 50/3-/20, flow rate: 1.0 mL/min, temperature: 40° C., wave length: 294 nm RT 14.313 min |
| 88 | 1H NMR (400 MHz, $CDCl_3$) δ6.93-6.74 (m, 3H), 6.09-5.92 (m, 1H), 4.21-3.86 (m, 7H), 3.81-3.3.68 (m, 1H), 3.62-3.33 (m, 5H), 3.16-2.45 (m, 3H), 2.34-2.11 (m, 4H), 1.92-1.70 (m, 5H), 1.51 (s, 3H), 1.62-1.37 (m, 8H), 1.21-1.00 (m, 10H). MS (ESI+) 659 (M + 1, 66%). CHIRALPAK ® IC (0.46 cmI.D. × 25 cmL), Mobile phase: n-hexane/ethanol/methanol = 50/3-/20, flow rate: 1.0 mL/min, temperature: 40° C., wave length: 294 nm RT 10.328 min |

Example 89

1-[({(3R)-3-[({7-Methyl-3-oxo-4-[2-(propanoylamino)ethyl]-3,4-dihydrospiro[1,4-benzoxazine-2, 1'-cyclobutan]-6-yl}carbonyl)(2-propanyl)amino]-1-piperidinyl}carbonyl)oxy]ethyl 3-pyridine carboxylate

[Chemical formula 247]

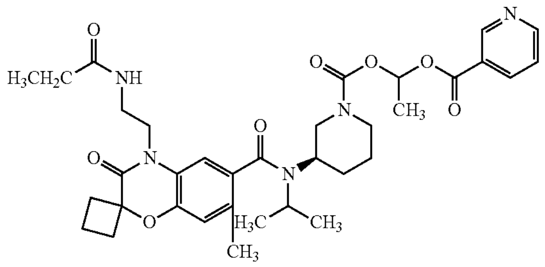

The title compound was synthesized according to the method disclosed in Reference Example 33 and Example 1 from the compound of Reference Example 57.

1H NMR (400 MHz, $CDCl_3$) δ 9.29-9.13 (m, 1H), 8.81-8.72 (m, 1H), 8.36-8.22 (m, 1H), 7.46-7.33 (m, 1H), 7.20-7.04 (m, 1H), 6.92-6.72 (m, 3H), 6.05 (brs, 1H), 4.25-3.26 (m, 6H), 3.18-2.59 (m, 4H), 2.51-2.09 (m, 9H), 2.05-1.44 (m, 9H), 1.31-0.90 (m, 9H).

MS (ESI+) 664 ($M^+$+1, 100%).

Examples 90 to 91

The compounds of Examples 90 and 91 were obtained according to the method disclosed in the corresponding Examples 52 and 53 using the compound of Example 16.

TABLE 29

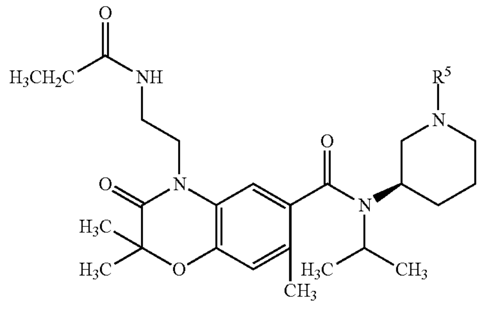

| Ex. No. | $R^5$ |
|---|---|
| 90 | 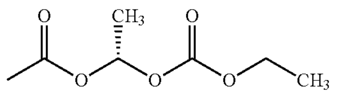 |
| 91 | 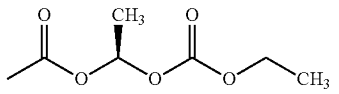 |

TABLE 30

| Ex. | Analytical Data |
|---|---|
| 90 | 1H NMR (400 MHz, $CDCl_3$) δ6.92-6.82 (m, 1H), 6.81-6.69 (m, 2H), 6.07-5.92 (m, 1H), 4.26-3.85 (m, 8H), 3.80-3.68 (m, 1H), 3.67-3.38 (m, 2H), 3.15-2.98 (m, 1H), 2.98-2.61 (m, 2H), 2.21 (s, 3H), 2.16 (q, J = 7.6 Hz, 2H), 1.90-1.75 (m, 2H), 1.74 (s, 3H), 1.59-1.49 (m, 6H), 1.43 (s, 3H), 1.30 (t, J = 7.1 Hz, 3H), 1.21-1.17 (m, 6H). MS (ESI+) 619 (M + 1, 6%). CHIRALPAK ® IC (0.46 cmI.D. × 25 cmL), Mobile phase: methanol, flow rate: 1.0 mL/min, temperature: 40° C., wave length: 295 nm RT 5.866 min |
| 91 | 1H NMR (400 MHz, $CDCl_3$) δ6.91-6.69 (m, 3H), 6.05-5.92 (m, 1H), 4.28-3.88 (m, 8H), 3.81-3.68 (m, 1H), 3.67-3.37 (m, 2H), 3.18-2.64 (m, 3H), 2.20 (s, 3H), 2.17 (q, J = 7.6 Hz, 2H), 1.90-1.70 (m, 2H), 1.66 (s, 3H), 1.62-1.49 (m, 6H), 1.44 (s, 3H), 1.35-1.26 (m, 3H), 1.23-1.17 (m, 6H). MS (ESI+) 619 (M + 1, 6%). CHIRALPAK ® IC (0.46 cmI.D. × 25 cmL), Mobile phase: methanol, flow rate: 1.0 mL/min, temperature: 40° C., wave length: 295 nm RT 5.168 min |

Example 92

1-[(2-Methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl)(2-propanyl)amino]-1-piperidinecarboxylate

[Chemical formula 248]

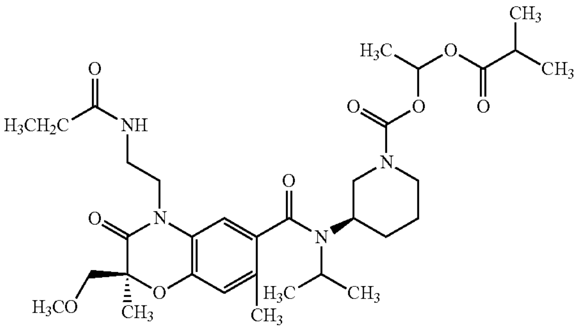

The title compound was obtained according to the method disclosed in the corresponding Reference Example 40 and Example 1 using the compound of Reference Example 66.

1H NMR (400 MHz, $CDCl_3$) δ 6.93-6.72 (m, 1H), 5.97 (brs, 1H), 4.23-3.88 (m, 5H), 3.82-3.38 (m, 8H), 3.16-2.74 (m, 3H), 2.65-2.45 (m. 1H), 2.31-2.09 (m. 5H), 1.91-1.69 (m, 2H), 1.66-1.32 (m, 8H), 1.30-1.01 (m, 14H).

MS (ESI+) 647 (M+1, 82%).

Examples 93 to 99

The compounds of Examples 93 and 94 were synthesized by collecting the compound of Example 92 under the following HPLC conditions. The compound of Example 95 was synthesized according to the method disclosed in the corresponding Reference Example 33 and Example 1 using the compound of Reference Example 40. The compound of Example 96 was synthesized according to Example 5 using the compound of Reference Example 57. The compound of Example 97 was synthesized according to the method disclosed in the corresponding Example 1 using the compound of Reference Example 57. The compounds of Example 98 and Example 99 were synthesized according to the method disclosed in the corresponding Example 1 and the literature (e.g., J. Med. Chem. 2008, 51, 1894, etc.) from the compound of Reference Example 29.

TABLE 31
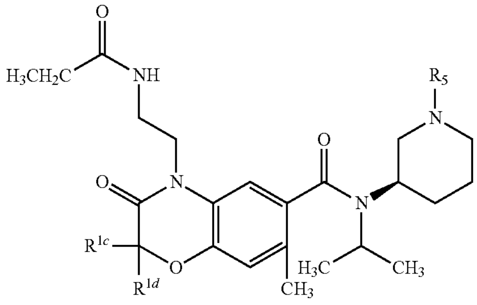
| Ex. No. | $R^{1c}$ | $R^{1d}$ | $R^5$ |
|---|---|---|---|
| 93 |  | 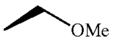 | 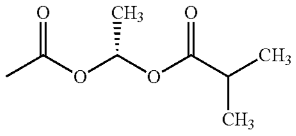 |
| 94 |  | 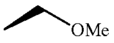 | 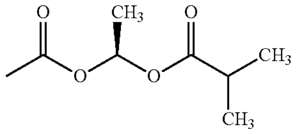 |
| 95 | Me | 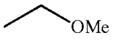 | 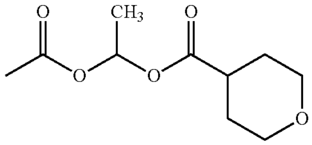 |
| 96 | 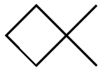 | | 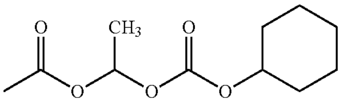 |
| 97 | 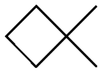 | | 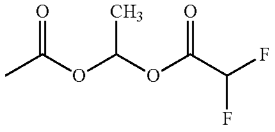 |
| 98 | Me | Me | 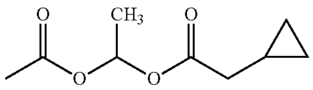 |
| 99 | Me | Me | 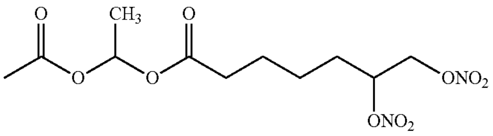 |

TABLE 32

| Ex. | Analytical Datal |
|---|---|
| 93 | 1H NMR (400 MHz, $d_6$-DMSO) δ.8.02-7.89 (m, 1H), 7.38-7.04 (m, 1H), 6.88-6.79 (m, 1H), 6.70-6.62 (m, 1H), 4.09-3.72 (m, 5H), 3.67-3.41 (m, 3H), 3.32 (s, 3H), 3.27-3.05 (m, 6H), 2.84-2.62 (m, 2H), 2.21-1.95 (m, 4H), 1.54-1.23 (m, 9H), 1.14-0.89 (m, 12H). MS (ESI+) 647 (M + 1, 91%). CHIRALPAK ® IC (0.46 cmI.D. x 25 cmL), Mobile phase: n-hexane/ethanol = 50/50, flow rate: 1.0 mL/min, temperature: 40° C., wave length: 254 nm RT 10.753 min |
| 94 | 1H NMR (400 MHz, $CDCl_3$) δ 6.92-6.74 (m, 3H), 5.97 (brs, 1H), 4.21-3.90 (m, 5H), 3.84-3.30 (m, 8H), 3.18-2.72 (m, 3H), 2.62-2.45 (m, 1H), 2.31-2.10 (m, 6H), 1.91-1.69 (m, 2H), 1.63-1.32 (m, 9H), 1.25-1.02 (m, 12H). MS (ESI+) 647 (M + 1, 26%). CHIRALPAK ® IC (0.46 cmI.D. x 25 cmL), Mobile phase: n-hexane/ethanol = 50/50, flow rate: 1.0 mL/min, temperature: 40° C., wave length: 254 nm RT 8.138 min |
| 95 | 1H NMR (400 MHz, $CDCl_3$) δ 6.88-6.71 (m, 3H), 5.96 (brs, 1H), 4.18-3.82 (m, 7H), 3.78-3.63 (m, 1H), 3.60-3.21 (m, 8H), 3.12-2.69 (m, 3H), 2.59-2.42 (m, 1H), 2.23-2.06 (m, 5H), 1.88-1.64 (m, 6H), 1.60-1.29 (m, 7H), 1.20-0.98 (m, 9H). MS (ESI+) 689 (M + 1, 100%). |
| 96 | 1H NMR (400 MHz, $CDCl_3$) δ6.90-5.74 (m, 3H), 6.01 (brs, 1H), 4.75-4.56 (m, 1H), 4.25-3.88 (m, 6H), 3.81-3.41 (m, 4H), 3.14-2.62 (m, 4H), 2.50-2.11 (m, 12H), 2.06-1.04 (m, 21H). MS (ESI+) 685 (M + 1, 20%). |
| 97 | 1H NMR (400 MHz, $CDCl_3$) δ.7.03-6.79 (m, 3H), 6.12-5.68 (m, 2H), 4.22-3.86 (m, 5H), 3.81-3.77 (m, 1H), 3.59-3.38 (m, 2H), 3.18-2.62 (m, 3H), 2.51-2.11 (m, 7H), 2.05-1.71 (m, 4H), 1.68-1.45 (m, 6H), 1.23-1.04 (m, 9H). MS (ESI+) 637 (M + 1, 17%). |
| 98 | 1H NMR (400 MHz, $CDCl_3$) δ.6.95-6.77 (m, 3H), 5.97 (brs, 1H), 4.22-3.88 (m, 5H), 3.81-3.36 (m, 3H), 3.16-2.70 (m, 2H), 2.32-2.10 (m, 8H), 1.90-1.70 (m, 2H), 1.66-1.37 (m, 9H), 1.25-0.98 (m, 11H), 0.69-0.49 (m, 2H), 0.21-0.12 (m, 2H). MS (ESI+) 629 (M + 1, 10%). |
| 99 | 1H NMR (400 MHz, $CDCl_3$) δ.6.95-6.72 (m, 4H), 6.10-5.92 (m, 1H), 5.34-5.22 (m, 1H), 4.82-4.69 (m, 1H), 4.53-4.41 (m, 1H), 4.22-3.86 (m, 5H), 3.82-3.66 (m, 1H), 3.62-3.35 (m, 3H), 3.19-2.70 (m, 3H), 2.46-2.10 (m, 8H), 1.92-1.34 (m, 12H), 1.29-1.01 (m, 12H). MS (ESI+) 481 (M + 1, 17%). |

Example 100

1-[(Cyclohexylcarbonyl)oxy]ethyl (3R)-3-[({2,2-dimethyl-3-oxo-4-[2-(propanyllamino)ethyl]-7-(trifluoromethyl)-3,4-dihydro-2H-1,4-benzoxazin-6-yl}carbonyl)(propan-2-yl)amino]piperidine-1-carboxylate

[Chemical formula 249]

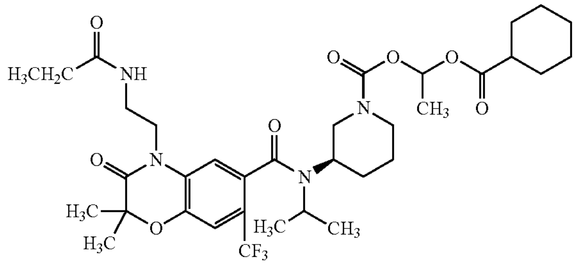

The title compound was obtained according to the method disclosed in the corresponding Example 1 from the compound of Reference Example 28.

1H NMR (300 MHz, $d_6$-DMSO) δ 8.06-8.03 (m, 1H), 7.60-7.31 (m, 2H), 6.67-6.65 (m, 1H), 4.08-3.91 (m, 3H), 3.33-3.06 (m, 3H), 2.72-2.68 (m, 2H), 2.11-1.97 (m, 2H), 1.75-0.81 (m, 35H).

MS (ESI+) 711 (M+1, 26%).

In addition to the compounds of the above-mentioned Examples, the compounds where the "$R^5$" in Compound No. 1 to 269 of the following Tables is replaced by a partial structure of P1 to P174 may also be prepared as compounds of Examples. In these cases, for example, the compound of No. 1 ($R^5$:P1) means the following compound.

TABLE 33

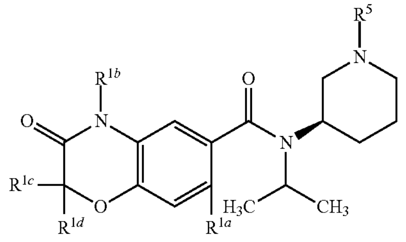

| Comp. No. | $R^{1a}$ | $R^{1b}$ | $R^{1c}$ | $R^{1d}$ |
|---|---|---|---|---|
| 1 | Br | $MeO(CH_2)_3$ | Me | Me |
| 2 | Cl | $MeO(CH_2)_3$ | Me | Me |
| 3 | CN | $MeO(CH_2)_3$ | Me | Me |
| 4 | Me | $MeO(CH_2)_3$ | Me | Me |
| 5 | Et | $MeO(CH_2)_3$ | Me | Me |
| 6 | n-Pr | $MeO(CH_2)_3$ | Me | Me |
| 7 | Cl | $MeO(CH_2)_4$ | Me | Me |
| 8 | Me | $MeO(CH_2)_4$ | Me | Me |
| 9 | Cl | $EtO(CH_2)_3$ | Me | Me |
| 10 | Br | $MeOC(O)NH(CH_2)_2$ | Me | Me |
| 11 | Cl | $MeOC(O)NH(CH_2)_2$ | Me | Me |
| 12 | Me | $MeOC(O)NH(CH_2)_2$ | Me | Me |
| 13 | Cl | $MeO(CH_2)_3$ | Et | Me |
| 14 | Br | $MeO(CH_2)_3$ | Et | Me |
| 15 | CN | $MeO(CH_2)_3$ | Et | Me |
| 16 | Cl | $MeO(CH_2)_3$ | H | (R)—Me |

TABLE 34

| Comp. No. | $R^{1a}$ | $R^{1b}$ | $R^{1c}$ | $R^{1d}$ |
|---|---|---|---|---|
| 17 | Br | $MeO(CH_2)_3$ | H | (R)—Me |
| 18 | Me | $MeO(CH_2)_3$ | H | (R)—Me |
| 19 | Cl | $MeO(CH_2)_4$ | H | (R)—Me |
| 20 | Br | $MeO(CH_2)_4$ | H | (R)—Me |
| 21 | Me | $MeO(CH_2)_4$ | H | (R)—Me |
| 22 | Cl | $MeOC(O)NH(CH_2)_2$ | H | (R)—Me |
| 23 | Br | $MeOC(O)NH(CH_2)_2$ | H | (R)—Me |
| 24 | Me | $MeOC(O)NH(CH_2)_2$ | H | (R)—Me |
| 25 | Cl | $MeO(CH_2)_3$ | H | Et |
| 26 | Cl | $MeO(CH_2)_4$ | $EtOCH_2$ | Me |
| 27 | Cl | $MeO(CH_2)_4$ | Me | $Me_2NC(O)$ |
| 28 | Cl | $MeO(CH_2)_4$ | Me | 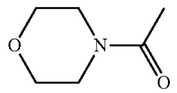 |
| 29 | Cl | $MeO(CH_2)_4$ | Me | 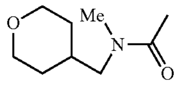 |

TABLE 34-continued

| Comp. No. | $R^{1a}$ | $R^{1b}$ | $R^{1c}$ | $R^{1d}$ |
|---|---|---|---|---|
| 30 | Cl | $MeOC(O)NH(CH_2)_2$ | Me | 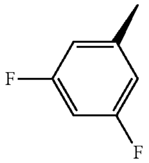 |
| 31 | Cl | $MeO(CH_2)_4$ | Me | $MeOCH_2$ |
| 32 | $CF_3$ | $MeO(CH_2)_3$ | Me | Me |

TABLE 35

| Comp. No. | $R^{1a}$ | $R^{1b}$ | $R^{1c}$ | $R^{1d}$ |
|---|---|---|---|---|
| 33 | $CF_3$ | $MeO(CH_2)_4$ | Me | Me |
| 34 | $CF_3$ | $MeOC(O)NH(CH_2)_2$ | Me | Me |
| 35 | Br | $MeO(CH_2)_4$ | Me | Me |
| 36 | Br | $MeOC(O)NH(CH_2)_2$ | Me | 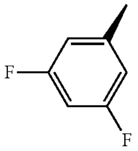 |

TABLE 35-continued

| Comp. No. | $R^{1a}$ | $R^{1b}$ | $R^{1c}$ | $R^{1d}$ |
|---|---|---|---|---|
| 37 | Me | $MeOC(O)NH(CH_2)_2$ | Me | 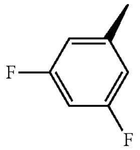 |
| 38 | OMe | $MeO(CH_2)_4$ | Me | Me |
| 39 | Me | $NC(CH_2)_4$ | Me | Me |
| 40 | ME | $Me_2NC(O)O(CH_2)_2$ | Me | Me |
| 41 | Br | $MeO(CH_2)_4$ | Me | $MeCH_2OCH_2$ |
| 42 | Me | $MeO(CH_2)_4$ | Me | $MeCH_2OCH_2$ |
| 43 | Cl | $MeO(CH_2)_4$ | 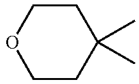 | |
| 44 | Me | $CH_3C(O)NH(CH_2)_2$ | Me | Me |
| 45 | Me | $CH_3S(O)_2NH(CH_2)_2$ | Me | Me |
| 46 | Me | 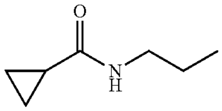 | Me | Me |
| 47 | Br | $MeO(CH_2)_4$ | 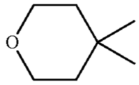 | |
| 48 | Me | $MeO(CH_2)_4$ | 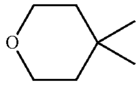 | |

TABLE 36

| Comp. No. | $R^{1a}$ | $R^{1b}$ | $R^{1c}$ | $R^{1d}$ |
|---|---|---|---|---|
| 49 | Me | $MeO(CH_2)_4$ | Me | EtO 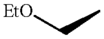 |
| 50 | Me | $CH_3CH_2C(O)NH(CH_2)_2$ | Me | Me |
| 51 | Me | $CH_3(CH_2)_5$ | Me | Me |
| 52 | Me | 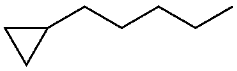 | Me | Me |
| 53 | Me | 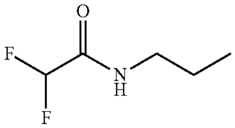 | Me | Me |
| 54 | Cl | $CH_3CH_2C(O)NH(CH_2)_2$ | Me | Me |
| 55 | Cl | 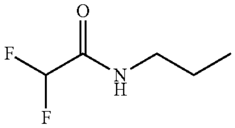 | Me | Me |
| 56 | Cl | 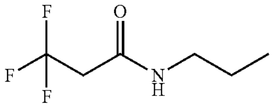 | Me | Me |

TABLE 36-continued
| Comp. No. | $R^{1a}$ | $R^{1b}$ | $R^{1c}$ | $R^{1d}$ |
|---|---|---|---|---|
| 57 | Me | $CH_3OC(O)NH(CH_2)_2$ | | 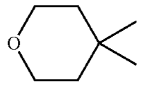 |
| 58 | Me | $MeO(CH_2)_4$ | Me | $MeOCH_2$ |
| 59 | Me | $MeO(CH_2)_4$ | Me | $CH_3CH_2NHC(O)OCH_2$ |
| 60 | Me | $MeO(CH_2)_4$ | Me | 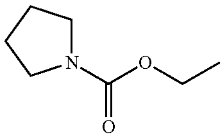 |
TABLE 37
| Comp. No. | $R^{1a}$ | $R^{1b}$ | $R^{1c}$ | $R^{1d}$ |
|---|---|---|---|---|
| 61 | $CF_3$ | 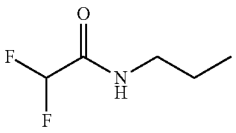 | Me | Me |
| 62 | Me | $MeO(CH_2)_4$ | Me | 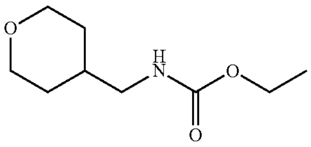 |
| 63 | $CF_3$ | 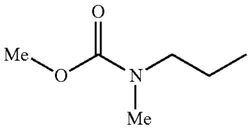 | Me | Me |
| 64 | Me | $MeO(CH_2)_4$ | 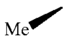 | 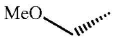 |
| 65 | Me | $MeO(CH_2)_4$ | 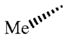 | 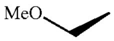 |
| 66 | $CF_3$ | $MeO(CH_2)_4$ | 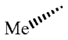 | H |
| 67 | Me | $CH_3CH_2C(O)(CH_2)_3$ | Me | Me |
| 68 | $CF_3$ | $MeO(CH_2)_4$ | Me | Me |
| 69 | $CF_3$ | $MeO(CH_2)_3$ | Me | $MeOCH_2$ |
| 70 | Me | $HO(CH_2)_4$ | Me | Me |
| 71 | $CF_3$ | $MeOC(O)NH(CH_2)_2$ | Me | Et |

TABLE 38
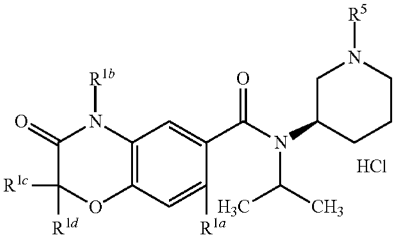
| Comp. No. | R[1a] | R[1b] | R[1c] | R[1d] |
|---|---|---|---|---|
| 72 | $CF_3$ | $CH_3CH_2C(O)NH(CH_2)_2$ | Me | Me |
| 73 | $CF_3$ | $MeO(CH_2)_4$ | 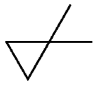 | |
| 74 | $CF_3$ | $CH_3OC(O)NH(CH_2)_2$ | 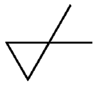 | |
| 75 | $CF_3$ | $CH_3CH_2C(S)NH(CH_2)_2$ | Me | Me |
| 76 | Me | 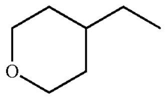 | Me | Me |
| 77 | $CF_3$ | $MeO(CH_2)_4$ | 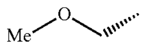 | 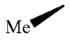 |
| 78 | $CF_3$ | $MeO(CH_2)_4$ | 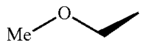 | 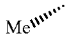 |
| 79 | Et | $MeO(CH_2)_4$ | Me | Me |
| 80 | Et | $CH_3OC(O)NH(CH_2)_2$ | Me | Me |
| 81 | Me | 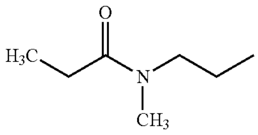 | Me | Me |
| 82 | Me | $CH_3NHC(O)(CH_2)_3$ | Me | Me |
| 83 | Me | $CH_3CH_2NHC(O)(CH_2)_3$ | Me | Me |
| 84 | Me | $CH_3(CH_2)_2NHC(O)(CH_2)_2$ | Me | Me |
| 85 | Me | 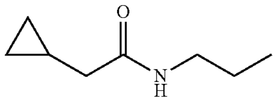 | Me | Me |
| 86 | Me | 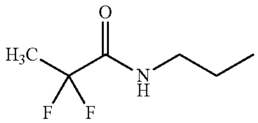 | Me | Me |
| 87 | Et | $CH_3CH_2C(O)NH(CH_2)_2$ | Me | Me |
| 88 | Et | 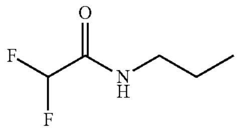 | Me | Me |
| 89 | $CHF_2$ | $MeO(CH_2)_4$ | Me | Me |

TABLE 39
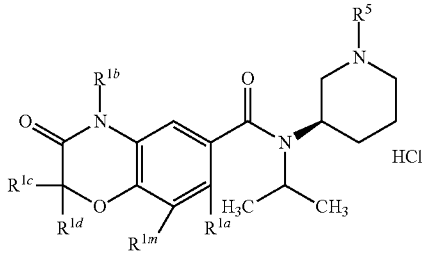
| Ex. No. | $R^{1a}$ | $R^{1m}$ | $R^{1b}$ | $R^{1c}$ | $R^{1d}$ |
|---|---|---|---|---|---|
| 90 | $CHF_2$ | F | $MeO(CH_2)_4$ | Me | Me |
| 91 | Me | H | 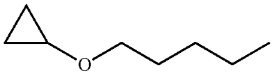 | Me | Me |
| 92 | Me | H | 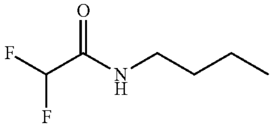 | Me | Me |
| 93 | $CF_3$ | H | 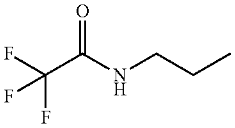 | Me | Me |
| 94 | Et | H | $MeO(CH_2)_4$ | H | 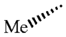 |
| 95 | $CF_3$ | H | $CH_3CH_2C(O)NH(CH_2)_2$ | | 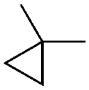 |
| 96 | $CF_3$ | H | $MeOC(O)NH(CH_2)_2$ | H | 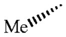 |
| 97 | Me | H | $MeO(CH_2)_4$ | H | 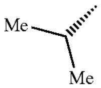 |
| 98 | Me | H | 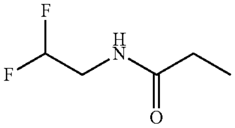 | Me | Me |
| 99 | Me | H | $CH_3CH_2C(O)NH(CH_2)_2$ | | 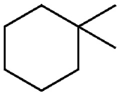 |
| 100 | Me | H | $CH_3C(O)NH(CH_2)_3$ | Me | Me |

TABLE 40
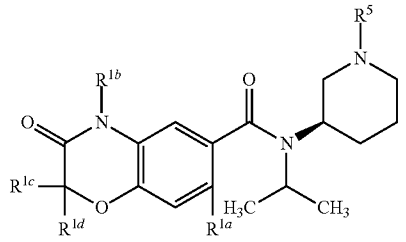
| Comp. No. | $R^{1a}$ | $R^{1b}$ | $R^{1c}$ | $R^{1d}$ |
|---|---|---|---|---|
| 101 | Me | 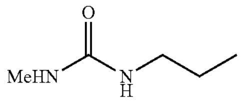 | Me | Me |
| 102 | $CF_3$ | 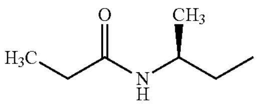 | Me | Me |
| 103 | Et | $CH_3C(O)NH(CH_2)_2$ | H | 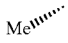 |
| 104 | Et | $CH_3CH_2C(O)NH(CH_2)_2$ | H | 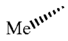 |
| 105 | Et | $HC(O)NH(CH_2)_2$ | H | 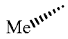 |
| 106 | $CF_3$ | 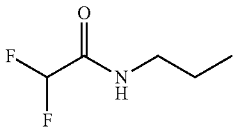 | Me | Me |
| 107 | Me | $CF_3(CH_2)_3$ | Me | Me |
| 108 | Me | $CF_3(CH_2)_4$ | Me | Me |
| 109 | Me | $CH_3CH_2C(O)NH(CH_2)_2$ | 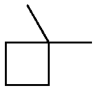 | |
| 110 | $CF_3$ | 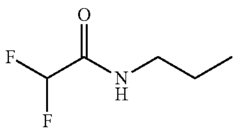 | 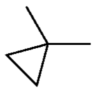 | |
| 111 | $CF_3$ | $EtOC(O)(CH_2)_2$ | Me | Me |
| 112 | $CF_3$ | $EtNHC(O)(CH_2)_2$ | Me | Me |
TABLE 41
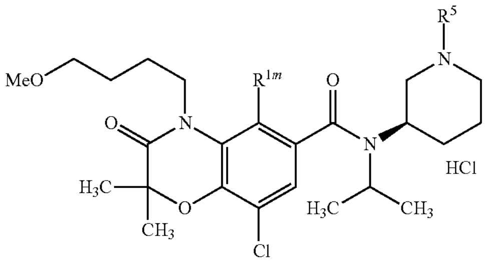
| Comp. No. | $R^{1m}$ |
|---|---|
| 113 | H |
| 114 | Cl |
| 115 | Br |
TABLE 42
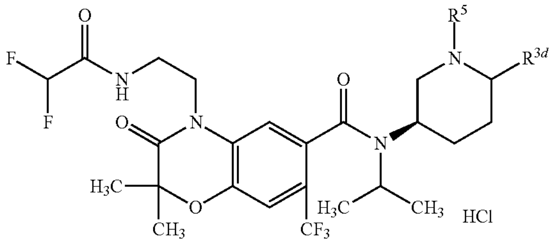
| Comp. No. | $R^{3d}$ |
|---|---|
| 116 | 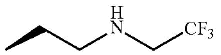 |
| 117 | 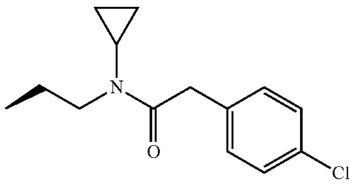 |
| 118 | 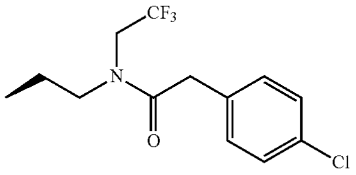 |
| 119 | 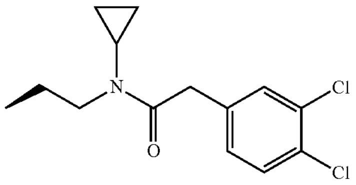 |
| 120 | 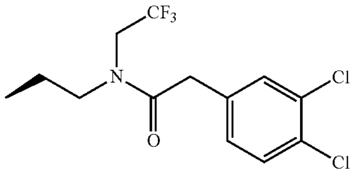 |
| 121 | 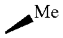 |
| 122 | 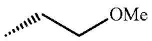 |

TABLE 43
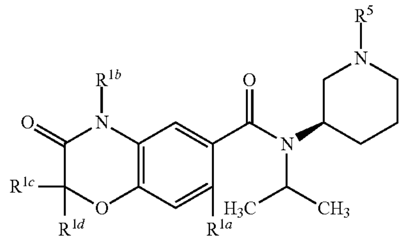
| Comp. No. | $R^{1a}$ | $R^{1b}$ | $R^{1c}$ | $R^{1d}$ |
|---|---|---|---|---|
| 123 | $CF_3$ | $MeNHC(O)(CH_2)_2$ | Me | Me |
| 124 | $CF_3$ | $FCH_2CH_2NHC(O)(CH_2)_2$ | Me | Me |
| 125 | $CF_3$ | $F_2CHCH_2NHC(O)(CH_2)_2$ | Me | Me |
| 127 | $CF_3$ | $CH_3CH_2C(O)NH(CH_2)_2$ | 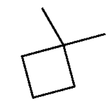 | |
| 129 | $CF_3$ | 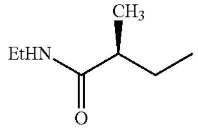 | Me | Me |
| 130 | $CF_3$ | 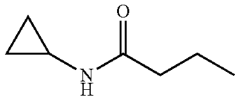 | Me | Me |
| 131 | Et | $EtOC(O)NH(CH_2)_2$ | Me | Me |
| 132 | Et | $CH_3(CH_2)_2C(O)NH(CH_2)_2$ | Me | Me |
TABLE 44
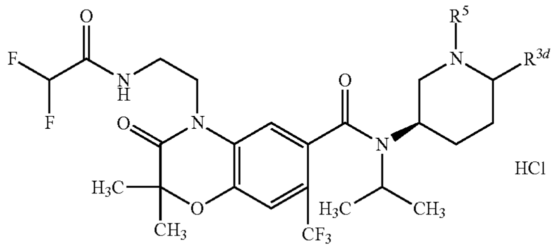
| Comp. No. | $R^{3d}$ |
|---|---|
| 133 | 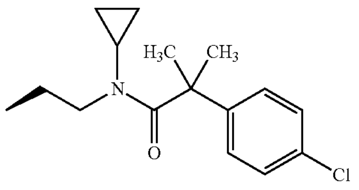 |
| 134 | 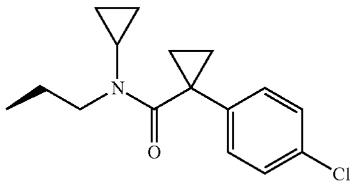 |
TABLE 45
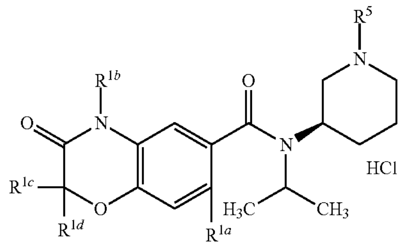
| Comp. No. | $R^{1a}$ | $R^{1b}$ | $R^{1c}$ | $R^{1d}$ |
|---|---|---|---|---|
| 135 | Me | $CH_3CH_2C(O)NH(CH_2)_2$ | 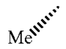 | 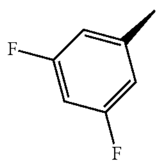 |
| 136 | $CF_3$ | $CH_3CH_2C(O)NH(CH_2)_2$ | 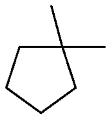 | |
| 137 | $CF_3$ | $FCH_2C(O)NH(CH_2)_2$ | Me | Me |
TABLE 46
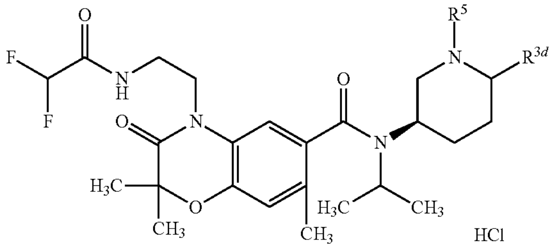
| Comp. No. | $R^{3d}$ |
|---|---|
| 138 | 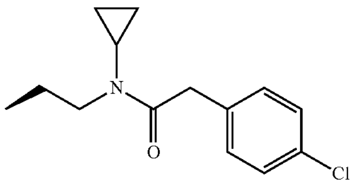 |
| 139 | 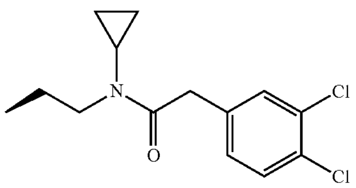 |
| 140 | 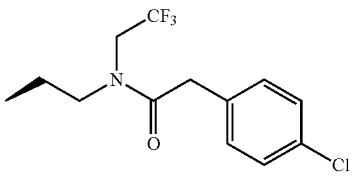 |

TABLE 47

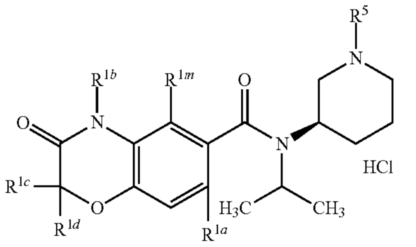

| Comp. No. | $R^{1a}$ | $R^{1m}$ | $R^{1b}$ | $R^{1c}$ | $R^{1d}$ |
|---|---|---|---|---|---|
| 141 | Me | H | $CH_3CH_2C(O)NH(CH_2)_2$ | F | F |
| 142 | H | Me | $CH_3CH_2C(O)NH(CH_2)_2$ | Me | Me |
| 143 | $CF_3$ | H | $CH_3CH_2C(O)NH(CH_2)_2$ | 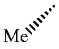 | 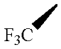 |
| 144 | $CF_3$ | H | $MeOC(O)NH(CH_2)_2$ | 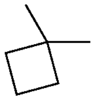 | |

TABLE 47-continued

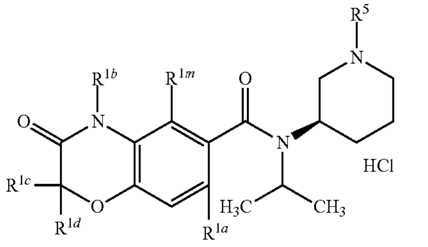

| Comp. No. | $R^{1a}$ | $R^{1m}$ | $R^{1b}$ | $R^{1c}$ | $R^{1d}$ |
|---|---|---|---|---|---|
| 145 | $CF_3$ | H | 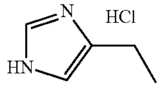 HCl | Me | Me |
| 146 | Cl | H | $CH_3CH_2C(O)NH(CH_2)_2$ | Me | Ph |
| 147 | Me | H | $CH_3CH_2C(O)NH(CH_2)_2$ | Me | Ph |
| 148 | $CF_3$ | H | $MeOC(O)NH(CH_2)_2$ | 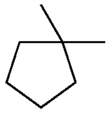 | |

TABLE 48

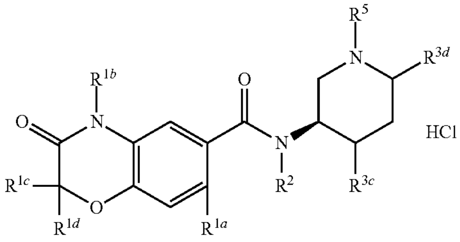

| Comp. No. | $R^{1a}$ | $R^{1b}$ | $R^{1c}$ | $R^{1d}$ | $R^2$ | $R^{3c}$ | $R^{3d}$ |
|---|---|---|---|---|---|---|---|
| 149 | $CF_3$ | $CH_3CH_2C(O)NH(CH_2)_2$ | Me | Me | H | H | H |
| 150 | $CF_3$ | $CH_3CH_2C(O)NH(CH_2)_2$ | Me | Me | Et | H | H |
| 151 | $CF_3$ | $CH_3CH_2C(O)NH(CH_2)_2$ | Me | Me | 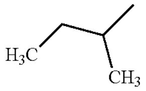 | H | H |
| 152 | $CF_3$ | $CH_3CH_2C(O)NH(CH_2)_2$ | Me | Me | Bn | H | H |
| 153 | $CF_3$ | $CH_3CH_2C(O)NH(CH_2)_2$ | Me | Ph | i-Pr | H | H |
| 154 | $CF_3$ | $CH_3O(CH_2)_4$ | Me | Me | H | H | H |
| 155 | $CF_3$ | $CH_3O(CH_2)_4$ | Me | Me | H | 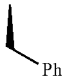 | H |
| 156 | $CF_3$ | $CH_3O(CH_2)_4$ | Me | Me | H | 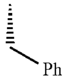 | H |
| 157 | $CF_3$ | $CH_3O(CH_2)_4$ | Me | Me | Me | H | H |
| 158 | $CF_3$ | $CH_3O(CH_2)_4$ | Me | Me | Me | 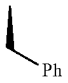 | H |
| 159 | $CF_3$ | $CH_3O(CH_2)_4$ | Me | Me | Me | 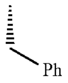 | H |

TABLE 48-continued

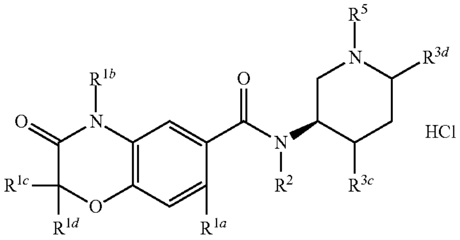

| Comp. No. | $R^{1a}$ | $R^{1b}$ | $R^{1c}$ | $R^{1d}$ | $R^2$ | $R^{3c}$ | $R^{3d}$ |
|---|---|---|---|---|---|---|---|
| 160 | $CF_3$ | $CH_3CH_2C(O)NH(CH_2)_2$ | Me | 3-MeOPh | i-Pr | H | H |
| 161 | $CF_3$ | $CH_3CH_2C(O)NH(CH_2)_2$ | H | 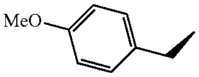 | i-Pr | H | H |
| 162 | CN | $CH_3O(CH_2)_4$ | Me | Me | i-Pr | H | H |
| 163 | Et | $CH_3O(CH_2)_4$ | | 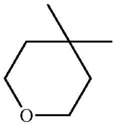 | i-Pr | H | H |
| 164 (TFAsalt) | Me | $HO_2C(CH_2)_3$ | Me | Me | i-Pr | H | H |
| 165 | Me | $CH_3(CH_2)_2O(CH_2)_2$ | Me | Me | i-Pr | H | H |
| 166 | Me | $CH_3CH_2CO_2CH_2CH_2$ | Me | Me | i-Pr | H | H |
| 167 | $CF_3$ | $CH_3O(CH_2)_4$ | H | 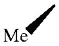 | i-Pr | H | H |
| 168 | $CF_3$ | 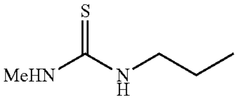 | Me | Me | i-Pr | H | 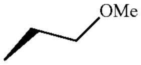 |
| 169 | $CF_3$ | $CH_3CH_2C(O)NH(CH_2)_2$ | H | 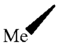 | i-Pr | H | H |

TABLE 49

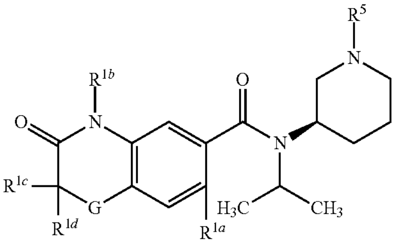

TABLE 49-continued

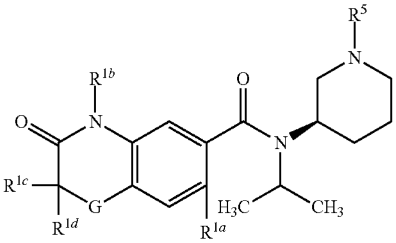

| Comp. No. | G | $R^{1a}$ | $R^{1b}$ | $R^{1c}$ | $R^{1d}$ |
|---|---|---|---|---|---|
| 170 | S | Me | $CH_3C(O)NH(CH_2)_2$ | Me | Me |
| 171 | S | Me | $MeO(CH_2)_4$ | Me | H |
| 172 | S | Me | $CH_3CH_2C(O)NH(CH_2)_2$ | Me | Me |
| 173 | S | $CF_3$ | $MeOC(O)NH(CH_2)_2$ | 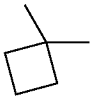 | |
| 174 | S | $CF_3$ | $CH_3CH_2C(O)NH(CH_2)_2$ | 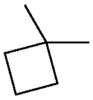 | |
| 175 | S | $CF_3$ | $MeOC(O)NH(CH_2)_2$ | 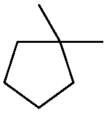 | |

TABLE 49-continued

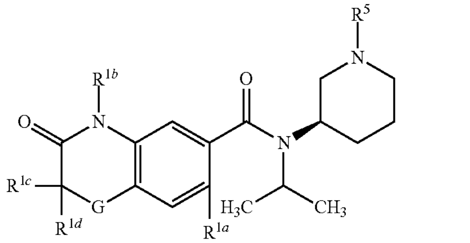

| Comp. No. | G | $R^{1a}$ | $R^{1b}$ | $R^{1c}$ | $R^{1d}$ |
|---|---|---|---|---|---|
| 176 | S | $CF_3$ | $CH_3CH_2C(O)NH(CH_2)_2$ | 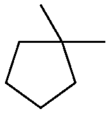 | |
| 177 | S | $CF_3$ | $MeO(CH_2)_4$ | $MeOCH_2$ | Me |
| 178 | S | $CF_3$ | $MeO(CH_2)_4$ | Me | H |
| 179 | S | Me | $MeOC(O)NH(CH_2)_2$ | Me | H |
| 180 | S | Me | $CH_3CH_2C(O)NH(CH_2)_2$ | Me | H |
| 181 | $SO_2$ | Me | $MeO(CH_2)_4$ | Me | Me |
| 182 | S | $CF_3$ | $CH_3CH_2C(O)NH(CH_2)_2$ | Me | H |
| 183 | S | $CF_3$ | $CH_3CH_2C(O)NH(CH_2)_2$ | Me | Me |
| 184 | S | Me | $MeOC(O)NH(CH_2)_2$ | 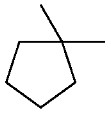 | |

TABLE 50

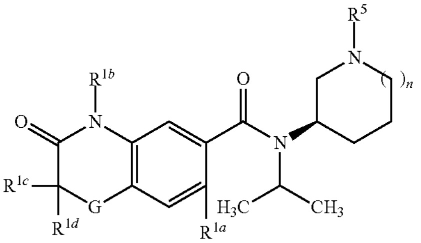

| Comp. No. | G | $R^{1a}$ | $R^{1b}$ | $R^{1c}$ | $R^{1d}$ | n |
|---|---|---|---|---|---|---|
| 185 | $CH_2$ | Cl | $MeO(CH_2)_4$ | Me | Me | 1 |
| 186 | $CH_2$ | Me | $MeO(CH_2)_4$ | Me | Me | 1 |
| 187 | $CH_2$ | Br | $MeOC(O)NH(CH_2)_2$ | Me | Me | 1 |
| 189 | $CH_2$ | Cl | $MeOC(O)NH(CH_2)_2$ | Me | Me | 1 |
| 190 | $CMe_2$ | Me | $MeO(CH_2)_4$ | H | H | 1 |
| 191 | $CH_2$ | Me | $MeOC(O)NH(CH_2)_2$ | Me | Me | 1 |
| 192 | $CH_2$ | Et | $MeOC(O)NH(CH_2)_2$ | Me | Me | 1 |
| 193 | $CH_2$ | Cl | $CH_3CH_2C(O)NH(CH_2)_2$ | Me | Me | 1 |
| 194 | $CH_2$ | Me | $CH_3CH_2C(O)NH(CH_2)_2$ | Me | Me | 1 |
| 195 | $CH_2$ | $CF_3$ | $CH_3CH_2C(O)NH(CH_2)_2$ | Me | Me | 1 |
| 196 | $CH_2$ | $CF_3$ | $CH_3CH_2C(O)NH(CH_2)_2$ | 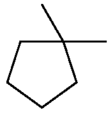 | | 1 |
| 200 | O | $CF_3$ | $MeO(CH_2)_4$ | Me | Me | 2 |
| 201 | O | $CF_3$ | $MeO(CH_2)_4$ | Me | Me | 0 |

TABLE 51

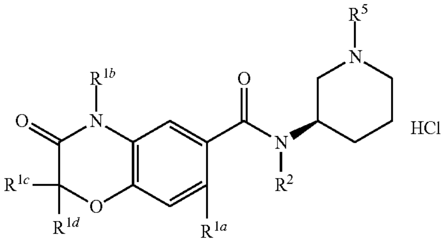

| Comp. No. | $R^{1a}$ | $R^{1b}$ | $R^{1c}$ | $R^{1d}$ | $R^2$ |
|---|---|---|---|---|---|
| 202 | $CF_3$ | $CH_3CH_2C(O)NH(CH_2)_2$ | Me | Me | 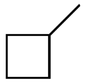 |
| 203 | $CF_3$ | $CH_3CH_2C(O)NH(CH_2)_2$ | Me | Me | 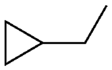 |
| 204 | $CF_3$ | $CH_3CH_2C(O)NH(CH_2)_2$ | Me | Me | 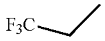 |
| 205 | $CF_3$ | $CH_3O(CH_2)_4$ | H | 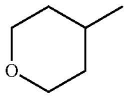 | i-Pr |
| 206 | $CF_3$ | $MeOC(O)NH(CH_2)_2$ | H | 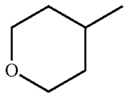 | i-Pr |
| 207 | $CF_3$ | $CH_3CH_2C(O)NH(CH_2)_2$ | Me | 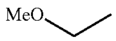 | i-Pr |

TABLE 51-continued

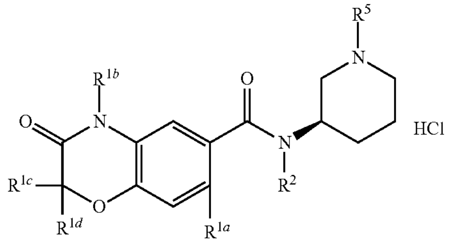

| Comp. No. | $R^{1a}$ | $R^{1b}$ | $R^{1c}$ | $R^{1d}$ | $R^2$ |
|---|---|---|---|---|---|
| 208 | $CF_3$ | $MeOC(O)NH(CH_2)_2$ | Me | 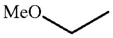 | i-Pr |
| 209 | $CF_3$ | $MeOC(O)NH(CH_2)_2$ | Me | 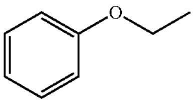 | i-Pr |
| 210 | $CF_3$ | $MeOC(O)NH(CH_2)_2$ | Me | 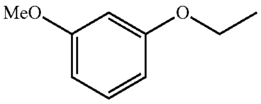 | i-Pr |
| 211 | $CF_3$ | $MeOC(O)NH(CH_2)_2$ | Me | 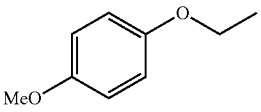 | i-Pr |
| 212 | $CF_3$ | $CH_3O(CH_2)_4$ | Me | 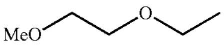 | i-Pr |
| 213 | $CF_3$ | $CH_3O(CH_2)_4$ | Me | 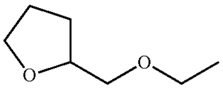 | i-Pr |
| 214 | $CF_3$ | $CH_3O(CH_2)_4$ | Me | 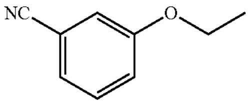 | i-Pr |
| 215 | $CF_3$ | $CH_3O(CH_2)_4$ | Me | 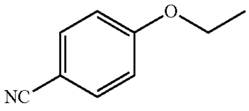 | i-Pr |
| 216 | $CF_3$ | $CH_3O(CH_2)_4$ | Me | 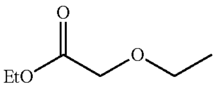 | i-Pr |
| 217 | $CF_3$ | $CH_3O(CH_2)_4$ | Me | 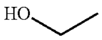 | i-Pr |
| 218 | $CF_3$ | $CH_3O(CH_2)_4$ | Me | 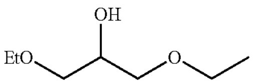 | i-Pr |
| 219 | $CF_3$ | $CH_3O(CH_2)_4$ | Me | 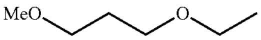 | i-Pr |
| 220 | $CF_3$ | $CH_3O(CH_2)_4$ | Me | 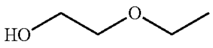 | i-Pr |
| 221 | $CF_3$ | $CH_3O(CH_2)_4$ | Me | 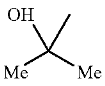 | i-Pr |
| 222 | $CF_3$ | $CHF_2C(O)NH(CH_2)_2$ | Me | 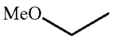 | i-Pr |

TABLE 51-continued

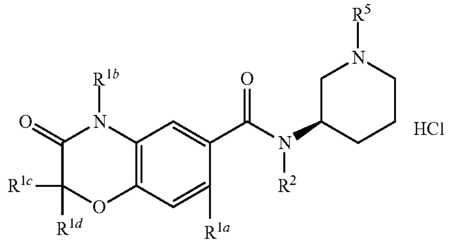

| Comp. No. | $R^{1a}$ | $R^{1b}$ | $R^{1c}$ | $R^{1d}$ | $R^2$ |
|---|---|---|---|---|---|
| 223 | $CF_3$ | $CHF_2C(O)NH(CH_2)_2$ | Me | 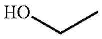 | i-Pr |

TABLE 52

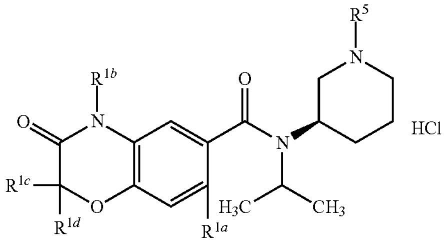

| Comp. No. | $R^{1a}$ | $R^{1b}$ | $R^{1c}$ | $R^{1d}$ |
|---|---|---|---|---|
| 224 | $CF_3$ | $CH_3CH_2C(O)NH(CH_2)_2$ | Me | 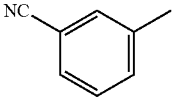 |
| 225 | $CF_3$ | $CH_3CH_2C(O)NH(CH_2)_2$ | Me | 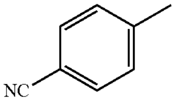 |
| 226 | $CF_3$ | $CH_3CH_2C(O)NH(CH_2)_2$ | Me | 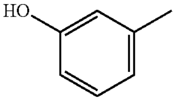 |
| 227 | $CF_3$ | $CH_3CH_2C(O)NH(CH_2)_2$ | Me | 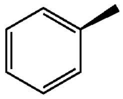 |
| 228 | $CF_3$ | $CH_3CH_2C(O)NH(CH_2)_2$ | Me | 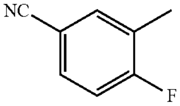 |
| 229 | $CF_3$ | $CH_3CH_2C(O)NH(CH_2)_2$ | Me | 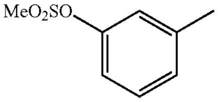 |
| 230 | $CF_3$ | $CH_3CH_2C(O)NH(CH_2)_2$ | Me | 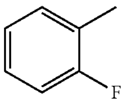 |

TABLE 52-continued

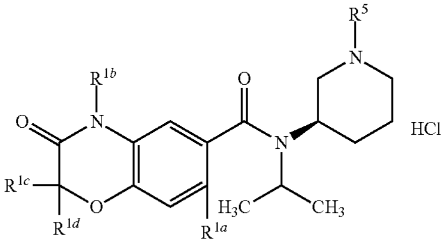

| Comp. No. | $R^{1a}$ | $R^{1b}$ | $R^{1c}$ | $R^{1d}$ |
|---|---|---|---|---|
| 231 | Me | $CH_3CH_2C(O)NH(CH_2)_2$ | Me | 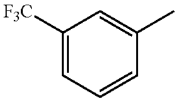 |
| 232 | Cl | $CH_3CH_2C(O)NH(CH_2)_2$ | Me | 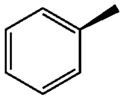 |
| 233 | Me | $CH_3CH_2C(O)NH(CH_2)_2$ | Me | 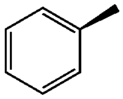 |
| 234 | $CF_3$ | $CH_3CH_2C(O)NH(CH_2)_2$ | Me | 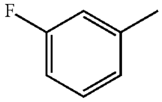 |
| 235 | Me | $CHF_2C(O)NH(CH_2)_2$ | | 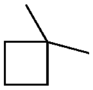 |
| 236 | Me | $CH_3CH_2C(O)NH(CH_2)_2$ | | 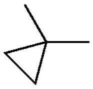 |
| 237 | Me | $CHF_2C(O)NH(CH_2)_2$ | | 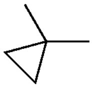 |

TABLE 53

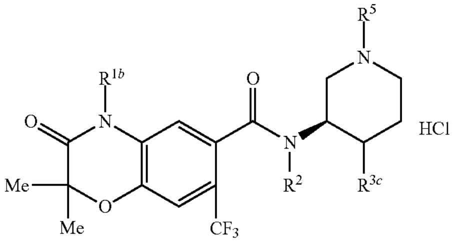

| Comp. No. | $R^{1a}$ | $R^{1b}$ | $R^2$ | $R^{3c}$ |
|---|---|---|---|---|
| 238 | $CF_3$ | $CH_3CH_2C(O)NH(CH_2)_2$ | i-Pr | 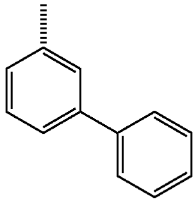 |
| 239 | $CF_3$ | $MeO(CH_2)_4$ | H | 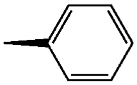 |
| 240 | $CF_3$ | $MeO(CH_2)_4$ | Et | 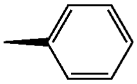 |
| 241 | $CF_4$ | $MeO(CH_2)_4$ | H | 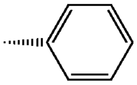 |
| 242 | $CF_3$ | $MeO(CH_2)_4$ | Et | 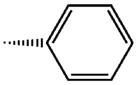 |
| 243 | $CF_3$ | $CH_3CH_2C(O)NH(CH_2)_2$ | Et | 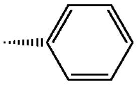 |
| 244 | F | $CH_3CH_2C(O)NH(CH_2)_2$ | Et | 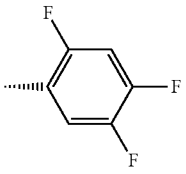 |

TABLE 54

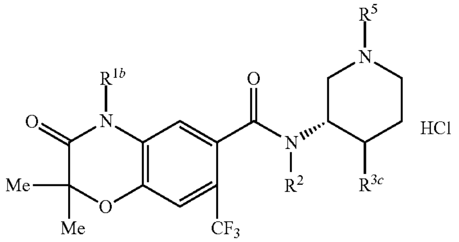

| Comp. No. | $R^{1b}$ | $R^2$ | $R^{3c}$ |
|---|---|---|---|
| 245 | $MeO(CH_2)_4$ | H | 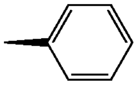 |
| 246 | $MeO(CH_2)_4$ | H | 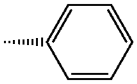 |
| 247 | $MeO(CH_2)_4$ | Et | 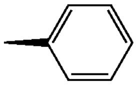 |
| 248 | $MeO(CH_2)_4$ | Et | 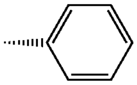 |
| 249 | $MeO(CH_2)_4$ | i-Pr | H |

TABLE 55

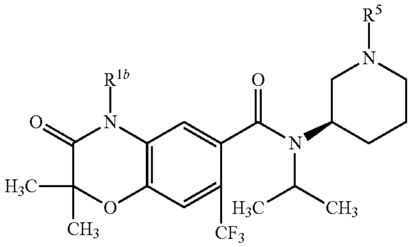

| Comp. No. | $R^{1a}$ | $R^{1b}$ | $R^{1c}$ | $R^{1d}$ |
|---|---|---|---|---|
| 250 | $CF_3$ | $CH_3CH_2CH(CF_3)NH(CH_2)_2$ | Me | Me |
| 251 | $CF_3$ | $MeOCH_2CH(OH)(CH_2)_2$ | Me | Me |
| 252 | $CF_3$ | $MeOCH_2C(O)(CH_2)_2$ | Me | Me |
| 253 | $CF_3$ | $MeOCH_2CH(OH)CH_2$ | Me | Me |
| 259 | $CH_3$ | $CHF_2C(O)NH(CH_2)_2$ | Me | Me |
| 260 | $CH_3$ | $CH_3CH_2C(O)NH(CH_2)_2$ | 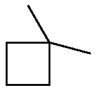 | |

TABLE 56

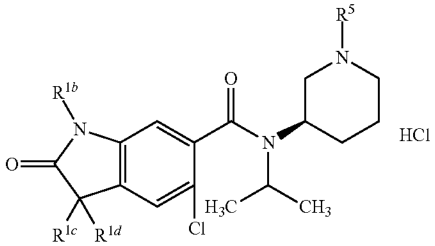

| Comp. No. | $R^{1b}$ | $R^{1c}$ | $R^{1d}$ |
|---|---|---|---|
| 254 | $MeO(CH_2)_4$ | Me | Me |
| 255 | $CH_3CH_2C(O)NH(CH_2)_2$ | Me | Me |
| 256 | $CHF_2C(O)NH(CH_2)_2$ | Me | Me |
| 257 | $CH_3CH_2C(O)NH(CH_2)_2$ | Et | Et |

Compound No. 258

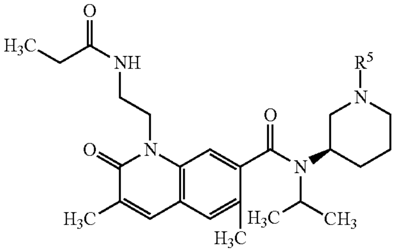

TABLE 57

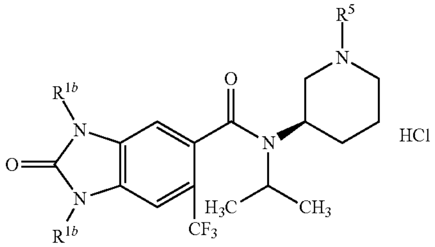

| Comp. No. | $R^{1b}$ | $R^{1b'}$ |
|---|---|---|
| 261 | $MeO(CH_2)_4$ | Et |
| 262 | $CH_3CH_2C(O)NH(CH_2)_2$ | Et |
| 263 | $CH_3C(O)NH(CH_2)_2$ | Et |
| 264 | $MeO(CH_2)_4$ | 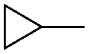 |

TABLE 58

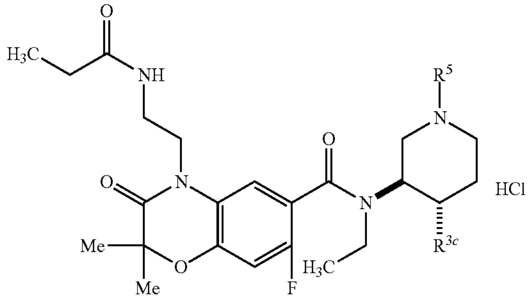

| Comp. No. | $R^{3c}$ |
|---|---|
| 265 | 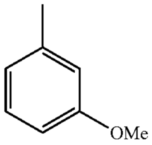 |
| 266 | 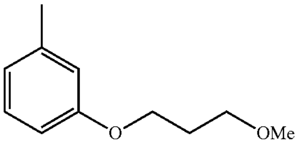 |

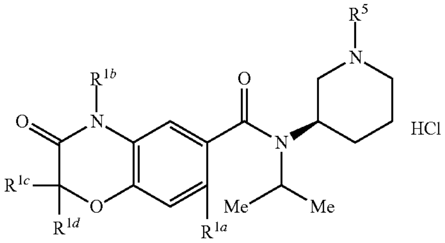

| Comp. No. | $R^{1a}$ | $R^{1b}$ | $R^{1c}$ | $R^{1d}$ |
|---|---|---|---|---|
| 267 | $CHF_2$ | $CH_3CH_2C(O)NH(CH_2)_2$ | Me | Me |
| 268 | $CHF_2$ | $CHF_2C(O)NH(CH_2)_2$ | Me | Me |
| 269 | $CF_3$ | $CH_3CH_2C(O)NH(CH_2)_2$ | Me | 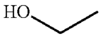 |

The above-mentioned compound Nos. 1 to 269 where $R^5$ is a hydrogen atom may be prepared according to Methods 1 to 33 as mentioned above. The analytical data of these compounds are shown in the following Tables.

TABLE 59

| Comp. No. | $^1H$ NMR (400 MHz, $CDCl_3$) |
|---|---|
| 1 | δ 9.78 (br, 2H), 7.15 (s, 1H), 6.91-6.90 (m, 1H), 4.21-4.12 (m, 1H), 3.99-3.86 (m, 3H), 3.73-3.69 (m, 1H), 3.48-3.34 (m, 4H), 3.31 (s, 3H), 2.95-2.86 (m, 2H), 2.11-2.00 (m, 2H), 1.90-1.82 (m, 3H), 1.56 (s, 3H), 1.43-1.41 (m, 3H), 1.38-1.12 (m, 6H). |
| 2 | δ 9.84 (br, 2H), 6.99 (s, 1H), 6.91 (s, 1H), 4.18 (br, 1H), 4.01-3.87 (m, 3H), 3.75-3.68 (m, 1H), 3.49-3.35 (m, 4H), 3.31 (s, 3H), 2.95-2.88 (m, 2H), 2.06-2.01 (m, 2H), 1.89-1.81 (m, 3H), 1.56 (s, 3H), 1.43-1.41 (m, 3H), 1.38-1.12 (m, 6H) |
| 3 | δ 9.83 (br, 2H), 7.22 (s, 1H), 7.06 (s, 1H), 4.18 (brs, 1H), 4.01-3.89 (m, 3H), 3.70-3.67 (m, 1H), 3.49-3.39 (m, 4H), 3.31 (s, 3H), 2.97-2.81 (m, 2H), 2.07-2.01 (m, 2H), 1.91-1.87 (m, 3H), 1.53-1.49 (m, 6H), 1.38-1.21 (m, 6H) |
| 4 | δ 9.89-9.77 (m, 2H), 6.79 (brs, 2H), 4.24-4.21 (m, 1H), 4.01-3.75 (m, 4H), 3.48-3.34 (m, 4H), 3.33-3.30 (m, 3H), 2.95-2.89 (m, 2H), 2.21-2.19 (m, 3H), 2.08-2.04 (m, 2H), 1.88-1.83 (m, 3H), 1.56 (s, 3H), 1.41-1.39 (m, 3H), 1.32-1.22 (m, 3H), 1.19-1.14 (m, 3H) |

TABLE 59-continued

| Comp. No. | $^1$H NMR (400 MHz, $CDCl_3$) |
|---|---|
| 5 | δ 9.81 (br, 2H), 6.86 (s, 1H), 6.78 (s, 1H), 4.22-4.19 (m, 1H), 3.99-3.78 (m, 4H), 3.42-3.36 (m, 4H), 3.33-3.30 (m, 3H), 2.93-2.89 (m, 2H), 2.56-2.47 (m, 2H), 2.02-1.87 (m, 5H), 1.56 (s, 3H), 1.42-1.40 (m, 3H), 1.31-1.15 (m, 9H) |
| 6 | δ 9.92-9.78 (m, 2H), 6.85-6.83 (m, 1H), 6.79-6.76 (m, 1H), 4.24-4.19 (m, 1H), 4.00-3.80 (m, 4H), 3.49-3.36 (m, 4H), 3.33-3.30 (m, 3H), 2.95-2.89 (m, 2H), 2.51-2.43 (m, 2H), 2.05-2.01 (m, 2H), 1.91-1.86 (m, 3H), 1.69-1.64 (m, 2H), 1.56 (s, 3H), 1.42-1.40 (m, 3H), 1.27-1.25 (m, 3H), 1.19-1.15 (m, 3H), 0.94 (t, J = 7.3 Hz, 3H) |
| 7 | δ 9.83 (br, 2H), 6.99-6.98 (m, 1H), 6.83-6.73 (m, 1H), 4.21-4.14 (m, 1H), 4.01-3.69 (m, 4H), 3.49-3.37 (m, 4H), 3.30 (s, 3H), 2.96-2.83 (m, 2H), 2.13-1.61 (m, 7H), 1.55 (s, 3H), 1.44 (s, 3H), 1.39-1.11 (m, 6H) |
| 8 | δ 9.87-9.85 (m, 2H), 6.79 (s, 1H), 6.70-6.62 (m, 1H), 4.24-4.20 (m, 1H), 3.99-3.95 (m, 1H), 3.86-3.75 (m, 3H), 3.48-3.32 (m, 4H), 3.29 (s, 3H), 2.93-2.88 (m, 2H), 2.20-2.18 (m, 3H), 2.12-1.59 (m, 7H), 1.54 (s, 3H), 1.41 (s, 3H), 1.30-1.13 (m, 6H) |
| 9 | δ 9.84-9.48 (m, 2H), 7.01 (s, 1H), 6.78-6.68 (m, 1H), 4.18-4.14 (m, 1H), 4.00-3.85 (m, 3H), 3.74-3.70 (m, 1H), 3.49-3.38 (m, 6H), 2.95-2.84 (m, 2H), 2.15-2.04 (m, 2H), 1.89-1.82 (m, 3H), 1.56 (s, 3H), 1.43-1.41 (m, 3H), 1.35-0.86 (m, 9H) |

TABLE 60

| | |
|---|---|
| 10 | δ 9.75 (br, 2H), 7.21-7.13 (m, 2H), 5.75 (brs, 0.5H), 5.04 (brs, 0.5H), 4.16-4.09 (m, 2H), 3.91-3.86 (m, 2H), 3.75-3.70 (m, 2H), 3.63-3.59 (m, 3H), 3.48-3.37 (m, 3H), 2.93-2.76 (m, 2H), 2.09-1.92 (m, 3H), 1.54 (s, 3H), 1.44 (s, 3H), 1.38-1.15 (m, 6H) |
| 11 | δ 9.87 (br, 2H), 7.26-7.21 (m, 1H), 6.99-6.97 (m, 1H), 5.67 (brs, 0.5H), 4.99 (brs, 0.5H), 4.15-4.11 (m, 2H), 3.96-3.88 (m, 2H), 3.72-3.66 (m, 2H), 3.59 (s, 3H), 3.48-3.38 (m, 3H), 2.94-2.79 (m, 2H), 2.09-1.90 (m, 3H), 1.54 (s, 3H), 1.43 (s, 3H), 1.37-1.30 (m, 3H), 1.24-1.15 (m, 3H) |
| 12 | δ 9.85 (br, 2H), 7.07-7.03 (m, 1H), 6.78 (s, 1H), 5.69 (brs, 0.5H), 5.04 (brs, 0.5H), 4.19-3.70 (m, 6H), 3.62-3.60 (m, 3H), 3.48-3.39 (m, 3H), 2.94-2.83 (m, 2H), 2.21-2.18 (m, 3H), 2.09-2.02 (m, 2H), 1.89-1.86 (m, 1H), 1.53 (s, 3H), 1.41 (s, 3H), 1.36-1.30 (m, 3H), 1.20-1.16 (m, 3H) |
| 13 | δ 9.86-9.76 (m, 2H), 7.00-6.98 (m, 1H), 6.90-6.87 (m, 1H), 4.20-4.16 (m, 1H), 3.99-3.85 (m, 3H), 3.78-3.69 (m, 1H), 3.49-3.36 (m, 4H), 3.32-3.30 (m, 3H), 2.95-2.84 (m, 2H), 2.16-1.78 (m, 7H), 1.52-1.39 (m, 3H), 1.37-1.12 (m, 6H), 1.01-0.89 (m, 3H) |
| 14 | δ 9.95-9.68 (br, 2H), 7.15-7.12 (m, 1H), 6.98-6.86 (m, 1H), 4.28-4.11 (m, 1H), 4.10-3.61 (m, 4H), 3.59-3.35 (m, 4H), 3.32-3.28 (m, 3H), 3.03-2.83 (m, 2H), 2.26-1.61 (m, 7H), 1.54-1.41 (m, 3H), 1.40-1.11 (m, 6H), 1.05-0.87 (m, 3H) |
| 15 | δ 9.83-9.68 (br, 2H), 7.25-7.12 (m, 1H), 6.98-6.90 (m, 1H), 4.18-4.04 (m, 1H), 4.02-3.77 (m, 3H), 3.70-3.58 (m, 1H), 3.47-3.25 (m, 4H), 3.23-3.17 (m, 3H), 2.92-2.72 (m, 2H), 2.15-1.72 (m, 7H), 1.70-1.60 (m, 3H), 1.53-1.15 (m, 6H), 0.97-0.83 (m, 3H) |
| 16 | δ 10.0-9.60 (br, 2H), 7.05-7.01 (m, 1H), 7.00-6.92 (m, 1H), 4.74-4.55 (m, 1H), 4.39-3.65 (m, 5H), 3.55-3.33 (m, 4H), 3.32-3.28 (m, 3H), 3.03-2.80 (m, 2H), 2.21-1.68 (m, 5H), 1.63-1.50 (m, 3H), 1.40-1.12 (m, 6H) |
| 17 | δ 9.95-9.60 (br, 2H), 7.13-7.11 (m, 1H), 6.89-6.83 (m, 1H), 4.68-4.48 (m, 1H), 4.18-3.52 (m, 5H), 3.45-3.28 (m, 4H), 3.26-3.23 (m, 3H), 2.95-2.75 (m, 2H), 2.15-1.71 (m, 5H), 1.55-1.40 (m, 3H), 1.38-1.02 (m, 6H) |
| 18 | δ 9.99-9.68 (br, 2H), 6.87-6.81 (m, 2H), 4.72-4.50 (m, 1H), 4.30-3.71 (m, 5H), 3.53-3.33 (m, 4H), 3.33-3.27 (m, 3H), 3.01-2.86 (m, 2H), 2.29-2.18 (m, 3H), 2.17-1.68 (m, 5H), 1.63-1.47 (m, 3H), 1.40-1.11 (m, 6H). MS (ESI+) 418 ($M^+$ + 1, 100%). |

TABLE 61

| | |
|---|---|
| 19 | δ 10.1-9.77 (br, 2H), 7.25-7.16 (m, 1H), 7.05-7.03 (m, 1H), 4.73-4.56 (m, 1H), 4.30-3.63 (m, 5H), 3.54-3.36 (m, 4H), 3.35-3.28 (m, 3H), 3.02-2.80 (m, 2H), 2.22-1.80 (m, 3H), 1.75-1.50 (m, 7H), 1.41-1.08 (m, 6H) |
| 20 | δ 10.2-9.65 (br, 2H), 7.22-7.18 (m, 1H), 7.05-6.86 (m, 1H), 4.72-4.55 (m, 1H), 4.31-3.60 (m, 5H), 3.55-3.38 (m, 4H), 3.33-3.28 (m, 3H), 3.04-2.73 (m, 2H), 2.23-1.50 (m, 10H), 1.49-1.10 (m, 6H) |
| 21 | δ 9.88-9.66 (br, 2H), 6.93-6.84 (m, 1H), 6.76-6.74 (m, 1H), 4.62-4.43 (m, 1H), 4.22-3.64 (m, 5H), 3.45-3.27 (m, 4H), 3.25-3.18 (m, 3H), 2.95-2.81 (m, 2H), 2.17-2.11 (m, 3H), 2.10-1.72 (m, 3H), 1.70-1.35 (m, 7H), 1.28-1.02 (m, 6H) |
| 22 | δ 9.95-9.58 (br, 2H), 7.26-7.17 (m, 1H), 7.04-7.01 (m, 1H), 5.83 (brs, 0.5H), 5.06 (brs, 0.5H), 4.75-4.57 (m, 1H), 4.27-4.10 (m, 2H), 4.08-3.82 (m, 2H), 3.80-3.65 (m, 2H), 3.65-3.50 (m, 3H), 3.49-3.28 (m, 3H), 3.05-2.80 (m, 2H), 2.18-1.85 (m, 3H), 1.65-1.46 (m, 3H), 1.43-1.11 (m, 6H) |

TABLE 61-continued

| | |
|---|---|
| 23 | δ 9.90-9.61 (br, 2H), 7.33-7.18 (m, 2H), 5.35 (brs, 0.5H), 5.04 (brs, 0.5H), 4.75-4.55 (m, 1H), 4.23-4.03 (m, 2H), 4.02-3.83 (m, 2H), 3.78-3.33 (m, 8H), 3.02-2.72 (m, 2H), 2.08-1.88 (m, 3H), 1.63-1.52 (m, 3H), 1.47-1.13 (m, 6H) |
| 24 | δ 9.95-9.65 (br, 2H), 7.20-7.05 (m, 1H), 6.83-6.80 (m, 1H), 5.70 (brs, 0.5H), 5.01 (brs, 0.5H), 4.71-4.53 (m, 1H), 4.32-3.71 (m, 6H), 3.70-3.51 (m, 3H), 3.50-3.28 (m, 3H), 2.98-2.75 (m, 2H), 2.28-2.12 (m, 3H), 2.10-1.88 (m, 3H), 1.64-1.45 (m, 3H), 1.43-1.10 (m, 6H) |
| 25 | δ 9.95-9.70 (br, 2H), 7.05-7.02 (m, 1H), 6.98-6.90 (m, 1H), 4.58-4.43 (m, 1H), 4.28-3.65 (m, 5H), 3.53-3.34 (m, 4H), 3.32-3.30 (m, 3H), 3.03-2.71 (m, 2H), 2.23-1.73 (m, 7H), 1.42-1.12 (m, 6H), 1.11-1.03 (m, 3H) |
| 26 | δ 9.95-9.70 (br, 2H), 7.03-6.98 (m, 1H), 6.87-6.67 (m, 1H), 4.30-3.43 (m, 10H), 3.42-3.33 (m, 3H), 3.32-3.25 (m, 3H), 3.07-2.80 (m, 2H), 2.28-1.61 (m, 7H), 1.55-1.38 (m, 3H), 1.37-1.12 (m, 6H), 1.11-1.03 (m, 3H) |

TABLE 62

| Comp. No. | $^1$H NMR (300 or 400 MHz, solvent)/MS (ESI+) |
|---|---|
| 27 | (400 MHz, DMSO-$d_6$) δ 9.10-8.71 (br, 2H), 7.41-7.13 (m, 2H), 4.13-3.99 (m, 1H), 3.95-3.73 (m, 2H), 3.72-2.93 (m, 10H), 2.95-2.49 (m, 7H), 1.95-1.64 (m, 3H), 1.62-1.31 (m, 7H), 1.25-1.15 (m, 6H) |
| 28 | (400 MHz, DMSO-$d_6$) δ 9.21-8.91 (br, 2H), 7.48-7.13 (m, 2H), 4.11-3.98 (m, 1H), 3.95-3.73 (m, 2H), 3.72-3.22 (m, 13H), 3.20-3.05 (m, 1H), 3.18 (s, 3H), 2.84-2.51 (m, 2H), 2.04-1.73 (m, 3H), 1.61-1.30 (m, 7H), 1.24-1.03 (m, 6H) |
| 29 | (400 MHz, $CDCl_3$) δ 9.87-9.23 (br, 2H), 7.08-6.65 (m, 2H), 4.23-2.48 (m, 20H), 2.31-1.38 (m, 18H), 1.37-0.97 (m, 6H) |
| 30 | RT 3.739 min (Shim-pack XR-ODS, 0.1% trifluoroacetic acid in water/acetonitrile, acetonitrile 30-90% 5.7 min, 1.0 ml/min). MS (ESI+) 579 ($M^+$ + 1, 100%). |
| 31 | (400 MHz, $CDCl_3$) δ 9.98-9.45 (br, 2H), 6.96-6.92 (m, 1H), 6.82-6.57 (m, 1H), 4.21-3.99 (m, 1H), 3.98-3.71 (m, 4H), 3.70-3.42 (m, 4H), 3.33 (s, 3H), 3.35-3.25 (m, 2H), 3.23 (s, 3H), 2.95-2.68 (m, 2H), 2.20-1.88 (m, 3H), 1.87-1.46 (m, 7H), 1.39-0.98 (m, 6H) |
| 32 | RT 3.548 min (Shim-pack XR-ODS, 0.1% trifluoroacetic acid in water/acetonitrile, acetonitrile 30-90% 5.7 min, 1.0 ml/min). MS (ESI+) 486 ($M^+$ + 1, 100%). |
| 33 | (400 MHz, DMSO-$d_6$) δ 9.18-9.72 (m, 2H), 7.08-7.26 (m, 2H), 2.50-4.22 (m, 17H), 1.28-1.97 (m, 10H), 0.97-1.22 (m, 6H) |
| 34 | (400 MHz, DMSO-$d_6$) δ 8.78-9.50 (m, 2H), 7.50 (brs, 1H), 7.24-7.42 (m, 2H), 2.96-3.98 (m, 12H), 2.52-2.85 (m, 2H), 1.60-1.96 (m, 3H), 1.48 (s, 3H), 1.42 (s, 3H), 0.98-1.19 (m, 6H) |
| 35 | RT 3.487 min (Shim-pack XR-ODS, 0.1% trifluoroacetic acid in water/acetonitrile, acetonitrile 30-90% 5.7min, 1.0 ml/min). MS (ESI+) 510 ($M^+$ + 1, 100%). |
| 36 | RT 3.894 min (Shim-pack XR-ODS, 0.1% trifluoroacetic acid in water/acetonitrile, acetonitrile 30-90% 5.7min, 1.0 ml/min). MS (ESI+) 623 ($M^+$ + 1, 100%). |
| 37 | RT 3.702 min (Shim-pack XR-ODS, 0.1% trifluoroacetic acid in water/acetonitrile, acetonitrile 30-90% 5.7min, 1.0 ml/min). MS (ESI+) 559 ($M^+$ + 1, 100%). |
| 38 | (300 MHz, DMSO-$d_6$) δ 9.39 (m, 1H), 7.00-6.89 (m, 1H), 6.78-6.75 (m, 1H), 3.95-3.60 (m, 7H), 3.38-3.02 (m, 8H), 2.73-2.51 (m, 3H), 1.91-1.65 (m, 3H), 1.49-1.37 (m, 10H), 1.16-1.01 (m, 5H) |
| 39 | (300 MHz, DMSO-$d_6$) δ 9.04 (m, 1H), 7.06-6.97 (m, 1H), 6.90 (m, 1H), 4.05-3.60 (m, 5H), 3.33-3.18 (m, 4H), 2.13 (s, 3H), 1.91-1.73 (m, 3H), 1.56-0.84 (m, 18H) |

TABLE 63

| | |
|---|---|
| 40 | (300 MHz, DMSO-$d_6$) δ 9.23 (m, 1H), 7.10-7.03 (m, 1H), 6.90 (m, 1H), 3.84-3.59 (m, 2H), 3.34-3.05 (m, 2H), 2.75-2.70 (m, 6H), 2.51-2.50 (m, 6H), 2.13 (s, 3H), 1.91-1.76 (m, 3H), 1.44-1.25 (m, 9H), 1.15-1.05 (m, 4H) |
| 41 | (400 MHz, $CDCl_3$) δ 9.95-9.36 (br, 2H), 6.77-6.75 (m, 1H), 6.64-6.50 (m, 1H), 4.32-4.04 (m, 1H), 4.01-3.61 (m, 6H), 3.59-3.15 (m, 6H), 3.22 (s, 3H), 2.97-2.65 (m, 2H), 2.18-1.48 (m, 10H), 1.39-0.90 (m, 9H) |
| 42 | (400 MHz, $CDCl_3$) δ 9.89-9.67 (br, 2H), 6.98-6.67 (m, 2H), 4.28-3.29 (m, 13H), 3.29-3.21 (m, 3H), 3.08-2.79 (m, 2H), 2.28-1.61 (m, 10H), 1.57-1.38 (m, 3H), 1.39-1.11 (m, 6H), 1.10-1.03 (m, 3H) |
| 43 | RT 2.823 min (Shim-pack XR-ODS, 0.1% trifluoroacetic acid in water/acetonitrile, acetonitrile 30-90% 5.7min, 1.0 ml/min). MS (ESI+) 508 ($M^+$ + 1, 100%). |
| 44 | (300 MHz, DMSO-$d_6$) δ 9.46-9.31 (m, 1H), 7.17-7.09 (m, 1H), 6.88 (m, 1H), 4.07-3.58 (m, 5H), 3.30-3.20 (m, 3H), 2.77-2.68 (m, 2H), 2.51-2.50 (m, 2H), 2.14 (s, 3H), 1.91-1.77 (m, 6H), 1.49-1.36 (m, 6H), 1.23-1.03 (m, 5H) |

TABLE 63-continued

| | |
|---|---|
| 45 | (300 MHz, DMSO-$d_6$) δ 9.35 (m, 1H), 7.05-6.96 (m, 1H), 6.87 (m, 1H), 3.93-3.50 (m, 4H), 3.35-3.09 (m, 5H), 2.95-2.78 (m, 3H), 2.49-2.48 (m, 2H), 2.12 (s, 3H), 1.90-1.73 (m, 3H), 1.44-1.39 (m, 6H), 1.17-1.01 (m, 6H) |
| 46 | (300 MHz, DMSO-$d_6$) δ 9.94-8.79 (m, 1H), 6.81-6.69 (m, 1H), 6.37 (m, 1H), 3.35-3.00 (m, 4H), 2.85-2.63 (m, 6H), 2.31-2.23 (m, 3H), 2.65 (s, 3H), 1.45-1.24 (m, 3H), 1.01-0.85 (m, 6H), 0.73-0.54 (m, 5H), 0.32-0.25 (m, 4H) |
| 47 | RT 2.995 min (Shim-pack XR-ODS, 0.1% trifluoroacetic acid in water/acetonitrile, 30-90% 5.7 min, 1.0 ml/min). MS (ESI+) 552 ($M^+$ + 1, 100%). |
| 48 | RT 2.730 min (Shim-pack XR-ODS, 0.1% trifluoroacetic acid in water/acetonitrile, acetonitrile 30-90% 5.7 min, 1.0 ml/min). MS (ESI+) 488 ($M^+$ + 1, 100%). |

TABLE 64

| Comp. No. | $^1$H NMR (300 or 400 MHz, solvent)/MS (ESI+) |
|---|---|
| 49 | RT 20.425 min (CHIRALPAK AD-H, hexane/0.1% diethylamine in 2-propanol = 80/20, 1.00 ml/min) MS (ESI+) 490 ($M^+$ + 1, 100%). |
| 50 | (300 MHz, DMSO-$d_6$) δ 9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 51 | (300 MHz, DMSO-$d_6$) δ 9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 52 | (300 MHz, DMSO-$d_6$) δ 9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 53 | (300 MHz, DMSO-$d_6$) δ 9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 54 | (300 MHz, DMSO-$d_6$) δ 9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 55 | (300 MHz, DMSO-$d_6$) δ 9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 56 | (300 MHz, DMSO-$d_6$) δ 9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 57 | (400 MHz, $CDCl_3$) δ 9.83-9.38 (br, 2H), 7.12-6.73 (m, 2H), 5.61 (brs, 0.5H), 4.99 (brs, 0.5H), 4.11-3.68 (m, 6H), 3.63-3.52 (m, 4H), 3.48-3.25 (m, 3H), 2.93-2.75 (m, 2H), 2.21-1.89 (m, 10H), 1.40-1.05 (m, 9H) |
| 58 | (400 MHz, $CDCl_3$) δ 9.95-9.60 (br, 2H), 6.97-6.81 (m, 2H), 4.15-3.72 (m, 6H), 3.54-3.41 (m, 2H), 3.37-3.28 (m, 2H), 3.31 (s, 3H), 3.22 (s, 3H), 2.92-2.77 (m, 2H), 2.10-1.89 (m, 2H), 1.77-1.51 (m, 6H), 1.41-1.29 (m, 6H), 1.25-1.01 (m, 6H) |
| 59 | (400 MHz, DMSO-$d_6$) δ 9.45-9.09 (br, 2H), 7.15-7.05 (m, 1H), 7.03-6.87 (m, 2H), 4.39-4.10 (m, 2H), 4.07-3.95 (m, 1H), 3.89-3.68 (m, 2H), 3.66-3.45 (m, 3H), 3.40-3.08 (m, 8H), 2.98-2.88 (m, 2H), 2.80-2.58 (m, 2H), 2.13 (s, 3H), 1.97-1.67 (m, 4H), 1.61-1.23 (m, 4H), 1.19-0.98 (m, 9H) |
| 60 | (400 MHz, DMSO-$d_6$) δ 9.29-8.99 (br, 2H), 7.07-6.85 (m, 2H), 4.38-4.15 (m, 2H), 4.11-3.68 (m, 3H), 3.66-3.52 (m, 3H), 3.28-2.95 (m, 7H), 2.75-2.55 (m, 3H), 2.12 (s, 3H), 1.95-1.57 (m, 7H), 1.52-1.32 (m, 9H), 1.29-1.03 (m, 6H) |
| 61 | (300 MHz, DMSO-$d_6$) δ 9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |

TABLE 65

| | |
|---|---|
| 62 | (400 MHz, DMSO-$d_6$) δ 9.45-9.10 (br, 2H), 7.28-7.12 (m, 1H), 7.08-6.79 (m, 2H), 4.40-4.16 (m, 2H), 4.08-3.98 (m, 1H), 3.88-3.51 (m, 7H), 3.23 (s, 3H), 3.18-3.10 (m, 5H), 2.85-2.58 (m, 4H), 2.13 (s, 3H), 1.90-1.63 (m, 3H), 1.63-1.21 (m, 12H), 1.20-1.01 (m, 6H) |
| 63 | (300 MHz, DMSO-$d_6$) δ 9.12-9.01 (m, 1H), 7.45-7.36 (m, 2H), 3.98-3.74 (m, 2H), 3.65-3.10 (m, 10H), 2.79-2.54 (m, 2H), 1.95-1.80 (m, 2H), 1.51-1.38 (m, 4H), 1.19-1.05 (m, 6H), 0.92-0.84 (m, 3H) |
| 64 | RT 9.395 min (CHIRALPAK AD-H, hexane/0.3% diethylamine in 2-propanol = 80/20, 1.00 ml/min). MS (ESI+) 476 ($M^+$ + 1, 100%). |
| 65 | RT 15.558 min (CHIRALPAK AD-H, hexane/0.3% diethylamine in 2-propanol = 80/20, 1.00 ml/min). MS (ESI+) 476 ($M^+$ + 1, 100 %). |

TABLE 65-continued

| | |
|---|---|
| 66 | (300 MHz, DMSO-$d_6$) δ 9.46-9.31 (m, 1H), 7.17-7.09 (m, 1H), 6.88 (m, 1H), 4.07-3.58 (m, 5H), 3.30-3.20 (m, 3H), 2.77-2.68 (m, 2H), 2.51-2.50 (m, 2H), 2.14 (s, 3H), 1.91-1.77 (m, 6H), 1.49-1.36 (m, 6H), 1.23-1.03 (m, 5H)<br>RT 3.499 min (Shim-pack XR-ODS, 0.1% trifluoroacetic acid in water/acetonitrile, acetonitrile 30-90% 5.7min, 1.0 ml/min).<br>MS (ESI+) 486 ($M^+$ + 1, 100%). |
| 67 | 1H NMR (300 MHz, DMSO-$d_6$) δ 9.00-8.78 (m, 1H), 6.73-6.64 (m, 2H), 4.31-3.44 (m, 8H), 2.99-2.80 (m, 3H), 2.49-2.37 (m, 2H), 2.18-2.10 (m, 2H), 2.04-1.81 (m, 7H), 1.48-0.84 (m, 14H) |
| 68 | $^1$H NMR (400 MHz, $CDCl_3$) δ 9.92-9.53 (br, 2H), 7.13-6.55 (m, 2H), 4.18-3.65 (m, 5H), 3.64-3.50 (m, 2H), 3.45-3.12 (m, 10H), 2.95-2.62 (m, 2H), 2.15-1.45 (m, 10H), 1.35-1.03 (m, 6H). |
| 69 | (400 MHz, DMSO-$d_6$) δ 9.70-9.23 (br, 2H), 7.32-7.08 (m, 2H), 4.21-3.86 (m, 2H), 3.85-3.62 (m, 3H), 3.60-3.42 (m, 2H), 3.40-3.23 (m, 4H), 3.21-3.05 (m, 6H), 2.83-2.47 (m, 2H), 1.93-1.57 (m, 4H), 1.52-1.38 (m, 4H), 1.28-0.98 (m, 6H) |
| 70 | (300 MHz, DMSO-$d_6$) δ 9.25-9.12 (m, 1H), 6.93-6.89 (m, 2H), 4.08-4.02 (m, 1H), 3.83-3.77 (m, 2H), 3.68-3.57 (m, 4H), 2.76-2.64 (m, 2H), 2.13 (s, 3H), 1.88-1.70 (m, 3H), 1.49-1.24 (m, 10H), 1.13-1.02 (m, 8H) |
| 71 | (300 MHz, DMSO-$d_6$) δ 9.09-8.94 (m, 1H), 7.40-7.33 (m, 2H), 3.98-3.74 (m, 2H), 3.60-3.04 (m, 7H), 2.79-2.58 (m, 2H), 1.99-1.60 (m, 5H), 1.49-1.36 (m, 4H), 1.17-1.01 (m, 6H), 0.92-0.84 (m, 3H) |

TABLE 66

| Comp. No. | $^1$H NMR (300 or 400 MHz, solvent)/MS (ESI+) |
|---|---|
| 72 | (300 MHz, DMSO-$d_6$) δ 9.18-9.05 (m, 1H), 7.35-7.30 (m, 2H), 4.02-3.23 (m, 8H), 3.03-2.38 (m, 3H), 2.21-1.68 (m, 3H), 1.53-1.34 (m, 8H), 1.18-0.85 (m, 9H) |
| 73 | (400 MHz, $CD_3OD$) δ 7.28 (s, 0.5H), 7.28 (s, 0.5H), 7.21 (s, 0.5H), 7.13 (s, 0.5H), 4.21-3.98 (m, 2H), 4.00-3.89 (m, 1H), 3.83-3.68 (m, 1H), 3.64-3.54 (m, 1H), 3.45-3.36 (m, 1H), 3.41 (t, J = 6.1 Hz, 2H), 3.31 (s, 3H), 3.13-2.91 (m, 1H), 2.90-2.66 (m, 1H), 2.15-2.04 (m, 1H), 2.05-1.94 (m, 2H), 1.94-1.77 (m, 2H), 1.75-1.64 (m, 2H), 1.67-1.56 (m, 2H), 1.41-1.37 (m, 2H), 1.31-1.26 (m, 2H), 1.26-1.21 (m, 3H), 1.21-1.16 (m, 3H) |
| 74 | (400 MHz, $CD_3OD$) δ 7.68 (s, 0.5H), 7.60 (s, 0.5H), 7.27 (s, 0.5H), 7.26 (s, 0.5H), 4.14-3.93 (m, 3H), 3.83-3.69 (m, 1H), 3.68-3.55 (m, 2H), 3.63 (s, 1.5H), 3.60 (s, 1.5H), 3.43-3.35 (m, 1H), 3.36-3.27 (m, 1H), 3.13-2.92 (m, 1H), 2.90-2.71 (m, 1H), 2.19-2.05 (m, 2H), 1.95-1.77 (m, 2H), 1.44-1.38 (m, 2H), 1.33-1.22 (m, 5H), 1.22-1.15 (m, 3H) |
| 75 | (300 MHz, DMSO-$d_6$) δ 10.33-10.25 (m, 1H), 9.03-8.83 (m, 1H), 7.58-7.54 (m, 1H), 7.35-7.34 (m, 1H), 4.11-4.06 (m, 2H), 3.83-3.57 (m, 4H), 3.43-2.53 (m, 5H), 1.90-1.56 (m, 3H), 1.50-1.36 (m, 7H), 1.19-1.01 (m, 10H) |
| 76 | (300 MHz, DMSO-$d_6$) δ 9.01-8.82 (m, 1H), 7.10-7.01 (m, 1H), 6.92-6.87 (m, 1H), 4.00-3.58 (m, 6H), 3.41-3.10 (m, 6H), 2.13 (s, 3H), 1.89-1.71 (m, 3H), 1.55-1.03 (m, 18H) |
| 77 | RT 9.275 min (CHIRALPAK AD-H, hexane/0.5% diethylamine in ethanol = 90/10, 1.00 ml/min)<br>MS (ESI+) 530 ($M^+$ + 1, 100%) |
| 78 | RT 21.608 min (CHIRALPAK AD-H, hexane/0.5% diethylamine in ethanol = 90/10, 1.00 ml/min)<br>MS (ESI+) 530 ($M^+$ + 1, 100%) |
| 79 | RT 3.414 min (Shim-pack XR-ODS, 0.1% trifluoroacetic acid in water/acetonitrile, acetonitrile 30-90% 5.7 min, 1.0 ml/min).<br>MS (ESI+) 460 ($M^+$ + 1, 100%). |
| 80 | RT 3.038 min (Shim-pack XR-ODS, 0.1% trifluoroacetic acid in water/acetonitrile, acetonitrile 30-90% 5.7 min, 1.0 ml/min).<br>MS (ESI+) 475 ($M^+$ + 1, 100%). |
| 81 | (300 MHz, DMSO-$d_6$) δ 9.16-9.07 (m, 1H), 7.20-7.12 (m, 1H), 6.90-6.85 (m, 1H), 3.94-3.83 (m, 2H), 2.97-2.65 (m, 4H), 2.23-1.97 (m, 5H), 1.90-1.74 (m, 6H), 1.43-1.33 (m, 7H), 1.16-0.95 (m, 6H), 0.91-0.80 (m, 3H) |
| 82 | (300 MHz, DMSO-$d_6$) δ 9.04-8.98 (m, 1H), 7.19-7.12 (m, 1H), 6.90-6.87 (m, 1H), 3.89-3.82 (m, 2H), 3.63-3.57 (m, 2H), 3.43-3.02 (m, 3H), 2.76-2.65 (m, 1H), 2.56-2.48 (m, 2H), 2.12 (s, 3H), 1.90-1.70 (m, 5H), 1.43-1.34 (m, 8H), 1.14-1.01 (m, 8H) |

TABLE 67

| | |
|---|---|
| 83 | (300 MHz, DMSO-$d_6$) δ 9.41-9.03 (m, 1H), 7.19-7.14 (m, 1H), 6.90-6.87 (m, 1H), 3.89-3.82 (m, 2H), 3.61-3.52 (m, 3H), 3.41-3.26 (m, 2H), 3.06-3.02 (m, 3H), 2.81-2.69 (m, 1H), 2.12 (s, 3H), 1.90-1.70 (m, 6H), 1.43-1.24 (m, 8H), 1.15-0.96 (m, 8H) |
| 84 | (300 MHz, DMSO-$d_6$) δ 9.20-9.11 (m, 1H), 7.24-7.19 (m, 1H), 6.91-6.86 (m, 1H), 3.84-3.80 (m, 3H), 3.63-3.57 (m, 3H), 3.37-3.19 (m, 2H), 2.94-2.72 (m, |

TABLE 67-continued

| | |
|---|---|
| | 1H), 2.21-2.12 (m, 3H), 2.02-1.97 (m, 1H), 1.90-1.73 (m, 3H), 1.55-1.34 (m, 10H), 1.15-0.98 (m, 6H), 0.88-0.79 (m, 4H) |
| 85 | (300 MHz, DMSO-$d_6$) δ 9.19-9.13 (m, 1H), 7.19-7.12 (m, 1H), 6.79-6.77 (m, 1H), 3.95-3.49 (m, 10H), 3.16-2.19 (m, 2H), 2.19-1.99 (m, 4H), 1.92-1.79 (m, 3H), 1.67-1.26 (m, 6H), 1.09-0.93 (m, 4H), 0.84-0.80 (m, 1H), 0.39-0.29 (m, 3H), 0.11-0.03 (m, 3H) |
| 86 | (300 MHz, DMSO-$d_6$) δ 9.15-9.09 (m, 1H), 7.14-7.04 (m, 1H), 6.89-6.83 (m, 1H), 3.95-3.84 (m, 2H), 3.63-3.57 (m, 2H), 3.35-3.09 (m, 2H), 2.76-2.67 (m, 3H), 2.12 (s, 3H), 1.90-1.58 (m, 6H), 1.42-1.33 (m, 7H), 1.13-1.01 (m, 7H) |
| 87 | RT 2.998 min (Shim-pack XR-ODS, 0.1% trifluoroacetic acid in water/acetonitrile, acetonitrile 30-90% 5.7 min, 1.0 ml/min). MS (ESI+) 473 ($M^+$ + 1, 100%). |
| 88 | RT 3.233 min (Shim-pack XR-ODS, 0.1% trifluoroacetic in water/acetonitrile, acetonitrile 30-90% 5.7min, 1.0 ml/min). MS (ESI+) 495 ($M^+$ + 1, 100%). |
| 89 | (400 MHz, $CDCl_3$) δ 9.97-9.35 (br, 2H), 7.14 (s, 1H), 6.94-6.50 (m, 2H), 4.30-3.65 (m, 5H), 3.55-3.30 (m, 4H), 3.22 (s, 3H), 2.95-2.68 (m, 2H), 2.32-1.75 (m, 5H), 1.71-1.28 (m, 8H), 1.22-0.99 (m, 6H) |

TABLE 68

| Comp. No. | $^1$H NMR (300 or 400 MHz, solvent)/MS (ESI+) |
|---|---|
| 90 | (400 MHz, $CDCl_3$) δ 9.95-9.38 (br, 2H), 6.89-6.47 (m, 2H), 4.24-3.45 (m, 6H), 3.33 (s, 3H), 3.26 (s, 3H), 2.95-2.61 (m, 2H), 2.19-1.75 (m, 5H), 1.68-1.38 (m, 8H), 1.32-0.94 (m, 6H) |
| 91 | (300 MHz, DMSO-$d_6$) δ 8.54-8.45 (m, 1H), 6.64-6.49 (m, 2H), 3.64-2.78 (m, 6H), 1.90-1.86 (m, 1H), 1.74 (s, 3H), 1.52-1.36 (m, 2H), 1.09-0.66 (m, 21H) |
| 92 | (300 MHz, DMSO-$d_6$) δ 9.10-8.84 (m, 1H), 7.00-6.89 (m, 2H), 3.99-3.84 (m, 2H), 3.63-3.52 (m, 2H), 3.14-2.99 (m, 2H), 2.82-2.62 (m, 1H), 2.12 (s, 3H), 1.90-1.69 (m, 5H), 1.43-1.34 (m, 7H), 1.11-1.01 (m, 10H) |
| 93 | (300 MHz, DMSO-$d_6$) δ 9.62-9.60 (m, 1H), 9.13-8.95 (m, 1H), 7.37-7.25 (m, 2H), 4.20-4.04 (m, 2H), 3.83-3.55 (m, 3H), 3.43-2.56 (m, 3H), 1.90-1.63 (m, 3H), 1.53-1.34 (m, 8H), 1.19-1.01 (m, 7H) |
| 94 | RT 3.233 min (Shim-pack XR-ODS, 0.1% trifluoroacetic acid in water/acetonitrile, acetonitrile 30-90% 5.7min, 1.0 ml/min). MS (ESI+) 446 ($M^+$ + 1, 100%). |
| 95 | (400 MHz, $CD_3OD$) δ 7.63 (s, 0.5H), 7.50 (s, 0.5H), 7.26 (s, 1H), 4.18-3.93 (m, 3H), 3.84-3.69 (m, 1H), 3.64-3.52 (m, 1H), 3.51-3.32 (m, 3H), 3.02-2.91 (m, 1H), 2.91-2.69 (m, 1H), 2.22-2.05 (m, 4H), 1.94-1.76 (m, 2H), 1.43-1.37 (m, 2H), 1.32-1.23 (m, 5H), 1.22-1.14 (m, 3H), 1.14-1.03 (m, 3H) |
| 96 | RT 2.834 min (Shim-pack XR-ODS, 0.1% trifluoroacetic acid in water/acetonitrile, acetonitrile 30-90% 5.7min, 1.0 ml/min). MS (ESI+) 461 ($M^+$ + 1, 100%). |
| 97 | (400 MHz, DMSO-$d_6$) δ 9.40-9.15 (m, 1H), 6.97 (s, 1H), 6.91 (s, 1H), 4.39-4.35 (m, 1H), 4.15-0.91 (m, 37H) |
| 98 | (300 MHz, DMSO-$d_6$) δ 9.19-9.15 (m, 1H), 6.88-6.60 (m, 2H), 4.66-4.48 (m, 2H), 3.83-3.81 (m, 1H), 3.63-3.36 (m, 5H), 3.11-3.05 (m, 2H), 2.27-2.62 (m, 2H), 2.11 (s, 3H), 1.97-1.68 (m, 3H), 1.44-1.38 (m, 6H), 1.11-0.99 (m, 6H) |
| 99 | (400 MHz, $CDCl_3$) δ 10.0-9.39 (br, 2H), 7.25-6.80 (m, 2H), 6.01 (brs, 0.5H), 5.35 (brs, 0.5H), 4.31-3.99 (m, 2H), 3.95-3.23 (m, 6H), 2.97-2.73 (m, 2H), 2.43-1.97 (m, 10H), 1.89-1.45 (m, 9H), 1.42-1.05 (m, 9H) |
| 100 | (300 MHz, DMSO-$d_6$) δ 9.19-9.13 (m, 1H), 6.98-6.89 (m, 2H), 3.96-3.80 (m, 2H), 3.63-2.62 (m, 5H), 2.12 (s, 3H), 1.93-1.63 (m, 9H), 1.42-1.34 (m, 6H), 1.11-1.01 (m, 6H) |
| 101 | (300 MHz, DMSO-$d_6$) δ 9.19-9.14 (m, 1H), 7.42-7.38 (m, 1H), 6.88-6.86 (m, 1H), 3.89-3.45 (m, 5H), 3.29-3.13 (m, 5H), 2.77-2.53 (m, 2H), 2.12 (s, 3H), 1.97-1.74 (m, 3H), 1.43-1.22 (m, 8H), 1.11-0.95 (m, 6H) |

TABLE 69

| Comp. No. | $^1$H NMR (300 or 400 MHz, solvent)/MS (ESI+) |
|---|---|
| 102 | (300 MHz, DMSO-$d_6$) δ 9.09-8.87 (m, 1H), 8.03-7.93 (m, 1H), 7.33-7.16 (m, 1H), 4.22-4.01 (m, 1H), 3.80-3.55 (m, 2H), 3.15-2.49 (m, 4H), 2.36-2.23 (m, 2H), 2.02-1.86 (m, 2H), 1.66-1.37 (m, 6H), 1.23-0.89 (m, 16H) |
| 103 | RT 2.656 min (Shim-pack XR-ODS, 0.1% trifluoroacetic acid in water/acetonitrile, acetonitrile 30-90% 5.7 min, 1.0 ml/min). MS (ESI+) 445 ($M^+$ + 1, 100%). |
| 104 | RT 2.805 min (Shim-pack XR-ODS, 0.1% trifluoroacetic acid in water/acetonitrile, acetonitrile 30-90% 5.7 min, 1.0 ml/min). MS (ESI+) 459 ($M^+$ + 1, 100%). |
| 105 | RT 2.659 min (Shim-pack XR-ODS, 0.1% trifluoroacetic acid in water/acetonitrile, acetonitrile 30-90% 5.7 min, 1.0 ml/min). MS (ESI+) 431 ($M^+$ + 1, 100%). |

TABLE 69-continued

| Comp. No. | $^1$H NMR (300 or 400 MHz, solvent)/MS (ESI+) |
|---|---|
| 106 | (400 MHz, $CDCl_3$) δ 7.52 (s, 1H), 7.22 (s, 1H), 6.06-5.75 (m, 1H), 4.37-3.89 (m, 3H), 3.78-3.49 (m, 9H), 3.30-3.20 (br, 1H), 2.63-2.36 (m, 2H), 2.19-1.73 (m, 6H), 1.57-1.48 (m, 6H), 1.41-1.15 (m, 6H) |
| 107 | (300 MHz, DMSO-$d_6$) δ 9.28-9.20 (m, 1H), 7.07-6.90 (m, 2H), 4.20-4.10 (m, 1H), 3.87-3.82 (m, 1H), 3.69-3.56 (m, 2H), 3.35-3.11 (m, 1H), 2.77-2.51 (m, 2H), 2.37-2.30 (m, 2H), 2.13 (s, 3H), 1.91-1.70 (m, 4H), 1.14-1.03 (m, 6H) |
| 108 | (300 MHz, DMSO-$d_6$) δ 9.27-9.25 (m, 1H), 7.07-6.90 (m, 2H), 4.10-3.58 (m, 4H), 3.37-2.64 (m, 5H), 2.34-2.23 (m, 2H), 2.13 (s, 3H), 1.91-1.69 (m, 3H), 1.56-1.35 (m, 10H), 1.15-1.03 (m, 6H) |
| 109 | (400 MHz, $CDCl_3$) δ 9.89-9.38 (br, 2H), 7.37-7.08 (m, 2H), 6.49 (br, 0.5H), 5.93 (br, 0.5H), 4.33-3.29 (m, 12H), 2.88-2.66 (m, 4H), 2.58-1.78 (m, 6H), 2.10 (s, 3H), 1.46-0.89 (m, 9H) |
| 110 | (400 MHz, $CD_3OD$) δ 7.61 (s, 0.5H), 7.50 (s, 0.5H), 7.28 (s, 0.5H), 7.27 (s, 0.5H), 6.02 (t, J = 54 Hz, 0.5H), 6.00 (t, J = 54 Hz, 0.5H), 4.20-3.95 (m, 3H), 3.84-3.67 (m, 1H), 3.68-3.32 (m, 4H), 3.01-2.90 (m, 1H), 2.88-2.68 (m, 1H), 2.18-2.01 (m, 1H), 1.92-1.77 (m, 1H), 1.46-1.35 (m, 2H), 1.33-1.21 (m, 5H), 1.22-1.13 (m, 3H) |
| 111 | (300 MHz, DMSO-$d_6$) δ 8.92-8.62 (m, 1H), 7.40-7.35 (m, 2H), 4.33-3.98 (m, 2H), 3.80-3.56 (m, 4H), 3.42-3.29 (m, 5H), 1.91-1.82 (m, 1H), 1.53-1.35 (m, 6H), 1.24-1.03 (m, 13H) |
| 112 | (300 MHz, DMSO-$d_6$) δ 9.01-8.85 (m, 1H), 7.35-7.24 (m, 2H), 4.15-4.10 (m, 2H), 3.63-3.54 (m, 2H), 3.03-2.97 (m, 2H), 2.36-2.34 (m, 1H), 1.90-1.75 (m, 2H), 1.48-1.35 (m, 7H), 1.19-0.90 (m, 15H) |
| 113 | δ 7.16 (s, 1H), 7.10 (s, 1H), 3.98-3.14 (m, 12H), 2.79-2.55 (m, 2H), 1.90-1.72 (m, 3H), 1.58-1.07 (m, 16H) |
| 114 | δ 7.30-7.18 (m, 1H), 4.12-3.08 (m, 12H), 2.85-2.55 (m, 2H), 1.88-1.75 (m, 3H), 1.54-1.07 (m, 16H) |
| 115 | δ 7.28-7.15 (m, 1H), 4.11-3.38 (m, 5H), 3.34-3.05 (m, 7H), 2.85-2.60 (m, 2H), 1.88-1.74 (m, 3H), 1.54-1.06 (m, 16H) |

TABLE 70

| Comp. No. | $^1$H NMR (400 MHz, solvent) |
|---|---|
| 116 | ($CDCl_3$) δ 7.70 (br, 1H), 7.23 (s, 1H), 6.08-5.81 (m, 1H), 4.28-3.17 (m, 11H), 2.82-2.60 (m, 2H), 2.30-2.18 (br, 1H), 1.88-1.72 (m, 6H), 1.57-1.48 (m, 6H), 1.33-1.13 (m, 6H) |
| 117 | ($CDCl_3$) δ 7.50 (s, 1H), 7.32-7.28 (m, 2H), 7.24-7.23 (m, 3H), 6.07-5.75 (m, 1H), 4.29-3.16 (m, 13H), 2.77 (br, 1H), 2.57-2.22 (m, 2H), 1.85-1.71 (m, 3H), 1.60-1.57 (m, 5H), 1.48 (s, 1H), 1.32-1.14 (m, 6H), 1.00-0.84 (m, 4H) |
| 118 | (3 $CDCl_3$) δ 7.53 (s, 1H), 7.40-7.16 (m, 5H), 6.08-5.75 (m, 1H), 4.35-3.23 (m, 16H), 2.77 (br, 1H), 2.55-1.84 (m, 6H), 1.58 (s, 3H), 1.48 (s, 3H), 1.24-1.13 (m, 6H) |
| 119 | ($CDCl_3$) δ 7.51-7.32 (m, 3H), 7.23-7.06 (m, 2H), 6.06-5.75 (m, 1H), 4.36-3.2 (m, 13H), 2.81 (br, 1H), 2.57 (br, 1H), 2.38-1.75 (m, 6H), 1.57 (s, 3H), 1.48 (s, 3H), 1.27-1.13 (m, 6H), 0.99-0.83 (m, 4H) |
| 120 | ($CDCl_3$) δ 7.53-7.34 (m, 3H), 7.25-6.98 (m, 2H), 6.09-5.75 (m, 1H), 4.38-3.22 (m, 14H), 2.91-1.73 (m, 7H), 1.57 (s, 3H), 1.48 (s, 3H), 1.24-1.14 (m, 6H) |
| 121 | ($CD_3OD$) δ 7.58-7.48 (m, 1H), 7.34-7.33 (m, 1H), 7.22-7.08 (m, 2H), 6.00 (dt, J = 9.2 Hz, 53.9 Hz, 1H), 4.17-4.06 (m, 3H), 3.79-3.28 (m, 6H), 3.16-3.11 (m, 1H), 2.88-2.75 (m, 1H), 2.07-1.85 (m, 2H), 1.81-1.77 (m, 1H), 1.54-1.46 (m, 9H), 1.26-1.16 (m, 6H). |
| 122 | ($CD_3OD$) δ 7.54-7.43 (m, 1H), 7.34-7.33 (m, 1H), 7.20-7.14 (m, 2H), 6.01 (dt, J = 11.0 Hz, 53.8 Hz, 1H), 4.16-4.07 (m, 3H), 3.85-3.28 (m, 11H), 2.90-2.79 (m, 1H), 2.21-2.05 (m, 2H), 2.01-1.88 (m, 2H), 1.79-1.47 (m, 8H), 1.28-1.17 (m, 6H). |

TABLE 71

| Comp. No. | $^1$H NMR (300 or 400 MHz, solvent)/MS (ESI+) |
|---|---|
| 123 | (300 MHz DMSO-$d_6$) δ 9.26-9.08 (m, 1H), 7.36-7.21 (m, 2H), 4.17-4.07 (m, 2H), 3.85-3.57 (m, 3H), 3.36-3.00 (m, 4H), 2.80-2.76 (m, 1H), 2.39-2.35 (m, 2H), 1.93-1.85 (m, 3H), 1.54-1.32 (m, 8H), 1.27-1.03 (m, 6H) |
| 124 | (300 MHz DMSO-$d_6$) δ 9.22-9.07 (m, 1H), 7.35-7.20 (m, 2H), 4.45-4.14 (m, 4H), 3.80-3.54 (m, 3H), 3.39-2.99 (m, 3H), 2.75-2.34 (m, 3H), 1.90-1.63 (m, 3H), 1.53-1.34 (m, 8H), 1.20-1.01 (m, 6H) |
| 125 | (300 MHz DMSO-$d_6$) δ 9.25-9.08 (m, 1H), 7.35-7.19 (m, 2H), 3.80-3.57 (m, 2H), 3.47-3.02 (m, 4H), 2.75-2.72 (m, 1H), 2.59-2.43 (m, 6H), 1.90-1.79 (m, 2H), 1.52-1.34 (m, 8H), 1.20-1.01 (m, 6H) |
| 126 | (400 MHz, $CDCl_3$) δ 9.75 (br, 2H), 6.81-6.77 (m, 2H), 4.19-4.06 (m, 1H), 4.06-3.83 (m, 4H), 3.53-3.35 (m, 4H), 3.30 (s, 3H), 2.97-2.74 (m, 2H), 2.18-1.59 (m, 7H), 1.54 (s, 6H), 1.39-1.12 (m, 6H) |

TABLE 71-continued

| Comp. No. | $^1$H NMR (300 or 400 MHz, solvent)/MS (ESI+) |
|---|---|
| 127 | (400 MHz, $CDCl_3$) δ 9.91-9.41 (br, 2H), 7.35-7.11 (m, 2H), 6.55 (br, 0.5H), 5.81 (br, 0.5H), 4.20-3.33 (m, 12H), 2.89-2.70 (m, 4H), 2.53-1.78 (m, 6H), 1.43-0.88 (m, 9H) |
| 129 | (300 MHz, DMSO-$d_6$) δ 9.12-9.07 (m, 1H), 7.35-7.19 (m, 2H), 4.01-3.57 (m, 2H), 3.11-2.64 (m, 5H), 1.90-1.76 (m, 3H), 1.53-1.31 (m, 8H), 1.27-0.79 (m, 15H) |
| 130 | (300 MHz, DMSO-$d_6$) δ 9.04-8.88 (m, 1H), 7.79-7.76 (m, 1H), 7.05-6.89 (m, 2H), 3.83-3.80 (m, 2H), 3.44-2.68 (m, 5H), 2.34-2.01 (m, 3H), 1.68-1.33 (m, 8H), 0.92-0.71 (m, 6H), 0.28-0.23 (m, 2H), 0.10-0.08 (m, 2H) |
| 131 | RT 3.316 min (Shim-pack XR-ODS, 0.1% trifluoroacetic acid in water/acetonitrile, acetonitrile 30-90% 5.7min, 1.0 ml/min). MS (ESI+) 489 ($M^+$ + 1, 100%). |
| 132 | RT 3.280 min (Shim-pack XR-ODS, 0.1% trifluoroacetic acid in water/ acetonitrile, acetonitrile 30-90% 5.7min, 1.0 ml/min). MS (ESI+) 487 ($M^+$ + 1, 100%). |
| 133 | δ 7.52 (s, 1H), 7.33-7.14 (m, 5H), 6.07-5.77 (m, 1H), 4.38-2.79 (m, 1 4H), 2.73-1.72 (m, 7H), 1.57-1.47 (m, 8H), 1.26-1.14 (m, 8H), 0.47 (br, 4H) |
| 134 | δ 7.53 (s, 1H), 7.44-7.11 (m, 5H), 6.07-5.76 (m, 1H), 4.38-3.91 (m, 4H), 3.78-1.82 (m, 15H), 1.57-1.47 (m, 8H), 1.30-1.16 (m, 8H), 0.68-0.61 (m, 4H) |
| 135 | ($CDCl_3$) δ 9.90-9.48 (br, 2H), 7.12-6.53 (m, 5H), 6.42 (br, 0.5H), 5.95 (br, 0.5H), 4.21-3.24 (m, 9H), 2.85-2.52 (m, 2H), 2.17 (s, 3H), 2.17-1.75 (m, 5H), 1.75 (s, 3H), 1.45-0.92 (m, 9H). |

TABLE 72

| | |
|---|---|
| 136 | (DMSO-$d_6$) δ 9.06-8.72 (br, 2H), 8.14-8.03 (m, 1H), 7.60-7.25 (m, 2H), 3.97-3.72 (m, 3H), 3.62-3.49 (m, 2H), 3.28-2.97 (m, 4H), 2.85-2.51 (m, 2H), 2.28-2.17 (m, 1H), 2.08-1.93 (m, 2H), 1.92-1.61 (m, 9H), 1.53-1.30 (m, 1H), 1.19-1.01 (m, 6H), 0.99-0.90 (m, 3H) |
| 137 | (DMSO-$d_6$) δ 9.02-8.94 (m, 1H), 7.39-7.32 (m, 2H), 4.01-3.88 (m, 1H), 3.80-3.55 (m, 3H), 3.04-2.60 (m, 3H), 1.90-1.63 (m, 2H), 1.54-1.36 (m, 8H), 1.17-1.01 (m, 11H) |
| 138 | δ 7.29-7.17 (m, 5H), 6.83-6.80 (m, 1H), 6.04-5.74 (m, 1H), 4.30-3.17 (m, 13H), 2.80-2.70 (br, 2H), 2.36-2.10 (m, 6H), 1.94-1.74 (m, 3H), 1.54 (s, 3H), 1.43 (s, 3H), 1.24-1.15 (m, 6H), 0.99-0.85 (m, 4H) |
| 139 | δ 7.27-7.10 (m, 4H), 6.83-6.80 (m, 1H), 6.04-5.74 (m, 1H), 4.31-3.11 (m, 13H), 2.87-2.69 (br, 2H), 2.21 (s, 4H), 2.00-1.81 (m, 5H), 1.54 (s, 3H), 1.44 (s, 3H), 1.24-1.17 (m, 6H), 1.01-0.86 (m, 4H) |
| 140 | δ 7.27-6.97 (m, 5H), 6.83-6.80 (m, 1H), 6.04-5.74 (m, 1H), 4.30-3.01 (m, 15H), 2.89-2.64 (br, 1H), 2.36-1.69 (m, 9H), 1.53 (s, 3H), 1.44 (s, 3H), 1.24-1.17 (m, 6H) |

TABLE 73

| Comp. No. | $^1$H NMR (400 MHz, solvent) |
|---|---|
| 141 | (DMSO-$d_6$) δ 9.32-9.10 (m, 1H), 8.07-7.99 (m, 1H), 7.43 (s, 1H), 7.30 (s, 1H), 4.15-0.90 (m, 28H) |
| 142 | (DMSO-$d_6$) δ 6.94-6.81 (m, 2H), 4.10-3.02 (m, 5H), 2.79-2.63 (m, 2H), 2.22 (s, 3H), 1.96-1.70 (m, 5H), 1.43-0.81 (m, 15H) |
| 143 | (DMSO-$d_6$) δ 9.25-8.93 (m, 1H), 8.14-8.07 (m, 1H), 7.68 (s, 1H), 7.54 (s, 1H), 4.07-0.91 (m, 28H) |
| 144 | (DMSO-$d_6$) δ 9.50-9.01 (br, 2H), 7.51-7.11 (m, 3H), 3.95-3.86 (m, 2H), 3.81-3.45 (m, 8H), 3.25-3.05 (m, 2H), 2.78-2.38 (m, 4H), 2.30-2.17 (m, 2H), 1.95-1.69 (m, 5H), 1.30-1.02 (m, 6H). |
| 145 | (DMSO-$d_6$) δ 9.30-9.25 (m, 1H), 8.98-8.96 (m, 1H), 7.49-7.33 (m, 2H), 5.47-5.41 (m, 1H), 5.19-5.11 (m, 1H), 3.65-3.60 (m, 3H), 3.15-2.98 (m, 1H), 2.77-2.72 (m, 1H), 1.90-1.77 (m, 3H), 1.55-1.44 (m, 8H), 1.35-1.33 (m, 1H), 1.16-1.14 (m, 1H), 1.04-0.85 (m, 6H) |
| 146 | (DMSO-$d_6$) δ 9.28-9.26 (m, 1H), 9.26-9.04 (m, 1H), 8.11-8.06 (m, 1H), 7.41-7.24 (m, 7H), 4.09-3.92 (m, 2H), 3.86-3.74 (m, 1H), 3.74-3.63 (m, 1H), 3.31-3.12 (m, 4H), 3.11-3.03 (m, 1H), 2.81-2.69 (m, 1H), 2.67-2.53 (m, 1H), 2.11-2.00 (m, 2H), 2.91-2.82 (m, 3H), 2.83-2.76 (m, 3H), 1.48-1.37 (m, 1H), 1.19-1.05 (m, 4H), 1.06-0.94 (m, 4H) |
| 147 | (DMSO-$d_6$) δ 9.14 (brs, 2H), 8.12-8.06 (m, 1H), 7.38-7.12 (m, 6H), 7.04-6.99 (m, 1H), 4.09-3.97 (m, 1H), 3.91-3.74 (m, 2H), 3.64-3.55 (m, 1H), 3.31-3.24 (m, 4H), 2.81-2.69 (m, 1H), 2.69-2.51 (m, 1H), 2.13-2.07 (m, 3H), 2.07-2.02 (m, 2H), 1.90-1.82 (m, 3H), 1.77 (s, 3H), 1.43-1.38 (m, 1H), 1.14-1.02 (m, 4H), 1.02-0.92 (m, 5H) |
| 148 | ($CD_3OD$) δ 7.62 (s, 0.5H), 7.53 (s, 0.5H), 7.31 (s, 0.5H), 7.31 (s, 0.5H), 4.12-3.90 (m, 3H), 3.82-3.68 (m, 1H), 3.66-3.50 (m, 2H), 3.62 (s, 1.5H), 3.59 (s, 1.5H), 3.44-3.33 (m, 1H), 3.03-2.91 (m, 1H), 2.88-2.70 (m, 1H), 2.30-2.18 (m, 1H), 2.18-2.02 (m, 2H), 2.06-1.73 (m, 9H), 1.30-1.22 (m, 3H), 1.23-1.14 (m, 3H) |

TABLE 74

| Comp. No. | $^1$H NMR (400 MHz, solvent)/MS (ESI+) |
|---|---|
| 149 | (DMSO-$d_6$) δ9.11-8.91 (br, 2H), 8.73-8.67 (br, 1H), 8.13-8.08 (br, 1H), 7.59 (s, 1H), 7.33 (s, 1H), 4.14-4.05 (m, 1H), 4.03-3.93 (m, 2H), 3.35-3.25 (m, 3H), 3.20-3.13 (m, 1H), 2.91-2.79 (m, 2H), 2.04 (q, J = 7.6 Hz, 2H), 1.95-1.85 (m, 2H), 1.82-1.50 (m, 2H), 1.44 (s, 6H), 0.99 (t, J = 7.6 Hz, 3H). |
| 150 | ($CDCl_3$) δ9.82-9.27 (br, 2H), 7.20-7.03 (m, 2H), 6.82 (brs, 0.5H), 6.65 (brs, 0.5H), 4.25-3.13 (m, 8H), 2.63-2.40 (m, 4H), 2.23-1.88 (m, 5H), 1.59-1.38 (m, 6H), 1.37-1.01 (m, 6H). |
| 151 | ($CDCl_3$) δ9.91-9.43 (br, 2H), 7.37-7.04 (m, 2H), 6.43 (brs, 0.5H), 5.27 (brs, 0.5H), 4.18-3.13 (m, 10H), 2.90-2.64 (m, 2H), 2.15-1.84 (m, 5H), 1.56-1.30 (m, 6H), 1.28-0.68 (m, 10H). |
| 152 | ($CDCl_3$) δ9.90-9.45 (br, 2H), 7.55-7.05 (m, 7H), 6.47 (brs, 0.5H), 6.24 (brs, 0.5H), 4.59-4.23 (m, 2H), 4.07-3.83 (m, 2H), 3.70-2.93 (m, 4H), 2.22-1.68 (m, 6H), 1.62-1.39 (m, 6H), 1.31-0.85 (m, 6H). |
| 153 | (DMSO-$d_6$) δ9.27-9.00 (m, 2H), 8.18-8.12 (m, 1H), 7.59-7.50 (m, 1.6H), 7.46 (s, 0.4H), 7.39-7.25 (m, 5H), 4.18-4.05 (m, 1H), 3.93-3.62 (m, 3H), 3.61-3.44 (m, 2H), 3.26-3.18 (m, 2H), 3.11-2.94 (m, 1H), 2.84-2.65 (m, 1H), 2.64-2.51 (m, 1H), 2.09-2.02 (m, 2H), 2.00-1.89 (m, 1H), 1.81 (s, 3H), 1.68-1.58 (m, 0.6H), 1.52-1.13 (m, 1.4H), 1.16 (d, J = 6.6 Hz, 1H), 1.12-0.92 (m, 8H) |
| 154 | (DMSO-$d_6$) δ9.05 (brs, 2H), 8.72 (d, J = 7.4 Hz, 1H), 7.34 (s, 1H), 7.33 (s, 1H), 4.10-4.08 (m, 1H), 3.98-3.95 (m, 2H), 3.37-3.28 (m, 3H), 3.20 (s, 3H), 3.17-3.14 (m, 1H), 2.86-2.80 (m, 1H), 2.76-2.71 (m, 1H), 1.91-1.85 (m, 2H), 1.72-1.68 (m, 1H), 1.61-1.45 (m, 5H), 1.42 (s, 6H). |
| 155 | (DMSO-$d_6$) δ8.99 (brs, 2H), 8.78 (d, J = 8.4 Hz, 1H), 7.52 (s, 1H), 7.37 (s, 1H), 7.31-7.27 (m, 2H), 7.21-7.17 (m, 3H), 4.39-4.36 (m, 1H), 4.08-4.05 (m, 2H), 3.37-3.27 (m, 1H), 3.22-3.14 (m, 5H), 2.88-2.82 (m, 1H), 2.79-2.75 (m, 1H), 2.53-2.45 (m, 1H), 2.15-2.13 (m, 1H), 1.75-1.61 (m, 3H), 1.57-1.52 (m, 3H), 1.49-1.43 (m, 7H). |
| 156 | (DMSO-$d_6$) δ8.90-8.27 (m, 3H), 7.38 (m, 1H), 7.31-7.27 (m, 3H), 7.21-7.18 (m, 3H), 4.00-3.91 (m, 3H), 3.39-3.35 (m, 1H), 3.26-3.23 (m, 2H), 3.19-3.16 (m, 1H), 3.12-3.08 (m, 4H), 2.78-2.72 (m, 1H), 2.67-2.61 (m, 1H), 2.29-2.23 (m, 1H), 1.90-1.85 (m, 1H), 1.63-1.56 (m, 3H), 1.51-1.35 (m, 9H). |
| 157 | (DMSO-$d_6$) δ9.03 (brs, 2H), 7.40-7.27 (m, 2H), 3.97-3.58 (m, 3H), 3.30-2.65 (m, 12H), 1.98-1.77 (m, 3H), 1.55-1.41 (m, 11H). |
| 158 | (DMSO-$d_6$) δ9.37 (brs, 2H), 7.40-7.27 (m, 4H), 7.25-7.15 (m, 3H), 4.00-3.80 (m, 3H), 3.59 (m, 1H), 3.44-3.37 (m, 1H), 3.25 (m, 1H), 3.20-3.11 (m, 4H), 3.04-2.80 (m, 6H), 2.62 (m, 1H), 1.71-1.34 (m, 13H). |

TABLE 75

| | |
|---|---|
| 159 | (DMSO-$d_6$) δ 8.90 (brs, 2H), 8.17-8.09 (m, 1H), 7.64-7.46 (m, 2H), 7.28-2.22 (m, 1H), 6.95-6.81 (m, 3H), 4.16-4.07 (m, 1H), 3.89-3.72 (m, 3H), 3.69 (s, 3H), 3.64-3.51 (m, 2H), 3.28-3.16 (m, 2H), 3.09-2.95 (m, 1H), 2.83-2.71 (m, 1H), 2.62-2.50 (m, 1H), 2.12-2.04 (m, 2H), 1.97-1.61 (m, 2H), 1.80 (s, 3H), 1.48-1.34 (m, 1H), 1.17-1.09 (m, 2H), 1.07-0.90 (m, 7H) |
| 160 | (DMSO-$d_6$) δ 8.90 (brs, 2H), 8.17-8.09 (m, 1H), 7.64-7.46 (m, 2H), 7.28-2.22 (m, 1H), 6.95-6.81 (m, 3H), 4.16-4.07 (m, 1H), 3.89-3.72 (m, 3H), 3.69 (s, 3H), 3.64-3.51 (m, 2H), 3.28-3.16 (m, 2H), 3.09-2.95 (m, 1H), 2.83-2.71 (m, 1H), 2.62-2.50 (m, 1H), 2.12-2.04 (m, 2H), 1.97-1.61 (m, 2H), 1.80 (s, 3H), 1.48-1.34 (m, 1H), 1.17-1.09 (m, 2H), 1.07-0.90 (m, 7H). |
| 161 | (DMSO-$d_6$) δ9.41-9.00 (m, 1H), 8.14 (m, 1H), 7.25-7.08 (m, 4H), 6.83 (s, 1H), 6.74 (s, 1H), 5.05 (d, 2H), 4.00-0.93 (m, 29H) |
| 162 | RT 3.164 min (Shim-pack XR-ODS, 0.1% trifluoroacetic acid in water/acetonitirile, acetonitirile 30-90% 5.7 min, 1.0 ml/min). MS (ESI+) 457 ($M^+$ + 1, 100%). |
| 163 | ($CD_3OD$)) δ7.11, 7.09 (s, 1H), 7.00, 6.93 (s, 1H), 4.05-4.12 (m, 2H), 3.65-3.90 (m, 8H), 3.38-3.44 (m, 4H), 3.28-3.29 (m, 2H), 2.94-2.99 (m, 1H), 2.81-2.84 (m, 1H), 2.56-2.61 (m, 2H), 1.91-2.19 (m, 5H), 1.56-1.77 (m, 7H), 1.20-1.29 (m, 9H). |
| 164 | (DMSO-$d_6$) δ7.68-7.65 (m, 1H), 6.91-6.89 (m, 2H), 4.00-3.91 (m, 4H), 2.78-2.33 (m, 5H), 1.86-1.01 (m, 22H). |
| 165 | (DMSO-$d_6$) δ9.17-9.12 (m, 1H), 7.09-7.03 (m, 1H), 6.87 (s, 1H), 4.12-3.97 (m, 2H), 3.62-3.50 (m, 3H), 3.35-3.13 (m, 6H), 2.78-2.62 (m, 2H), 2.12 (s, 3H), 1.90-1.72 (m, 3H), 1.43-1.33 (m, 9H), 1.14-1.01 (m, 5H), 0.78-0.73 (m, 3H). |
| 166 | (DMSO-$d_6$) δ9.09-9.03 (m, 1H), 7.07-7.00 (m, 1H), 6.89-6.87 (m, 1H), 4.22-4.16 (m, 6H), 3.61-3.53 (m, 1H), 2.20-2.12 (m, 6H), 1.87-1.75 (m, 4H), 1.43-1.33 (m, 6H), 1.13-0.90 (m, 8H). |
| 167 | ($CD_3OD$) δ7.37 (d, J = 2.9 Hz, 1H), 7.23 (s, 0.5H), 7.15 (s, 0.5H), 4.81-4.75 (m, 1H), 4.23-3.94 (m, 3H), 3.76-3.63 (m, 3H), 3.44-3.39 (m, 3H), 3.31-3.29 (m, 3H), 3.03-2.70 (m, 2H), 2.11-1.86 (m, 3H), 1.70-1.48 (m, 8H), 1.26-1.16 (m, 6H). |
| 168 | ($CDCl_3$) δ 7.55 (br, 1H), 7.23 (m, 1H), 4.22-4.13 (m, 3H), 3.89 (m, 3H), 3.71-3.53 (m, 5H), 3.36 (m, 3H), 2.94-2.79 (m, 3H), 2.62 (br, 1H), 2.36-2.18 (m, 2H), 2.01-1.77 (m, 2H), 1.59 (m, 3H), 1.48 (s, 3H), 1.33-1.14 (m, 6H). |
| 169 | RT = 3.082 min (Shim-pack XR-ODS, 0.1% trifluoroacetic acid in water/acetonitirile, acetonitirile acetonitirile 30-90% 5.7 min, 1.0 ml/min). MS (ESI+) 499 ($M^+$ + 1, 100%). |

TABLE 76

| Comp. No. | $^{1}H$ NMR (400 MHz, solvent)/MS (ESI+) |
|---|---|
| 170 | RT 2.773 min (Shim-pack XR-ODS, 0.1% trifluoroacetic acid in water/acetonitirile, acetonitirile 30-90% 5.7 min, 1.0 ml/min). MS ($ESI^+$) 476 ($M^+$ + 1, 100%). |
| 171 | ($CD_3OD$) δ7.34 (s, 1H), 7.14, 7.09 (S × 2, 1H), 3.91-4.28 (m, 3H), 3.72-3.88 (m, 1H), 3.51-3.69 (m, 2H), 3.31-3.48 (m, 4H), 3.26 (s, 3H), 2.75-3.05 (m, 2H), 2.25 (s, 3H), 2.08 (m, 1H), 1.86-1.99 (m, 2H), 1.53-1.62 (m, 4H), 1.36-1.42 (m, 3H), 1.20-1.29 (m, 6H) |
| 172 | ($CDCl_3$) δ9.74-9.60 (brs, 2H), 7.14-7.06 (m, 2H), 5.98 (brs, 1H), 4.22-4.01 (m, 2H), 3.98-3.76 (m, 2H), 3.76-3.62 (m, 2H), 3.56-3.31 (m, 3H), 2.96-2.74 (m, 2H), 2.16 (s, 3H), 2.15-2.06 (m, 2H), 2.03-1.85 (m, 3H), 1.48-1.38 (m, 3H), 1.39-1.15 (m, 6H), 1.16-1.05 (m, 3H), 1.05-0.98 (m, 3H) |
| 173 | ($CD_3OD$) δ7.80 (s, 0.5H), 7.80 (s, 0.5H), 7.77 (s, 0.5H), 7.67 (s, 0.5H), 4.17-3.90 (m, 3H), 3.82-3.52 (m, 2H), 3.63 (s, 1.5H), 3.59 (s, 1.5H), 3.45-3.22 (m, 2H), 3.04-2.91 (m, 1H), 2.90-2.70 (m, 2H), 2.63-2.50 (m, 1H), 2.30-1.78 (m, 9H), 1.31-1.23 (m, 3H), 1.22-1.14 (m, 3H) |
| 174 | ($CD_3OD$) δ7.79 (s, 0.5H), 7.74 (s, 0.5H), 7.58 (s, 0.5H), 7.56 (s, 0.5H), 4.18-3.91 (m, 3H), 3.82-3.43 (m, 3H), 3.45-3.31 (m, 1H), 3.04-2.67 (m, 3H), 2.61-2.48 (m, 1H), 2.39-1.76 (m, 10H), 1.25 (d, J = 6.6 Hz, 1H), 1.22-1.13 (m, 3H), 1.12-1.02 (m, 3H) |
| 175 | ($CD_3OD$) δ7.82 (s, 0.5H), 7.77 (s, 1H), 7.73 (s, 0.5H), 4.18-3.90 (m, 3H). 3.82-3.67 (m, 1H), 3.68-3.52 (m, 2H), 3.64 (s, 1.5H), 3.63 (s, 1.5H), 3.45-3.34 (m, 2H), 3.04-2.91 (m, 1H), 2.89-2.70 (m, 1H), 2.58-2.37 (m, 1H), 2.16-2.04 (m, 1H), 1.94-1.60 (m, 9H), 1.35-1.22 (m, 3H), 1.25-1.13 (m, 3H) |
| 176 | ($CD_3OD$) δ7.77 (s, 0.5H), 7.75 (s, 0.5H), 7.75 (s, 0.5H), 7.63 (s, 0.5H), 4.19-3.91 (m, 3H), 3.83-3.52 (m, 3H), 3.53-3.33 (m, 2H), 3.13-2.90 (m, 1H), 2.90-2.67 (m, 1H), 2.52-2.41 (m, 1H), 2.24-2.00 (m, 4H), 1.98-1.57 (m, 9H), 1.30-1.22 (m, 3H), 1.22-1.13 (m, 3H), 1.13-1.03 (m, 3H) |
| 177 | ($CD_3OD$) δ7.79 (s, 0.5H), 7.76 (s, 0.5H), 7.26 (s, 0.5H), 7.16 (s, 0.5H), 4.31-4.13 (m, 1H), 4.14-3.96 (m, 2H), 3.81-3.68 (m, 1H), 3.70-3.20 (m, 6H), 3.39 (s, 3H), 3.27 (s, 1.5H), 3.24 (s, 1.5H), 3.03-2.90 (m, 1H), 2.90-2.66 (m, 1H), 2.15-2.04 (m, 1H), 2.05-1.95 (m, 1H), 1.95-1.70 (m, 2H), 1.73-1.50 (m, 4H), 1.49 (s, 3H), 1.27-1.12 (m, 6H) |
| 178 | ($CD_3OD$) δ7.82 (s, 0.5H), 7.82 (s, 0.5H), 7.33 (s, 0.5H), 7.26 (s, 0.5H), 4.38-4.12 (m, 1H), 4.14-3.95 (m, 2H), 3.50-3.31 (m, 4H), 3.27 (s, 1.5H), 3.26 (s, 1.5H), 3.05-2.89 (m, 1H), 2.91-2.68 (m, 1H), 2.13-2.04 (m, 1H), 2.04-1.92 (m, 1H), 1.95-1.75 (m, 2H), 1.70-1.49 (m, 4H), 1.45 (d, J = 7.0 Hz, 1.5H), 1.40 (d, J = 7.0 Hz, 1.5H), 1.27-1.13 (m, 3H) |
| 179 | ($CD_3OD$) δ7.50, 7.43 (d, J = 15 Hz, 1H), 7.30 (s, 3H), 3.87-4.16 (m, 3H), 3.72-3.85 (m, 1H), 3.51-3.67 (m, 6H), 3.32-3.43 (m, 3H), 2.95-3.05 (m, 1H), 2.79-2.91 (m, 1H), 2.25 (s, 3H), 2.09-2.12 (m, 1H), 1.88-1.96 (m, 2H), 1.55-1.62 (m, 1H), 1.44, 1.38 (d, J = 7 Hz, 3H), 1.23-1.26 (m, 6H) |

TABLE 77

| Comp. No. | $^{1}H$ NMR (400 MHz, solvent)/MS (ESI+) |
|---|---|
| 180 | RT 2.421 min (Shim-pack XR-ODS, 0.1% trifluoroacetic acid in water/acetonitrile, acetonitirile 30-90% 5.7 min, 1.0 ml/min). MS ($ESI^+$) 460 ($M^+$ + 1, 100%). |
| 181 | ($CD_3OD$) δ7.86 (s, 1H), 7.43, 7.37 (s, 1H), 4.22-4.31 (m, 1H), 4.02-4.17 (m, 1H), 3.61-3.77 (m, 3H), 3.32-3.48 (m, 4H), 3.27 (s, 3H), 2.96-3.04 (m, 1H), 2.77-2.86 (m, 1H), 2.36 (m, 3H), 2.09-2.13 (m, 1H), 1.85-2.02 (m, 2H), 1.62-1.69 (m, 2H), 1.58-1.60 (m, 6H), 1.45 (s, 3H), 1.21-1.27 (m, 6H) |
| 182 | ($CD_3OD$) δ7.56-7.82 (m, 2H), 4.05-4.24 (m, 3H), 3.62-3.83 (m, 5H), 3.32-3.55 (m, 3H), 2.93-3.00 (m, 1H), 2.75-2.86 (m, 1H), 2.18-2.28 (m, 3H), 1.82-1.97 (m, 2H), 1.47, 1.41 (d, J = 7 Hz, 3H), 1.05-1.27 (m, 10H) |
| 183 | ($CD_3OD$) δ7.78 (d, J = 18 Hz, 1H), 7.70 (d, J = 41 Hz, 1H), 3.92-4.22 (m, 3H), 3.57-3.82 (m, 3H), 3.25-3.48 (m, 3H), 2.91-3.05 (m, 2H), 2.71-2.90 (m, 1H), 2.08-2.22 (m, 4H), 1.89-1.99 (m, 2H), 1.51 (s, 3H), 1.37 (s, 3H), 1.26 (d, J = 6.52, 3H), 1.19 (t, J = 6.8 Hz, 3H), 1.03-1.12 (m, 3H) |
| 184 | ($CD_3OD$) δ8.18 (s, 0.5H), 7.51 (s, 0.5H), 7.25 (s, 0.5H), 7.26 (s, 0.5H), 4.18-3.82 (m, 3H), 3.85-3.13 (m, 5H), 3.62 (s, 1.5H), 3.60 (s, 1.5H), 3.03-2.75 (m, 2H), 2.50-2.31 (m, 1H), 2.06-1.51 (m, 11H), 1.37-1.10 (m, 6H) |
| 185 | ($CDCl_3$) δ9.81-9.78 (brs 2H), 7.16 (brs, 1H), 6.92 (brs, 2H), 4.18 (brs, 1H), 4.01-3.84 (m, 4H), 3.50-3.38 (m, 4H), 3.32 (s, 3H), 3.92-2.81 (m, 2H), 2.76 (s, 2H), 2.19-2.04 (m, 2H), 1.88 (brs, 1H), 1.78 (brs, 1H), 1.67-1.61 (m, 4H), 1.32 (brs, 2H), 1.38-1.31 (m, 3H), 1.16 (d, J = 2.0 Hz, 5H) |
| 186 | ($CDCl_3$) δ9.83 (brs, 2H), 6.96 (s, 1H), 6.65 (s, 1H), 4.23 (brs, 1H), 4.03-3.75 (m, 5H), 3.52-3.45 (m, 2H), 3.45-3.39 (m, 3H), 3.27 (s, 3H), 2.93 (brs, 2H), 2.77-2.61 (m, 2H), 2.29-2.05 (m, 6H), 1.94-1.85 (m, 1H), 1.46-1.25 (m, 4H), 1.25-1.14 (m, 6H), 1.09 (d, J = 2.0 Hz, 3H) |
| 187 | ($CDCl_3$) δ7.32 (brs, 2H), 4.52-3.94 (m, 3H), 3.94-3.64 (m, 5H), 3.63-3.28 (m, 2H), 3.26-2.71 (m, 5H), 2.44-1.83 (m, 7H), 1.71-1.07 (m, 12H) |
| 189 | ($CDCl_3$) δ9.93-9.78 (m, 2H), 7.26 (d, J = 4 Hz, 1H), 7.16 (d, J = 4 Hz, 1H), 4.28-4.11 (m, 2H), 3.98-3.83 (m, 2H), 3.77-3.68 (m, 1H), 3.68-3.58 (m, 3H), 3.51- |

TABLE 77-continued

| Comp. No. | $^1$H NMR (400 MHz, solvent)/MS (ESI+) |
|---|---|
| | 3.30 (m, 4H), 3.02-2.88 (m, 2H), 2.94-2.67 (m, 2H), 2.08-2.00 (m, 2H), 1.99-1.72 (m, 2H), 1.42-1.36 (m, 3H), 1.31-1.16 (m, 6H), 1.15-1.05 (m, 3H) |
| 190 | ($CDCl_3$) δ9.98-9.45 (brs, 2H), 7.12 (m, 1H), 6.88 (m, 1H), 4.48-4.36 (m, 1H), 4.26-4.17 (m, 1H), 4.12-3.95 (m, 2H), 3.62-3.36 (m, 4H), 3.37-3.26 (m, 6H), 2.96-2.76 (m, 2H), 2.33 (s, 3H), 2.18-1.93 (m, 4H), 1.57-1.47 (m, 3H), 1.41-1.34 (m, 3H), 1.30-1.17 (m, 6H), 1.16-1.11 (m, 3H) |

TABLE 78

| | |
|---|---|
| 191 | ($CDCl_3$) δ 9.84 (brs, 2H), 7.13 (s, 0.6H), 7.09 (s, 0.4H), 6.95 (s, 1H), 5.80 (t, J = 5.4 Hz, 0.4H), 5.28 (t, J = 5.8 Hz, 0.6H), 4.25-4.12 (m, 1H), 4.08-3.82 (m, 3H), 3.78-3.69 (m, 1H), 3.68-3.55 (m, 3H), 3.55-3.27 (m, 3H), 2.99-2.81 (m, 2H), 2.81-2.53 (m, 3H), 2.23-2.17 (m, 3H), 2.18-1.99 (m, 2H), 1.96-1.82 (m, 1H), 1.41-1.24 (m, 3H), 1.24-1.11 (m, 6H), 1.07 (s, 3H) |
| 192 | ($CDCl_3$) δ9.64-9.51 (m, 2H), 7.01 (s, 0.5H), 6.98 (s, 0.5H), 6.94 (s, 1H), 5.69 (m, 0.5H), 5.19 (t, J = 5.4 Hz, 0.5H), 4.20-4.14 (m, 1H), 4.13-3.96 (m, 1H), 3.96-3.76 (m, 2H), 3.74-3.63 (m, 1H), 3.61-3.50 (m, 4H), 3.48-3.22 (m, 3H), 2.93-2.78 (m, 2H), 2.78-2.59 (m, 2H), 2.55-2.26 (m, 2H), 2.15-1.97 (m, 1H), 2.05-1.90 (m, 1H), 1.88-1.75 (m, 1H), 1.34-1.22 (m, 3H), 1.22-1.09 (m, 9H), 1.06 (s, 3H) |
| 193 | ($CDCl_3$) δ9.84-9.53 (m, 2H), 7.20 (s, 1H), 7.08 (s, 1H), 4.18-3.77 (m, 4H), 3.71-3.56 (m, 3H), 3.54-3.32 (m, 3H), 2.94-2.83 (m, 1H), 2.83-2.61 (m, 2H), 2.21-1.94 (m, 9H), 1.46-1.24 (m, 2H), 1.24-1.05 (m, 10H) |
| 194 | ($CDCl_3$) δ9.69 (brs, 2H), 7.18-6.93 (m, 2H), 4.33-4.14 (m, 1H), 4.16-3.84 (m, 3H), 3.84-3.74 (m, 2H), 3.64-3.34 (m, 3H), 3.04-2.84 (m, 2H), 2.84-2.68 (m, 2H), 2.58-2.42 (m, 3H), 2.31-2.11 (m, 6H), 1.44-1.15 (m, 7H), 1.15-1.06 (m, 8H) |
| 195 | (DMSO-$d_6$) δ9.51-9.46 (brs, 1H), 9.32-9.27 (m, 0.6H), 9.24-9.22 (m, 0.4H), 8.17-8.10 (m, 1H), 7.66-7.57 (m, 1.6H), 7.53 (s, 0.4H), 3.91-3.82 (m, 2H), 3.82-3.75 (m, 2H), 3.29-3.25 (m, 1H), 3.21-3.12 (m, 2H), 3.03-3.00 (m, 1H), 2.93-2.82 (m, 2H), 2.76-2.69 (m, 1H), 2.64-2.58 (m, 1H), 2.09-2.02 (m, 2H), 1.87 (brs, 2H), 1.69-1.64 (m, 1H), 1.52-1.50 (m, 0.6H), 1.40-1.36 (m, 0.4H), 1.20-1.12 (d, J = 6.7 Hz, 2H), 1.14-1.03 (m, 5H), 1.01-0.81 (m, 8H) |
| 196 | (DMSO-$d_6$) δ 9.18 (brs, 2H), 8.16-8.08 (m, 1H), 7.66-7.58 (m, 1.6H), 7.50 (s, 0.4H), 3.91-3.77 (m, 3H), 3.71-3.66 (m, 1H), 3.57-3.51 (m, 1H), 3.38-3.25 (m, 1H), 3.22-3.15 (m, 2H), 3.08-3.02 (m, 1H), 2.82-2.73 (m, 1H), 2.64-2.58 (m, 1H), 2.09-2.02 (m, 4H), 1.94-1.78 (m, 2H), 1.70-1.59 (m, 6H), 1.43-1.35 (m, 3H), 1.19-1.17 (d, J = 6.6 HZ, 2H), 1.14-1.09 (m, 2H), 1.00 (d, J = 2.4 Hz, 2H), 0.99-0.91 (m, 3H) |
| 200 | (DMSO-$d_6$) δ 9.41 (brs, 1H), 8.63 (brs, 1H), 7.39-7.16 (m, 2H), 4.12-4.09 (m, 1H) 3.91-3.88 (m, 1H), 3.79 (m, 1H), 3.65-3.50 (m, 2H), 3.45-3.42 (m, 1H), 3.21-3.16 (m, 5H), 3.11-3.03 (m, 1H), 2.40-2.28 (m, 1H), 1.90-1.76 (m, 4H), 1.60-1.48 (m, 9H), 1.41 (s, 3H), 1.17-1.03 (m, 6H) |
| 201 | 1H-NMR (400 MHz, DMSO-$d_6$) δ 9.44 (m, 2H), 7.38-7.24 (m, 2H), 4.25 (m, 1H), 4.10 (m, 1H), 3.89 (m, 1H), 3.71 (m, 1H), 3.58-3.54 (m, 2H), 3.16 (s, 3H), 3.08 (m, 1H), 2.22 (m, 2H), 2.00 (m, 1H), 1.51-1.48 (m, 7H), 1.41 (s, 3H), 1.31-1.30 (m, 2H), 1.14-1.11 (m, 3H), 1.05-1.02 (m, 3H).<br>MS (ESI+) 486 (M + 1, 100%). |

TABLE 79

| Comp. No. | $^1$H NMR (400 MHz, solvent)/MS (ESI+) |
|---|---|
| 202 | RT 2.350 min (Shim-pack XR-ODS, 0.1% trifluoroacetic acid in water/acetonitrile, acetonitrile 30-90% 5.7 min, 1.0 ml/min).<br>MS (ESI+) 525 ($M^+$ + 1, 100%). |
| 203 | RT 2.346 min (Shim-pack XR-ODS, 0.1% trifluoroacetic acid in water/acetonitrile, acetonitrile 30-90% 5.7 min, 1.0 ml/min).<br>MS (ESI+) 525 ($M^+$ + 1, 100%). |
| 204 | RT 2.156 min (Shim-pack XR-ODS, 0.1% trifluoroacetic acid in water/acetonitrile, acetonitrile 30-90% 5.7 min, 1.0 ml/min).<br>MS (ESI+) 553 ($M^+$ + 1, 100%). |
| 205 | RT 2.435 min (Shim-pack XR-ODS, 0.1% trifluoroacetic acid in water/acetonitrile, acetonitrile 30-90% 5.7 min, 1.0 ml/min).<br>MS (ESI+) 556 ($M^+$ + 1, 100%). |
| 206 | RT 1.881 min (Shim-pack XR-ODS, 0.1% trifluoroacetic acid in water/acetonitrile, acetonitrile 30-90% 5.7 min, 1.0 ml/min).<br>MS (ESI+) 571 ($M^+$ + 1, 100%). |
| 207 | ($CD_3OD$) δ7.56-7.43 (m, 2H), 7.29-7.27 (m, 2H), 4.25-3.99 (m, 4H), 3.88-3.61 (m, 4H), 3.68-3.52 (m, 3H), 3.44-3.29 (m, 4H), 3.01-2.71 (m, 4H), 2.20-1.85 (m, 4H), 1.52-1.44 (m, 2H), 1.28-1.15 (m, 6H), 1.11-1.02 (m, 3H) |
| 208 | ($CD_3OD$) δ7.61-7.52 (m, 2H), 7.29-7.26 (m, 2H), 4.11-3.98 (m, 4H), 3.88-3.61 (m, 4H), 3.65 (s, 3H), 3.60-3.52 (m, 1H), 3.42-3.25 (m, 4H), 3.01-2.65 (m, 4H), 2.27-1.85 (m, 4H), 1.53-1.45 (m, 2H), 1.28-1.16 (m, 6H) |

TABLE 79-continued

| Comp. No. | $^1$H NMR (400 MHz, solvent)/MS (ESI+) |
|---|---|
| 209 | RT 3.025 min (Shim-pack XR-ODS, 0.1% trifluoroacetic acid in water/acetonitrile, acetonitrile 30-90% 5.7 min, 1.0 ml/min). MS (ESI+) 607 ($M^+$ + 1, 100%). |
| 210 | RT 3.018 min (Shim-pack XR-ODS, 0.1% trifluoroacetic acid in water/acetonitrile, acetonitrile 30-90% 5.7 min, 1.0 ml/min). MS (ESI+) 637 ($M^+$ + 1, 100%). |
| 211 | RT 2.907 min (Shim-pack XR-ODS, 0.1% trifluoroacetic acid in water/acetonitrile, acetonitrile 30-90% 5.7 min, 1.0 ml/min). MS (ESI+) 637 ($M^+$ + 1, 100%). |
| 212 | RT 2.526 min (Shim-pack XR-ODS, 0.1% trifluoroacetic acid in water/acetonitrile, acetonitrile 30-90% 5.7 min, 1.0 ml/min). MS (ESI+) 574 ($M^+$ + 1, 100%). |
| 213 | RT 2.640 min (Shim-pack XR-ODS, 0.1% trifluoroacetic acid in water/acetonitrile, acetonitrile 30-90% 5.7 min, 1.0 ml/min). MS (ESI+) 600 ($M^+$ + 1, 100%). |
| 214 | RT 3.108 min (Shim-pack XR-ODS, 0.1% trifluoroacetic acid in water/acetonitrile, acetonitrile 30-90% 5.7 min, 1.0 ml/min). MS (ESI+) 617 ($M^+$ + 1, 100%). |
| 215 | RT 2.973 min (Shim-pack XR-ODS, 0.1% trifluoroacetic acid in water/acetonitrile, acetonitrile 30-90% 5.7 min, 1.0 ml/min). MS (ESI+) 617 ($M^+$ + 1, 100%). |
| 216 | RT 2.680 min (Shim-pack XR-ODS, 0.1% trifluoroacetic acid in water/acetonitrile, acetonitrile 30-90% 5.7 min, 1.0 ml/min). MS (ESI+) 602 ($M^+$ + 1, 100%). |

TABLE 80

| Comp. No. | $^1$H NMR (400 MHz, solvent)/MS (ESI+) |
|---|---|
| 217 | RT 1.690 min (Shim-pack XR-ODS, 0.1% trifluoroacetic acid in water/acetonitrile, acetonitrile 30-90% 5.7 min, 1.0 ml/min). MS (ESI+) 516 ($M^+$ + 1, 100%). |
| 218 | RT 2.280 min (Shim-pack XR-ODS, 0.1% trifluoroacetic acid in water/acetonitrile, acetonitrile 30-90% 5.7 min, 1.0 ml/min). MS (ESI+) 618 ($M^+$ + 1, 100%). |
| 219 | RT 1.848 min (Shim-pack XR-ODS, 0.1% trifluoroacetic acid in water/acetonitrile, acetonitrile 30-90% 5.7 min, 1.0 ml/min). MS (ESI+) 560 ($M^+$ + 1, 100%). |
| 220 | RT 2.695 min (Shim-pack XR-ODS, 0.1% trifluoroacetic acid in water/acetonitrile, acetonitrile 30-90% 5.7 min, 1.0 ml/min). MS (ESI+) 588 ($M^+$ + 1, 100%). |
| 221 | RT 2.527 min (Shim-pack XR-ODS, 0.1% trifluoroacetic acid in water/acetonitrile, acetonitrile 30-90% 5.7 min, 1.0 ml/min). MS (ESI+) 544 ($M^+$ + 1, 100%). |
| 222 | ($CD_3OD$) δ7.53, 7.42 (s, 1H), 7.31 (s, 1H), 6.14, 6.02, 5.87 (s, 1H), 4.02-4.22 (m, 2H), 3.72-3.91 (m, 2H), 3.34-3.70 (m, 6H), 3.24 (s, 3H), 2.92-3.02 (m, 1H), 2.72-2.88 (m, 1H), 1.80-2.17 (m, 4H), 1.53-1.64 (m, 2H), 1.51, 1.46 (s, 3H), 1.16-1.33 (m, 6H). MS (ESI+) 565(M + 1, 100%). |
| 223 | ($CD_3OD$) δ7.53, 7.42 (s, 1H), 7.33 (s, 1H), 6.15, 6.02, 5.88 (s, 1H), 4.02-4.17 (m, 2H), 3.63-3.99 (m, 3H), 3.34-3.62 (m, 5H), 3.15-3.34 (m, 1H), 2.92-3.02 (m, 1H), 2.70-2.86 (m, 1H), 1.75-2.15 (m, 4H), 1.47-1.73 (m, 2H), 1.42, 1.46 (s, 3H), 1.23-1.28 (m, 3H), 1.15-1.23 (m, 3H). MS (ESI+) 551(M + 1, 100%). |
| 224 | (DMSO-$d_6$) δ8.18-7.46 (m, 6H), 4.06-3.88 (m, 3H), 3.80-3.23 (m, 5H), 2.80-2.51 (m, 3H), 2.07-1.99 (m, 2H), 1.80 (s, 3H), 1.46-1.30 (m, 3H), 1.16-0.90 (m, 8H). MS (ESI+) 600(M + 1, 100%). |
| 225 | (DMSO-$d_6$) δ8.15-7.45 (m, 6H), 4.08-3.58 (m, 3H), 3.56-3.22 (m, 5H), 2.81-2.54 (m, 3H), 2.09-1.90 (m, 2H), 1.84 (s, 3H), 1.46-1.22 (m, 3H), 1.16-0.91 (m, 8H). MS (ESI+) 600(M + 1, 100%). |
| 226 | ($CD_3OD$) δ8.13-8.04 (m, 1H), 7.55 (brs, 0.5H), 7.51-7.40 (m, 1.5H), 7.16-7.06 (m, 1H), 6.86-6.74 (m, 2H), 6.70-6.62 (m, 1H), 4.28-4.12 (m, 1.5H), 4.12-3.96 (m, 1.5H), 3.86-3.74 (m, 1H), 3.71-3.50 (m, 4H), 3.44-3.32 (m, 2H), 3.31-3.24 (m, 1H), 2.99-2.88 (m, 1H), 2.86-2.68 (m, 1H), 2.24-2.18 (m, 3H), 2.16-2.02 (m, 2H), 1.99-1.86 (m, 3H), 1.33-1.25 (m, 1.5H), 1.24-1.16 (m, 1.5H), 1.16-1.04 (m, 6H). MS (ESI+) 591(M + 1, 100%). |

TABLE 81

| | |
|---|---|
| 227 | ($CDCl_3$) δ9.86-9.52 (m, 2H), 7.38-7.15 (m, 5H), 7.14-7.01 (m, 2H), 4.24-4.05 (m, 2H), 3.93-3.80 (m, 2H), 3.81-3.75 (m, 1H), 3.74-3.67 (m, 1H), 3.63-3.37 (m, 3H), |

TABLE 81-continued

| | |
|---|---|
| | 3.41-3.28 (m, 1H), 2.92-2.81 (m, 1H), 2.84-2.69 (m, 1H), 2.26-2.19 (m, 2H), 2.04-1.83 (m, 6H), 1.32-1.23 (m, 3H), 1.24-1.23 (m, 3H), 1.16-1.00 (m, 3H). MS (ESI+) 575(M + 1, 100%). |
| 228 | ($CD_3OD$) δ8.00-7.96 (m, 0.5H), 7.88-7.76 (m, 1.5H), 7.64-7.62 (m, 0.5H), 7.54-7.48 (m, 0.5H), 7.43-7.37 (m, 2H), 4.19-4.02 (m, 3H), 3.86-.75 (m, 1H), 3.62-3.44 (m, 2H), 3.42-3.24 (m, 4H), 3.03-2.91 (m, 1H), 2.89-2.68 (m, 1H), 2.21-2.04 (m, 4H), 2.00-1.76 (m, 5H), 1.28-1.21 (m, 1.5H), 1.19-1.11 (m, 1.5H),1.11-1.02 (m, 6H). MS (ESI+) 618 (M + 1, 100%). |
| 229 | ($CD_3OD$) δ7.58-7.54 (m, 1.5H), 7.48-7.44 (m, 3.5H), 7.24-7.20 (m, 1H), 4.28-4.11 (m, 1.5H), 4.08-3.94 (m, 1.5H), 3.82-3.63 (m, 1H), 3.62-3.50 (m, 2H), 3.46-3.21 (m, 4H), 3.21-3.14 (m, 3H), 3.02-2.89 (m, 1H), 2.84-2.67 (m, 1H), 2.23-2.04 (m, 4H), 1.94-1.71 (m, 5H), 1.27-1.25 (m, 1.5H), 1.21-1.24 (m, 1.5H), 1.14-1.04 (m, 6H). MS (ESI+) 669 (M + 1, 100%). |
| 230 | ($CD_3OD$) δ7.51-7.29 (m, 4H), 7.22-7.03 (m, 2H), 4.26-4.04 (m, 3H), 3.84-3.73 (m, 1H), 3.72-3.55 (m, 3H), 3.46-3.35 (m, 2H), 3.31-3.24 (m, 1H), 2.99-2.92 (m, 1H), 2.88-2.73 (m, 1H), 2.26-2.04 (m, 4H), 2.01-1.94 (m, 3H), 1.95-1.82 (m, 2H), 1.31-1.25 (m, 1.5H), 1.22-1.16 (m, 1.5H), 1.16-1.04 (m, 6H). MS (ESI+) 593 (M + 1, 100%). |
| 231 | ($CDCl_3$) δ9.84-9.64 (brs, 2H), 7.68-7.36 (m, 4H), 7.03-6.84 (m, 2H), 4.20-4.04 (m, 2H), 3.94-3.74 (m, 3H), 3.58-3.31 (m, 4H), 2.94-2.71 (m, 2H), 2.21-2.02 (m, 5H), 2.01-1.94 (m, 2H), 2.93-1.82 (m, 4H), 1.34-1.00 (m, 9H). MS (ESI+) 589 (M + 1, 100%). |
| 232 | ($CDCl_3$) δ9.84-9.54 (m, 2H), 7.36-7.17 (m, 5H), 7.16-7.04 (m, 2H), 4.20-4.04 (m, 2H), 3.91-3.81 (m, 2H), 3.80-3.74 (m, 1H), 3.71-3.64 (m, 1H), 3.60-3.36 (m, 3H), 3.39-3.28 (m, 1H), 2.91-2.81 (m, 1H), 2.81-2.68 (m, 1H), 2.24-2.21 (m, 2H), 2.02-1.84 (m, 6H), 1.34-1.26 (m, 3H), 1.26-1.22 (m, 3H), 1.14-1.01 (m, 3H). MS (ESI+) 521 (M + 1, 100%). |
| 233 | ($CDCl_3$) δ9.77-9.50 (m, 2H), 7.29-7.11 (m, 5H), 6.87-6.79 (m, 2H), 4.16-3.89 (m, 2H), 3.84-3.74 (m, 1H), 3.69-3.53 (m, 2H), 3.52-3.24 (m, 4H), 2.84-2.68 (m, 2H), 2.48-2.31 (m, 2H), 2.12 (s, 3H), 2.08-1.94 (m, 2H), 1.93-1.73 (m, 5H), 1.31-1.18 (m, 3H), 1.21-0.96 (m, 6H). MS (ESI+) 541 (M+, 100%). |
| 234 | (DMSO-$d_6$) δ7.66-7.11 (m, 6H), 4.11-3.75 (m, 3H), 3.60-3.22 (m, 5H), 3.10-2.52 (m, 2H), 2.30-2.03 (m, 3H), 1.83 (s, 3H), 1.56-1.38 (m, 3H), 1.19-0.92 (m, 8H). MS (ESI+) 593 (M + 1, 100%). |

TABLE 82

| | |
|---|---|
| 235 | (DMSO-$d_6$) δ7.08-6.96 (s, 1H), 6.30-6.03 (m, 1H), 4.00-3.61 (m, 4H), 3.15-3.13 (m, 1H), 2.80-2.50 (m, 4H), 2.49-2.40 (m, 1H), 2.39-2.13 (m, 3H), 2.14 (s, 3H), 1.98-1.72 (m, 6H), 1.46-1.43 (m, 1H), 1.12 (m, 6H). MS (ESI+) 493 (M + 1, 100%). |
| 236 | ($CD_3OD$) δ7.30, 7.20 (s, 1H), 6.83 (s, 1H), 4.12 (t, 2H), 3.81-4.08 (m, 2H), 3.55-3.68 (m, 1H), 3.33-3.55 (m, 4H), 2.77-3.03 (m, 2H), 2.12-2.26 (m, 6H), 1.85-2.12 (m, 4H), 1.52-1.63 (m, 1H), 1.05-1.38 (m, 12H). MS (ESI+) 457 (M + 1, 100%). |
| 237 | ($CD_3OD$) δ7.31, 7.23 (s, 1H), 6.83 (s, 1H), 6.14, 6.00, 5.87 (s, 1H), 4.08-4.14 (m, 2H), 3.98-4.02 (m, 1H), 3.82-3.86 (m, 1H), 3.3.34-3.67 (m, 3H), 2.92-3.03 (m, 1H), 2.77-2.92 (m, 1H), 2.23 (d, 4H), 1.82-2.13 (m, 6H), 1.53-1.64 (m, 1H), 1.19-1.39 (m, 9H). MS (ESI+) 479 (M + 1, 100%). |
| 238 | ($CDCl_3$) δ 7.68-7.33 (m, 11H), 4.46(br, 1H), 4.18-3.93 (m, 3H), 3.78-3.51 (m, 4H), 3.24-2.95 (br, 2H), 2.68 (br, 1H), 2.23 (br, 1H), 2.07-2.01 (m, 2H), 1.55-1.40 (m, 7H), 1.23 (br, 4H), 1.02 (m, 3H), 0.46 (m, 3H). MS (ESI+) 665 (M + 1, 80%). |
| 239 | (DMSO-$d_6$) δ9.07 (brs, 2H), 8.80 (d, J = 9.6 Hz, 1H), 7.30-7.19 (m, 6H), 6.99 (s, 1H), 4.75-4.73 (m, 1H), 4.06-3.93 (m, 2H), 3.45-3.25 (m, 6H), 3.21 (s, 3H), 3.09 (m, 1H), 2.58-2.49 (m, 1H), 1.92-1.89 (m, 1H), 1.67-1.53 (m, 4H), 1.42 (s, 3H), 1.39 (s, 3H). MS (ESI+) 434 (M + 1, 100%). |
| 240 | (DMSO-$d_6$) δ9.33-9.31 (m, 2H), 8.30-6.52 (m, 7H), 4.32-3.70 (m, 3H), 3.67-3.30 (m, 8H), 3.25-3.20 (m, 2H), 3.15 (s, 3H), 2.88-2.66 (m, 2H), 2.22-1.84 (m, 2H), 1.46-0.55 (m, 12H). MS (ESI+) 462 (M + 1, 100%). |
| 241 | (DMSO-$d_6$) δ9.07 (brs, 2H), 8.68-8.66 (m, 1H), 7.37-7.24 (m, 6H), 6.52 (s, 1H), 4.48-4.45 (m, 1H), 3.76-3.74 (m, 2H), 3.39-3.28 (m, 1H), 3.23 (s, 3H), 3.05-2.91 (m, 2H), 2.84-2.78 (m, 1H), 1.99-1.94 (m, 2H), 1.46-1.39 (m, 10H). MS (ESI+) 434 (M + 1, 100%). |
| 242 | (DMSO-$d_6$) δ9.22 (brs, 2H), 7.45-6.14 (m, 7H), 4.03-3.86 (m, 2H), 3.73 (m, 2H), 3.56-3.54 (m, 1H), 3.43-3.17 (m, 3H), 3.12-3.06 (m, 2H), 2.85 (brs, 1H), 2.29-1.97 (m, 2H), 1.54-1.23 (m, 11H), 0.87-0.58 (m, 3H). MS (ESI+) 462 (M + 1, 100%). |

TABLE 82-continued

| | |
|---|---|
| 243 | (DMSO-$d_6$) δ9.10 (brs, 2H), 7.76-6.15 (m, 8H), 4.01-3.68 (m, 5H), 3.38-3.07 (m, 8H), 2.08-1.90 (m, 3H), 1.57-0.73 (m, 12H). MS (ESI+) 575 (M + 1, 100%). |
| 244 | (DMSO-$d_6$) δ9.60-9.08 (m, 2H), 8.32-6.92 (m, 5H), 4.43-4.07 (m, 1H), 3.95-3.86 (m, 3H), 3.66-3.05 (m, 9H), 2.12-1.83 (m, 4H), 1.53-0.75 (m, 9H). MS (ESI+) 579 (M + 1, 100%). |

TABLE 83

| | |
|---|---|
| 245 | (DMSO-$d_6$) δ9.07 (brs, 2H), 8.68-8.66 (m, 1H), 7.37-7.24 (m, 6H), 6.52 (s, 1H), 4.48-4.45 (m, 1H), 3.76-3.74 (m, 2H), 3.39-3.28 (m, 1H), 3.23 (s, 3H), 3.05-2.91 (m, 2H), 2.84-2.78 (m, 1H), 1.99-1.94 (m, 2H), 1.46-1.39 (m, 10H). MS (ESI+) 434 (M + 1, 100%). |
| 246 | (DMSO-$d_6$) δ9.07 (brs, 2H), 8.80 (d, J = 9.6 Hz, 1H), 7.30-7.19 (m, 6H), 6.99 (s, 1H), 4.75-4.73 (m, 1H), 4.06-3.93 (m, 2H), 3.45-3.25 (m, 6H), 3.21 (s, 3H), 3.09 (m, 1H), 2.58-2.49 (m, 1H), 1.92-1.89 (m, 1H), 1.67-1.53 (m, 4H), 1.42 (s, 3H), 1.39 (s, 3H). MS (ESI+) 434 (M + 1, 100%). |
| 247 | (DMSO-$d_6$) δ9.22 (brs, 2H), 7.45-6.14 (m, 7H), 4.03-3.86 (m, 2H), 3.73 (m, 2H), 3.56-3.54 (m, 1H), 3.43-3.17 (m, 3H), 3.12-3.06 (m, 2H), 2.85 (brs, 1H), 2.29-1.97 (m, 2H), 1.54-1.23 (m, 11H), 0.87-0.58 (m, 3H). MS (ESI+) 462 (M + 1, 100%). |
| 248 | (DMSO-$d_6$) δ9.33-9.31 (m, 2H), 8.30-6.52 (m, 7H), 4.32-3.70 (m, 3H), 3.67-3.30 (m, 8H), 3.25-3.20 (m, 2H), 3.15 (s, 3H), 2.88-2.66 (m, 2H), 2.22-1.84 (m, 2H), 1.46-0.55 (m, 12H). MS (ESI+) 462 (M + 1, 100%). |
| 249 | ($CDCl_3$) δ9.92-9.53 (br, 2H), 7.13-6.55 (m, 2H), 4.18-3.65 (m, 5H), 3.64-3.50 (m, 2H), 3.45-3.12 (m, 10H), 2.95-2.62 (m, 2H), 2.15-1.45 (m, 10H), 1.35-1.03 (m, 6H). MS (ESI+) 500 (M + 1, 100%). |
| 250 | ($CDCl_3$) δ 7.91-7.35 (m, 2H), 4.46 (br, 2H), 4.06 (m, 2H), 3.75-3.57 (m, 3H), 3.38-3.31 (m, 2H), 2.98-2.70 (m, 2H), 2.11-1.85 (m, 6H), 1.55-1.51 (m, 6H), 1.33-1.13 (m, 5H). MS (ESI+) 567 (M + 1, 12%). |
| 251 | RT 2.293 min (Shim-pack XR-ODS, 0.1% trifluoroacetic acid in water/acetonitrile, acetonitrile 30-90% 5.7 min, 1.0 ml/min). MS (ESI+) 516 ($M^+$ + 1, 100%). |
| 252 | RT 2.333 min (Shim-pack XR-ODS, 0.1% trifluoroacetic acid in water/acetonitrile, acetonitrile 30-90% 5.7 min, 1.0 ml/min). MS (ESI+) 514 ($M^+$ + 1, 100%). |
| 253 | RT 2.102 min (Shim-pack XR-ODS, 0.1% trifluoroacetic acid in water/acetonitrile, acetonitrile30-90% 5.7 min, 1.0 ml/min). MS (ESI+) 502 ($M^+$ + 1, 100%). |
| 254 | 1H NMR (400 MHz, $CD_3OD$) δ7.57-7.55(m, 1H), 7.15-7.05 (m, 1H), 3.82-3.46 (m, 3H), 3.44-3.29 (m, 2H), 3.27-3.25 (m, 3H), 3.19-3.07 (m, 4H), 2.80-2.59 (m, 1H), 1.87-1.70 (m, 2H), 1.57-1.45 (m, 4H), 1.28-1.17 (m, 10H), 1.10-1.00 (m, 4H). MS (ESI+) 450 (M + 1, 100%). |
| 255 | 1H NMR (400 MHz, $CD_3OD$) δ7.53-7.49 (m, 1H), 7.14-7.01 (m, 1H), 3.83-3.39 (m, 6H), 3.27-3.11 (m, 3H), 2.91-2.50 (m, 3H), 2.07-1.75 (m, 7H), 1.30-1.01 (m, 8H), 0.91-0.76 (m, 4H). MS (ESI+) 463 (M + 1, 100%). |
| 256 | 1H NMR (400 MHz, $CD_3OD$) δ7.61-7.49 (m, 1H), 7.14-7.09 (m, 1H), 3.80-3.55 (m, 5H), 3.19-3.04 (m, 2H), 2.88-2.61 (m, 2H), 1.89-1.75 (m, 3H), 1.26-1.01 (m, 15H). MS (ESI+) 487 (M + 1, 100%). |

TABLE 84

| | |
|---|---|
| 257 | 1H NMR (400 MHz, $CD_3OD$) δ7.48-7.43 (m, 1H), 7.23-7.05 (m, 1H), 3.86-3.74 (m, 4H), 3.65-3.55 (m, 2H), 3.30-3.13 (m, 3H), 2.90-2.51 (m, 2H), 2.09-1.78 (m, 6H), 1.23-1.02 (m, 9H), 0.87-0.80 (m, 3H), 0.53-0.48 (m, 6H). MS (ESI+) 457 (M + 1, 100%). |
| 258 | RT 2.230 min (Shim-pack XR-ODS, 0.1% trifluoroacetic acid in water/acetonitrile, acetonitrile 30-90% 5.7 min, 1.0 ml/min). MS (ESI+) 441 ($M^+$ + 1, 100%). |
| 259 | 1H NMR (400 MHz, $CD_3OD$) δ7.47 (s, 0.5H), 7.37 (s, 0.5H), 7.28 (s, 1H), 6.01 (t, J = 54 Hz, 0.5H), 5.99 (t, J = 54 Hz, 0.5H), 4.17-3.94 (m, 3H), 3.88-3.73 (m, 1H), 3.62-3.50 (m, 2H), 3.45-3.30 (m, 2H), 3.02-2.75 (m, 2H), 2.26 (s, 0.6H), 2.25 (s, 0.4H), 2.14-2.05 (m, 1H), 2.00-1.78 (m, 2H), 1.63-1.51 (m, 1H), 1.44 (s, 3H), 1.34 (s, 3H), 1.30-1.15 (m, 6H). |
| 260 | 1H NMR (400 MHz, $CD_3OD$) δ7.40 (s, 0.5H), 7.32 (s, 0.5H), 7.31 (s, 0.5H), 7.29 (s, 0.5H), 4.17-3.91 (m, 3H), 3.86-3.74 (m, 1H), 3.65-3.51 (m, 2H), 3.44-3.10 (m, 2H), 3.03-2.92 (m, 1H), 2.90-2.76 (m, 2H), 2.55-2.44 (m, 1H), 2.25 (s, 1.5H), 2.24 (s, 1.5H), 2.22-2.04 (m, 4H), 2.03-1.80 (m, 5H), 1.64-1.50 (m, 1H), 1.27-1.16 (m, 6H), 1.12-1.03 (m, 3H). |

TABLE 84-continued

| | |
|---|---|
| 261 | RT 1.948 min (Shim-pack XR-ODS, 0.1% trifluoroacetic acid in water/acetonitrile, acetonitrile 30-90% 5.7 min, 1.0 ml/min). MS (ESI+) 485 ($M^+$ + 1, 100%). |
| 262 | RT 1.635 min (Shim-pack XR-ODS, 0.1% trifluoroacetic acid in water/acetonitrile, acetonitrile 30-90% 5.7 min, 1.0 ml/min). MS (ESI+) 498 ($M^+$ + 1, 100%). |
| 263 | RT 1.496 min (Shim-pack XR-ODS, 0.1% trifluoroacetic acid in water/acetonitrile, acetonitrile 30-90% 5.7 min, 1.0 ml/min). MS (ESI+) 484 ($M^+$ + 1, 100%). |
| 264 | RT 2.093 min (Shim-pack XR-ODS, 0.1% trifluoroacetic acid in water/acetonitrile, acetonitrile 30-90% 5.7 min, 1.0 ml/min). MS (ESI+) 497 ($M^+$ + 1, 100%). |
| 265 | 1H NMR (400 MHz, DMSO-$d_6$) δ9.11 n (brs, 2H), 8.25-5.99 (m, 7H), 4.30-3.61 (m, 8H), 3.03-2.89 (m, 3H), 2.25-1.84 (m, 6H), 1.53-0.79 (m, 14H). MS (ESI+) 555 (M + 1, 100%). |
| 266 | 1H NMR (400 MHz, DMSO-$d_6$) δ9.40 (m, 2H), 8.32-5.97 (m, 7H), 3.99-3.73 (m, 6H), 3.49-3.43 (m, 3H), 3.17-3.04 (m, 5H), 2.07-1.80 (m, 7H), 1.53-1.37 (m, 7H), 1.23-0.79 (m, 8H). MS (ESI+) 613 (M + 1, 100%). |
| 267 | 1H NMR (400 MHz, DMSO-$d_6$) δ9.10-9.40 (br, 2H), 8.15 (brs, 1H), 6.76-7.56 (m, 3H), 2.60-3.92 (m, 12H), 1.80-2.04 (m, 2H), 1.39-1.52 (m, 8H), 0.94-1.21 (m, 9H). |
| 268 | 1H NMR (400 MHz, DMSO-$d_6$) δ8.90-9.20 (br, 2H), 6.70-7.31 (m, 3H), 6.17 (t, J = 53 Hz, 1H), 2.60-3.92 (m, 7H), 1.80-2.04 (m, 2H), 1.39-1.52 (m, 8H), 0.94-1.21 (m, 9H). |
| 269 | 1H NMR (400 MHz, $CD_3OD$) δ7.30-7.34 (m, 2H), 3.91-4.16 (m, 4H), 3.65-3.75 (m, 3H), 3.30-3.35 (m, 4H), 2.93-2.96 (m, 1H), 2.70-2.82 (m, 2H), 2.13-2.17 (m, 2H), 1.73-1.82 (m, 2H), 1.57-1.58 (m, 3H), 1.39-1.40 (m, 2H), 1.28-1.31 (m, 2H), 1.20-1.24 (m, 2H), 1.12-1.15 (m, 2H), 1.04-1.08 (m, 4H). MS (ESI+) 529 (M + 100%). |

Experiment 1: In Vitro Renin Inhibitory Activity Assay

Recombinant human renin (4.2 ng/mL) was reacted in 0.1M HEPES buffer (pH 7.4) containing 0.1M NaCl, 1 mM EDTA and 0.1 mg/mL BSA together with a substrate and a test compound at 37° C. for one hour. As the substrate, Arg-Glu(EDANS)-Ile-His-Pro-Phe-His-Leu-Val-Ile-His-Thr-Lys(DABCYL)-Arg (SEQ ID NO: 1) or DABCYL-γ-Abu-Ile-His-Pro-Phe-His-Leu-Val-Ile-His-Thr-EDANS (SEQ ID NO: 2) was added in such an amount so that the final concentration thereof became 4 μM. The elevated fluorescence intensity at the exciting wavelength 340 nm and the fluorescence wavelength 500 nm was measured by a fluorescence plate reader. The concentration of a test compound to be needed to inhibit an enzyme activity in the presence of a test compound in several concentrations by 50% was calculated as an $IC_{50}$ value. The test compounds were diluted in DMSO and used in this Experiment.

TABLE 85

| Test Compound | Human renin inhibitory activity $IC_{50}$ (nM) |
|---|---|
| Example 1 | 160 |
| Example 2 | 5.1 |
| Example 4 | 42 |
| Example 7 | 1.3 |
| Example 8 | 410 |
| Example 9 | 140 |
| Example 11 | 460 |
| Example 12 | 160 |
| Example 13 | 5.1 |
| Example 14 | 17 |
| Example 18 | 3.6 |
| Example 19 | 11 |
| Example 20 | 91 |
| Example 21 | 62 |
| Example 22 | 85 |
| Example 26 | 21 |

TABLE 85-continued

| Test Compound | Human renin inhibitory activity $IC_{50}$ (nM) |
|---|---|
| Example 27 | 2.9 |
| Example 30 | 2.2 |
| Example 31 | 0.38 |
| Example 32 | 2.6 |
| Example 33 | 1.2 |
| Example 34 | 140 |
| Example 35 | 2.7 |
| Example 36 | 58 |
| Example 38 | 58 |
| Example 39 | 3.6 |
| Example 40 | 2.6 |
| Example 41 | 68 |
| Example 42 | 15 |
| Example 43 | 69 |
| Example 44 | 1.9 |
| Example 45 | 52 |
| Example 46 | 74 |
| Example 47 | 76 |
| Example 48 | 340 |
| Example 49 | 14 |
| Example 50 | 15 |
| Example 52 | 42 |
| Example 53 | 48 |
| Example 54 | 13 |
| Example 59 | 38 |
| Example 60 | 3.2 |
| Example 62 | 2.8 |
| Example 63 | 0.96 |
| Example 66 | 1230 |
| Example 67 | 250 |
| Example 71 | 2.5 |
| Example 72 | 22 |
| Example 74 | 22 |
| Example 75 | 0.74 |
| Example 76 | 0.56 |
| Example 78 | 20 |
| Example 79 | 5.3 |
| Example 81 | 1.7 |
| Example 82 | 530 |
| Example 83 | 505 |

TABLE 85-continued

| Test Compound | Human renin inhibitory activity $IC_{50}$ (nM) |
|---|---|
| Example 84 | 21 |
| Example 86 | 14 |
| Example 87 | 9.6 |
| Example 88 | 9.6 |
| Example 89 | 1.9 |
| Example 90 | 730 |
| Example 91 | 710 |
| Example 93 | 1896 |
| Example 94 | 1890 |
| Example 97 | 0.13 |
| Example 98 | 9.1 |
| Example 99 | 19 |

Experiment 2: Testing for Irritation by Single Subcutaneous Administration to Rats The abdominal skin of CD male rats were divided in quarters, and a test compound (0.1 ml) was administered thereto once, and the administered sites were observed at one day and three days after the administration, and the inflammation changes were evaluated. A test compound was measured and dissolved in DMSO and a saline solution in a concentration of 2%.

TABLE 86

| Test Compound | Observation at Administration Site | |
|---|---|---|
| | One day after administration | Three days after administration |
| Example 2 | — | — |
| Example 27 | **** | *** |
| Example 67 | ** | — |
| Example 79 | *** | *** |
| Example 81 | ** | — |
| Example 82 | ** | — |
| Example 87 | — | — |
| Example 93 | — | — |
| Example 96 | *** | *** |
| Comparative Example 1 | *** | **** |
| Comparative Example 2 | **** | **** |
| Comparative Example 3 | **** | **** |
| Comparative Example 4 | **** | **** |

Amount of Inflammation: * <  < * < ****,

— No inflammation

Comparative Example 1

4-(4-methoxybutyl)-2,2-dimethyl-3-oxo-N-[(3R)-3-piperidinyl]-N-(2-propanyl)-7-(trifluoromethyl)-3,4-dihydro-2H-1,4-benzoxazine-6-carboxamide hydrochloride Comparative Example 2

2,2-dimethyl-3-oxo-N-[(3R)-3-piperidinyl]-4-[2-(propanoylamino)ethyl]-N-(2-propanyl)-7-(trifluoromethyl)-3,4-dihydro-2H-1,4-benzoxazine-6-carboxamide hydrochloride Comparative Example 3

N-isopropyl-7-methyl-3-oxo-N-[(3R)-piperidin-3-yl]-4-[2-(propionylamino)ethyl]-3,4-dihydrospiro[1,4-benzoxazine-2,1'-cyclobutane]-6-carboxamide hydrochloride Comparative Example 4

N-isopropyl-2,2-dimethyl-3-oxo-N-[(3R)-piperidin-3-yl]-4-[2-(propionylamino)ethyl]-7-(trifluoromethyl)-3,4-dihydro-2H-1,4-benzoxazine-6-carboxamide hydrochloride The compounds of Comparative Examples 1 to 4 are all the compounds having a cyclic amino moiety (precisely a piperidine ring) where the nitrogen atom is not substituted, and they cause inflammation when administered subcutaneously. On the other hand, with respect to the present compounds having the piperidine ring within a nitrogen atom substituted by a specific substituent, the inflammation stimulation activity thereof was decreased. Namely, when the compounds of Comparative Examples 1 to 4 were administered, the intense inflammation was induced and observed already at one day after the administration, and such intense inflammation was sustained even at three days after the administration. On the other hand, when the present compounds were administered, an inflammation was not observed, or in cases the inflammation was observed, it was mild.

Experiment 3: Hypotensive Evaluation Test Using Double Transgenic Rats, and Combination Effect Test Using dTGR (double transgenic: rats transgenic for human renin/angiotensinogen), the hypotensive effects were evaluated by a single administration of a single drug or two drugs. It has been reported that dTGR shows serious hypertension at 3 weeks old, accompanied by severe organ damage and finally died till 8 weeks old (Pilz, B., et al. Hypertension 46(3): 569-576, 2005). Then, in order to keep them alive, enalapril was administered to dTGR rats in drinking water for 5 weeks from 3 weeks old (30 mg/kg/day). After cessation of enalapril, the rats were washed out from drugs at least for 3 weeks, and the animals having 150 mmHg or more of 24-hour average of average blood pressure were used for evaluation. The average for 24 hours before the drug-administration was considered as a baseline value for every individual, the amount of change of the average blood pressure after the administration was calculated. Each test compound was administered once in the form of a single drug or two drugs. The dosage of valsartan was 2 mg/kg, the dosage of amlodipine besylate was 5 mg/kg, the dosage of hydrochlorothiazide was 20 mg/kg, and the dosage of the compounds of Examples 2, 27, 67, 81, 82, 87 were 3 mg/kg or 10 mg/kg.

TABLE 87

| Test compound | Decreased amount of Average blood pressure (mmHg) |
|---|---|
| valsartan | 29.5 |
| Example 27 | 30.7 |
| valsartan + Example 27 | 41.2 |
| Example 87 | 34.9 |
| valsartan + Example 87 | 50.0 |
| amlodipine besylate | 27.5 |
| Example 81 | 27.7 |
| amlodipine besylate + Example 81 | 41.4 |
| Example 67 | 27.9 |
| amlodipine besylate + Example 67 | 41.0 |
| hydrochlorothiazide | 12.5 |
| Example 82 | 30.9 |
| hydrochlorothiazide + Example 82 | 37.1 |
| Example 2 | 30.9 |
| hydrochlorothiazide + Example 2 | 36.6 |

n = 3,
Decreased amount of average blood pressure: Amount of change from the data before the administration The compounds of the present invention showed more excellent hypotensive activity as compared to well-known compounds having renin inhibitory activity (for example, compounds disclosed in the above-mentioned patent document 5) in dTGR. In addition, the compounds of the present invention showed hypotensive activity as equal to or more excellent than those conventional hypotensive agents such as valsartan, amlodipine besylate or hydrochlorothiazide in dTGR.

The combined effects of the compounds of the present invention with existing hypotensive agents valsartan, amlodipine besylate or hydrochlorothiazide were examined. In the results, the hypotensive effects of a combination with any launched agent were increased, and it was confirmed that a combination use of the compound of the present invention with a conventional hypotensive agent may be therapeutically useful.

INDUSTRIAL APPLICABILITY

The compounds of the present invention are useful as a therapeutic agent for treatment of hypertension. These compounds are also useful in the control of acute and chronic congestive heart failure. These compounds can also be expected to be useful in the treatment of primary and secondary pulmonary hypertension, primary and secondary hyperaldosteronism, renovascular hypertension, primary and secondary kidney diseases such as glomerulonephritis, IgA nephropathy, diabetic nephropathy, hypertensive nephropathy (nephrosclerosis), nephrotic syndrome, kidney failure, left ventricular hypertrophy, left ventricular fibrosis, left ventricular diastolic failure, left ventricular failure, atrial fibrillation, unstable angina pectoris, cardiac infarction, cardiomyopathy, stroke, restenosis after vascular reconstruction, diabetic retinopathy, cognition disorder such as Alzheimer's disease, cerebrovascular dementia, and also useful in inhibition of angiopathy such as migraine, Raynaud's disease, and atherosclerosis process as much as possible. In addition, these compounds are useful in the treatment of diseases relating to elevated intraocular pressure such as glaucoma.

Sequence Listing Free Text

The amino acid sequence disclosed in Seq ID:1 is an amino acid sequence used in the renin inhibitory activity assay.

The amino acid sequence disclosed in Seq ID:2 is an amino acid sequence used in the renin inhibitory activity assay.

The invention claimed is:

1. A compound of formula (I):

(I)

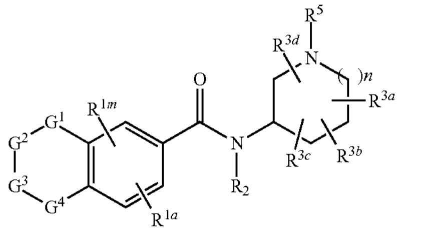

wherein $R^{1a}$ is halogen atom, hydroxyl, formyl, carboxy, cyano, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{5-6}$ cycloalkenyl, optionally substituted $C_{1-6}$ alkylthio, optionally substituted $C_{6-10}$ arylthio, optionally substituted $C_{1-6}$ alkylsulfonyl, optionally substituted $C_{1-6}$ alkoxy, optionally substituted $C_{3-6}$ cycloalkoxy, optionally substituted $C_{5-6}$ cycloalkenyloxy, optionally substituted amino, optionally substituted aminocarbonyl, optionally substituted $C_{1-4}$ alkoxycarbonyl, optionally substituted $C_{1-4}$ alkylcarbonyl, optionally substituted $C_{6-10}$ arylcarbonyl, optionally substituted $C_{6-10}$ aryl, optionally substituted $C_{6-10}$ aryloxy, optionally substituted $C_{7-14}$ aralkyloxy, or optionally substituted 5- to 10-membered monocyclic or polycyclic heteroaryl;

$R^{1m}$ is hydrogen atom, halogen atom, $C_{1-6}$ alkyl, $C_{3-6}$ cycloalkyl, $C_{1-6}$ alkoxy, or $C_{3-6}$ cycloalkoxy;

$G^1$ is —N($R^{1b}$)—, $G^2$ is —CO—, $G^3$ is —C($R^{1c}$)($R^{1d}$)—, and $G^4$ is —C($R^{1x}$)($R^{1y}$)—, —$SO_2$—, oxygen, sulfur, or absent;

$R^{1b}$ is optionally substituted $C_{1-6}$ alkyl, optionally substituted $C_{2-6}$ alkenyl, optionally substituted $C_{2-6}$ alkynyl, or optionally substituted 5- to 10-membered monocyclic or polycyclic heteroaryl $C_{1-4}$ alkyl;

$R^{1c}$ and $R^{1d}$ are independently hydrogen atom, halogen atom, hydroxyl, carboxy, optionally substituted $C_{2-6}$ alkenyl, optionally substituted $C_{5-6}$ cycloalkenyl, optionally substituted $C_{2-6}$ alkynyl, optionally substituted $C_{1-6}$ alkyl, optionally substituted $C_{3-6}$ cycloalkyl, optionally substituted aminocarbonyl, optionally substituted saturated heterocyclyl, optionally substituted $C_{1-6}$ alkoxy, optionally substituted $C_{3-6}$ cycloalkoxy, optionally substituted aminocarbonyl, optionally substituted $C_{1-4}$ alkoxycarbonyl, optionally substituted $C_{1-4}$ alkylcarbonyl, optionally substituted $C_{6-10}$ arylcarbonyl, optionally substituted 5- to 10-membered monocyclic or polycyclic heteroaryl, cyano, optionally substituted $C_{6-10}$ aryloxy, optionally substituted 5- to 10-membered monocyclic or polycyclic heteroaryloxy, optionally substituted $C_{7-14}$ aralkyloxy, optionally substituted $C_{7-14}$ aralkyl, optionally substituted amino, optionally substituted saturated heterocyclyloxy, optionally substituted 5- to 10-membered monocyclic or polycyclic heteroaryl $C_{1-4}$ alkyl, or a group of the following formula:

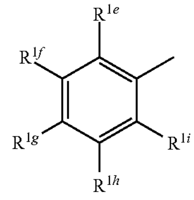

(wherein, $R^{1e}$, $R^{1f}$, $R^{1g}$, $R^{1h}$ and $R^{1i}$ are independently (a) hydrogen atom, (b) halogen atom, (c) cyano, (d) $C_{1-4}$ alkyl (optionally substituted by 5- to 6-membered saturated heterocyclyloxy, $C_{1-4}$ alkoxy (optionally substituted by $C_{1-4}$ alkoxy or $C_{3-6}$ alkoxy), or 1 to 3 fluorine atoms), (e) $C_{1-4}$ alkoxy (optionally substituted by 1 to 3 halogen atoms, $C_{1-4}$ alkoxy or $C_{1-6}$ alkylaminocarbonyl), (f) $C_{3-6}$ cycloalkoxy (optionally substituted by $C_{1-4}$ alkoxy), (g) 5- to 6-membered saturated heterocyclyloxy, (h) $C_{1-6}$ alkylaminocarbonyl, (i) hydroxyl, or (j) $C_{1-4}$ alkylsulfonyl, or $R^{1e}$, $R^{1h}$ and $R^{1i}$ are each independently hydrogen atom, and $R^{1f}$ and $R^{1g}$ combine with each other to form a condensed ring), or alternatively, $R^{1c}$ and $R^{1d}$ combine with each other to form a group of the following formula:

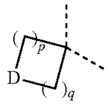

(wherein D is oxygen, sulfur, —$SO_2$—, —$NR^{4a}$—, —$NR^{4a}$CO—, —$NR^{4a}SO_2$—, —$NR^{4a}CONR^{4a}$—, —CH($R^{4b}$)—, or —CH($R^{4b}$)$CH_2$—, $R^{4a}$ is hydrogen atom, optionally substituted $C_{1-6}$ alkyl, optionally substituted $C_{1-4}$ alkoxycarbonyl, optionally substituted $C_{1-4}$ alkylsulfonyl, or optionally substituted $C_{6-10}$ arylsulfonyl, $R^{4b}$ is hydrogen atom, halogen atom, hydroxyl, optionally substituted $C_{1-6}$ alkoxy, optionally substituted $C_{3-6}$ cycloalkoxy, optionally substituted $C_{7-14}$ aralkyloxy, or optionally substituted aminocarbonyloxy, p and q are independently 0, 1 or 2);

$R^{1x}$ and $R^{1y}$ are independently hydrogen atom, halogen atom, or $C_{1-4}$ alkyl, or alternatively, $R^{1x}$ and $R^{1y}$ combine with each other to form a group of the following formula:

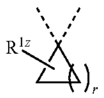

(wherein $R^{1z}$ is hydrogen atom, halogen atom, $C_{1-4}$ alkyl or $C_{1-4}$ alkoxy, r is 1, 2, 3 or 4);

$R^2$ is hydrogen atom, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted $C_{5-6}$ cycloalkenyl, optionally substituted $C_{6-10}$ aryl, optionally substituted $C_{7-14}$ aralkyl, or optionally substituted 5- to 10-membered monocyclic or polycyclic heteroaryl;

$R^{3a}$, $R^{3b}$, $R^{3c}$, and $R^{3d}$ are independently halogen atom, hydroxyl, formyl, carboxy, cyano, or a group: -A-B (wherein A is a single bond, $—(CH_2)_sO—$, $—(CH_2)_sN(R^{4c})—$, $—(CH_2)_sSO_2—$, $—(CH_2)_sCO—$, $—(CH_2)_sCOO—$, $—(CH_2)_sN(R^{4c})CO—$, $—(CH_2)_sN(R^{4c})SO_2—$, $—(CH_2)_sN(R^{4c})COO—$, $—(CH_2)_sOCON(R^{4c})—$, $—(CH_2)_sO—CO—$, $—(CH_2)_sCON(R^{4c})—$, $—(CH_2)_sN(R^{4c})CON(R^{4c})—$, or $—(CH_2)_sSO_2N(R^{4c})—$, B is hydrogen atom, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted $C_{5-6}$ cycloalkenyl, optionally substituted $C_{6-10}$ aryl, optionally substituted $C_{7-14}$ aralkyl, optionally substituted 5- to 10-membered monocyclic or polycyclic heteroaryl, optionally substituted 5- to 10-membered monocyclic or polycyclic heteroaryl $C_{1-4}$ alkyl, or optionally substituted saturated heterocyclyl, provided that if A is $—(CH_2)_sN(R^{4c})—$, $—(CH_2)_sOCON(R^{4c})—$, $—(CH_2)_sCON(R^{4c})—$, $—(CH_2)_sN(R^{4c})CON(R^{4c})—$ and $—(CH_2)_sSO_2N(R^{4c})—$, $R^{4c}$ and B may combine with each other to form a ring, $R^{4c}$ is hydrogen atom, optionally substituted $C_{1-6}$ alkyl, optionally substituted $C_{3-10}$ cycloalkyl, optionally substituted $C_{6-10}$ aryl, optionally substituted $C_{7-14}$ aralkyl, or optionally substituted 5- to 10-membered monocyclic or polycyclic heteroaryl, s is 0, 1 or 2, provided that if A is $—(CH_2)_sN(R^{4c})—$, s is 0 or 2, provided that if A is $—(CH_2)_nCON(R^{4c})—$, s is 1 or 2), or alternatively, any two of $R^{3a}$, $R^{3b}$, $R^{3c}$ and $R^{3d}$ are hydrogen atom, and the other two combine with each other together with the adjacent heterocyclyl to form a bridged ring;

n is 0, 1 or 2;

$R^5$ is

1: $C_{1-6}$ alkyl (in which the group is substituted by (a) amino, (b) hydroxy, or (c) a group of the following formula:

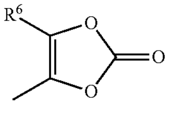

(wherein $R^6$ is (i) $C_{1-4}$ alkyl (optionally substituted by $C_{1-4}$ alkoxy), (ii) $C_{3-6}$ cycloalkyl, or (iii) $C_{6-10}$ aryl (optionally substituted by $C_{1-4}$ alkoxy))), 2: $C_{1-4}$ alkylcarbonyl (optionally substituted by (a) amino, or (b) hydroxy)

3: $C_{1-4}$ alkoxycarbonyl (in which the group is substituted by a group of the following formula:

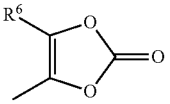

(wherein $R^6$ has the same meaning as defined above)), or

4: a group of the following formula:

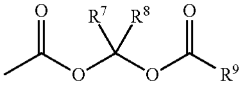

(wherein $R^7$ and $R^8$ are each independently (a) hydrogen atom, (b) $C_{1-4}$ alkyl (optionally substituted by $C_{1-4}$ alkoxy, $C_{3-6}$ cycloalkyl (optionally substituted by $C_{1-4}$ alkoxy), 5- to 6-membered saturated heterocyclyl, or 5- to 6-membered saturated heterocyclyloxy), (c) $C_{3-10}$ cycloalkyl (optionally substituted by 1 to 2 fluorine atoms, or $C_{1-4}$ alkoxy), (d) $C_6$-10 aryl (optionally substituted by halogen atom, or ($C_{6-10}$ aryl optionally substituted by halogen atom or $C_{1-4}$ alkoxy), (e) 5- to 6-membered saturated heterocyclyl, or (f) 5- to 10-membered monocyclic or polycyclic heteroaryl (optionally substituted by $C_{1-4}$ alkyl, or $C_{1-4}$ alkoxy), $R^9$ is (a) $C_{1-6}$ alkyl (optionally substituted by
1 to 3 fluorine atoms,
hydroxy,
$C_{1-4}$ alkoxy,
carboxy,
5- to 6-membered saturated heterocyclyl,
$C_{3-6}$ cycloalkyl,
$C_{1-4}$ alkoxycarbonyl,
$C_{1-4}$ alkoxycarbonylamino,
amino,
mono- or di-($C_{1-6}$ alkyl)amino,
5- to 7-membered cyclic amine,
1 to 2 nitroxy,
aminocarbonyl, or
5- to 7-membered cyclic aminocarbonyl), (b) $C_3$-10 cycloalkyl (optionally substituted by hydroxy), (c)$C_{6-10}$ aryl (in which the group is substituted by $C_{1-4}$ alkyl, $C_{1-4}$ alkoxy, or $C_{1-4}$ alkylcarbonyloxy), (d) $C_{1-4}$ alkylcarbonyl (optionally substituted by hydroxy), (e) 5- to 10-membered monocyclic or polycyclic heteroaryl, (f) 5- to 6-membered saturated heterocyclyl(optionally substituted by $C_{1-4}$ alkyl optionally substituted by $C_{1-4}$ alkoxy), (g) $C_{1-6}$ alkoxy (optionally substituted by $C_{3-6}$ cycloalkyl), (h) $C_{3-6}$ cycloalkyloxy (optionally substituted by $C_{1-4}$ alkoxy), or (i) 5- to 6-membered saturated heterocyclyloxy); or a pharmaceutically acceptable salt thereof.

2. The compound of claim 1, wherein $G^1$ is —N($R^{1b}$)—, $G^2$ is —CO—, $G^3$ is —C($R^{1c}$)($R^{1d}$) and $G^4$ is —C($R^{1x}$)($R^{1y}$)—, —$SO_2$—, oxygen, sulfur, or absent, or (ii), or a pharmaceutically acceptable salt thereof.

3. The compound of claim 2, wherein $G^4$ is oxygen, or a pharmaceutically acceptable salt thereof.

4. The compound of claim 2, wherein $G^4$ is sulfur, or a pharmaceutically acceptable salt thereof.

5. The compound of claim 1, wherein $R^{1a}$ and $R^{1m}$ bind to the adjacent ring in either binding position of the following formula (A) or (B):

(A)

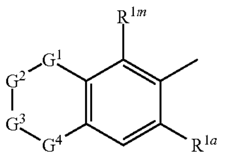

(B)

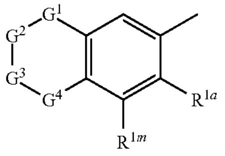

or a pharmaceutically acceptable salt thereof.

6. The compound of claim 1, wherein $R^{1a}$ is $C_{1-6}$ alkyl optionally substituted by 1 to 3 fluorine atoms, or a pharmaceutically acceptable salt thereof.

7. The compound of claim 6, wherein $R^{1a}$ is methyl, or trifluoromethyl, or a pharmaceutically acceptable salt thereof.

8. The compound of claim 1, wherein $R^{1m}$ is hydrogen atom, or a pharmaceutically acceptable salt thereof.

9. The compound of claim 1, wherein $R^{1b}$ is $C_{1-6}$ alkyl which is optionally substituted by $C_{1-4}$ alkylcarbonylamino optionally substituted by 1 to 3 fluorine atoms, or a pharmaceutically acceptable salt thereof.

10. The compound of claim 9, wherein $R^{1b}$ is 2-(ethylcarbonylamino)ethyl, or a pharmaceutically acceptable salt thereof.

11. The compound of claim 1, wherein $R^{1c}$ is hydrogen atom, halogen atom, or $C_{1-6}$ alkyl optionally substituted by $C_{1-4}$ alkoxy, or a pharmaceutically acceptable salt thereof.

12. The compound of claim 1, wherein $R^{1d}$ is one group selected from the group consisting of 1: hydrogen atom;

2: halogen atom;

3: cyano;

4: $C_{2-6}$ alkenyl (optionally substituted by $C_{6-10}$ aryl optionally substituted by $C_{1-4}$ alkoxy);

5: $C_{2-6}$ alkynyl (optionally substituted by $C_{6-10}$ aryl optionally substituted by $C_{1-4}$ alkoxy);

6: $C_{1-6}$ alkyl (optionally substituted by same or different 1 to 2 groups selected from the group consisting of (a) 1 to 3 halogen atoms, (b) cyano, (c) $C_{3-6}$ cycloalkyl (optionally substituted by halogen atom, $C_{1-4}$ alkyl, or $C_{1-4}$ alkoxy), (d) hydroxy, (e) $C_{1-4}$ alkoxy (optionally substituted by same or different 1 to 3 groups selected from the group consisting of halogen atom, cyano, $C_{3-6}$ cycloalkoxy optionally substituted by mono- or di-($C_{1-6}$ alkyl)aminocarbonyl, mono- or di-($C_{1-6}$ alkyl)aminosulfonyl, $C_{1-6}$ alkylsulfonyl, aminocarbonyl optionally substituted by mono- or di-($C_{1-6}$ alkyl), $C_{1-4}$ alkylcarbonyl, 5- to 7-membered cyclic aminocarbonyl, hydroxy, $C_{1-4}$ alkoxy, 5- to 6-membered saturated heterocyclyl, and $C_{1-4}$ alkoxycarbonyl), (f) $C_{3-6}$ cycloalkoxy (optionally substituted by $C_{1-4}$ alkyl optionally substituted by $C_{1-4}$ alkoxy), (g) $C_{6-10}$ aryloxy (optionally substituted by same or different 1 to 3 groups selected from the group consisting of halogen atom, cyano, and $C_{1-4}$ alkoxy), (h) amino (in which amino is substituted by same or different 1 to 2 groups selected from the group consisting of $C_{1-6}$ alkyl, $C_{3-6}$ cycloalkyl, $C_{3-6}$ cycloalkyl$C_{1-4}$ alkyl optionally substituted by aminocarbonyl, $C_{3-6}$ cycloalkyl$C_{1-4}$ alkoxycarbonyl, $C_{1-4}$ alkylcarbonyl, $C_{3-6}$ cycloalkylcarbonyl optionally substituted by $C_{1-4}$ alkylsulfonylamino, 5- to 6-membered saturated heterocyclyl$C_{1-4}$ alkyl optionally substituted by $C_{1-4}$ alkyl, 5- to 6-membered saturated heterocyclylcarbonyl, 5- to 6-membered saturated heterocyclyloxycarbonyl, 5- to 6-membered saturated heterocyclyl$C_{1-4}$ alkylcarbonyl, and $C_{1-4}$ alkylsulfonyl), (i) 5- to 7-membered cyclic amino (optionally substituted by same or different 1 to 4 groups selected from the group consisting of $C_{1-4}$ alkyl, $C_{7-14}$ aralkyl, and oxo), (j) mono- or di-($C_{1-6}$ alkyl)aminocarbonyl, (k) 4- to 7-membered cyclic aminocarbonyl (optionally substituted by $C_{1-4}$ alkyl), (l) aminocarbonyloxy (in which amino is substituted by same or different 1 to 2 groups selected from the group consisting of $C_{1-6}$ alkyl optionally substituted by 5- to 6-membered saturated heterocyclyl, $C_{3-6}$ cycloalkyl optionally substituted by hydroxy, and 5- to 6-membered saturated heterocyclyl), (m) 5- to 7-membered cyclic aminocarbonyloxy (in which cyclic amino may be optionally substituted by 1 to 2 fluorine atoms), (n) 5- to 7-membered cyclic aminocarbonyl$C_{1-4}$ alkoxy, (O) mono- or di-($C_{1-6}$ alkyl)aminocarbonyl$C_{1-4}$ alkoxy, (p) 5- to 6-membered saturated heterocyclyl (optionally substituted by same or different groups selelcted from the group consisting of $C_{1-4}$ alkyl and oxo), (q) 5- to 6-membered saturated heterocyclyl$C_{1-4}$ alkoxy (in which heterocyclyl is optionally substituted by $C_{1-4}$ alkyl), (r) 5- to 6-membered saturated heterocyclyloxy (in which heterocyclyl is optionally substituted by same or different 1 to 2 groups selected from the group consisting of $C_{1-4}$ alkyl and oxo), (s) mono- or di-$C_{1-4}$ alkylaminosulfonyl, (t) carboxy, (u) $C_{1-4}$ alkoxycarbonyl, (v) $C_{6-10}$ arylcarbonyl (optionally substituted by $C_{14}$ alkoxy), (w) $C_{1-4}$ alkoxycarbonylamino, (x) $C_{6-10}$ aryloxycarbonylamino (in which aryl is optionally substituted by halogen atom), (y) 5- to 6-membered monocyclic heteroaryloxycarbonylamino, and (z) N—($C_{1-4}$ alkylaminocarbonyl)-N—($C_{1-6}$ alkyl) amino);

7: $C_{3-10}$ cycloalkyl (optionally substituted by (a) halogen atom, (b) hydroxy, or (c) $C_{1-4}$ alkoxy);

8: $C_{7-14}$ aralkyl (optionally substituted by same or different 1 to 3 groups selected from the group consisting of (a) halogen atom, (b) cyano, (c) hydroxy, (d) $C_{1-4}$ alkoxy, and (e) $C_{1-4}$ alkyl optionally substituted by $C_{1-4}$ alkoxy);

9: $C_{1-6}$ alkoxy (optionally substituted by (a) $C_{1-4}$ alkoxycarbonylamino, (b) N—($C_{1-6}$alkylsulfonyl)-N—($C_{1-6}$alkyl)aminocarbonyl, (c) mono- or di-($C_{1-6}$alkyl)aminocarbonyl, or (d) 5- to 7-membered cyclic aminocarbonyl);

10: $C_{3-6}$ cycloalkoxy;

11: $C_{7-14}$ aralkyloxy (in which aralkyl is optionally substituted by $C_{1-4}$ alkoxy);

12: mono- or di-substituted aminocarbonyl (in which amino is optionally substituted by $C_{1-6}$ alkyl optionally substituted by 5- to 6-membered saturated heterocyclyl);

13: 5- to 7-membered cyclic aminocarbonyl (optionally substituted by a group selected from the group consisting of (a) halogen atom, (b) $C_{1-4}$ alkoxy, and (c) $C_{6-10}$ aryl optionally substituted by halogen atom);

14: saturated heterocyclyl (optionally substituted by same or different 1 to 4 groups selected from the group consisting of (a) $C_{1-4}$ alkyl, (b) $C_{6-10}$ aryl optionally substituted by 1 to 3 halogen atoms, and (c) oxo);

15: saturated heterocyclyloxy (optionally substituted by $C_{1-4}$ alkoxycarbonyl, or $C_{1-4}$ alkylcarbonyl);

16: 5- to 10-membered monocyclic or polycyclic heteroaryl (optionally substituted by same or different 1 to 2 groups selected from the group consisting of (a) halogen atom, (b) $C_{1-4}$ alkyl optionally substituted by 1 to 3 fluorine atoms, and (c) $C_{1-4}$ alkoxy optionally substituted by mono- or di-($C_{1-6}$alkyl)aminocarbonyl);

17: 5- to 10-membered monocyclic or polycyclic heteroaryl$C_{1-4}$ alkyl;

18: amino (in which amino is optionally substituted by (a) $C_{3-6}$ cycloalkyl$C_{1-4}$ alkyl (in which cycloalkyl is optionally substituted by aminocarbonyl), (b) $C_{1-4}$ alkylcarbonyl (in which alkyl is optionally substituted by $C_{1-4}$ alkoxy), (c) $C_{3-6}$ cycloalkylcarbonyl (in which cycloalkyl is optionally substituted by $C_{1-4}$ alkylsulfonylamino), or (d) 5- to 6-membered saturated heterocyclyloxycarbonyl);

19: hydroxyl, and

20: a group of the following formula:

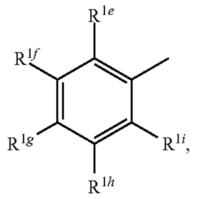

or a pharmaceutically acceptable salt thereof.

13. The compound of claim 1, wherein $R^{1c}$ and $R^{1d}$ combine with each other to form a group of the following formula:

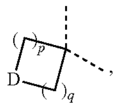

or a pharmaceutically acceptable salt thereof.

14. The compound of claim 13, wherein D, p and q are any of the following (i) to (iii) (in which (i) D is oxygen, and p and q are the same and 2, (ii) D is —$CH_2$—, and p and q are the same and 1 or 2, or (iii) D is —$CH_2CH_2$—, and p and q are the same and 0 or 1); or a pharmaceutically acceptable salt thereof.

15. The compound of claim 1, wherein $R^{1c}$ and $R^{1d}$ combine with each other to form a group of the following formula:

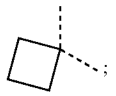

or a pharmaceutically acceptable salt thereof.

16. The compound of claim 1, wherein $R^2$ is $C_{1-6}$ alkyl, or a pharmaceutically acceptable salt thereof.

17. The compound of claim 16, wherein $R^2$ is isopropyl, or a pharmaceutically acceptable salt thereof.

18. The compound of claim 1, wherein $R^{3a}$, $R^{3b}$, $R^{3c}$ and $R^{3d}$ are a group: -A-B (wherein A is a single bond, and B is hydrogen atom), or a pharmaceutically acceptable salt thereof.

19. The compound of claim 1, wherein n is 1, or a pharmaceutically acceptable salt thereof.

20. The compound of claim 1, wherein $R^5$ is $C_{1-4}$ alkoxycarbonyl (in which the group is substituted by a group of the following formula:

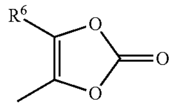

in which $R^6$ is the same as defined above), or a pharmaceutically acceptable salt thereof.

21. The compound of claim 1, wherein $R^5$ is a group of the following formula:

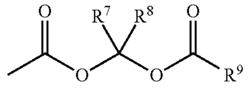

(in which $R^7$ and $R^8$ are independently, hydrogen atom, or $C_{1-4}$ alkyl, and $R^9$ is (a) $C_{1-6}$ alkyl (optionally substituted by 1 to 3 fluorine atoms, amino, hydroxy, $C_{1-4}$-alkoxy, carboxy, $C_{1-4}$-alkoxycarbonyl, $C_{1-4}$-alkoxycarbonylamino, or 1 to 2 nitroxy), (b) $C_{3-10}$ cycloalkyl, (c) $C_{1-4}$ alkylcarbonyl (optionally substituted by hydroxy), (d) $C_{6-10}$ aryl (in which the group is substituted by $C_{1-4}$ alkyl, or $C_{1-4}$ alkylcarbonyloxy), (e) 5- to 10-membered monocyclic or polycyclic heteroaryl, (f) 5- to 6-membered saturated heterocyclyl, (g) $C_{1-6}$alkoxy (optionally substituted by $C_{3-6}$ cycloalkyl), (h) $C_{3-6}$ cycloalkyloxy, or (i) 5- to 6-membered saturated heterocyclyloxy), or a pharmaceutically acceptable salt thereof.

22. The compound of claim 21, wherein $R^7$ is hydrogen atom, and $R^8$ is methyl, or a pharmaceutically acceptable salt thereof.

23. The compound of claim 21, wherein $R^9$ is

1: $C_{1-4}$ alkyl,

2: $C_{3-6}$ cycloalkyl,

3: $C_{1-6}$ alkoxy (optionally substituted by $C_{3-6}$ cycloalkyl),

4: $C_{3-6}$ cycloalkyloxy, or

5: 5- to 6-membered saturated heterocyclyloxy, or a pharmaceutically acceptable salt thereof.

24. The compound of claim 23, wherein $R^9$ is

1: $C_{1-4}$ alkyl, or

2: $C_{1-6}$ alkoxy, or a pharmaceutically acceptable salt thereof.

25. The compound of claim 1, selected from the group consisting of:

1-(isobutyryloxy)ethyl (3R)-3-[isopropyl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (5-methyl-2-oxo-1,3-dioxol-4-yl)methyl (3R)-3-[isopropyl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(cyclohexylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate,

[(2-methylpropanoyl)oxy]methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperazine-1-carboxylate, {[(propan-2-yloxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (acetyloxy)methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (2-oxo-5-phenyl-1,3-dioxol-4-yl)methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-{[(propan-2-yloxy)carbonyl]oxy}ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate,

[(methoxycarbonyl)oxy]methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate,

[(ethoxycarbonyl)oxy]methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, {[(cyclopropylmethoxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, {[(cyclobutyloxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, {[(tetrahydro-2H-pyran-4-yloxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, {[(pentan-3-yloxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, {[(cyclopentyloxy)carbonyl]oxy}methyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(acetyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(propanoyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(acetyloxy)-2-methylpropyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 2-methyl-1-(propanoyloxy)propyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 2-(acetyloxy)propan-2-yl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 2,2-dimethyl-3-oxo-4-[2-(propanoylamino)ethyl]-N-(propan-2-yl)-7-(trifluoromethyl)-N—[(3R)-1-(L-valyl)piperidin-3-yl]-3,4-dihydro-2H-1,4-benzoxazine-6-carboxamide, N-[(3R)-1-(L-alanyl)piperidin-3-yl]-2,2-dimethyl-3-oxo-4-[2-(propanoylamino)ethyl]-N-(propan-2-yl)-7-(trifluoromethyl)-3,4-dihydro-2H-1,4-benzoxazine-6-carboxamide, N-{(3R)-1-[(2S)-2-hydroxypropanoyl]piperidin-3-yl}-2,2-dimethyl-3-oxo-4-[2-(propanoylamino)ethyl]-N-(propan-2-yl)-7-(trifluoromethyl)-3,4-dihydro-2H-1,4-benzoxazine-6-carboxamide, N-[(3R)-1-acetylpiperidin-3-yl]-2,2-dimethyl-3-oxo-4-[2-(propanoylamino)ethyl]-N-(propan-2-yl)-7-(trifluoromethyl)-3,4-dihydro-2H-1,4-benzoxazine-6-carboxamide, 1-[(2-methylpropanoyl)oxy]ethyl (3R)-3-[({2,2-dimethyl-3-oxo-4-[2-(propanoylamino)ethyl]-7-(trifluoromethyl)-3,4-dihydro-2H-1,4-benzoxazin-6-yl}carbonyl)(propan-2-yl)amino]piperidine-1-carboxylate, (5-methyl-2-oxo-1,3-dioxol-4-yl)methyl (3R)-3-[({2,2-dimethyl-3-oxo-4-[2-(propanoylamino)ethyl]-7-(trifluoromethyl)-3,4-dihydro-2H-1,4-benzoxazin-6-yl}carbonyl)(propan-2-yl)amino]piperidine-1-carboxylate, {[(propan-2-yloxy)carbonyl]oxy}methyl (3R)-3-[({2,2-dimethyl-3-oxo-4-[2-(propanoylamino)ethyl]-7-(trifluoromethyl)-3,4-dihydro-2H-1,4-benzoxazin-6-yl}carbonyl)-(propan-2-yl)amino]piperidine-1-carboxylate, {[(tetrahydro-2H-pyran-4-yloxy)carbonyl]oxy}methyl (3R)-3-[({2,2-dimethyl-3-oxo-4-[2-(propanoylamino)ethyl]-7-(trifluoromethyl)-3,4-dihydro-2H-1,4-benzoxazin-6-yl}carbonyl)-(propan-2-yl)amino]piperidine-1-carboxylate, (5-methyl-2-oxo-1,3-dioxol-4-yl)methyl (3R)-3-[({2,2-dimethyl-3-oxo-4-[2-(propanoylamino)ethyl]-7-(trifluoromethyl)-3,4-dihydro-2H-1,4-benzothiazin-6-yl}carbonyl)(propan-2-yl)amino]piperidine-1-carboxylate, 2,2-dimethyl-N-{(3R)-1-[(5-methyl-2-oxo-1,3-dioxol-4-yl)methyl]piperidin-3-yl}-3-oxo-4-[2-(propanoylamino)ethyl]-N-(propan-2-yl)-7-(trifluoromethyl)-3,4-dihydro-2H-1,4-benzoxazine-6-carboxamide, 2,2,7-trimethyl-3-oxo-N-{(3R)-1-[(2-oxo-5-phenyl-1,3-dioxol-4-yl)methyl]piperidin-3-yl}-4-[2-(propanoylamino)ethyl]-N-(propan-2-yl)-3,4-dihydro-2H-1,4-benzoxazine-6-carboxamide, 1-(acetyloxy)ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl) (propan-2-yl)amino]piperidine-1-carboxylate, 1-[(ethoxycarbonyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-(acetyloxy)-2-methylpropyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-(propanoyloxy)ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl) (propan-2-yl)amino]piperidine-1-carboxylate, 1-(propanoyloxy)ethyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, 1-[(ethoxycarbonyl)oxy]ethyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, (5-methyl-2-oxo-1,3-dioxol-4-yl)methyl (3R)-3-{[(4-{2-[(difluoroacetyl)amino]ethyl}-7-methyl-3-oxo-3,4-dihydrospiro[1,4-benzoxazine-2,1'-cyclopropan]-6-yl)carbonyl](propan-2-yl)amino}piperidine-1-carboxylate, (5-methyl-2-oxo-1,3-dioxol-4-yl)methyl (3R)-3-[({7-methyl-3-oxo-4-[2-(propanoylamino)ethyl]-3,4-dihydrospiro[1,4-benzoxazine-2,1'-cyclopropan]-6-yl}carbonyl)(propan-2-yl)amino]piperidine-1-carboxylate, 1-(propanoyloxy)ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)(propan-2-yl)amino]piperidine-1-carboxylate, 1-[(2-methylpropanoyl)oxy]ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)(propan-2-yl)amino]piperidine-1-carboxylate, 1-[(tetrahydro-2H-pyran-4-ylcarbonyl)oxy]ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)-(propan-2-yl)amino]piperidine-1-carboxylate, (5-methyl-2-oxo-1,3-dioxol-4-yl)methyl (3R)-3-{[(4-{2-[(difluoroacetyl)amino]ethyl}-7-methyl-3-oxo-3,4-dihydrospiro[1,4-benzoxazine-2,1'-cyclobutan]-6-yl)carbonyl](propan-2-yl)amino}piperidine-1-carboxylate, 2-methyl-1-[(2-methylpropanoyl)oxy]propyl (3R)-3-[({7-methyl-3-oxo-4-[2-(propanoylamino)ethyl]-3,4-dihydrospiro[1,4-benzoxazine-2,1'-cyclobutan]-6-yl}carbonyl)-(propan-2-yl)amino]piperidine-1-carboxylate, 2-methyl-1-(propanoyloxy)propyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(2-methylpropanoyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(tetrahydro-2H-pyran-4-ylcarbonyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)-(propan-2-yl)amino]piperidine-1-carboxylate, 1-[(methoxyacetyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(3-hydroxy-3-methylbutanoyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 2-methyl-1-[(2-methylpropanoyl)oxy]propyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1S)-1-(propanoyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-(propanoyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-{[(cyclohexyloxy)carbonyl]oxy}ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, tert-butyl 1-[({(3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidin-1-yl}carbonyl)oxy]ethyl butanedioate, 4-oxo-4-{1-[({(3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidin-1-yl}carbonyl)oxy]ethoxy}-butanoic acid, 1-{[N-(tert-butoxycarbonyl)glycyl]oxy}ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(glycyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[({(3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidin-1-yl}carbonyl)oxy]ethylpyridine-3-carboxylate, 1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(methoxyacetyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(L-valyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(4-hydroxybutanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-({[2-(acetyloxy)phenyl]carbonyl}oxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(2-oxopropanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1S)-1-[(2-methylpropanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-[(2-methylpropanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(3-hydroxy-3-methylbutanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (5-methyl-2-oxo-1,3-dioxol-4-yl)methyl (3R)-3-[{[2-(hydroxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, (5-methyl-2-oxo-1,3-dioxol-4-yl)methyl (3R)-3-[{[2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}(propan-2-yl)amino]piperidine-1-carboxylate, (5-methyl-2-oxo-1,3-dioxol-4-yl)methyl (3R)-3-[{[4-{2-[(difluoroacetyl)amino]ethyl}-3-oxo-7-(trifluoromethyl)-3,4-dihydrospiro[1,4-benzoxazin-2,1'-cyclopropan]-6-yl]carbonyl}-(propan-2-yl)amino]piperidine-1-carboxylate, 1-[(2-methylpropanoyl)oxy]ethyl (3R)-3-[{[4-{2-[(difluoroacetyl)amino]ethyl}-3-oxo-7-(trifluoromethyl)-3,4-dihydrospiro[1,4-benzoxazin-2,1'-cyclopropan]-6-yl]carbonyl}(propan-2-yl)amino]piperidine-1-carboxylate, (5-methyl-2-oxo-1,3-dioxol-4-yl)methyl (3R)-3-[{[(2R)-2-methyl-3-oxo-4-[2-(propanoylamino)ethyl]-2,7-bis(trifluoromethyl)-3,4-dihydro-2H-1,4-benzoxazin-6-yl]-carbonyl}(propan-2-yl)amino]piperidine-1-carboxylate, 1-[(2-methylpropanoyl)oxy]ethyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, 2-methyl-1-(propanoyloxy)propyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, 2-methyl-1-[(2-methylpropanoyloxy)oxy]propyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}(propan-2-yl)amino]piperidine-1-carboxylate, (5-methyl-2-oxo-1,3-dioxol-4-yl)methyl (3R)-3-{[(4-{2-[(difluoroacetyl)amino]ethyl}-2,2,7-trimethyl-3-oxo-3,4-dihydro-2H-1,4-benzothiazin-6-yl)carbonyl](propan-2-yl)amino}-piperidine-1-carboxylate, (5-methyl-2-oxo-1,3-dioxol-4-yl)methyl (3R)-3-[({7-methyl-3-oxo-4-[2-(propanoylamino)ethyl]-3,4-dihydrospiro[1,4-benzothiazine-2,1'-cyclobutan]-6-yl}carbonyl)(propan-2-yl)amino]piperidine-1-carboxylate, 1-{[(4-methylphenyl)carbonyl]oxy}ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, (1R)-1-[(2-methylpropanoyl)oxy]ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]piperidine-1-carboxylate, (5-methyl-2-oxo-1,3-dioxol-4-yl)methyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, (1R)-1-[(2-methylpropanoyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, (1S)-1-[(2-methylpropanoyl)oxy]ethyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, 1-[(4-methoxybutanoyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(4-methoxybutanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(propanoyloxy)ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]-piperidine-1-carboxylate, (1R)-1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1S)-1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[({(3R)-3-[({7-methyl-3-oxo-4-[2-(propanoylamino)ethyl]-3,4-dihydrospiro[1,4-benzoxazin-2,1'-cyclobutan]-6-yl}carbonyl)(propan-2-yl)amino]piperidin-1-yl}carbonyl)oxy]-ethylpyridine-3-carboxylate, (1S)-1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]piperidine-1-carboxylate, (1R)-1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl) (propan-2-yl)amino]piperidine-1-carboxylate, (1S)-1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl) (propan-2-yl)amino]piperidine-1-carboxylate, 1-[(tetrahydro-2H-pyran-4-ylcarbonyl)oxy]ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]piperidine-1-carboxylate, 1-{[(cyclohexyloxy)carbonyl]oxy}ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(difluoroacetyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(cyclopropylacetyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-{[6,7-bis(nitroxy)heptanoyl]oxy}ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, and 1-[(cyclohexylcarbonyl)oxy]ethyl (3R)-3-[({2,2-dimethyl-3-oxo-4-[2-(propanoylamino)ethyl]-7-(trifluoromethyl)-3,4-dihydro-2H-1,4-benzoxazin-6-yl}carbonyl)(propan-2-yl)amino]piperidine-1-carboxylate, or a pharmaceutically acceptable salt thereof.

26. The compound of claim 1, selected from the group consisting of:

(5-methyl-2-oxo-1,3-dioxol-4-yl)methyl (3R)-3-[isopropyl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (5-methyl-2-oxo-1,3-dioxol-4-yl)methyl (3R)-3-[({2,2-dimethyl-3-oxo-4-[2-(propanoylamino)ethyl]-7-(trifluoromethyl)-3,4-dihydro-2H-1,4-benzoxazin-6-yl}carbonyl)(propan-2-yl)amino]piperidine-1-carboxylate, (5-methyl-2-oxo-1,3-dioxol-4-yl)methyl (3R)-3-[({2,2-dimethyl-3-oxo-4-[2-(propanoylamino)ethyl]-7-(trifluoromethyl)-3,4-dihydro-2H-1,4-benzothiazin-6-yl}carbonyl)(propan-2-yl)amino]piperidine-1-carboxylate, (5-methyl-2-oxo-1,3-dioxol-4-yl)methyl (3R)-3-{[(4-{2-[(difluoroacetyl)amino]ethyl}-7-methyl-3-oxo-3,4-dihydrospiro[1,4-benzoxazine-2,1'-cyclopropan]-6-yl)carbonyl](propan-2-yl)amino}piperidine-1-carboxylate, (5-methyl-2-oxo-1,3-dioxol-4-yl)methyl (3R)-3-[({7-methyl-3-oxo-4-[2-(propanoylamino)ethyl]-3,4-dihydrospiro[1,4-benzoxazine-2,1'-cyclopropan]-6-yl}carbonyl)(propan-2-yl)amino]piperidine-1-carboxylate, (5-methyl-2-oxo-1,3-dioxol-4-yl)methyl (3R)-3-{[(4-{2-[(difluoroacetyl)amino]ethyl}-7-methyl-3-oxo-3,4-dihydrospiro[1,4-benzoxazine-2,1'-cyclobutan]-6-yl)carbonyl](propan-2-yl)-amino}piperidine-1-carboxylate, (5-methyl-2-oxo-1,3-dioxol-4-yl)methyl (3R)-3-[{[2-(hydroxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, (5-methyl-2-oxo-1,3-dioxol-4-yl)methyl (3R)-3-[{[2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}(propan-2-yl)amino]piperidine-1-carboxylate, (5-methyl-2-oxo-1,3-dioxol-4-yl)methyl (3R)-3-[{[4-{2-[(difluoroacetyl)amino]ethyl}-3-oxo-7-(trifluoromethyl)-3,4-dihydrospiro[1,4-benzoxazin-2,1'-cyclopropan]-6-yl]carbonyl}-(propan-2-yl)amino]piperidine-1-carboxylate, (5-methyl-2-oxo-1,3-dioxol-4-yl)methyl (3R)-3-[{[(2R)-2-methyl-3-oxo-4-[2-(propanoylamino)ethyl]-2,7-bis(trifluoromethyl)-3,4-dihydro-2H-1,4-benzoxazin-6-yl]-carbonyl}(propan-2-yl)amino]piperidine-1-carboxylate, (5-methyl-2-oxo-1,3-dioxol-4-yl)methyl (3R)-3-{[(4-{2-[(difluoroacetyl)amino]ethyl}-2,2,7-trimethyl-3-oxo-3,4-dihydro-2H-1,4-benzothiazin-6-yl)carbonyl](propan-2-yl)amino}-piperidine-1-carboxylate, (5-methyl-2-oxo-1,3-dioxol-4-yl)methyl (3R)-3-[({7-methyl-3-oxo-4-[2-(propanoylamino)ethyl]-3,4-dihydrospiro[1,4-benzothiazine-2,1'-cyclobutan]-6-yl}carbonyl)(propan-2-yl)amino]piperidine-1-carboxylate, and (5-methyl-2-oxo-1,3-dioxol-4-yl)methyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, or a pharmaceutically acceptable salt thereof.

27. The compound of claim 1, selected from the group consisting of:

1-(isobutyryloxy)ethyl (3R)-3-[isopropyl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-(propanoyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(2-methylpropanoyl)oxy]ethyl (3R)-3-[({2,2-dimethyl-3-oxo-4-[2-(propanoylamino)ethyl]-7-(trifluoromethyl)-3,4-dihydro-2H-1,4-benzoxazin-6-yl}carbonyl)(propan-2-yl)amino]piperidine-1-carboxylate, 1-[(ethoxycarbonyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl) (propan-2-yl)amino]piperidine-1-carboxylate, 1-(propanoyloxy)ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl) (propan-2-yl)amino]piperidine-1-carboxylate, 1-(propanoyloxy)ethyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, 1-[(ethoxycarbonyl)oxy]ethyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, 1-(propanoyloxy)ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)(propan-2-yl)amino]piperidine-1-carboxylate, 1-[(2-methylpropanoyl)oxy]ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)(propan-2-yl)amino]piperidine-1-carboxylate, 1-[(tetrahydro-2H-pyran-4-ylcarbonyl)oxy]ethyl (3R)-3-[({7-methyl-3-oxo-4-[2-(propanoylamino)ethyl]-3,4-dihydrospiro[1,4-benzoxazine-2,1'-cyclopropan]-6-yl}carbonyl)-(propan-2-yl)amino]piperidine-1-carboxylate, 1-[(2-methylpropanoyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(tetrahydro-2H-pyran-4-ylcarbonyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)-(propan-2-yl)amino]piperidine-1-carboxylate, (1S)-1-(propanoyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-(propanoyloxy)ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1S)-1-[(2-methylpropanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-[(2-methylpropanoyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(2-methylpropanoyl)oxy]ethyl (3R)-3-[{[4-{2-[(difluoroacetyl)amino]ethyl}-3-oxo-7-(trifluoromethyl)-3,4-dihydrospiro[1,4-benzoxazine-2,1'-cyclopropan]-6-yl]carbonyl}(propan-2-yl)amino]piperidine-1-carboxylate, 1-[(2-methylpropanoyl)oxy]ethyl (3R)-3-[{[(2S)-2-(methoxymethyl)-2-methyl-3-oxo-4-[2-(propanoylamino)ethyl]-7-(trifluoromethyl)-3,4-dihydro-2H-1,4-benzoxazin-6-yl]carbonyl}-(propan-2-yl)amino]piperidine-1-carboxylate, (1R)-1-[(2-methylpropanoyl)oxy]ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl) (propan-2-yl)amino]piperidine-1-carboxylate, (1R)-1-[(2-methylpropanoyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, (1S)-1-[(2-methylpropanoyl)oxy]ethyl (3R)-3-[({7-methyl-3-oxo-4-[2-(propanoylamino)-ethyl]-3,4-dihydrospiro[1,4-benzoxazine-2,1'-cyclobutan]-6-yl}carbonyl)(propan-2-yl)amino]-piperidine-1-carboxylate, 1-(propanoyloxy)ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]-piperidine-1-carboxylate, (1R)-1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1S)-1-[(tetrahydro-2H-pyran-4-ylcarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1S)-1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, (1R)-1-[(ethoxycarbonyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, 1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl) (propan-2-yl)amino]piperidine-1-carboxylate, (1R)-1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl) (propan-2-yl)amino]piperidine-1-carboxylate, (1S)-1-[(2-methylpropanoyl)oxy]ethyl (3R)-3-[({(2S)-2-(methoxymethyl)-2,7-dimethyl-3-oxo-4-[2-(propanoylamino)ethyl]-3,4-dihydro-2H-1,4-benzoxazin-6-yl}carbonyl) (propan-2-yl)amino]piperidine-1-carboxylate, 1-[(tetrahydro-2H-pyran-4-ylcarbonyl)oxy]ethyl (3R)-3-[({2-(methoxymethyl)-2,7-dimethyl-3-oxo-4-[2-(propanoylamino)ethyl]-3,4-dihydro-2H-1,4-benzoxazin-6-yl}carbonyl)(propan-2-yl)amino]piperidine-1-carboxylate, 1-{[(cyclohexyloxy)carbonyl]oxy}ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl)(propan-2-yl)amino]piperidine-1-carboxylate, 1-[(difluoroacetyl)oxy]ethyl (3R)-3-[({7-methyl-3-oxo-4-[2-(propanoylamino)ethyl]-3,4-dihydrospiro[1,4-benzoxazine-2,1'-cyclobutan]-6-yl}carbonyl) (propan-2-yl)amino]piperidine-1-carboxylate, and 1-[(cyclopropylacetyl)oxy]ethyl (3R)-3-[propan-2-yl({2,2,7-trimethyl-3-oxo-4-[2-(propanoylamino)ethyl]-3,4-dihydro-2H-1,4-benzoxazin-6-yl}carbonyl)amino]piperidine-1-carboxylate, or a pharmaceutically acceptable salt thereof.

28. A pharmaceutical composition, comprising as the active ingredient the compound of claim 1 or a pharmaceutically acceptable salt thereof.

29. A method of treating diseases caused by renin inhibitory effects, comprising administering an effective amount of the compound of claim 1 or a pharmaceutically acceptable salt thereof to a patient in need thereof, wherein the disease is hypertension.

30. A medication, comprising the compound of claim 1 or a pharmaceutically acceptable salt thereof in combination with at least one or more drugs selected from the following Drug Group (A):

wherein Drug Group (A) is the group consisting of insulin formulation, an improving agent of insulin resistance, α-glucosidase inhibitor, biguanide preparation, insulin secretagogue, GLP-1, GLP-1 analog, protein tyrosine phosphatase inhibitor, β3 agonist, DPPIV inhibitor, aldose reductase inhibitor, neurotrophic factor, PKC inhibitor, AGE inhibitor, active oxygen-eliminating agent, cerebral vasodilator, HMG-CoA reductase inhibitor, squalene synthetase inhibitor, ACAT inhibitor, angiotensin converting enzyme inhibitor, angiotensin II antagonist, calcium antagonist, ACE/NEP inhibitor, β blocking agent, α blocking agent, αβ blocking agent, central anti-obesity drug, pancreatic lipase inhibitor, peptidic anorexiant, cholecystokinin agonist, xanthine derivative, thiazide preparation, anti-aldosterone preparation, carbonic anhydrase inhibitor, chlorobenzene sulfonamide preparation, azosemide, isosorbide, ethacrynic acid, piretanide, bumetanide, and furosemide.

31. A method of treating diseases caused by renin inhibitory effects, comprising administering an effective amount of the compound of claim 1 or a pharmaceutically acceptable salt thereof in combination with at least one or more drugs selected from Drug Group (A) defined in claim 30 to a patient in need thereof, wherein the disease is hypertension.

32. A compound of formula (III):

(III)

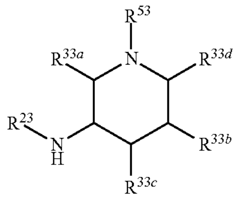

wherein $R^{23}$ is hydrogen atom, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted $C_{5-6}$ cycloalkenyl, optionally substituted $C_{6-10}$ aryl, optionally substituted $C_{7-14}$ aralkyl, or optionally substituted 5- to 10-membered monocyclic or polycyclic heteroaryl;

$R^{33a}$, $R^{33b}$, $R^{33c}$, and $R^{33d}$ are independently halogen atom, hydroxyl, formyl, carboxy, cyano, or a group: $-A^3-B^3$ (wherein $A^3$ is a single bond, $-(CH_2)_{s3}O-$, $-(CH_2)_{s3}N(R^{43c})-$, $-(CH_2)_{s3}SO_2-$, $-(CH_2)_{s3}CO-$, $-(CH_2)_{s3}COO-$, $-(CH_2)_{s3}N(R^{43c})CO-$, $-(CH_2)_{s3}N(R^{43c})SO_2-$, $-(CH_2)_{s3}N(R^{43c})COO-$, $-(CH_2)_{s3}OCON(R^{43c})-$, $-(CH_2)_{s3}O-CO-$, $-(CH_2)_{s3}CON(R^{43c})-$, $-(CH_2)_{s3}N(R^{43c})CON(R^{43c})-$, or $-(CH_2)_{s3}SO_2N(R^{43c})-$, $B^3$ is hydrogen atom, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted $C_{5-6}$ cycloalkenyl, optionally substituted $C_{6-10}$ aryl, optionally substituted $C_{7-14}$ aralkyl, optionally substituted 5- to 10-membered monocyclic or polycyclic heteroaryl, optionally substituted 5- to 10-membered monocyclic or polycyclic heteroaryl$C_{1-4}$ alkyl, or optionally substituted saturated heterocyclyl, provided that if $A^3$ is $-(CH_2)_{s3}N(R^{43c})-$, $-(CH_2)_{s3}OCON(R^{43c})-$, $-(CH_2)_{s3}CON(R^{43c})-$, $-(CH_2)_{s3}N(R^{43c})CON(R^{43c})-$, and $-(CH_2)_{s3}SO_2N(R^{43c})-$, $R^{43c}$ and $B^3$ may combine with each other to form a ring, $R^{43c}$ is hydrogen atom, optionally substituted $C_{1-6}$ alkyl, optionally substituted $C_{3-10}$ cycloalkyl, optionally substituted $C_{6-10}$ aryl, optionally substituted $C_{7-14}$ aralkyl, or optionally substituted 5- to 10-membered monocyclic or polycyclic heteroaryl, s3 is 0, 1 or 2, provided that if $A^3$ is $-(CH_2)_{s3}N(R^{43c})-$, s3 is 0 or 2, provided that if $A^3$ is $-(CH_2)_{s3}CON(R^{43c})-$, s3 is 1 or 2), or alternatively any two of $R^{33a}$, $R^{33b}$, $R^{33c}$ and $R^{33d}$ are hydrogen atom, the other two combine with each other together with the adjacent heterocyclyl to form a bridged ring;

$R^{53}$ is

1: $C_{1-4}$ alkoxycarbonyl (in which the group is substituted by a group of the following formula:

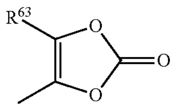

(in which $R^{63}$ is (a) $C_{1-4}$ alkyl (optionally substituted by $C_{1-4}$ alkoxy)

(b) $C_{3-6}$ cycloalkyl, or (c) $C_{6-10}$ aryl (optionally substituted by $C_{1-4}$ alkoxy))), or 2: a group of the following formula:

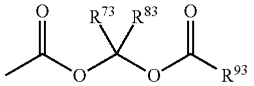

(wherein $R^{73}$ and $R^{83}$ are independently, (a) hydrogen atom, (b) $C_{1-4}$ alkyl (optionally substituted by $C_{1-4}$ alkoxy, $C_{3-6}$ cycloalkyl optionally substituted by $C_{1-4}$ alkoxy, 5- to 6-membered saturated heterocyclyl, or 5- to 6-membered saturated heterocyclyloxy), (c) $C_{3-10}$ cycloalkyl (optionally substituted by 1 to 2 fluorine atoms, or $C_{1-4}$ alkoxy), (d) $C_{6-10}$ aryl (optionally substituted by halogen atom, or $C_{6-10}$ aryl optionally substituted by halogen atom or $C_{1-4}$ alkoxy), (e) 5- to 6-membered saturated heterocyclyl, or (f) 5- to 10-membered monocyclic or polycyclic heteroaryl (optionally substituted by $C_{1-4}$ alkyl, or $C_{1-4}$ alkoxy), and $R^{93}$ is (a) $C_{1-6}$ alkyl (optionally substituted by
1 to 3 fluorine atoms,
hydroxy,
$C_{1-4}$ alkoxy,
carboxy,
5- to 6-membered saturated heterocyclyl,
$C_{3-6}$ cycloalkyl,
$C_{1-4}$ alkoxycarbonyl,
$C_{1-4}$ alkoxycarbonylamino,
amino,
mono- or di-($C_{1-6}$ alkyl)amino,
5- to 7-membered cyclic amine,
1 to 2 nitroxy,
aminocarbonyl, or
5- to 7-membered cyclic aminocarbonyl), (b) $C_{3-10}$ cycloalkyl (optionally substituted by hydroxy), (c) $C_{6-10}$ aryl (in which the group is substituted by $C_{1-4}$ alkyl, $C_{1-4}$ alkoxy, or $C_{1-4}$ alkylcarbonyloxy), (d) $C_{1-4}$ alkylcarbonyl (optionally substituted by hydroxy), (e) 5- to 10-membered monocyclic or polycyclic heteroaryl, (f) 5- to 6-membered saturated heterocyclyl (optionally substituted by $C_{1-4}$ alkyl optionally substituted by $C_{1-4}$ alkoxy), (g) $C_{1-6}$ alkoxy (optionally substituted by $C_{3-6}$cycloalkyl), (h) $C_{3-6}$cycloalkyloxy (optionally substituted by $C_{1-4}$ alkoxy), or (i) 5- to 6-membered saturated heterocyclyloxy), or a pharmaceutically acceptable salt thereof.

33. The compound of claim 32, wherein $R^{23}$ is $C_{1-6}$ alkyl, or a pharmaceutically acceptable salt thereof.

34. The compound of claim 32, wherein $R^{33a}$, $R^{33b}$, $R^{33c}$ and $R^{33d}$ are independently a group: $-A^3-B^3$ (wherein $A^3$ is a single bond, and $B^3$ is hydrogen atom), or a pharmaceutically acceptable salt thereof.

35. The compound of claim 32, wherein $R^{53}$ is $C_{1-4}$ alkoxycarbonyl (in which the group is substituted by a group of the following formula:

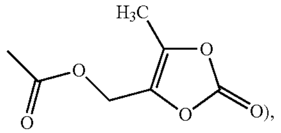

or a pharmaceutically acceptable salt thereof.

36. The compound of claim 32, wherein $R^{53}$ is a group of the following formula:

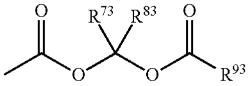

(wherein $R^{73}$ and $R^{83}$ are independently hydrogen atom, or $C_{1-4}$ alkyl, $R^{93}$ is (a) $C_{1-6}$ alkyl (optionally substituted by 1 to 3 fluorine atoms, amino, hydroxy, $C_{1-4}$ alkoxy, carboxy, $C_{1-4}$ alkoxycarbonyl, $C_{1-4}$ alkoxycarbonylamino, or 1 to 2 nitroxy), (b) $C_{3-10}$ cycloalkyl, (c) $C_{1-4}$ alkylcarbonyl (optionally substituted by hydroxy), (d) $C_{6-10}$ aryl (in which the group is substituted by $C_{1-4}$ alkyl, or $C_{1-4}$ alkylcarbonyloxy), (e) 5- to 10-membered monocyclic or polycyclic heteroaryl, (f) 5- to 6-membered saturated heterocyclyl, (g) $C_{1-6}$ alkoxy (optionally substituted by $C_{3-6}$ cycloalkyl), (h) $C_{3-6}$ cycloalkyloxy, or (i) 5- to 6-membered saturated heterocyclyloxy), or a pharmaceutically acceptable salt thereof.

* * * * *